US012364769B2

(12) United States Patent
Geall et al.

(10) Patent No.: US 12,364,769 B2
(45) Date of Patent: Jul. 22, 2025

(54) NUCLEIC ACID-POLYPEPTIDE COMPOSITIONS AND USES THEREOF

(71) Applicant: Avidity Biosciences, Inc., La Jolla, CA (US)

(72) Inventors: Andrew John Geall, Carlsbad, CA (US); Venkata Ramana Doppalapudi, San Diego, CA (US); Joel Daniel Arias, San Diego, CA (US); David Sai-Ho Chu, San Diego, CA (US); Michael Caramian Cochran, La Jolla, CA (US); Rob Burke, Encinitas, CA (US); Philip Kovach, San Diego, CA (US); Barbora Malecova, San Diego, CA (US)

(73) Assignee: AVIDITY BIOSCIENCES, INC., San Diego, CA (US)

( * ) Notice: Subject to any disclaimer, the term of this patent is extended or adjusted under 35 U.S.C. 154(b) by 176 days.

(21) Appl. No.: 17/364,765

(22) Filed: Jun. 30, 2021

(65) Prior Publication Data
US 2022/0395580 A1 Dec. 15, 2022

Related U.S. Application Data

(62) Division of application No. 16/152,324, filed on Oct. 4, 2018, now Pat. No. 11,110,180.

(60) Provisional application No. 62/568,238, filed on Oct. 4, 2017.

(51) Int. Cl.
C07H 21/04 (2006.01)
A61K 31/713 (2006.01)
A61K 47/60 (2017.01)
A61K 47/64 (2017.01)
A61K 47/68 (2017.01)
A61P 35/00 (2006.01)
C07H 17/00 (2006.01)
C07K 16/28 (2006.01)
C12N 15/113 (2010.01)

(52) U.S. Cl.
CPC ........ A61K 47/6807 (2017.08); A61K 31/713 (2013.01); A61K 47/60 (2017.08); A61K 47/64 (2017.08); A61K 47/6811 (2017.08); A61K 47/6849 (2017.08); A61K 47/6883 (2017.08); A61P 35/00 (2018.01); C07H 17/00 (2013.01); C07K 16/2863 (2013.01); C12N 15/113 (2013.01); C12N 2310/312 (2013.01); C12N 2310/3125 (2013.01); C12N 2310/315 (2013.01); C12N 2310/3513 (2013.01); C12N 2310/3515 (2013.01)

(58) Field of Classification Search
CPC .. A61K 47/6807; A61K 31/713; A61K 47/64; A61K 47/6849; A61K 47/6883; C12N 15/113
See application file for complete search history.

(56) References Cited

U.S. PATENT DOCUMENTS

| | | |
|---|---|---|
| 4,694,778 A | 9/1987 | Learn et al. |
| 5,142,047 A | 8/1992 | Summerton et al. |
| 5,185,444 A | 2/1993 | Summerton et al. |
| 5,736,557 A | 4/1998 | Hofheinz et al. |
| 5,889,136 A | 3/1999 | Scaringe et al. |
| 6,008,400 A | 12/1999 | Scaringe et al. |
| 6,111,086 A | 8/2000 | Scaringe |
| 6,821,783 B1 | 11/2004 | Comely et al. |
| 6,884,869 B2 | 4/2005 | Senter et al. |
| 7,498,298 B2 | 3/2009 | Doronina et al. |
| 7,850,975 B2 | 12/2010 | Mullis |
| 7,943,762 B2 | 5/2011 | Weller et al. |
| 8,288,352 B2 | 10/2012 | Doronina et al. |
| 8,501,930 B2 | 8/2013 | Rozema et al. |
| 8,591,910 B2 | 11/2013 | Mullis |
| 8,604,184 B2 | 12/2013 | Mullis et al. |
| 8,609,105 B2 | 12/2013 | Senter et al. |
| 8,697,688 B2 | 4/2014 | Howard et al. |
| 8,936,910 B2 | 1/2015 | Mitsch et al. |
| 9,089,614 B2 | 7/2015 | Lin et al. |
| 9,481,905 B2 | 11/2016 | Chen et al. |
| 9,725,474 B2 | 8/2017 | Murata et al. |
| 9,809,817 B2 | 11/2017 | Khvorova et al. |
| 10,881,743 B2 | 1/2021 | Geall et al. |
| 11,084,844 B2 * | 8/2021 | Prakash ............... C12N 15/113 |
| 11,110,180 B2 | 9/2021 | Geall et al. |
| 11,208,419 B2 | 12/2021 | Miao et al. |
| 11,208,429 B2 | 12/2021 | Takahashi et al. |

(Continued)

FOREIGN PATENT DOCUMENTS

| | | |
|---|---|---|
| CN | 109526222 A | 3/2019 |
| EP | 0532423 A1 | 3/1993 |

(Continued)

OTHER PUBLICATIONS

Watts et al. (Drug Discovery Today col. Oct. 13, 2008).*
Haraszti et al. (Nucleic Acids Research, 2017 7581-7592).*
Debacker et al. Improving gene silencing oligonucleotides by incorporation of peptide nucleic acids. Thesis (Doctoral) (Sep. 1, 2017) Retrieved from the Internet: URL:https://eprints.soton.ac.uk/422159/ [retrieved on Jul. 26, 2021].
Haraszti et al. 5′-Vinylphosphonate improves tissue accumulation and efficacy of conjugated siRNAs in vivo. Nucleic Acids Res. 45(13):7581-7592 (2017).

(Continued)

Primary Examiner — Kimberly Chong
(74) Attorney, Agent, or Firm — WILSON SONSINI GOODRICH & ROSATI

(57) ABSTRACT

Disclosed herein are compositions and pharmaceutical formulations that comprise a binding moiety conjugated to a modified polynucleic acid molecule and a polymer. Also described herein include methods for treating a cancer which utilize a composition or a pharmaceutical formulation comprising a binding moiety conjugated to a polynucleic acid molecule and a polymer.

12 Claims, 14 Drawing Sheets

Specification includes a Sequence Listing.

(56) References Cited

U.S. PATENT DOCUMENTS

| | | | |
|---|---|---|---|
| 12,006,499 | B2 | 6/2024 | Doppalapudi et al. |
| 2004/0012626 | A1 | 1/2004 | Brookins |
| 2007/0004665 | A1 | 1/2007 | McSwiggen et al. |
| 2011/0293512 | A1 | 12/2011 | Violette et al. |
| 2012/0065169 | A1 | 3/2012 | Hanson et al. |
| 2012/0157511 | A1 | 6/2012 | Manoharan et al. |
| 2013/0028919 | A1 | 1/2013 | Howard et al. |
| 2013/0116420 | A1 | 5/2013 | Prakash et al. |
| 2013/0309256 | A1 | 11/2013 | Lyon et al. |
| 2013/0323836 | A1* | 12/2013 | Manoharan .......... C07H 19/067 536/26.3 |
| 2014/0127239 | A1 | 5/2014 | Howard |
| 2014/0194610 | A1 | 7/2014 | Verdine et al. |
| 2014/0286970 | A1 | 9/2014 | Jeffrey et al. |
| 2014/0294851 | A1 | 10/2014 | Nguyen |
| 2014/0296321 | A1 | 10/2014 | Iversen |
| 2015/0037360 | A1 | 2/2015 | Smith |
| 2015/0064181 | A1 | 3/2015 | Armstrong |
| 2015/0080457 | A1 | 3/2015 | Manoharan et al. |
| 2015/0105539 | A1 | 4/2015 | Miao et al. |
| 2015/0105540 | A1 | 4/2015 | Miao et al. |
| 2015/0211006 | A1 | 7/2015 | Butler et al. |
| 2016/0016983 | A1 | 1/2016 | Murata et al. |
| 2016/0046939 | A1 | 2/2016 | Prakash et al. |
| 2016/0186185 | A1 | 6/2016 | Prakash et al. |
| 2016/0376577 | A1 | 12/2016 | Madison et al. |
| 2017/0035796 | A1 | 2/2017 | Wooddell et al. |
| 2017/0051286 | A1 | 2/2017 | Smith |
| 2017/0081425 | A1 | 3/2017 | Colletti et al. |
| 2017/0281795 | A1 | 10/2017 | Geall et al. |
| 2019/0240346 | A1* | 8/2019 | Sugo ...................... A61K 48/00 |
| 2020/0385414 | A1 | 12/2020 | Doppalapudi et al. |
| 2020/0385725 | A1 | 12/2020 | Doppalapudi et al. |
| 2021/0095283 | A1 | 4/2021 | Geall et al. |
| 2022/0395589 | A1 | 12/2022 | Green et al. |
| 2023/0234978 | A1 | 7/2023 | Doppalapudi et al. |

FOREIGN PATENT DOCUMENTS

| | | |
|---|---|---|
| EP | 1579015 A2 | 9/2005 |
| EP | 1068241 B1 | 10/2007 |
| EP | 2344637 B1 | 12/2014 |
| EP | 2421971 B1 | 7/2016 |
| EP | 2486141 B1 | 1/2018 |
| JP | 2005504020 A | 2/2005 |
| JP | 2005508634 A | 4/2005 |
| JP | 2017525705 A | 9/2017 |
| JP | 2018529732 A | 10/2018 |
| KR | 20130105294 A | 9/2013 |
| WO | WO-9207065 A1 | 4/1992 |
| WO | WO-9315187 A1 | 8/1993 |
| WO | WO-9734631 A1 | 9/1997 |
| WO | WO-9813526 A1 | 4/1998 |
| WO | WO-03004602 A2 | 1/2003 |
| WO | WO-03037909 A1 | 5/2003 |
| WO | WO-2008036127 A2 | 3/2008 |
| WO | WO-2008147824 A2 | 12/2008 |
| WO | WO-2009061941 A2 | 5/2009 |
| WO | WO-2009099942 A2 | 8/2009 |
| WO | WO-2009126933 A2 | 10/2009 |
| WO | WO-2011005860 A2 | 1/2011 |
| WO | WO-2011139699 A2 | 11/2011 |
| WO | WO-2011139702 A2 | 11/2011 |
| WO | WO-2011150408 A2 | 12/2011 |
| WO | WO-2012031243 A2 | 3/2012 |
| WO | WO-2013166155 A1 | 11/2013 |
| WO | WO-2014080251 A1 | 5/2014 |
| WO | WO-2014100505 A1 | 6/2014 |
| WO | WO-2014140317 A2 | 9/2014 |
| WO | WO-2014145090 A1 | 9/2014 |
| WO | WO-2014177042 A1 | 11/2014 |
| WO | WO-2014197854 A1 | 12/2014 |
| WO | WO-2015038426 A1 | 3/2015 |
| WO | WO-2015057699 A2 | 4/2015 |
| WO | WO-2015069587 A2 | 5/2015 |
| WO | WO-2015107425 A2 | 7/2015 |
| WO | WO-2016028649 A1 | 2/2016 |
| WO | WO-2016187425 A1 | 11/2016 |
| WO | WO-2017059223 A2 | 4/2017 |
| WO | WO-2017148879 A1 | 9/2017 |
| WO | WO-2017173304 A1 | 10/2017 |
| WO | WO-2017173408 A1 | 10/2017 |
| WO | WO-2017221883 A1 | 12/2017 |
| WO | WO-2018045317 A1 | 3/2018 |
| WO | WO-2018129384 A1 | 7/2018 |
| WO | WO-2019071028 A1 | 4/2019 |
| WO | WO-2019136180 A2 | 7/2019 |
| WO | WO-2020247782 A1 | 12/2020 |
| WO | WO-2020247818 A1 | 12/2020 |

OTHER PUBLICATIONS

Haringsma et al. mRNA knockdown by single strand RNA is improved by chemical modifications. Nucleic Acids Res 40(9):4125-4136 (2012).

Kang et al. HER2 Rna Aptamer-and Cell Penetrating Peptide-Mediated Delivery of Multimeric Antisense Strands of siRNAs for Gene Silencing: Multimeric antisense strands of siRNAs. Bull. Korean Chem. Soc. 37(9):1440-1444 (2016).

Kumar et al. 5'-Morpholino modification of the sense strand of an siRNA makes it a more effective passenger. Chemical Comm 55(35):5139-5142 (2019) Retrieved from the Internet: URL:https://pubs.rsc.org/en/content/articlepdf/2019/cc/c9cc00977a.

Shukla et al. Exploring Chemical Modifications for siRNA Therapeutics: A Structural and Functional Outlook. ChemMedChem 5(3):328-349 (2010).

Zhang et al. RNA interference in mammalian cells by siRNAs modified with morpholino nucleoside analogues. Bioorg Med Chem 17(6):2441-2446 (2009).

Abramova et al. Novel oligonucleotide analogues based on morpholino nucleoside subunits-antisense technologies: new chemical possibilities. Indian Journal of Chemistry 48B:1721-1726 (2009).

Agarwal et al. A Pictet-Spengler ligation for protein chemical modification. PNAS 110(1):46-51 (2013).

Albarran et al. Efficient intracellular delivery of a pro-apoptotic peptide with a pH-responsive carrier. React Funct Polym 71:261-265 (2011).

Augustyns et al., Incorporation of hexose nucleoside analogues into oligonucleotides: synthesis, base-pairing properties and enzymatic stability. Nucleic Acids Research 20(18):4711-4716 (1992).

Axup et al. Synthesis of site-specific antibody-drug conjugates using unnatural amino acids. PNAS 109(40):16101-16106 (2012).

Bell et al. Epidermal Growth Factor Receptor Mutations and Gene Amplification in Non-Small-Cell Lung Cancer: Molecular Analysis of the IDEAL/INTACT Gefitinib Trials. J Clin Oncol 23(31):8081-8092 (2005).

Berge et al. Pharmaceutical Salts. Journal of Pharmaceutical Sciences 66(1):1-19 (Jan. 1977).

Bird et al. Single-chain antigen-binding proteins. Science 242:423-442 (1988).

Blaney et al. Traceless solid-phase organic synthesis. Chem. Rev. 102:2607-2024 (2002.

Bulmus et al. A new pH-responsive and glutathione-reactive, endosomal membrane-disruptive polymeric carrier for intracellular delivery of biomolecular drugs. J Controlled Release 93:105-120 (2003).

Burke et al. siRNA-mediated knockdown of P450 oxidoreductase in rats: a tool to reduce metabolism by CYPs and increase exposure of high clearance compounds. Pharm. Res. 31(12):3445-3460 (2014).

Casi et al. Site-specific traceless coupling of potent cytotoxic drugs to recombinant antibodies for pharmacodelivery. J Am Chem Soc 134(13):5887-5892 (2012).

Castaneda et al. Acid-cleavable thiomaleamic acid linker for homogeneous antibody-drug conjugation, Chem. Commun. 49:8187-8189 (2013).

Clackson et al. Making antibody fragments using phage display libraries. Nature 352(6336):624-628 (1991).

(56) References Cited

OTHER PUBLICATIONS

Colberre-Garapin et al. A new dominant hybrid selective marker for higher eukaryotic cells. J Mol Biol 150:1-14 (1981).
Cole et al. The EBV-hybridoma technique and its application to human lung cancer. In, Monoclonal Antibodies and Cancer Therapy (vol. 27, UCLA Symposia on Molecular and Cellular Biology, New Series) (eds. R.A. Reisfeld and S.Sell), New York: Alan R. Liss, Inc. pp. 77-96 (1985).
Collis, Aec. The synthesis of vinylphosphonate-linked RNA. [Ph.D. Thesis] Retrieved from http://eprints.nottingham.ac.uk/10541/1/Alana_Collis_Thesis.pdf (2008).
Co-pending U.S. Appl. No. 17/364,754, inventors Geall; Andrew John et al., filed Jun. 30, 2021.
Crouse et al. Expression and amplification of engineered mouse dihydrofolate reductase minigenes. Mol Cell Biol 3(2):257-266 (1983).
Dawson et al. Modulation of Reactivity in Native Chemical Ligation through the Use of Thiol Additives. J. Am. Chem. Soc. 119:4325-4329 (1997).
Dawson et al. Synthesis of proteins by native chemical ligation. Science 266(5186):776-779 (1994).
Dimasi et al. Development of a trispecific antibody designed to simultaneously and efficiently target three different antigens on tumor cells. Mol Pharm 12(9):3490-3501 (2015).
Donner et al. Co-administration of an excipient oligonucleotide helps delineate pathways of productive and nonproductive uptake of phosphorothioate antisense oligonucleotides in the liver. Nucleic Acid Therapeutics 27(4): 209-220 (2017).
Duncan et al. A polymer-Triton X-100 conjugate capable of pH-dependent red blood cell lysis: a model system illustrating the possibility of drug delivery within acidic intracellular compartments. J Drug Target 2:341-347 (1994).
Elkayam et al., siRNA carrying an (E)-vinylphosphonate moiety at the 5' end of the guide strand augments gene silencing by enhanced binding to human Argonaute-2. Nucleic Acids Research 45(6):3528-3536 (2017).
El-Sayed et al. Rational design of composition and activity correlations for pH-responsive and glutathione-reactive polymer therapeutics. J Control Release 104:417-427 (2005).
Flanary et al. Antigen delivery with poly(propylacrylic acid) conjugation enhanced MHC-1 presentation and T-cell activation. Bioconjugate Chem. 20:241-248 (2009).
Goldspiel et al. Human gene therapy. Clin Pharm 12:488-505 (1993).
Griffey et al. 2'-0-aminopropyl ribonucleotides: a zwitterionic modification that enhances the exonuclease resistance and biological activity of antisense oligonucleotides, J. Med. Chem. 39(26):5100-5109 (1997).
Hackeng et al. Protein synthesis by native chemical ligation: Expanded scope by using straightforward methodology. Pnas USA 96:10068-10073 (1999).
Hanes et al. In vitro selection and evolution of functional proteins by using ribosome display. PNAS USA 94:4937-4942 (1997).
Hejesen et al. A traceless aryl-triazene linker for DNA-directed chemistry. Org Biomol Chem 11(15):2493-2497 (2013).
Henry et al. pH-responsive poly(styrene-alt-maleic anhydride) alkylamide copolymers for intracellular drug delivery. Biomacromolecules 7:2407-2414 (2006).
Huse et al. Generation of a large combinatorial library of the immunoglobulin repertoire in phage lambda. Science 246(4935):1275-1281 (1989).
Huston et al. Protein engineering of antibody binding sites: recovery of specific activity in an anti-digoxin single-chain Fv analogue produced in *Escherichia coli*. PNAS USA 85:5879-5883 (1988).
Jones et al. Poly(2-alkylacrylic acid) polymers deliver molecules to the cytosol by pH-sensitive disruption of endosomal vesicles. Biochem J 372:65-75 (2003).
Khormaee et al. Endosomolytic anionic polymer for the cytoplasmic delivery of siRNAs in localized in vivo applications. Adv Funct Mater 23:565-574 (2013).
Kohler et al. Continuous cultures of fused cells secreting antibody of predefined specificity. Nature 256:495-497 (1975).
Koizumi. ENA oligonucleotides as therapeutics. Curr Opin Mol Ther 8(2):144-149 (2006).
Kozbor et al. The production of monoclonal antibodies from human lymphocytes. Immunology Today 4:72-79 (1983).
Kutmeier et al. Assembly of humanized antibody genes from synthetic oligonucleotides using a single-round PCR. BioTechniques 17:242 (1994).
Lowy et al., Isolation of transforming DNA: Cloning the hamster aprt gene. Cell 22:817-823 (1980).
Lyon et al. Self-hydrolyzing maleimides improve the stability and pharmacological properties of antibody-drug conjugates. Nat. Biotechnol. 32(10):1059-1062 (2014).
McEnaney et al. Antibody-recruiting molecules: an emerging paradigm for engaging immune function in treating human disease. ACS Chem Biol. 7(7):1139-1151 (2012).
Miller et al., Stabilin-mediated cellular internalization of phosphorothioate-modified antisense oligonucleotides (ASOs). https://digitalcommons.unl.edu/cgi/viewcontent.cgi?filename=0&article=1019&context=ucareresearch (2016).
Morgan et al. Human gene therapy. Ann Rev Biochem 62:191-217 (1993).
Morrison et al. Chimeric human antibody molecules: mouse antigen-binding domains with human constant region domains. PNAS USA 81(21):6851-6855 (1984).
Mulligan et al. Selection for animal cells that express the *Escherichia coli* gene coding for xanthine-guanine phosphoribosyltransferase. PNAS USA 78(4):2072-2076 (1981).
Mulligan. The basic science of gene therapy. Science 260(5110):926-932 (1993).
Naisbitt et al. Disposition of amodiaquine and related antimalarial agents in human neutrophils: implications for drug design. J Pharmacol Exp Ther 280:884-893 (1997) .
Neuberger et al. Recombinant antibodies possessing novel effector functions. Nature 312(5995):604-608 (1984).
Obika et al. Synthesis of 2'-0,4'-C-methyleneuridine and-cytidine. Novel bicyclic nucleosides having a fixed C3'-endo sugar puckering. Tetrahedron Lett. 38(50):8735-8738 (1997).
O'Hare et al. Transformation of mouse fibroblasts to methotrexate resistance by a recombinant plasmid expressing a prokaryotic dihydrofolate reductase. PNAS USA 78:1527-1531 (1981).
Parmar et al. 5'-(E)-Vinylphosphonate: A Stable Phosphate Mimic Can Improve the RNAi Activity of siRNA-GalNAc Conjugates. Chembiochem 17(11):985-989 (2016).
PCT/US2018/054444 International Search Report and Written Opinion dated Feb. 15, 2019.
PCT/US2018/54444 Invitation to Pay Additional Fees dated Dec. 27, 2018.
PCT/US2019/012223 International Search Report and Written Opinion dated Jul. 5, 2019.
PCT/US2020/036369 International Search Report and Written Opinion dated Oct. 20, 2020.
PCT/US2020/036369 Invitation to Pay Additional Fees dated Aug. 13, 2020.
PCT/US2020/036420 International Search Report and Written Opinion dated Oct. 5, 2020.
PCT/US2020/036420 Invitation to Pay Additional Fees dated Aug. 14, 2020.
Pei et al. Quantitative evaluation of siRNA delivery in vivo. RNA 16:2553-2563 (2010).
Prakash et al. Synergistic effect of phosphorothioate, 5'-vinylphosphonate and GalNAc modifications for enhancing activity of synthetic siRNA. Bioorg Med Chem Lett 26(12):2817-2820 (2016).
PubChem CID 89552245. Feb. 13, 2015, pp. 1-10. Retrieved from the Internet <url :<a href="https://pubchem.ncbi.nlm.nih.gov/compound/89552245">https://pubchem.ncbi.nlm.nih.gov/compound/89552245</url :<a>.
Santerre et al. Expression of prokaryotic genes for hygromycin B and G418 resistance as dominant-selection markers in mouse L cells. Gene 30(1-3):147-156 (1984).
Skerra et al. Assembly of a functional Immunoglobulin Fv fragment in *Escherichia coli*. Science 240(4855):1038-1041 (1988).

(56) References Cited

OTHER PUBLICATIONS

Strop et al. Location matters: site of conjugation modulates stability and pharmacokinetics of antibody drug conjugates. Chem Biol 20(2):161-167 (2013).

Suriano et al. Beta-catenin (CTNNB1) gene amplification: a new mechanism of protein overexpression in cancer. Genes Chromosomes Cancer 42(3):238-246 (2005).

Szybalska et al. Genetics of human cell line. IV. DNA-mediated heritable transformation of a biochemical trait. PNAS USA 48:2026-2034 (1962).

Takeda et al. Construction of chimaeric processed immunoglobulin genes containing mouse variable and human constant region sequences. Nature 314(6010):452-454 (1985).

Talasila et al. EGFR Wild-type Amplification and Activation Promote Invasion and Development of Glioblastoma Independent of Angiogenesis. Acta Neuropathol. 125(5):683-698 (2013).

Tolstoshev. Gene Therapy, Concepts, Current Trials and Future Directions. Ann. Rev. Pharmacol. Toxicol. 32:573-596 (1993).

U.S. Appl. No. 16/152,324 Office Action dated Oct. 16, 2020.

Valtorta et al. KRAS gene amplification in colorectal cancer and impact on response to EGFR-targeted therapy. Int J Cancer 133:1259-1266 (2013).

Walker et al. Improved cellular delivery of antisense oligonucleotides using transferrin receptor antibody-oligonucleotide conjugates. Pharmaceutical research 12(10):1548-1553 (1995).

Ward et al. Binding activities of a repertoire of single immunoglobulin variable domains secreted from *Escherichia coli*. Nature 341(6242):544-546 (1989).

Wigler et al. Transfer of purified herpes virus thymidine kinase gene to cultured mouse cells. Cell 11:223-232 (1977).

Wigler et al. Transformation of mammalian cells with an amplifiable dominant-acting gene. PNAS USA 77:3567-3570 (1980).

Wu et al. Building complex glycopeptides: Development of a cysteine-free native chemical ligation protocol. Angew. Chem. Int. Ed. 45:4116-4125 (2006).

Wu et al. Delivery systems for gene therapy. Biotherapy 3:87-95 (1991).

Wu et al. Site-specific chemical modification of recombinant proteins produced in mammalian cells by using the genetically encoded aldehyde tag. PNAS USA 106(9):3000-3005 (2009).

Yessine et al. Characterization of the membrane-destabilizing properties of different pH-sensitive methacrylic acid copolymers. Biochimica et Biophysica Acta 1613:28-38 (2003).

Zhang et al. A remote arene-binding site on prostate specific membrane antigen revealed by antibody-recruiting small molecules. J Am Chem Soc. 132(36):12711-12716 (2010).

Prakash et al. Identification of metabolically stable 5'-phosphate analogs that support single-stranded siRNA activity. Nucleic Acids Res. 43(6):2993-3011 (2015).

Schiaffino et al. Mechanisms regulating skeletal muscle growth and atrophy. FEBS J 280(17):4294-4314 (2013).

U.S. Appl. No. 16/894,648 Office Action dated Jul. 3, 2023.

Habus et al. Oligonucleotides containing acyclic nucleoside analogues with carbamate internucleoside linkages. Nucleosides, Nucleotides & Nucleic Acids 14(9-10):1853-1859 (1995).

Karlsen et al. Pyrene-modified unlocked nucleic acids: synthesis, thermodynamic studies, and fluorescent properties. Chembiochem 13(4):590-601 (2012).

Karlsen et al. Synthesis of an unlocked nucleic acid terpyridine monomer and binding of divalent metal ion in nucleic acid duplexes. J Org Chem 74(22):8838-8841 (2009).

Vaish et al. Improved specificity of gene silencing by siRNAs containing unlocked nucleobase analogs. Nucleic Acids Res 39(5):1823-1832 (2011).

Watts et al. Chemically modified siRNA: tools and applications. Drug Discov Today 13(19-20):842-855 (2008).

\* cited by examiner

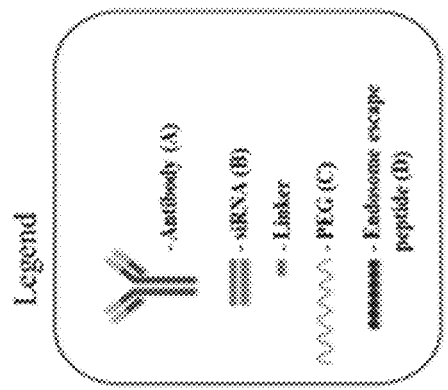
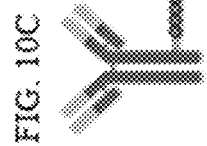
FIG. 10A  A-B-C
FIG. 10B  A-B-D-C
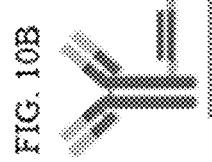
FIG. 10C  A-D-B-C
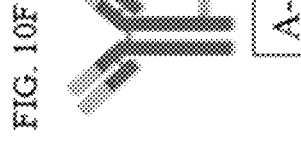
FIG. 10D  A-B-D
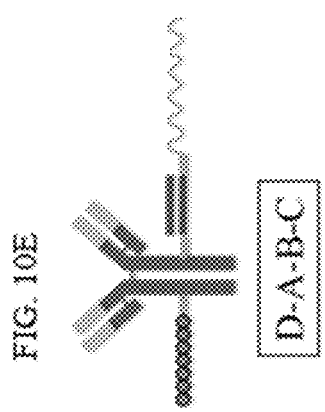
FIG. 10E  D-A-B-C
FIG. 10F  A-D-B
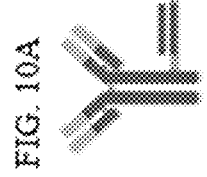
FIG. 10G  A-C-B
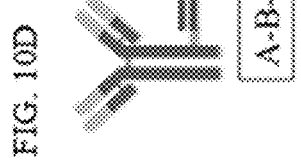
FIG. 10H  A-B-(D)$_k$
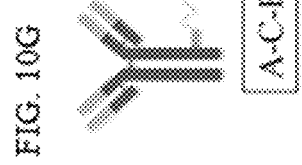
FIG. 10I  A-B-(D)$_k$

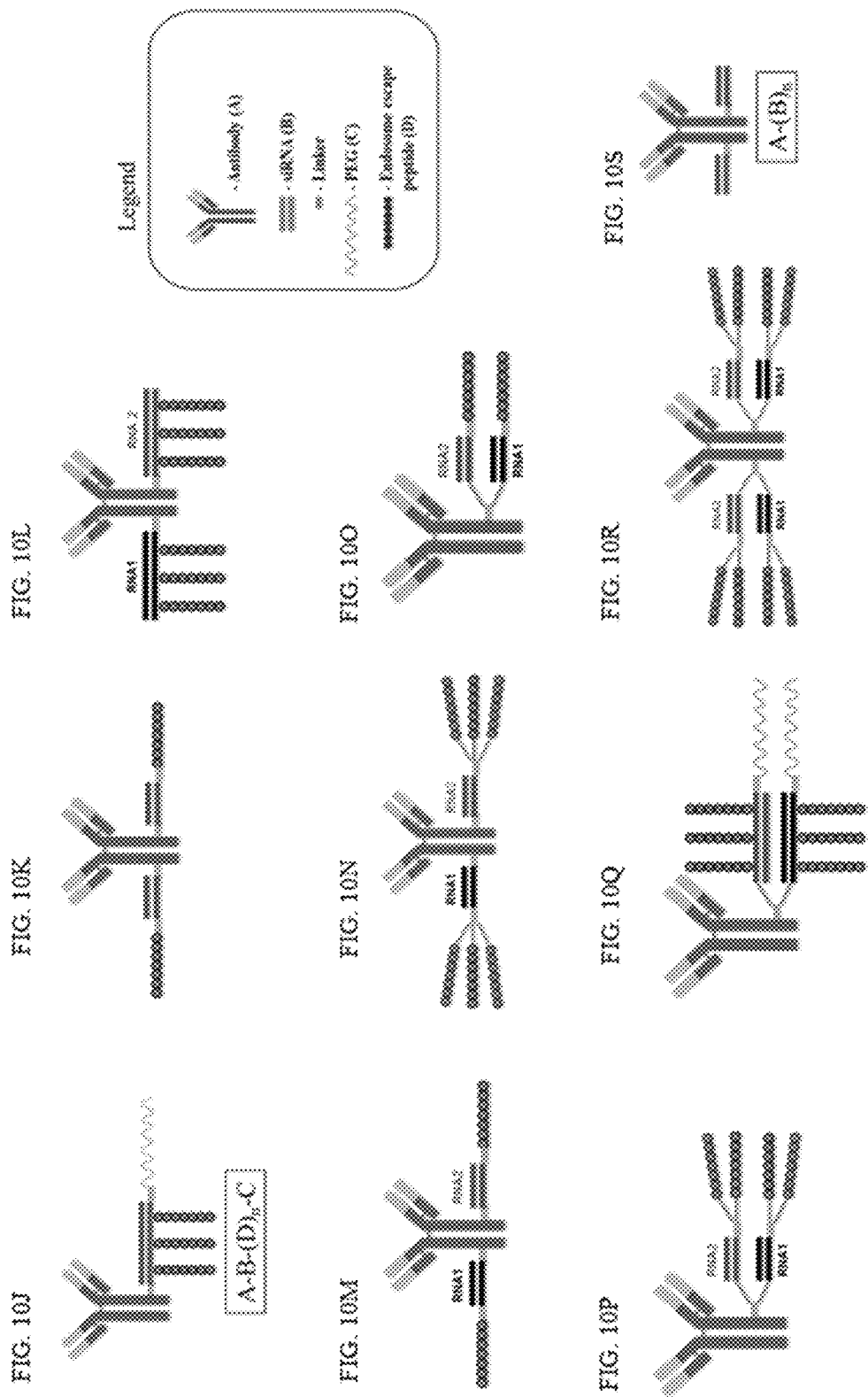

NUCLEIC ACID-POLYPEPTIDE COMPOSITIONS AND USES THEREOF

CROSS-REFERENCE

This application is a divisional of U.S. patent application Ser. No. 16/152,324, filed on Oct. 4, 2018, which claims the benefit of U.S. Provisional Patent Application No. 62/568,238, filed on Oct. 4, 2017, which is incorporated herein by reference in its entirety.

SEQUENCE LISTING

The instant application contains a Sequence Listing which has been submitted electronically in ASCII format and is hereby incorporated by reference in its entirety. Said ASCII copy, created on Jan. 9, 2019, is named 45532-719-402_SL.txt and is 340,395 bytes in size.

BACKGROUND OF THE DISCLOSURE

Gene suppression by RNA-induced gene silencing provides several levels of control: transcription inactivation, small interfering RNA (siRNA)-induced mRNA degradation, and siRNA-induced transcriptional attenuation. In some instances, RNA interference (RNAi) provides long lasting effect over multiple cell divisions. As such, RNAi represents a viable method useful for drug target validation, gene function analysis, pathway analysis, and disease therapeutics.

SUMMARY OF THE DISCLOSURE

Disclosed herein, in certain embodiments, are compositions and pharmaceutical formulations that comprise a binding moiety conjugated to a polynucleic acid molecule and a polymer. In some embodiments, also described herein include methods for treating a disease or condition (e.g., cancer) that utilize a composition or a pharmaceutical formulation comprising a binding moiety conjugated to a polynucleic acid molecule and a polymer.

Disclosed herein, in certain embodiments, is a molecule of Formula (I):

A-X-B-Y-C            Formula I wherein,
A is a binding moiety;
B is a polynucleotide;
C is a polymer;
X is a bond or a first linker; and
Y is a bond or a second linker; and
wherein the polynucleotide comprises at least one 5'-vinylphosphonate modified nucleotide.

In some embodiments, the polynucleotide comprises a single strand. In some embodiments, the polynucleotide comprises two or more strands. In some embodiments, the polynucleotide comprises a first polynucleotide and a second polynucleotide hybridized to the first polynucleotide to form a double-stranded polynucleic acid molecule. In some embodiments, the second polynucleotide comprises at least one modification.

In some embodiments, the first polynucleotide and the second polynucleotide are RNA molecules. In some embodiments, the first polynucleotide and the second polynucleotide are siRNA molecules.

In some embodiments, the first polynucleotide comprises a sequence having at least 60%, 65%, 70%, 75%, 80%, 85%, 90%, 95%, 96%, 97%, 98%, 99%, or 100% sequence identity to SEQ ID NOs: 16-45, 422-1173, 1195-1214, or 1215-1242. In some embodiments, the first polynucleotide consists of a sequence selected from SEQ ID NOs: 16-45, 422-1173, 1195-1214, or 1215-1242.

In some embodiments, the second polynucleotide comprises a sequence having at least 60%, 65%, 70%, 75%, 80%, 85%, 90%, 95%, 96%, 97%, 98%, 99%, or 100% sequence identity to SEQ ID NOs: 16-45, 422-1173, 1195-1214, or 1215-1242. In some embodiments, the second polynucleotide consists of a sequence selected from SEQ ID NOs: 16-45, 422-1173, 1195-1214, or 1215-1242.

In some embodiments, X and Y are independently a bond or a non-polymeric linker group. In some embodiments, X is a bond. In some embodiments, X is a $C_1$-$C_6$ alkyl group. In some embodiments, Y is a $C_1$-$C_6$ alkyl group. In some embodiments, X is a homobifunctional linker or a heterobifunctional linker, optionally conjugated to a $C_1$-$C_6$ alkyl group. In some embodiments, Y is a homobifunctional linker or a heterobifunctional linker.

In some embodiments, the binding moiety is an antibody or binding fragment thereof. In some embodiments, the antibody or binding fragment thereof comprises a humanized antibody or binding fragment thereof, chimeric antibody or binding fragment thereof, monoclonal antibody or binding fragment thereof, monovalent Fab', divalent Fab2, single-chain variable fragment (scFv), diabody, minibody, nanobody, single-domain antibody (sdAb), or camelid antibody or binding fragment thereof. In some embodiments, the antibody or binding fragment thereof is an anti-EGFR antibody or binding fragment thereof.

In some embodiments, C is polyethylene glycol. In some embodiments, C has a molecular weight of about 5000 Da.

In some embodiments, A-X is conjugated to the 5' end of B and Y-C is conjugated to the 3' end of B. In some embodiments, Y-C is conjugated to the 5' end of B and A-X is conjugated to the 3' end of B. In some embodiments, A-X, Y-C or a combination thereof is conjugated to an internucleotide linkage group.

In some embodiments, the molecule further comprises D. In some embodiments, D is conjugated to C or to A.

In some embodiments, D is conjugated to the molecule of Formula (I) according to Formula (II):

(A-X-B-Y-$C_n$)-L-D            Formula II wherein,
A is a binding moiety;
B is a polynucleotide;
C is a polymer;
X is a bond or a first linker;
Y is a bond or a second linker;
L is a bond or a third linker;
D is an endosomolytic moiety; and
n is an integer between 0 and 1; and
wherein the polynucleotide comprises at least one 5'-vinylphosphonate modified nucleotide; and
D is conjugated anywhere on A, B, or C.
In some embodiments, D is INF7 or melittin.
In some embodiments, D is an endosomolytic polymer.
In some embodiments, L is a $C_1$-$C_6$ alkyl group. In some embodiments, L is a homobifuctional linker or a heterobifunctional linker.

In some embodiments, the molecule further comprises at least a second binding moiety A. In some embodiments, the at least second binding moiety A is conjugated to A, to B, or to C. In some embodiments, the at least second binding moiety A is cholesterol.

In some embodiments, the molecule further comprises at least an additional polynucleotide B. In some embodiments, the at least an additional polynucleotide B is conjugated to A, to B, or to C.

In some embodiments, the molecule further comprises at least an additional polymer C. In some embodiments, the at least an additional polymer C is conjugated to A, to B, or to C.

Disclosed herein, in certain embodiments, is a molecule of Formula (I): A-X-B-Y-C (Formula I), wherein A is an antibody or its binding fragments thereof; B is a polynucleotide; C is a polymer; X is a bond or first non-polymeric linker; and Y is a bond or second linker; wherein the polynucleotide comprises at least one 5'-vinylphosphonate modified nucleotide; and wherein A and C are not attached to B at the same terminus. In some embodiments, the at least one modified internucleotide linkage comprises a phosphorothioate linkage or a phosphorodithioate linkage. In some embodiments, the at least one inverted abasic moiety is at at least one terminus. In some embodiments, the polynucleotide comprises a single strand. In some embodiments, the polynucleotide comprises a first polynucleotide and a second polynucleotide hybridized to the first polynucleotide to form a double-stranded polynucleic acid molecule. In some embodiments, the second polynucleotide comprises at least one modification. In some embodiments, the first polynucleotide and the second polynucleotide are RNA molecules. In some embodiments, the first polynucleotide comprises a sequence having at least 80%, 85%, 90%, 95%, 96%, 97%, 98%, 99%, or 100% sequence identity to SEQ ID NOs: 16-45, 422-1173, 1195-1214, or 1215-1242. In some embodiments, the second polynucleotide comprises a sequence having at least 80%, 85%, 90%, 95%, 96%, 97%, 98%, 99%, or 100% sequence identity to SEQ ID NOs: 16-45, 422-1173, 1195-1214, or 1215-1242. In some embodiments, Y is a non-polymeric linker group. In some embodiments, X is a bond. In some embodiments, X is a $C_1$-$C_6$ alkyl group. In some embodiments, Y is a $C_1$-$C_6$ alkyl group. In some embodiments, X is a homobifuctional linker or a heterobifunctional linker, optionally conjugated to a $C_1$-$C_6$ alkyl group. In some embodiments, Y is a homobifuctional linker or a heterobifunctional linker. In some embodiments, the antibody or binding fragment thereof comprises a humanized antibody or binding fragment thereof, chimeric antibody or binding fragment thereof, monoclonal antibody or binding fragment thereof, monovalent Fab', divalent Fab2, single-chain variable fragment (scFv), diabody, minibody, nanobody, single-domain antibody (sdAb), or camelid antibody or binding fragment thereof. In some embodiments, C is polyethylene glycol. In some embodiments, C has a molecular weight of about 1000 Da, 2000 Da, or 5000 Da. In some embodiments, A-X is conjugated to the 5' end of B and Y-C is conjugated to the 3' end of B. In some embodiments, Y-C is conjugated to the 5' end of B and A-X is conjugated to the 3' end of B. In some embodiments, the molecule further comprises D. In some embodiments, D is conjugated to C or to A. In some embodiments, D is conjugated to the molecule of Formula (I) according to Formula (II): (A-X-B-Y-$C_c$)-L-D (Formula II), wherein A is an antibody or its binding fragments thereof; B is a polynucleotide; C is a polymer; X is a bond or first non-polymeric linker; Y is a bond or second linker; L is a bond or third linker; D is an endosomolytic moiety; and c is an integer between 0 and 1; wherein the polynucleotide comprises at least one 2' modified nucleotide, at least one modified internucleotide linkage, or at least one inverted abasic moiety; wherein A and C are not attached to B at the same terminus; and wherein D is conjugated anywhere on A or C or to a terminus of B. In some embodiments, D is INF7 or melittin. In some embodiments, D is an endosomolytic polymer. In some embodiments, L is a $C_1$-$C_6$ alkyl group. In some embodiments, L is a homobifuctional linker or a heterobifunctional linker. In some embodiments, the molecule further comprises at least a second binding moiety. In some embodiments, the at least second binding moiety is conjugated to A, to B, or to C. In some embodiments, the at least second binding moiety is cholesterol. In some embodiments, the molecule further comprises at least an additional polynucleotide B. In some embodiments, the at least an additional polynucleotide B is conjugated to A, to B, or to C. In some embodiments, the molecule further comprises at least an additional polymer C. In some embodiments, the at least an additional polymer C is conjugated to A, to B, or to C.

Disclosed herein, in certain embodiments, is a pharmaceutical composition comprising a molecule described above, and a pharmaceutically acceptable excipient. In some embodiments, the pharmaceutical composition is formulated as a nanoparticle formulation. In some embodiments, the pharmaceutical composition is formulated for parenteral, oral, intranasal, buccal, rectal, or transdermal administration.

Disclosed herein, in certain embodiments, is a method of treating a disease or disorder in a patient in need thereof, comprising administering to the patient a composition comprising a molecule described above. In some embodiments, the disease or disorder is a cancer. In some embodiments, the cancer is a solid tumor. In some embodiments, the cancer is a hematologic malignancy. In some embodiments, the cancer comprises a KRAS-associated, an EGFR-associated, an AR-associated cancer, a β-catenin associated cancer, a PIK3C-associated cancer, or a MYC-associated cancer. In some embodiments, the cancer comprises bladder cancer, breast cancer, colorectal cancer, endometrial cancer, esophageal cancer, glioblastoma multiforme, head and neck cancer, kidney cancer, lung cancer, ovarian cancer, pancreatic cancer, prostate cancer, or thyroid cancer. In some embodiments, the cancer comprises acute myeloid leukemia, CLL, DLBCL, or multiple myeloma. In some embodiments, the method is an immuno-oncology therapy.

Disclosed herein, in certain embodiments, is a method of inhibiting the expression of a target gene in a primary cell of a patient, comprising administering a molecule described above to the primary cell. In some embodiments, the method is an in vivo method. In some embodiments, the patient is a human.

Disclosed herein, in certain embodiments, is an immuno-oncology therapy comprising a molecule described above for the treatment of a disease or disorder in a patient in need thereof.

Disclosed herein, in certain embodiments, is a kit comprising a molecule described above.

BRIEF DESCRIPTION OF THE DRAWINGS

FIGS. 10A-10S illustrate cartoon representations of molecules described herein.

DETAILED DESCRIPTION OF THE DISCLOSURE

Figure 1A:
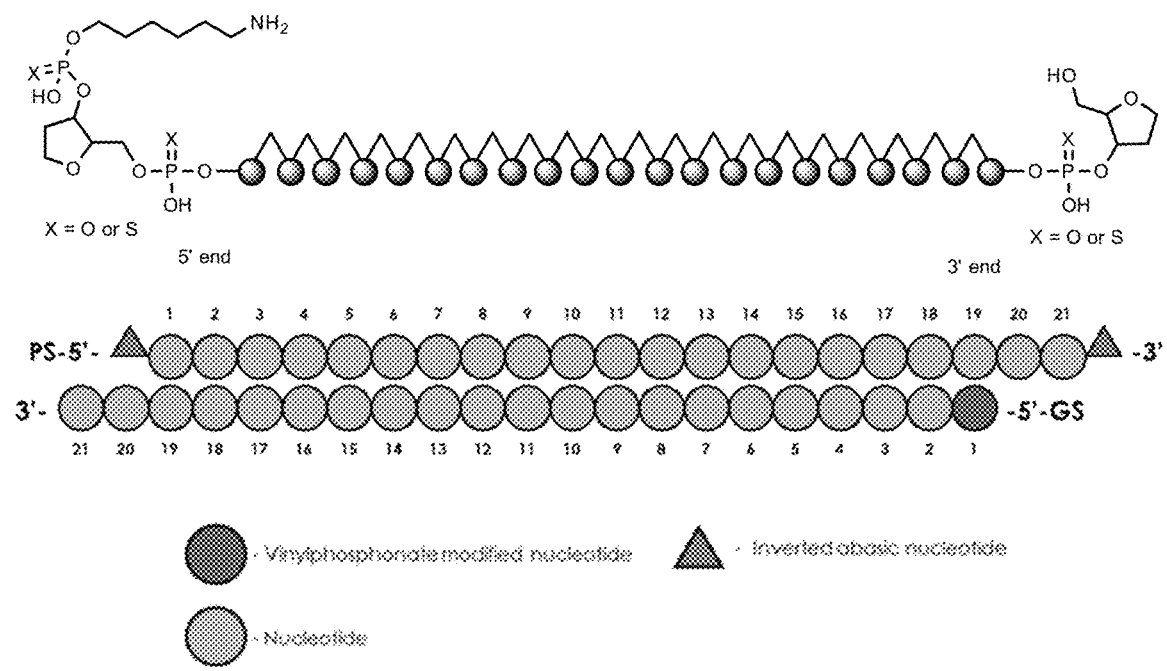
FIG. 1A shows a cartoon representation of the structure of a 21 mer duplex with 19 bases of complementarity and 3' dinucleotide overhangs, as described in example 10.

Nucleic acid (e.g., RNAi) therapy is a targeted therapy with high selectivity and specificity. However, in some instances, nucleic acid therapy is also hindered by poor intracellular uptake, limited blood stability and non-specific immune stimulation. To address these issues, various modifications of the nucleic acid composition are explored, such as for example, novel linkers for better stabilizing and/or lower toxicity, optimization of binding moiety for increased target specificity and/or target delivery, and nucleic acid polymer modifications for increased stability and/or reduced off-target effect.

In some embodiments, the arrangement or order of the different components that make-up the nucleic acid composition further effects intracellular uptake, stability, toxicity, efficacy, and/or non-specific immune stimulation. For example, if the nucleic acid component includes a binding moiety, a polymer, and a polynucleic acid molecule (or polynucleotide), the order or arrangement of the binding moiety, the polymer, and/or the polynucleic acid molecule (or polynucleotide) (e.g., binding moiety-polynucleic acid molecule-polymer, binding moiety-polymer-polynucleic acid molecule, or polymer-binding moiety-polynucleic acid molecule) further effects intracellular uptake, stability, toxicity, efficacy, and/or non-specific immune stimulation.

In some embodiments, described herein include a molecule those arrangement of the nucleic acid components effects intracellular uptake, stability, toxicity, efficacy, and/or non-specific immune stimulation. In some instances, the molecule comprises a binding moiety conjugated to a polynucleic acid molecule and a polymer. In some embodiments, the molecule comprises a molecule according to Formula (I): A-X-B-Y-C; in which A is a binding moiety, B is a polynucleotide comprising at least one 5'-vinylphosphonate modified nucleotide, C is a polymer, X is a bond or first linker, and Y is a bond or second linker. In some instances, the polynucleotide comprises at least one 5'-vinylphosphonate modified nucleotide. In some instances, the molecule of Formula (I) further comprises D, an endosomolytic moiety.

In some embodiments, a molecule comprising a binding moiety conjugated to a polynucleic acid molecule and a polymer arranged as described herein enhances intracellular uptake, stability, and/or efficacy. In some instances, a molecule comprising a binding moiety conjugated to a polynucleic acid molecule and a polymer arranged as described herein reduces toxicity and/or non-specific immune stimulation. In some cases, the molecule comprises a molecule according to Formula (I): A-X-B-Y-C; in which A is a binding moiety, B is a polynucleotide comprising at least one 5'-vinylphosphonate modified nucleotide, C is a polymer, X is a bond or first linker, and Y is a bond or second linker. In some instances, the polynucleotide comprises at least one 5'-vinylphosphonate modified nucleotide. In some instances, the molecule of Formula (I) further comprises D, an endosomolytic moiety.

In some embodiments, a molecule described herein is further used to treat a disease or disorder. In some instances, a molecule for the treatment of a disease or disorder is a molecule according to Formula (I): A-X-B-Y-C; in which A is a binding moiety, B is a polynucleotide comprising at least one 5'-vinylphosphonate modified nucleotide, C is a polymer, X is a bond or first linker, and Y is a bond or second linker. In some instances, the polynucleotide comprises at least one 5'-vinylphosphonate modified nucleotide. In some instances, the molecule of Formula (I) further comprises D, an endosomolytic moiety.

In some embodiments, a molecule described herein is also used for inhibiting the expression of a target gene in a primary cell of a patient in need thereof. In such instances, a molecule for such use is a molecule according to Formula (I): A-X-B-Y-C; in which A is a binding moiety, B is a polynucleotide comprising at least one 5'-vinylphosphonate modified nucleotide, C is a polymer, X is a bond or first linker, and Y is a bond or second linker. In some instances, the polynucleotide comprises at least one 5'-vinylphosphonate modified nucleotide, at least one modified internucleotide linkage, or at least one inverted abasic moiety. In some instances, the molecule of Formula (I) further comprises D, an endosomolytic moiety.

In some embodiments, a molecule described herein is additionally used as an immuno-oncology therapy for the treatment of a disease or disorder. In some instance, the molecule is a molecule according to Formula (I): A-X-B-Y-C; in which A is a binding moiety, B is a polynucleotide comprising at least one 5'-vinylphosphonate modified nucleotide, C is a polymer, X is a bond or first linker, and Y is a bond or second linker. In some instances, the polynucleotide comprises at least one 5'-vinylphosphonate modified nucleotide, at least one modified internucleotide linkage, or at least one inverted abasic moiety. In some instances, the molecule of Formula (I) further comprises D, an endosomolytic moiety.

In additional embodiments, described herein include a kit, which comprises one or more of the molecules described herein.

Therapeutic Molecule Platform

In some embodiments, a molecule (e.g., a therapeutic molecule) described herein comprises a binding moiety conjugated to a polynucleic acid molecule comprising at least one 5'-vinylphosphonate modified nucleotide and a polymer. In some embodiments, a molecule (e.g., a therapeutic molecule) comprises a molecule according to Formula (I):

A-X-B-Y-C                                                       Formula I wherein,
A is a binding moiety;
B is a polynucleotide;
C is a polymer;
X is a bond or a first linker; and
Y is a bond or a second linker; and
wherein the polynucleotide comprises at least one 5'-vinylphosphonate modified nucleotide.

In some instances, the molecule of Formula (I) further comprises D, an endosomolytic moiety.

In some embodiments, at least one A and/or at least one C are conjugated to the 5' terminus of B, the 3' terminus of B, an internal site on B, or in any combinations thereof. In some instances, at least one A is conjugated at one terminus of B while at least one C is conjugated at the opposite terminus of B. In some instances, at least one of A is conjugated at one terminus of B while at least one of C is conjugated at an internal site on B.

In some cases, A and C are not conjugated or attached to B at the same terminus. In some cases, A is attached or conjugated to B at a first terminus of B. In some cases, C is attached or conjugated to B at a second terminus of B, and the second terminus of B is different than the first terminus. In some cases, A is attached or conjugated to B at the 5' terminus of B, and C is attached or conjugated to B at the 3' terminus of B. In other cases, A is attached or conjugated to B at the 3' terminus of B, and C is attached or conjugated to B at the 5' terminus of B.

In some embodiments, A is an antibody or binding fragment thereof. In some cases, C is a polymer. In some cases, A and C are not conjugated or attached to B at the same terminus. In some cases, A is attached or conjugated to B at a first terminus of B. In some cases, C is attached or conjugated to B at a second terminus of B, and the second terminus of B is different than the first terminus. In some cases, A is attached or conjugated to B at the 5' terminus of B, and C is attached or conjugated to B at the 3' terminus of B. In other cases, A is attached or conjugated to B at the 3' terminus of B, and C is attached or conjugated to B at the 5' terminus of B. In some cases, X which connects A to B is a bond or a non-polymeric linker. In some cases, X is a non-peptide linker (or a linker that does not comprise an amino acid residue). In some cases, Y which connects B to C is a bond or a second linker. In some instances, X connects A to the 5' terminus of B, and Y connects C to the 3' terminus of B. In other instances, X connects A to the 3' terminus of B, and Y connects C to the 5' terminus of B.

In some embodiments, X-B is conjugated or attached to the N-terminus, C-terminus, a constant region, a hinge region, or a Fc region of A. In some instances, X-B is conjugated or attached to the N-terminus of A. In some instances, X-B is conjugated or attached to the C-terminus of A. In some instances, X-B is conjugated or attached to a hinge region of A. In some instances, X-B is conjugated or attached to a constant region of A. In some instances, X-B is conjugated or attached to the Fc region of A.

In some instances, at least one B and/or at least one C, and optionally at least one D are conjugated to a first A. In some instances, the at least one B is conjugated at a terminus (e.g., a 5' terminus or a 3' terminus) to the first A or are conjugated via an internal site to the first A. In some cases, the at least one C is conjugated either directly to the first A or indirectly via the two or more Bs. If indirectly via the two or more Bs, the two or more Cs are conjugated either at the same terminus as the first A on B, at opposing terminus from the first A, or independently at an internal site. In some instances, at least one additional A is further conjugated to the first A, to B, or to C. In additional instances, the at least one D is optionally conjugated either directly or indirectly to the first A, to the at least one B, or to the at least one C. If directly to the first A, the at least one D is also optionally conjugated to the at least one B to form a A-D-B conjugate or is optionally conjugated to the at least one B and the at least one C to form a A-D-B-C conjugate. In some cases, the at least one additional A is different than the first A.

In some cases, two or more Bs and/or two or more Cs are conjugated to a first A. In some instances, the two or more Bs are conjugated at a terminus (e.g., a 5' terminus or a 3' terminus) to the first A or are conjugated via an internal site to the first A. In some instances, the two or more Cs are conjugated either directly to the first A or indirectly via the two or more Bs. If indirectly via the two or more Bs, the two or more Cs are conjugated either at the same terminus as the first A on B, at opposing terminus from the first A, or independently at an internal site. In some instances, at least one additional A is further conjugated to the first A, to two or more Bs, or to two or more Cs. In additional instances, at least one D is optionally conjugated either directly or indirectly to the first A, to the two or more Bs, or to the two or more Cs. If indirectly to the first A, the at least one D is conjugated to the first A through the two or more Bs, through the two or more Cs, through a B-C orientation to form a A-B-C-D type conjugate, or through a C-B orientation to form a A-C-B-D type conjugate. In some cases, the at least one additional A is different than the first A. In some cases, the two or more Bs are different. In other cases, the two or more Bs are the same. In some instances, the two or more Cs are different. In other instances, the two or more Cs are the same. In additional instances, the two or more Ds are different. In additional instances, the two or more Ds are the same.

In other cases, two or more Bs and/or two or more Ds, optionally two or more Cs are conjugated to a first A. In some instances, the two or more Bs are conjugated at a terminus (e.g., a 5' terminus or a 3' terminus) to the first A or are conjugated via an internal site to the first A. In some instances, the two or more Ds are conjugated either directly to the first A or indirectly via the two or more Bs. If indirectly via the two or more Bs, the two or more Ds are conjugated either at the same terminus as the first A on B, at opposing terminus from the first A, or independently at an internal site. In some instances, at least one additional A is further conjugated to the first A, to the two or more Bs, or to the two or more Ds. In additional instances, the two or more Cs are optionally conjugated either directly or indirectly to the first A, to the two or more Bs, or to the two or more Ds. In some cases, the at least one additional A is different than the first A. In some cases, the two or more Bs are different. In other cases, the two or more Bs are the same. In some instances, the two or more Cs are different. In other instances, the two or more Cs are the same. In additional instances, the two or more Ds are different. In additional instances, the two or more Ds are the same.

In some embodiments, a molecule (e.g., a therapeutic molecule) described herein comprises a molecule according to Formula (II):

(A-X-B-Y-C$_c$)-L-D      Formula II wherein,
A is a binding moiety;
B is a polynucleotide;
C is a polymer;
X is a bond or a first linker;
Y is a bond or a second linker;
L is a bond or a third linker;
D is an endosomolytic moiety; and
c is an integer between 0 and 1; and
wherein the polynucleotide comprises at least one 5'-vinylphosphonate modified nucleotide; and D is conjugated anywhere on A, B, or C.

In some embodiments, a molecule (e.g., a therapeutic molecule) described herein comprises a molecule according to Formula (III):

A$_a$-X-B$_b$-Y-C$_c$-L-D$_n$      Formula III wherein,
A is a binding moiety;
B is a polynucleotide;
C is a polymer;
D is an endosomolytic moiety;
X is a bond or a first linker;
Y is a bond or a second linker;
L is a bond or a third linker;
a and b are independently an integer between 1-3;
c is an integer between 0 and 3; and
n is an integer between 0 and 10; and
wherein the polynucleotide comprises at least one 5'-vinylphosphonate modified nucleotide; A is conjugated anywhere on B, C, or D; B is conjugated anywhere on A, C, or D; C is conjugated anywhere on A, B, or D; and D is conjugated anywhere on A, B, or C.

In some embodiments, a molecule (e.g., a therapeutic molecule) described herein comprises a molecule according to Formula (IIIa): A-X-B-L-D-Y-C.

In some embodiments, a molecule (e.g., a therapeutic molecule) described herein comprises a molecule according to Formula (IIIb): A$_a$-X-B$_b$-L-D$_n$.

In some embodiments, a molecule (e.g., a therapeutic molecule) described herein comprises a molecule according to Formula (IV):

A-X-(B$_b$-Y-C$_c$-L-D$_n$)$_m$ wherein,
A is a binding moiety;
B is a polynucleotide;
C is a polymer;
D is an endosomolytic moiety;
X is a bond or a first linker;
Y is a bond or a second linker;
L is a bond or a third linker;
a and b are independently an integer between 1-3;
c is an integer between 0 and 3;
n is an integer between 0 and 10; and
m is an integer between 1-3; and
wherein the polynucleotide comprises at least one 5'-vinylphosphonate modified nucleotide; C is conjugated anywhere on B or D; and D is conjugated anywhere on B or C.

In some embodiments, a molecule (e.g., a therapeutic molecule) described herein comprises a molecule according to Formula (IVa): A-X-(B$_b$-L-D$_n$-Y-C$_c$)$_m$.

In some embodiments, a molecule (e.g., a therapeutic molecule) is a molecule as illustrated in FIG. 10A.
In some embodiments, a molecule (e.g., a therapeutic molecule) is a molecule as illustrated in FIG. 10B.
In some embodiments, a molecule (e.g., a therapeutic molecule) is a molecule as illustrated in FIG. 10C.
In some embodiments, a molecule (e.g., a therapeutic molecule) is a molecule as illustrated in FIG. 10D.
In some embodiments, a molecule (e.g., a therapeutic molecule) is a molecule as illustrated in FIG. 10E.
In some embodiments, a molecule (e.g., a therapeutic molecule) is a molecule as illustrated illustrated in FIG. 10F.
In some embodiments, a molecule (e.g., a therapeutic molecule) is a molecule as illustrated in FIG. 10G.
In some embodiments, a molecule (e.g., a therapeutic molecule) is a molecule as illustrated in FIG. 10H.
In some embodiments, a molecule (e.g., a therapeutic molecule) is a molecule as illustrated in FIG. 10I.
In some embodiments, a molecule (e.g., a therapeutic molecule) is a molecule as illustrated in FIG. 10J.
In some embodiments, a molecule (e.g., a therapeutic molecule) is a molecule as illustrated in FIG. 10K.
In some embodiments, a molecule (e.g., a therapeutic molecule) is a molecule as illustrated in FIG. 10L.
In some embodiments, a molecule (e.g., a therapeutic molecule) is a molecule as illustrated in FIG. 10M.
In some embodiments, a molecule (e.g., a therapeutic molecule) is a molecule as illustrated in FIG. 10N.
In some embodiments, a molecule (e.g., a therapeutic molecule) is a molecule as illustrated in FIG. 10O.
In some embodiments, a molecule (e.g., a therapeutic molecule) is a molecule as illustrated in FIG. 10P.
In some embodiments, a molecule (e.g., a therapeutic molecule) is a molecule as illustrated in FIG. 10Q.
In some embodiments, a molecule (e.g., a therapeutic molecule) is a molecule as illustrated in FIG. 10R.
In some embodiments, a molecule (e.g., a therapeutic molecule) is a molecule as illustrated in FIG. 10S.

The antibody as illustrated above is for representation purposes only and encompasses a humanized antibody or binding fragment thereof, chimeric antibody or binding fragment thereof, monoclonal antibody or binding fragment thereof, monovalent Fab', divalent Fab2, single-chain variable fragment (scFv), diabody, minibody, nanobody, single-domain antibody (sdAb), or camelid antibody or binding fragment thereof.

Polynucleic Acid Molecule Targets

In some embodiments, the polynucleic acid molecule B is a polynucleic acid molecule (or polynucleotide) that hybridizes to a target region on an oncogene. In some instances, oncogenes are further classified into several categories: growth factors or mitogens, receptor tyrosine kinases, cytoplasmic tyrosine kinases, cytoplasmic serine/threonine kinases, regulatory GTPases, and transcription factors. Exemplary growth factors include c-Sis. Exemplary receptor tyrosine kinases include epidermal growth factor receptor (EGFR), platelet-derived growth factor receptor (PDGFR), vascular endothelial growth factor receptor (VEGFR), and HER2/neu. Exemplary cytoplasmic tyrosine kinases include Src-family tyrosine kinases, Syk-ZAP-70 family of tyrosine kinases, BTK family of tyrosine kinases, and Abl gene in CML. Exemplary cytoplasmic serine/threonine kinases include Raf kinase and cyclin-dependent kinases. Exemplary regulatory GTPases include Ras family of proteins such as KRAS. Exemplary transcription factors include MYC gene. In some instances, an oncogene described herein comprises an oncogene selected from growth factors or mitogens, receptor tyrosine kinases, cytoplasmic tyrosine kinases, cytoplasmic serine/threonine kinases, regulatory GTPases, or transcription factors. In some embodiments, the polynucleic acid molecule is a polynucleic acid molecule that hybridizes to a target region of an oncogene selected from growth factors or mitogens, receptor tyrosine kinases, cytoplasmic tyrosine kinases, cytoplasmic serine/threonine kinases, regulatory GTPases, or transcription factors.

In some embodiments, an oncogene described herein comprises Abl, AKT-2, ALK, AML1 (or RUNX1), AR, AXL, BCL-2, 3, 6, BRAF, c-MYC, EGFR, ErbB-2 (Her2, Neu), Fms, FOS, GLI1, HPRT1, IL-3, INTS2, JUN, KIT, KS3, K-sam, LBC (AKAP13), LCK, LYL1, MAS1, MDM2, MET, MLL (KMT2A), MOS, MYB, MYH11/CBFB, NOTCH1 (TAN1), NTRK1 (TRK), OST (SLC51B), PAX5, PIM1, PRAD-1, RAF, RAR/PML, HRAS, KRAS, NRAS, REL/NRG, RET, ROS, SKI, SRC, TIAM1, or TSC2. In some embodiments, the polynucleic acid molecule is a polynucleic acid molecule that hybridizes to a target region of Abl, AKT-2, ALK, AML1 (or RUNX1), AR, AXL, BCL-2, 3, 6, BRAF, c-MYC, EGFR, ErbB-2 (Her2, Neu), Fms, FOS, GLI1, HPRT1, IL-3, INTS2, JUN, KIT, KS3, K-sam, LBC (AKAP13), LCK, LYL1, MAS1, MDM2, MET, MLL (KMT2A), MOS, MYB, MYH11/CBFB, NOTCH1 (TAN1), NTRK1 (TRK), OST (SLC51B), PAX5, PRAD-1, RAF, RAR/PML, HRAS, KRAS, NRAS, REL/ NRG, RET, ROS, SKI, SRC, TIAM1, or TSC2.

In some embodiments, an oncogene described herein comprises KRAS, EGFR, AR, HPRT1, CNNTB1 (β-catenin), or β-catenin associated genes. In some embodiments, the polynucleic acid molecule B is a polynucleic acid molecule that hybridizes to a target region of KRAS, EGFR, AR, HPRT1, CNNTB1 (β-catenin), or β-catenin associated genes. In some embodiments, the polynucleic acid molecule B is a polynucleic acid molecule that hybridizes to a target region of KRAS. In some embodiments, the polynucleic acid molecule B is a polynucleic acid molecule that hybridizes to a target region of EGFR. In some embodiments, the polynucleic acid molecule B is a polynucleic acid molecule that hybridizes to a target region of AR. In some embodiments, the polynucleic acid molecule B is a polynucleic acid molecule that hybridizes to a target region of CNNTB1 (β-catenin). In some embodiments, the polynucleic acid molecule B is a polynucleic acid molecule that hybridizes to a target region of CNNTB1 (β-catenin) associated genes. In some instances, the β-catenin associated genes comprise PIK3CA, PIK3CB, and Myc. In some instances, the polynucleic acid molecule B is a polynucleic acid molecule that hybridizes to a target region of HPRT1.

Polynucleic Acid Molecules that Target Kirsten Rat Sarcoma Viral Oncogene Homolog (KRAS)

Kirsten Rat Sarcoma Viral Oncogene Homolog (also known as GTPase KRas, V-Ki-ras2 Kirsten rat sarcoma viral oncogene homolog, or KRAS) is involved in regulating cell division. The K-Ras protein is a GTPase belonging to the Ras superfamily. In some instances, K-Ras modulates cell cycle progression, as well as induces growth arrest, apoptosis, and replicative senescence under different environmental triggers (e.g., cellular stress, ultraviolet, heat shock, or ionizing irradiation). In some cases, wild type KRAS gene has been shown to be frequently lost during tumor progression in different types of cancer, while mutations of KRAS gene have been linked to cancer development. In some instances, KRAS amplification has also been implicated in cancer development (see, for example, Valtorta et al. "KRAS gene amplification in colorectal cancer and impact on response to EGFR-targeted therapy," *Int. J. Cancer* 133: 1259-1266 (2013)). In such cases, the cancer pertains to a refractory cancer in which the patient has acquired resistance to a particular inhibitor or class of inhibitors.

In some embodiments, the KRAS gene is wild type or comprises a mutation. In some instances, KRAS mRNA is wild type or comprises a mutation. In some instances, the polynucleic acid molecule is a polynucleic acid molecule that hybridizes to a target region of wild type KRAS DNA or RNA. In some instances, the polynucleic acid molecule is a polynucleic acid molecule that hybridizes to a target region of KRAS DNA or RNA comprising a mutation (e.g., a substitution, a deletion, or an addition).

In some embodiments, KRAS DNA or RNA comprises one or more mutations. In some embodiments, KRAS DNA or RNA comprises one or more mutations at codons 12 or 13 in exon 1. In some instances, KRAS DNA or RNA comprises one or more mutations at codons 61, 63, 117, 119, or 146. In some instances, KRAS DNA or RNA comprises one or more mutations at positions corresponding to amino acid residues 12, 13, 18, 19, 20, 22, 24, 26, 36, 59, 61, 63, 64, 68, 110, 116, 117, 119, 146, 147, 158, 164, 176, or a combination thereof of the KRAS polypeptide. In some embodiments, KRAS DNA or RNA comprises one or more mutations at positions corresponding to amino acid residues selected from G12V, G12D, G12C, G12A, G12S, G12F, G13C, G13D, G13V, A18D, L19F, T20R, Q22K, I24N, N26K, I36L, I36M, A59G, A59E, Q61K, Q61H, Q61L, Q61R, E63K, Y64D, Y64N, R68S, P110S, K117N, C118S, A146T, A146P, A146V, K147N, T158A, R164Q, K176Q, or a combination thereof of the KRAS polypeptide.

In some embodiments, the polynucleic acid molecule hybridizes to a target region of KRAS DNA or RNA comprising one or more mutations. In some embodiments, the polynucleic acid molecule hybridizes to a target region of KRAS DNA or RNA comprising one or more mutations at codons 12 or 13 in exon 1. In some embodiments, the polynucleic acid molecule hybridizes to a target region of KRAS DNA or RNA comprising one or more mutations at codons 61, 63, 117, 119, or 146. In some embodiments, the polynucleic acid molecule hybridizes to a target region of KRAS DNA or RNA comprising one or more mutations at positions corresponding to amino acid residues 12, 13, 18, 19, 20, 22, 24, 26, 36, 59, 61, 63, 64, 68, 110, 116, 117, 119, 146, 147, 158, 164, 176, or a combination thereof of the KRAS polypeptide. In some embodiments, the polynucleic acid molecule hybridizes to a target region of KRAS DNA or RNA comprising one or more mutations corresponding to amino acid residues selected from G12V, G12D, G12C, G12A, G12S, G12F, G13C, G13D, G13V, A18D, L19F, T20R, Q22K, I24N, N26K, I36L, I36M, A59G, A59E, Q61K, Q61H, Q61L, Q61R, E63K, Y64D, Y64N, R68S, P110S, K117N, C118S, A146T, A146P, A146V, K147N, T158A, R164Q, K176Q, or a combination thereof of the KRAS polypeptide.

Polynucleic Acid Molecules that Target Epidermal Growth Factor Receptor (EGFR)

Epidermal growth factor receptor (EGFR, ErbB-1, or HER1) is a transmembrane tyrosine kinase receptor and a member of the ErbB family of receptors, which also include HER2/c-neu (ErbB-2), Her3 (ErbB-3) and Her4 (ErbB-4). In some instances, EGFR mutations drive the downstream activation of RAS/RAF/MAPK, PI3K/AKT, and/or JAK/ STAT pathways, leading to mitosis, cell proliferation, and suppression of apoptosis. In addition, amplification of wild-type EGFR gene has been implicated in the development of cancers such as glioblastomas and non-small cell lung cancer (Talasila, et al., "EGFR Wild-type Amplification and Activation Promote Invasion and Development of Glioblastoma Independent of Angiogenesis," *Acta Neuropathol.* 125 (5): 683-698 (2013); Bell et al., "Epidermal Growth Factor Receptor Mutations and Gene Amplification in Non-Small-Cell Lung Cancer: Molecular Analysis of the IDEAL/INTACT Gefitinib Trials," *J. Clinical Oncology* 23(31): 8081-8092 (2005)).

In some embodiments, EGFR DNA or RNA is wild type EGFR or EGFR comprising a mutation. In some instances, EGFR is wild type EGFR. In some instances, EGFR DNA or RNA comprises a mutation. In some instances, the polynucleic acid molecule hybridizes to a target region of wild type EGFR DNA or RNA. In some instances, the polynucleic acid molecule hybridizes to a target region of EGFR DNA or RNA comprising a mutation (e.g., a substitution, a deletion, or an addition).

In some instances, EGFR DNA or RNA comprises one or more mutations. In some embodiments, EGFR DNA or RNA comprises one or more mutations within one or more exons. In some instances, the one or more exons comprise exon 18, exon 19, exon 20, exon 21 or exon 22. In some instances, EGFR DNA or RNA comprises one or more mutations in exon 18, exon 19, exon 20, exon 21, exon 22 or a combination thereof.

In some instances, EGFR DNA or RNA comprises one or more mutations at positions corresponding to amino acid residues 34, 38, 45, 62, 63, 77, 78, 108, 114, 120, 140, 148, 149, 160, 177, 178, 189, 191, 198, 220, 222, 223, 229, 237, 240, 244, 252, 254, 255, 256, 263, 270, 273, 276, 282, 288, 289, 301, 303, 304, 309, 314, 326, 331, 354, 363, 373, 337, 380, 384, 393, 427, 428, 437, 441, 447, 465, 475, 515, 526, 527, 531, 536, 541, 546, 571, 588, 589, 596, 596, 598, 602, 614, 620, 628, 636, 641, 645, 651, 671, 689, 694, 700, 709, 712, 714, 715, 716, 719, 720, 721, 731, 733, 739-744, 742, 746-750, 746-752, 746, 747, 747-749, 747-751, 747-753, 751, 752, 754, 752-759, 750, 761-762, 761, 763, 765, 767-768, 767-769, 768, 769, 769-770, 770-771, 772, 773-774, 773, 774, 774-775, 776, 779, 783, 784, 786, 790, 792, 794, 798, 803, 805, 807, 810, 826, 827, 831, 832, 833, 835, 837, 838, 839, 842, 843, 847, 850, 851, 853, 854, 856, 858, 861, 863, 894, 917, 967, 1006, 1019, 1042, 1100, 1129, 1141, 1153, 1164, 1167, or a combination thereof of the EGFR polypeptide. In some embodiments, EGFR DNA or RNA comprises one or more mutations at positions corresponding to amino acid residues 747, 761, 790, 854, 858, or a combination thereof of the EGFR polypeptide. In some embodiments, EGFR DNA or RNA comprises one or more mutations at positions corresponding to amino acid residues 761, 790, 858, or a combination thereof of the EGFR polypeptide. In some embodiments, EGFR DNA or RNA comprises a mutation at a position corresponding to amino acid residue 747 of the EGFR polypeptide. In some embodiments, EGFR DNA or RNA comprises a mutation at a position corresponding to amino acid residue 761 of the EGFR polypeptide. In some embodiments, EGFR DNA or RNA comprises a mutation at a position corresponding to amino acid residue 790 of the EGFR polypeptide. In some embodiments, EGFR DNA or RNA comprises a mutation at a position corresponding to amino acid residue 854 of the EGFR polypeptide. In some embodiments, EGFR DNA or RNA comprises a mutation at a position corresponding to amino acid residue 858 of the EGFR polypeptide.

In some embodiments, EGFR DNA or RNA comprises one or more mutations selected from T34M, L38V, E45Q, L62R, G63R, G63K, S77F, F78L, R108K, R108G, E114K, A120P, L140V, V148M, R149W, E160K, S177P, M178I, K189T, D191N, S198R, S220P, R222L, R222C, S223Y, S229C, A237Y, C240Y, R244G, R252C, R252P, F254I, R255 (nonsense mutation), D256Y, T263P, Y270C, T273A, Q276 (nonsense), E282K, G288 (frame shift), A289D, A289V, A289T, A289N, A289D, V301 (deletion), D303H, H304Y, R309Q, D314N, C326R, G331R, T354M, T363I, P373Q, R337S, S380 (frame shift), T384S, D393Y, R427L, G428S, S437Y, V441I, S447Y, G465R, I475V, C515S, C526S, R527L, R531 (nonsense), V536M, L541I, P546Q, C571S, G588S, P589L, P596L, P596S, P596R, P596L, G598V, G598A, E602G, G614D, C620Y, C620W, C628Y, C628F, C636Y, T638M, P641H, S645C, V651M, R671C, V689M, P694S, N700D, E709A, E709K, E709Q, E709K, F712L, K714N, I715S, K716R, G719A, G719C, G719D, G719S, S720C, S720F, G721V, W731Stop, P733L, K739-I744 (insertion), V742I, V742A, E746-A750 (deletion), E746K, L747S, L747-E749 (deletion), L747-T751 (deletion), L747-P753 (deletion), G746-S752 (deletion), T751I, S752Y, K754 (deletion), S752-I759 (deletion), A750P, D761-E762 (e.g., residues EAFQ insertion (SEQ ID NO: 1276)), D761N, D761Y, A763V, V765A, A767-S768 (e.g., residues TLA insertion), A767-V769 (e.g., residues ASV insertion), S768I, S768T, V769L, V769M, V769-D770 (e.g., residue Y insertion), 770-771 (e.g., residues GL insertion), 770-771 (e.g., residue G insertion), 770-771 (e.g., residues CV insertion), 770-771 (e.g., residues SVD insertion), P772R, 773-774 (e.g., residues NPH insertion), H773R, H773L, V774M, 774-775 (e.g., residues HV insertion), R776H, R776C, G779F, T783A, T784F, T854A, V786L, T790M, L792P, P794H, L798F, R803W, H805R, D807H, G810S, N826S, Y827 (nonsense), R831H, R832C, R832H, L833F, L833V, H835L, D837V, L838M, L838P, A839V, N842H, V843L, T847K, T8471, H850N, V851A, I853T, F856L, L858R, L858M, L861Q, L861R, G863D, Q894L, G917A, E967A, D1006Y, P1019L, S1042N, R1100S, H1129Y, T1141S, S1153I, Q1164R, L1167M, or a combination thereof of the EGFR polypeptide.

In some instances, the polynucleic acid molecule hybridizes to a target region of EGFR DNA or RNA comprising one or more mutations. In some embodiments, the polynucleic acid molecule hybridizes to a target region of EGFR DNA or RNA comprising one or more mutations in exon 18, exon 19, exon 20, exon 21, exon 22 or a combination thereof.

In some embodiments, the polynucleic acid molecule hybridizes to a target region of EGFR DNA or RNA comprising one or more mutations at positions corresponding to amino acid residues 34, 38, 45, 62, 63, 77, 78, 108, 114, 120, 140, 148, 149, 160, 177, 178, 189, 191, 198, 220, 222, 223, 229, 237, 240, 244, 252, 254, 255, 256, 263, 270, 273, 276, 282, 288, 289, 301, 303, 304, 309, 314, 326, 331, 354, 363, 373, 337, 380, 384, 393, 427, 428, 437, 441, 447, 465, 475, 515, 526, 527, 531, 536, 541, 546, 571, 588, 589, 596, 596, 598, 602, 614, 620, 628, 636, 641, 645, 651, 671, 689, 694, 700, 709, 712, 714, 715, 716, 719, 720, 721, 731, 733, 739-744, 742, 746-750, 746-752, 746, 747, 747-749, 747-751, 747-753, 751, 752, 754, 752-759, 750, 761-762, 761, 763, 765, 767-768, 767-769, 768, 769, 769-770, 770-771, 772, 773-774, 773, 774, 774-775, 776, 779, 783, 784, 786, 790, 792, 794, 798, 803, 805, 807, 810, 826, 827, 831, 832, 833, 835, 837, 838, 839, 842, 843, 847, 850, 851, 853, 854, 856, 858, 861, 863, 894, 917, 967, 1006, 1019, 1042, 1100, 1129, 1141, 1153, 1164, 1167, or a combination thereof of the EGFR polypeptide. In some embodiments, the polynucleic acid molecule hybridizes to a target region of EGFR DNA or RNA comprising one or more mutations at positions corresponding to amino acid residues 747, 761, 790, 854, 858, or a combination thereof of the EGFR polypeptide. In some embodiments, the polynucleic acid molecule hybridizes to a target region of EGFR DNA or RNA comprising one or more mutations at positions corresponding to amino acid residues 761, 790, 858, or a combination thereof of the EGFR polypeptide. In some embodiments, the polynucleic acid molecule hybridizes to a target region of EGFR DNA or RNA comprising a mutation at a position corresponding to amino acid residue 747 of the EGFR polypeptide. In some embodiments, the polynucleic acid molecule hybridizes to a target region of EGFR DNA or RNA comprising a mutation at a position corresponding to amino acid residue 761 of the EGFR polypeptide. In some embodiments, the polynucleic acid molecule hybridizes to a target region of EGFR DNA or RNA comprising a mutation at a position corresponding to amino acid residue 790 of the EGFR polypeptide. In some embodiments, the polynucleic acid molecule hybridizes to a target region of EGFR DNA or RNA comprising a mutation at a position corresponding to amino acid residue 854 of the EGFR polypeptide. In some embodiments, the polynucleic acid molecule hybridizes to a target region of EGFR DNA or RNA comprising a mutation at a position corresponding to amino acid residue 858 of the EGFR polypeptide.

In some embodiments, the polynucleic acid molecule hybridizes to a target region of EGFR DNA or RNA comprising one or more mutations selected from T34M, L38V, E45Q, L62R, G63R, G63K, S77F, F78L, R108K, R108G, E114K, A120P, L140V, V148M, R149W, E160K, S177P, M178I, K189T, D191N, S198R, S220P, R222L, R222C, S223Y, S229C, A237Y, C240Y, R244G, R252C, R252P, F254I, R255 (nonsense mutation), D256Y, T263P, Y270C, T273A, Q276 (nonsense), E282K, G288 (frame shift), A289D, A289V, A289T, A289N, A289D, V301 (deletion), D303H, H304Y, R309Q, D314N, C326R, G331R, T354M, T363I, P373Q, R337S, S380 (frame shift), T384S, D393Y, R427L, G428S, S437Y, V441I, S447Y, G465R, I475V, C515S, C526S, R527L, R531 (nonsense), V536M, L541I, P546Q, C571S, G588S, P589L, P596L, P596S, P596R, P596L, G598V, G598A, E602G, G614D, C620Y, C620W, C628Y, C628F, C636Y, T638M, P641H, S645C, V651M, R671C, V689M, P694S, N700D, E709A, E709K, E709Q, E709K, F712L, K714N, I715S, K716R, G719A, G719C, G719D, G719S, S720C, S720F, G721V, W731Stop, P733L, K739-I744 (insertion), V742I, V742A, E746-A750 (deletion), E746K, L747S, L747-E749 (deletion), L747-T751 (deletion), L747-P753 (deletion), G746-S752 (deletion), T751I, S752Y, K754 (deletion), S752-1759 (deletion), A750P, D761-E762 (e.g., residues EAFQ insertion (SEQ ID NO: 1276)), D761N, D761Y, A763V, V765A, A767-5768 (e.g., residues TLA insertion), A767-V769 (e.g., residues ASV insertion), S768I, S768T, V769L, V769M, V769-D770 (e.g., residue Y insertion), 770-771 (e.g., residues GL insertion), 770-771 (e.g., residue G insertion), 770-771 (e.g., residues CV insertion), 770-771 (e.g., residues SVD insertion), P772R, 773-774 (e.g., residues NPH insertion), H773R, H773L, V774M, 774-775 (e.g., residues HV insertion), R776H, R776C, G779F, T783A, T784F, T854A, V786L, T790M, L792P, P794H, L798F, R803W, H805R, D807H, G810S, N826S, Y827 (nonsense), R831H, R832C, R832H, L833F, L833V, H835L, D837V, L838M, L838P, A839V, N842H, V843L, T847K, T8471, H850N, V851A, I853T, F856L, L858R, L858M, L861Q, L861R, G863D, Q894L, G917A, E967A, D1006Y, P1019L, S1042N, R1100S, H1129Y, T1141S, S1153I, Q1164R, L1167M, or a combination thereof of the EGFR polypeptide. In some embodiments, the polynucleic acid molecule hybridizes to a target region of EGFR DNA or RNA comprising one or more mutations selected from L747S, D761Y, T790M, T854A, L858R, or a combination thereof of the EGFR polypeptide. In some embodiments, the polynucleic acid molecule hybridizes to a target region of EGFR DNA or RNA comprising one or more mutations selected from D761Y, T790M, L858R, or a combination thereof of the EGFR polypeptide. In some embodiments, the polynucleic acid molecule hybridizes to a target region of EGFR DNA or RNA comprising mutation L747S of the EGFR polypeptide. In some embodiments, the polynucleic acid molecule hybridizes to a target region of EGFR DNA or RNA comprising mutation D761Y of the EGFR polypeptide. In some embodiments, the polynucleic acid molecule hybridizes to a target region of EGFR DNA or RNA comprising mutation T790M of the EGFR polypeptide. In some embodiments, the polynucleic acid molecule hybridizes to a target region of EGFR DNA or RNA comprising mutation T854A of the EGFR polypeptide. In some embodiments, the polynucleic acid molecule hybridizes to a target region of EGFR DNA or RNA comprising mutation L858R of the EGFR polypeptide.

Polynucleic Acid Molecules that Target Androgen Receptor (AR)

Androgen receptor (AR) (also known as NR3C4, nuclear receptor subfamily 3, group C, gene 4) belongs to the steroid hormone group of nuclear receptor superfamily along with related members: estrogen receptor (ER), glucocorticoid receptor (GR), progesterone receptor (PR), and mineralocorticoid receptor (MR). Androgens, or steroid hormones, modulate protein synthesis and tissue remodeling through the androgen receptor. The AR protein is a ligand-inducible zinc finger transcription factor that regulates target gene expression. The presence of mutations in the AR gene has been observed in several types of cancers (e.g., prostate cancer, breast cancer, bladder cancer, or esophageal cancer), and in some instances, has been linked to metastatic progression.

In some embodiments, AR DNA or RNA is wild type or comprises one or more mutations and/or splice variants. In some instances, AR DNA or RNA comprises one or more mutations. In some instances, AR DNA or RNA comprises one or more splice variants selected from AR splice variants including but not limited to AR1/2/2b, ARV2, ARV3, ARV4, AR1/2/3/2b, ARV5, ARV6, ARV7, ARV9, ARV10, ARV11, ARV12, ARV13, ARV14, ARV15, ARV16, and ARV (v567es). In some instances, the polynucleic acid molecule hybridizes to a target region of AR DNA or RNA comprising a mutation (e.g., a substitution, a deletion, or an addition) or a splice variant.

In some embodiments, AR DNA or RNA comprises one or more mutations. In some embodiments, AR DNA or RNA comprises one or more mutations within one or more exons. In some instances, the one or more exons comprise exon 1, exon 2, exon 3, exon 4, exon 5, exon 6, exon 7, or exon 8. In some embodiments, AR DNA or RNA comprises one or more mutations within exon 1, exon 2, exon 3, exon 4, exon 5, exon 6, exon 7, exon 8 or a combination thereof. In some instances, AR DNA or RNA comprises one or more mutations at positions corresponding to amino acid residues 2, 14, 16, 29, 45, 54, 57, 64, 106, 112, 176, 180, 184, 194, 198, 204, 214, 221, 222, 233, 243, 252, 255, 266, 269, 287, 288, 334, 335, 340, 363, 368, 369, 390, 403, 443, 491, 505, 513, 524, 524, 528, 533, 547, 548, 564, 567, 568, 574, 547, 559, 568, 571, 573, 575, 576, 577, 578, 579, 580, 581, 582, 585, 586, 587, 596, 597, 599, 601, 604, 607, 608, 609, 610, 611, 615, 616, 617, 619, 622, 629, 630, 638, 645, 647, 653, 662, 664, 670, 671, 672, 674, 677, 681, 682, 683, 684, 687, 688, 689, 690, 695, 700, 701, 702, 703, 705, 706, 707, 708, 710, 711, 712, 715, 717, 720, 721, 722, 723, 724, 725, 726, 727, 728, 730, 732, 733, 737, 739, 741, 742, 743, 744, 745, 746, 748, 749, 750, 751, 752, 754, 755, 756, 757, 758, 759, 762, 763, 764, 765, 766, 767, 768, 771, 772, 774, 777, 779, 786, 795, 780, 782, 784, 787, 788, 790, 791, 793, 794, 798, 802, 803, 804, 806, 807, 812, 813, 814, 819, 820, 821, 824, 827, 828, 830, 831, 834, 840, 841, 842, 846, 854, 855, 856, 863, 864, 866, 869, 870, 871, 874, 875, 877, 879, 880, 881, 886, 888, 889, 891, 892, 895, 896, 897, 898, 902, 903, 904, 907, 909, 910, 911, 913, 916, 919, or a combination thereof of the AR polypeptide. In some embodiments, AR DNA or RNA comprises one or more mutations at positions corresponding to amino acid residues selected from E2K, P14Q, K16N, V29M, S45T, L54S, L57Q, Q64R, Y106C, Q112H, S176S, K180R, L184P, Q194R, E198G, G204S, G214R, K221N, N222D, D233K, S243L, A252V, L255P, M266T, P269S, A287D, E288K, S334P, S335T, P340L, Y363N, L368V, A369P, P390R, P390S, P390L, A403V, Q443R, G491S, G505D, P513S, G524D, G524S, D528G, P533S, L547F, P548S, D564Y, S567F, G568W, L574P, L547F, C559Y, G568W, G568V, Y571C, Y571H, A573D, T575A, C576R, C576F, G577R, S578T, C579Y, C579F, K580R, V581F, F582Y, F582S, R585K, A586V, A587S, A596T, A596S, S597G, S5971, N599Y, C601F, D604Y, R607Q, R608K, K609N, D610T, C611Y, R615H, R615P, R615G, R616C, L616R, L616P, R617P, C619Y, A622V, R629W, R629Q, K630T, L638M, A645D, S647N, E653K, S662 (nonsense), I664N, Q670L, Q670R, P671H, I672T, L674P, L677P, E681L, P682T, G683A, V684I, V684A, A687V, G688Q, H689P, D690V, D695N, D695V, D695H, L700M, L701P, L701I, H701H, S702A, S703G, N705S, N705Y, E706 (nonsense), L707R, G708A, R710T, Q711E, L712F, V715M, K717Q, K720E, A721T, L722F, P723S, G724S, G724D, G724N, F725L, R726L, N727K, L728S, L728I, V730M, D732N, D732Y, D732E, Q733H, I737T, Y739D, W741R, M742V, M742I, G743R, G743V, L744F, M745T, V746M, A748D, A748V, A748T, M749V, M749I, G750S, G750D, W751R, R752Q, F754V, F754L, T755A, N756S, N756D, V757A, N758T, S759F, S759P, L762F, Y763H, Y763C, F764L, A765T, A765V, P766A, P766S, D767E, L768P, L768M, N771H, E772G, E772A, R774H, R774C, K777T, R779W, R786Q, G795V, M780I, S782N, C784Y, M787V, R788S, L790F, S791P, E793D, F794S, Q798E, Q802R, G803L, F804L, C806Y, M807V, M807R, M807I, L812P, F813V, S814N, N819Q, G820A, L821V, Q824L, Q824R, F827L, F827V, D828H, L830V, L830P, R831Q, R831L, Y834C, R840C, R840H, I841S, I842T, R846G, R854K, R855C, R855H, F856L, L863R, D864N, D864E, D864G, V866L, V866M, V866E, I869M, A870G, A870V, R871G, H874Y, H874R, Q875K, T877S, T877A, D879T, D879G, L880Q, L881V, M886V, S888L, V889M, F891L, P892L, M895T, A896T, E897D, I898T, Q902R, V903M, P904S, P904H, L907F, G909R, G909E, K910R, V911L, P913S, F916L, Q919R, or a combination thereof of the AR polypeptide.

In some embodiments, the polynucleic acid molecule hybridizes to a target region of AR DNA or RNA comprising one or more mutations. In some embodiments the polynucleic acid hybridizes to one or more AR splice variants. In some embodiments the polynucleic acid hybridizes to AR DNA or RNA comprising one or more AR splice variants including but not limited to AR1/2/2b, ARV2, ARV3, ARV4, AR1/2/3/2b, ARV5, ARV6, ARV7, ARV9, ARV10, ARV11, ARV12, ARV13, ARV14, ARV15, ARV16, and ARV (v567es). In some embodiments, the polynucleic acid molecule hybridizes to a target region of AR DNA or RNA comprising one or more mutations within exon 1, exon 2, exon 3, exon 4, exon 5, exon 6, exon 7, exon 8 or a combination thereof. In some embodiments, the polynucleic acid molecule hybridizes to a target region of AR DNA or RNA comprising one or more mutations at positions corresponding to amino acid residues 2, 14, 16, 29, 45, 54, 57, 64, 106, 112, 176, 180, 184, 194, 198, 204, 214, 221, 222, 233, 243, 252, 255, 266, 269, 287, 288, 334, 335, 340, 363, 368, 369, 390, 403, 443, 491, 505, 513, 524, 524, 528, 533, 547, 548, 564, 567, 568, 574, 547, 559, 568, 571, 573, 575, 576, 577, 578, 579, 580, 581, 582, 585, 586, 587, 596, 597, 599, 601, 604, 607, 608, 609, 610, 611, 615, 616, 617, 619, 622, 629, 630, 638, 645, 647, 653, 662, 664, 670, 671, 672, 674, 677, 681, 682, 683, 684, 687, 688, 689, 690, 695, 700, 701, 702, 703, 705, 706, 707, 708, 710, 711, 712, 715, 717, 720, 721, 722, 723, 724, 725, 726, 727, 728, 730, 732, 733, 737, 739, 741, 742, 743, 744, 745, 746, 748, 749, 750, 751, 752, 754, 755, 756, 757, 758, 759, 762, 763, 764, 765, 766, 767, 768, 771, 772, 774, 777, 779, 786, 795, 780, 782, 784, 787, 788, 790, 791, 793, 794, 798, 802, 803, 804, 806, 807, 812, 813, 814, 819, 820, 821, 824, 827, 828, 830, 831, 834, 840, 841, 842, 846, 854, 855, 856, 863, 864, 866, 869, 870, 871, 874, 875, 877, 879, 880, 881, 886, 888, 889, 891, 892, 895, 896, 897, 898, 902, 903, 904, 907, 909, 910, 911, 913, 916, 919, or a combination thereof of the AR polypeptide. In some embodiments, the polynucleic acid molecule hybridizes to a target region of AR DNA or RNA comprising one or more mutations selected from E2K, P14Q, K16N, V29M, S45T, L54S, L57Q, Q64R, Y106C, Q112H, S176S, K180R, L184P, Q194R, E198G, G204S, G214R, K221N, N222D, D233K, S243L, A252V, L255P, M266T, P269S, A287D, E288K, S334P, S335T, P340L, Y363N, L368V, A369P, P390R, P390S, P390L, A403V, Q443R, G491S, G505D, P513S, G524D, G524S, D528G, P533S, L547F, P548S, D564Y, S567F, G568W, L574P, L547F, C559Y, G568W, G568V, Y571C, Y571H, A573D, T575A, C576R, C576F, G577R, S578T, C579Y, C579F, K580R, V581F, F582Y, F582S, R585K, A586V, A587S, A596T, A596S, S597G, S5971, N599Y, C601F, D604Y, R607Q, R608K, K609N, D610T, C611Y, R615H, R615P, R615G, R616C, L616R, L616P, R617P, C619Y, A622V, R629W, R629Q, K630T, L638M, A645D, S647N, E653K, S662 (nonsense), I664N, Q670L, Q670R, P671H, I672T, L674P, L677P, E681L, P682T, G683A, V684I, V684A, A687V, G688Q, H689P, D690V, D695N, D695V, D695H, L700M, L701P, L701I, H701H, S702A, S703G, N705S, N705Y, E706 (nonsense), L707R, G708A, R710T, Q711E, L712F, V715M, K717Q, K720E, A721T, L722F, P723S, G724S, G724D, G724N, F725L, R726L, N727K, L728S, L728I, V730M, D732N, D732Y, D732E, Q733H, I737T, Y739D, W741R, M742V, M742I, G743R, G743V, L744F, M745T, V746M, A748D, A748V, A748T, M749V, M749I, G750S, G750D, W751R, R752Q, F754V, F754L, T755A, N756S, N756D, V757A, N758T, S759F, S759P, L762F, Y763H, Y763C, F764L, A765T, A765V, P766A, P766S, D767E, L768P, L768M, N771H, E772G, E772A, R774H, R774C, K777T, R779W, R786Q, G795V, M780I, S782N, C784Y, M787V, R788S, L790F, S791P, E793D, F794S, Q798E, Q802R, G803L, F804L, C806Y, M807V, M807R, M807I, L812P, F813V, S814N, N819Q, G820A, L821V, Q824L, Q824R, F827L, F827V, D828H, L830V, L830P, R831Q, R831L, Y834C, R840C, R840H, I841S, I842T, R846G, R854K, R855C, R855H, F856L, L863R, D864N, D864E, D864G, V866L, V866M, V866E, I869M, A870G, A870V, R871G, H874Y, H874R, Q875K, T877S, T877A, D879T, D879G, L880Q, L881V, M886V, S888L, V889M, F891L, P892L, M895T, A896T, E897D, I898T, Q902R, V903M, P904S, P904H, L907F, G909R, G909E, K910R, V911L, P913S, F916L, Q919R, or a combination thereof of the AR polypeptide.

Polynucleic Acid Molecules that Target B-Catenin and B-Catenin-Associated Genes

Catenin beta-1 (also known as CTNNB1, β-catenin, or beta-catenin) is a member of the catenin protein family. In humans, it is encoded by the CTNNB1 gene and is known for its dual functions—cell-cell adhesion and gene transcription. Beta-catenin is an integral structural component of cadherin-based adherens junctions and regulates cell growth and adhesion between cells and anchors the actin cytoskeleton. In some instance, beta-catenin is responsible for transmitting the contact inhibition signal that causes the cells to stop dividing once the epithelial sheet is complete. Beta-catenin is also a key nuclear effector of the Wnt signaling pathway. In some instances, imbalance in the structural and signaling properties of beta-catenin results in diseases and deregulated growth connected to malignancies such as cancer. For example, overexpression of beta-catenin has been linked to cancers such as gastric cancer (Suriano, et al., "Beta-catenin (CTNNB1) gene amplification: a new mechanism of protein overexpression in cancer," Genes Chromosomes Cancer 42(3): 238-246 (2005)). In some cases, mutations in CTNNB1 gene have been linked to cancer development (e.g., colon cancer, melanoma, hepatocellular carcinoma, ovarian cancer, endometrial cancer, medulloblastoma pilomatricomas, or prostrate cancer), and in some instances, has been linked to metastatic progression. In additional cases, mutations in the CTNNB1 gene cause beta-catenin to translocate to the nucleus without any external stimulus and drive the transcription of its target genes continuously. In some cases, the potential of beta-catenin to change the previously epithelial phenotype of affected cells into an invasive, mesenchyme-like type contributes to metastasis formation.

In some embodiments, CTNNB1 gene is wild type CTNNB1 or CTNNB1 comprising one or more mutations. In some instances, CTNNB1 is wild type CTNNB1. In some instances, CTNNB1 is CTNNB1 comprising one or more mutations. In some instances, the polynucleic acid molecule is a polynucleic acid molecule that hybridizes to a target region of wild type CTNNB1. In some instances, the polynucleic acid molecule is a polynucleic acid molecule that hybridizes to a target region of CTNNB1 comprising a mutation (e.g., a substitution, a deletion, or an addition).

In some embodiments, CTNNB1 DNA or RNA comprises one or more mutations. In some embodiments, CTNNB1 DNA or RNA comprises one or more mutations within one or more exons. In some instances, the one or more exons comprise exon 3. In some instances, CTNNB1 DNA or RNA comprises one or more mutations at codons 32, 33, 34, 37, 41, 45, 183, 245, 287 or a combination thereof. In some instances, CTNNB1 DNA or RNA comprises one or more mutations at positions corresponding to amino acid residues 25, 31, 32, 33, 34, 35, 36, 37, 41, 45, 140, 162, 170, 199, 213, 215, 257, 303, 322, 334, 354, 367, 373, 383, 387, 402, 426, 453, 474, 486, 515, 517, 535, 553, 555, 582, 587, 619, 623, 641, 646, 688, 703, 710, 712, 714, 724, 738, 777, or a combination thereof of the CTNNB1 polypeptide. In some embodiments, CTNNB1 DNA or RNA comprises one or more mutations at positions corresponding to amino acid residues selected from W25 (nonsense mutation), L31M, D32A, D32N, D32Y, D32G, D32H, S33C, S33Y, S33F, S33P, G34R, G34E, G34V, I35S, H36Y, S37F, S37P, S37C, S37A, T41N, T41A, T41I, S45Y, S45F, S45C, I140T, D162E, K170M, V199I, C213F, A215T, T257I, I303M, Q322K, E334K, K354T, G367V, P373S, W383G, N387K, L402F, N426D, R453L, R453Q, R474 (nonsense mutation), R486C, R515Q, L517F, R535 (nonsense mutation), R535Q, M553V, G555A, R582Q, R587Q, C619Y, Q623E, T64I (frame shift), S646F, M688T, Q703H, R710H, D712N, P714R, Y724H, E738K, F777S, or a combination thereof of the CTNNB1 polypeptide.

In some embodiments, the polynucleic acid molecule hybridizes to a target region of CTNNB1 DNA or RNA comprising one or more mutations. In some embodiments, the polynucleic acid molecule hybridizes to a target region of CTNNB1 DNA or RNA comprising one or more mutations within exon 3. In some embodiments, the polynucleic acid molecule hybridizes to a target region of CTNNB1 DNA or RNA comprising one or more mutations at codons 32, 33, 34, 37, 41, 45, 183, 245, 287 or a combination thereof. In some embodiments, the polynucleic acid molecule hybridizes to a target region of CTNNB1 DNA or RNA comprising one or more mutations at positions corresponding to amino acid residues 25, 31, 32, 33, 34, 35, 36, 37, 41, 45, 140, 162, 170, 199, 213, 215, 257, 303, 322, 334, 354, 367, 373, 383, 387, 402, 426, 453, 474, 486, 515, 517, 535, 553, 555, 582, 587, 619, 623, 641, 646, 688, 703, 710, 712, 714, 724, 738, 777, or a combination thereof of the CTNNB1 polypeptide. In some embodiments, the polynucleic acid molecule hybridizes to a target region of CTNNB1 DNA or RNA comprising one or more mutations selected from W25 (nonsense mutation), L31M, D32A, D32N, D32Y, D32G, D32H, S33C, S33Y, S33F, S33P, G34R, G34E, G34V, I35S, H36Y, S37F, S37P, S37C, S37A, T41N, T41A, T41I, S45Y, S45F, S45C, I140T, D162E, K170M, V199I, C213F, A215T, T257I, I303M, Q322K, E334K, K354T, G367V, P373S, W383G, N387K, L402F, N426D, R453L, R453Q, R474 (nonsense mutation), R486C, R515Q, L517F, R535 (nonsense mutation), R535Q, M553V, G555A, R582Q, R587Q, C619Y, Q623E, T64I (frame shift), S646F, M688T, Q703H, R710H, D712N, P714R, Y724H, E738K, F777S, or a combination thereof of the CTNNB1 polypeptide.

In some embodiments, beta-catenin associated genes further comprise PIK3CA, PIK3CB, and MYC. In some embodiments, beta-catenin associated genes further comprise PIK3CA DNA or RNA. PIK3CA (phosphatidylinositol-4,5-bisphosphate 3-kinase, catalytic subunit alpha or p110a protein) is a class i PI3-kinase catalytic subunit that uses ATP to phosphorylate phosphatidylinositols. In some embodiments, PIK3CA gene is wild type PIK3CA or PIK3CA comprising one or more mutations. In some instances, PIK3CA DNA or RNA is wild type PIK3CA. In some instances, PIK3CA DNA or RNA comprises one or more mutations. In some instances, the polynucleic acid molecule hybridizes to a target region of wild type PIK3CA DNA or RNA. In some instances, the polynucleic acid molecule hybridizes to a target region of PIK3CA DNA or RNA comprising a mutation (e.g., a substitution, a deletion, or an addition).

In some embodiments, PIK3CA DNA or RNA comprises one or more mutations. In some embodiments, PIK3CA DNA or RNA comprises one or more mutation within one or more exons. In some instances, PIK3CA DNA or RNA comprises one or more mutation within exons 9 and/or 20. In some instances, PIK3CA DNA or RNA comprises one or more mutations at positions corresponding to amino acid residues 1, 4, 10-16, 11-18, 11, 12, 38, 39, 65, 72, 75, 79, 81, 83, 88, 90, 93, 102, 103, 103-104, 103-106, 104, 105-108, 106, 106-107, 106-108, 107, 108, 109-112, 110, 111, 113, 115, 137, 170, 258, 272, 279, 320, 328, 335, 342, 344, 345, 350, 357, 359, 363, 364, 365, 366, 378, 398, 401, 417, 420, 447-455, 449, 449-457, 451, 453, 454, 455, 455-460, 463-465, 471, 495, 522, 538, 539, 542, 545, 546, 547, 576, 604, 614, 617, 629, 643, 663, 682, 725, 726, 777, 791, 818, 866, 901, 909, 939, 951, 958, 970, 971, 975, 992, 1004, 1007, 1016, 1017, 1021, 1025, 1029, 1037, 1040, 1043, 1044, 1045, 1047, 1048, 1049, 1052, 1065, 1069, or a combination thereof of the PIK3CA polypeptide. In some embodiments, PIK3CA DNA or RNA comprises one or more mutations at positions corresponding to amino acid residues selected from M1V, R4 (nonsense mutation), L10-M16 (deletion), W11-P18 (deletion), W11L, G12D, R38L, R38H, R38C, R38S, E39K, E39G, E65K, S72G, Q75E, R79M, E81K, E81 (deletion), F83Y, R88Q, C90Y, C90G, R93Q, R93W, I102 (deletion), E103G, E103-P104 (deletion), E103-G106 (deletion), P104L, V105-R108 (deletion), G106V, G106-N107 (deletion), G106-R108 (deletion), G106R, N107S, R108L, R108H, E109-I112 (deletion), E110 (deletion), K111E, K111R, K111N, K111 (deletion), L113 (deletion), R115L, Q137L, N170S, D258N, Y272 (nonsense mutation), L279I, G320V, W328S, R335G, T342S, V344G, V344M, V344A, N345K, N345I, N345T, D350N, D350G, R357Q, G359R, G363A, G364R, E365K, E365V, P366R, C378R, C378Y, R398H, R401Q, E417K, C420R, C420G, P447-L455 (deletion), P449L, P449-N457 (deletion), G451R, G451V, E453K, E453Q, E453D, D454Y, L455 (frame shift insertion), L455-G460 (deletion), G463-N465 (deletion), P471L, P471A, H495L, H495Y, E522A, D538N, P539R, E542K, E542V, E542G, E542Q, E542A, E545K, E545A, E545G, E545Q, E545D, Q546K, Q546R, Q546P, E547D, S576Y, C604R, F614I, A617W, S629C, Q643H, I663S, Q682 (deletion), D725N, W726K, R777M, E791Q, R818C, L866W, C901F, F909L, D939G, R951C, Q958R, E970K, C971R, R975S, R992P, M1004I, G1007R, F1016C, D1017H, Y1021H, Y1021C, T1025A, T1025S, D1029H, E1037K, M1040V, M1043V, M1043I, N1044K, N1044Y, D1045V, H1047R, H1047L, H1047Y, H1047Q, H1048R, G1049R, T1052K, H1065L, 1069W (nonstop mutation), or a combination thereof of the PIK3CA polypeptide.

In some embodiments, the polynucleic acid molecule hybridizes to a target region of PIK3CA DNA or RNA comprising one or more mutations. In some embodiments, the polynucleic acid molecule hybridizes to a target region of PIK3CA DNA or RNA comprising one or more mutations within an exon. In some embodiments, the polynucleic acid molecule hybridizes to a target region of PIK3CA DNA or RNA comprising one or more mutations within exon 9 or exon 20. In some embodiments, the polynucleic acid molecule hybridizes to a target region of PIK3CA DNA or RNA comprising one or more mutations at positions corresponding to amino acid residues 1, 4, 10-16, 11-18, 11, 12, 38, 39, 65, 72, 75, 79, 81, 83, 88, 90, 93, 102, 103, 103-104, 103-106, 104, 105-108, 106, 106-107, 106-108, 107, 108, 109-112, 110, 111, 113, 115, 137, 170, 258, 272, 279, 320, 328, 335, 342, 344, 345, 350, 357, 359, 363, 364, 365, 366, 378, 398, 401, 417, 420, 447-455, 449, 449-457, 451, 453, 454, 455, 455-460, 463-465, 471, 495, 522, 538, 539, 542, 545, 546, 547, 576, 604, 614, 617, 629, 643, 663, 682, 725, 726, 777, 791, 818, 866, 901, 909, 939, 951, 958, 970, 971, 975, 992, 1004, 1007, 1016, 1017, 1021, 1025, 1029, 1037, 1040, 1043, 1044, 1045, 1047, 1048, 1049, 1052, 1065, 1069, or a combination thereof of the PIK3CA polypeptide. In some embodiments, the polynucleic acid molecule is a polynucleic acid molecule that hybridizes to a target region of PIK3CA DNA or RNA comprising one or more mutations at positions corresponding to amino acid residues selected from M1V, R4 (nonsense mutation), L10-M16 (deletion), W11-P18 (deletion), W11L, G12D, R38L, R38H, R38C, R38S, E39K, E39G, E65K, S72G, Q75E, R79M, E81K, E81 (deletion), F83Y, R88Q, C90Y, C90G, R93Q, R93W, I102 (deletion), E103G, E103-P104 (deletion), E103-G106 (deletion), P104L, V105-R108 (deletion), G106V, G106-N107 (deletion), G106-R108 (deletion), G106R, N107S, R108L, R108H, E109-I112 (deletion), E110 (deletion), K111E, K111R, K111N, K111 (deletion), L113 (deletion), R115L, Q137L, N170S, D258N, Y272 (nonsense mutation), L279I, G320V, W328S, R335G, T342S, V344G, V344M, V344A, N345K, N345I, N345T, D350N, D350G, R357Q, G359R, G363A, G364R, E365K, E365V, P366R, C378R, C378Y, R398H, R401Q, E417K, C420R, C420G, P447-L455 (deletion), P449L, P449-N457 (deletion), G451R, G451V, E453K, E453Q, E453D, D454Y, L455 (frame shift insertion), L455-G460 (deletion), G463-N465 (deletion), P471L, P471A, H495L, H495Y, E522A, D538N, P539R, E542K, E542V, E542G, E542Q, E542A, E545K, E545A, E545G, E545Q, E545D, Q546K, Q546R, Q546P, E547D, S576Y, C604R, F614I, A617W, S629C, Q643H, I663S, Q682 (deletion), D725N, W726K, R777M, E791Q, R818C, L866W, C901F, F909L, D939G, R951C, Q958R, E970K, C971R, R975S, R992P, M1004I, G1007R, F1016C, D1017H, Y1021H, Y1021C, T1025A, T1025S, D1029H, E1037K, M1040V, M1043V, M1043I, N1044K, N1044Y, D1045V, H1047R, H1047L, H1047Y, H1047Q, H1048R, G1049R, T1052K, H1065L, 1069W (nonstop mutation), or a combination thereof of the PIK3CB polypeptide.

In some embodiments, beta-catenin associated genes further comprise PIK3CB. In some embodiments, PIK3CB gene is wild type or comprises one or more mutations. In some instances, PIK3CB DNA or RNA is wild type PIK3CB DNA or RNA. In some instances, PIK3CB DNA or RNA comprises one or more mutations. In some instances, the polynucleic acid molecule hybridizes to a target region of wild type PIK3CB DNA or RNA. In some instances, the polynucleic acid molecule hybridizes to a target region of PIK3CB DNA or RNA comprising a mutation (e.g., a substitution, a deletion, or an addition).

In some embodiments, PIK3CB DNA or RNA comprises one or more mutations. In some embodiments, PIK3CB DNA or RNA comprises one or more mutations within one or more exons. In some instances, PIK3CB DNA or RNA comprises one or more mutations at positions corresponding to amino acid residues 18, 19, 21, 28, 50, 61, 68, 103, 135, 140, 167, 252, 270, 290, 301, 304, 321, 369, 417, 442, 470, 497, 507, 512, 540, 551, 552, 554, 562, 567, 593, 595, 619, 628, 668, 768, 805, 824, 830, 887, 967, 992, 1005, 1020, 1036, 1046, 1047, 1048, 1049, 1051, 1055, 1067, or a combination thereof of the PIK3CB polypeptide. In some embodiments, PIK3CB DNA or RNA comprises one or more mutations at positions corresponding to amino acid residues selected from W18 (nonsense mutation), A19V, D21H, G28S, A50P, K61T, M68I, R103K, H135N, L140S, S167C, G252W, R270W, K290N, E301V, I304R, R321Q, V369I, T417M, N442K, E470K, E497D, P507S, I512M, E540 (nonsense mutation), C551R, E552K, E554K, R562 (nonsense mutation), E567D, A593V, L595P, V619A, R628 (nonsense mutation), R668W, L768F, K805E, D824E, A830T, E887 (nonsense mutation), V967A, I992T, A1005V, D1020H, E1036K, D1046N, E1047K, A1048V, L1049R, E1051K, T1055A, D1067V, D1067A, or a combination thereof of the PIK3CB polypeptide.

In some embodiments, the polynucleic acid molecule hybridizes to a target region of PIK3CB DNA or RNA comprising one or more mutations. In some embodiments, the polynucleic acid molecule hybridizes to a target region of PIK3CB DNA or RNA comprising one or more mutations within an exon. In some embodiments, the polynucleic acid molecule hybridizes to a target region of PIK3CB DNA or RNA comprising one or more mutations at positions corresponding to amino acid residues 18, 19, 21, 28, 50, 61, 68, 103, 135, 140, 167, 252, 270, 290, 301, 304, 321, 369, 417, 442, 470, 497, 507, 512, 540, 551, 552, 554, 562, 567, 593, 595, 619, 628, 668, 768, 805, 824, 830, 887, 967, 992, 1005, 1020, 1036, 1046, 1047, 1048, 1049, 1051, 1055, 1067, or a combination thereof of the PIK3CB polypeptide. In some embodiments, the polynucleic acid molecule hybridizes to a target region of PIK3CB DNA or RNA comprising one or more mutations at positions corresponding to amino acid residues selected from W18 (nonsense mutation), A19V, D21H, G28S, A50P, K61T, M68I, R103K, H135N, L140S, S167C, G252W, R270W, K290N, E301V, I304R, R321Q, V369I, T417M, N442K, E470K, E497D, P507S, I512M, E540 (nonsense mutation), C551R, E552K, E554K, R562 (nonsense mutation), E567D, A593V, L595P, V619A, R628 (nonsense mutation), R668W, L768F, K805E, D824E, A830T, E887 (nonsense mutation), V967A, I992T, A1005V, D1020H, E1036K, D1046N, E1047K, A1048V, L1049R, E1051K, T1055A, D1067V, D1067A, or a combination thereof of the PIK3CB polypeptide.

In some embodiments, beta-catenin associated genes further comprise MYC. In some embodiments, MYC gene is wild type MYC or MYC comprising one or more mutations. In some instances, MYC is wild type MYC DNA or RNA. In some instances, MYC DNA or RNA comprises one or more mutations. In some instances, the polynucleic acid molecule hybridizes to a target region of wild type MYC DNA or RNA. In some instances, the polynucleic acid molecule is a polynucleic acid molecule that hybridizes to a target region of MYC DNA or RNA comprising a mutation (e.g., a substitution, a deletion, or an addition).

In some embodiments, MYC DNA or RNA comprises one or more mutations. In some embodiments, MYC DNA or RNA comprises one or more mutation within one or more exons. In some instances, MYC DNA or RNA comprises one or more mutations within exon 2 or exon 3. In some instances, MYC DNA or RNA comprises one or more mutations at positions corresponding to amino acid residues 2, 7, 17, 20, 32, 44, 58, 59, 76, 115, 138, 141, 145, 146, 169, 175, 188, 200, 202, 203, 248, 251, 298, 321, 340, 369, 373, 374, 389, 395, 404, 419, 431, 439, or a combination thereof. In some embodiments, MYC DNA or RNA comprises one or more mutations at positions corresponding to amino acid residues selected from P2L, F7L, D17N, Q20E, Y32N, A44V, A44T, T58I, P59L, A76V, F115L, F138S, A141S, V145I, S146L, S169C, S175N, C188F, N200S, S202N, S203T, T248S, D251E, S298Y, Q321E, V340D, V369D, T373K, H374R, F389L, Q395H, K404N, L419M, E431K, R439Q, or a combination thereof of the MYC polypeptide.

In some embodiments, the polynucleic acid molecule hybridizes to a target region of MYC DNA or RNA comprising one or more mutations. In some embodiments, the polynucleic acid molecule hybridizes to a target region of MYC DNA or RNA comprising one or more mutations within an exon. In some embodiments, the polynucleic acid molecule hybridizes to a target region of MYC DNA or RNA comprising one or more mutations within exon 2 or exon 3. In some embodiments, the polynucleic acid molecule hybridizes to a target region of MYC DNA or RNA comprising one or more mutations at positions corresponding to amino acid residues 2, 7, 17, 20, 32, 44, 58, 59, 76, 115, 138, 141, 145, 146, 169, 175, 188, 200, 202, 203, 248, 251, 298, 321, 340, 369, 373, 374, 389, 395, 404, 419, 431, 439, or a combination thereof of the MYC polypeptide. In some embodiments, the polynucleic acid molecule hybridizes to a target region of MYC DNA or RNA comprising one or more mutations at positions corresponding to amino acid residues selected from P2L, F7L, D17N, Q20E, Y32N, A44V, A44T, T58I, P59L, A76V, F115L, F138S, A141S, V145I, S146L, S169C, S175N, C188F, N200S, S202N, S203T, T248S, D251E, S298Y, Q321E, V340D, V369D, T373K, H374R, F389L, Q395H, K404N, L419M, E431K, R439Q, or a combination thereof of the MYC polypeptide.

Polynucleic Acid Molecules that Target Hypoxanthine Phosphoribosyltransferase 1 (HPRT1)

Hypoxanthine-guanine phosphoribosyltransferase (HGPRT) is a transferase that catalyzes the conversion of hypoxanthine to inosine monophosphate and guanine to guanosine monophosphate. HGPRT is encoded by the hypoxanthine Phosphoribosyltransferase 1 (HPRT1) gene.

In some embodiments, HPRT1 DNA or RNA is wild type or comprises one or more mutations. In some instances, HPRT1 DNA or RNA comprises one or more mutations within one or more exons. In some instances, the one or more exons comprise exon 2, exon 3, exon 4, exon 6, exon 8, or exon 9. In some instances, HPRT1 DNA or RNA comprises one or more mutations at positions corresponding to amino acid residues 35, 48, 56, 74, 87, 129, 154, 162, 195, 200, 210, or a combination thereof of the HPRT1 polypeptide. In some embodiments, the polynucleic acid molecule hybridizes to a target region of HPRT1 DNA or RNA comprising one or more mutations selected from V35M, R48H, E56D, F74L, R87I, N129 (splice-site mutation), N154H, S162 (splice-site mutation), Y195C, Y195N, R200M, E210K, or a combination thereof of the HPRT1 polypeptide.

In some embodiments, the polynucleic acid molecule hybridizes to a target region of HPRT1 DNA or RNA comprising one or more mutations. In some embodiments, the polynucleic acid molecule hybridizes to a target region of HPRT1 DNA or RNA comprising one or more mutations within exon 2, exon 3, exon 4, exon 6, exon 8, or exon 9. In some embodiments, the polynucleic acid molecule hybridizes to a target region of HPRT1 DNA or RNA comprising one or more mutations at positions corresponding to amino acid residues 35, 48, 56, 74, 87, 129, 154, 162, 195, 200, 210, or a combination thereof of the HPRT1 polypeptide. In some embodiments, the polynucleic acid molecule hybridizes to a target region of HPRT1 DNA or RNA comprising one or more mutations selected from V35M, R48H, E56D, F74L, R87I, N129 (splice-site mutation), N154H, S162 (splice-site mutation), Y195C, Y195N, R200M, E210K, or a combination thereof of the HPRT1 polypeptide.

Polynucleic Acid Molecule Sequences

In some embodiments, the polynucleic acid molecule comprises a sequence that hybridizes to a target sequence illustrated in Tables 1, 3, 5, 6, or 7. In some instances, the polynucleic acid molecule is B. In some instances, the polynucleic acid molecule B comprises a sequence that hybridizes to a target sequence illustrated in Table 1 (KRAS target sequences). In some instances, the polynucleic acid molecule B comprises a sequence that hybridizes to a target sequence illustrated in Table 3 (EGFR target sequences). In some cases, the polynucleic acid molecule B comprises a sequence that hybridizes to a target sequence illustrated in Table 5 (AR target sequences). In some cases, the polynucleic acid molecule B comprises a sequence that hybridizes to a target sequence illustrated in Table 6 (β-catenin target sequences). In additional cases, the polynucleic acid molecule B comprises a sequence that hybridizes to a target sequence illustrated in Table 7 (PIK3CA and PIK3CB target sequences).

In some embodiments, the polynucleic acid molecule B comprises a sequence having at least 50%, 55%, 60%, 65%, 70%, 75%, 80%, 85%, 90%, 95%, 96%, 97%, 98%, 99%, or 100% sequence identity to a sequence listed in Table 2. In some embodiments, the polynucleic acid molecule comprises a sequence having at least 50%, 55%, 60%, 65%, 70%, 75%, 80%, 85%, 90%, 95%, 96%, 97%, 98%, 99%, or 100% sequence identity to SEQ ID NOs: 16-45. In some embodiments, the polynucleic acid molecule comprises a sequence having at least 50% sequence identity to SEQ ID NOs: 16-45. In some embodiments, the polynucleic acid molecule comprises a sequence having at least 60% sequence identity to SEQ ID NOs: 16-45. In some embodiments, the polynucleic acid molecule comprises a sequence having at least 70% sequence identity to SEQ ID NOs: 16-45. In some embodiments, the polynucleic acid molecule comprises a sequence having at least 75% sequence identity to SEQ ID NOs: 16-45. In some embodiments, the polynucleic acid molecule comprises a sequence having at least 80% sequence identity to SEQ ID NOs: 16-45. In some embodiments, the polynucleic acid molecule comprises a sequence having at least 85% sequence identity to SEQ ID NOs: 16-45. In some embodiments, the polynucleic acid molecule comprises a sequence having at least 90% sequence identity to SEQ ID NOs: 16-45. In some embodiments, the polynucleic acid molecule comprises a sequence having at least 95% sequence identity to SEQ ID NOs: 16-45. In some embodiments, the polynucleic acid molecule comprises a sequence having at least 96% sequence identity to SEQ ID NOs: 16-45. In some embodiments, the polynucleic acid molecule comprises a sequence having at least 97% sequence identity to SEQ ID NOs: 16-45. In some embodiments, the polynucleic acid molecule comprises a sequence having at least 98% sequence identity to SEQ ID NOs: 16-45. In some embodiments, the polynucleic acid molecule comprises a sequence having at least 99% sequence identity to SEQ ID NOs: 16-45. In some embodiments, the polynucleic acid molecule consists of SEQ ID NOs: 16-45.

In some embodiments, the polynucleic acid molecule B comprises a first polynucleotide and a second polynucleotide. In some instances, the first polynucleotide comprises a sequence having at least 50%, 55%, 60%, 65%, 70%, 75%, 80%, 85%, 90%, 95%, 96%, 97%, 98%, 99%, or 100% sequence identity to SEQ ID NOs: 16-45. In some cases, the second polynucleotide comprises a sequence having at least 50%, 55%, 60%, 65%, 70%, 75%, 80%, 85%, 90%, 95%, 96%, 97%, 98%, 99%, or 100% sequence identity to SEQ ID NOs: 16-45. In some cases, the polynucleic acid molecule comprises a first polynucleotide having at least 50%, 55%, 60%, 65%, 70%, 75%, 80%, 85%, 90%, 95%, 96%, 97%, 98%, 99%, or 100% sequence identity to SEQ ID NOs: 16-45 and a second polynucleotide having at least 50%, 55%, 60%, 65%, 70%, 75%, 80%, 85%, 90%, 95%, 96%, 97%, 98%, 99%, or 100% sequence identity to SEQ ID NOs: 16-45.

In some embodiments, the polynucleic acid molecule B comprises a sequence having at least 50%, 55%, 60%, 65%, 70%, 75%, 80%, 85%, 90%, 95%, 96%, 97%, 98%, 99%, or 100% sequence identity to a sequence listed in Table 4. In some embodiments, the polynucleic acid molecule comprises a sequence having at least 50%, 55%, 60%, 65%, 70%, 75%, 80%, 85%, 90%, 95%, 96%, 97%, 98%, 99%, or 100% sequence identity to SEQ ID NOs: 422-1173. In some embodiments, the polynucleic acid molecule comprises a sequence having at least 50% sequence identity to SEQ ID NOs: 422-1173. In some embodiments, the polynucleic acid molecule comprises a sequence having at least 60% sequence identity to SEQ ID NOs: 422-1173. In some embodiments, the polynucleic acid molecule comprises a sequence having at least 70% sequence identity to SEQ ID NOs: 422-1173. In some embodiments, the polynucleic acid molecule comprises a sequence having at least 75% sequence identity to SEQ ID NOs: 422-1173. In some embodiments, the polynucleic acid molecule comprises a sequence having at least 80% sequence identity to SEQ ID NOs: 422-1173. In some embodiments, the polynucleic acid molecule comprises a sequence having at least 85% sequence identity to SEQ ID NOs: 422-1173. In some embodiments, the polynucleic acid molecule comprises a sequence having at least 90% sequence identity to SEQ ID NOs: 422-1173. In some embodiments, the polynucleic acid molecule comprises a sequence having at least 95% sequence identity to SEQ ID NOs: 422-1173. In some embodiments, the polynucleic acid molecule comprises a sequence having at least 96% sequence identity to SEQ ID NOs: 422-1173. In some embodiments, the polynucleic acid molecule comprises a sequence having at least 97% sequence identity to SEQ ID NOs: 422-1173. In some embodiments, the polynucleic acid molecule comprises a sequence having at least 98% sequence identity to SEQ ID NOs: 422-1173. In some embodiments, the polynucleic acid molecule comprises a sequence having at least 99% sequence identity to SEQ ID NOs: 422-1173. In some embodiments, the polynucleic acid molecule consists of SEQ ID NOs: 422-1173.

In some embodiments, the polynucleic acid molecule B comprises a first polynucleotide and a second polynucleotide. In some instances, the first polynucleotide comprises a sequence having at least 50%, 55%, 60%, 65%, 70%, 75%, 80%, 85%, 90%, 95%, 96%, 97%, 98%, 99%, or 100% sequence identity to SEQ ID NOs: 422-1173. In some cases, the second polynucleotide comprises a sequence having at least 50%, 55%, 60%, 65%, 70%, 75%, 80%, 85%, 90%, 95%, 96%, 97%, 98%, 99%, or 100% sequence identity to SEQ ID NOs: 422-1173. In some cases, the polynucleic acid molecule comprises a first polynucleotide having at least 50%, 55%, 60%, 65%, 70%, 75%, 80%, 85%, 90%, 95%, 96%, 97%, 98%, 99%, or 100% sequence identity to SEQ ID NOs: 422-1173 and a second polynucleotide having at least 50%, 55%, 60%, 65%, 70%, 75%, 80%, 85%, 90%, 95%, 96%, 97%, 98%, 99%, or 100% sequence identity to SEQ ID NOs: 422-1173.

In some embodiments, the polynucleic acid molecule B comprises a sequence having at least 50%, 55%, 60%, 65%, 70%, 75%, 80%, 85%, 90%, 95%, 96%, 97%, 98%, 99%, or 100% sequence identity to a sequence listed in Table 8. In some embodiments, the polynucleic acid molecule comprises a sequence having at least 50%, 55%, 60%, 65%, 70%, 75%, 80%, 85%, 90%, 95%, 96%, 97%, 98%, 99%, or 100% sequence identity to SEQ ID NOs: 1195-1214. In some embodiments, the polynucleic acid molecule comprises a sequence having at least 50% sequence identity to SEQ ID NOs: 1195-1214. In some embodiments, the polynucleic acid molecule comprises a sequence having at least 60% sequence identity to SEQ ID NOs: 1195-1214. In some embodiments, the polynucleic acid molecule comprises a sequence having at least 70% sequence identity to SEQ ID NOs: 1195-1214. In some embodiments, the polynucleic acid molecule comprises a sequence having at least 75% sequence identity to SEQ ID NOs: 1195-1214. In some embodiments, the polynucleic acid molecule comprises a sequence having at least 80% sequence identity to SEQ ID NOs: 1195-1214. In some embodiments, the polynucleic acid molecule comprises a sequence having at least 85% sequence identity to SEQ ID NOs: 1195-1214. In some embodiments, the polynucleic acid molecule comprises a sequence having at least 90% sequence identity to SEQ ID NOs: 1195-1214. In some embodiments, the polynucleic acid molecule comprises a sequence having at least 95% sequence identity to SEQ ID NOs: 1195-1214. In some embodiments, the polynucleic acid molecule comprises a sequence having at least 96% sequence identity to SEQ ID NOs: 1195-1214. In some embodiments, the polynucleic acid molecule comprises a sequence having at least 97% sequence identity to SEQ ID NOs: 1195-1214. In some embodiments, the polynucleic acid molecule comprises a sequence having at least 98% sequence identity to SEQ ID NOs: 1195-1214. In some embodiments, the polynucleic acid molecule comprises a sequence having at least 99% sequence identity to SEQ ID NOs: 1195-1214. In some embodiments, the polynucleic acid molecule consists of SEQ ID NOs: 1195-1214.

In some embodiments, the polynucleic acid molecule B comprises a first polynucleotide and a second polynucleotide. In some instances, the first polynucleotide comprises a sequence having at least 50%, 55%, 60%, 65%, 70%, 75%, 80%, 85%, 90%, 95%, 96%, 97%, 98%, 99%, or 100% sequence identity to SEQ ID NOs: 1195-1214. In some cases, the second polynucleotide comprises a sequence that is complementary to a sequence having at least 50%, 55%, 60%, 65%, 70%, 75%, 80%, 85%, 90%, 95%, 96%, 97%, 98%, 99%, or 100% sequence identity to SEQ ID NOs: 1195-1214. In some instances, the polynucleic acid molecule comprises a first polynucleotide having at least 50%, 55%, 60%, 65%, 70%, 75%, 80%, 85%, 90%, 95%, 96%, 97%, 98%, 99%, or 100% sequence identity to SEQ ID NOs: 1195-1214, and a second polynucleotide that is complementary to a sequence having at least 50%, 55%, 60%, 65%, 70%, 75%, 80%, 85%, 90%, 95%, 96%, 97%, 98%, 99%, or 100% sequence identity to SEQ ID NOs: 1195-1214.

In some embodiments, the polynucleic acid molecule B comprises a sequence having at least 50%, 55%, 60%, 65%, 70%, 75%, 80%, 85%, 90%, 95%, 96%, 97%, 98%, 99%, or 100% sequence identity to a sequence listed in Table 9. In some embodiments, the polynucleic acid molecule comprises a sequence having at least 50%, 55%, 60%, 65%, 70%, 75%, 80%, 85%, 90%, 95%, 96%, 97%, 98%, 99%, or 100% sequence identity to SEQ ID NOs: 1215-1242. In some embodiments, the polynucleic acid molecule comprises a sequence having at least 50% sequence identity to SEQ ID NOs: 1215-1242. In some embodiments, the polynucleic acid molecule comprises a sequence having at least 60% sequence identity to SEQ ID NOs: 1215-1242. In some embodiments, the polynucleic acid molecule comprises a sequence having at least 70% sequence identity to SEQ ID NOs: 1215-1242. In some embodiments, the polynucleic acid molecule comprises a sequence having at least 75% sequence identity to SEQ ID NOs: 1215-1242. In some embodiments, the polynucleic acid molecule comprises a sequence having at least 80% sequence identity to SEQ ID NOs: 1215-1242. In some embodiments, the polynucleic acid molecule comprises a sequence having at least 85% sequence identity to SEQ ID NOs: 1215-1242. In some embodiments, the polynucleic acid molecule comprises a sequence having at least 90% sequence identity to SEQ ID NOs: 1215-1242. In some embodiments, the polynucleic acid molecule comprises a sequence having at least 95% sequence identity to SEQ ID NOs: 1215-1242. In some embodiments, the polynucleic acid molecule comprises a sequence having at least 96% sequence identity to SEQ ID NOs: 1215-1242. In some embodiments, the polynucleic acid molecule comprises a sequence having at least 97% sequence identity to SEQ ID NOs: 1215-1242. In some embodiments, the polynucleic acid molecule comprises a sequence having at least 98% sequence identity to SEQ ID NOs: 1215-1242. In some embodiments, the polynucleic acid molecule comprises a sequence having at least 99% sequence identity to SEQ ID NOs: 1215-1242. In some embodiments, the polynucleic acid molecule consists of SEQ ID NOs: 1215-1242.

In some embodiments, the polynucleic acid molecule B comprises a first polynucleotide and a second polynucleotide. In some instances, the first polynucleotide comprises a sequence having at least 50%, 55%, 60%, 65%, 70%, 75%, 80%, 85%, 90%, 95%, 96%, 97%, 98%, 99%, or 100% sequence identity to SEQ ID NOs: 1215-1242. In some cases, the second polynucleotide comprises a sequence having at least 50%, 55%, 60%, 65%, 70%, 75%, 80%, 85%, 90%, 95%, 96%, 97%, 98%, 99%, or 100% sequence identity to SEQ ID NOs: 1215-1242. In some cases, the polynucleic acid molecule comprises a first polynucleotide having at least 50%, 55%, 60%, 65%, 70%, 75%, 80%, 85%, 90%, 95%, 96%, 97%, 98%, 99%, or 100% sequence identity to SEQ ID NOs: 1215-1242 and a second polynucleotide having at least 50%, 55%, 60%, 65%, 70%, 75%, 80%, 85%, 90%, 95%, 96%, 97%, 98%, 99%, or 100% sequence identity to SEQ ID NOs: 1215-1242.

Polynucleic Acid Molecules

In some embodiments, the polynucleic acid molecule described herein comprises RNA or DNA. In some cases, the polynucleic acid molecule comprises RNA. In some instances, RNA comprises short interfering RNA (siRNA), short hairpin RNA (shRNA), microRNA (miRNA), double-stranded RNA (dsRNA), transfer RNA (tRNA), ribosomal RNA (rRNA), or heterogeneous nuclear RNA (hnRNA). In some instances, RNA comprises shRNA. In some instances, RNA comprises miRNA. In some instances, RNA comprises dsRNA. In some instances, RNA comprises tRNA. In some instances, RNA comprises rRNA. In some instances, RNA comprises hnRNA. In some instances, the RNA comprises siRNA. In some instances, the polynucleic acid molecule comprises siRNA. In some cases, B comprises siRNA.

In some embodiments, the polynucleic acid molecule is from about 10 to about 50 nucleotides in length. In some instances, the polynucleic acid molecule is from about 10 to about 30, from about 15 to about 30, from about 18 to about 25, from about 18 to about 24, from about 19 to about 23, or from about 20 to about 22 nucleotides in length.

In some embodiments, the polynucleic acid molecule is about 50 nucleotides in length. In some instances, the polynucleic acid molecule is about 45 nucleotides in length. In some instances, the polynucleic acid molecule is about 40 nucleotides in length. In some instances, the polynucleic acid molecule is about 35 nucleotides in length. In some instances, the polynucleic acid molecule is about 30 nucleotides in length. In some instances, the polynucleic acid molecule is about 25 nucleotides in length. In some instances, the polynucleic acid molecule is about 20 nucleotides in length. In some instances, the polynucleic acid molecule is about 19 nucleotides in length. In some instances, the polynucleic acid molecule is about 18 nucleotides in length. In some instances, the polynucleic acid molecule is about 17 nucleotides in length. In some instances, the polynucleic acid molecule is about 16 nucleotides in length. In some instances, the polynucleic acid molecule is about 15 nucleotides in length. In some instances, the polynucleic acid molecule is about 14 nucleotides in length. In some instances, the polynucleic acid molecule is about 13 nucleotides in length. In some instances, the polynucleic acid molecule is about 12 nucleotides in length. In some instances, the polynucleic acid molecule is about 11 nucleotides in length. In some instances, the polynucleic acid molecule is about 10 nucleotides in length. In some instances, the polynucleic acid molecule is from about 10 to about 50 nucleotides in length. In some instances, the polynucleic acid molecule is from about 10 to about 45 nucleotides in length. In some instances, the polynucleic acid molecule is from about 10 to about 40 nucleotides in length. In some instances, the polynucleic acid molecule is from about 10 to about 35 nucleotides in length. In some instances, the polynucleic acid molecule is from about 10 to about 30 nucleotides in length. In some instances, the polynucleic acid molecule is from about 10 to about 25 nucleotides in length. In some instances, the polynucleic acid molecule is from about 10 to about 20 nucleotides in length. In some instances, the polynucleic acid molecule is from about 15 to about 25 nucleotides in length. In some instances, the polynucleic acid molecule is from about 15 to about 30 nucleotides in length. In some instances, the polynucleic acid molecule is from about 12 to about 30 nucleotides in length.

In some embodiments, the polynucleic acid molecule comprises a first polynucleotide. In some instances, the polynucleic acid molecule comprises a second polynucleotide. In some instances, the polynucleic acid molecule comprises a first polynucleotide and a second polynucleotide. In some instances, the first polynucleotide is a sense strand or passenger strand. In some instances, the second polynucleotide is an antisense strand or guide strand.

In some embodiments, the polynucleic acid molecule is a first polynucleotide. In some embodiments, the first polynucleotide is from about 10 to about 50 nucleotides in length. In some instances, the first polynucleotide is from about 10 to about 30, from about 15 to about 30, from about 18 to about 25, from about 18 to about 24, from about 19 to about 23, or from about 20 to about 22 nucleotides in length.

In some instances, the first polynucleotide is about 50 nucleotides in length. In some instances, the first polynucleotide is about 45 nucleotides in length. In some instances, the first polynucleotide is about 40 nucleotides in length. In some instances, the first polynucleotide is about 35 nucleotides in length. In some instances, the first polynucleotide is about 30 nucleotides in length. In some instances, the first polynucleotide is about 25 nucleotides in length. In some instances, the first polynucleotide is about 20 nucleotides in length. In some instances, the first polynucleotide is about 19 nucleotides in length. In some instances, the first polynucleotide is about 18 nucleotides in length. In some instances, the first polynucleotide is about 17 nucleotides in length. In some instances, the first polynucleotide is about 16 nucleotides in length. In some instances, the first polynucleotide is about 15 nucleotides in length. In some instances, the first polynucleotide is about 14 nucleotides in length. In some instances, the first polynucleotide is about 13 nucleotides in length. In some instances, the first polynucleotide is about 12 nucleotides in length. In some instances, the first polynucleotide is about 11 nucleotides in length. In some instances, the first polynucleotide is about 10 nucleotides in length. In some instances, the first polynucleotide is from about 10 to about 50 nucleotides in length. In some instances, the first polynucleotide is from about 10 to about 45 nucleotides in length. In some instances, the first polynucleotide is from about 10 to about 40 nucleotides in length. In some instances, the first polynucleotide is from about 10 to about 35 nucleotides in length. In some instances, the first polynucleotide is from about 10 to about 30 nucleotides in length. In some instances, the first polynucleotide is from about 10 to about 25 nucleotides in length. In some instances, the first polynucleotide is from about 10 to about 20 nucleotides in length. In some instances, the first polynucleotide is from about 15 to about 25 nucleotides in length. In some instances, the first polynucleotide is from about 15 to about 30 nucleotides in length. In some instances, the first polynucleotide is from about 12 to about 30 nucleotides in length.

In some embodiments, the polynucleic acid molecule is a second polynucleotide. In some embodiments, the second polynucleotide is from about 10 to about 50 nucleotides in length. In some instances, the second polynucleotide is from about 10 to about 30, from about 15 to about 30, from about 18 to about 25, from about 18 to about 24, from about 19 to about 23, or from about 20 to about 22 nucleotides in length.

In some instances, the second polynucleotide is about 50 nucleotides in length. In some instances, the second polynucleotide is about 45 nucleotides in length. In some instances, the second polynucleotide is about 40 nucleotides in length. In some instances, the second polynucleotide is about 35 nucleotides in length. In some instances, the second polynucleotide is about 30 nucleotides in length. In some instances, the second polynucleotide is about 25 nucleotides in length. In some instances, the second polynucleotide is about 20 nucleotides in length. In some instances, the second polynucleotide is about 19 nucleotides in length. In some instances, the second polynucleotide is about 18 nucleotides in length. In some instances, the second polynucleotide is about 17 nucleotides in length. In some instances, the second polynucleotide is about 16 nucleotides in length. In some instances, the second polynucleotide is about 15 nucleotides in length. In some instances, the second polynucleotide is about 14 nucleotides in length. In some instances, the second polynucleotide is about 13 nucleotides in length. In some instances, the second polynucleotide is about 12 nucleotides in length. In some instances, the second polynucleotide is about 11 nucleotides in length. In some instances, the second polynucleotide is about 10 nucleotides in length. In some instances, the second polynucleotide is from about 10 to about 50 nucleotides in length. In some instances, the second polynucleotide is from about 10 to about 45 nucleotides in length. In some instances, the second polynucleotide is from about 10 to about 40 nucleotides in length. In some instances, the second polynucleotide is from about 10 to about 35 nucleotides in length. In some instances, the second polynucleotide is from about 10 to about 30 nucleotides in length. In some instances, the second polynucleotide is from about 10 to about 25 nucleotides in length. In some instances, the second polynucleotide is from about 10 to about 20 nucleotides in length. In some instances, the second polynucleotide is from about 15 to about 25 nucleotides in length. In some instances, the second polynucleotide is from about 15 to about 30 nucleotides in length. In some instances, the second polynucleotide is from about 12 to about 30 nucleotides in length.

In some embodiments, the polynucleic acid molecule comprises a first polynucleotide and a second polynucleotide. In some instances, the polynucleic acid molecule further comprises a blunt terminus, an overhang, or a combination thereof. In some instances, the blunt terminus is a 5' blunt terminus, a 3' blunt terminus, or both. In some cases, the overhang is a 5' overhang, 3' overhang, or both. In some cases, the overhang comprises 1, 2, 3, 4, 5, 6, 7, 8, 9, or 10 non-base pairing nucleotides. In some cases, the overhang comprises 1, 2, 3, 4, 5, or 6 non-base pairing nucleotides. In some cases, the overhang comprises 1, 2, 3, or 4 non-base pairing nucleotides. In some cases, the overhang comprises 1 non-base pairing nucleotide. In some cases, the overhang comprises 2 non-base pairing nucleotides. In some cases, the overhang comprises 3 non-base pairing nucleotides. In some cases, the overhang comprises 4 non-base pairing nucleotides.

In some embodiments, the sequence of the polynucleic acid molecule is at least 40%, 50%, 55%, 60%, 65%, 70%, 75%, 80%, 85%, 90%, 95%, 98%, 99%, or 99.5% complementary to a target sequence described herein. In some embodiments, the sequence of the polynucleic acid molecule is at least 50% complementary to a target sequence described herein. In some embodiments, the sequence of the polynucleic acid molecule is at least 60% complementary to a target sequence described herein. In some embodiments, the sequence of the polynucleic acid molecule is at least 70% complementary to a target sequence described herein. In some embodiments, the sequence of the polynucleic acid molecule is at least 80% complementary to a target sequence described herein. In some embodiments, the sequence of the polynucleic acid molecule is at least 90% complementary to a target sequence described herein. In some embodiments, the sequence of the polynucleic acid molecule is at least 95% complementary to a target sequence described herein. In some embodiments, the sequence of the polynucleic acid molecule is at least 99% complementary to a target sequence described herein. In some instances, the sequence of the polynucleic acid molecule is 100% complementary to a target sequence described herein.

In some embodiments, the sequence of the polynucleic acid molecule has 5 or less mismatches to a target sequence described herein. In some embodiments, the sequence of the polynucleic acid molecule has 4 or less mismatches to a target sequence described herein. In some instances, the sequence of the polynucleic acid molecule may has 3 or less mismatches to a target sequence described herein. In some cases, the sequence of the polynucleic acid molecule may has 2 or less mismatches to a target sequence described herein. In some cases, the sequence of the polynucleic acid molecule may has 1 or less mismatches to a target sequence described herein.

In some embodiments, the specificity of the polynucleic acid molecule that hybridizes to a target sequence described herein is a 95%, 98%, 99%, 99.5%, or 100% sequence complementarity of the polynucleic acid molecule to a target sequence. In some instances, the hybridization is a high stringent hybridization condition.

In some embodiments, the polynucleic acid molecule hybridizes to at least 8, 9, 10, 11, 12, 13, 14, 15, 16, 17, 18, 19, 20, or more contiguous bases of a target sequence described herein. In some embodiments, the polynucleic acid molecule hybridizes to at least 8 contiguous bases of a target sequence described herein. In some embodiments, the polynucleic acid molecule hybridizes to at least 9 contiguous bases of a target sequence described herein. In some embodiments, the polynucleic acid molecule hybridizes to at least 10 contiguous bases of a target sequence described herein. In some embodiments, the polynucleic acid molecule hybridizes to at least 11 contiguous bases of a target sequence described herein. In some embodiments, the polynucleic acid molecule hybridizes to at least 12 contiguous bases of a target sequence described herein. In some embodiments, the polynucleic acid molecule hybridizes to at least 13 contiguous bases of a target sequence described herein. In some embodiments, the polynucleic acid molecule hybridizes to at least 14 contiguous bases of a target sequence described herein. In some embodiments, the polynucleic acid molecule hybridizes to at least 15 contiguous bases of a target sequence described herein. In some embodiments, the polynucleic acid molecule hybridizes to at least 16 contiguous bases of a target sequence described herein. In some embodiments, the polynucleic acid molecule hybridizes to at least 17 contiguous bases of a target sequence described herein. In some embodiments, the polynucleic acid molecule hybridizes to at least 18 contiguous bases of a target sequence described herein. In some embodiments, the polynucleic acid molecule hybridizes to at least 19 contiguous bases of a target sequence described herein. In some embodiments, the polynucleic acid molecule hybridizes to at least 20 contiguous bases of a target sequence described herein.

In some embodiments, the polynucleic acid molecule has reduced off-target effect. In some instances, "off-target" or "off-target effects" refer to any instance in which a polynucleic acid polymer directed against a given target causes an unintended effect by interacting either directly or indirectly with another mRNA sequence, a DNA sequence or a cellular protein or other moiety. In some instances, an "off-target effect" occurs when there is a simultaneous degradation of other transcripts due to partial homology or complementarity between that other transcript and the sense and/or antisense strand of the polynucleic acid molecule.

In some embodiments, the polynucleic acid molecule comprises natural, synthetic, or artificial nucleotide analogues or bases. In some cases, the polynucleic acid molecule comprises combinations of DNA, RNA and/or nucleotide analogues. In some instances, the synthetic or artificial nucleotide analogues or bases comprise modifications at one or more of ribose moiety, phosphate moiety, nucleoside moiety, or a combination thereof.

In some embodiments, a nucleotide analogue or artificial nucleotide base described above comprises a 5'-vinylphosphonate modified nucleotide nucleic acid with a modification at a 5' hydroxyl group of the ribose moiety. In some embodiments, the 5'-vinylphosphonate modified nucleotide is selected from the nucleotide provided below.

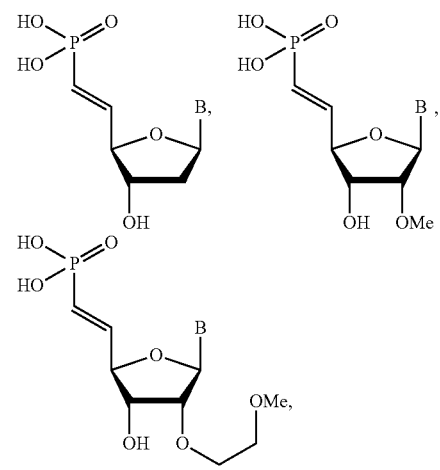

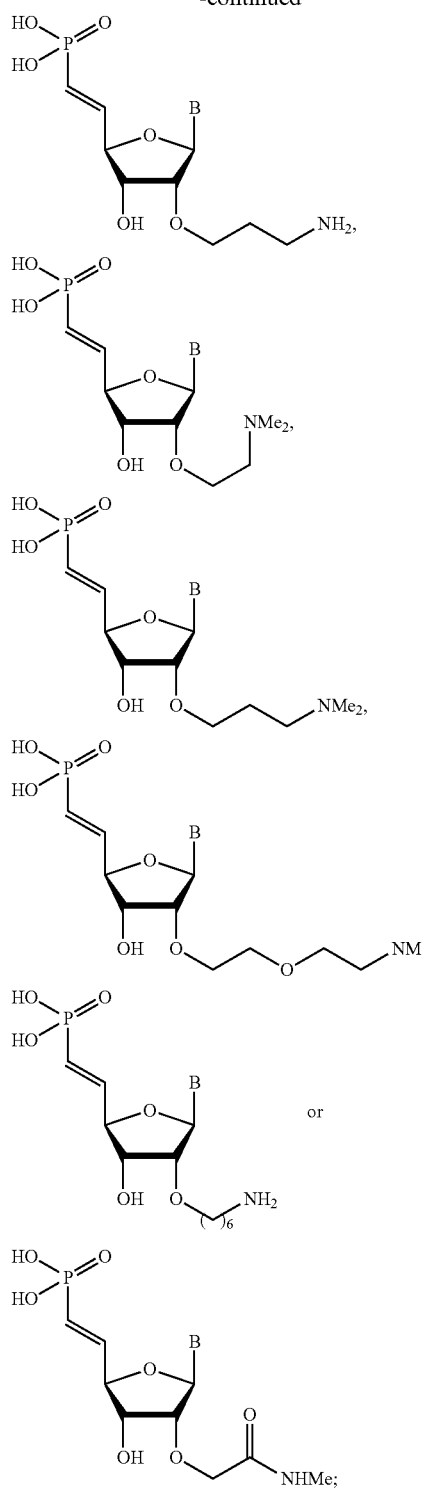

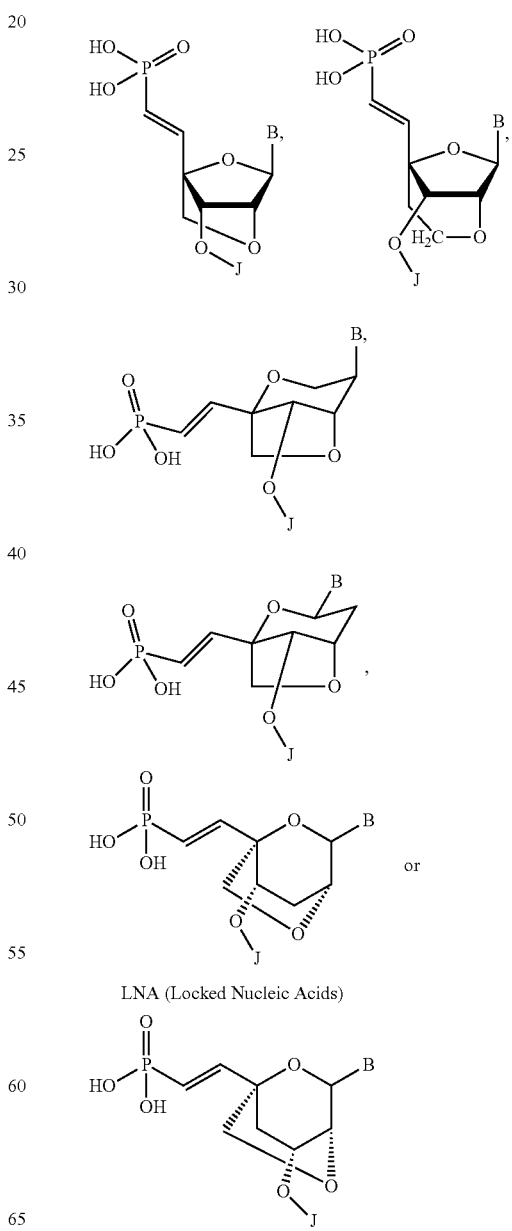

LNA (Locked Nucleic Acids)

In some instances, the modification at the 2' hydroxyl group is a 2'-O-aminopropyl modification in which an extended amine group comprising a propyl linker binds the amine group to the 2' oxygen. In some instances, this modification neutralizes the phosphate-derived overall negative charge of the oligonucleotide molecule by introducing one positive charge from the amine group per sugar and thereby improves cellular uptake properties due to its zwitterionic properties.

In some instances, the 5'-vinylphosphonate modified nucleotide is further modified at the 2' hydroxyl group in a locked or bridged ribose modification (e.g., locked nucleic acid or LNA) in which the oxygen molecule bound at the 2' carbon is linked to the 4' carbon by a methylene group, thus forming a 2'-C,4'-C-oxy-methylene-linked bicyclic ribonucleotide monomer. Exemplary representations of the chemical structure of 5'-vinylphosphonate modified LNA are illustrated below, wherein J is an internucleotide linkage.

In some embodiments, additional modifications at the 2' hydroxyl group include 2'-deoxy, T-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), or 2'-O-N-methylacetamido (2'-O-NMA).

In some embodiments, a nucleotide analogue comprises a modified base such as, but not limited to, 5-propynyluridine, 5-propynylcytidine, 6-methyladenine, 6-methylguanine, N,N,-dimethyladenine, 2-propyladenine, 2propylguanine, 2-aminoadenine, 1-methylinosine, 3-methyluridine, 5-methylcytidine, 5-methyluridine and other nucleotides having a modification at the 5 position, 5-(2-amino) propyl uridine, 5-halocytidine, 5-halouridine, 4-acetylcytidine, 1-methyladenosine, 2-methyladenosine, 3-methylcytidine, 6-methyluridine, 2-methylguanosine, 7-methylguanosine, 2, 2-dimethylguanosine, 5-methylaminoethyluridine, 5-methyloxyuridine, deazanucleotides (such as 7-deaza-adenosine, 6-azouridine, 6-azocytidine, or 6-azothymidine), 5-methyl-2-thiouridine, other thio bases (such as 2-thiouridine, 4-thiouridine, and 2-thiocytidine), dihydrouridine, pseudouridine, queuosine, archaeosine, naphthyl and substituted naphthyl groups, any O- and N-alkylated purines and pyrimidines (such as N6-methyladenosine, 5-methylcarbonylmethyluridine, uridine 5-oxyacetic acid, pyridine-4-one, or pyridine-2-one), phenyl and modified phenyl groups such as aminophenol or 2,4, 6-trimethoxy benzene, modified cytosines that act as G-clamp nucleotides, 8-substituted adenines and guanines, 5-substituted uracils and thymines, azapyrimidines, carboxyhydroxyalkyl nucleotides, carboxyalkylaminoalkyi nucleotides, and alkylcarbonylalkylated nucleotides. 5'-Vinylphosphonate modified nucleotides also include those nucleotides that are modified with respect to the sugar moiety, as well as 5'-vinylphosphonate modified nucleotides having sugars or analogs thereof that are not ribosyl. For example, the sugar moieties, in some cases are or are based on, mannoses, arabinoses, glucopyranoses, galactopyranoses, 4'-thioribose, and other sugars, heterocycles, or carbocycles. The term nucleotide also includes what are known in the art as universal bases. By way of example, universal bases include but are not limited to 3-nitropyrrole, 5-nitroindole, or nebularine.

In some embodiments, a 5'-vinylphosphonate modified nucleotide analogue further comprises a morpholino, a peptide nucleic acid (PNA), a methylphosphonate nucleotide, a thiolphosphonate nucleotide, a 2'-fluoro N3-P5'-phosphoramidite, or a 1', 5'-anhydrohexitol nucleic acid (HNA). Morpholino or phosphorodiamidate morpholino oligo (PMO) comprises synthetic molecules whose structure mimics natural nucleic acid structure but deviates from the normal sugar and phosphate structures. In some instances, the five member ribose ring is substituted with a six member morpholino ring containing four carbons, one nitrogen, and one oxygen. In some cases, the ribose monomers are linked by a phosphordiamidate group instead of a phosphate group. In such cases, the backbone alterations remove all positive and negative charges making morpholinos neutral molecules capable of crossing cellular membranes without the aid of cellular delivery agents such as those used by charged oligonucleotides. A non-limiting example of a 5'-vinylphosphonate modified morpholino oligonucleotide is illustrated below.

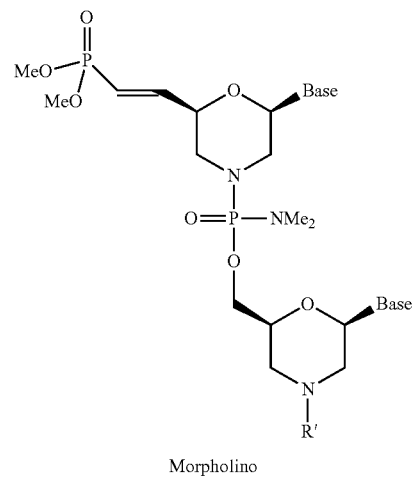

Morpholino

In some embodiments, a 5'-vinylphosphonate modified morpholino or PMO described above is a PMO comprising a positive or cationic charge. In some instances, the PMO is PMOplus (Sarepta). PMOplus refers to phosphorodiamidate morpholino oligomers comprising any number of (1-piperazino)phosphinylideneoxy, (1-(4-(omega-guanidino-alkanoyl))-piperazino)phosphinylideneoxy linkages (e.g., as such those described in PCI Publication No. WO2008/036127. In some cases, the PMO is a PMO described in U.S. Pat. No. 7,943,762.

In some embodiments, a morpholino or PMO described above is a PMO-X (Sarepta). In some cases, PMO-X refers to phosphorodiamidate morpholino oligomers comprising at least one linkage or at least one of the disclosed terminal modifications, such as those disclosed in PCT Publication No. WO2011/150408 and U.S. Publication No. 2012/0065169.

In some embodiments, a morpholino or PMO described above is a PMO as described in Table 5 of U.S. Publication No. 2014/0296321.

Exemplary representations of the chemical structure of 5'-vinylphosphonate modified nucleic acids are illustrated below, wherein J is an internucleotide linkage.

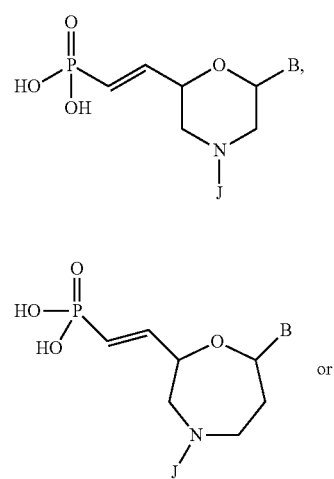

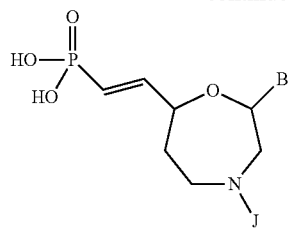

In some embodiments, peptide nucleic acid (PNA) does not contain sugar ring or phosphate linkage and the bases are attached and appropriately spaced by oligoglycine-like molecules, therefore, eliminating a backbone charge.

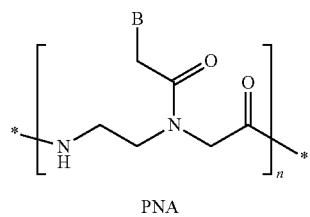

PNA

In some embodiments, one or more modifications of the 5'-vinylphosphonate modified oligonucleotide optionally occur at the internucleotide linkage. In some instances, modified internucleotide linkage includes, but is not limited to, phosphorothioates; phosphorodithioates; methylphosphonates; 5'-alkylenephosphonates; 5'-methylphosphonate; 3'-alkylene phosphonates; borontrifluoridates; borano phosphate esters and selenophosphates of 3'-5'linkage or 2'-5'linkage; phosphotriesters; thionoalkylphosphotriesters; hydrogen phosphonate linkages; alkyl phosphonates; alkylphosphonothioates; arylphosphonothioates; phosphoroselenoates; phosphorodiselenoates; phosphinates; phosphoramidates; 3'-alkylphosphoramidates; aminoalkylphosphoramidates; thionophosphoramidates; phosphoropiperazidates; phosphoroanilothioates; phosphoroanilidates; ketones; sulfones; sulfonamides; carbonates; carbamates; methylenehydrazos; methylenedimethylhydrazos; formacetals; thioformacetals; oximes; methyleneiminos; methylenemethyliminos; thioamidates; linkages with riboacetyl groups; aminoethyl glycine; silyl or siloxane linkages; alkyl or cycloalkyl linkages with or without heteroatoms of, for example, 1 to 10 carbons that are saturated or unsaturated and/or substituted and/or contain heteroatoms; linkages with morpholino structures, amides, or polyamides wherein the bases are attached to the aza nitrogens of the backbone directly or indirectly; and combinations thereof.

In some instances, the modification is a methyl or thiol modification such as methylphosphonate or thiolphosphonate modification. Exemplary thiolphosphonate nucleotide (left), phosphorodithioates (center) and methylphosphonate nucleotide (right) are illustrated below.

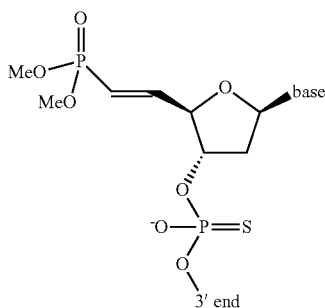

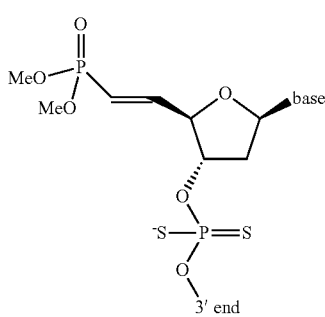

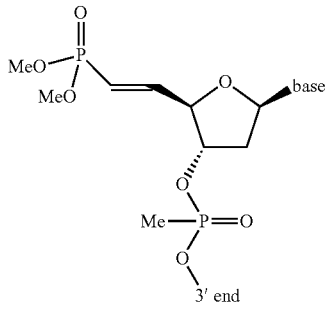

In some instances, a 5'-vinylphosphonate modified nucleotide includes, but is not limited to, phosphoramidites illustrated as:

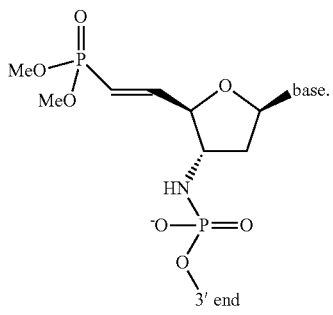

In some instances, the modified internucleotide linkage is a phosphorodiamidate linkage. A non-limiting example of a phosphorodiamidate linkage with a morpholino system is shown below.

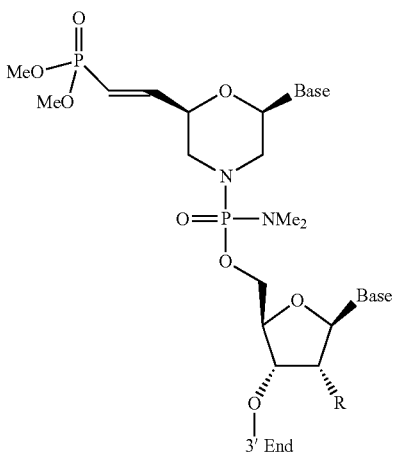

In some instances, the modified internucleotide linkage is a methylphosphonate linkage. A non-limiting example of a methylphosphonate linkage is shown below.

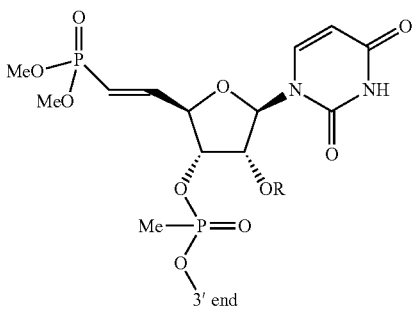

In some instances, the modified internucleotide linkage is a amide linkage. A non-limiting example of an amide linkage is shown below.

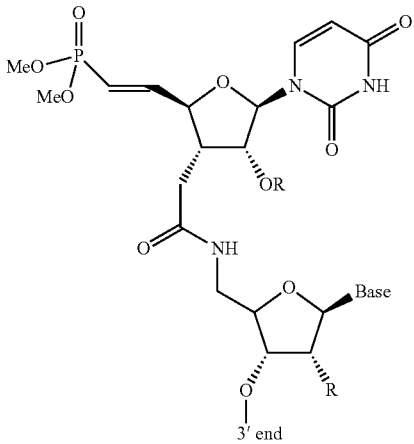

In some instances, a 5'-vinylphosphonate modified nucleotide includes, but is not limited to, the modified nucleic acid illustrated illustrated below.

In some embodiments, one or more modifications comprise a modified phosphate backbone in which the modification generates a neutral or uncharged backbone. In some instances, the phosphate backbone is modified by alkylation to generate an uncharged or neutral phosphate backbone. As used herein, alkylation includes methylation, ethylation, and propylation. In some cases, an alkyl group, as used herein in the context of alkylation, refers to a linear or branched saturated hydrocarbon group containing from 1 to 6 carbon atoms. In some instances, exemplary alkyl groups include, but are not limited to, methyl, ethyl, n-propyl, isopropyl, n-butyl, isobutyl, sec-butyl, tert-butyl, n-pentyl, isopentyl, neopentyl, hexyl, isohexyl, 1, 1-dimethylbutyl, 2,2-dimethylbutyl, 3,3-dimethylbutyl, and 2-ethylbutyl groups. In some cases, a modified phosphate is a phosphate group as described in U.S. Pat. No. 9,481,905.

In some embodiments, additional modified phosphate backbones comprise methylphosphonate, ethylphosphonate, methylthiophosphonate, or methoxyphosphonate. In some cases, the modified phosphate is methylphosphonate. In some cases, the modified phosphate is ethylphosphonate. In some cases, the modified phosphate is methylthiophosphonate. In some cases, the modified phosphate is methoxyphosphonate.

In some embodiments, one or more modifications further optionally include modifications of the ribose moiety, phosphate backbone and the nucleoside, or modifications of the nucleotide analogues at the 3' or the 5' terminus. For example, the 3' terminus optionally include a 3' cationic group, or by inverting the nucleoside at the 3'-terminus with a 3'-3' linkage. In another alternative, the 3'-terminus is optionally conjugated with aminoalkyl group, e.g., a 3' C5-aminoalkyl dT. In an additional alternative, the 3'-terminus is optionally conjugated with an abasic site, e.g., with an apurinic or apyrimidinic site.

In some embodiments, the polynucleic acid molecule comprises one or more of the artificial nucleotide analogues described herein. In some instances, the 5'-vinylphosphonate modified polynucleic acid molecule comprises 1, 2, 3, 4, 5, 6, 7, 8, 9, 10, 11, 12, 13, 14, 15, 16, 17, 18, 20, 25, or more of the artificial 5'-vinylphosphonate modified nucleotide analogues described herein. In some embodiments, the artificial 5'-vinylphosphonate modified nucleotide analogues include 2'-O-methyl, 2'-O-methoxyethyl (2'-O-MOE), 2'-O-aminopropyl, 2'-deoxy, T-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), or 2'-O-N-methylacetamido (2'-O-NMA) modified, LNA, ENA, PNA, HNA, morpholino, methylphosphonate nucleotides, thiolphosphonate nucleotides, 2'-fluoro N3-P5'-phosphoramidites, or a combination thereof. In some instances, the 5'-vinylphosphonate modified polynucleic acid molecule comprises 1, 2, 3, 4, 5, 6, 7, 8, 9, 10, 11, 12, 13, 14, 15, 16, 17, 18, 20, 25, or more of the artificial nucleotide analogues selected from 2'-O-methyl, 2'-O-methoxyethyl (2'-O-MOE), 2'-O-aminopropyl, 2'-deoxy, T-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), or 2'-O-N-methylacetamido (2'-O-NMA) modified, LNA, ENA, PNA, HNA, morpholino, methylphosphonate nucleotides, thiolphosphonate nucleotides, 2'-fluoro N3-P5'-phosphoramidites, or a combination thereof. In some instances, the 5'-vinylphosphonate modified polynucleic acid molecule comprises 1, 2, 3, 4, 5, 6, 7, 8, 9, 10, 11, 12, 13, 14, 15, 16, 17, 18, 20, 25, or more of 2'-O-methyl modified nucleotides. In some instances, the 5'-vinylphosphonate modified polynucleic acid molecule comprises 1, 2, 3, 4, 5, 6, 7, 8, 9, 10, 11, 12, 13, 14, 15, 16, 17, 18, 20, 25, or more of 2'-O-methoxyethyl (2'-O-MOE) modified nucleotides. In some instances, the 5'-vinylphosphonate modified polynucleic acid molecule comprises 1, 2, 3, 4, 5, 6, 7, 8, 9, 10, 11, 12, 13, 14, 15, 16, 17, 18, 20, 25, or more of thiolphosphonate nucleotides.

In some embodiments, the 5'-vinylphosphonate modified polynucleic acid molecule comprises at least about 1, about 2, about 3, about 4, about 5, about 6, about 7, about 8, about 9, about 10, about 11, about 12, about 13, about 14, about 15, about 16, about 17, about 18, about 19, about 20, about 21, about 22, or more modifications. In some instances, the polynucleic acid molecule is a polynucleic acid molecule of SEQ ID NOs: 16-45, 422-1173, 1195-1214, or 1215-1242

In some instances, the 5'-vinylphosphonate modified polynucleic acid molecule comprises at least about 1, about 2, about 3, about 4, about 5, about 6, about 7, about 8, about 9, about 10, about 11, about 12, about 13, about 14, about 15, about 16, about 17, about 18, about 19, about 20, about 21, about 22, or more modified nucleotides. In some instances, the polynucleic acid molecule is a polynucleic acid molecule of SEQ ID NOs: 16-45, 422-1173, 1195-1214, or 1215-1242.

In some instances, the 5'-vinylphosphonate modified polynucleic acid molecule comprises at least one of: from about 5% to about 100% modification, from about 10% to about 100% modification, from about 20% to about 100% modification, from about 30% to about 100% modification, from about 40% to about 100% modification, from about 50% to about 100% modification, from about 60% to about 100% modification, from about 70% to about 100% modification, from about 80% to about 100% modification, and from about 90% to about 100% modification. In some instances, the polynucleic acid molecule is a polynucleic acid molecule of SEQ ID NOs: 16-45, 422-1173, 1195-1214, or 1215-1242.

In some instances, about 5 to about 100% of the 5'-vinylphosphonate modified polynucleic acid molecule comprise the artificial nucleotide analogues described herein. In some instances, about 5%, 10%, 15%, 20%, 25%, 30%, 35%, 40%, 45%, 50%, 55%, 60%, 65%, 70%, 75%, 80%, 85%, 90%, 95%, or 100% of the polynucleic acid molecule comprise the artificial nucleotide analogues described herein. In some instances, about 5%, 10%, 15%, 20%, 25%, 30%, 35%, 40%, 45%, 50%, 55%, 60%, 65%, 70%, 75%, 80%, 85%, 90%, 95%, or 100% of a polynucleic acid molecule of SEQ ID NOs: 16-45, 422-1173, 1195-1214, or 1215-1242 comprise the artificial nucleotide analogues described herein. In some instances, about 5%, 10%, 15%, 20%, 25%, 30%, 35%, 40%, 45%, 50%, 55%, 60%, 65%, 70%, 75%, 80%, 85%, 90%, 95%, or 100% of a polynucleic acid molecule of SEQ ID NOs: 16-45 comprise the artificial nucleotide analogues described herein. In some instances, about 5%, 10%, 15%, 20%, 25%, 30%, 35%, 40%, 45%, 50%, 55%, 60%, 65%, 70%, 75%, 80%, 85%, 90%, 95%, or 100% of a polynucleic acid molecule of SEQ ID NOs: 422-1173 comprise the artificial nucleotide analogues described herein. In some instances, about 5%, 10%, 15%, 20%, 25%, 30%, 35%, 40%, 45%, 50%, 55%, 60%, 65%, 70%, 75%, 80%, 85%, 90%, 95%, or 100% of a polynucleic acid molecule of SEQ ID NOs: 1195-1214 comprise the artificial nucleotide analogues described herein. In some instances, about 5%, 10%, 15%, 20%, 25%, 30%, 35%, 40%, 45%, 50%, 55%, 60%, 65%, 70%, 75%, 80%, 85%, 90%, 95%, or 100% of a polynucleic acid molecule of SEQ ID NOs: 1215-1242 comprise the artificial nucleotide analogues described herein. In some embodiments, the artificial nucleotide analogues include 2'-O-methyl, 2'-O-methoxyethyl (2'-O-MOE), 2'-O-aminopropyl, 2'-deoxy, T-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), or 2'-O-N-methylacetamido (2'-O-NMA) modified, LNA, ENA, PNA, HNA, morpholino, methylphosphonate nucleotides, thiolphosphonate nucleotides, 2'-fluoro N3-P5'-phosphoramidites, or a combination thereof.

In some cases, one or more of the artificial 5'-vinylphosphonate modified nucleotide analogues described herein are resistant toward nucleases such as for example ribonuclease such as RNase H, deoxyribonuclease such as DNase, or exonuclease such as 5'-3' exonuclease and 3'-5' exonuclease when compared to natural polynucleic acid molecules. In some instances, artificial nucleotide analogues comprising 2'-O-methyl, 2'-O-methoxyethyl (2'-O-MOE), 2'-O-aminopropyl, 2'-deoxy, T-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), or 2'-O-N-methylacetamido (2'-O-NMA) modified, LNA, ENA, PNA, HNA, morpholino, methylphosphonate nucleotides, thiolphosphonate nucleotides, 2'-fluoro N3-P5'-phosphoramidites, or combinations thereof are resistant toward nucleases such as for example ribonuclease such as RNase H, deoxyribunuclease such as DNase, or exonuclease such as 5'-3' exonuclease and 3'-5' exonuclease. In some instances, 2'-O-methyl modified polynucleic acid molecule is nuclease resistant (e.g., RNase H, DNase, 5'-3' exonuclease or 3'-5' exonuclease resistant). In some instances, 2'O-methoxyethyl (2'-O-MOE) modified polynucleic acid molecule is nuclease resistant (e.g., RNase H, DNase, 5'-3' exonuclease or 3'-5' exonuclease resistant). In some instances, 2'-O-aminopropyl modified polynucleic acid molecule is nuclease resistant (e.g., RNase H, DNase, 5'-3' exonuclease or 3'-5' exonuclease resistant). In some instances, 2'-deoxy modified polynucleic acid molecule is nuclease resistant (e.g., RNase H, DNase, 5'-3' exonuclease or 3'-5' exonuclease resistant). In some instances, T-deoxy-2'-fluoro modified polynucleic acid molecule is nuclease resistant (e.g., RNase H, DNase, 5'-3' exonuclease or 3'-5' exonuclease resistant). In some instances, 2'-O-aminopropyl (2'-O-AP) modified polynucleic acid molecule is nuclease resistant (e.g., RNase H, DNase, 5'-3' exonuclease or 3'-5' exonuclease resistant). In some instances, 2'-O-dimethylaminoethyl (2'-O-DMAOE) modified polynucleic acid molecule is nuclease resistant (e.g., RNase H, DNase, 5'-3' exonuclease or 3'-5' exonuclease resistant). In some instances, 2'-0-dimethylaminopropyl (2'-O-DMAP) modified polynucleic acid molecule is nuclease resistant (e.g., RNase H, DNase, 5'-3' exonuclease or 3'-5' exonuclease resistant). In some instances, T-O-dimethylaminoethyloxyethyl (2'-O-DMAEOE) modified polynucleic acid molecule is nuclease resistant (e.g., RNase H, DNase, 5'-3' exonuclease or 3'-5' exonuclease resistant). In some instances, 2'-O-N-methylacetamido (2'-O-NMA) modified polynucleic acid molecule is nuclease resistant (e.g., RNase H, DNase, 5'-3' exonuclease or 3'-5' exonuclease resistant). In some instances, LNA-modified polynucleic acid molecule is nuclease resistant (e.g., RNase H, DNase, 5'-3' exonuclease or 3'-5' exonuclease resistant). In some instances, ENA-modified polynucleic acid molecule is nuclease resistant (e.g., RNase H, DNase, 5'-3' exonuclease or 3'-5' exonuclease resistant). In some instances, HNA-modified polynucleic acid molecule is nuclease resistant (e.g., RNase H, DNase, 5'-3' exonuclease or 3'-5' exonuclease resistant). Morpholinos may be nuclease resistant (e.g., RNase H, DNase, 5'-3' exonuclease or 3'-5' exonuclease resistant). In some instances, PNA-modified polynucleic acid molecule is resistant to nucleases (e.g., RNase H, DNase, 5'-3' exonuclease or 3'-5' exonuclease resistant). In some instances, methylphosphonate nucleotide-modified polynucleic acid molecule is nuclease resistant (e.g., RNase H, DNase, 5'-3' exonuclease or 3'-5' exonuclease resistant). In some instances, thiolphosphonate nucleotide-modified polynucleic acid molecule is nuclease resistant (e.g., RNase H, DNase, 5'-3' exonuclease or 3'-5' exonuclease resistant). In some instances, polynucleic acid molecule comprising 2'-fluoro N3-P5'-phosphoramidites is nuclease resistant (e.g., RNase H, DNase, 5'-3' exonuclease or 3'-5' exonuclease resistant). In some instances, the 5' conjugates described herein inhibit 5'-3' exonucleolytic cleavage. In some instances, the 3' conjugates described herein inhibit exonucleolytic cleavage.

In some embodiments, one or more of the artificial 5'-vinylphosphonate modified nucleotide analogues described herein have increased binding affinity toward their mRNA target relative to an equivalent natural polynucleic acid molecule. The one or more of the artificial nucleotide analogues comprising 2'-O-methyl, 2'-O-methoxyethyl (2'-O-MOE), 2'-O-aminopropyl, 2'-deoxy, T-deoxy-2'-fluoro, 2'-O-aminopropyl (2'-0-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), or 2'-O-N-methylacetamido (2'-O-NMA) modified, LNA, ENA, PNA, HNA, morpholino, methylphosphonate nucleotides, thiolphosphonate nucleotides, or 2'-fluoro N3-P5'-phosphoramidites can have increased binding affinity toward their mRNA target relative to an equivalent natural polynucleic acid molecule. In some instances, 2'-O-methyl modified polynucleic acid molecule has increased binding affinity toward their mRNA target relative to an equivalent natural polynucleic acid molecule. In some instances, 2'-O-methoxyethyl (2'-O-MOE) modified polynucleic acid molecule has increased binding affinity toward their mRNA target relative to an equivalent natural polynucleic acid molecule. In some instances, 2'-O-aminopropyl modified polynucleic acid molecule has increased binding affinity toward their mRNA target relative to an equivalent natural polynucleic acid molecule. In some instances, 2'-deoxy modified polynucleic acid molecule has increased binding affinity toward their mRNA target relative to an equivalent natural polynucleic acid molecule. In some instances, T-deoxy-2'-fluoro modified polynucleic acid molecule has increased binding affinity toward their mRNA target relative to an equivalent natural polynucleic acid molecule. In some instances, 2'-O-aminopropyl (2'-O-AP) modified polynucleic acid molecule has increased binding affinity toward their mRNA target relative to an equivalent natural polynucleic acid molecule. In some instances, 2'-O-dimethylaminoethyl (2'-O-DMAOE) modified polynucleic acid molecule has increased binding affinity toward their mRNA target relative to an equivalent natural polynucleic acid molecule. In some instances, 2'-O-dimethylaminopropyl (2'-O-DMAP) modified polynucleic acid molecule has increased binding affinity toward their mRNA target relative to an equivalent natural polynucleic acid molecule. In some instances, T-O-dimethylaminoethyloxyethyl (2'-O-DMAEOE) modified polynucleic acid molecule has increased binding affinity toward their mRNA target relative to an equivalent natural polynucleic acid molecule. In some instances, 2'-O-N-methylacetamido (2'-O-NMA) modified polynucleic acid molecule has increased binding affinity toward their mRNA target relative to an equivalent natural polynucleic acid molecule. In some instances, LNA-modified polynucleic acid molecule has increased binding affinity toward their mRNA target relative to an equivalent natural polynucleic acid molecule. In some instances, ENA-modified polynucleic acid molecule has increased binding affinity toward their mRNA target relative to an equivalent natural polynucleic acid molecule. In some instances, PNA-modified polynucleic acid molecule has increased binding affinity toward their mRNA target relative to an equivalent natural polynucleic acid molecule. In some instances, HNA-modified polynucleic acid molecule has increased binding affinity toward their mRNA target relative to an equivalent natural polynucleic acid molecule. In some instances, morpholino-modified polynucleic acid molecule has increased binding affinity toward their mRNA target relative to an equivalent natural polynucleic acid molecule. In some instances, methylphosphonate nucleotide-modified polynucleic acid molecule has increased binding affinity toward their mRNA target relative to an equivalent natural polynucleic acid molecule. In some instances, thiolphosphonate nucleotide-modified polynucleic acid molecule has increased binding affinity toward their mRNA target relative to an equivalent natural polynucleic acid molecule. In some instances, polynucleic acid molecule comprising 2'-fluoro N3-P5'-phosphoramidites has increased binding affinity toward their mRNA target relative to an equivalent natural polynucleic acid molecule. In some cases, the increased affinity is illustrated with a lower Kd, a higher melt temperature (Tm), or a combination thereof.

In some embodiments, a 5'-vinylphosphonate modified polynucleic acid molecule described herein is a chirally pure (or stereo pure) polynucleic acid molecule, or a polynucleic acid molecule comprising a single enantiomer. In some instances, the polynucleic acid molecule comprises L-nucleotide. In some instances, the polynucleic acid molecule comprises D-nucleotides. In some instance, a polynucleic acid molecule composition comprises less than 30%, 25%, 20%, 15%, 10%, 5%, 4%, 3%, 2%, 1%, or less of its mirror enantiomer. In some cases, a polynucleic acid molecule composition comprises less than 30%, 25%, 20%, 15%, 10%, 5%, 4%, 3%, 2%, 1%, or less of a racemic mixture. In some instances, the polynucleic acid molecule is a polynucleic acid molecule described in: U.S. Patent Publication Nos: 2014/194610 and 2015/211006; and PCT Publication No.: WO2015107425.

In some embodiments, a polynucleic acid molecule described herein is further modified to include an aptamer-conjugating moiety. In some instances, the aptamer conjugating moiety is a DNA aptamer-conjugating moiety. In some instances, the aptamer-conjugating moiety is Alphamer (Centauri Therapeutics), which comprises an aptamer portion that recognizes a specific cell-surface target and a portion that presents a specific epitopes for attaching to circulating antibodies. In some instance, a polynucleic acid molecule described herein is further modified to include an aptamer-conjugating moiety as described in: U.S. Pat. Nos. 8,604,184, 8,591,910, and 7,850,975.

In additional embodiments, a polynucleic acid molecule described herein is modified to increase its stability. In some embodiment, the polynucleic acid molecule is RNA (e.g., siRNA), the polynucleic acid molecule is modified to increase its stability. In some instances, the polynucleic acid molecule is modified by one or more of the modifications described above to increase its stability. In some cases, the polynucleic acid molecule is modified at the 2' hydroxyl position, such as by 2'-O-methyl, 2'-O-methoxyethyl (2'-O-MOE), 2'-O-aminopropyl, 2'-deoxy, T-deoxy-2'-fluoro, 2'-O-aminopropyl (2'-0-AP), 2'-O-dimethylaminoethyl (2'-O-

DMAOE), 2'-O-dimethylaminopropyl (2'-O-DMAP), T-O-dimethylaminoethyloxyethyl (2'-O-DMAEOE), or 2'-O-N-methylacetamido (2'-O-NMA) modification or by a locked or bridged ribose conformation (e.g., LNA or ENA). In some cases, the polynucleic acid molecule is modified by 2'-O-methyl and/or 2'-O-methoxyethyl ribose. In some cases, the polynucleic acid molecule also includes morpholinos, PNAs, HNA, methylphosphonate nucleotides, thiolphosphonate nucleotides, and/or 2'-fluoro N3-P5'-phosphoramidites to increase its stability. In some instances, the polynucleic acid molecule is a chirally pure (or stereo pure) polynucleic acid molecule. In some instances, the chirally pure (or stereo pure) polynucleic acid molecule is modified to increase its stability. Suitable modifications to the RNA to increase stability for delivery will be apparent to the skilled person.

In some embodiments, a polynucleic acid molecule described herein has RNAi activity that modulates expression of RNA encoded by a gene described supra. In some instances, a polynucleic acid molecule described herein is a double-stranded siRNA molecule that down-regulates expression of a gene, wherein one of the strands of the double-stranded siRNA molecule comprises a nucleotide sequence that is complementary to a nucleotide sequence of the gene or RNA encoded by the gene or a portion thereof, and wherein the second strand of the double-stranded siRNA molecule comprises a nucleotide sequence substantially similar to the nucleotide sequence of the gene or RNA encoded by the gene or a portion thereof. In some cases, a polynucleic acid molecule described herein is a double-stranded siRNA molecule that down-regulates expression of a gene, wherein each strand of the siRNA molecule comprises about 15 to 25, 18 to 24, or 19 to about 23 nucleotides, and wherein each strand comprises at least about 14, 17, or 19 nucleotides that are complementary to the nucleotides of the other strand. In some cases, a polynucleic acid molecule described herein is a double-stranded siRNA molecule that down-regulates expression of a gene, wherein each strand of the siRNA molecule comprises about 19 to about 23 nucleotides, and wherein each strand comprises at least about 19 nucleotides that are complementary to the nucleotides of the other strand. In some instances, the gene is KRAS, EGFR, AR, HPRT1, CNNTB1 (β-catenin), or β-catenin associated genes.

In some embodiments, a polynucleic acid molecule described herein is constricted using chemical synthesis and/or enzymatic ligation reactions using procedures known in the art. For example, a polynucleic acid molecule is chemically synthesized using naturally occurring nucleotides or variously modified nucleotides designed to increase the biological stability of the molecules or to increase the physical stability of the duplex formed between the polynucleic acid molecule and target nucleic acids. Exemplary methods include those described in: U.S. Pat. Nos. 5,142,047; 5,185,444; 5,889,136; 6,008,400; and 6,111,086; PCT Publication No. WO2009099942; or European Publication No. 1579015 Additional exemplary methods include those described in: Griffey et al., "2'-O-aminopropyl ribonucleotides: a zwitterionic modification that enhances the exonuclease resistance and biological activity of antisense oligonucleotides," *J. Med. Chem.* 39(26):5100-5109 (1997)); Obika, et al. "Synthesis of 2'-O,4'-C-methyleneuridine and -cytidine. Novel bicyclic nucleosides having a fixed C3,-endo sugar puckering". *Tetrahedron Letters* 38 (50): 8735 (1997); Koizumi, M. "ENA oligonucleotides as therapeutics". *Current opinion in molecular therapeutics* 8 (2): 144-149 (2006); and Abramova et al., "Novel oligonucleotide analogues based on morpholino nucleoside subunits-antisense technologies: new chemical possibilities," Indian Journal of Chemistry 48B:1721-1726 (2009). Alternatively, the polynucleic acid molecule is produced biologically using an expression vector into which a polynucleic acid molecule has been subcloned in an antisense orientation (i.e., RNA transcribed from the inserted polynucleic acid molecule will be of an antisense orientation to a target polynucleic acid molecule of interest).

One embodiment provides a molecule of Formula (I):

A-X-B-Y-C            Formula I wherein,
A is a binding moiety,
B is a polynucleotide;
C is a polymer;
X is a bond or a first non-polymeric linker; and
Y is a bond or a second linker;
wherein the polynucleotide comprises at least one 5'-vinylphosphonate modified non-natural nucleotide; and
wherein A and C are not attached to B at the same terminus.

Another embodiment provides the molecule of Formula (I), wherein the polynucleotide further comprises, at least one modified internucleotide linkage, or at least one inverted abasic moiety;

Another embodiment provides the molecule of Formula (I), wherein the at least one 5'-vinylphosphonate modified non-natural nucleotide is located at the 5'-terminus of the polynucleotide.

Another embodiment provides the molecule of Formula (I), wherein the at least one 5'-vinylphosphonate modified non-natural nucleotide is located at an internucleotide linkage of the polynucleotide.

Another embodiment provides the molecule of Formula (I), wherein the at least one 5'-vinylphosphonate modified non-natural nucleotide is further modified at the 2'-position.

Another embodiment provides the molecule of Formula (I), wherein the 2'-modification is selected from 2'-O-methyl, 2'-O-methoxyethyl (2'-O-MOE), 2'-deoxy, T-deoxy-2'-fluoro, 2'-O-aminopropyl (2?-O-AP), 2?-O-dimethylaminoethyl (2'-O-DMAOE), 2?-O-dimethylaminopropyl (2'-O-DMAP), T-O-dimethylaminoethyloxyethyl (2'-O-DMAEOE), or 2'-O-N-methylacetamido (2'-O-NMA) modified nucleotide.

Another embodiment provides the molecule of Formula (I), wherein the at least one 5'-vinylphosphonate modified non-natural nucleotide is selected from:

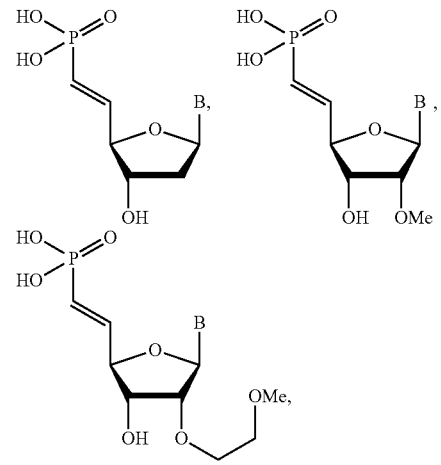

-continued

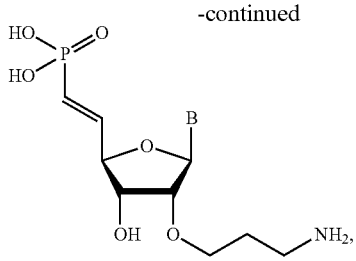

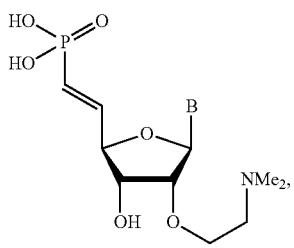

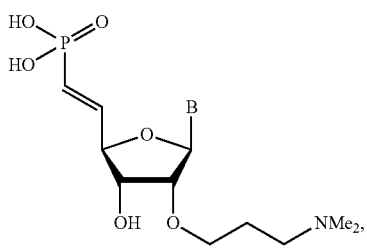

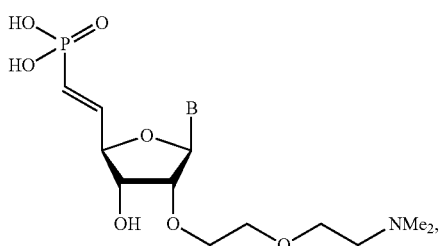

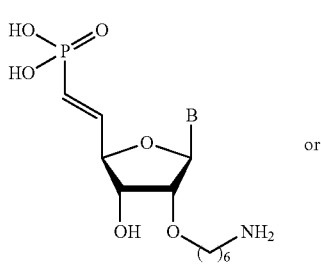

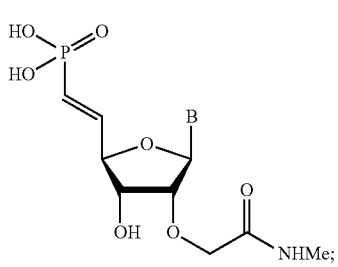

wherein B is a heterocyclic base moiety.

Another embodiment provides the molecule of Formula (I), wherein the at least one 5'-vinylphosphonate modified non-natural nucleotide is selected from:

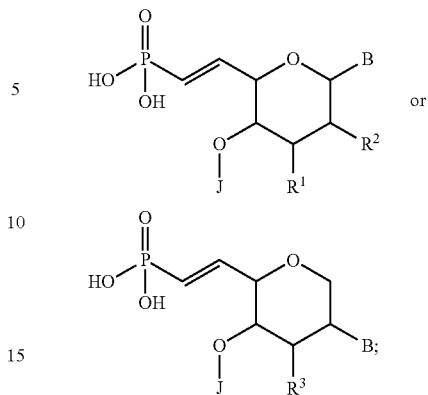

wherein B is a heterocyclic base moiety;

R1, R2, and R3 are independently selected from hydrogen, halogen, alkyl or alkoxy; and J is an internucleotide linking group linking to the adjacent nucleotide of the polynucleotide.

Another embodiment provides the molecule of Formula (I), wherein the at least one 5'-vinylphosphonate modified non-natural nucleotide is selected from:

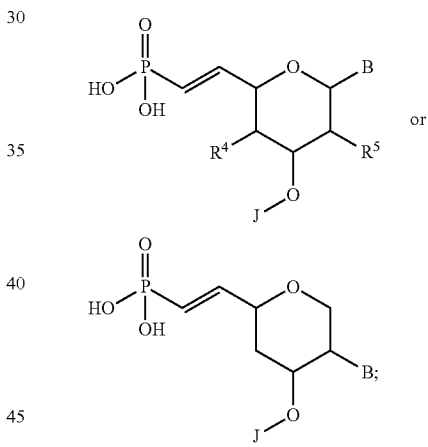

wherein B is a heterocyclic base moiety;

R4, and R5 are independently selected from hydrogen, halogen, alkyl or alkoxy; and J is an internucleotide linking group linking to the adjacent nucleotide of the polynucleotide.

Another embodiment provides the molecule of Formula (I), wherein the at least one 5'-vinylphosphonate modified non-natural nucleotide is selected from:

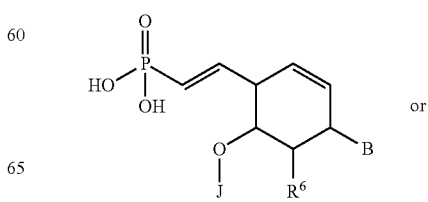

-continued

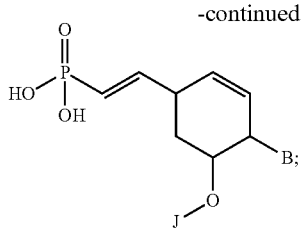

wherein B is a heterocyclic base moiety;
R6 is selected from hydrogen, halogen, alkyl or alkoxy; and
J is an internucleotide linking group linking to the adjacent nucleotide of the polynucleotide.

Another embodiment provides the molecule of Formula (I), wherein the at least one 5'-vinylphosphonate modified non-natural nucleotide is selected from locked nucleic acid (LNA) or ethylene nucleic acid (ENA).

Another embodiment provides the molecule of Formula (I), wherein the at least one 5'-vinylphosphonate modified non-natural nucleotide is selected from:

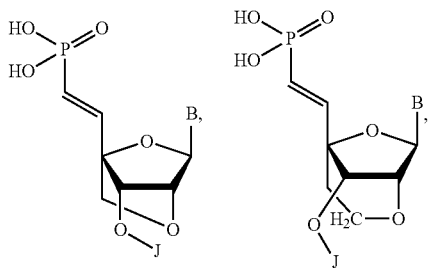

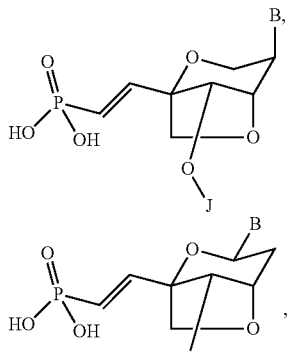

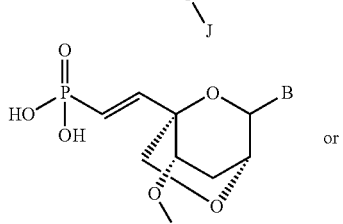

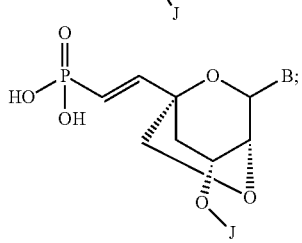

wherein B is a heterocyclic base moiety; and
J is an internucleotide linking group linking to the adjacent nucleotide of the polynucleotide.

Another embodiment provides the molecule of Formula (I), wherein the at least one 5'-vinylphosphonate modified non-natural nucleotide is selected from:

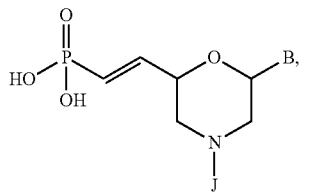

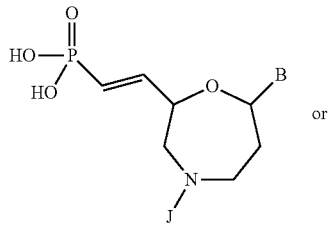

or

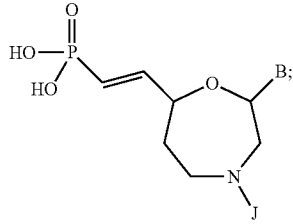

wherein B is a heterocyclic base moiety; and
J is an internucleotide linking group linking to the adjacent nucleotide of the polynucleotide.

Another embodiment provides the molecule of Formula (I), wherein the at least one 5'-vinylphosphonate modified non-natural nucleotide is:

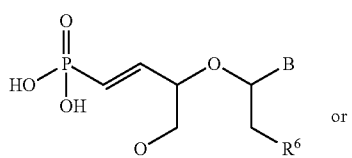

or

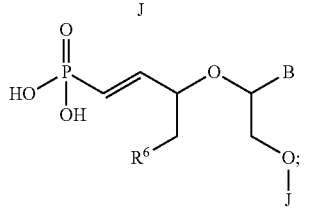

wherein B is a heterocyclic base moiety;
R6 is selected from hydrogen, halogen, alkyl or alkoxy; and
J is an internucleotide linking group linking to the adjacent nucleotide of the polynucleotide.

Another embodiment provides the molecule of Formula (I), wherein the at least one modified internucleotide linkage comprises a phosphorothioate linkage, phosphorodithioate linkage, a phosphorodiamidate linkage, a methylphosphonate linkage, or an amide linkage.

Another embodiment provides the molecule of Formula (I), wherein the at least one inverted abasic moiety is at least one terminus.

One embodiment provides an oligonucleotide of Formula (II), wherein the oligonucleotide comprises at least one 5'-vinylphosphonate modified non-natural nucleotide.

Another embodiment provides the oligonucleotide of Formula (II), wherein the oligonucleotide further comprises, at least one modified internucleotide linkage, or at least one inverted abasic moiety;

Another embodiment provides the oligonucleotide of Formula (II), wherein the at least one 5'-vinylphosphonate modified non-natural nucleotide is located at the 5'-terminus of the polynucleotide.

Another embodiment provides the oligonucleotide of Formula (II), wherein the at least one 5'-vinylphosphonate modified non-natural nucleotide is located at an internucleotide linkage of the polynucleotide.

Another embodiment provides the oligonucleotide of Formula (II), wherein the at least one 5'-vinylphosphonate modified non-natural nucleotide is further modified at the 2'-position. Another embodiment provides the oligonucleotide of Formula (II), wherein the 2'-modification is selected from 2' O-methyl, 2'-O-methoxyethyl (2'-O-MOE), 2'-deoxy, T-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), or 2'-O-N-methylacetamido (2'-O-NMA) modified nucleotide.

Another embodiment provides the oligonucleotide of Formula (II), wherein the at least one 5'-vinylphosphonate modified non-natural nucleotide is selected from:

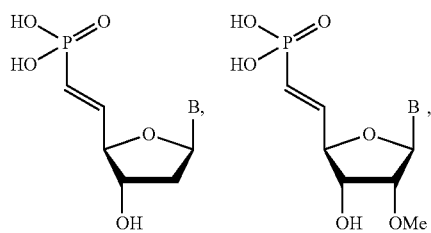

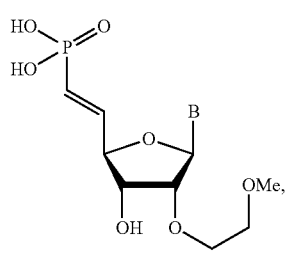

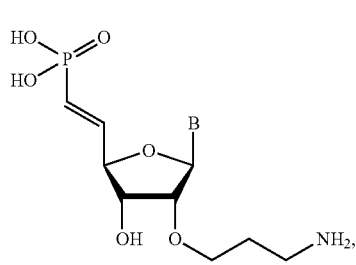

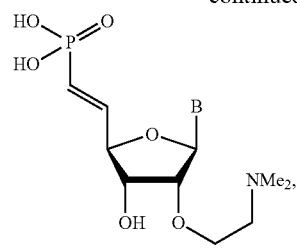

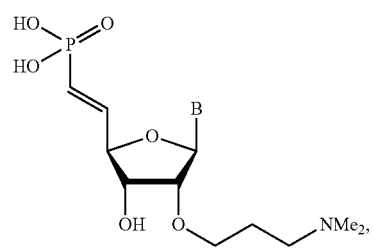

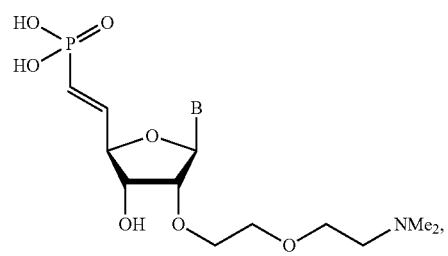

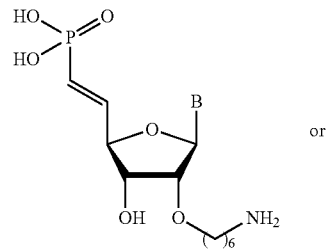

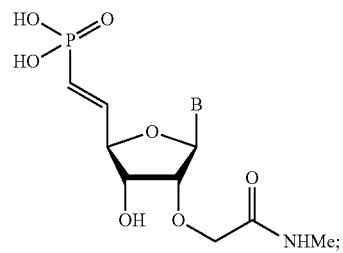

wherein B is a heterocyclic base moiety.

Another embodiment provides the oligonucleotide of Formula (II), wherein the at least one 5'-vinylphosphonate modified non-natural nucleotide is selected from:

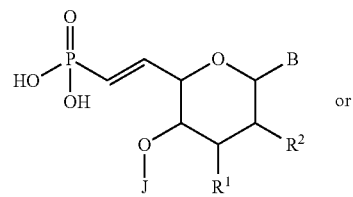

-continued

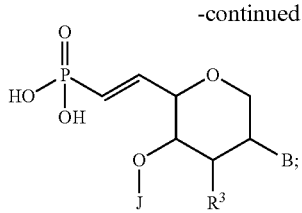

wherein B is a heterocyclic base moiety;
R1, R2, and R3 are independently selected from hydrogen, halogen, alkyl or alkoxy; and
J is an internucleotide linking group linking to the adjacent nucleotide of the polynucleotide.

Another embodiment provides the oligonucleotide of Formula (II), wherein the at least one 5'-vinylphosphonate modified non-natural nucleotide is selected from:

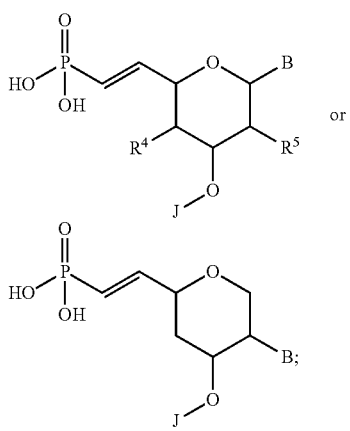

wherein B is a heterocyclic base moiety;
R4, and R5 are independently selected from hydrogen, halogen, alkyl or alkoxy; and
J is an internucleotide linking group linking to the adjacent nucleotide of the polynucleotide.

Another embodiment provides the oligonucleotide of Formula (II), wherein the at least one 5'-vinylphosphonate modified non-natural nucleotide is selected from:

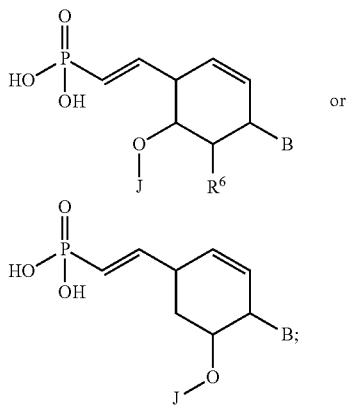

wherein B is a heterocyclic base moiety;
R6 is selected from hydrogen, halogen, alkyl or alkoxy; and
J is an internucleotide linking group linking to the adjacent nucleotide of the polynucleotide.

Another embodiment provides the oligonucleotide of Formula (II), wherein the at least one 5'-vinylphosphonate modified non-natural nucleotide is selected from locked nucleic acid (LNA) or ethylene nucleic acid (ENA).

Another embodiment provides the oligonucleotide of Formula (II), wherein the at least one 5'-vinylphosphonate modified non-natural nucleotide is selected from:

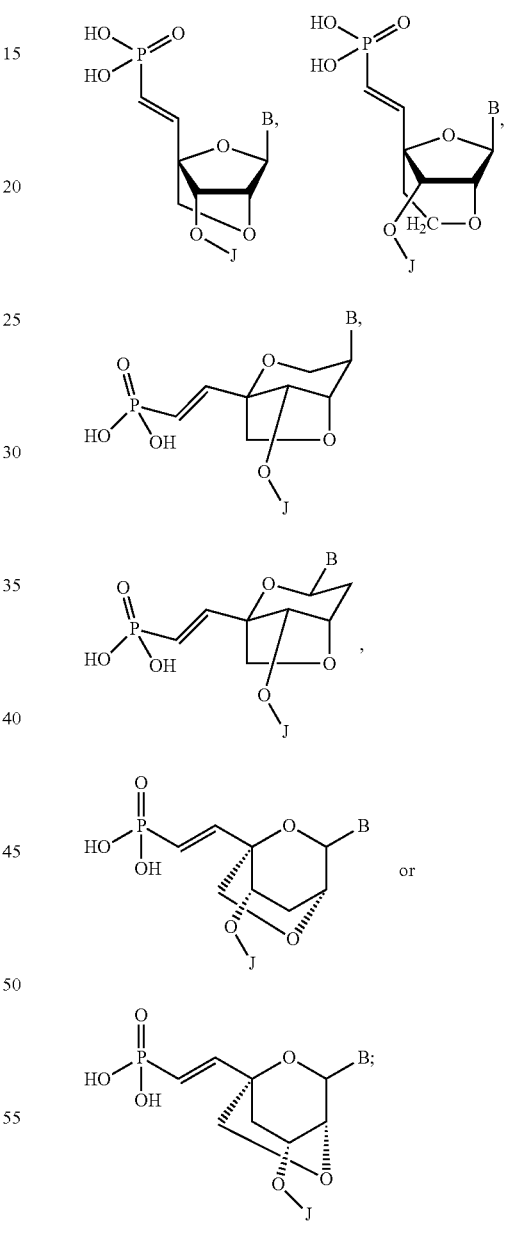

wherein B is a heterocyclic base moiety; and
J is an internucleotide linking group linking to the adjacent nucleotide of the polynucleotide.

Another embodiment provides the oligonucleotide of Formula (II), wherein the at least one 5'-vinylphosphonate modified non-natural nucleotide is selected from:

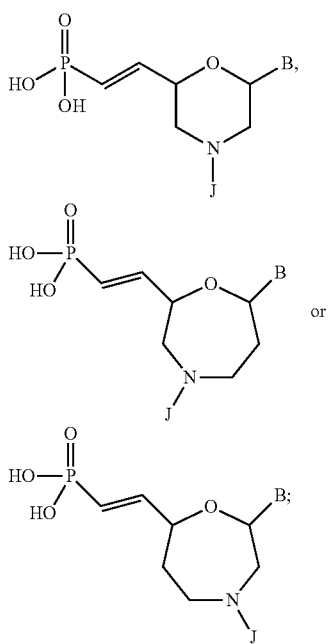

wherein B is a heterocyclic base moiety; and

J is an internucleotide linking group linking to the adjacent nucleotide of the polynucleotide.

Another embodiment provides the oligonucleotide of Formula (II), wherein the at least one 5'-vinylphosphonate modified non-natural nucleotide is:

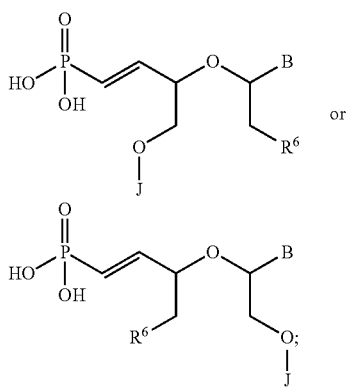

wherein B is a heterocyclic base moiety;

R6 is selected from hydrogen, halogen, alkyl or alkoxy; and

J is an internucleotide linking group linking to the adjacent nucleotide of the polynucleotide.

Another embodiment provides the oligonucleotide of Formula (II), wherein the at least one modified internucleotide linkage comprises a phosphorothioate linkage, phosphorodithioate linkage, a phosphorodiamidate linkage, a methylphosphonate linkage, or an amide linkage.

Another embodiment provides the oligonucleotide of Formula (II), wherein the at least one inverted abasic moiety is at least one terminus.

Another embodiment provides the oligonucleotide of Formula (II), wherein the oligonucleotide is single stranded.

Another embodiment provides the oligonucleotide of Formula (II), wherein the oligonucleotide is double stranded stranded.

Another embodiment provides the oligonucleotide of Formula (II), wherein the oligonucleotide is from 2 to about 100 residues in length. Another embodiment provides the oligonucleotide of Formula (II), wherein the oligonucleotide is from 2 to about 90 residues in length. Another embodiment provides the oligonucleotide of Formula (II), wherein the oligonucleotide is from 2 to about 80 residues in length. Another embodiment provides the oligonucleotide of Formula (II), wherein the oligonucleotide is from 2 to about 70 residues in length. Another embodiment provides the oligonucleotide of Formula (II), wherein the oligonucleotide is from 2 to about 60 residues in length. Another embodiment provides the oligonucleotide of Formula (II), wherein the oligonucleotide is from 2 to about 50 residues in length. Another embodiment provides the oligonucleotide of Formula (II), wherein the oligonucleotide is from 2 to about 40 residues in length. Another embodiment provides the oligonucleotide of Formula (II), wherein the oligonucleotide is from 2 to about 30 residues in length. Another embodiment provides the oligonucleotide of Formula (II), wherein the oligonucleotide is from 2 to about 20 residues in length. Another embodiment provides the oligonucleotide of Formula (II), wherein the oligonucleotide is from 2 to about 10 residues in length. Another embodiment provides the oligonucleotide of Formula (II), wherein the oligonucleotide is from 8 to about 30 residues in length. Another embodiment provides the oligonucleotide of Formula (II), wherein the oligonucleotide is from 10 to about 30 residues in length. Another embodiment provides the oligonucleotide of Formula (II), wherein the oligonucleotide is from 14 to about 30 residues in length. Another embodiment provides the oligonucleotide of Formula (II), wherein the oligonucleotide is from 18 to about 30 residues in length. Another embodiment provides the oligonucleotide of Formula (II), wherein the oligonucleotide is from 22 to about 30 residues in length. Another embodiment provides the oligonucleotide of Formula (II), wherein the oligonucleotide is from 26 to about 30 residues in length.

One embodiment provides a compound suitable for the synthesis of oligonucleotides selected from the group:

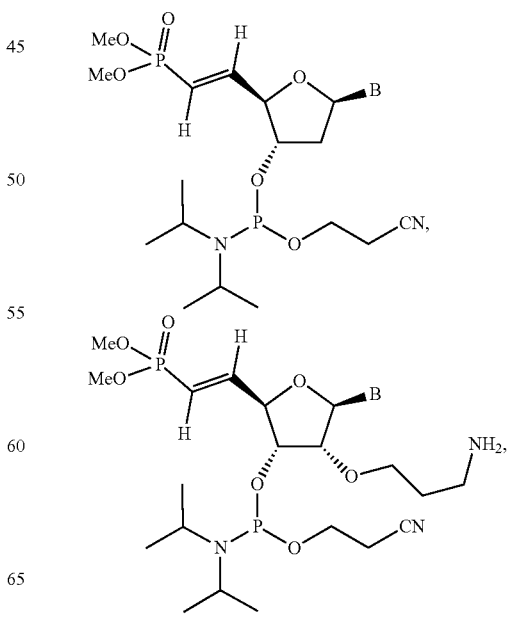

57
-continued
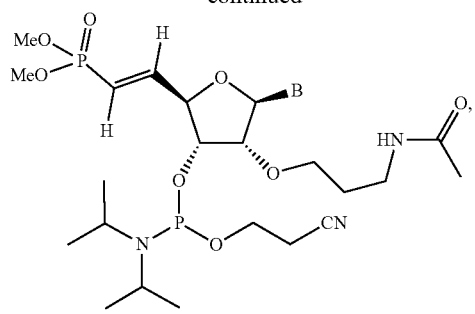
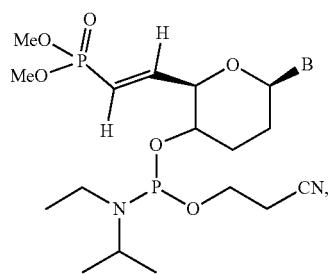
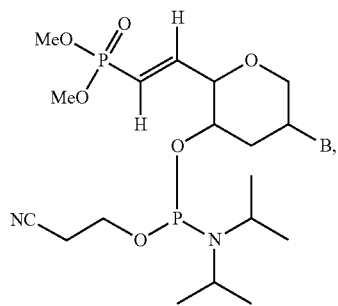
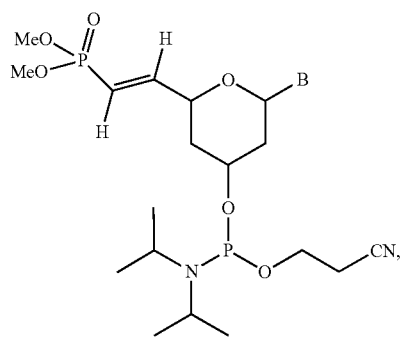
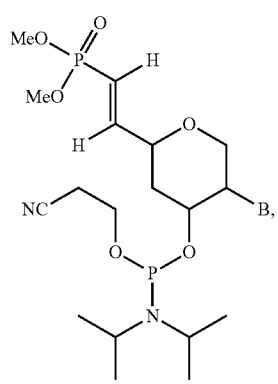
58
-continued
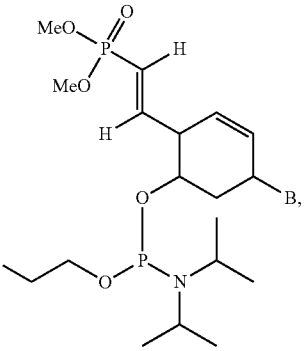
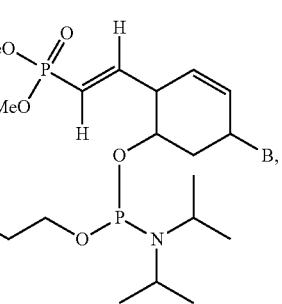
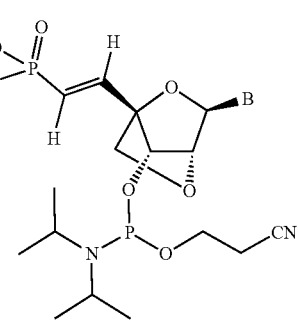
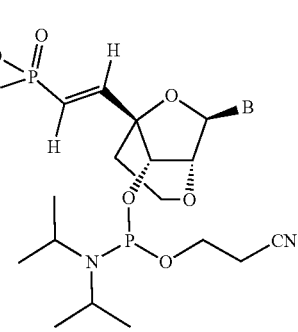
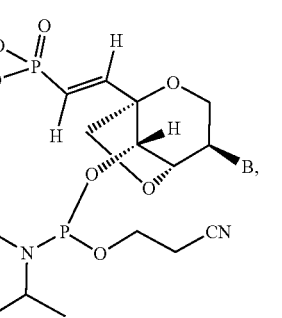

-continued

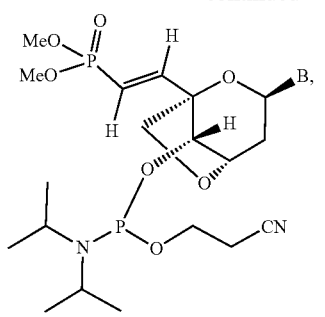
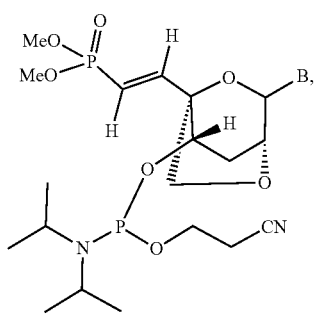
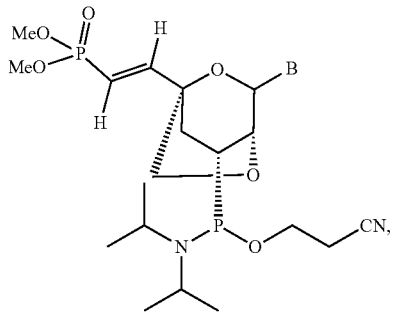
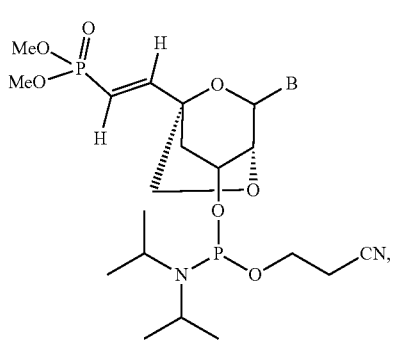
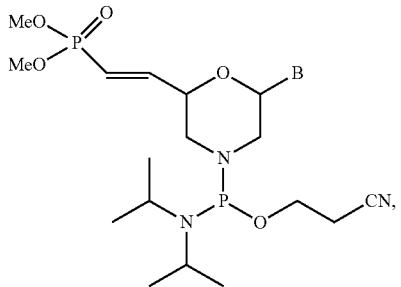

-continued

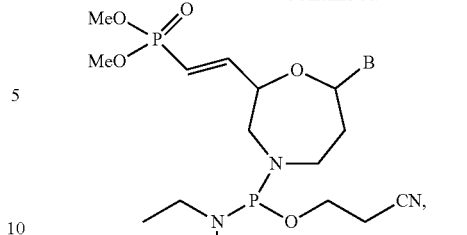
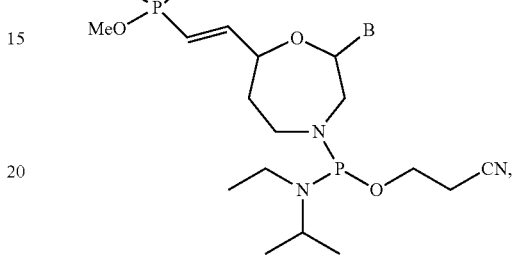
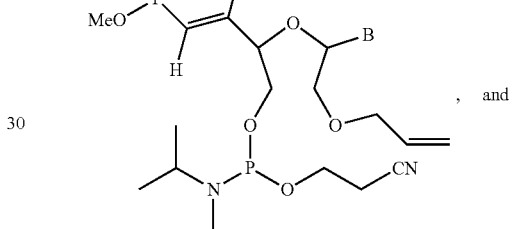
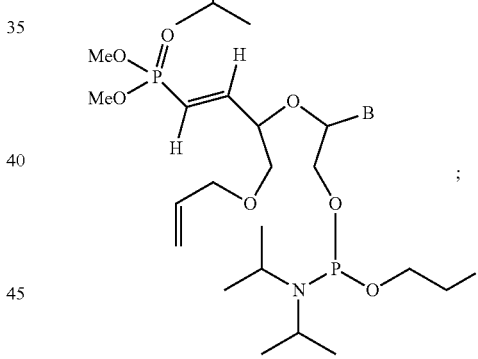

wherein B is a heterocyclic base moiety.

Conjugation Chemistry

In some embodiments, a polynucleic acid molecule is conjugated to a binding moiety. In some instances, the binding moiety comprises amino acids, peptides, polypeptides, proteins, antibodies, antigens, toxins, hormones, lipids, nucleotides, nucleosides, sugars, carbohydrates, polymers such as polyethylene glycol and polypropylene glycol, as well as analogs or derivatives of all of these classes of substances. Additional examples of binding moiety also include steroids, such as cholesterol, phospholipids, di- and triacylglycerols, fatty acids, hydrocarbons (e.g., saturated, unsaturated, or contains substitutions), enzyme substrates, biotin, digoxigenin, and polysaccharides. In some instances, the binding moiety is an antibody or binding fragment thereof. In some instances, the polynucleic acid molecule is further conjugated to a polymer, and optionally an endosomolytic moiety.

In some embodiments, the polynucleic acid molecule is conjugated to the binding moiety by a chemical ligation process. In some instances, the polynucleic acid molecule is conjugated to the binding moiety by a native ligation. In some instances, the conjugation is as described in: Dawson, et al. "Synthesis of proteins by native chemical ligation," *Science* 1994, 266, 776-779; Dawson, et al. "Modulation of Reactivity in Native Chemical Ligation through the Use of Thiol Additives," *J. Am. Chem. Soc.* 1997, 119, 4325-4329; Hackeng, et al. "Protein synthesis by native chemical ligation: Expanded scope by using straightforward methodology.," *Proc. Natl. Acad. Sci. USA* 1999, 96, 10068-10073; or Wu, et al. "Building complex glycopeptides: Development of a cysteine-free native chemical ligation protocol," *Angew. Chem. Int. Ed.* 2006, 45, 4116-4125. In some instances, the conjugation is as described in U.S. Pat. No. 8,936,910. In some embodiments, the polynucleic acid molecule is conjugated to the binding moiety either site-specifically or non-specifically via native ligation chemistry.

In some instances, the polynucleic acid molecule is conjugated to the binding moiety by a site-directed method utilizing a "traceless" coupling technology (Philochem). In some instances, the "traceless" coupling technology utilizes an N-terminal 1,2-aminothiol group on the binding moiety which is then conjugate with a polynucleic acid molecule containing an aldehyde group. (see Casi et al., "Site-specific traceless coupling of potent cytotoxic drugs to recombinant antibodies for pharmacodelivery," *JACS* 134(13): 5887-5892 (2012))

In some instances, the polynucleic acid molecule is conjugated to the binding moiety by a site-directed method utilizing an unnatural amino acid incorporated into the binding moiety. In some instances, the unnatural amino acid comprises p-acetylphenylalanine (pAcPhe). In some instances, the keto group of pAcPhe is selectively coupled to an alkoxy-amine derivatived conjugating moiety to form an oxime bond. (see Axup et al., "Synthesis of site-specific antibody-drug conjugates using unnatural amino acids," *PNAS* 109(40): 16101-16106 (2012)).

In some instances, the polynucleic acid molecule is conjugated to the binding moiety by a site-directed method utilizing an enzyme-catalyzed process. In some instances, the site-directed method utilizes SMARTag™ technology (Redwood). In some instances, the SMARTag™ technology comprises generation of a formylglycine (FGly) residue from cysteine by formylglycine-generating enzyme (FGE) through an oxidation process under the presence of an aldehyde tag and the subsequent conjugation of FGly to an alkylhydraine-functionalized polynucleic acid molecule via hydrazino-Pictet-Spengler (HIPS) ligation. (see Wu et al., "Site-specific chemical modification of recombinant proteins produced in mammalian cells by using the genetically encoded aldehyde tag," *PNAS* 106(9): 3000-3005 (2009); Agarwal, et al., "A Pictet-Spengler ligation for protein chemical modification," *PNAS* 110(1): 46-51 (2013))

In some instances, the enzyme-catalyzed process comprises microbial transglutaminase (mTG). In some cases, the polynucleic acid molecule is conjugated to the binding moiety utilizing a microbial transglutaminze catalyzed process. In some instances, mTG catalyzes the formation of a covalent bond between the amide side chain of a glutamine within the recognition sequence and a primary amine of a functionalized polynucleic acid molecule. In some instances, mTG is produced from *Streptomyces mobarensis*. (see Strop et al., "Location matters: site of conjugation modulates stability and pharmacokinetics of antibody drug conjugates," *Chemistry and Biology* 20(2) 161-167 (2013))

In some instances, the polynucleic acid molecule is conjugated to the binding moiety by a method as described in PCT Publication No. WO2014/140317, which utilizes a sequence-specific transpeptidase.

In some instances, the polynucleic acid molecule is conjugated to the binding moiety by a method as described in U.S. Patent Publication Nos. 2015/0105539 and 2015/0105540.

Binding Moiety

In some embodiments, the binding moiety A is a polypeptide. In some instances, the polypeptide is an antibody or its fragment thereof. In some cases, the fragment is a binding fragment. In some instances, the antibody or binding fragment thereof comprises a humanized antibody or binding fragment thereof, murine antibody or binding fragment thereof, chimeric antibody or binding fragment thereof, monoclonal antibody or binding fragment thereof, monovalent Fab', divalent Fab$_2$, F(ab)'$_3$ fragments, single-chain variable fragment (scFv), bis-scFv, (scFv)$_2$, diabody, minibody, nanobody, triabody, tetrabody, disulfide stabilized Fv protein (dsFv), single-domain antibody (sdAb), Ig NAR, camelid antibody or binding fragment thereof, bispecific antibody or biding fragment thereof, or a chemically modified derivative thereof.

In some instances, A is an antibody or binding fragment thereof. In some instances, A is a humanized antibody or binding fragment thereof, murine antibody or binding fragment thereof, chimeric antibody or binding fragment thereof, monoclonal antibody or binding fragment thereof, monovalent Fab', divalent Fab$_2$, F(ab)'$_3$ fragments, single-chain variable fragment (scFv), bis-scFv, (scFv)$_2$, diabody, minibody, nanobody, triabody, tetrabody, disulfide stabilized Fv protein ("dsFv"), single-domain antibody (sdAb), Ig NAR, camelid antibody or binding fragment thereof, bispecific antibody or biding fragment thereof, or a chemically modified derivative thereof. In some instances, A is a humanized antibody or binding fragment thereof. In some instances, A is a murine antibody or binding fragment thereof. In some instances, A is a chimeric antibody or binding fragment thereof. In some instances, A is a monoclonal antibody or binding fragment thereof. In some instances, A is a monovalent Fab'. In some instances, A is a diavalent Fab$_2$. In some instances, A is a single-chain variable fragment (scFv).

In some embodiments, the binding moiety A is a bispecific antibody or binding fragment thereof. In some instances, the bispecific antibody is a trifunctional antibody or a bispecific mini-antibody. In some cases, the bispecific antibody is a trifunctional antibody. In some instances, the trifunctional antibody is a full length monoclonal antibody comprising binding sites for two different antigens. Exemplary trifunctional antibodies include catumaxomab (which targets EpCAM and CD3; Fresenius Biotech/Trion Pharma), ertumaxomab (targets HER2/neu/CD3; Fresenius Biotech/Trion Pharma), lymphomun FBTA05 (targets CD20/CD3; Fresenius Biotech/Trion Pharma), RG7221 (RO5520985; targets Angiopoietin 2/VEGF; Roche), RG7597 (targets Her1/Her3; Genentech/Roche), MM141 (targets IGF1R/Her3; Merrimack), ABT122 (targets TNFα/IL17; Abbvie), ABT981 (targets IL1α/IL1β; Abbott), LY3164530 (targets Her1/cMET; Eli Lilly), and TRBS07 (Ektomab; targets GD2/CD3; Trion Research Gmbh). Additional exemplary trifunctional antibodies include mAb[2] from F-star Biotechnology Ltd. In some instances, A is a bispecific trifunctional antibody. In some embodiments, A is a bispecific trifunctional antibody selected from: catumaxomab (which targets EpCAM and CD3; Fresenius Biotech/Trion Pharma), ertumaxomab (targets HER2/neu/CD3; Fresenius Biotech/Trion Pharma), lymphomun FBTA05 (targets CD20/CD3; Fresenius Biotech/Trion Pharma), RG7221 (RO5520985; targets Angiopoietin 2/VEGF; Roche), RG7597 (targets Her1/Her3; Genentech/Roche), MM141 (targets IGF1R/Her3; Merrimack), ABT122 (targets TNFα/IL17; Abbvie), ABT981 (targets IL1α/IL1β; Abbott), LY3164530 (targets Her1/cMET; Eli Lilly), TRBS07 (Ektomab; targets GD2/CD3; Trion Research Gmbh), and a mAb$^2$ from F-star Biotechnology Ltd.

In some cases, the bispecific antibody is a bispecific mini-antibody. In some instances, the bispecific mini-antibody comprises divalent Fab$_2$, F(ab)'$_3$ fragments, bis-scFv, (scFv)$_2$, diabody, minibody, triabody, tetrabody or a bi-specific T-cell engager (BiTE). In some embodiments, the bi-specific T-cell engager is a fusion protein that contains two single-chain variable fragments (scFvs) in which the two scFvs target epitopes of two different antigens. Exemplary bispecific mini-antibodies include, but are not limited to, DART (dual-affinity re-targeting platform; MacroGenics), blinatumomab (MT103 or AMG103; which targets CD19/CD3; Micromet), MT111 (targets CEA/CD3; Micromet/Amegen), MT112 (BAY2010112; targets PSMA/CD3; Micromet/Bayer), MT110 (AMG 110; targets EPCAM/CD3; Amgen/Micromet), MGD006 (targets CD123/CD3; MacroGenics), MGD007 (targets GPA33/CD3; MacroGenics), BI1034020 (targets two different epitopes on β-amyloid; Ablynx), ALX0761 (targets IL17A/IL17F; Ablynx), TF2 (targets CEA/hepten; Immunomedics), IL-17/IL-34 biAb (BMS), AFM13 (targets CD30/CD16; Affimed), AFM11 (targets CD19/CD3; Affimed), and domain antibodies (dAbs from Domantis/GSK).

In some embodiments, the binding moiety A is a bispecific mini-antibody. In some instances, A is a bispecific Fab$_2$. In some instances, A is a bispecific F(ab)'$_3$ fragment. In some cases, A is a bispecific bis-scFv. In some cases, A is a bispecific (scFv)$_2$. In some embodiments, A is a bispecific diabody. In some embodiments, A is a bispecific minibody. In some embodiments, A is a bispecific triabody. In other embodiments, A is a bispecific tetrabody. In other embodiments, A is a bi-specific T-cell engager (BiTE). In additional embodiments, A is a bispecific mini-antibody selected from: DART (dual-affinity re-targeting platform; MacroGenics), blinatumomab (MT103 or AMG103; which targets CD19/CD3; Micromet), MT111 (targets CEA/CD3; Micromet/Amegen), MT112 (BAY2010112; targets PSMA/CD3; Micromet/Bayer), MT110 (AMG 110; targets EPCAM/CD3; Amgen/Micromet), MGD006 (targets CD123/CD3; MacroGenics), MGD007 (targets GPA33/CD3; MacroGenics), BI1034020 (targets two different epitopes on β-amyloid; Ablynx), ALX0761 (targets IL17A/IL17F; Ablynx), TF2 (targets CEA/hepten; Immunomedics), IL-17/IL-34 biAb (BMS), AFM13 (targets CD30/CD16; Affimed), AFM11 (targets CD19/CD3; Affimed), and domain antibodies (dAbs from Domantis/GSK).

In some embodiments, the binding moiety A is a trispecific antibody. In some instances, the trispecific antibody comprises F(ab)'$_3$ fragments or a triabody. In some instances, A is a trispecific F(ab)'$_3$ fragment. In some cases, A is a triabody. In some embodiments, A is a trispecific antibody as described in Dimas, et al., "Development of a trispecific antibody designed to simultaneously and efficiently target three different antigens on tumor cells," Mol. Pharmaceutics, 12(9): 3490-3501 (2015).

In some embodiments, the binding moiety A is an antibody or binding fragment thereof that recognizes a cell surface protein. In some instances, the cell surface protein is an antigen expressed by a cancerous cell. Exemplary cancer antigens include, but are not limited to, alpha fetoprotein, ASLG659, B7-H3, BAFF-R, Brevican, CA125 (MUC16), CA15-3, CA19-9, carcinoembryonic antigen (CEA), CA242, CRIPTO (CR, CR1, CRGF, CRIPTO, TDGF1, teratocarcinoma-derived growth factor), CTLA-4, CXCR5, E16 (LAT1, SLC7A5), FcRH2 (IFGP4, IRTA4, SPAP1A (SH2 domain containing phosphatase anchor protein 1a), SPAP1B, SPAP1C), epidermal growth factor, ETBR, Fc receptor-like protein 1 (FCRH1), GEDA, HLA-DOB (Beta subunit of MHC class II molecule (Ia antigen), human chorionic gonadotropin, ICOS, IL-2 receptor, IL20Ra, Immunoglobulin superfamily receptor translocation associated 2 (IRTA2), L6, Lewis Y, Lewis X, MAGE-1, MAGE-2, MAGE-3, MAGE 4, MART1, mesothelin, MDP, MPF (SMR, MSLN), MCP1 (CCL2), macrophage inhibitory factor (MIF), MPG, MSG783, mucin, MUC1-KLH, Napi3b (SLC34A2), nectin-4, Neu oncogene product, NCA, placental alkaline phosphatase, prostate specific membrane antigen (PMSA), prostatic acid phosphatase, PSCA hlg, p97, Purinergic receptor P2X ligand-gated ion channel 5 (P2X5), LY64 (Lymphocyte antigen 64 (RP105), gp100, P21, six transmembrane epithelial antigen of prostate (STEAP1), STEAP2, Sema 5b, tumor-associated glycoprotein 72 (TAG-72), TrpM4 (BR22450, FLJ20041, TRPM4, TRPM4B, transient receptor potential cation channel, subfamily M, member 4) and the like.

In some instances, the cell surface protein comprises clusters of differentiation (CD) cell surface markers. Exemplary CD cell surface markers include, but are not limited to, CD1, CD2, CD3, CD4, CD5, CD6, CD7, CD8, CD9, CD10, CD11a, CD11b, CD11c, CD11d, CDw12, CD13, CD14, CD15, CD15s, CD16, CDw17, CD18, CD19, CD20, CD21, CD22, CD23, CD24, CD25, CD26, CD27, CD28, CD29, CD30, CD31, CD32, CD33, CD34, CD35, CD36, CD37, CD38, CD39, CD40, CD41, CD42, CD43, CD44, CD45, CD45RO, CD45RA, CD45RB, CD46, CD47, CD48, CD49a, CD49b, CD49c, CD49d, CD49e, CD49f, CD50, CD51, CD52, CD53, CD54, CD55, CD56, CD57, CD58, CD59, CDw60, CD61, CD62E, CD62L (L-selectin), CD62P, CD63, CD64, CD65, CD66a, CD66b, CD66c, CD66d, CD66e, CD79 (e.g., CD79a, CD79b), CD90, CD95 (Fas), CD103, CD104, CD125 (IL5RA), CD134 (OX40), CD137 (4-1BB), CD152 (CTLA-4), CD221, CD274, CD279 (PD-1), CD319 (SLAMF7), CD326 (EpCAM), and the like.

In some instances, the binding moiety A is an antibody or binding fragment thereof that recognizes a cancer antigen. In some instances, the binding moiety A is an antibody or binding fragment thereof that recognizes alpha fetoprotein, ASLG659, B7-H3, BAFF-R, Brevican, CA125 (MUC16), CA15-3, CA19-9, carcinoembryonic antigen (CEA), CA242, CRIPTO (CR, CR1, CRGF, CRIPTO, TDGF1, teratocarcinoma-derived growth factor), CTLA-4, CXCR5, E16 (LAT1, SLC7A5), FcRH2 (IFGP4, IRTA4, SPAP1A (SH2 domain containing phosphatase anchor protein 1a), SPAP1B, SPAP1C), epidermal growth factor, ETBR, Fc receptor-like protein 1 (FCRH1), GEDA, HLA-DOB (Beta subunit of MHC class II molecule (Ia antigen), human chorionic gonadotropin, ICOS, IL-2 receptor, IL20Ra, Immunoglobulin superfamily receptor translocation associated 2 (IRTA2), L6, Lewis Y, Lewis X, MAGE-1, MAGE-2, MAGE-3, MAGE 4, MART1, mesothelin, MCP1 (CCL2), MDP, macrophage inhibitory factor (MIF), MPF (SMR, MSLN), MPG, MSG783, mucin, MUC1-KLH, Napi3b (SLC34A2), nectin-4, Neu oncogene product, NCA, placental alkaline phosphatase, prostate specific membrane antigen (PMSA), prostatic acid phosphatase, PSCA hlg, p97, Purinergic receptor P2X ligand-gated ion channel 5 (P2X5), LY64 (Lymphocyte antigen 64 (RP105), gp100, P21, six transmembrane epithelial antigen of prostate (STEAP1), STEAP2, Sema 5b, tumor-associated glycoprotein 72 (TAG-72), TrpM4 (BR22450, FLJ20041, TRPM4, TRPM4B, transient receptor potential cation channel, subfamily M, member 4) or a combination thereof.

In some instances, the binding moiety A is an antibody or binding fragment thereof that recognizes a CD cell surface marker. In some instances, the binding moiety A is an antibody or binding fragment thereof that recognizes CD1, CD2, CD3, CD4, CD5, CD6, CD7, CD8, CD9, CD10, CD11a, CD11b, CD11c, CD11d, CDw12, CD13, CD14, CD15, CD15s, CD16, CDw17, CD18, CD19, CD20, CD21, CD22, CD23, CD24, CD25, CD26, CD27, CD28, CD29, CD30, CD31, CD32, CD33, CD34, CD35, CD36, CD37, CD38, CD39, CD40, CD41, CD42, CD43, CD44, CD45, CD45RO, CD45RA, CD45RB, CD46, CD47, CD48, CD49a, CD49b, CD49c, CD49d, CD49e, CD49f, CD50, CD51, CD52, CD53, CD54, CD55, CD56, CD57, CD58, CD59, CDw60, CD61, CD62E, CD62L (L-selectin), CD62P, CD63, CD64, CD65, CD66a, CD66b, CD66c, CD66d, CD66e, CD79 (e.g., CD79a, CD79b), CD90, CD95 (Fas), CD103, CD104, CD125 (IL5RA), CD134 (OX40), CD137 (4-1BB), CD152 (CTLA-4), CD221, CD274, CD279 (PD-1), CD319 (SLAMF7), CD326 (EpCAM), or a combination thereof In some embodiments, the antibody or binding fragment thereof comprises zalutumumab (HuMax-EFGr, Genmab), abagovomab (Menarini), abituzumab (Merck), adecatumumab (MT201), alacizumab pegol, alemtuzumab (Campath®, MabCampath, or Campath-1H; Leukosite), AlloMune (BioTransplant), amatuximab (Morphotek, Inc.), anti-VEGF (Genetech), anatumomab mafenatox, apolizumab (hu1D10), ascrinvacumab (Pfizer Inc.), atezolizumab (MPDL3280A; Genentech/Roche), B43.13 (OvaRex, AltaRex Corporation), basiliximab (Simulect®, Novartis), belimumab (Benlysta®, GlaxoSmithKline), bevacizumab (Avastin®, Genentech), blinatumomab (Blincyto, AMG103; Amgen), BEC2 (ImGlone Systems Inc.), carlumab (Janssen Biotech), catumaxomab (Removab, Trion Pharma), CEAcide (Immunomedics), Cetuximab (Erbitux®, ImClone), citatuzumab bogatox (VB6-845), cixutumumab (IMC-A12, ImClone Systems Inc.), conatumumab (AMG 655, Amgen), dacetuzumab (SGN-40, huS2C6; Seattle Genetics, Inc.), daratumumab (Darzalex®, Janssen Biotech), detumomab, drozitumab (Genentech), durvalumab (MedImmune), dusigitumab (MedImmune), edrecolomab (MAb17-1A, Panorex, Glaxo Wellcome), elotuzumab (Empliciti™, Bristol-Myers Squibb), emibetuzumab (Eli Lilly), enavatuzumab (Facet Biotech Corp.), enfortumab vedotin (Seattle Genetics, Inc.), enoblituzumab (MGA271, MacroGenics, Inc.), ensituxumab (Neogenix Oncology, Inc.), epratuzumab (LymphoCide, Immunomedics, Inc.), ertumaxomab (Rexomun®, Trion Pharma), etaracizumab (Abegrin, MedImmune), farletuzumab (MORAb-003, Morphotek, Inc), FBTA05 (Lymphomun, Trion Pharma), ficlatuzumab (AVEO Pharmaceuticals), figitumumab (CP-751871, Pfizer), flanvotumab (ImClone Systems), fresolimumab (GC1008, Aanofi-Aventis), futuximab, glaximab, ganitumab (Amgen), girentuximab (Rencarex®, Wilex AG), IMAB362 (Claudiximab, Ganymed Pharmaceuticals AG), imalumab (Baxalta), IMC-1C11 (ImClone Systems), IMC-C225 (Imclone Systems Inc.), imgatuzumab (Genentech/Roche), intetumumab (Centocor, Inc.), ipilimumab (Yervoy®, Bristol-Myers Squibb), iratumumab (Medarex, Inc.), isatuximab (SAR650984, Sanofi-Aventis), labetuzumab (CEA-CIDE, Immunomedics), lexatumumab (ETR2-ST01, Cambridge Antibody Technology), lintuzumab (SGN-33, Seattle Genetics), lucatumumab (Novartis), lumiliximab, mapatumumab (HGS-ETR1, Human Genome Sciences), matuzumab (EMD 72000, Merck), milatuzumab (hLL1, Immunomedics, Inc.), mitumomab (BEC-2, ImClone Systems), narnatumab (ImClone Systems), necitumumab (Portrazza™, Eli Lilly), nesvacumab (Regeneron Pharmaceuticals), nimotuzumab (h-R3, BIOMAb EGFR, TheraCIM, Theraloc, or CIMAher; Biotech Pharmaceutical Co.), nivolumab (Opdivo®, Bristol-Myers Squibb), obinutuzumab (Gazyva or Gazyvaro; Hoffmann-La Roche), ocaratuzumab (AME-133v, LY2469298; Mentrik Biotech, LLC), ofatumumab (Arzerra®, Genmab), onartuzumab (Genentech), Ontuxizumab (Morphotek, Inc.), oregovomab (OvaRex®, AltaRex Corp.), otlertuzumab (Emergent BioSolutions), panitumumab (ABX-EGF, Amgen), pankomab (Glycotope GMBH), parsatuzumab (Genentech), patritumab, pembrolizumab (Keytruda®, Merck), pemtumomab (Theragyn, Antisoma), pertuzumab (Perjeta, Genentech), pidilizumab (CT-011, Medivation), polatuzumab vedotin (Genentech/Roche), pritumumab, racotumomab (Vaxira®, Recombio), ramucirumab (Cyramza®, ImClone Systems Inc.), rituximab (Rituxan®, Genentech), robatumumab (Schering-Plough), Seribantumab (Sanofi/Merrimack Pharmaceuticals, Inc.), sibrotuzumab, siltuximab (Sylvant™, Janssen Biotech), Smart MI95 (Protein Design Labs, Inc.), Smart ID10 (Protein Design Labs, Inc.), tabalumab (LY2127399, Eli Lilly), taplitumomab paptox, tenatumomab, teprotumumab (Roche), tetulomab, TGN1412 (CD28-SuperMAB or TAB08), tigatuzumab (CD-1008, Daiichi Sankyo), tositumomab, trastuzumab (Herceptin®), tremelimumab (CP-672,206; Pfizer), tucotuzumab celmoleukin (EMD Pharmaceuticals), ublituximab, urelumab (BMS-663513, Bristol-Myers Squibb), volociximab (M200, Biogen Idec), zatuximab, and the like.

In some embodiments, the binding moiety A comprises zalutumumab (HuMax-EFGr, Genmab), abagovomab (Menarini), abituzumab (Merck), adecatumumab (MT201), alacizumab pegol, alemtuzumab (Campath®, MabCampath, or Campath-1H; Leukosite), AlloMune (BioTransplant), amatuximab (Morphotek, Inc.), anti-VEGF (Genetech), anatumomab mafenatox, apolizumab (hu1D10), ascrinvacumab (Pfizer Inc.), atezolizumab (MPDL3280A; Genentech/Roche), B43.13 (OvaRex, AltaRex Corporation), basiliximab (Simulect®, Novartis), belimumab (Benlysta®, GlaxoSmithKline), bevacizumab (Avastin®, Genentech), blinatumomab (Blincyto, AMG103; Amgen), BEC2 (ImGlone Systems Inc.), carlumab (Janssen Biotech), catumaxomab (Removab, Trion Pharma), CEAcide (Immunomedics), Cetuximab (Erbitux®, ImClone), citatuzumab bogatox (VB6-845), cixutumumab (IMC-A12, ImClone Systems Inc.), conatumumab (AMG 655, Amgen), dacetuzumab (SGN-40, huS2C$_6$; Seattle Genetics, Inc.), daratumumab (Darzalex®, Janssen Biotech), detumomab, drozitumab (Genentech), durvalumab (MedImmune), dusigitumab (MedImmune), edrecolomab (MAb17-1A, Panorex, Glaxo Wellcome), elotuzumab (Empliciti™, Bristol-Myers Squibb), emibetuzumab (Eli Lilly), enavatuzumab (Facet Biotech Corp.), enfortumab vedotin (Seattle Genetics, Inc.), enoblituzumab (MGA271, MacroGenics, Inc.), ensituxumab (Neogenix Oncology, Inc.), epratuzumab (LymphoCide, Immunomedics, Inc.), ertumaxomab (Rexomun®, Trion Pharma), etaracizumab (Abegrin, MedImmune), farletuzumab (MORAb-003, Morphotek, Inc), FBTA05 (Lymphomun, Trion Pharma), ficlatuzumab (AVEO Pharmaceuticals), figitumumab (CP-751871, Pfizer), flanvotumab (ImClone Systems), fresolimumab (GC1008, Aanofi-Aventis), futuximab, glaximab, ganitumab (Amgen), girentuximab (Rencarex®, Wilex AG), IMAB362 (Claudiximab, Ganymed Pharmaceuticals AG), imalumab (Baxalta), IMC-1C11 (ImClone Systems), IMC-C225 (Imclone Systems Inc.), imgatuzumab (Genentech/Roche), intetumumab (Centocor, Inc.), ipilimumab (Yervoy®, Bristol-Myers Squibb), iratumumab (Medarex, Inc.), isatuximab (SAR650984, Sanofi-Aventis), labetuzumab (CEA-CIDE, Immunomedics), lexatumumab (ETR2-ST01, Cambridge Antibody Technology), lintuzumab (SGN-33, Seattle Genetics), lucatumumab (Novartis), lumiliximab, mapatumumab (HGS-ETR1, Human Genome Sciences), matuzumab (EMD 72000, Merck), milatuzumab (hLL1, Immunomedics, Inc.), mitumomab (BEC-2, ImClone Systems), narnatumab (ImClone Systems), necitumumab (Portrazza™, Eli Lilly), nesvacumab (Regeneron Pharmaceuticals), nimotuzumab (h-R3, BIOMAb EGFR, TheraCIM, Theraloc, or CIMAher; Biotech Pharmaceutical Co.), nivolumab (Opdivo®, Bristol-Myers Squibb), obinutuzumab (Gazyva or Gazyvaro; Hoffmann-La Roche), ocaratuzumab (AME-133v, LY2469298; Mentrik Biotech, LLC), ofatumumab (Arzerra®, Genmab), onartuzumab (Genentech), Ontuxizumab (Morphotek, Inc.), oregovomab (OvaRex®, AltaRex Corp.), otlertuzumab (Emergent BioSolutions), panitumumab (ABX-EGF, Amgen), pankomab (Glycotope GMBH), parsatuzumab (Genentech), patritumab, pembrolizumab (Keytruda®, Merck), pemtumomab (Theragyn, Antisoma), pertuzumab (Perjeta, Genentech), pidilizumab (CT-011, Medivation), polatuzumab vedotin (Genentech/Roche), pritumumab, racotumomab (Vaxira®, Recombio), ramucirumab (Cyramza®, ImClone Systems Inc.), rituximab (Rituxan®, Genentech), robatumumab (Schering-Plough), Seribantumab (Sanofi/Merrimack Pharmaceuticals, Inc.), sibrotuzumab, siltuximab (Sylvant™, Janssen Biotech), Smart MI95 (Protein Design Labs, Inc.), Smart ID10 (Protein Design Labs, Inc.), tabalumab (LY2127399, Eli Lilly), taplitumomab paptox, tenatumomab, teprotumumab (Roche), tetulomab, TGN1412 (CD28-SuperMAB or TAB08), tigatuzumab (CD-1008, Daiichi Sankyo), tositumomab, trastuzumab (Herceptin®), tremelimumab (CP-672,206; Pfizer), tucotuzumab celmoleukin (EMD Pharmaceuticals), ublituximab, urelumab (BMS-663513, Bristol-Myers Squibb), volociximab (M200, Biogen Idec), or zatuximab. In some embodiments, the binding moiety A is zalutumumab (HuMax-EFGr, by Genmab).

In some embodiments, the binding moiety A is conjugated according to Formula (I) to a polynucleic acid molecule (B), and a polymer (C), and optionally an endosomolytic moiety (D) according to Formula (II) described herein. In some instances, the polynucleic acid molecule comprises a sequence having at least 50%, 55%, 60%, 65%, 70%, 75%, 80%, 85%, 90%, 95%, 96%, 97%, 98%, 99%, or 100% sequence identity to a sequence listed in Tables 2, 4, 8, or 9. In some embodiments, the polynucleic acid molecule comprises a sequence having at least 50%, 55%, 60%, 65%, 70%, 75%, 80%, 85%, 90%, 95%, 96%, 97%, 98%, 99%, or 100% sequence identity to SEQ ID NOs: 16-45, 422-1173, 1195-1214, or 1215-1242. In some instances, the polynucleic acid molecule comprises a sequence selected from SEQ ID NOs: 16-45, 422-1173, 1195-1214, or 1215-1242. In some instances, the polymer C comprises polyalkylen oxide (e.g., polyethylene glycol). In some embodiments, the endosomolytic moiety D comprises INF7 or melittin, or their respective derivatives.

In some embodiments, the binding moiety A is conjugated to a polynucleic acid molecule (B), and a polymer (C), and optionally an endosomolytic moiety (D). In some instances, the binding moiety A is an antibody or binding fragment thereof.

In some embodiments, the binding moiety A is conjugated to a polynucleic acid molecule (B) non-specifically. In some instances, the binding moiety A is conjugated to a polynucleic acid molecule (B) via a lysine residue or a cysteine residue, in a non-site specific manner. In some instances, the binding moiety A is conjugated to a polynucleic acid molecule (B) via a lysine residue in a non-site specific manner. In some cases, the binding moiety A is conjugated to a polynucleic acid molecule (B) via a cysteine residue in a non-site specific manner. In some instances, the binding moiety A is an antibody or binding fragment thereof.

In some embodiments, the binding moiety A is conjugated to a polynucleic acid molecule (B) in a site-specific manner. In some instances, the binding moiety A is conjugated to a polynucleic acid molecule (B) through a lysine residue, a cysteine residue, at the 5'-terminus, at the 3'-terminus, an unnatural amino acid, or an enzyme-modified or enzyme-catalyzed residue, via a site-specific manner. In some instances, the binding moiety A is conjugated to a polynucleic acid molecule (B) through a lysine residue via a site-specific manner. In some instances, the binding moiety A is conjugated to a polynucleic acid molecule (B) through a cysteine residue via a site-specific manner. In some instances, the binding moiety A is conjugated to a polynucleic acid molecule (B) at the 5'-terminus via a site-specific manner. In some instances, the binding moiety A is conjugated to a polynucleic acid molecule (B) at the 3'-terminus via a site-specific manner. In some instances, the binding moiety A is conjugated to a polynucleic acid molecule (B) through an unnatural amino acid via a site-specific manner. In some instances, the binding moiety A is conjugated to a polynucleic acid molecule (B) through an enzyme-modified or enzyme-catalyzed residue via a site-specific manner. In some instances, the binding moiety A is an antibody or binding fragment thereof.

In some embodiments, one or more regions of a binding moiety A (e.g., an antibody or binding fragment thereof) is conjugated to a polynucleic acid molecule (B). In some instances, the one or more regions of a binding moiety A comprise the N-terminus, the C-terminus, in the constant region, at the hinge region, or the Fc region of the binding moiety A. In some instances, the polynucleic acid molecule (B) is conjugated to the N-terminus of the binding moiety A (e.g., the N-terminus of an antibody or binding fragment thereof). In some instances, the polynucleic acid molecule (B) is conjugated to the C-terminus of the binding moiety A (e.g., the N-terminus of an antibody or binding fragment thereof). In some instances, the polynucleic acid molecule (B) is conjugated to the constant region of the binding moiety A (e.g., the constant region of an antibody or binding fragment thereof). In some instances, the polynucleic acid molecule (B) is conjugated to the hinge region of the binding moiety A (e.g., the constant region of an antibody or binding fragment thereof). In some instances, the polynucleic acid molecule (B) is conjugated to the Fc region of the binding moiety A (e.g., the constant region of an antibody or binding fragment thereof).

In some embodiments, one or more polynucleic acid molecule (B) is conjugated to a binding moiety A. In some instances, about 1, 2, 3, 4, 5, 6, 7, 8, 9, 10, 11, 12, 13, 14, 15, 16, or more polynucleic acid molecules are conjugated to one binding moiety A. In some instances, about 1 polynucleic acid molecule is conjugated to one binding moiety A. In some instances, about 2 polynucleic acid molecules are conjugated to one binding moiety A. In some instances, about 3 polynucleic acid molecules are conjugated to one binding moiety A. In some instances, about 4 polynucleic acid molecules are conjugated to one binding moiety A. In some instances, about 5 polynucleic acid molecules are conjugated to one binding moiety A. In some instances, about 6 polynucleic acid molecules are conjugated to one binding moiety A. In some instances, about 7 polynucleic acid molecules are conjugated to one binding moiety A. In some instances, about 8 polynucleic acid molecules are conjugated to one binding moiety A. In some instances, about 9 polynucleic acid molecules are conjugated to one binding moiety A. In some instances, about 10 polynucleic acid molecules are conjugated to one binding moiety A. In some instances, about 11 polynucleic acid molecules are conjugated to one binding moiety A. In some instances, about 12 polynucleic acid molecules are conjugated to one binding moiety A. In some instances, about 13 polynucleic acid molecules are conjugated to one binding moiety A. In some instances, about 14 polynucleic acid molecules are conjugated to one binding moiety A. In some instances, about 15 polynucleic acid molecules are conjugated to one binding moiety A. In some instances, about 16 polynucleic acid molecules are conjugated to one binding moiety A. In some cases, the one or more polynucleic acid molecules are the same. In other cases, the one or more polynucleic acid molecules are different. In some instances, the binding moiety A is an antibody or binding fragment thereof.

In some embodiments, the number of polynucleic acid molecule (B) conjugated to a binding moiety A (e.g., an antibody or binding fragment thereof) forms a ratio. In some instances, the ratio is referred to as a DAR (drug-to-antibody) ratio, in which the drug as referred to herein is the polynucleic acid molecule (B). In some instances, the DAR ratio of the polynucleic acid molecule (B) to binding moiety A is about 1, 2, 3, 4, 5, 6, 7, 8, 9, 10, 11, 12, 13, 14, 15, 16, or greater. In some instances, the DAR ratio of the polynucleic acid molecule (B) to binding moiety A is about 1 or greater. In some instances, the DAR ratio of the polynucleic acid molecule (B) to binding moiety A is about 2 or greater. In some instances, the DAR ratio of the polynucleic acid molecule (B) to binding moiety A is about 3 or greater. In some instances, the DAR ratio of the polynucleic acid molecule (B) to binding moiety A is about 4 or greater. In some instances, the DAR ratio of the polynucleic acid molecule (B) to binding moiety A is about 5 or greater. In some instances, the DAR ratio of the polynucleic acid molecule (B) to binding moiety A is about 6 or greater. In some instances, the DAR ratio of the polynucleic acid molecule (B) to binding moiety A is about 7 or greater. In some instances, the DAR ratio of the polynucleic acid molecule (B) to binding moiety A is about 8 or greater. In some instances, the DAR ratio of the polynucleic acid molecule (B) to binding moiety A is about 9 or greater. In some instances, the DAR ratio of the polynucleic acid molecule (B) to binding moiety A is about 10 or greater. In some instances, the DAR ratio of the polynucleic acid molecule (B) to binding moiety A is about 11 or greater. In some instances, the DAR ratio of the polynucleic acid molecule (B) to binding moiety A is about 12 or greater.

In some instances, the DAR ratio of the polynucleic acid molecule (B) to binding moiety A (e.g., an antibody or binding fragment thereof) is about 1, 2, 3, 4, 5, 6, 7, 8, 9, 10, 11, 12, 13, 14, 15, or 16. In some instances, the DAR ratio of the polynucleic acid molecule (B) to binding moiety A is about 1. In some instances, the DAR ratio of the polynucleic acid molecule (B) to binding moiety A is about 2. In some instances, the DAR ratio of the polynucleic acid molecule (B) to binding moiety A is about 3. In some instances, the DAR ratio of the polynucleic acid molecule (B) to binding moiety A is about 4. In some instances, the DAR ratio of the polynucleic acid molecule (B) to binding moiety A is about 5. In some instances, the DAR ratio of the polynucleic acid molecule (B) to binding moiety A is about 6. In some instances, the DAR ratio of the polynucleic acid molecule (B) to binding moiety A is about 7. In some instances, the DAR ratio of the polynucleic acid molecule (B) to binding moiety A is about 8. In some instances, the DAR ratio of the polynucleic acid molecule (B) to binding moiety A is about 9. In some instances, the DAR ratio of the polynucleic acid molecule (B) to binding moiety A is about 10. In some instances, the DAR ratio of the polynucleic acid molecule (B) to binding moiety A is about 11. In some instances, the DAR ratio of the polynucleic acid molecule (B) to binding moiety A is about 12. In some instances, the DAR ratio of the polynucleic acid molecule (B) to binding moiety A is about 13. In some instances, the DAR ratio of the polynucleic acid molecule (B) to binding moiety A is about 14. In some instances, the DAR ratio of the polynucleic acid molecule (B) to binding moiety A is about 15. In some instances, the DAR ratio of the polynucleic acid molecule (B) to binding moiety A is about 16.

In some instances, the DAR ratio of the polynucleic acid molecule (B) to binding moiety A is 1, 2, 3, 4, 5, 6, 7, 8, 9, 10, 11, 12, 13, 14, 15, or 16. In some instances, the DAR ratio of the polynucleic acid molecule (B) to binding moiety A is 1. In some instances, the DAR ratio of the polynucleic acid molecule (B) to binding moiety A is 2. In some instances, the DAR ratio of the polynucleic acid molecule (B) to binding moiety A is 4. In some instances, the DAR ratio of the polynucleic acid molecule (B) to binding moiety A is 6. In some instances, the DAR ratio of the polynucleic acid molecule (B) to binding moiety A is 8. In some instances, the DAR ratio of the polynucleic acid molecule (B) to binding moiety A is 12.

In some embodiments, an antibody or its binding fragment is further modified using conventional techniques known in the art, for example, by using amino acid deletion, insertion, substitution, addition, and/or by recombination and/or any other modification (e.g. posttranslational and chemical modifications, such as glycosylation and phosphorylation) known in the art either alone or in combination. In some instances, the modification further comprises a modification for modulating interaction with Fc receptors. In some instances, the one or more modifications include those described in, for example, International Publication No. WO97/34631, which discloses amino acid residues involved in the interaction between the Fc domain and the FcRn receptor. Methods for introducing such modifications in the nucleic acid sequence underlying the amino acid sequence of an antibody or its binding fragment is well known to the person skilled in the art.

In some instances, an antibody binding fragment further encompasses its derivatives and includes polypeptide sequences containing at least one CDR.

In some instances, the term "single-chain" as used herein means that the first and second domains of a bi-specific single chain construct are covalently linked, preferably in the form of a co-linear amino acid sequence encodable by a single nucleic acid molecule.

In some instances, a bispecific single chain antibody construct relates to a construct comprising two antibody derived binding domains. In such embodiments, bi-specific single chain antibody construct is tandem bi-scFv or diabody. In some instances, a scFv contains a VH and VL domain connected by a linker peptide. In some instances, linkers are of a length and sequence sufficient to ensure that each of the first and second domains can, independently from one another, retain their differential binding specificities.

In some embodiments, binding to or interacting with as used herein defines a binding/interaction of at least two antigen-interaction-sites with each other. In some instances, antigen-interaction-site defines a motif of a polypeptide that shows the capacity of specific interaction with a specific antigen or a specific group of antigens. In some cases, the binding/interaction is also understood to define a specific recognition. In such cases, specific recognition refers to that the antibody or its binding fragment is capable of specifically interacting with and/or binding to at least two amino acids of each of a target molecule. For example, specific recognition relates to the specificity of the antibody molecule, or to its ability to discriminate between the specific regions of a target molecule. In additional instances, the specific interaction of the antigen-interaction-site with its specific antigen results in an initiation of a signal, e.g. due to the induction of a change of the conformation of the antigen, an oligomerization of the antigen, etc. In further embodiments, the binding is exemplified by the specificity of a "key-lock-principle". Thus in some instances, specific motifs in the amino acid sequence of the antigen-interaction-site and the antigen bind to each other as a result of their primary, secondary or tertiary structure as well as the result of secondary modifications of said structure. In such cases, the specific interaction of the antigen-interaction-site with its specific antigen results as well in a simple binding of the site to the antigen.

In some instances, specific interaction further refers to a reduced cross-reactivity of the antibody or its binding fragment or a reduced off-target effect. For example, the antibody or its binding fragment that bind to the polypeptide/protein of interest but do not or do not essentially bind to any of the other polypeptides are considered as specific for the polypeptide/protein of interest. Examples for the specific interaction of an antigen-interaction-site with a specific antigen comprise the specificity of a ligand for its receptor, for example, the interaction of an antigenic determinant (epitope) with the antigenic binding site of an antibody.

Additional Binding Moieties

In some embodiments, the binding moiety is a plasma protein. In some instances, the plasma protein comprises albumin. In some instances, the binding moiety A is albumin. In some instances, albumin is conjugated by one or more of a conjugation chemistry described herein to a polynucleic acid molecule. In some instances, albumin is conjugated by native ligation chemistry to a polynucleic acid molecule. In some instances, albumin is conjugated by lysine conjugation to a polynucleic acid molecule.

In some instances, the binding moiety is a steroid. Exemplary steroids include cholesterol, phospholipids, di- and triacylglycerols, fatty acids, hydrocarbons that are saturated, unsaturated, comprise substitutions, or combinations thereof. In some instances, the steroid is cholesterol. In some instances, the binding moiety is cholesterol. In some instances, cholesterol is conjugated by one or more of a conjugation chemistry described herein to a polynucleic acid molecule. In some instances, cholesterol is conjugated by native ligation chemistry to a polynucleic acid molecule. In some instances, cholesterol is conjugated by lysine conjugation to a polynucleic acid molecule.

In some instances, the binding moiety is a polymer, including but not limited to poly nucleic acid molecule aptamers that bind to specific surface markers on cells. In this instance the binding moiety is a polynucleic acid that does not hybridize to a target gene or mRNA, but instead is capable of selectively binding to a cell surface marker similarly to an antibody binding to its specific epitope of a cell surface marker.

In some cases, the binding moiety is a peptide. In some cases, the peptide comprises between about 1 and about 3 kDa. In some cases, the peptide comprises between about 1.2 and about 2.8 kDa, about 1.5 and about 2.5 kDa, or about 1.5 and about 2 kDa. In some instances, the peptide is a bicyclic peptide. In some cases, the bicyclic peptide is a constrained bicyclic peptide. In some instances, the binding moiety is a bicyclic peptide (e.g., bicycles from Bicycle Therapeutics).

In additional cases, the binding moiety is a small molecule. In some instances, the small molecule is an antibody-recruiting small molecule. In some cases, the antibody-recruiting small molecule comprises a target-binding terminus and an antibody-binding terminus, in which the target-binding terminus is capable of recognizing and interacting with a cell surface receptor. For example, in some instances, the target-binding terminus comprising a glutamate urea compound enables interaction with PSMA, thereby, enhances an antibody interaction with a cell (e.g., a cancerous cell) that expresses PSMA. In some instances, a binding moiety is a small molecule described in Zhang et al., "A remote arene-binding site on prostate specific membrane antigen revealed by antibody-recruiting small molecules," J Am Chem Soc. 132(36): 12711-12716 (2010); or McEnaney, et al., "Antibody-recruiting molecules: an emerging paradigm for engaging immune function in treating human disease," ACS Chem Biol. 7(7): 1139-1151 (2012).

Production of Antibodies or Binding Fragments Thereof

In some embodiments, polypeptides described herein (e.g., antibodies and its binding fragments) are produced using any method known in the art to be useful for the synthesis of polypeptides (e.g., antibodies), in particular, by chemical synthesis or by recombinant expression, and are preferably produced by recombinant expression techniques.

In some instances, an antibody or its binding fragment thereof is expressed recombinantly, and the nucleic acid encoding the antibody or its binding fragment is assembled from chemically synthesized oligonucleotides (e.g., as described in Kutmeier et al., 1994, *BioTechniques* 17:242), which involves the synthesis of overlapping oligonucleotides containing portions of the sequence encoding the antibody, annealing and ligation of those oligonucleotides, and then amplification of the ligated oligonucleotides by PCR.

Alternatively, a nucleic acid molecule encoding an antibody is optionally generated from a suitable source (e.g., an antibody cDNA library, or cDNA library generated from any tissue or cells expressing the immunoglobulin) by PCR amplification using synthetic primers hybridizable to the 3' and 5' ends of the sequence or by cloning using an oligonucleotide probe specific for the particular gene sequence.

In some instances, an antibody or its binding is optionally generated by immunizing an animal, such as a rabbit, to generate polyclonal antibodies or, more preferably, by generating monoclonal antibodies, e.g., as described by Kohler and Milstein (1975, *Nature* 256:495-497) or, as described by Kozbor et al. (1983, *Immunology Today* 4:72) or Cole et al.

(1985 in *Monoclonal Antibodies and Cancer Therapy*, Alan R. Liss, Inc., pp. 77-96). Alternatively, a clone encoding at least the Fab portion of the antibody is optionally obtained by screening Fab expression libraries (e.g., as described in Huse et al., 1989, *Science* 246:1275-1281) for clones of Fab fragments that bind the specific antigen or by screening antibody libraries (See, e.g., Clackson et al., 1991, *Nature* 352:624; Hane et al., 1997 *Proc. Natl. Acad. Sci. USA* 94:4937).

In some embodiments, techniques developed for the production of "chimeric antibodies" (Morrison et al., 1984, *Proc. Natl. Acad. Sci.* 81:851-855; Neuberger et al., 1984, *Nature* 312:604-608; Takeda et al., 1985, *Nature* 314:452-454) by splicing genes from a mouse antibody molecule of appropriate antigen specificity together with genes from a human antibody molecule of appropriate biological activity are used. A chimeric antibody is a molecule in which different portions are derived from different animal species, such as those having a variable region derived from a murine monoclonal antibody and a human immunoglobulin constant region, e.g., humanized antibodies.

In some embodiments, techniques described for the production of single chain antibodies (U.S. Pat. No. 4,694,778; Bird, 1988, *Science* 242:423-42; Huston et al., 1988, *Proc. Natl. Acad. Sci. USA* 85:5879-5883; and Ward et al., 1989, *Nature* 334:544-54) are adapted to produce single chain antibodies. Single chain antibodies are formed by linking the heavy and light chain fragments of the Fv region via an amino acid bridge, resulting in a single chain polypeptide. Techniques for the assembly of functional Fv fragments in *E. coli* are also optionally used (Skerra et al., 1988, *Science* 242:1038-1041).

In some embodiments, an expression vector comprising the nucleotide sequence of an antibody or the nucleotide sequence of an antibody is transferred to a host cell by conventional techniques (e.g., electroporation, liposomal transfection, and calcium phosphate precipitation), and the transfected cells are then cultured by conventional techniques to produce the antibody. In specific embodiments, the expression of the antibody is regulated by a constitutive, an inducible or a tissue, specific promoter.

In some embodiments, a variety of host-expression vector systems is utilized to express an antibody or its binding fragment described herein. Such host-expression systems represent vehicles by which the coding sequences of the antibody is produced and subsequently purified, but also represent cells that are, when transformed or transfected with the appropriate nucleotide coding sequences, express an antibody or its binding fragment in situ. These include, but are not limited to, microorganisms such as bacteria (e.g., *E. coli* and *B. subtilis*) transformed with recombinant bacteriophage DNA, plasmid DNA or cosmid DNA expression vectors containing an antibody or its binding fragment coding sequences; yeast (e.g., *Saccharomyces Pichia*) transformed with recombinant yeast expression vectors containing an antibody or its binding fragment coding sequences; insect cell systems infected with recombinant virus expression vectors (e.g., baculovirus) containing an antibody or its binding fragment coding sequences; plant cell systems infected with recombinant virus expression vectors (e.g., cauliflower mosaic virus (CaMV) and tobacco mosaic virus (TMV)) or transformed with recombinant plasmid expression vectors (e.g., Ti plasmid) containing an antibody or its binding fragment coding sequences; or mammalian cell systems (e.g., COS, CHO, BH, 293, 293T, 3T3 cells) harboring recombinant expression constructs containing promoters derived from the genome of mammalian cells (e.g., metallothionein promoter) or from mammalian viruses (e.g. the adenovirus late promoter; the vaccinia virus 7.5K promoter).

For long-term, high-yield production of recombinant proteins, stable expression is preferred. In some instances, cell lines that stably express an antibody are optionally engineered. Rather than using expression vectors that contain viral origins of replication, host cells are transformed with DNA controlled by appropriate expression control elements (e.g., promoter, enhancer, sequences, transcription terminators, polyadenylation sites, etc.), and a selectable marker. Following the introduction of the foreign DNA, engineered cells are then allowed to grow for 1-2 days in an enriched media, and then are switched to a selective media. The selectable marker in the recombinant plasmid confers resistance to the selection and allows cells to stably integrate the plasmid into their chromosomes and grow to form foci that in turn are cloned and expanded into cell lines. This method can advantageously be used to engineer cell lines which express the antibody or its binding fragments.

In some instances, a number of selection systems are used, including but not limited to the herpes simplex virus thymidine kinase (Wigler et al., 1977, *Cell* 11:223), hypoxanthine-guanine phosphoribosyltransferase (Szybalska & Szybalski, 192, *Proc. Natl. Acad. Sci. USA* 48:202), and adenine phosphoribosyltransferase (Lowy et al., 1980, *Cell* 22:817) genes are employed in tk–, hgprt– or aprt– cells, respectively. Also, antimetabolite resistance are used as the basis of selection for the following genes: dhfr, which confers resistance to methotrexate (Wigler et al., 1980, *Proc. Natl. Acad. Sci. USA* 77:357; O'Hare et al., 1981, *Proc. Natl. Acad. Sci. USA* 78:1527); gpt, which confers resistance to mycophenolic acid (Mulligan & Berg, 1981, *Proc. Natl. Acad. Sci. USA* 78:2072); neo, which confers resistance to the aminoglycoside G-418 (*Clinical Pharmacy* 12:488-505; Wu and Wu, 1991, *Biotherapy* 3:87-95; Tolstoshev, 1993, *Ann. Rev. Pharmacol. Toxicol.* 32:573-596; Mulligan, 1993, *Science* 260:926-932; and Morgan and Anderson, 1993, *Ann. Rev. Biochem.* 62:191-217; May, 1993, *TIB TECH* 11(5):155-215) and hygro, which confers resistance to hygromycin (Santerre et al., 1984, *Gene* 30:147). Methods commonly known in the art of recombinant DNA technology which can be used are described in Ausubel et al. (eds., 1993, *Current Protocols in Molecular Biology*, John Wiley & Sons, NY; Kriegler, 1990, *Gene Transfer and Expression, A Laboratory Manual*, Stockton Press, NY; and in Chapters 12 and 13, Dracopoli et al. (eds), 1994, *Current Protocols in Human Genetics*, John Wiley & Sons, NY.; Colberre-Garapin et al., 1981, *J. Mol. Biol.* 150:1).

In some instances, the expression levels of an antibody are increased by vector amplification (for a review, see Bebbington and Hentschel, *The use of vectors based on gene amplification for the expression of cloned genes in mammalian cells in DNA cloning*, Vol. 3. (Academic Press, New York, 1987)). When a marker in the vector system expressing an antibody is amplifiable, an increase in the level of inhibitor present in culture of host cell will increase the number of copies of the marker gene. Since the amplified region is associated with the nucleotide sequence of the antibody, production of the antibody will also increase (Crouse et al., 1983, *Mol. Cell Biol.* 3:257).

In some instances, any method known in the art for purification of an antibody is used, for example, by chromatography (e.g., ion exchange, affinity, particularly by affinity for the specific antigen after Protein A, and sizing column chromatography), centrifugation, differential solubility, or by any other standard technique for the purification of proteins.

Polymer Conjugating Moiety

In some embodiments, a polymer moiety C is further conjugated to a polynucleic acid molecule described herein, a binding moiety described herein, or in combinations thereof. In some instances, a polymer moiety C is conjugated a polynucleic acid molecule. In some cases, a polymer moiety C is conjugated to a binding moiety. In other cases, a polymer moiety C is conjugated to a polynucleic acid molecule-binding moiety molecule. In additional cases, a polymer moiety C is conjugated, and as discussed under the Therapeutic Molecule Platform section.

In some instances, the polymer moiety C is a natural or synthetic polymer, consisting of long chains of branched or unbranched monomers, and/or cross-linked network of monomers in two or three dimensions. In some instances, the polymer moiety C includes a polysaccharide, lignin, rubber, or polyalkylen oxide (e.g., polyethylene glycol). In some instances, the at least one polymer moiety C includes, but is not limited to, alpha-, omega-dihydroxylpolyethyleneglycol, biodegradable lactone-based polymer, e.g. polyacrylic acid, polylactide acid (PLA), poly(glycolic acid) (PGA), polypropylene, polystyrene, polyolefin, polyamide, polycyanoacrylate, polyimide, polyethylenterephthalat (PET, PETG), polyethylene terephthalate (PETE), polytetramethylene glycol (PTG), or polyurethane as well as mixtures thereof. As used herein, a mixture refers to the use of different polymers within the same compound as well as in reference to block copolymers. In some cases, block copolymers are polymers wherein at least one section of a polymer is build up from monomers of another polymer. In some instances, the polymer moiety C comprises polyalkylene oxide. In some instances, the polymer moiety C comprises PEG. In some instances, the polymer moiety C comprises polyethylene imide (PEI) or hydroxy ethyl starch (HES).

In some instances, C is a PEG moiety. In some instances, the PEG moiety is conjugated at the 5' terminus of the polynucleic acid molecule while the binding moiety is conjugated at the 3' terminus of the polynucleic acid molecule. In some instances, the PEG moiety is conjugated at the 3' terminus of the polynucleic acid molecule while the binding moiety is conjugated at the 5' terminus of the polynucleic acid molecule. In some instances, the PEG moiety is conjugated to an internal site of the polynucleic acid molecule. In some instances, the PEG moiety, the binding moiety, or a combination thereof, are conjugated to an internal site of the polynucleic acid molecule. In some instances, the conjugation is a direct conjugation. In some instances, the conjugation is via native ligation.

In some embodiments, the polyalkylene oxide (e.g., PEG) is a polydispers or monodispers compound. In some instances, polydispers material comprises disperse distribution of different molecular weight of the material, characterized by mean weight (weight average) size and dispersity. In some instances, the monodisperse PEG comprises one size of molecules. In some embodiments, C is poly- or monodispersed polyalkylene oxide (e.g., PEG) and the indicated molecular weight represents an average of the molecular weight of the polyalkylene oxide, e.g., PEG, molecules.

In some embodiments, the molecular weight of the polyalkylene oxide (e.g., PEG) is about 200, 300, 400, 500, 600, 700, 800, 900, 1000, 1100, 1200, 1300, 1400, 1450, 1500, 1600, 1700, 1800, 1900, 2000, 2100, 2200, 2300, 2400, 2500, 2600, 2700, 2800, 2900, 3000, 3250, 3350, 3500, 3750, 4000, 4250, 4500, 4600, 4750, 5000, 5500, 6000, 6500, 7000, 7500, 8000, 10,000, 12,000, 20,000, 35,000, 40,000, 50,000, 60,000, or 100,000 Da.

In some embodiments, C is polyalkylene oxide (e.g., PEG) and has a molecular weight of about 200, 300, 400, 500, 600, 700, 800, 900, 1000, 1100, 1200, 1300, 1400, 1450, 1500, 1600, 1700, 1800, 1900, 2000, 2100, 2200, 2300, 2400, 2500, 2600, 2700, 2800, 2900, 3000, 3250, 3350, 3500, 3750, 4000, 4250, 4500, 4600, 4750, 5000, 5500, 6000, 6500, 7000, 7500, 8000, 10,000, 12,000, 20,000, 35,000, 40,000, 50,000, 60,000, or 100,000 Da. In some embodiments, C is PEG and has a molecular weight of about 200, 300, 400, 500, 600, 700, 800, 900, 1000, 1100, 1200, 1300, 1400, 1450, 1500, 1600, 1700, 1800, 1900, 2000, 2100, 2200, 2300, 2400, 2500, 2600, 2700, 2800, 2900, 3000, 3250, 3350, 3500, 3750, 4000, 4250, 4500, 4600, 4750, 5000, 5500, 6000, 6500, 7000, 7500, 8000, 10,000, 12,000, 20,000, 35,000, 40,000, 50,000, 60,000, or 100,000 Da. In some instances, the molecular weight of C is about 200 Da. In some instances, the molecular weight of C is about 300 Da. In some instances, the molecular weight of C is about 400 Da. In some instances, the molecular weight of C is about 500 Da. In some instances, the molecular weight of C is about 600 Da. In some instances, the molecular weight of C is about 700 Da. In some instances, the molecular weight of C is about 800 Da. In some instances, the molecular weight of C is about 900 Da. In some instances, the molecular weight of C is about 1000 Da. In some instances, the molecular weight of C is about 1100 Da. In some instances, the molecular weight of C is about 1200 Da. In some instances, the molecular weight of C is about 1300 Da. In some instances, the molecular weight of C is about 1400 Da. In some instances, the molecular weight of C is about 1450 Da. In some instances, the molecular weight of C is about 1500 Da. In some instances, the molecular weight of C is about 1600 Da. In some instances, the molecular weight of C is about 1700 Da. In some instances, the molecular weight of C is about 1800 Da. In some instances, the molecular weight of C is about 1900 Da. In some instances, the molecular weight of C is about 2000 Da. In some instances, the molecular weight of C is about 2100 Da. In some instances, the molecular weight of C is about 2200 Da. In some instances, the molecular weight of C is about 2300 Da. In some instances, the molecular weight of C is about 2400 Da. In some instances, the molecular weight of C is about 2500 Da. In some instances, the molecular weight of C is about 2600 Da. In some instances, the molecular weight of C is about 2700 Da. In some instances, the molecular weight of C is about 2800 Da. In some instances, the molecular weight of C is about 2900 Da. In some instances, the molecular weight of C is about 3000 Da. In some instances, the molecular weight of C is about 3250 Da. In some instances, the molecular weight of C is about 3350 Da. In some instances, the molecular weight of C is about 3500 Da. In some instances, the molecular weight of C is about 3750 Da. In some instances, the molecular weight of C is about 4000 Da. In some instances, the molecular weight of C is about 4250 Da. In some instances, the molecular weight of C is about 4500 Da. In some instances, the molecular weight of C is about 4600 Da. In some instances, the molecular weight of C is about 4750 Da. In some instances, the molecular weight of C is about 5000 Da. In some instances, the molecular weight of C is about 5500 Da. In some instances, the molecular weight of C is about 6000 Da. In some instances, the molecular weight of C is about 6500 Da. In some instances, the molecular weight of C is about 7000 Da. In some instances, the molecular weight of C is about 7500 Da. In some instances, the molecular weight of C is about 8000 Da. In some instances, the molecular weight of C is about 10,000 Da. In some instances, the molecular weight of C is about 12,000 Da. In some instances, the molecular weight of C is about 20,000 Da. In some instances, the molecular weight of C is about 35,000 Da. In some instances, the molecular weight of C is about 40,000 Da. In some instances, the molecular weight of C is about 50,000 Da. In some instances, the molecular weight of C is about 60,000 Da. In some instances, the molecular weight of C is about 100,000 Da.

In some embodiments, the polyalkylene oxide (e.g., PEG) is a discrete PEG, in which the discrete PEG is a polymeric PEG comprising more than one repeating ethylene oxide units. In some instances, a discrete PEG (dPEG) comprises from 2 to 60, from 2 to 50, or from 2 to 48 repeating ethylene oxide units. In some instances, a dPEG comprises about 2, 3, 4, 5, 6, 7, 8, 9, 10, 11, 12, 13, 14, 15, 16, 17, 18, 19, 20, 22, 24, 26, 28, 30, 35, 40, 42, 48, 50 or more repeating ethylene oxide units. In some instances, a dPEG comprises about 2 or more repeating ethylene oxide units. In some instances, a dPEG comprises about 3 or more repeating ethylene oxide units. In some instances, a dPEG comprises about 4 or more repeating ethylene oxide units. In some instances, a dPEG comprises about 5 or more repeating ethylene oxide units. In some instances, a dPEG comprises about 6 or more repeating ethylene oxide units. In some instances, a dPEG comprises about 7 or more repeating ethylene oxide units. In some instances, a dPEG comprises about 8 or more repeating ethylene oxide units. In some instances, a dPEG comprises about 9 or more repeating ethylene oxide units. In some instances, a dPEG comprises about 10 or more repeating ethylene oxide units. In some instances, a dPEG comprises about 11 or more repeating ethylene oxide units. In some instances, a dPEG comprises about 12 or more repeating ethylene oxide units. In some instances, a dPEG comprises about 13 or more repeating ethylene oxide units. In some instances, a dPEG comprises about 14 or more repeating ethylene oxide units. In some instances, a dPEG comprises about 15 or more repeating ethylene oxide units. In some instances, a dPEG comprises about 16 or more repeating ethylene oxide units. In some instances, a dPEG comprises about 17 or more repeating ethylene oxide units. In some instances, a dPEG comprises about 18 or more repeating ethylene oxide units. In some instances, a dPEG comprises about 19 or more repeating ethylene oxide units. In some instances, a dPEG comprises about 20 or more repeating ethylene oxide units. In some instances, a dPEG comprises about 22 or more repeating ethylene oxide units. In some instances, a dPEG comprises about 24 or more repeating ethylene oxide units. In some instances, a dPEG comprises about 26 or more repeating ethylene oxide units. In some instances, a dPEG comprises about 28 or more repeating ethylene oxide units. In some instances, a dPEG comprises about 30 or more repeating ethylene oxide units. In some instances, a dPEG comprises about 35 or more repeating ethylene oxide units. In some instances, a dPEG comprises about 40 or more repeating ethylene oxide units. In some instances, a dPEG comprises about 42 or more repeating ethylene oxide units. In some instances, a dPEG comprises about 48 or more repeating ethylene oxide units. In some instances, a dPEG comprises about 50 or more repeating ethylene oxide units. In some cases, a dPEG is synthesized as a single molecular weight compound from pure (e.g., about 95%, 98%, 99%, or 99.5%) staring material in a step-wise fashion. In some cases, a dPEG has a specific molecular weight, rather than an average molecular weight. In some cases, a dPEG described herein is a dPEG from Quanta Biodesign, LMD.

In some embodiments, the polymer moiety C comprises a cationic mucic acid-based polymer (cMAP). In some instances, cMPA comprises one or more subunit of at least one repeating subunit, and the subunit structure is represented as Formula (III):

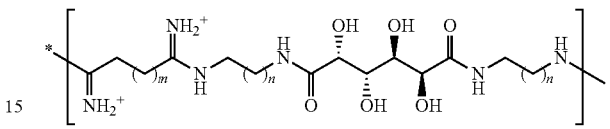

Formula III wherein m is independently at each occurrence 1, 2, 3, 4, 5, 6, 7, 8, 9, or 10, preferably 4-6 or 5; and n is independently at each occurrence 1, 2, 3, 4, or 5. In some embodiments, m and n are, for example, about 10.

In some instances, cMAP is further conjugated to a PEG moiety, generating a cMAP-PEG copolymer, an mPEG-cMAP-PEGm triblock polymer, or a cMAP-PEG-cMAP triblock polymer. In some instances, the PEG moiety is in a range of from about 500 Da to about 50,000 Da. In some instances, the PEG moiety is in a range of from about 500 Da to about 1000 Da, greater than 1000 Da to about 5000 Da, greater than 5000 Da to about 10,000 Da, greater than 10,000 to about 25,000 Da, greater than 25,000 Da to about 50,000 Da, or any combination of two or more of these ranges.

In some instances, the polymer moiety C is cMAP-PEG copolymer, an mPEG-cMAP-PEGm triblock polymer, or a cMAP-PEG-cMAP triblock polymer. In some cases, the polymer moiety C is cMAP-PEG copolymer. In other cases, the polymer moiety C is an mPEG-cMAP-PEGm triblock polymer. In additional cases, the polymer moiety C is a cMAP-PEG-cMAP triblock polymer.

In some embodiments, the polymer moiety C is conjugated to the polynucleic acid molecule, the binding moiety, and optionally to the endosomolytic moiety.

Endosomolytic Moiety

In some embodiments, a molecule of Formula (I): A-X-B-Y-C, further comprises an additional conjugating moiety. In some instances, the additional conjugating moiety is an endosomolytic moiety. In some cases, the endosomolytic moiety is a cellular compartmental release component, such as a compound capable of releasing from any of the cellular compartments known in the art, such as the endosome, lysosome, endoplasmic reticulum (ER), golgi apparatus, microtubule, peroxisome, or other vesicular bodies with the cell. In some cases, the endosomolytic moiety comprises an endosomolytic polypeptide, an endosomolytic polymer, an endosomolytic lipid, or an endosomolytic small molecule. In some cases, the endosomolytic moiety comprises an endosomolytic polypeptide. In other cases, the endosomolytic moiety comprises an endosomolytic polymer.

Endosomolytic Polypeptides

In some embodiments, a molecule of Formula (I): A-X-B-Y-C, is further conjugated with an endosomolytic polypeptide. In some cases, the endosomolytic polypeptide is a pH-dependent membrane active peptide. In some cases, the endosomolytic polypeptide is an amphipathic polypeptide. In additional cases, the endosomolytic polypeptide is a peptidomimetic. In some instances, the endosomolytic polypeptide comprises INF, melittin, meucin, or their respective derivatives thereof. In some instances, the endosomolytic polypeptide comprises INF or its derivatives thereof. In other cases, the endosomolytic polypeptide comprises melittin or its derivatives thereof. In additional cases, the endosomolytic polypeptide comprises meucin or its derivatives thereof.

In some instances, INF7 is a 24 residue polypeptide those sequence comprises CGIFGEIEELIEEGLENLIDWGNA (SEQ ID NO: 1243), or GLFEAIEGFIENGWEG-MIDGWYGC (SEQ ID NO: 1244). In some instances, INF7 or its derivatives comprise a sequence of: GLFEAIEGFIEN-GWEGMIWDYGSGSCG (SEQ ID NO: 1245), GLFEAIEGFIENGWEGMIDG WYG-(PEG)6-NH2 (SEQ ID NO: 1246), or GLFEAIEGFIENGWEGMIWDYG-SGSC-K(GalNAc)2 (SEQ ID NO: 1247).

In some cases, melittin is a 26 residue polypeptide those sequence comprises CLIGAILKVLATGLPTLISWIKNK-RKQ (SEQ ID NO: 1248), or GIGAVLKVLTTGLPAL-ISWIKRKRQQ (SEQ m NO: 1249), In some instances, melittin comprises a polypeptide sequence as described in U.S. Pat. No. 8,501,930.

In some instances, meucin is an antimicrobial peptide (AMP) derived from the venom gland of the scorpion *Mesobuthus eupeus*. In some instances, meucin comprises of meucin-13 those sequence comprises IFGAIAGLLKNIF-NH$_2$ (SEQ ID NO: 1250) and meucin-18 those sequence comprises FFGHLFKLATKIIPSLFQ (SEQ ID NO: 1251).

In some instances, the endosomolytic polypeptide comprises a polypeptide in which its sequence is at least 50%, 60%, 70%, 80%, 90%, 95%, or 99% sequence identity to INF7 or its derivatives thereof, melittin or its derivatives thereof, or meucin or its derivatives thereof. In some instances, the endosomolytic moiety comprises INF7 or its derivatives thereof, melittin or its derivatives thereof, or meucin or its derivatives thereof.

In some instances, the endosomolytic moiety is INF7 or its derivatives thereof. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NOs: 1243-1247. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NO: 1243. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NO: 1244-1247. In some cases, the endosomolytic moiety comprises SEQ ID NO: 1243. In some cases, the endosomolytic moiety comprises SEQ ID NO: 1244-1247. In some cases, the endosomolytic moiety consists of SEQ ID NO: 1243. In some cases, the endosomolytic moiety consists of SEQ ID NO: 1244-1247.

In some instances, the endosomolytic moiety is melittin or its derivatives thereof. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NOs: 1248 or 1249. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NO: 1248. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NO: 1249. In some cases, the endosomolytic moiety comprises SEQ ID NO: 1248. In some cases, the endosomolytic moiety comprises SEQ ID NO: 1249. In some cases, the endosomolytic moiety consists of SEQ ID NO: 1248. In some cases, the endosomolytic moiety consists of SEQ ID NO: 1249.

In some instances, the endosomolytic moiety is meucin or its derivatives thereof. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NOs: 1250 or 1251. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NO: 1250. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NO: 1251. In some cases, the endosomolytic moiety comprises SEQ ID NO: 1250. In some cases, the endosomolytic moiety comprises SEQ ID NO: 1251. In some cases, the endosomolytic moiety consists of SEQ ID NO: 1250. In some cases, the endosomolytic moiety consists of SEQ ID NO: 1251.

In some instances, the endosomolytic moiety comprises a sequence as illustrated in Table 10.

TABLE 10

| Name | Origin | Amino Acid Sequence | SEQ ID NO: | Type |
|---|---|---|---|---|
| Pep-1 | NLS from Simian Virus 40 large antigen and Reverse transcriptase of HIV | KETWWETWWTEWSQPKKKRKV | 1252 | Primary amphipathic |
| pVEC | VE-cadherin | LLIILRRRRIRKQAHAHSK | 1253 | Primary amphipathic |
| VT5 | Synthetic peptide | DPKGDPKGVTVTVTVTVTGKGDP KPD | 1254 | β-sheet amphipathic |
| C105Y | 1-antitrypsin | CSIPPEVKFNKPFVYLI | 1255 | — |
| Transportan | Galanin and mastoparan | GWTLNSAGYLLGKINLKALAALA KKIL | 1256 | Primary amphipathic |
| TP10 | Galanin and mastoparan | AGYLLGKINLKALAALAKKIL | 1257 | Primary amphipathic |

TABLE 10-continued

| Name | Origin | Amino Acid Sequence | SEQ ID NO: | Type |
|---|---|---|---|---|
| MPG | A hydrofobic domain from the fusion sequence of HIV gp41 and NLS of SV40 T antigen | GALFLGFLGAAGSTMGA | 1258 | β-sheet amphipathic |
| gH625 | Glycoprotein gH of HSV type I | HGLASTLTRWAHYNALIRAF | 1259 | Secondary amphipathic α-helical |
| CADY | PPTG1 peptide | GLWRALWRLLRSLWRLLWRA | 1260 | Secondary amphipathic α-helical |
| GALA | Synthetic peptide | WEAALAEALAEALAEHLAEALAE ALEALAA | 1261 | Secondary amphipathic α-helical |
| INF | Influenza HA2 fusion peptide | GLFEAIEGFIENGWEGMIDGWYGC | 1262 | Secondary amphipathic α-helical/pH-dependent membrane active peptide |
| HA2E5-TAT | Influenza HA2 subunit of influenza virus X31 strain fusion peptide | GLFGAIAGFIENGWEGMIDGWYG | 1263 | Secondary amphipathic α-helical/pH-dependent membrane active peptide |
| HA2-penetratin | Influenza HA2 subunit of influenza virus X31 strain fusion peptide | GLFGAIAGFIENGWEGMIDGRQIKI WFQNRRMKW KK-amide | 1264 | pH-dependent membrane active peptide |
| HA-K4 | Influenza HA2 subunit of influenza virus X31 strain fusion peptide | GLFGAIAGFIENGWEGMIDG-SSKKKK | 1265 | pH-dependent membrane active peptide |
| HA2E4 | Influenza HA2 subunit of influenza virus X31 strain fusion peptide | GLFEAIAGFIENGWEGMIDGGGYC | 1266 | pH-dependent membrane active peptide |
| H5WYG | HA2 analogue | GLFHAIAHFIHGGWH GLIHGWYG | 1267 | pH-dependent membrane active peptide |
| GALA-INF3-(PEG)6-NH | INF3 fusion peptide | GLFEAIEGFIENGWEGLAEALAEAL EALAA-(PEG)6-NH2 | 1268 | pH-dependent membrane active peptide |
| CM18-TAT11 | Cecropin-A-Melittin$_{2-12}$ (CM$_{18}$) fusion peptide | KWKLFKKIGAVLKVLTTG-YGRKKIMQRRR | 1269 | pH-dependent membrane active peptide |

In some cases, the endosomolytic moiety comprises a Bak BH3 polypeptide which induces apoptosis through antago- nization of suppressor targets such as Bcl-2 and/or Bcl-x$_L$. In some instances, the endosomolytic moiety comprises a Bak BH3 polypeptide described in Albarran, et al., "Efficient intracellular delivery of a pro-apoptotic peptide with a pH-responsive carrier," *Reactive &Functional Polymers* 71: 261-265 (2011).

In some instances, the endosomolytic moiety comprises a polypeptide (e.g., a cell-penetrating polypeptide) as described in PCT Publication Nos. WO2013/166155 or WO2015/069587.

Endosomolytic Polymers

In some embodiments, a molecule of Formula (I): A-X-B-Y-C, is further conjugated with an endosomolytic polymer. As used herein, an endosomolytic polymer comprises a linear, a branched network, a star, a comb, or a ladder type of polymer. In some instances, an endosomolytic polymer is a homopolymer or a copolymer comprising two or more different types of monomers. In some cases, an endosomolytic polymer is a polycation polymer. In other cases, an endosomolytic polymer is a polyanion polymer.

In some instances, a polycation polymer comprises monomer units that are charge positive, charge neutral, or charge negative, with a net charge being positive. In other cases, a polycation polymer comprises a non-polymeric molecule that contains two or more positive charges. Exemplary cationic polymers include, but are not limited to, poly(L-lysine) (PLL), poly(L-arginine) (PLA), polyethyleneimine (PEI), poly[α-(4-aminobutyl)-L-glycolic acid] (PAGA), 2-(dimethylamino)ethyl methacrylate (DMAEMA), or N,N-Diethylaminoethyl Methacrylate (DEAEMA).

In some cases, a polyanion polymer comprises monomer units that are charge positive, charge neutral, or charge negative, with a net charge being negative. In other cases, a polyanion polymer comprises a non-polymeric molecule that contains two or more negative charges. Exemplary anionic polymers include p(alkylacrylates) (e.g., poly(propyl acrylic acid) (PPAA)) or poly(N-isopropylacrylamide) (NIPAM). Additional examples include PP75, a L-phenylalanine-poly(L-lysine isophthalamide) polymer described in Khormaee, et al., "Edosomolytic anionic polymer for the cytoplasmic delivery of siRNAs in localized in vivo applications," *Advanced Functional Materials* 23: 565-574 (2013).

In some embodiments, an endosomolytic polymer described herein is a pH-responsive endosomolytic polymer. A pH-responsive polymer comprises a polymer that increases in size (swell) or collapses depending on the pH of the environment. Polyacrylic acid and chitosan are examples of pH-responsive polymers.

In some instances, an endosomolytic moiety described herein is a membrane-disruptive polymer. In some cases, the membrane-disruptive polymer comprises a cationic polymer, a neutral or hydrophobic polymer, or an anionic polymer. In some instances, the membrane-disruptive polymer is a hydrophilic polymer.

In some instances, an endosomolytic moiety described herein is a pH-responsive membrane-disruptive polymer. Exemplary pH-responsive membrane-disruptive polymers include p(alkylacrylic acids), poly(N-isopropylacrylamide) (NIPAM) copolymers, succinylated p(glycidols), and p(β-malic acid) polymers.

In some instances, p(alkylacrylic acids) include poly (propylacrylic acid) (polyPAA), poly(methacrylic acid) (PMAA), poly(ethylacrylic acid) (PEAA), and poly(propyl acrylic acid) (PPAA). In some instances, a p(alkylacrylic acid) include a p(alkylacrylic acid) described in Jones, et al., *Biochemistry Journal* 372: 65-75 (2003).

In some embodiments, a pH-responsive membrane-disruptive polymer comprises p(butyl acrylate-co-methacrylic acid). (see Bulmus, et al., *Journal of Controlled Release* 93: 105-120 (2003); and Yessine, et al., *Biochimica et Biophysica Acta* 1613: 28-38 (2003))

In some embodiments, a pH-responsive membrane-disruptive polymer comprises p(styrene-alt-maleic anhydride). (see Henry, et al., *Biomacromolecules* 7: 2407-2414 (2006))

In some embodiments, a pH-responsive membrane-disruptive polymer comprises pyridyldisulfide acrylate (PDSA) polymers such as poly(MAA-co-PDSA), poly(EAA-co-PDSA), poly(PAA-co-PDSA), poly(MAA-co-BA-co-PDSA), poly(EAA-co-BA-co-PDSA), or poly(PAA-co-BA-co-PDSA) polymers. (see El-Sayed, et al., "Rational design of composition and activity correlations for pH-responsive and glutathione-reactive polymer therapeutics," *Journal of Controlled Release* 104: 417-427 (2005); or Flanary et al., "Antigen delivery with poly(propylacrylic acid) conjugation enhanced MHC-1 presentation and T-cell activation," *Bioconjugate Chem.* 20: 241-248 (2009))

In some embodiments, a pH-responsive membrane-disruptive polymer comprises a lytic polymer comprising the base structure of:

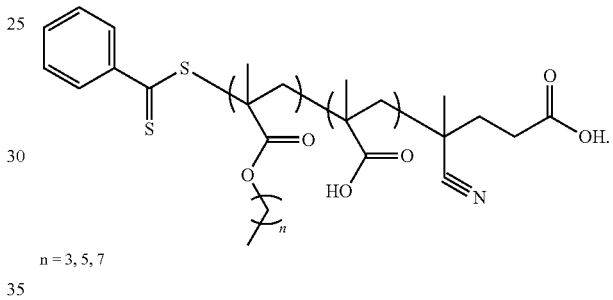

n = 3, 5, 7

In some instances, an endosomolytic moiety described herein is further conjugated to an additional conjugate, e.g., a polymer (e.g., PEG), or a modified polymer (e.g., cholesterol-modified polymer).

In some instances, the additional conjugate comprises a detergent (e.g., Triton X-100). In some instances, an endosomolytic moiety described herein comprises a polymer (e.g., a poly(amidoamine)) conjugated with a detergent (e.g., Triton X-100). In some instances, an endosomolytic moiety described herein comprises poly(amidoamine)-Triton X-100 conjugate (Duncan, et al., "A polymer-Triton X-100 conjugate capable of pH-dependent red blood cell lysis: a model system illustrating the possibility of drug delivery within acidic intracellular compartments," *Journal of Drug Targeting* 2: 341-347 (1994)).

Endosomolytic Lipids

In some embodiments, the endosomolytic moiety is a lipid (e.g., a fusogenic lipid). In some embodiments, a molecule of Formula (I): A-X-B-Y-C, is further conjugated with an endosomolytic lipid (e.g., fusogenic lipid). Exemplary fusogenic lipids include 1,2-dileoyl-sn-3-phosphoethanolamine (DOPE), phosphatidylethanolamine (POPE), palmitoyloleoylphosphatidylcholine (POPC), (6Z,9Z,28Z, 31Z)-heptatriaconta-6,9,28,31-tetraen-19-ol (Di-Lin), N-methyl(2,2-di((9Z,12Z)-octadeca-9,12-dienyl)-1,3-dioxolan-4-yl)methanamine (DLin-k-DMA) and N-methyl-2-(2,2-di((9Z,12Z)-octadeca-9,12-dienyl)-1,3-dioxolan-4-yl) ethanamine (XTC).

In some instances, an endosomolytic moiety is a lipid (e.g., a fusogenic lipid) described in PCT Publication No. WO09/126,933.

Endosomolytic Small Molecules

In some embodiments, the endosomolytic moiety is a small molecule. In some embodiments, a molecule of Formula (I): A-X-B-Y-C, is further conjugated with an endosomolytic small molecule. Exemplary small molecules suitable as endosomolytic moieties include, but are not limited to, quinine, chloroquine, hydroxychloroquines, amodiaquins (carnoquines), amopyroquines, primaquines, mefloquines, nivaquines, halofantrines, quinone imines, or a combination thereof. In some instances, quinoline endosomolytic moieties include, but are not limited to, 7-chloro-4-(4-diethyl-amino-1-methylbutyl-amino)quinoline (chloroquine); 7-chloro-4-(4-ethyl-(2-hydroxyethyl)-amino-1-methyl-butyl-amino)quinoline (hydroxychloroquine); 7-fluoro-4-(4-diethylamino-1-methylbutyl-amino)quinoline; 4-(4-diethylamino-1-methylbutylamino) quinoline; 7-hydroxy-4-(4-diethyl-amino-1-methylbutylamino)quinoline; 7-chloro-4-(4-diethylamino-1-butylamino)quinoline (desmethyl-chloroquine); 7-fluoro-4-(4-diethylamino-1-butylamino) quinoline); 4-(4-diethyl-amino-1-butylamino)quinoline; 7-hydroxy-4-(4-diethylamino-1-butylamino)quinoline; 7-chloro-4-(1-carboxy-4-diethylamino-1-butylamino)qui-noline; 7-fluoro-4-(1-carboxy-4-diethyl-amino-1-buty-lamino)quinoline; 4-(1-carboxy-4-diethylamino-1-buty-lamino) quinoline; 7-hydroxy-4-(1-carboxy-4-diethyl-amino-1-butylamino)quinoline; 7-chloro-4-(1-carboxy-4-diethylamino-1-methylbutylamino)quinoline; 7-fluoro-4-(1-carboxy-4-diethyl-amino-1-methylbutylamino)quinoline; 4-(1-carboxy-4-diethylamino-1-methylbutylamino)quino-line; 7-hydroxy-4-(1-carboxy-4-diethylamino-1-methyl-butylamino)quinoline; 7-fluoro-4-(4-ethyl-(2-hydroxy-ethyl)-amino-1-methylbutylamino)quinoline; 4-(4-ethyl-(2-hydroxy-ethyl)-amino-1-methylbutylamino-)quinoline; 7-hydroxy-4-(4-ethyl-(2-hydroxyethyl)-amino-1-methyl-butylamino)quinoline; hydroxychloroquine phosphate; 7-chloro-4-(4-ethyl-(2-hydroxyethyl-1)-amino-1-buty-lamino)quinoline (desmethylhydroxychloroquine); 7-fluoro-4-(4-ethyl-(2-hydroxyethyl)-amino-1-butylamino) quinoline; 4-(4-ethyl-(2-hydroxyethyl)-amino-1-buty-lamino)quinoline; 7-hydroxy-4-(4-ethyl-(2-hydroxyethyl)-amino-1-butylamino) quinoline; 7-chloro-4-(1-carboxy-4-ethyl-(2-hydroxyethyl)-amino-1-butylamino)quinoline; 7-fluoro-4-(1-carboxy-4-ethyl-(2-hydroxyethyl)-amino-1-butylamino)quinoline; 4-(1-carboxy-4-ethyl-(2-hydroxy-ethyl)-amino-1-butylamino)quinoline; 7-hydroxy-4-(1-car-boxy-4-ethyl-(2-hydroxyethyl)-amino-1-butylamino) quinoline; 7-chloro-4-(1-carboxy-4-ethyl-(2-hydroxyethyl)-amino-1-methylbutylamino)quinoline; 7-fluoro-4-(1-car-boxy-4-ethyl-(2-hydroxyethyl)-amino-1-methylbutylamino) quinoline; 4-(1-carboxy-4-ethyl-(2-hydroxyethyl)-amino-1-methylbutylamino)quinoline; 7-hydroxy-4-(1-carboxy-4-ethyl-(2-hydroxyethyl)-amino-1-methylbutylamino)qui-noline; 8-[(4-aminopentyl)amino-6-methoxydihydrochlo-ride quinoline; 1-acetyl-1,2,3,4-tetrahydroquinoline; 8-[(4-aminopentyl)amino]-6-methoxyquinoline dihydrochloride; 1-butyryl-1,2,3,4-tetrahydroquinoline; 3-chloro-4-(4-hy-droxy-alpha,alpha'-bis(2-methyl-1-pyrrolidinyl)-2,5-xylidi-noquinoline, 4-[(4-diethyl-amino)-1-methylbutyl-amino]-6-methoxyquinoline; 3-fluoro-4-(4-hydroxy-alpha,alpha'-bis (2-methyl-1-pyrrolidinyl)-2,5-xylidinoquinoline, 4-[(4-diethylamino)-1-methylbutyl-amino]-6-methoxyquinoline; 4-(4-hydroxy-alpha,alpha'-bis(2-methyl-1-pyrrolidinyl)-2, 5-xylidinoquinoline; 4-[(4-diethylamino)-1-methylbutyl-amino]-6-methoxyquinoline; 3,4-dihydro-1-(2H)-quinolin-ecarboxaldehyde; 1,1'-pentamethylene diquinoleinium diiodide; 8-quinolinol sulfate and amino, aldehyde, carbox-ylic, hydroxyl, halogen, keto, sulfhydryl and vinyl deriva-tives or analogs thereof. In some instances, an endosomo-lytic moiety is a small molecule described in Naisbitt et al (1997, J Pharmacol Exp Therapy 280:884-893) and in U.S. Pat. No. 5,736,557.

Formula (I) Molecule—Endosomolytic Moiety Conjugates

In some embodiments, one or more endosomolytic moieties are conjugated to a molecule comprising at least one binding moiety, at least one polynucleotide, at least one polymer, or any combinations thereof. In some instances, the endosomolytic moiety is conjugated according to Formula (II):

$$(A\text{-}X\text{-}B\text{-}Y\text{-}C_c)\text{-}L\text{-}D \qquad \text{Formula II}$$

wherein,
A is a binding moiety;
B is a polynucleotide;
C is a polymer;
X is a bond or a first linker;
Y is a bond or a second linker;
L is a bond or a third linker;
D is an endosomolytic moiety; and
c is an integer between 0 and 1; and
wherein the polynucleotide comprises at least one 5'-vi-nylphosphonate modified nucleotide; and D is conjugated anywhere on A, B, or C.

In some embodiments, A and C are not attached to B at the same terminus.

In some embodiments, the at least one 2' modified nucleotide comprises 2'-O-methyl, 2'-O-methoxyethyl (2'-O-MOE), 2'-O-aminopropyl, 2'-deoxy, T-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), or 2'-O-N-methylacetamido (2'-O-NMA) modified nucleotide. In some instances, the at least one 2' modified nucleotide comprises locked nucleic acid (LNA) or ethylene nucleic acid (ENA). In some cases, the at least one modified internucleotide linkage comprises a phosphorothioate linkage or a phospho-rodithioate linkage. In some embodiments, the polynucleotide comprises a first polynucleotide and a second polynucleotide hybridized to the first polynucleotide to form a double-stranded polynucleic acid molecule. In some instances, the second polynucleotide comprises at least one modification. In some cases, the first polynucleotide and the second polynucleotide are RNA molecules. In some cases, the first polynucleotide and the second polynucleotide are siRNA molecules. In some embodiments, X, Y, and L are independently a bond or a non-polymeric linker group. In some instances, A is an antibody or binding fragment thereof. In some instances, the antibody or binding fragment thereof comprises a humanized antibody or binding fragment thereof, chimeric antibody or binding fragment thereof, monoclonal antibody or binding fragment thereof, monovalent Fab', divalent Fab2, single-chain variable fragment (scFv), diabody, minibody, nanobody, single-domain antibody (sdAb), or camelid antibody or binding fragment thereof. In some cases, C is polyethylene glycol.

In some instances, the endosomolytic moiety comprises a polypeptide, a polymer, a lipid, or a small molecule. In some instances, the endosomolytic moiety is an endosomolytic polypeptide. In some cases, the endosomolytic moiety is an endosomolytic polymer. In other cases, the endosomolytic moiety is an endosomolytic lipid. In additional cases, the endosomolytic moiety is an endosomolytic small molecule.

In some instances, the endosomolytic moiety is INF7 or its derivatives thereof. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NOs: 1243. In some cases, the endosomolytic moiety comprises SEQ ID NO: 1243. In some cases, the endosomolytic moiety consists of SEQ ID NO: 1243.

In some instances, the endosomolytic moiety is melittin or its derivatives thereof. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NOs: 1248. In some cases, the endosomolytic moiety comprises SEQ ID NO: 1248. In some cases, the endosomolytic moiety consists of SEQ ID NO: 1248.

In some instances, the endosomolytic moiety is a sequence as illustrated in Table 10.

In additional cases, the endosomolytic moiety is an endosomolytic polymer, such as for example, a pH-responsive endosomolytic polymer, a membrane-disruptive polymer, a polycation polymer, a polyanion polymer, a pH-responsive membrane-disruptive polymer, or a combination thereof. In additional cases, the endosomolytic moiety comprises a p(alkylacrylic acid) polymer, a p(butyl acrylate-co-methacrylic acid) polymer, a p(styrene-alt-maleic anhydride) polymer, a pyridyldisulfide acrylate (PDSA) polymer, a polymer-PEG conjugate, a polymer-detergent conjugate, or a combination thereof.

In some embodiments, the endosomolytic moiety conjugate is according to Formula (IIa):

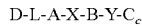　　　　　　　　　　　　　　　　　Formula IIa wherein,
A is a binding moiety;
B is a polynucleotide;
C is a polymer;
X is a bond or a first linker;
Y is a bond or a second linker;
L is a bond or a third linker;
D is an endosomolytic moiety; and
c is an integer of 1; and
wherein the polynucleotide comprises at least one 5'-vinylphosphonate modified nucleotide.

In some embodiments, A and C are not attached to B at the same terminus.

In some embodiments, the at least one 2' modified nucleotide comprises 2'-O-methyl, 2'-O-methoxyethyl (2'-O-MOE), 2'-O-aminopropyl, 2'-deoxy, T-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), or 2'-O-N-methylacetamido (2'-O-NMA) modified nucleotide. In some instances, the at least one 2' modified nucleotide comprises locked nucleic acid (LNA) or ethylene nucleic acid (ENA). In some cases, the at least one modified internucleotide linkage comprises a phosphorothioate linkage or a phosphorodithioate linkage. In some embodiments, the polynucleotide comprises a first polynucleotide and a second polynucleotide hybridized to the first polynucleotide to form a double-stranded polynucleic acid molecule. In some instances, the second polynucleotide comprises at least one modification. In some cases, the first polynucleotide and the second polynucleotide are RNA molecules. In some cases, the first polynucleotide and the second polynucleotide are siRNA molecules. In some embodiments, X, Y, and L are independently a bond or a non-polymeric linker group. In some instances, A is an antibody or binding fragment thereof. In some instances, the antibody or binding fragment thereof comprises a humanized antibody or binding fragment thereof, chimeric antibody or binding fragment thereof, monoclonal antibody or binding fragment thereof, monovalent Fab', divalent Fab2, single-chain variable fragment (scFv), diabody, minibody, nanobody, single-domain antibody (sdAb), or camelid antibody or binding fragment thereof. In some cases, C is polyethylene glycol.

In some instances, the endosomolytic moiety comprises a polypeptide, a polymer, a lipid, or a small molecule. In some instances, the endosomolytic moiety is an endosomolytic polypeptide. In some cases, the endosomolytic moiety is an endosomolytic polymer. In other cases, the endosomolytic moiety is an endosomolytic lipid. In additional cases, the endosomolytic moiety is an endosomolytic small molecule.

In some instances, the endosomolytic moiety is INF7 or its derivatives thereof. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NOs: 1243. In some cases, the endosomolytic moiety comprises SEQ ID NO: 1243. In some cases, the endosomolytic moiety consists of SEQ ID NO: 1243.

In some instances, the endosomolytic moiety is melittin or its derivatives thereof. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NOs: 1248. In some cases, the endosomolytic moiety comprises SEQ ID NO: 1248. In some cases, the endosomolytic moiety consists of SEQ ID NO: 1248.

In some instances, the endosomolytic moiety is a sequence as illustrated in Table 10.

In additional cases, the endosomolytic moiety is an endosomolytic polymer, such as for example, a pH-responsive endosomolytic polymer, a membrane-disruptive polymer, a polycation polymer, a polyanion polymer, a pH-responsive membrane-disruptive polymer, or a combination thereof. In additional cases, the endosomolytic moiety comprises a p(alkylacrylic acid) polymer, a p(butyl acrylate-co-methacrylic acid) polymer, a p(styrene-alt-maleic anhydride) polymer, a pyridyldisulfide acrylate (PDSA) polymer, a polymer-PEG conjugate, a polymer-detergent conjugate, or a combination thereof.

In some instances, the endosomolytic moiety conjugate is according to Formula (IIb):

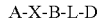　　　　　　　　　　　　　　　　　Formula IIb wherein,
A is a binding moiety;
B is a polynucleotide;
X is a bond or a first linker;
L is a bond or a third linker; and
D is an endosomolytic moiety; and
wherein the polynucleotide comprises at least one 5'-vinylphosphonate modified nucleotide.

In some embodiments, A and C are not attached to B at the same terminus.

In some embodiments, the at least one 2' modified nucleotide comprises 2'-O-methyl, 2'-O-methoxyethyl (2'-O-MOE), 2'-O-aminopropyl, 2'-deoxy, T-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), or 2'-O-N-methylacetamido (2'-O-NMA) modified nucleotide. In some instances, the at least one 2' modified nucleotide comprises locked nucleic acid (LNA) or ethylene nucleic acid (ENA). In some cases, the at least one modified internucleotide linkage comprises a phosphorothioate linkage or a phosphorodithioate linkage. In some embodiments, the polynucleotide comprises a first polynucleotide and a second polynucleotide hybridized to the first polynucleotide to form a double-stranded polynucleic acid molecule. In some instances, the second polynucleotide comprises at least one modification. In some cases, the first polynucleotide and the second polynucleotide are RNA molecules. In some cases, the first polynucleotide and the second polynucleotide are siRNA molecules. In some embodiments, X and L are independently a bond or a non-polymeric linker group. In some instances, A is an antibody or binding fragment thereof. In some instances, the antibody or binding fragment thereof comprises a humanized antibody or binding fragment thereof, chimeric antibody or binding fragment thereof, monoclonal antibody or binding fragment thereof, monovalent Fab', divalent Fab2, single-chain variable fragment (scFv), diabody, minibody, nanobody, single-domain antibody (sdAb), or camelid antibody or binding fragment thereof. In some cases, C is polyethylene glycol.

In some instances, the endosomolytic moiety comprises a polypeptide, a polymer, a lipid, or a small molecule. In some instances, the endosomolytic moiety is an endosomolytic polypeptide. In some cases, the endosomolytic moiety is an endosomolytic polymer. In other cases, the endosomolytic moiety is an endosomolytic lipid. In additional cases, the endosomolytic moiety is an endosomolytic small molecule.

In some instances, the endosomolytic moiety is INF7 or its derivatives thereof. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NOs: 1243. In some cases, the endosomolytic moiety comprises SEQ ID NO: 1243. In some cases, the endosomolytic moiety consists of SEQ ID NO: 1243.

In some instances, the endosomolytic moiety is melittin or its derivatives thereof. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NOs: 1248. In some cases, the endosomolytic moiety comprises SEQ ID NO: 1248. In some cases, the endosomolytic moiety consists of SEQ ID NO: 1248.

In some instances, the endosomolytic moiety is a sequence as illustrated in Table 10.

In additional cases, the endosomolytic moiety is an endosomolytic polymer, such as for example, a pH-responsive endosomolytic polymer, a membrane-disruptive polymer, a polycation polymer, a polyanion polymer, a pH-responsive membrane-disruptive polymer, or a combination thereof. In additional cases, the endosomolytic moiety comprises a p(alkylacrylic acid) polymer, a p(butyl acrylate-co-methacrylic acid) polymer, a p(styrene-alt-maleic anhydride) polymer, a pyridyldisulfide acrylate (PDSA) polymer, a polymer-PEG conjugate, a polymer-detergent conjugate, or a combination thereof.

In some instances, the endosomolytic moiety conjugate is according to Formula (IIc):

$$A\text{-}X\text{-}B\text{-}Y\text{-}C_c\text{-}L\text{-}D \qquad \text{Formula IIc}$$

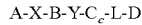

wherein,
A is a binding moiety;
B is a polynucleotide;
C is a polymer;
X is a bond or a first linker;
Y is a bond or a second linker;
L is a bond or a third linker;
D is an endosomolytic moiety; and
c is an integer of 1; and
wherein the polynucleotide comprises at least one 5'-vinylphosphonate modified nucleotide.

In some embodiments, A and C are not attached to B at the same terminus.

In some embodiments, the at least one 2' modified nucleotide comprises 2'-O-methyl, 2'-O-methoxyethyl (2'-O-MOE), 2'-O-aminopropyl, 2'-deoxy, T-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), or 2'-O-N-methylacetamido (2'-O-NMA) modified nucleotide. In some instances, the at least one 2' modified nucleotide comprises locked nucleic acid (LNA) or ethylene nucleic acid (ENA). In some cases, the at least one modified internucleotide linkage comprises a phosphorothioate linkage or a phosphorodithioate linkage. In some embodiments, the polynucleotide comprises a first polynucleotide and a second polynucleotide hybridized to the first polynucleotide to form a double-stranded polynucleic acid molecule. In some instances, the second polynucleotide comprises at least one modification. In some cases, the first polynucleotide and the second polynucleotide are RNA molecules. In some cases, the first polynucleotide and the second polynucleotide are siRNA molecules. In some embodiments, X, Y, and L are independently a bond or a non-polymeric linker group. In some instances, A is an antibody or binding fragment thereof. In some instances, the antibody or binding fragment thereof comprises a humanized antibody or binding fragment thereof, chimeric antibody or binding fragment thereof, monoclonal antibody or binding fragment thereof, monovalent Fab', divalent Fab2, single-chain variable fragment (scFv), diabody, minibody, nanobody, single-domain antibody (sdAb), or camelid antibody or binding fragment thereof. In some cases, C is polyethylene glycol.

In some instances, the endosomolytic moiety comprises a polypeptide, a polymer, a lipid, or a small molecule. In some instances, the endosomolytic moiety is an endosomolytic polypeptide. In some cases, the endosomolytic moiety is an endosomolytic polymer. In other cases, the endosomolytic moiety is an endosomolytic lipid. In additional cases, the endosomolytic moiety is an endosomolytic small molecule.

In some instances, the endosomolytic moiety is INF7 or its derivatives thereof. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NOs: 1243. In some cases, the endosomolytic moiety comprises SEQ ID NO: 1243. In some cases, the endosomolytic moiety consists of SEQ ID NO: 1243.

In some instances, the endosomolytic moiety is melittin or its derivatives thereof. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NOs: 1248. In some cases, the endosomolytic moiety comprises SEQ ID NO: 1248. In some cases, the endosomolytic moiety consists of SEQ ID NO: 1248.

In some instances, the endosomolytic moiety is a sequence as illustrated in Table 10.

In additional cases, the endosomolytic moiety is an endosomolytic polymer, such as for example, a pH-responsive endosomolytic polymer, a membrane-disruptive polymer, a polycation polymer, a polyanion polymer, a pH-responsive membrane-disruptive polymer, or a combination thereof. In additional cases, the endosomolytic moiety comprises a p(alkylacrylic acid) polymer, a p(butyl acrylate-co-methacrylic acid) polymer, a p(styrene-alt-maleic anhydride) polymer, a pyridyldisulfide acrylate (PDSA) polymer, a polymer-PEG conjugate, a polymer-detergent conjugate, or a combination thereof.

In some instances, the endosomolytic moiety conjugate is according to Formula (IId):

A-L-D-X-B-Y-C$_c$    Formula IId wherein,
A is a binding moiety;
B is a polynucleotide;
C is a polymer;
X is a bond or a first linker;
Y is a bond or a second linker;
L is a bond or a third linker;
D is an endosomolytic moiety; and
c is an integer of 1; and
wherein the polynucleotide comprises at least one 5'-vinylphosphonate modified nucleotide.

In some embodiments, A and C are not attached to B at the same terminus.

In some embodiments, the at least one 2' modified nucleotide comprises 2'-O-methyl, 2'-O-methoxyethyl (2'-O-MOE), 2'-O-aminopropyl, 2'-deoxy, T-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), or 2'-O-N-methylacetamido (2'-O-NMA) modified nucleotide. In some instances, the at least one 2' modified nucleotide comprises locked nucleic acid (LNA) or ethylene nucleic acid (ENA). In some cases, the at least one modified internucleotide linkage comprises a phosphorothioate linkage or a phosphorodithioate linkage. In some embodiments, the polynucleotide comprises a first polynucleotide and a second polynucleotide hybridized to the first polynucleotide to form a double-stranded polynucleic acid molecule. In some instances, the second polynucleotide comprises at least one modification. In some cases, the first polynucleotide and the second polynucleotide are RNA molecules. In some cases, the first polynucleotide and the second polynucleotide are siRNA molecules. In some embodiments, X, Y, and L are independently a bond or a non-polymeric linker group. In some instances, A is an antibody or binding fragment thereof. In some instances, the antibody or binding fragment thereof comprises a humanized antibody or binding fragment thereof, chimeric antibody or binding fragment thereof, monoclonal antibody or binding fragment thereof, monovalent Fab', divalent Fab2, single-chain variable fragment (scFv), diabody, minibody, nanobody, single-domain antibody (sdAb), or camelid antibody or binding fragment thereof. In some cases, C is polyethylene glycol.

In some instances, the endosomolytic moiety comprises a polypeptide, a polymer, a lipid, or a small molecule. In some instances, the endosomolytic moiety is an endosomolytic polypeptide. In some cases, the endosomolytic moiety is an endosomolytic polymer. In other cases, the endosomolytic moiety is an endosomolytic lipid. In additional cases, the endosomolytic moiety is an endosomolytic small molecule.

In some instances, the endosomolytic moiety is INF7 or its derivatives thereof. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NOs: 1243. In some cases, the endosomolytic moiety comprises SEQ ID NO: 1243. In some cases, the endosomolytic moiety consists of SEQ ID NO: 1243.

In some instances, the endosomolytic moiety is melittin or its derivatives thereof. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NOs: 1248. In some cases, the endosomolytic moiety comprises SEQ ID NO: 1248. In some cases, the endosomolytic moiety consists of SEQ ID NO: 1248.

In some instances, the endosomolytic moiety is a sequence as illustrated in Table 10.

In additional cases, the endosomolytic moiety is an endosomolytic polymer, such as for example, a pH-responsive endosomolytic polymer, a membrane-disruptive polymer, a polycation polymer, a polyanion polymer, a pH-responsive membrane-disruptive polymer, or a combination thereof. In additional cases, the endosomolytic moiety comprises a p(alkylacrylic acid) polymer, a p(butyl acrylate-co-methacrylic acid) polymer, a p(styrene-alt-maleic anhydride) polymer, a pyridyldisulfide acrylate (PDSA) polymer, a polymer-PEG conjugate, a polymer-detergent conjugate, or a combination thereof.

Linkers

In some embodiments, a linker described herein is a cleavable linker or a non-cleavable linker. In some instances, the linker is a cleavable linker. In some instances, the linker is an acid cleavable linker. In some instances, the linker is a non-cleavable linker. In some instances, the linker includes a $C_1$-$C_6$ alkyl group (e.g., a $C_5$, $C_4$, $C_3$, $C_2$, or $C_1$ alkyl group). In some instances, the linker includes homobifunctional cross linkers, heterobifunctional cross linkers, and the like. In some instances, the liker is a traceless linker (or a zero-length linker). In some instances, the linker is a non-polymeric linker. In some cases, the linker is a non-peptide linker or a linker that does not contain an amino acid residue.

In some instances, the linker comprises a homobifunctional linker. Exemplary homobifunctional linkers include, but are not limited to, Lomant's reagent dithiobis (succinimidylpropionate) DSP, 3'3'-dithiobis(sulfosuccinimidyl proprionate (DTSSP), disuccinimidyl suberate (DSS), bis(sulfosuccinimidyl)suberate (BS), disuccinimidyl tartrate (DST), disulfosuccinimidyl tartrate (sulfo DST), ethylene glycobis (succinimidylsuccinate) (EGS), disuccinimidyl glutarate (DSG), N,N'-disuccinimidyl carbonate (DSC), dimethyl adipimidate (DMA), dimethyl pimelimidate (DMP), dimethyl suberimidate (DMS), dimethyl-3,3'-dithiobispropionimidate (DTBP), 1,4-di-3'-(2'-pyridyldithio)propionamido)butane (DPDPB), bismaleimidohexane (BMH), aryl halide-containing compound (DFDNB), such as e.g. 1,5-difluoro-2,4-dinitrobenzene or 1,3-difluoro-4,6-dinitrobenzene, 4,4'-difluoro-3,3'-dinitrophenylsulfone (DFDNPS), bis-[β-(4-azidosalicylamido)ethyl]disulfide (BASED), formaldehyde, glutaraldehyde, 1,4-butanediol diglycidyl ether, adipic acid dihydrazide, carbohydrazide, o-toluidine, 3,3'-dimethylbenzidine, benzidine, α,α'-p-diaminodiphenyl, diiodo-p-xylene sulfonic acid, N,N'-ethylene-bis(iodoacetamide), or N,N'-hexamethylene-bis(iodoacetamide).

In some embodiments, the linker comprises a heterobifunctional linker. Exemplary heterobifunctional linker include, but are not limited to, amine-reactive and sulfhydryl cross-linkers such as N-succinimidyl 3-(2-pyridyldithio) propionate (sPDP), long-chain N-succinimidyl 3-(2-pyridyldithio)propionate (LC-sPDP), water-soluble-long-chain N-succinimidyl 3-(2-pyridyldithio) propionate (sulfo-LC-sPDP), succinimidyloxycarbonyl-α-methyl-α-(2-pyridyldithio)toluene (sMPT), sulfosuccinimidyl-6-[α-methyl-α-(2-pyridyldithio)toluamido]hexanoate (sulfo-LC-sMPT), succinimidyl-4-(N-maleimidomethyl)cyclohexane-1-carboxylate (sMCC), sulfosuccinimidyl-4-(N-maleimidomethyl)cyclohexane-1-carboxylate (sulfo-sMCC), m-maleimidobenzoyl-N-hydroxysuccinimide ester (MBs), m-maleimidobenzoyl-N-hydroxysulfosuccinimide ester (sulfo-MBs), N-succinimidyl(4-iodoacteyl)aminobenzoate (sIAB), sulfosuccinimidyl(4-iodoacteyl)aminobenzoate (sulfo-sIAB), succinimidyl-4-(p-maleimidophenyl)butyrate (sMPB), sulfosuccinimidyl-4-(p-maleimidophenyl)butyrate (sulfo-sMPB), N-(γ-maleimidobutyryloxy)succinimide ester (GMBs), N-(γ-maleimidobutyryloxy)sulfosuccinimide ester (sulfo-GMBs), succinimidyl 6-((iodoacetyl)amino)hexanoate (sIAX), succinimidyl 6-[6-(((iodoacetyl)amino) hexanoyl)amino]hexanoate (sIAXX), succinimidyl 4-(((iodoacetyl)amino)methyl)cyclohexane-1-carboxylate (sIAC), succinimidyl 6-((((4-iodoacetyl)amino)methyl)cyclohexane-1-carbonyl)amino) hexanoate (sIACX), p-nitrophenyl iodoacetate (NPIA), carbonyl-reactive and sulfhydryl-reactive cross-linkers such as 4-(4-N-maleimidophenyl) butyric acid hydrazide (MPBH), 4-(N-maleimidomethyl) cyclohexane-1-carboxyl-hydrazide-8 ($M_2C_2H$), 3-(2-pyridyldithio)propionyl hydrazide (PDPH), amine-reactive and photoreactive cross-linkers such as N-hydroxysuccinimidyl-4-azidosalicylic acid (NHs-AsA), N-hydroxysulfosuccinimidyl-4-azidosalicylic acid (sulfo-NHs-AsA), sulfosuccinimidyl-(4-azidosalicylamido)hexanoate (sulfo-NHs-LC-AsA), sulfosuccinimidyl-2-(p-azidosalicylamido)ethyl-1,3'-dithiopropionate (sAsD), N-hydroxysuccinimidyl-4-azidobenzoate (HsAB), N-hydroxysulfosuccinimidyl-4-azidobenzoate (sulfo-HsAB), N-succinimidyl-6-(4'-azido-2'-nitrophenylamino)hexanoate (sANPAH), sulfosuccinimidyl-6-(4'-azido-2'-nitrophenylamino)hexanoate (sulfo-sANPAH), N-5-azido-2-nitrobenzoyloxysuccinimide (ANB-NOs), sulfosuccinimidyl-2-(m-azido-o-nitrobenzamido)-ethyl-1,3'-dithiopropionate (sAND), N-succinimidyl-4(4-azidophenyl)-1,3'-dithiopropionate (sADP), N-sulfosuccinimidyl(4-azidophenyl)-1,3'-dithiopropionate (sulfo-sADP), sulfosuccinimidyl 4-(p-azidophenyl)butyrate (sulfo-sAPB), sulfosuccinimidyl 2-(7-azido-4-methylcoumarin-3-ace tamide)ethyl-1,3'-dithiopropionate (sAED), sulfosuccinimidyl 7-azido-4-methylcoumain-3-acetate (sulfo-sAMCA), ρ-nitrophenyl diazopyruvate (ρNPDP), ρ-nitrophenyl-2-diazo-3,3,3-trifluoropropionate (PNP-DTP), sulfhydryl-reactive and photoreactive cross-linkers such as 1-(ρ-Azidosalicylamido)-4-(iodoacetamido)butane (AsIB), N-[4-(ρ-azidosalicylamido)butyl]-3'-(2'-pyridyldithio)propionamide (APDP), benzophenone-4-iodoacetamide, benzophenone-4-maleimide carbonyl-reactive and photoreactive cross-linkers such as ρ-azidobenzoyl hydrazide (ABH), carboxylate-reactive and photoreactive cross-linkers such as 4-(ρ-azidosalicylamido)butylamine (AsBA), and arginine-reactive and photoreactive cross-linkers such as ρ-azidophenyl glyoxal (APG).

In some instances, the linker comprises a reactive functional group. In some cases, the reactive functional group comprises a nucleophilic group that is reactive to an electrophilic group present on a binding moiety. Exemplary electrophilic groups include carbonyl groups—such as aldehyde, ketone, carboxylic acid, ester, amide, enone, acyl halide or acid anhydride. In some embodiments, the reactive functional group is aldehyde. Exemplary nucleophilic groups include hydrazide, oxime, amino, hydrazine, thiosemicarbazone, hydrazine carboxylate, and arylhydrazide.

In some embodiments, the linker comprises a maleimide group. In some instances, the maleimide group is also referred to as a maleimide spacer. In some instances, the maleimide group further encompasses a caproic acid, forming maleimidocaproyl (mc). In some cases, the linker comprises maleimidocaproyl (mc). In some cases, the linker is maleimidocaproyl (mc). In other instances, the maleimide group comprises a maleimidomethyl group, such as succinimidyl-4-(N-maleimidomethyl)cyclohexane-1-carboxylate (sMCC) or sulfosuccinimidyl-4-(N-maleimidomethyl)cyclohexane-1-carboxylate (sulfo-sMCC) described above.

In some embodiments, the maleimide group is a self-stabilizing maleimide. In some instances, the self-stabilizing maleimide utilizes diaminopropionic acid (DPR) to incorporate a basic amino group adjacent to the maleimide to provide intramolecular catalysis of tiosuccinimide ring hydrolysis, thereby eliminating maleimide from undergoing an elimination reaction through a retro-Michael reaction. In some instances, the self-stabilizing maleimide is a maleimide group described in Lyon, et al., "Self-hydrolyzing maleimides improve the stability and pharmacological properties of antibody-drug conjugates," *Nat. Biotechnol.* 32(10): 1059-1062 (2014). In some instances, the linker comprises a self-stabilizing maleimide. In some instances, the linker is a self-stabilizing maleimide.

In some embodiments, the linker comprises a peptide moiety. In some instances, the peptide moiety comprises at least 2, 3, 4, 5, 6, 7, 8, or more amino acid residues. In some instances, the peptide moiety is a cleavable peptide moiety (e.g., either enzymatically or chemically). In some instances, the peptide moiety is a non-cleavable peptide moiety. In some instances, the peptide moiety comprises Val-Cit (valine-citrulline), Gly-Gly-Phe-Gly (SEQ ID NO: 1270), Phe-Lys, Val-Lys, Gly-Phe-Lys, Phe-Phe-Lys, Ala-Lys, Val-Arg, Phe-Cit, Phe-Arg, Leu-Cit, Ile-Cit, Trp-Cit, Phe-Ala, Ala-Leu-Ala-Leu (SEQ ID NO: 1271), or Gly-Phe-Leu-Gly (SEQ ID NO: 1272). In some instances, the linker comprises a peptide moiety such as: Val-Cit (valine-citrulline), Gly-Gly-Phe-Gly (SEQ ID NO: 1270), Phe-Lys, Val-Lys, Gly-Phe-Lys, Phe-Phe-Lys, Ala-Lys, Val-Arg, Phe-Cit, Phe-Arg, Leu-Cit, Ile-Cit, Trp-Cit, Phe-Ala, Ala-Leu-Ala-Leu (SEQ ID NO: 1271), or Gly-Phe-Leu-Gly (SEQ ID NO: 1272). In some cases, the linker comprises Val-Cit. In some cases, the linker is Val-Cit.

In some embodiments, the linker comprises a benzoic acid group, or its derivatives thereof. In some instances, the benzoic acid group or its derivatives thereof comprise paraaminobenzoic acid (PABA). In some instances, the benzoic acid group or its derivatives thereof comprise gamma-aminobutyric acid (GABA).

In some embodiments, the linker comprises one or more of a maleimide group, a peptide moiety, and/or a benzoic acid group, in any combination. In some embodiments, the linker comprises a combination of a maleimide group, a peptide moiety, and/or a benzoic acid group. In some instances, the maleimide group is maleimidocaproyl (mc). In some instances, the peptide group is val-cit. In some instances, the benzoic acid group is PABA. In some instances, the linker comprises a mc-val-cit group. In some cases, the linker comprises a val-cit-PABA group. In additional cases, the linker comprises a mc-val-cit-PABA group.

In some embodiments, the linker is a self-immolative linker or a self-elimination linker. In some cases, the linker is a self-immolative linker. In other cases, the linker is a self-elimination linker (e.g., a cyclization self-elimination linker). In some instances, the linker comprises a linker described in U.S. Pat. No. 9,089,614 or PCT Publication No. WO2015038426.

In some embodiments, the linker is a dendritic type linker. In some instances, the dendritic type linker comprises a branching, multifunctional linker moiety. In some instances, the dendritic type linker is used to increase the molar ratio of polynucleotide B to the binding moiety A. In some instances, the dendritic type linker comprises PAMAM dendrimers.

In some embodiments, the linker is a traceless linker or a linker in which after cleavage does not leave behind a linker moiety (e.g., an atom or a linker group) to a binding moiety A, a polynucleotide B, a polymer C, or an endosomolytic moiety D. Exemplary traceless linkers include, but are not limited to, germanium linkers, silicium linkers, sulfur linkers, selenium linkers, nitrogen linkers, phosphorus linkers, boron linkers, chromium linkers, or phenylhydrazide linker. In some cases, the linker is a traceless aryl-triazene linker as described in Hejesen, et al., "A traceless aryl-triazene linker for DNA-directed chemistry," *Org Biomol Chem* 11(15): 2493-2497 (2013). In some instances, the linker is a traceless linker described in Blaney, et al., "Traceless solid-phase organic synthesis," *Chem. Rev.* 102: 2607-2024 (2002). In some instances, a linker is a traceless linker as described in U.S. Pat. No. 6,821,783.

In some instances, the linker comprises a functional group that exerts steric hinderance at the site of bonding between the linker and a conjugating moiety (e.g., A, B, C, or D described herein). In some instances, the steric hinderance is a steric hindrance around a disulfide bond. Exemplary linkers that exhibit steric hinderance comprises a heterobifuctional linker, such as a heterobifunctional linker described above. In some cases, a linker that exhibits steric hinderance comprises SMCC and SPDB.

In some instances, the linker is an acid cleavable linker. In some instances, the acid cleavable linker comprises a hydrazone linkage, which is susceptible to hydrolytic cleavage. In some cases, the acid cleavable linker comprises a thiomaleamic acid linker. In some cases, the acid cleavable linker is a thiomaleamic acid linker as described in Castaneda, et al, "Acid-cleavable thiomaleamic acid linker for homogeneous antibody-drug conjugation," *Chem. Commun.* 49: 8187-8189 (2013).

In some instances, the linker is a linker described in U.S. Pat. Nos. 6,884,869; 7,498,298; 8,288,352; 8,609,105; or 8,697,688; U.S. Patent Publication Nos. 2014/0127239; 2013/028919; 2014/286970; 2013/0309256; 2015/037360; or 2014/0294851; or PCT Publication Nos. WO2015057699; WO2014080251; WO2014197854; WO2014145090; or WO2014177042.

In some embodiments, X, Y, and L are independently a bond or a linker. In some instances, X, Y, and L are independently a bond. In some cases, X, Y, and L are independently a linker.

In some instances, X is a bond or a linker. In some instances, X is a bond. In some instances, X is a linker. In some instances, the linker is a $C_1$-$C_6$ alkyl group. In some cases, X is a $C_1$-$C_6$ alkyl group, such as for example, a $C_5$, $C_4$, $C_3$, $C_2$, or $C_1$ alkyl group. In some cases, the $C_1$-$C_6$ alkyl group is an unsubstituted $C_1$-$C_6$ alkyl group. As used in the context of a linker, and in particular in the context of X, alkyl means a saturated straight or branched hydrocarbon radical containing up to six carbon atoms. In some instances, X is a non-polymeric linker. In some instances, X includes a homobifunctional linker or a heterobifunctional linker described supra. In some cases, X includes a heterobifunctional linker. In some cases, X includes sMCC. In other instances, X includes a heterobifuctional linker optionally conjugated to a $C_1$-$C_6$ alkyl group. In other instances, X includes sMCC optionally conjugated to a $C_1$-$C_6$ alkyl group. In additional instances, X does not include a homobifuctional linker or a heterobifunctional linker described supra.

In some instances, Y is a bond or a linker. In some instances, Y is a bond. In other cases, Y is a linker. In some embodiments, Y is a $C_1$-$C_6$ alkyl group. In some instances, Y is a homobifuctional linker or a heterobifunctional linker described supra. In some instances, Y is a homobifuctional linker described supra. In some instances, Y is a heterobifunctional linker described supra. In some instances, Y comprises a maleimide group, such as maleimidocaproyl (mc) or a self-stabilizing maleimide group described above. In some instances, Y comprises a peptide moiety, such as Val-Cit. In some instances, Y comprises a benzoic acid group, such as PABA. In additional instances, Y comprises a combination of a maleimide group, a peptide moiety, and/or a benzoic acid group. In additional instances, Y comprises a mc group. In additional instances, Y comprises a mc-val-cit group. In additional instances, Y comprises a val-cit-PABA group. In additional instances, Y comprises a mc-val-cit-PABA group.

In some instances, L is a bond or a linker. In some cases, L is a bond. In other cases, L is a linker. In some embodiments, L is a $C_1$-$C_6$ alkyl group. In some instances, L is a homobifuctional linker or a heterobifunctional linker described supra. In some instances, L is a homobifuctional linker described supra. In some instances, L is a heterobifunctional linker described supra. In some instances, L comprises a maleimide group, such as maleimidocaproyl (mc) or a self-stabilizing maleimide group described above. In some instances, L comprises a peptide moiety, such as Val-Cit. In some instances, L comprises a benzoic acid group, such as PABA. In additional instances, L comprises a combination of a maleimide group, a peptide moiety, and/or a benzoic acid group. In additional instances, L comprises a mc group. In additional instances, L comprises a mc-val-cit group. In additional instances, L comprises a val-cit-PABA group. In additional instances, L comprises a mc-val-cit-PABA group.

Methods of Use

In some embodiments, a composition or a pharmaceutical formulation described herein comprising a binding moiety conjugated to a polynucleic acid molecule and a polymer is used for the treatment of a disease or disorder. In some instances, the disease or disorder is a cancer. In some embodiments, a composition or a pharmaceutical formulation described herein is used as an immunotherapy for the treatment of a disease or disorder. In some instances, the immunotherapy is an immuno-oncology therapy.

Cancer

In some embodiments, a composition or a pharmaceutical formulation described herein is used for the treatment of cancer. In some instances, the cancer is a solid tumor. In some instances, the cancer is a hematologic malignancy. In some instances, the cancer is a relapsed or refractory cancer, or a metastatic cancer. In some instances, the solid tumor is a relapsed or refractory solid tumor, or a metastatic solid tumor. In some cases, the hematologic malignancy is a relapsed or refractory hematologic malignancy, or a metastatic hematologic malignancy.

In some embodiments, the cancer is a solid tumor. Exemplary solid tumor includes, but is not limited to, anal cancer, appendix cancer, bile duct cancer (i.e., cholangiocarcinoma), bladder cancer, brain tumor, breast cancer, cervical cancer, colon cancer, cancer of Unknown Primary (CUP), esophageal cancer, eye cancer, fallopian tube cancer, gastroenterological cancer, kidney cancer, liver cancer, lung cancer, medulloblastoma, melanoma, oral cancer, ovarian cancer, pancreatic cancer, parathyroid disease, penile cancer, pituitary tumor, prostate cancer, rectal cancer, skin cancer, stomach cancer, testicular cancer, throat cancer, thyroid cancer, uterine cancer, vaginal cancer, or vulvar cancer.

In some instances, a composition or a pharmaceutical formulation described herein comprising a binding moiety conjugated to a polynucleic acid molecule and a polymer is used for the treatment of a solid tumor. In some instances, a composition or a pharmaceutical formulation described herein comprising a binding moiety conjugated to a polynucleic acid molecule and a polymer is used for the treatment of anal cancer, appendix cancer, bile duct cancer (i.e., cholangiocarcinoma), bladder cancer, brain tumor, breast cancer, cervical cancer, colon cancer, cancer of Unknown Primary (CUP), esophageal cancer, eye cancer, fallopian tube cancer, gastroenterological cancer, kidney cancer, liver cancer, lung cancer, medulloblastoma, melanoma, oral cancer, ovarian cancer, pancreatic cancer, parathyroid disease, penile cancer, pituitary tumor, prostate cancer, rectal cancer, skin cancer, stomach cancer, testicular cancer, throat cancer, thyroid cancer, uterine cancer, vaginal cancer, or vulvar cancer. In some instances, the solid tumor is a relapsed or refractory solid tumor, or a metastatic solid tumor.

In some instances, the cancer is a hematologic malignancy. In some instances, the hematologic malignancy is a leukemia, a lymphoma, a myeloma, a non-Hodgkin's lymphoma, or a Hodgkin's lymphoma. In some instances, the hematologic malignancy comprises chronic lymphocytic leukemia (CLL), small lymphocytic lymphoma (SLL), high risk CLL, a non-CLL/SLL lymphoma, prolymphocytic leukemia (PLL), follicular lymphoma (FL), diffuse large B-cell lymphoma (DLBCL), mantle cell lymphoma (MCL), Waldenström's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis.

In some instances, a composition or a pharmaceutical formulation described herein comprising a binding moiety conjugated to a polynucleic acid molecule and a polymer is used for the treatment of a hematologic malignancy. In some instances, a composition or a pharmaceutical formulation described herein comprising a binding moiety conjugated to a polynucleic acid molecule and a polymer is used for the treatment of a leukemia, a lymphoma, a myeloma, a non-Hodgkin's lymphoma, or a Hodgkin's lymphoma. In some instances, the hematologic malignancy comprises chronic lymphocytic leukemia (CLL), small lymphocytic lymphoma (SLL), high risk CLL, a non-CLL/SLL lymphoma, prolymphocytic leukemia (PLL), follicular lymphoma (FL), diffuse large B-cell lymphoma (DLBCL), mantle cell lymphoma (MCL), Waldenström's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis. In some cases, the hematologic malignancy is a relapsed or refractory hematologic malignancy, or a metastatic hematologic malignancy.

In some instances, the cancer is a KRAS-associated, EGFR-associated, AR-associated cancer, HPRT1-associated cancer, or β-catenin associated cancer. In some instances, a composition or a pharmaceutical formulation described herein comprising a binding moiety conjugated to a polynucleic acid molecule and a polymer is used for the treatment of a KRAS-associated, EGFR-associated, AR-associated cancer, HPRT1-associated cancer, or β-catenin associated cancer. In some instances, a composition or a pharmaceutical formulation described herein comprising a binding moiety conjugated to a polynucleic acid molecule and a polymer is used for the treatment of a KRAS-associated cancer. In some instances, a composition or a pharmaceutical formulation described herein comprising a binding moiety conjugated to a polynucleic acid molecule and a polymer is used for the treatment of an EGFR-associated cancer. In some instances, a composition or a pharmaceutical formulation described herein comprising a binding moiety conjugated to a polynucleic acid molecule and a polymer is used for the treatment of an AR-associated cancer. In some instances, a composition or a pharmaceutical formulation described herein comprising a binding moiety conjugated to a polynucleic acid molecule and a polymer is used for the treatment of an HPRT1-associated cancer. In some instances, a composition or a pharmaceutical formulation described herein comprising a binding moiety conjugated to a polynucleic acid molecule and a polymer is used for the treatment of a β-catenin associated cancer. In some instances, the cancer is a solid tumor. In some instances, the cancer is a hematologic malignancy. In some instances, the solid tumor is a relapsed or refractory solid tumor, or a metastatic solid tumor. In some cases, the hematologic malignancy is a relapsed or refractory hematologic malignancy, or a metastatic hematologic malignancy. In some instances, the cancer comprises bladder cancer, breast cancer, colorectal cancer, endometrial cancer, esophageal cancer, glioblastoma multiforme, head and neck cancer, kidney cancer, lung cancer, ovarian cancer, pancreatic cancer, prostate cancer, thyroid cancer, acute myeloid leukemia, CLL, DLBCL, or multiple myeloma. In some instances, the β-catenin associated cancer further comprises PIK3C-associated cancer and/or MYC-associated cancer.

Immunotherapy

In some embodiments, a composition or a pharmaceutical formulation described herein is used as an immunotherapy for the treatment of a disease or disorder. In some instances, the immunotherapy is an immuno-oncology therapy. In some instances, immuno-oncology therapy is categorized into active, passive, or combinatory (active and passive) methods. In active immuno-oncology therapy method, for example, tumor-associated antigens (TAAs) are presented to the immune system to trigger an attack on cancer cells presenting these TAAs. In some instances, the active immune-oncology therapy method includes tumor-targeting and/or immune-targeting agents (e.g., checkpoint inhibitor agents such as monoclonal antibodies), and/or vaccines, such as in situ vaccination and/or cell-based or non-cell based (e.g., dendritic cell-based, tumor cell-based, antigen, anti-idiotype, DNA, or vector-based) vaccines. In some instances, the cell-based vaccines are vaccines which are generated using activated immune cells obtained from a patient's own immune system which are then activated by the patient's own cancer. In some instances, the active immune-oncology therapy is further subdivided into non-specific active immunotherapy and specific active immunotherapy. In some instances, non-specific active immunotherapy utilizes cytokines and/or other cell signaling components to induce a general immune system response. In some cases, specific active immunotherapy utilizes specific TAAs to elicite an immune response.

In some embodiments, a composition or a pharmaceutical formulation described herein is used as an active immuno-oncology therapy method for the treatment of a disease or disorder (e.g., cancer). In some embodiments, the composition or a pharmaceutical formulation described herein comprises a tumor-targeting agent. In some instances, the tumor-targeting agent is encompassed by a binding moiety A. In other instances, the tumor-targeting agent is an additional agent used in combination with a molecule of Formula (I). In some instances, the tumor-targeting agent is a tumor-directed polypeptide (e.g., a tumor-directed antibody). In some instances, the tumor-targeting agent is a tumor-directed antibody, which exerts its antitumor activity through mechanisms such as direct killing (e.g., signaling-induced apoptosis), complement-dependent cytotoxicity (CDC), and/or antibody-dependent cell-mediated cytotoxicity (ADCC). In additional instances, the tumor-targeting agent elicits an adaptive immune response, with the induction of antitumor T cells.

In some embodiments, the binding moiety A is a tumor-directed polypeptide (e.g., a tumor-directed antibody). In some instances, the binding moiety A is a tumor-directed antibody, which exerts its antitumor activity through mechanisms such as direct killing (e.g., signaling-induced apoptosis), complement-dependent cytotoxicity (CDC), and/or antibody-dependent cell-mediated cytotoxicity (ADCC). In additional instances, the binding moiety A elicits an adaptive immune response, with the induction of antitumor T cells.

In some embodiments, the composition or a pharmaceutical formulation described herein comprises an immune-targeting agent. In some instances, the immune-targeting agent is encompassed by a binding moiety A. In other instances, the immune-targeting agent is an additional agent used in combination with a molecule of Formula (I). In some instances, the immune-targeting agent comprises cytokines, checkpoint inhibitors, or a combination thereof.

In some embodiments, the immune-targeting agent is a checkpoint inhibitor. In some cases, an immune checkpoint molecule is a molecule presented on the cell surface of CD4 and/or CD8 T cells. Exemplary immune checkpoint molecules include, but are not limited to, Programmed Death-Ligand 1 (PD-L1, also known as B7-H1, CD274), Programmed Death 1 (PD-1), CTLA-4, B7H1, B7H4, OX-40, CD137, CD40, 2B4, IDOL IDO2, VISTA, CD27, CD28, PD-L2 (B7-DC, CD273), LAG3, CD80, CD86, PDL2, B7H3, HVEM, BTLA, KIR, GAL9, TIM3, A2aR, MARCO (macrophage receptor with collageneous structure), PS (phosphatidylserine), ICOS (inducible T cell costimulator), HAVCR2, CD276, VTCN1, CD70, and CD160.

In some instances, an immune checkpoint inhibitor refers to any molecule that modulates or inhibits the activity of an immune checkpoint molecule. In some instances, immune checkpoint inhibitors include antibodies, antibody-derivatives (e.g., Fab fragments, scFvs, minobodies, diabodies), antisense oligonucleotides, siRNA, aptamers, or peptides. In some embodiments, an immune checkpoint inhibitor is an inhibitor of Programmed Death-Ligand 1 (PD-L1, also known as B7-H1, CD274), Programmed Death 1 (PD-1), CTLA-4, PD-L2 (B7-DC, CD273), LAG3, TIM3, 2B4, A2aR, B7H1, B7H3, B7H4, BTLA, CD2, CD27, CD28, CD30, CD40, CD70, CD80, CD86, CD137, CD160, CD226, CD276, DR3, GAL9, GITR, HAVCR2, HVEM, IDO1, IDO2, ICOS (inducible T cell costimulator), KIR, LAIR1, LIGHT, MARCO (macrophage receptor with col-lageneous structure), PS (phosphatidylserine), OX-40, SLAM, TIGHT, VISTA, VTCN1, or any combinations thereof.

In some embodiments, exemplary checkpoint inhibitors include:
PD-L1 inhibitors such as Genentech's MPDL3280A (RG7446), Anti-mouse PD-L1 antibody Clone 10F.9G2 (Cat #BE0101) from BioXcell, anti-PD-L1 monoclonal antibody MDX-1105 (BMS-936559) and BMS-935559 from Bristol-Meyer's Squibb, MSB0010718C, mouse anti-PD-L1 Clone 29E.2A3, and AstraZeneca's MEDI4736;
PD-L2 inhibitors such as GlaxoSmithKline's AMP-224 (Amplimmune), and rHIgM12B7;
PD-1 inhibitors such as anti-mouse PD-1 antibody Clone J43 (Cat #BE0033-2) from BioXcell, anti-mouse PD-1 antibody Clone RMP1-14 (Cat #BE0146) from BioXcell, mouse anti-PD-1 antibody Clone EH12, Merck's MK-3475 anti-mouse PD-1 antibody (Keytruda, pembrolizumab, lambrolizumab), AnaptysBio's anti-PD-1 antibody known as ANB011, antibody MDX-1 106 (ONO-4538), Bristol-Myers Squibb's human IgG4 monoclonal antibody nivolumab (Opdivo®, BMS-936558, MDX1106), AstraZeneca's AMP-514 and AMP-224, and Pidilizumab (CT-011) from CureTech Ltd;
CTLA-4 inhibitors such as Bristol Meyers Squibb's anti-CTLA-4 antibody ipilimumab (also known as Yervoy®, MDX-010, BMS-734016 and MDX-101), anti-CTLA4 Antibody, clone 9H10 from Millipore, Pfizer's tremelimumab (CP-675,206, ticilimumab), and anti-CTLA4 antibody clone BNI3 from Abcam;
LAG3 inhibitors such as anti-Lag-3 antibody clone eBioC9B7W (C9B7W) from eBioscience, anti-Lag3 antibody LS-B2237 from LifeSpan Biosciences, IMP321 (ImmuFact) from Immutep, anti-Lag3 antibody BMS-986016, and the LAG-3 chimeric antibody A9H12;
B7-H3 inhibitors such as MGA271;
KIR inhibitors such as Lirilumab (IPH2101);
CD137 (41BB) inhibitors such as urelumab (BMS-663513, Bristol-Myers Squibb), PF-05082566 (anti-4-1BB, PF-2566, Pfizer), or XmAb-5592 (Xencor);
PS inhibitors such as Bavituximab;
and inhibitors such as an antibody or fragments (e.g., a monoclonal antibody, a human, humanized, or chimeric antibody) thereof, RNAi molecules, or small molecules to TIM3, CD52, CD30, CD20, CD33, CD27, OX40 (CD134), GITR, ICOS, BTLA (CD272), CD160, 2B4, LAIR1, TIGHT, LIGHT, DR3, CD226, CD2, or SLAM.

In some embodiments, a binding moiety A comprising an immune checkpoint inhibitor is used for the treatment of a disease or disorder (e.g., cancer). In some instances, the binding moiety A is a bispecific antibody or a binding fragment thereof that comprises an immune checkpoint inhibitor. In some cases, a binding moiety A comprising an inhibitor of Programmed Death-Ligand 1 (PD-L1, also known as B7-H1, CD274), Programmed Death 1 (PD-1), CTLA-4, PD-L2 (B7-DC, CD273), LAG3, TIM3, 2B4, A2aR, B7H1, B7H3, B7H4, BTLA, CD2, CD27, CD28, CD30, CD40, CD70, CD80, CD86, CD137, CD160, CD226, CD276, DR3, GAL9, GITR, HAVCR2, HVEM, IDO1, IDO2, ICOS (inducible T cell costimulator), KIR, LAIR1, LIGHT, MARCO (macrophage receptor with col-lageneous structure), PS (phosphatidylserine), OX-40, SLAM, TIGHT, VISTA, VTCN1, or any combinations thereof, is used for the treatment of a disease or disorder (e.g., cancer).

In some embodiments, a molecule of Formula (I) in combination with an immune checkpoint inhibitor is used for the treatment of a disease or disorder (e.g., cancer). In some instances, the immune checkpoint inhibitor comprises an inhibitor of Programmed Death-Ligand 1 (PD-L1, also known as B7-H1, CD274), Programmed Death 1 (PD-1), CTLA-4, PD-L2 (B7-DC, CD273), LAG3, TIM3, 2B4, A2aR, B7H1, B7H3, B7H4, BTLA, CD2, CD27, CD28, CD30, CD40, CD70, CD80, CD86, CD137, CD160, CD226, CD276, DR3, GAL9, GITR, HAVCR2, HVEM, IDO1, IDO2, ICOS (inducible T cell costimulator), KIR, LAIR1, LIGHT, MARCO (macrophage receptor with collageneous structure), PS (phosphatidylserine), OX-40, SLAM, TIGHT, VISTA, VTCN1, or any combinations thereof. In some cases, a molecule of Formula (I) is used in combination with ipilimumab, tremelimumab, nivolumab, pembrolizumab, pidilizumab, MPDL3280A, MEDI4736, MSB0010718C, MK-3475, or BMS-936559, for the treatment of a disease or disorder (e.g., cancer).

In some embodiments, the immune-targeting agent is a cytokine. In some cases, cytokine is further subgrouped into chemokine, interferon, interleukin, and tumor necrosis factor. In some embodiments, chemokine plays a role as a chemoattractant to guide the migration of cells, and is classified into four subfamilies: CXC, CC, CX3C, and XC. Exemplary chemokines include chemokines from the CC subfamily: CCL1, CCL2 (MCP-1), CCL3, CCL4, CCL5 (RANTES), CCL6, CCL7, CCL8, CCL9 (or CCL10), CCL11, CCL12, CCL13, CCL14, CCL15, CCL16, CCL17, CCL18, CCL19, CCL20, CCL21, CCL22, CCL23, CCL24, CCL25, CCL26, CCL27, and CCL28; the CXC subfamily: CXCL1, CXCL2, CXCL3 CXCL4, CXCL5, CXCL6, CXCL7, CXCL8, CXCL9, CXCL10, CXCL11, CXCL12, CXCL13, CXCL14, CXCL15, CXCL16, and CXCL17, the XC subfamily XCL1 and XCL2; and the CX3C subfamily CX3CL1.

Interferon (IFNs) comprises interferon type I (e.g. IFN-α, IFN-β, IFN-ε, IFN-κ, and IFN-ω), interferon type II (e.g. IFN-γ), and interferon type III. In some embodiments, IFN-α is further classified into about 13 subtypes which include IFNA1, IFNA2, IFNA4, IFNA5, IFNA6, IFNA7, IFNA8, IFNA10, IFNA13, IFNA14, IFNA16, IFNA17, and IFNA21.

Interleukin is expressed by leukocyte or white blood cell and promote the development and differentiation of T and B lymphocytes and hematopoietic cells. Exemplary interleukins include IL-1, IL-2, IL-3, IL-4, IL-5, IL-6, IL-7, IL-8 (CXCL8), IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-35, and IL-36.

Tumor necrosis factors (TNFs) are a group of cytokines that modulate apoptosis. In some instances, there are about 19 members within the TNF family, including, not limited to, TNFα, lymphotoxin-alpha (LT-alpha), lymphotoxin-beta (LT-beta). T cell antigen gp39 (CD40L), CD27L, CD30L, FASL, OX40L, and TNF-related apoptosis inducing ligand (TRAIL).

In some embodiments, a molecule of Formula (I) in combination with a cytokine is used for the treatment of a disease or disorder (e.g., cancer). In some cases, a molecule of Formula (I) in combination with a chemokine is used for the treatment of a disease or disorder (e.g., cancer). In some cases, a molecule of Formula (I) in combination with an interferon is used for the treatment of a disease or disorder (e.g., cancer). In some cases, a molecule of Formula (I) in combination with an interleukin is used for the treatment of a disease or disorder (e.g., cancer). In some cases, a molecule of Formula (I) in combination with a tumor necrosis factor is used for the treatment of a disease or disorder (e.g., cancer). In some instances, a molecule of Formula (I) in combination with IL-1β, IL-2, IL-7, IL-8, IL-15, MCP-1 (CCL2), MIP-1α, RANTES, MCP-3, MIP5, CCL19, CCL21, CXCL2, CXCL9, CXCL10, or CXCL11 is used for the treatment of a disease or disorder (e.g., cancer).

In some embodiments, the composition or a pharmaceutical formulation described herein comprises a vaccine. In some instances, the vaccine is an in situ vaccination. In some instances, the vaccine is a cell-based vaccine. In some instances, the vaccine is a non-cell based vaccine. In some instances, a molecule of Formula (I) in combination with dendritic cell-based vaccine is used for the treatment of a disease or disorder (e.g., cancer). In some instances, a molecule of Formula (I) in combination with tumor cell-based vaccine is used for the treatment of a disease or disorder (e.g., cancer). In some instances, a molecule of Formula (I) in combination with antigen vaccine is used for the treatment of a disease or disorder (e.g., cancer). In some instances, a molecule of Formula (I) in combination with anti-idiotype vaccine is used for the treatment of a disease or disorder (e.g., cancer). In some instances, a molecule of Formula (I) in combination with DNA vaccine is used for the treatment of a disease or disorder (e.g., cancer). In some instances, a molecule of Formula (I) in combination with vector-based vaccine is used for the treatment of a disease or disorder (e.g., cancer).

In some embodiments, a composition or a pharmaceutical formulation described herein is used as a passive immuno-oncology therapy method for the treatment of a disease or disorder (e.g., cancer). The passive method, in some instances, utilizes adoptive immune system components such as T cells, natural killer (NK) T cells, and/or chimeric antigen receptor (CAR) T cells generated exogenously to attack cancer cells.

In some embodiments, a molecule of Formula (I) in combination with a T-cell based therapeutic agent is used for the treatment of a disease or disorder (e.g., cancer). In some cases, the T-cell based therapeutic agent is an activated T-cell agent that recognizes one or more of a CD cell surface marker described above. In some instances, the T-cell based therapeutic agent comprises an activated T-cell agent that recognizes one or more of CD2, CD3, CD4, CD5, CD8, CD27, CD28, CD80, CD134, CD137, CD152, CD154, CD160, CD200R, CD223, CD226, CD244, CD258, CD267, CD272, CD274, CD278, CD279, or CD357. In some instances, a molecule of Formula (I) in combination with an activated T-cell agent recognizing one or more of CD2, CD3, CD4, CD5, CD8, CD27, CD28, CD80, CD134, CD137, CD152, CD154, CD160, CD200R, CD223, CD226, CD244, CD258, CD267, CD272, CD274, CD278, CD279, or CD357 is used for the treatment of a disease or disorder (e.g., cancer).

In some embodiments, a molecule of Formula (I) in combination with natural killer (NK) T cell-based therapeutic agent is used for the treatment of a disease or disorder (e.g., cancer). In some instances, the NK-based therapeutic agent is an activated NK agent that recognizes one or more of a CD cell surface marker described above. In some cases, the NK-based therapeutic agent is an activated NK agent that recognizes one or more of CD2, CD11a, CD11b, CD16, CD56, CD58, CD62L, CD85j, CD158a/b, CD158c, CD158e/f/k, CD158h/j, CD159a, CD162, CD226, CD314, CD335, CD337, CD244, or CD319. In some instances, a molecule of Formula (I) in combination with an activated NK agent recognizing one or more of CD2, CD11a, CD11b, CD16, CD56, CD58, CD62L, CD85j, CD158a/b, CD158c, CD158e/f/k, CD158h/j, CD159a, CD162, CD226, CD314, CD335, CD337, CD244, or CD319 is used for the treatment of a disease or disorder (e.g., cancer).

In some embodiments, a molecule of Formula (I) in combination with CAR-T cell-based therapeutic agent is used for the treatment of a disease or disorder (e.g., cancer).

In some embodiments, a molecule of Formula (I) in combination with an additional agent that destabilizes the endosomal membrane (or disrupts the endosomal-lysosomal membrane trafficking) is used for the treatment of a disease or disorder (e.g., cancer). In some instances, the additional agent comprises an antimitotic agent. Exemplary antimitotic agents include, but are not limited to, taxanes such as paclitaxel and docetaxel; vinca alkaloids such as vinblastine, vincristine, vindesine, and vinorelbine; cabazitaxel; colchicine; eribulin; estramustine; etoposide; ixabepilone; podophyllotoxin; teniposide; or griseofulvin. In some instances, the additional agent comprises paclitaxel, docetaxel, vinblastine, vincristine, vindesine, vinorelbine, cabazitaxel, colchicine, eribulin, estramustine, etoposide, ixabepilone, podophyllotoxin, teniposide, or griseofulvin. In some instances, the additional agent comprises taxol. In some instances, the additional agent comprises paclitaxel. In some instances, the additional agent comprises etoposide. In other instances, the additional agent comprises vitamin K3.

In some embodiments, a composition or a pharmaceutical formulation described herein is used as a combinatory method (including for both active and passive methods) in the treatment of a disease or disorder (e.g., cancer).

Pharmaceutical Formulation

In some embodiments, the pharmaceutical formulations described herein are administered to a subject by multiple administration routes, including but not limited to, parenteral (e.g., intravenous, subcutaneous, intramuscular), oral, intranasal, buccal, rectal, or transdermal administration routes. In some instances, the pharmaceutical composition describe herein is formulated for parenteral (e.g., intravenous, subcutaneous, intramuscular) administration. In other instances, the pharmaceutical composition describe herein is formulated for oral administration. In still other instances, the pharmaceutical composition describe herein is formulated for intranasal administration.

In some embodiments, the pharmaceutical formulations include, but are not limited to, aqueous liquid dispersions, self-emulsifying dispersions, solid solutions, liposomal dispersions, aerosols, solid dosage forms, powders, immediate-release formulations, controlled-release formulations, fast melt formulations, tablets, capsules, pills, delayed release formulations, extended release formulations, pulsatile release formulations, multiparticulate formulations (e.g., nanoparticle formulations), and mixed immediate and controlled release formulations.

In some instances, the pharmaceutical formulation includes multiparticulate formulations. In some instances, the pharmaceutical formulation includes nanoparticle formulations. In some instances, nanoparticles comprise cMAP, cyclodextrin, or lipids. In some cases, nanoparticles comprise solid lipid nanoparticles, polymeric nanoparticles, self-emulsifying nanoparticles, liposomes, microemulsions, or micellar solutions. Additional exemplary nanoparticles include, but are not limited to, paramagnetic nanoparticles, superparamagnetic nanoparticles, metal nanoparticles, fullerene-like materials, inorganic nanotubes, dendrimers (such as with covalently attached metal chelates), nanofibers, nanohorns, nano-onions, nanorods, nanoropes and quantum dots. In some instances, a nanoparticle is a metal nanoparticle, e.g., a nanoparticle of scandium, titanium, vanadium, chromium, manganese, iron, cobalt, nickel, copper, zinc, yttrium, zirconium, niobium, molybdenum, ruthenium, rhodium, palladium, silver, cadmium, hafnium, tantalum, tungsten, rhenium, osmium, iridium, platinum, gold, gadolinium, aluminum, gallium, indium, tin, thallium, lead, bismuth, magnesium, calcium, strontium, barium, lithium, sodium, potassium, boron, silicon, phosphorus, germanium, arsenic, antimony, and combinations, alloys or oxides thereof.

In some instances, a nanoparticle includes a core or a core and a shell, as in a core-shell nanoparticle.

In some instances, a nanoparticle is further coated with molecules for attachment of functional elements (e.g., with one or more of a polynucleic acid molecule or binding moiety described herein). In some instances, a coating comprises chondroitin sulfate, dextran sulfate, carboxymethyl dextran, alginic acid, pectin, carragheenan, fucoidan, agaropectin, porphyran, karaya gum, gellan gum, xanthan gum, hyaluronic acids, glucosamine, galactosamine, chitin (or chitosan), polyglutamic acid, polyaspartic acid, lysozyme, cytochrome C, ribonuclease, trypsinogen, chymotrypsinogen, α-chymotrypsin, polylysine, polyarginine, histone, protamine, ovalbumin, dextrin, or cyclodextrin. In some instances, a nanoparticle comprises a graphene-coated nanoparticle.

In some cases, a nanoparticle has at least one dimension of less than about 500 nm, 400 nm, 300 nm, 200 nm, or 100 nm.

In some instances, the nanoparticle formulation comprises paramagnetic nanoparticles, superparamagnetic nanoparticles, metal nanoparticles, fullerene-like materials, inorganic nanotubes, dendrimers (such as with covalently attached metal chelates), nanofibers, nanohorns, nano-onions, nanorods, nanoropes or quantum dots. In some instances, a polynucleic acid molecule or a binding moiety described herein is conjugated either directly or indirectly to the nanoparticle. In some instances, at least 1, 5, 10, 15, 20, 30, 40, 50, 60, 70, 80, 90, 100, or more polynucleic acid molecules or binding moieties described herein are conjugated either directly or indirectly to a nanoparticle.

In some embodiments, the pharmaceutical formulations include a carrier or carrier materials selected on the basis of compatibility with the composition disclosed herein, and the release profile properties of the desired dosage form. Exemplary carrier materials include, e.g., binders, suspending agents, disintegration agents, filling agents, surfactants, solubilizers, stabilizers, lubricants, wetting agents, diluents, and the like. Pharmaceutically compatible carrier materials include, but are not limited to, acacia, gelatin, colloidal silicon dioxide, calcium glycerophosphate, calcium lactate, maltodextrin, glycerine, magnesium silicate, polyvinylpyrrollidone (PVP), cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like. See, e.g., *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pennsylvania 1975; Liberman, H. A. and Lachman, L., Eds., *Pharmaceutical Dosage*

*Forms*, Marcel Decker, New York, N.Y., 1980; and *Pharmaceutical Dosage Forms and* Drug Delivery Systems, Seventh Ed. (Lippincott Williams & Wilkins 1999).

In some instances, the pharmaceutical formulations further include pH-adjusting agents or buffering agents which include acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

In some instances, the pharmaceutical formulation includes one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

In some instances, the pharmaceutical formulations further include diluent which are used to stabilize compounds because they can provide a more stable environment. Salts dissolved in buffered solutions (which also can provide pH control or maintenance) are utilized as diluents in the art, including, but not limited to a phosphate buffered saline solution. In certain instances, diluents increase bulk of the composition to facilitate compression or create sufficient bulk for homogenous blend for capsule filling. Such compounds can include e.g., lactose, starch, mannitol, sorbitol, dextrose, microcrystalline cellulose such as Avicel®; dibasic calcium phosphate, dicalcium phosphate dihydrate; tricalcium phosphate, calcium phosphate; anhydrous lactose, spray-dried lactose; pregelatinized starch, compressible sugar, such as Di-Pac® (Amstar); mannitol, hydroxypropylmethylcellulose, hydroxypropylmethylcellulose acetate stearate, sucrose-based diluents, confectioner's sugar; monobasic calcium sulfate monohydrate, calcium sulfate dihydrate; calcium lactate trihydrate, dextrates; hydrolyzed cereal solids, amylose; powdered cellulose, calcium carbonate; glycine, kaolin; mannitol, sodium chloride; inositol, bentonite, and the like.

In some cases, the pharmaceutical formulations include disintegration agents or disintegrants to facilitate the breakup or disintegration of a substance. The term "disintegrate" include both the dissolution and dispersion of the dosage form when contacted with gastrointestinal fluid. Examples of disintegration agents include a starch, e.g., a natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol), cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

In some instances, the pharmaceutical formulations include filling agents such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

Lubricants and glidants are also optionally included in the pharmaceutical formulations described herein for preventing, reducing or inhibiting adhesion or friction of materials. Exemplary lubricants include, e.g., stearic acid, calcium hydroxide, talc, sodium stearyl fumerate, a hydrocarbon such as mineral oil, or hydrogenated vegetable oil such as hydrogenated soybean oil)(Sterotex®, higher fatty acids and their alkali-metal and alkaline earth metal salts, such as aluminum, calcium, magnesium, zinc, stearic acid, sodium stearates, glycerol, talc, waxes, Stearowet®, boric acid, sodium benzoate, sodium acetate, sodium chloride, leucine, a polyethylene glycol (e.g., PEG-4000) or a methoxypolyethylene glycol such as Carbowax™, sodium oleate, sodium benzoate, glyceryl behenate, polyethylene glycol, magnesium or sodium lauryl sulfate, colloidal silica such as Syloid™, Cab-O-Sil®, a starch such as corn starch, silicone oil, a surfactant, and the like.

Plasticizers include compounds used to soften the microencapsulation material or film coatings to make them less brittle. Suitable plasticizers include, e.g., polyethylene glycols such as PEG 300, PEG 400, PEG 600, PEG 1450, PEG 3350, and PEG 800, stearic acid, propylene glycol, oleic acid, triethyl cellulose and triacetin. Plasticizers can also function as dispersing agents or wetting agents.

Solubilizers include compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, dimethyl isosorbide, and the like.

Stabilizers include compounds such as any antioxidation agents, buffers, acids, preservatives and the like.

Suspending agents include compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol can have a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

Surfactants include compounds such as sodium lauryl sulfate, sodium docusate, Tween 60 or 80, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. Additional surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40. Sometimes, surfactants is included to enhance physical stability or for other purposes.

Viscosity enhancing agents include, e.g., methyl cellulose, xanthan gum, carboxymethyl cellulose, hydroxypropyl cellulose, hydroxypropylmethyl cellulose, hydroxypropylmethyl cellulose acetate stearate, hydroxypropylmethyl cellulose phthalate, carbomer, polyvinyl alcohol, alginates, acacia, chitosans and combinations thereof.

Wetting agents include compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium docusate, sodium oleate, sodium lauryl sulfate, sodium doccusate, triacetin, Tween 80, vitamin E TPGS, ammonium salts and the like.

Therapeutic Regimens

In some embodiments, the pharmaceutical compositions described herein are administered for therapeutic applications. In some embodiments, the pharmaceutical composition is administered once per day, twice per day, three times per day or more. The pharmaceutical composition is administered daily, every day, every alternate day, five days a week, once a week, every other week, two weeks per month, three weeks per month, once a month, twice a month, three times per month, or more. The pharmaceutical composition is administered for at least 1 month, 2 months, 3 months, 4 months, 5 months, 6 months, 7 months, 8 months, 9 months, 10 months, 11 months, 12 months, 18 months, 2 years, 3 years, or more.

In some embodiments, one or more pharmaceutical compositions are administered simultaneously, sequentially, or at an interval period of time. In some embodiments, one or more pharmaceutical compositions are administered simultaneously. In some cases, one or more pharmaceutical compositions are administered sequentially. In additional cases, one or more pharmaceutical compositions are administered at an interval period of time (e.g., the first administration of a first pharmaceutical composition is on day one followed by an interval of at least 1, 2, 3, 4, 5, or more days prior to the administration of at least a second pharmaceutical composition).

In some embodiments, two or more different pharmaceutical compositions are coadministered. In some instances, the two or more different pharmaceutical compositions are coadministered simultaneously. In some cases, the two or more different pharmaceutical compositions are coadministered sequentially without a gap of time between administrations. In other cases, the two or more different pharmaceutical compositions are coadministered sequentially with a gap of about 0.5 hour, 1 hour, 2 hour, 3 hour, 12 hours, 1 day, 2 days, or more between administrations.

In the case wherein the patient's status does improve, upon the doctor's discretion the administration of the composition is given continuously; alternatively, the dose of the composition being administered is temporarily reduced or temporarily suspended for a certain length of time (i.e., a "drug holiday"). In some instances, the length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday is from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, are optionally reduced, as a function of the symptoms, to a level at which the improved disease, disorder or condition is retained.

In some embodiments, the amount of a given agent that correspond to such an amount varies depending upon factors such as the particular compound, the severity of the disease, the identity (e.g., weight) of the subject or host in need of treatment, but nevertheless is routinely determined in a manner known in the art according to the particular circumstances surrounding the case, including, e.g., the specific agent being administered, the route of administration, and the subject or host being treated. In some instances, the desired dose is conveniently presented in a single dose or as divided doses administered simultaneously (or over a short period of time) or at appropriate intervals, for example as two, three, four or more sub-doses per day.

The foregoing ranges are merely suggestive, as the number of variables in regard to an individual treatment regime is large, and considerable excursions from these recommended values are not uncommon. Such dosages are altered depending on a number of variables, not limited to the activity of the compound used, the disease or condition to be treated, the mode of administration, the requirements of the individual subject, the severity of the disease or condition being treated, and the judgment of the practitioner.

In some embodiments, toxicity and therapeutic efficacy of such therapeutic regimens are determined by standard pharmaceutical procedures in cell cultures or experimental animals, including, but not limited to, the determination of the LD50 (the dose lethal to 50% of the population) and the ED50 (the dose therapeutically effective in 50% of the population). The dose ratio between the toxic and therapeutic effects is the therapeutic index and it is expressed as the ratio between LD50 and ED50. Compounds exhibiting high therapeutic indices are preferred. The data obtained from cell culture assays and animal studies are used in formulating a range of dosage for use in human. The dosage of such compounds lies preferably within a range of circulating concentrations that include the ED50 with minimal toxicity. The dosage varies within this range depending upon the dosage form employed and the route of administration utilized.

Kits/Article of Manufacture

Disclosed herein, in certain embodiments, are kits and articles of manufacture for use with one or more of the compositions and methods described herein. Such kits include a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In one embodiment, the containers are formed from a variety of materials such as glass or plastic.

The articles of manufacture provided herein contain packaging materials. Examples of pharmaceutical packaging materials include, but are not limited to, blister packs, bottles, tubes, bags, containers, bottles, and any packaging material suitable for a selected formulation and intended mode of administration and treatment.

For example, the container(s) include a molecule of Formula (I): A-X-B-Y-C, optionally conjugated to an endosomolytic moiety D as disclosed herein. Such kits optionally include an identifying description or label or instructions relating to its use in the methods described herein.

A kit typically includes labels listing contents and/or instructions for use and package inserts with instructions for use. A set of instructions will also typically be included.

In one embodiment, a label is on or associated with the container. In one embodiment, a label is on a container when letters, numbers, or other characters forming the label are attached, molded or etched into the container itself; a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

In certain embodiments, the pharmaceutical compositions are presented in a pack or dispenser device which contains one or more unit dosage forms containing a compound provided herein. The pack, for example, contains metal or plastic foil, such as a blister pack. In one embodiment, the pack or dispenser device is accompanied by instructions for administration. In one embodiment, the pack or dispenser is also accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In one embodiment, compositions containing a compound provided herein formulated in a compatible pharmaceutical carrier are also prepared, placed in an appropriate container, and labeled for treatment of an indicated condition.

Certain Terminology

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

As used herein, ranges and amounts can be expressed as "about" a particular value or range. About also includes the exact amount. Hence "about 5 µL" means "about 5 µL" and also "5 µL." Generally, the term "about" includes an amount that is expected to be within experimental error.

The section headings used herein are for organizational purposes only and are not to be construed as limiting the subject matter described.

As used herein, the terms "individual(s)", "subject(s)" and "patient(s)" mean any mammal. In some embodiments, the mammal is a human. In some embodiments, the mammal is a non-human. None of the terms require or are limited to situations characterized by the supervision (e.g. constant or intermittent) of a health care worker (e.g. a doctor, a registered nurse, a nurse practitioner, a physician's assistant, an orderly or a hospice worker).

EXAMPLES

These examples are provided for illustrative purposes only and not to limit the scope of the claims provided herein.

Chemical Synthesis Examples

Example 1. Preparation of Compound 1-3, and 5-8

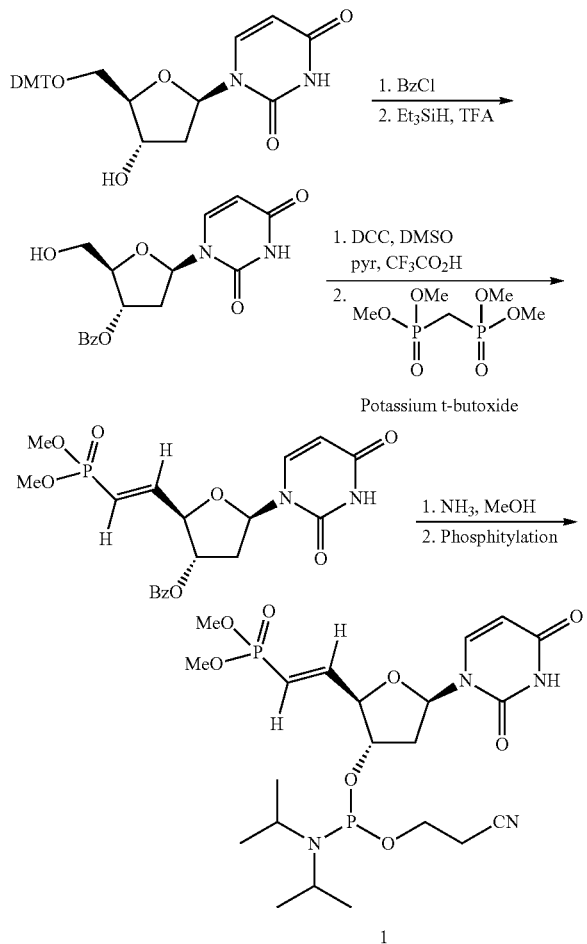

or as follows

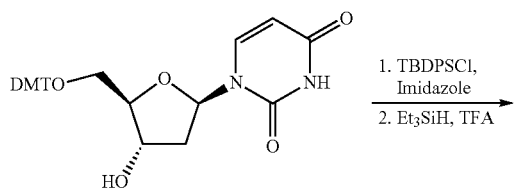

111
-continued
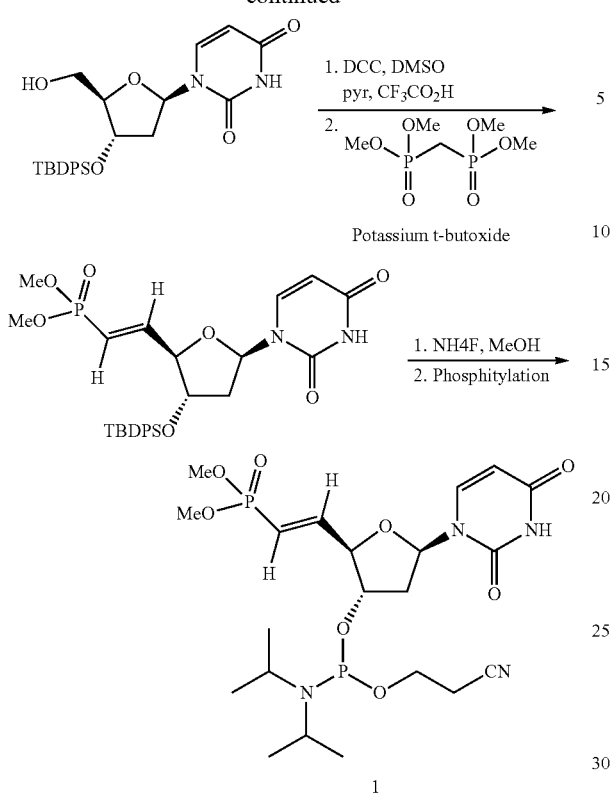
Compounds 2, 3, and 5-8 were prepared as per procedures illustrated in Example 1.
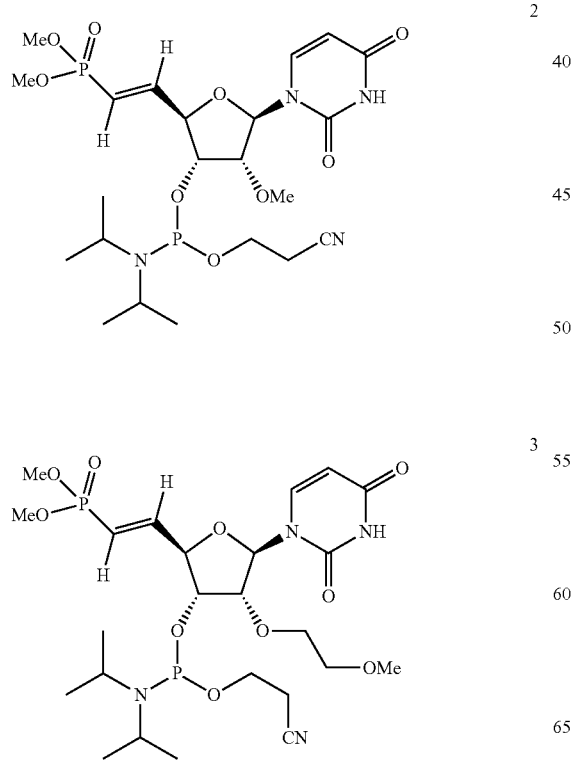
112
-continued
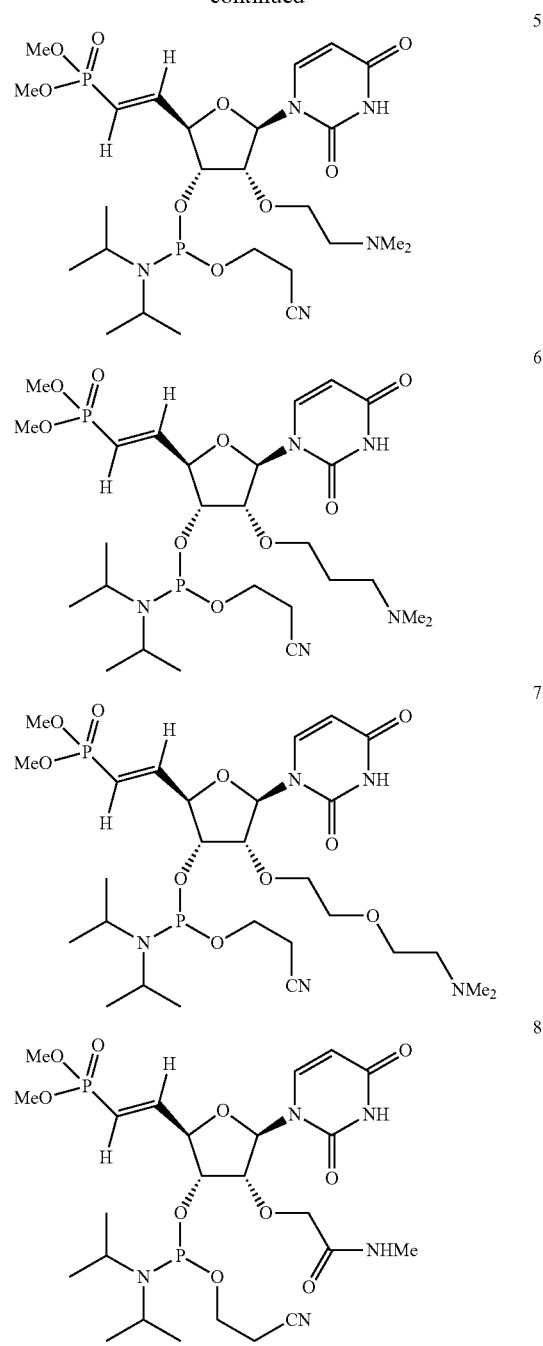
Example 2. Preparation of Compound 4
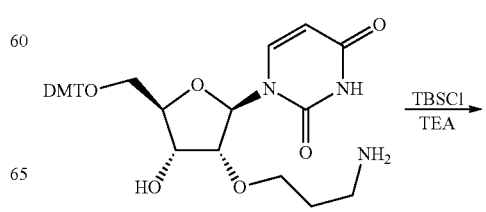

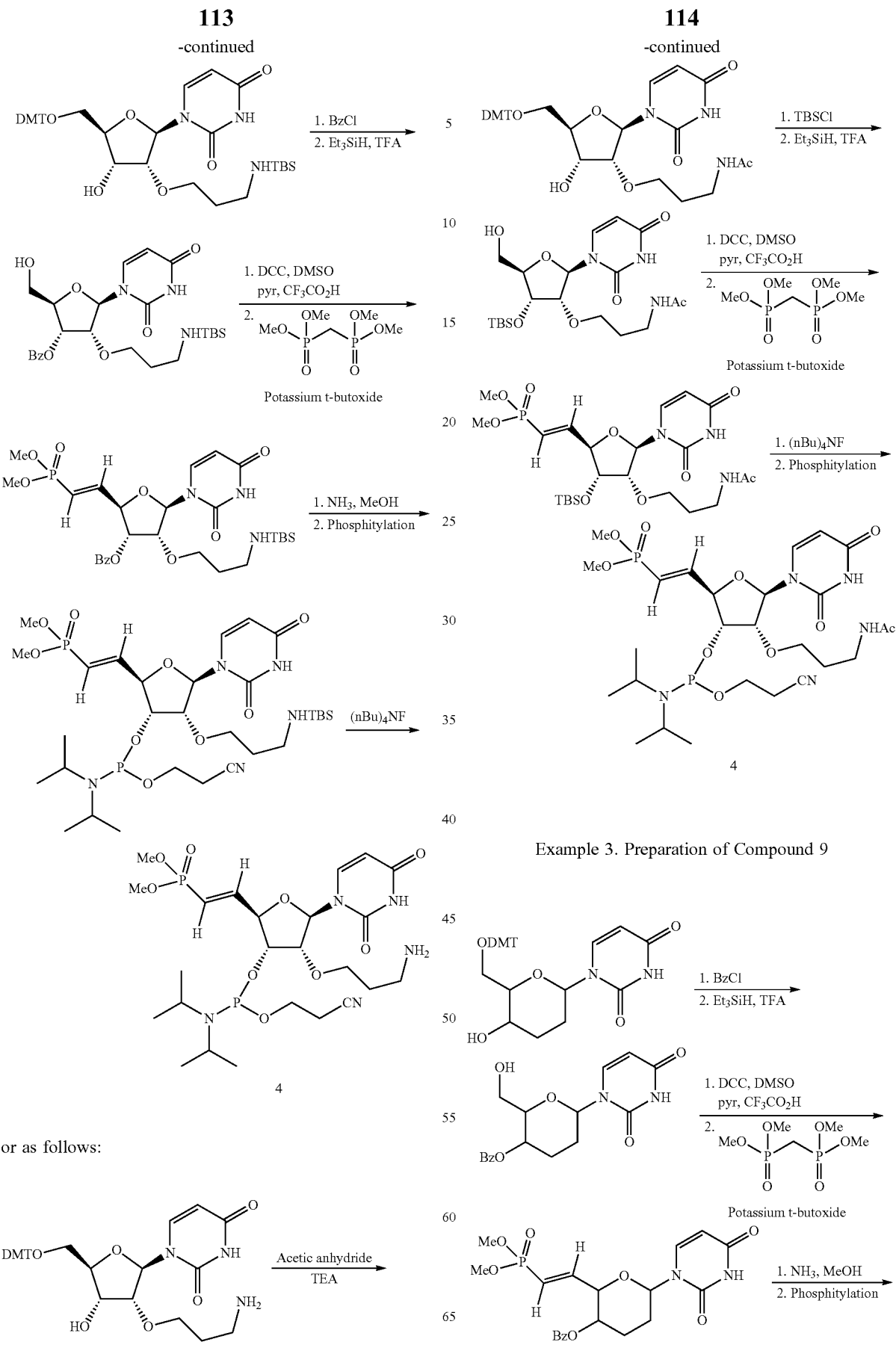
Example 3. Preparation of Compound 9

-continued
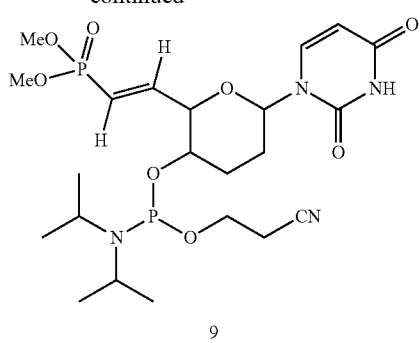
9
or as follows:
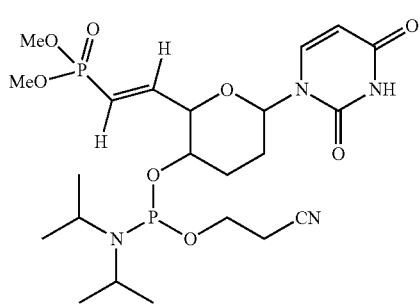
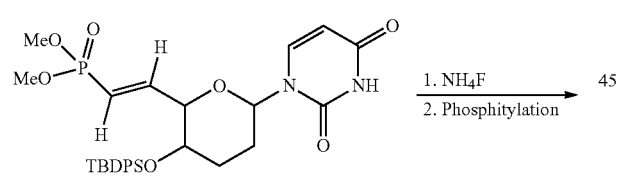
Example 4. Preparation of Compound 10
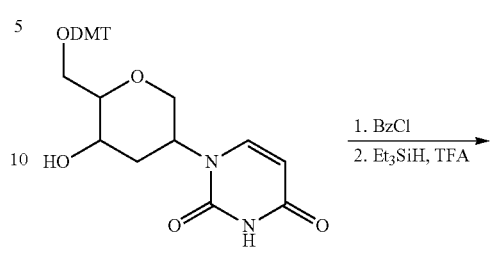
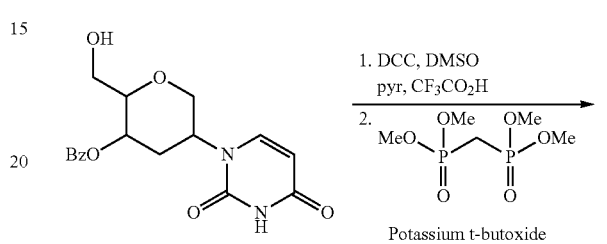
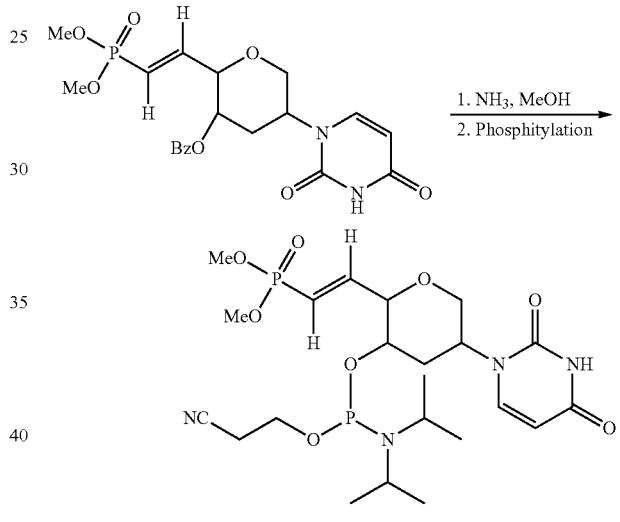
10
or as follows:

117
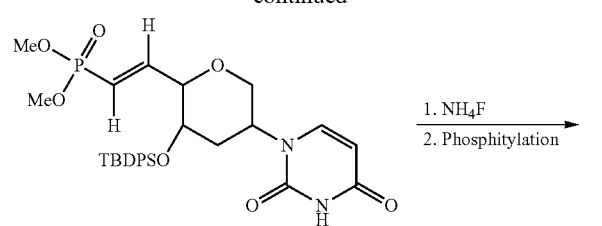
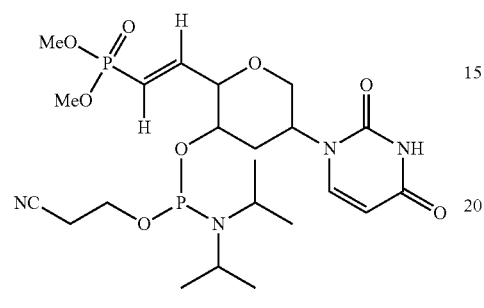
Example 5. Preparation of Compound 11
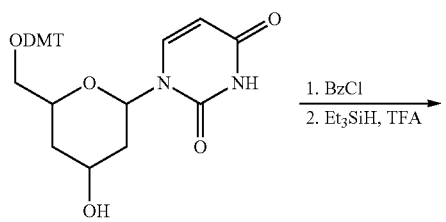
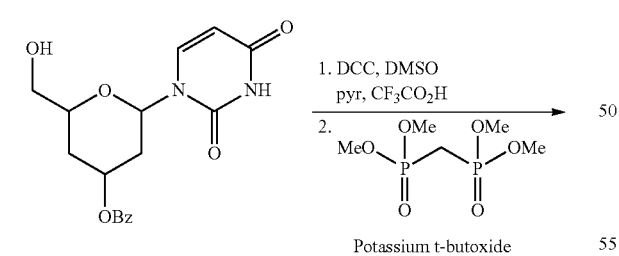
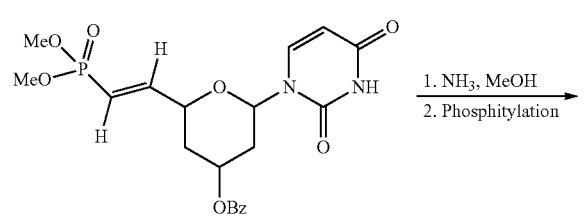
118
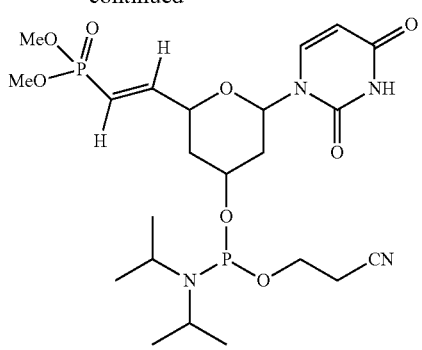
11
or as follows:
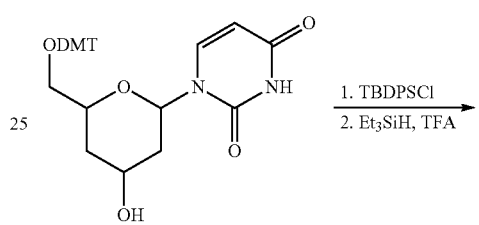
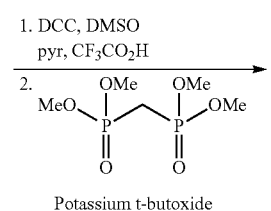
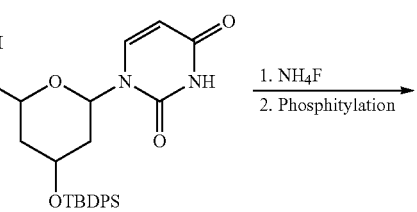
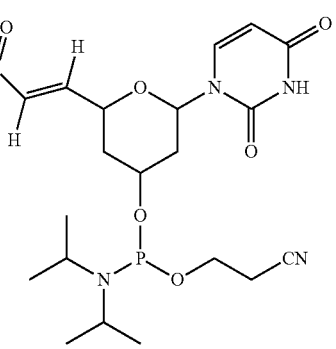
11

Example 6. Preparation of Compound 12
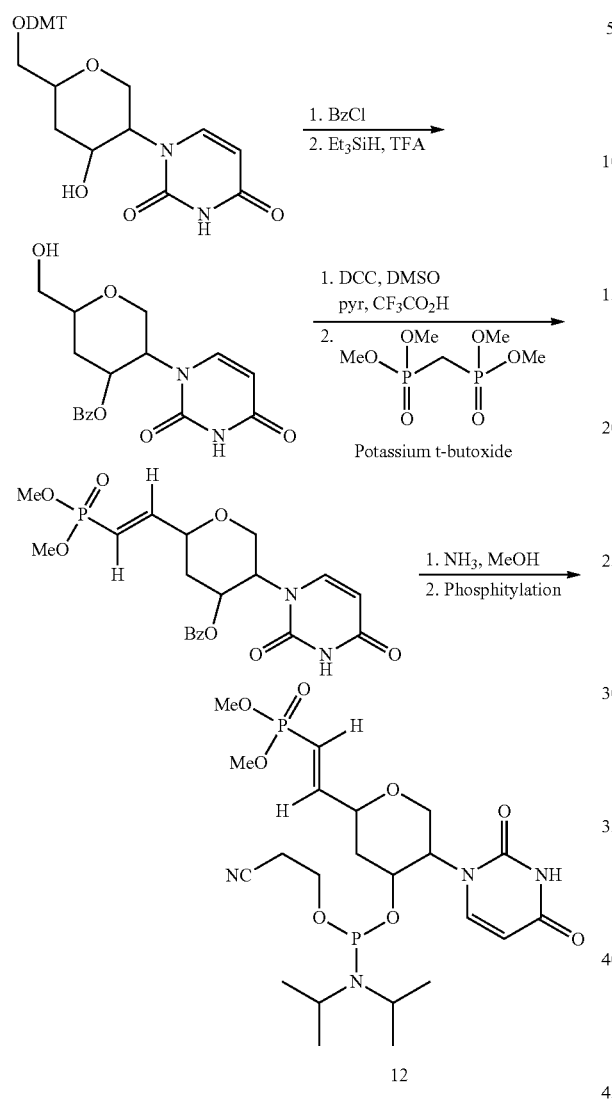
or as follows:
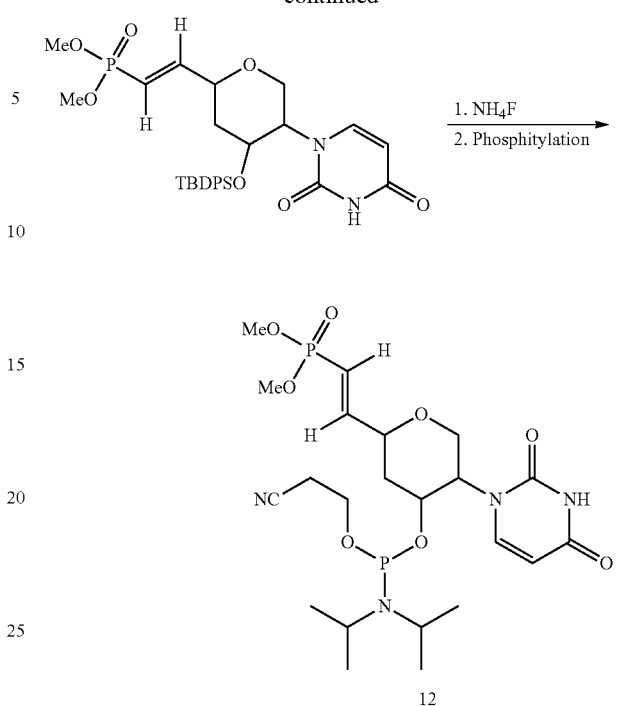
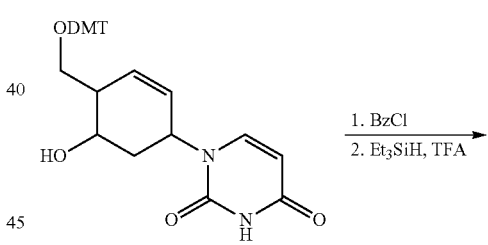
Example 7. Preparation of Compound 14
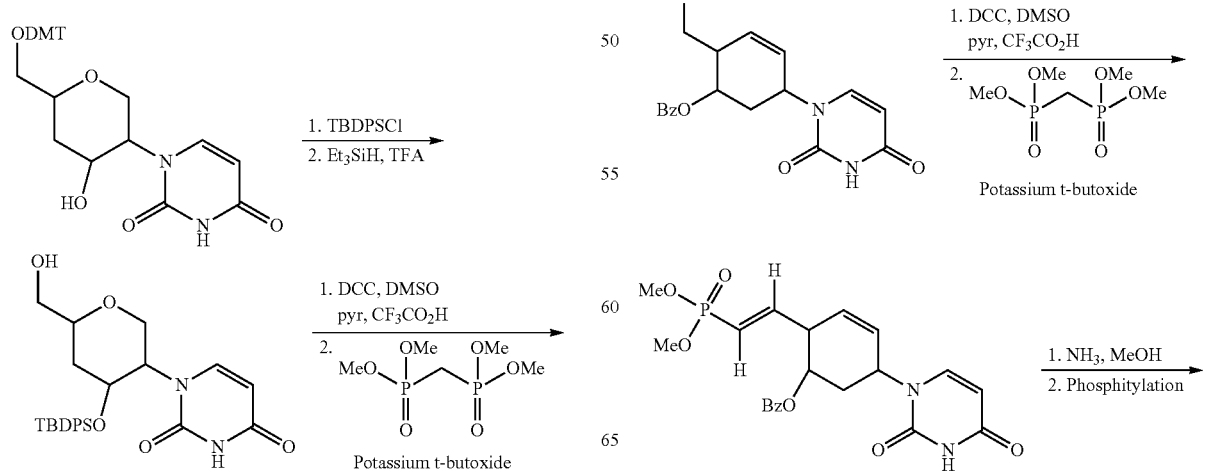

-continued
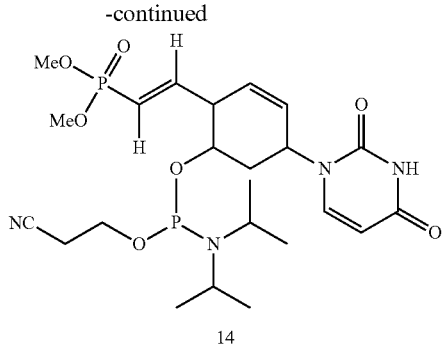
14
or as follows:
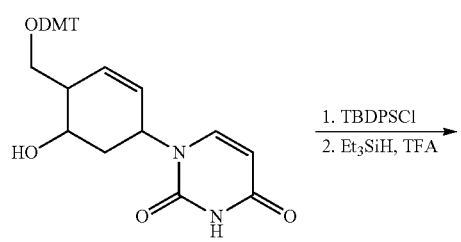
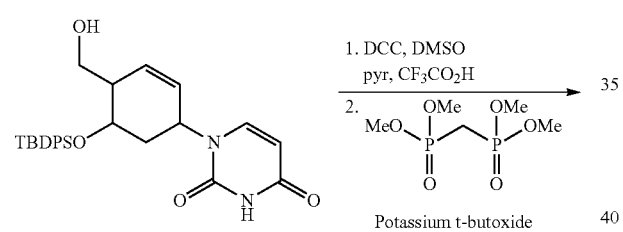
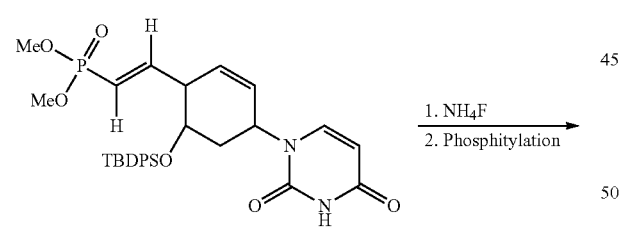
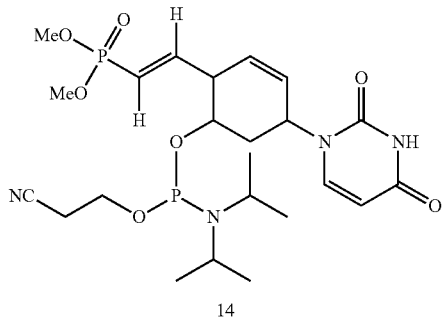
14
Example 8. Preparation of Compound 15
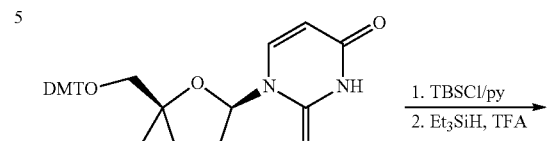
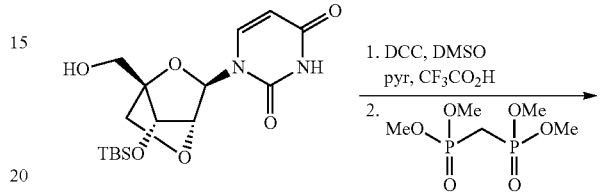
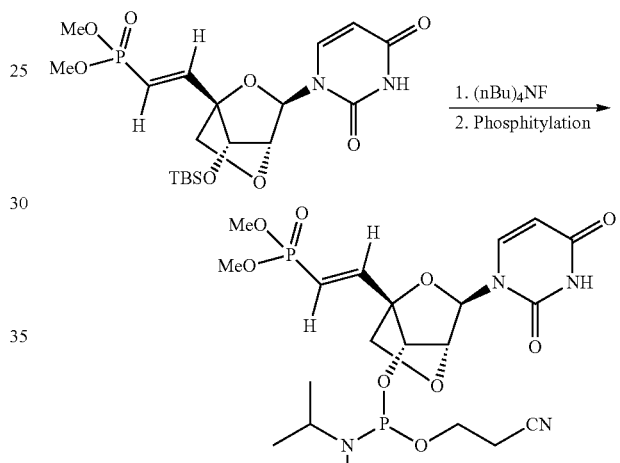
15
Example 9. Preparation of Compound 16
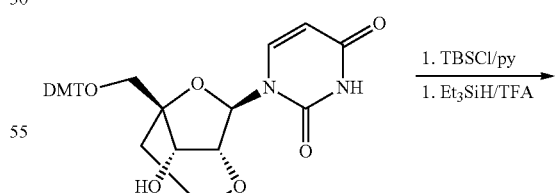
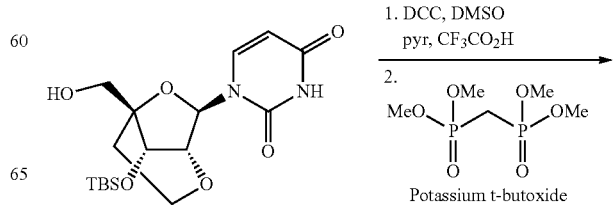

Example 10. Preparation of Compound 17
Example 11. Preparation of Compound 18
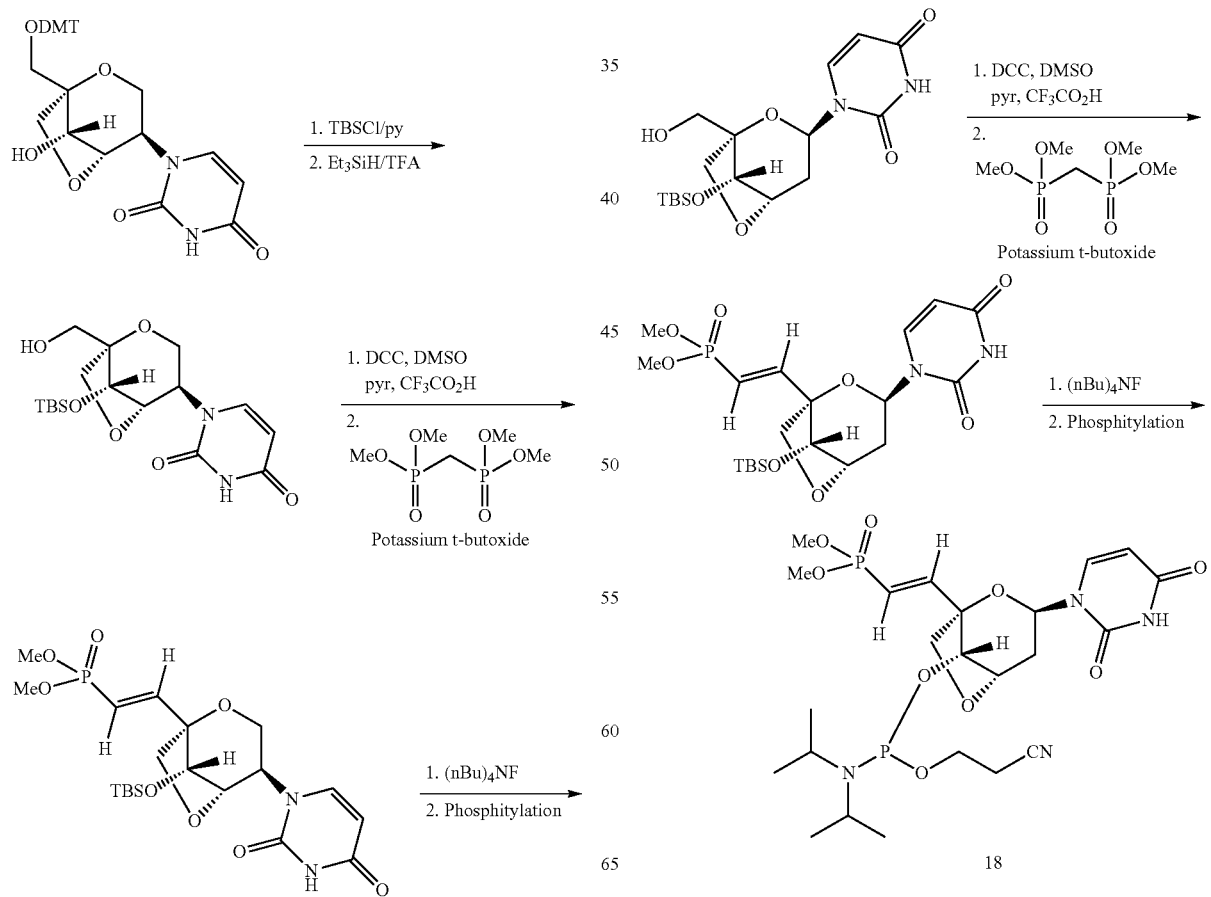

Example 12. Preparation of Compound 19
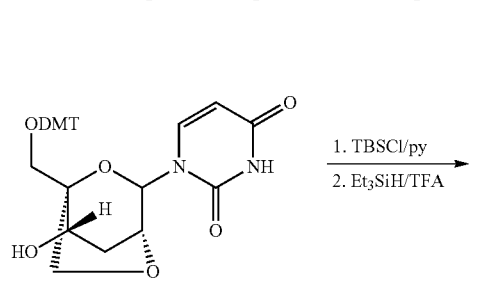
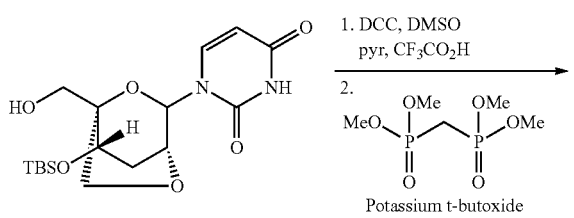
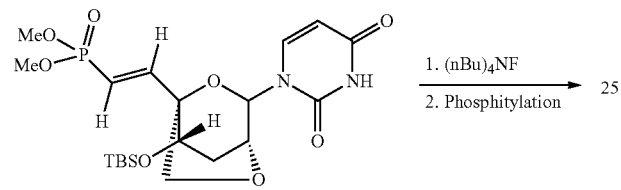
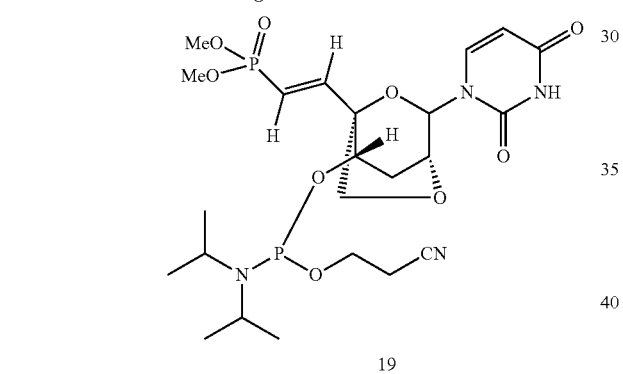
Example 13. Preparation of Compound 20
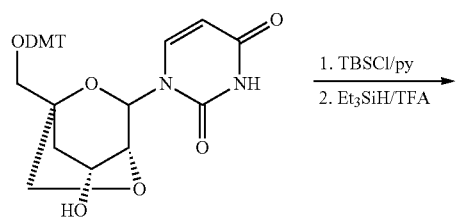
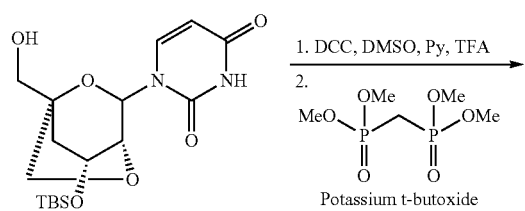
-continued
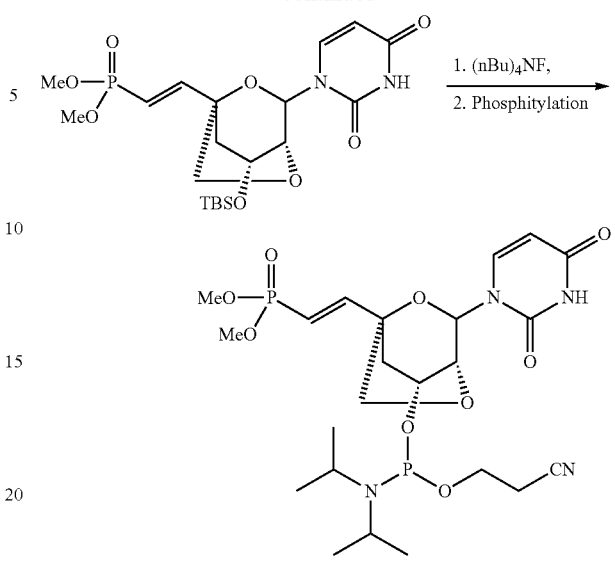
Example 14. Preparation of Compound 21
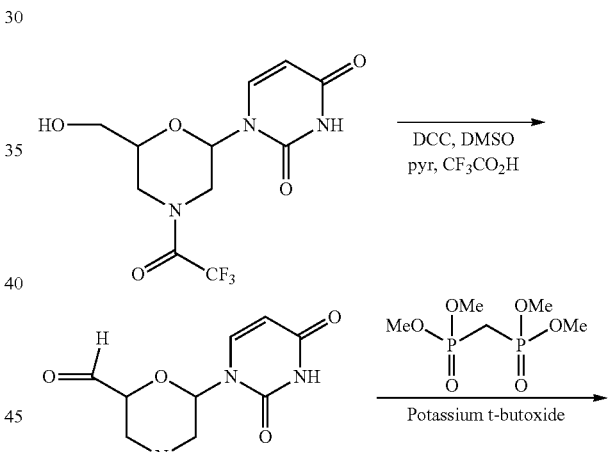
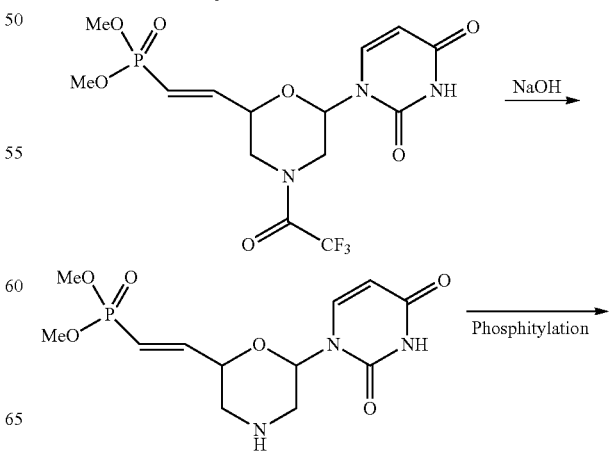

127 128
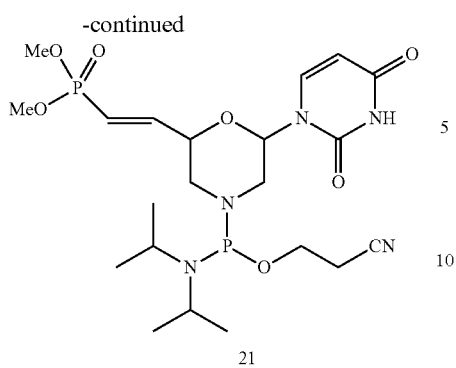 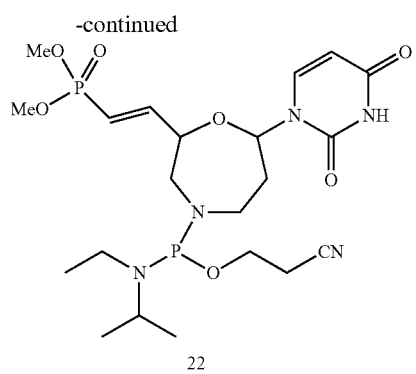
Example 15. Preparation of Compound 22
Example 16. Preparation of Compound 23
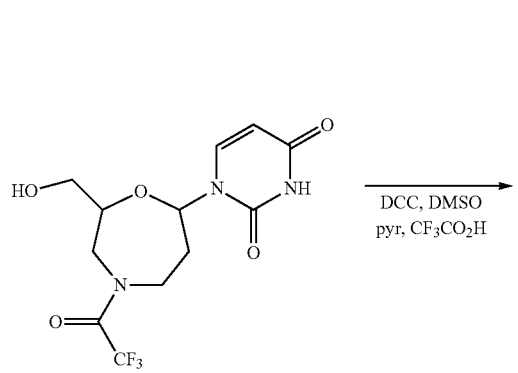
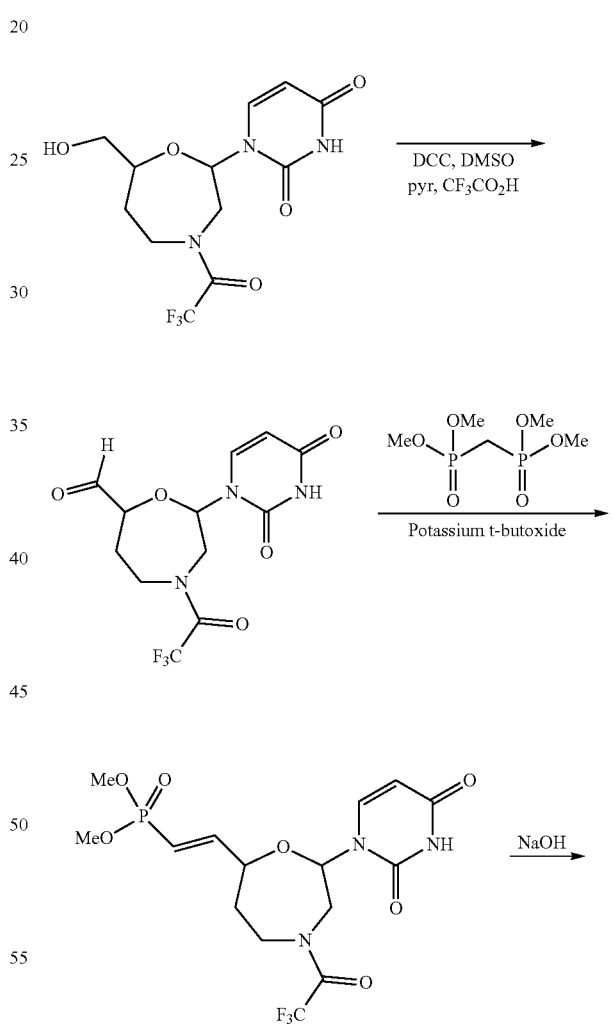
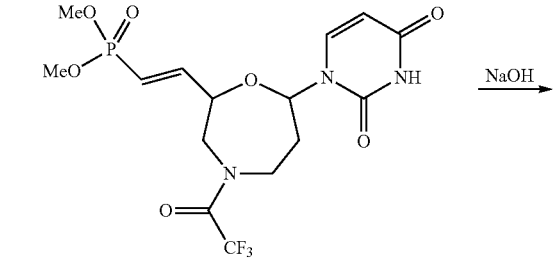
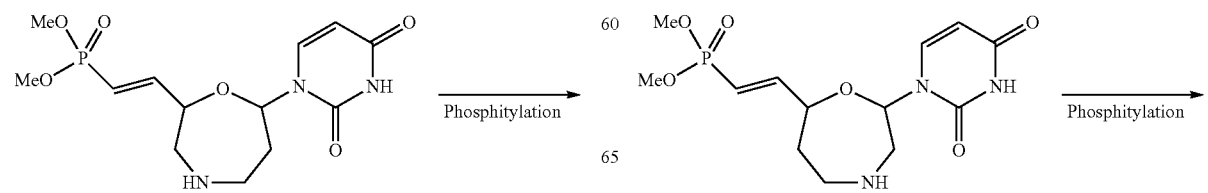

129
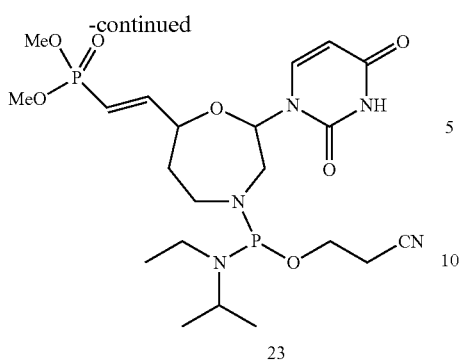
23
130
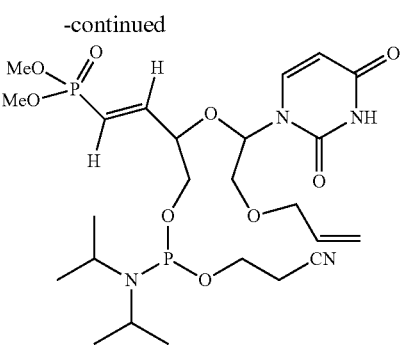
24
Example 17. Preparation of Compound 24
Example 18. Preparation of Compound 25
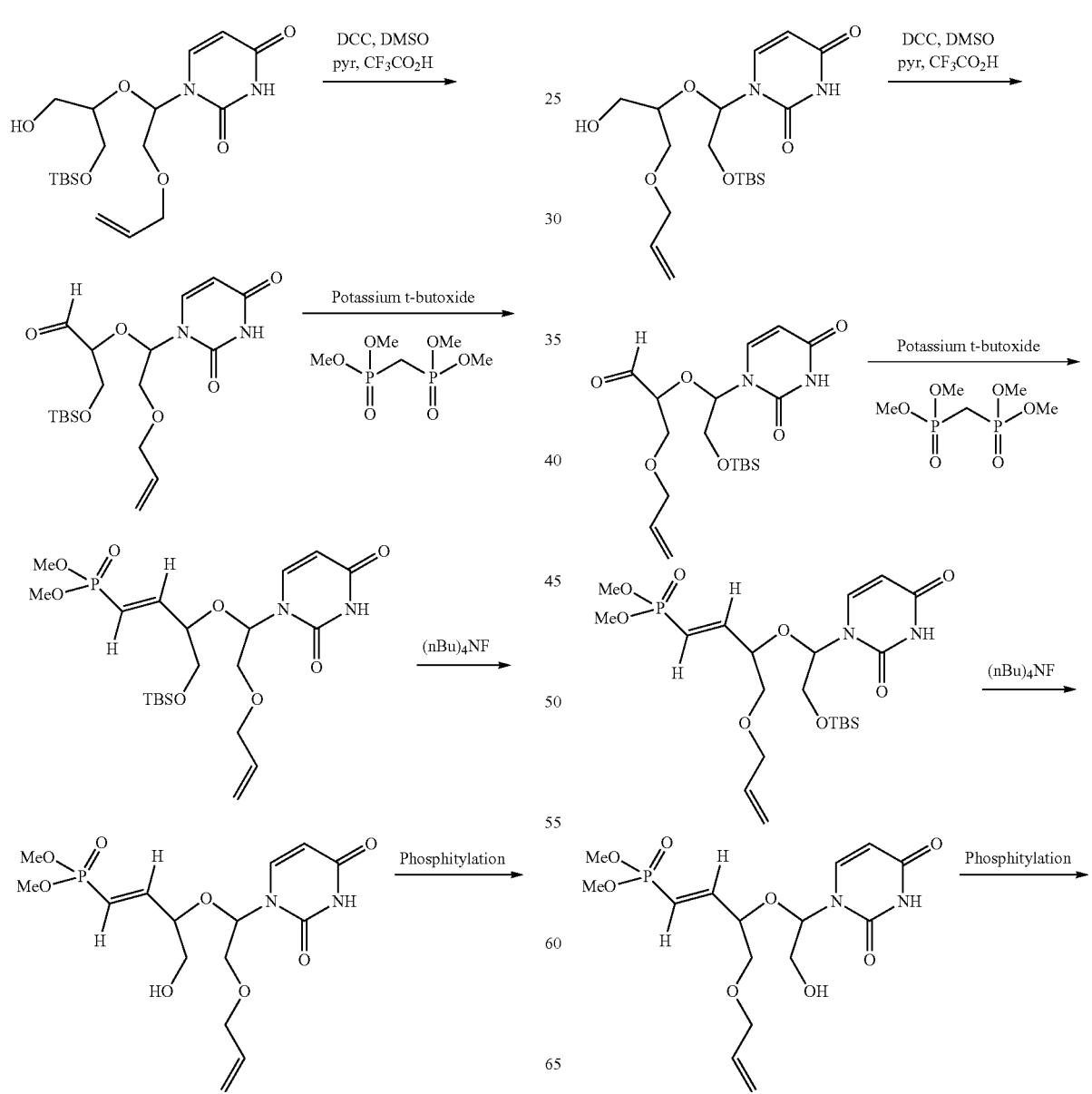

Example 19. Preparation of Compound 26
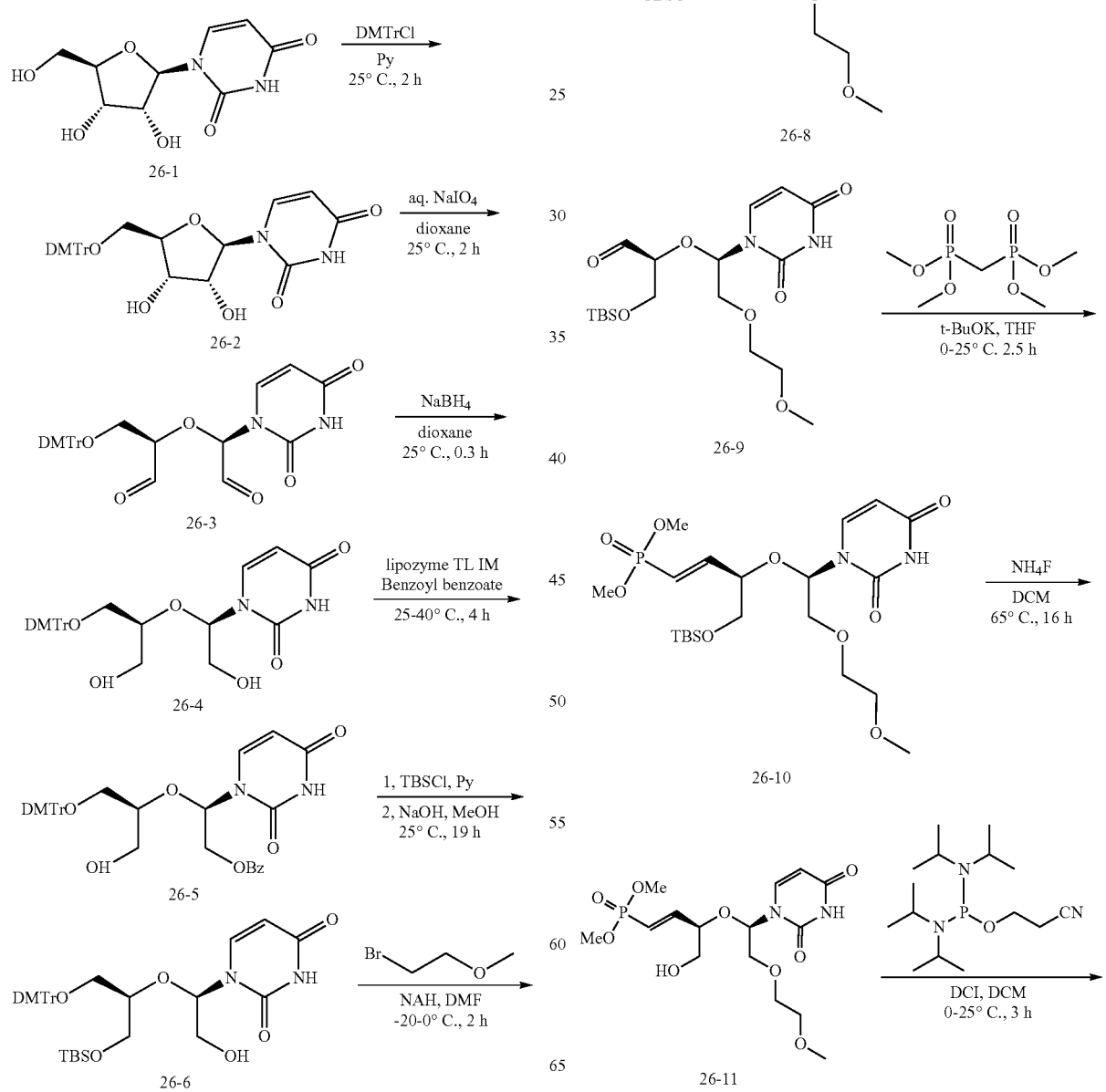

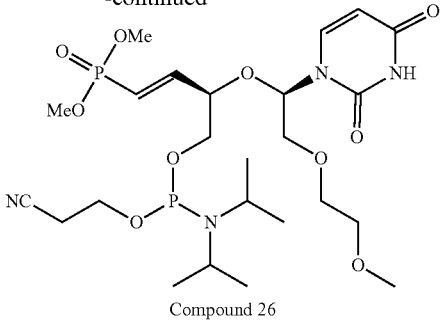

Compound 26

Synthetic Procedures for the Preparation of Compound 26

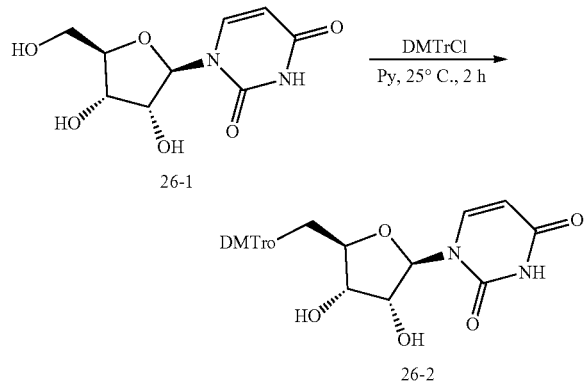

To a solution of compound 26-1 (500 g, 2.05 mol, 1.00 eq) in Py (3500 mL) was added DMTrCl (763 g, 2.25 mol, 1.10 eq). The mixture was stirred at 25° C. for 2 h. TLC (DCM/MeOH=10/1, compound 26-2: $R_f$=0.60) indicated compound 26-1 was consumed completely. The reaction mixture was diluted with DCM (5.00 L) and washed with NaHCO$_3$ (2.00 L×2). The combined organic layers were washed with Brine (2.00 L), dried over Na$_2$SO$_4$, filtered and concentrated under reduced pressure to give a residue. The residue was purified by column chromatography (SiO$_2$, Petroleum ether/Ethyl acetate/TEA=50/1/0.5% to 0/1/0.5%). Compound 26-2 (700 g, 56.3% yield, 90.0% purity) was obtained as a white solid.

$^1$H NMR: 400 MHz, DMSO-d$_6$ δ ppm 11.35 (s, 1H), 7.72 (d, J=8.0 Hz, 1H), 7.36-7.41 (m, 2H), 7.32 (t, J=7.6 Hz, 2H), 7.20-7.28 (m, 5H), 6.90 (d, J=8.6 Hz, 4H), 5.48 (d, J=4.8 Hz, 1H), 5.31 (d, J=8.0 Hz, 1H), 5.14 (d, J=5.6 Hz, 1H), 4.09 (q, J=5.4 Hz, 2H), 3.92-3.99 (m, 1H), 3.70-3.78 (m, 6H), 3.18-3.30 (m, 2H).

Compound 26-3

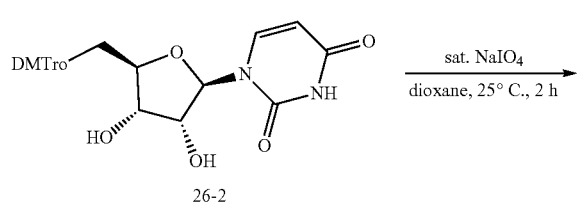

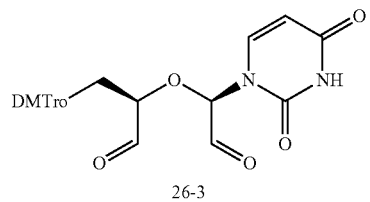

To a solution of compound 26-2 (250 g, 457 mmol, 1.00 eq) in dioxane (2500 mL) was added sat NaIO$_4$ (103 g, 484 mmol, 4.85 mL, 1.06 eq) solution. The mixture was stirred at 25° C. for 2 h. TLC (DCM/MeOH=10/1, compound 26-3: $R_f$=0.49) indicated compound 26-2 was consumed completely. The reaction mixture was filtered. The crude product compound 26-3 (250 g) was obtained as a colorless oil and used in the next step without further purification.

Compound 26-4

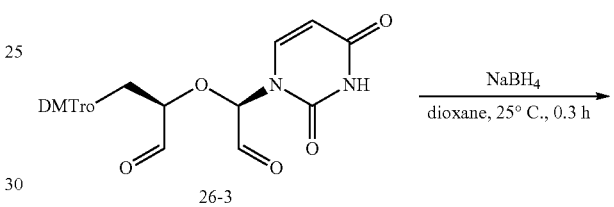

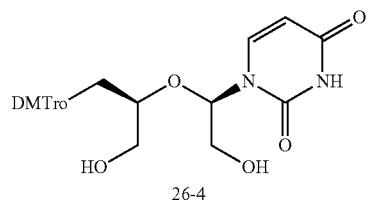

To a solution of compound 26-3 (250 g, 459 mmol, 1.00 eq) in dioxane (3000 mL) was added NaBH$_4$ (17.3 g, 459 mmol, 1.00 eq). The mixture was stirred at 25° C. for 0.3 h. TLC (DCM/MeOH=10/1, compound 26-4: $R_f$=0.41) indicated compound 26-3 was consumed completely. The reaction mixture was quenched with acetone, neutralized with 20% acetic acid, and concentrated to give a residue under reduced pressure. The residue was diluted with DCM (2.00 L), washed with H$_2$O (2.00 L), dried over Na$_2$SO$_4$, filtered and concentrated under reduced pressure to give a residue. The product was used into the next step without further purification. Compound 26-4 (250 g) was obtained as a colorless oil.

$^1$H NMR: 400 MHz, DMSO-d$_6$ δ ppm 11.35 (s, 1H), 7.65 (d, J=8.0 Hz, 1H), 7.28-7.33 (m, 4H), 7.17-7.21 (m, 5H), 6.86 (d, J=8.0 Hz, 4H), 5.83 (t, J=6.4 Hz, 1H), 5.53 (d, J=8.0 Hz, 1H), 5.13 (t, J=8.0 Hz, 1H), 4.75 (t, J=5.2 Hz, 1H), 3.76 (s, 6H), 3.68-3.73 (m, 1H), 3.60-3.64 (m, 2H), 3.42 (t, J=5.2 Hz, 2H), 2.96-3.02 (m, 2H)

Compound 26-5

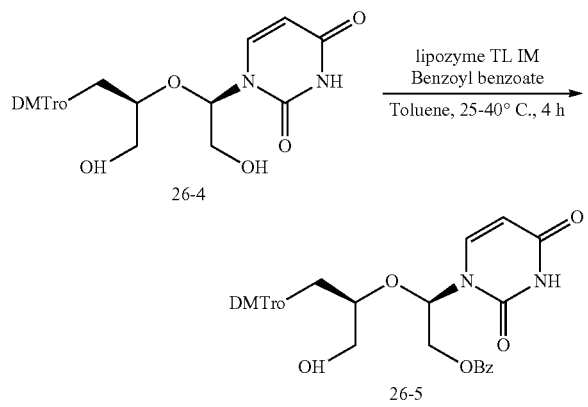

To a solution of compound 26-4 (50.0 g, 91.1 mmol, 1.00 eq) in toluene (2500 mL) was added benzoyl benzoate (30.9 g, 136 mmol, 25.7 mL, 1.50 eq) and lipozyme TL IM (30.0 g, 29.2 mmol) at 25° C. The mixture was stirred at 40° C. for 4 h. TLC (DCM/MeOH=20/1, compound 26-5: $R_f$=0.58) indicated compound 26-4 was consumed completely. The reaction mixture was filtered, quenched by addition methanol (250 mL), concentrated under reduced pressure to give a residue, which was purified by column chromatography (SiO$_2$, Petroleum ether/Ethyl acetate/TEA=10/1/0.5% to 1/2/0.5%). Compound 26-5 (37.5 g, 63.0% yield) was obtained as a white solid.

Compound 26-6

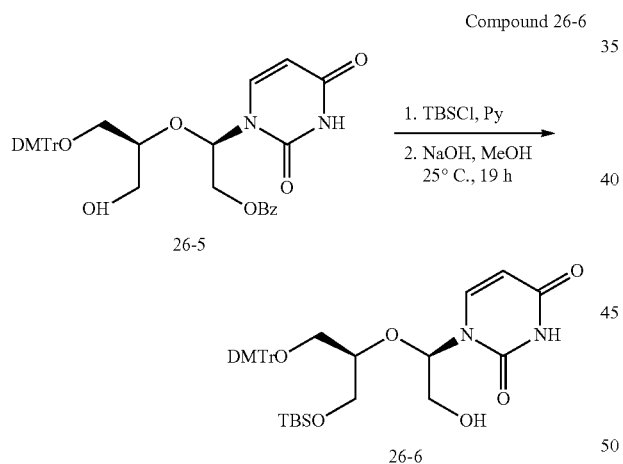

To a solution of compound 26-5 (340 g, 520 mmol, 1.00 eq) in Py (1700 mL) was added TBSCl (157 g, 1.04 mol, 127 mL, 2.00 eq) below 25° C. The mixture was stirred at 25° C. for 19 h. TLC (DCM/MeOH=20/1, compound 26-6: $R_f$=0.37) indicated compound 26-5 was consumed completely. Water (340 mL) was added to the reaction mixture. The resulting mixture containing the nucleoside was dissolved in MeOH (1.00 L), then added dropwise NaOH in MeOH (1.00 L, pH=10) at 0° C., then stirred for 2.5 h at 0° C. The mixture was concentrated under reduced pressure to give a residue. Sat. aq NH$_4$Cl (1.00 L) was added to the mixture, which was stirred for 10 min. Water (1.00 L) was added and the mixture extracted with DCM (1.00 L), dried over Na$_2$SO$_4$, filtered and concentrated under reduced pressure to give a residue, which was purified by column chromatography (SiO$_2$, Petroleum ether/Ethyl acetate/TEA=10/1/0.5% to 0/1/0.5%). Compound 26-6 (250 g, 339 mmol, 65.2% yield, 90.0% purity) was obtained as a white solid.

$^1$H NMR: 400 MHz, DMSO-d$_6$ δ ppm 11.35 (s, 1H), 7.65 (d, J=8.0 Hz, 1H), 7.24-7.33 (m, 4H), 7.14-7.22 (m, 5H), 6.82-6.88 (m, 4H), 5.83 (t, J=5.8 Hz, 1H), 5.47-5.57 (m, 1H), 5.11 (t, J=5.8 Hz, 1H), 3.72 (d, J=0.8 Hz, 6H), 3.57-3.67 (m, 4H), 3.46-3.55 (m, 1H), 2.94-3.00 (m, 2H), 0.72-0.78 (m, 9H), −0.04 (d, J=8.2 Hz, 5H)

Compound 26-7

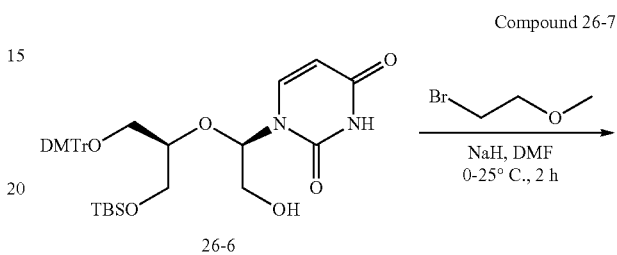

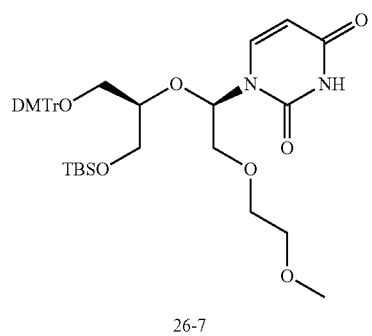

To a solution of compound 26-6 (50.0 g, 75.4 mmol, 1.00 eq) in DMF (500 mL) was added NaH (9.96 g, 248. mmol, 1.81 uL, 60% purity, 3.30 eq) at −20° C. and stirred at −20° C. for 0.5 h. Then the alkoxy bromide (15.7 g, 113. mmol, 10.6 mL, 1.50 eq) was added to the reaction. The mixture was stirred at 0° C. for 1.5 h. TLC (Petroleum ether/Ethyl acetate=1/2, compound 7: $R_f$=0.43) indicated compound 26-6 was consumed completely. The reaction mixture was quenched by addition NH$_4$Cl (1.00 L×2) at 25° C., and then diluted with ethyl acetate (500 mL) and washed with water (500 mL). The combined organic layers were washed with brine (500 mL), dried over Na$_2$SO$_4$, filtered and concentrated under reduced pressure to give a residue. The residue was purified by column chromatography (SiO$_2$, Petroleum ether/Ethyl acetate/TEA=10/1/0.5% to 0/1/0.5%). Compound 26-7 (34.0 g, 47.1 mmol, 62.5% yield) was obtained as a colorless oil.

$^1$H NMR: 400 MHz DMSO-d$_6$ δ ppm 11.40 (d, J=1.8 Hz, 1H), 7.68 (d, J=8.2 Hz, 1H), 7.24-7.33 (m, 5H), 7.14-7.22 (m, 5H), 6.81-6.88 (m, 4H), 5.96-6.02 (m, 1H), 5.55 (dd, J=8.0, 2.0 Hz, 1H), 3.73 (d, J=0.8 Hz, 6H), 3.70 (dd, J=6.0, 2.2 Hz, 2H), 3.62-3.66 (m, 2H), 3.53-3.57 (m, 2H), 3.50-3.53 (m, 1H), 3.38-3.42 (m, 2H), 3.20-3.22 (m, 3H), 2.94-3.00 (m, 2H), 0.72-0.82 (m, 9H), −0.04 (d, J=7.4 Hz, 5H)

Compound 26-8

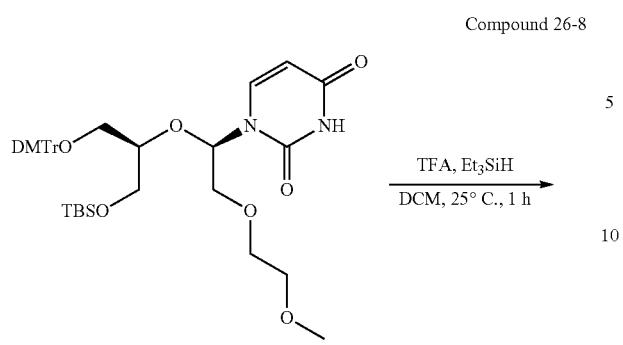

26-7

26-8

To a solution of compound 26-7 (46.8 g, 64.9 mmol, 1.00 eq) in DCM (468 mL) was added TFA (43.1 g, 378 mmol, 28.0 mL, 5.83 eq) and Et₃SiH (15.1 g, 129 mmol, 20.7 mL, 2.00 eq). The mixture was stirred at 25° C. for 1 hr. TLC (Petroleum ether/Ethyl acetate=0/1, compound 26-8: $R_f$=0.43) indicated compound 26-7 was consumed completely. The reaction mixture was diluted with DCM (500 mL) and washed with H₂O (500 mL). The combined organic layers were washed with NaHCO₃ (500 mL×3) and brine (500 mL), dried over Na₂SO₄, filtered and concentrated under reduced pressure to give a residue. The residue was purified by column chromatography (SiO₂, Petroleum ether/Ethyl acetate=10/1 to 0/1). Compound 26-8 (17.0 g, 36.5 mmol, 56.3% yield, 90.0% purity) was obtained as a colorless oil.

¹H NMR: 400 MHz, DMSO-d₆ δ ppm 11.87 (s, 1H), 8.17 (d, J=8.2 Hz, 1H), 7.75-7.87 (m, 4H), 7.63-7.74 (m, 5H), 7.36 (dd, J=9.0, 2.6 Hz, 4H), 6.34 (t, J=5.8 Hz, 1H), 6.05 (d, J=8.0 Hz, 1H), 5.62 (t, J=5.8 Hz, 1H), 4.24 (s, 6H), 4.09-4.20 (m, 4H), 4.02 (d, J=4.6 Hz, 1H), 3.83 (s, 1H), 2.95-3.09 (m, 4H), 1.28 (s, 9H), 0.48 (d, J=8.2 Hz, 6H).

Compound 26-9

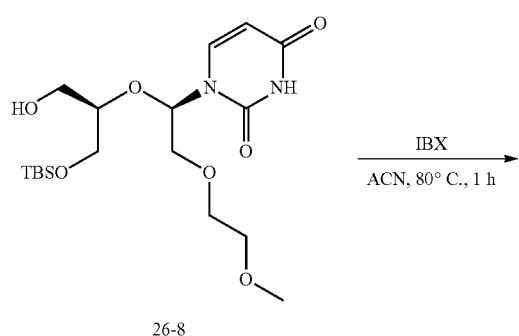

26-8

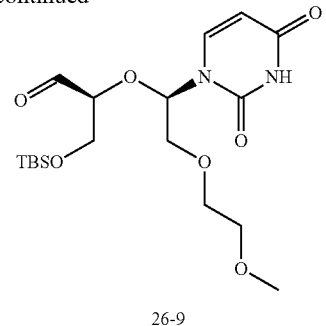

26-9

To a solution of compound 26-8 (17.0 g, 40.6 mmol, 1.00 eq) in ACN (170 mL) was added IBX (17.1 g, 60.9 mmol, 1.50 eq). The mixture was stirred at 80° C. for 1 hr. LC-MS showed compound 26-8 was consumed completely. The reaction mixture was filtered and concentrated under reduced pressure to give a residue. The crude product compound 26-9 (17.0 g, crude) was obtained as a colorless oil and used in the next step without further purification.

Compound 26-10

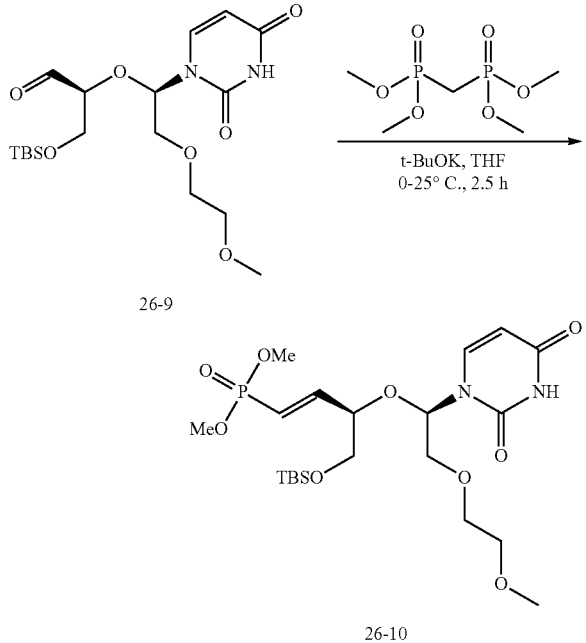

26-9

26-10

To a solution of compound tetramethyl methylenediphosphonate (15.1 g, 65.3 mmol, 1.60 eq) in THF (100 mL) was added dropwise t-BuOK (6.87 g, 61.2 mmol, 1.50 eq) at 0° C., and the mixture stirred at 25° C. for 0.5 hr. The mixture was then added dropwise to compound 26-9 (17.0 g, 40.8 mmol, 1.00 eq) in THF (70.0 mL) and stirred at 0° C. for 1 h, allowed to reach 25° C. and stirred at 25° C. for 1 h. TLC (Petroleum ether/Ethyl acetate=0/1, compound 10: $R_f$=0.07) indicated compound 26-9 was consumed completely. The reaction mixture was quenched by addition NH₄Cl (500 mL), and then diluted with ethyl acetate (200 mL) and extracted. The combined organic layers were washed with brine (200 mL), dried over Na₂SO₄, filtered and concentrated under reduced pressure to give a residue. The residue was purified by column chromatography (SiO₂, petroleum ether/ethyl acetate=10/1 to 0/1). Compound 26-10 (11.4 g, 16.3 mmol, 40.1% yield, 75.0% purity) was obtained as a white solid.

¹H NMR: 400 MHz, CDCl₃ δ ppm 9.19 (s, 1H), 7.43 (d, J=8.16 Hz, 1H), 6.51-6.67 (m, 1H), 6.13 (t, J=4.78 Hz, 1H), 5.82-5.95 (m, 1H), 5.72 (dd, J=8.04, 1.88 Hz, 1H), 4.20 (s, 1H), 3.63-3.78 (m, 12H), 3.45-3.54 (m, 2H), 3.31-3.37 (m, 3H), 0.82-0.94 (m, 9H), 0.00-0.10 (m, 6H).

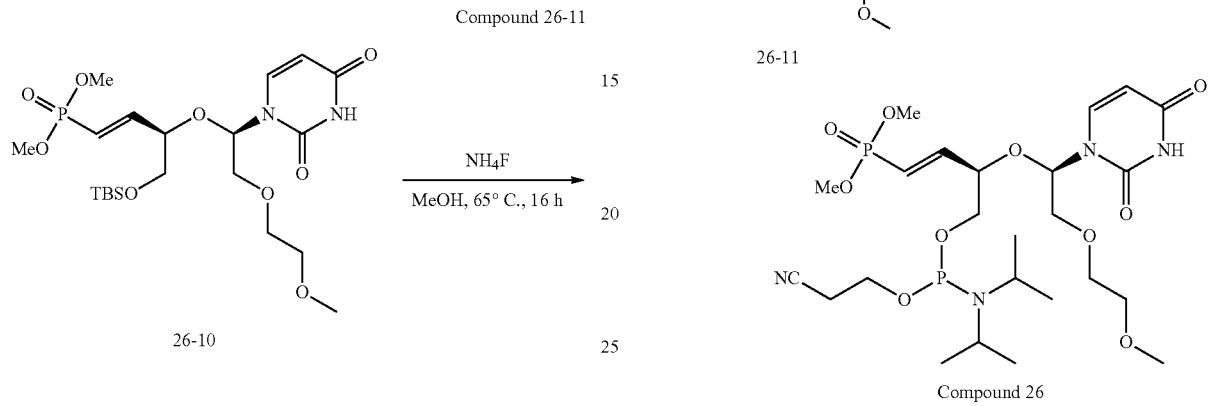

To a solution of compound 26-10 (11.4 g, 21. mmol, 1.00 eq) in methanol (114 mL) was added NH₄F (6.46 g, 174 mmol, 8.00 eq). The mixture was stirred at 65° C. for 16 h. TLC (DCM/MeOH=20/1, compound 10: R$_f$=0.28) indicated compound 26-10 was consumed completely. The reaction mixture was concentrated under reduced pressure to give a residue. The residue was purified by column chromatography (SiO₂, Ethyl acetate/MeOH=100/1 to 10/1). Compound 26-11 (5.90 g, 13.0 mmol, 59.6% yield, 90.0% purity) was obtained as a colorless oil.

¹H NMR: 400 MHz DMSO-d₆, δ ppm 11.29 (s, 1H) 7.74 (d, J=8.0 Hz, 1H) 6.42-6.62 (m, 1H) 5.90-5.98 (m, 2H) 5.62 (dd, J=8.0, 1.2 Hz, 1H) 5.01 (t, J=5.6 Hz, 1H) 4.18 (d, J=1.6 Hz, 1H) 4.10 (q, J=5.2 Hz, 1H) 3.70-3.76 (m, 2H) 3.50-3.58 (m, 8H) 3.43-3.49 (m, 1H) 3.36-3.41 (m, 2H) 3.21 (s, 3H) 3.17 (d, J=5.2 Hz, 2H) 1.91 (s, 1H)

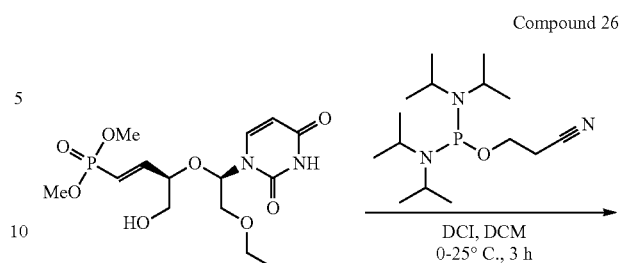

To a solution of compound 26-11 (4.90 g, 12.0 mmol, 1.00 eq) in DCM (49.0 mL) was added DCI (2.27 g, 19.2 mmol, 1.60 eq) and 2-Cyanoethyl N,N,N',N-tetraisopropylphosphorodiamidite (6.51 g, 21.6 mmol, 6.86 mL, 1.80 eq) at 0° C. The mixture was stirred at 25° C. for 3 hrs. TLC (DCM/MeOH=10/1, Compound 26: R$_f$=0.58) indicated compound 26-11 was consumed completely. The reaction mixture was diluted with DCM (50.0 mL) and washed with aq. NaHCO₃ (50.0 mL×2). The combined organic layers were washed with brine (50.0 mL), dried over Na₂SO₄, filtered and concentrated under reduced pressure to give a residue. The residue was purified by column chromatography (SiO₂, Petroleum ether/Ethyl acetate/TEA=100/1/0.5% to 0/1/0.5%). Compound 26 (5.40 g, 8.52 mmol, 70.9% yield, 96.0% purity) was obtained as a colorless oil.

³¹P decoupled ¹H NMR: (400 MHz, CD₃CN): δ 7.42-7.45 (dd, J=8 Hz, 1H), δ 6.42-6.47 (dd, J=17.2 Hz, 1H), 5.97-5.84 (m, 2H), 5.54-5.52 (d, J=8 Hz, 1H), 4.27-4.23 (m, 1H), 3.75-3.50 (br, 12H), 3.36-3.30 (br, 2H), 3.18 (s, 3H), 2.60-2.57 (m, 2H), 1.10-1.09 (d, 12H)

³¹P NMR (400 MHz, CD₃CN) δ 148.6, 148.4, 19.24, 19.22

MS (ESI) calculated for $C_{24}H_{42}N_4O_{10}P_2$ (M-H)⁻ m/z=607.2, found 607.2.

Example 20. Preparation of Compound 27

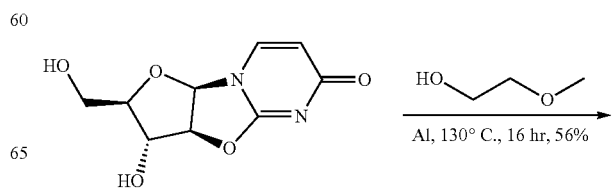

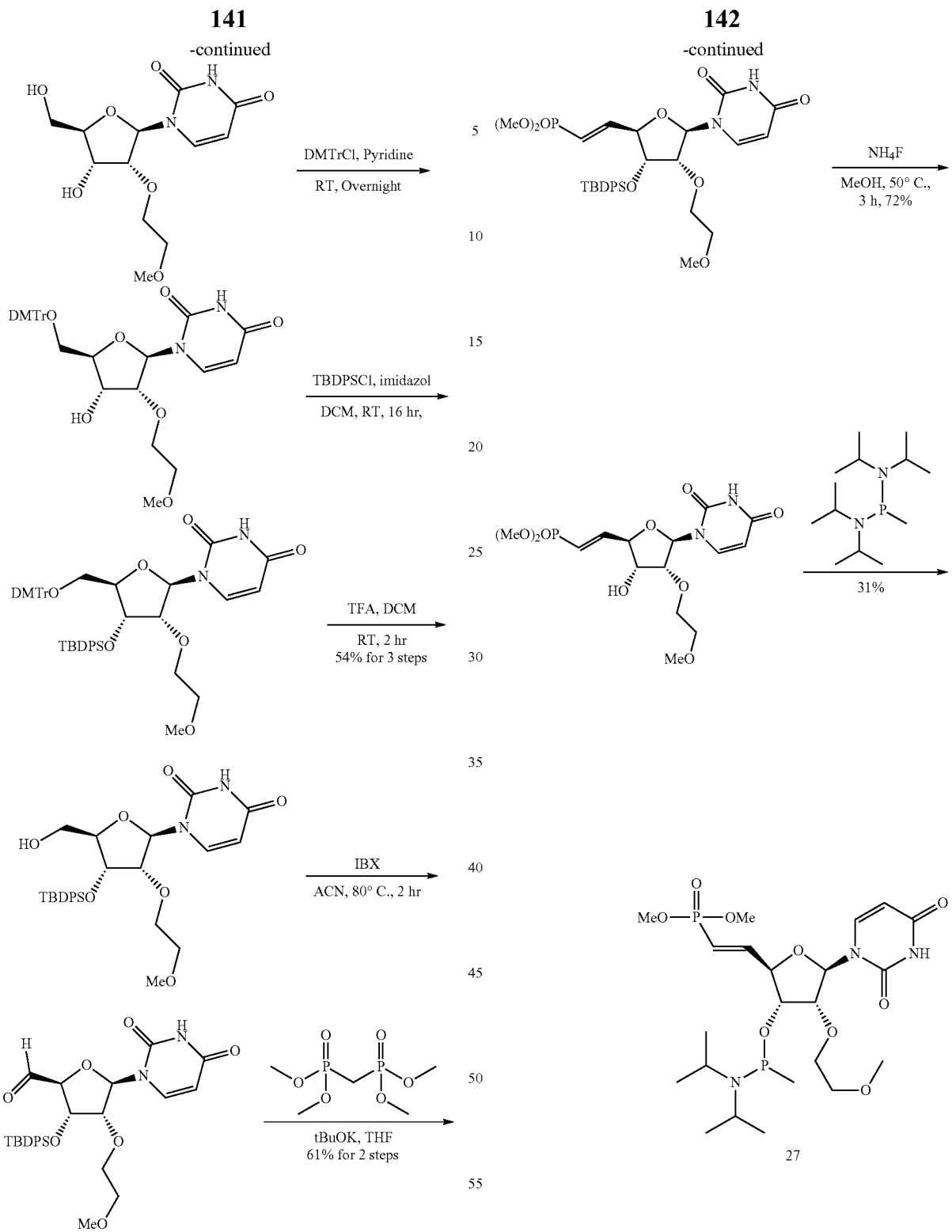
Example 21. Preparation of Compound 28
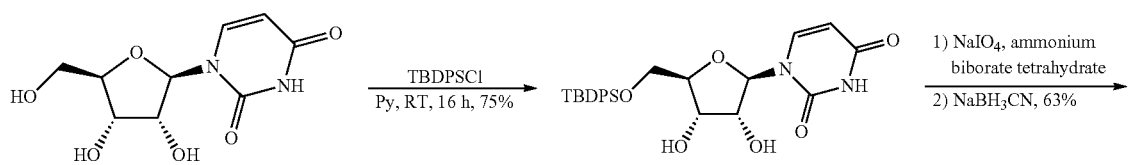

143
-continued
144
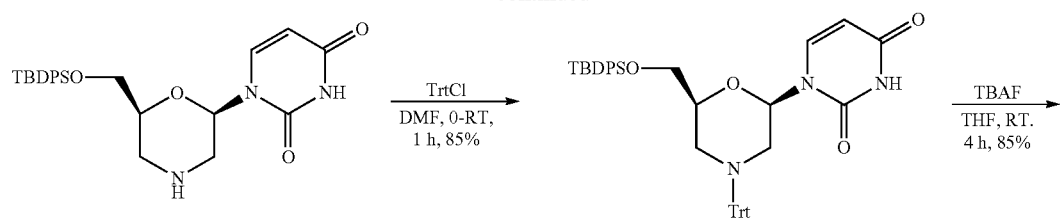
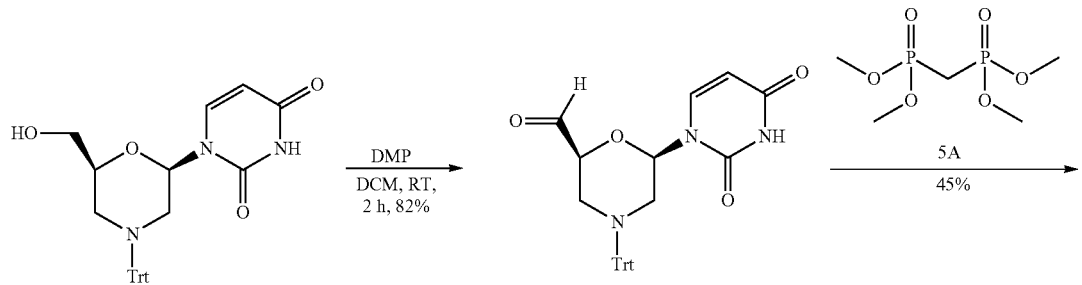
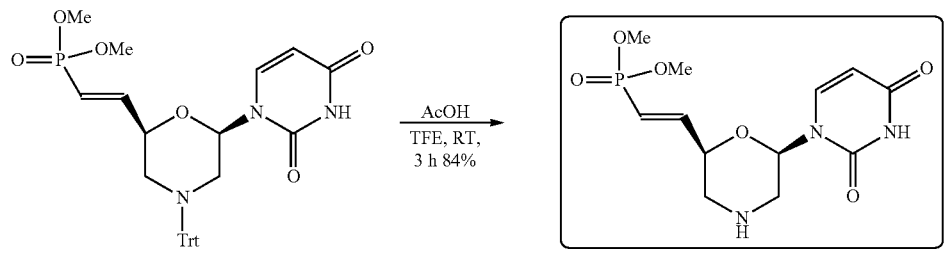
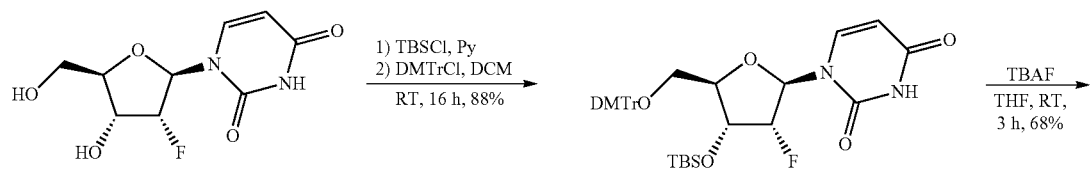
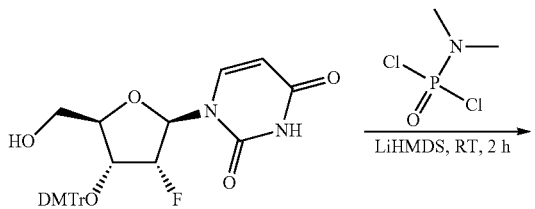
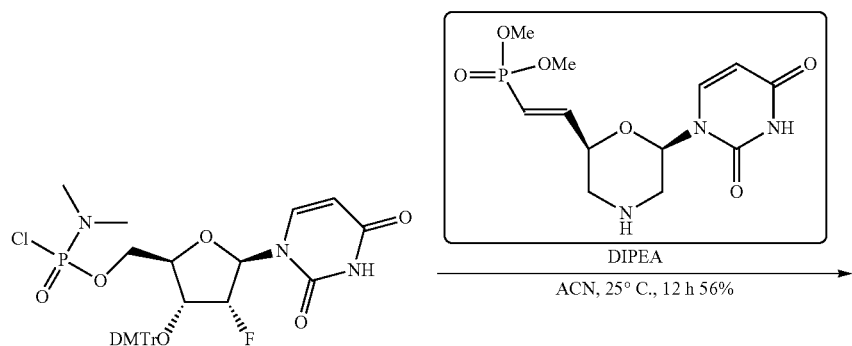

-continued
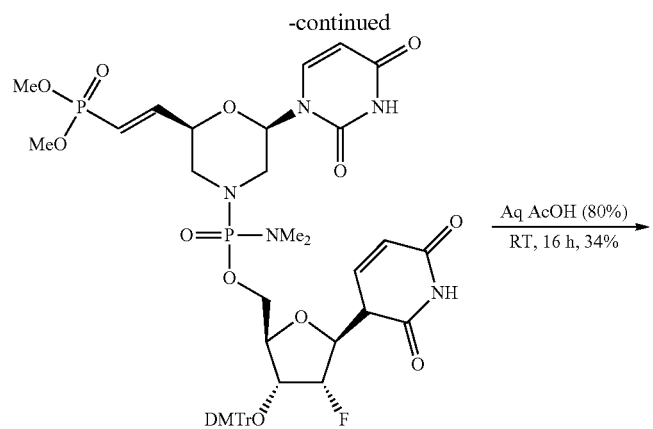
Aq AcOH (80%)
RT, 16 h, 34%
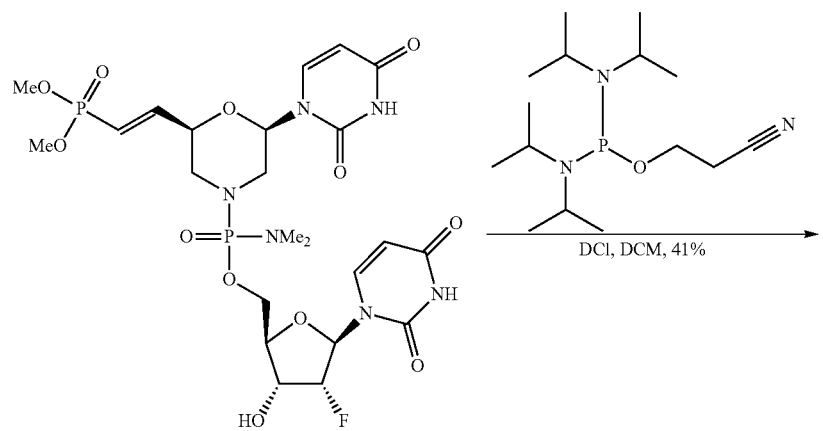
DCl, DCM, 41%
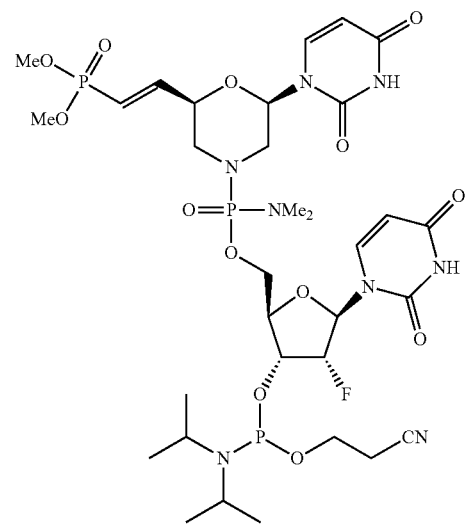
28

Example 22. Preparation of Compound 29
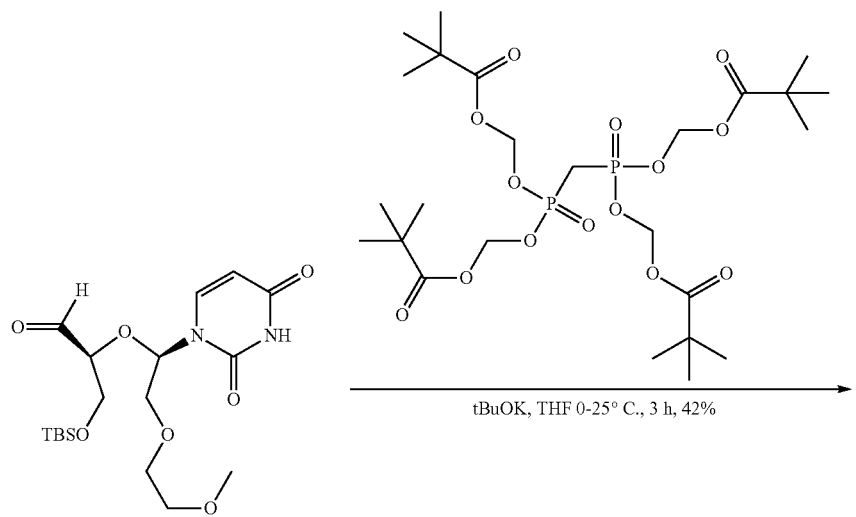
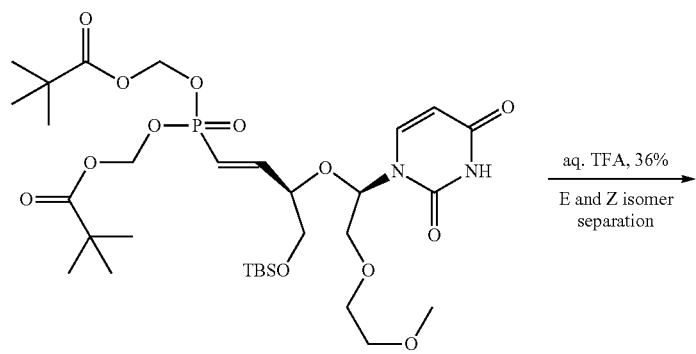
Mixture of E and Z isomers
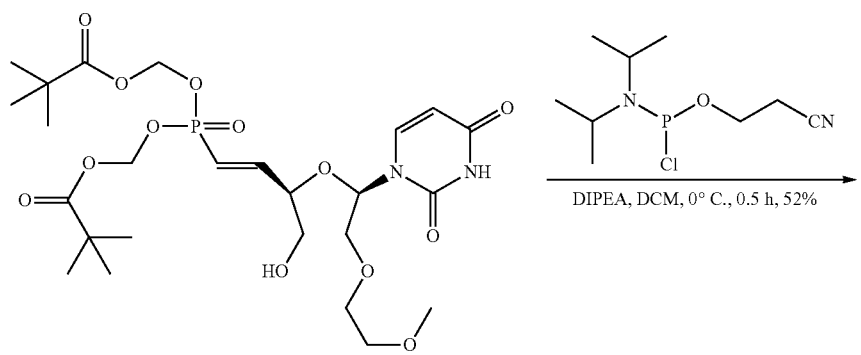

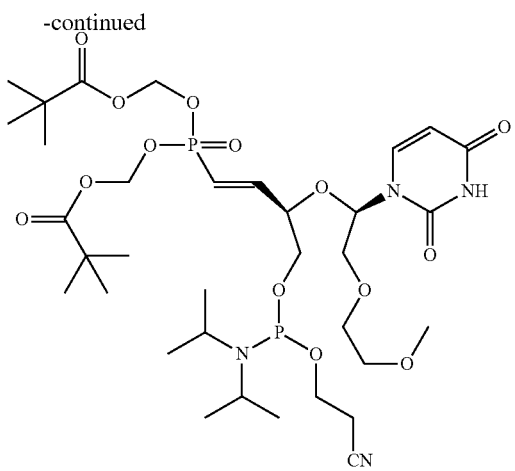
29
Example 23. Preparation of Compound 30
Example 24. Preparation of Compound 31
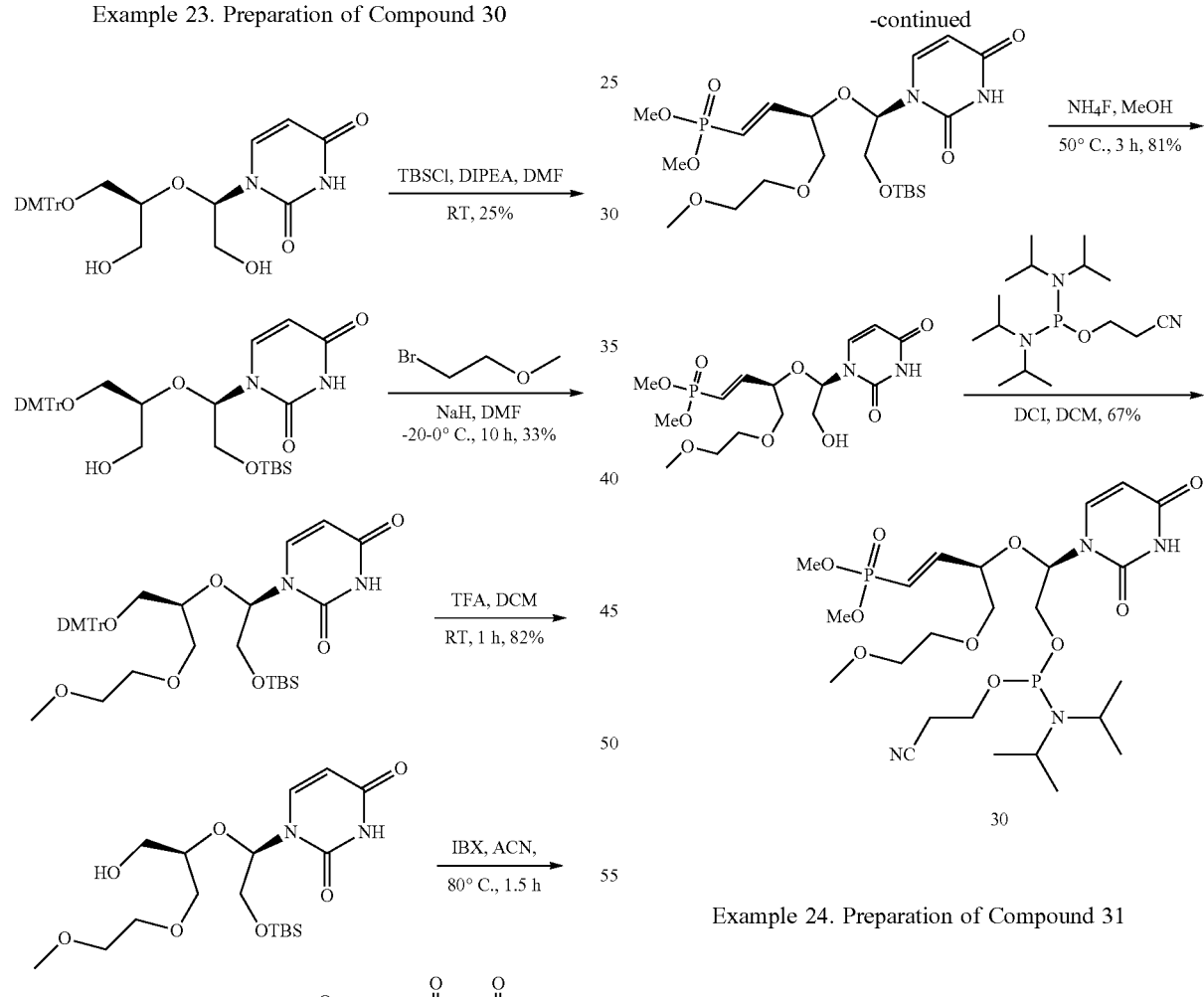
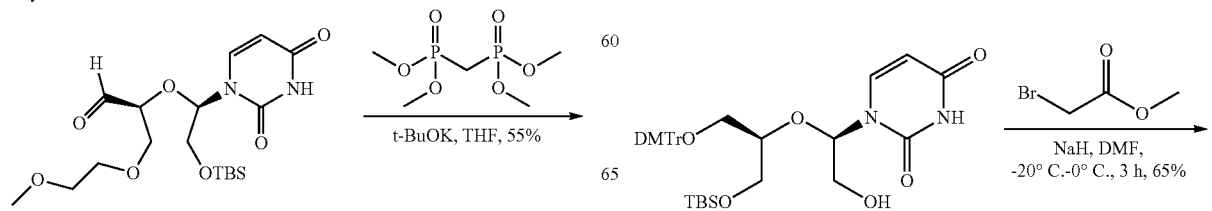

-continued
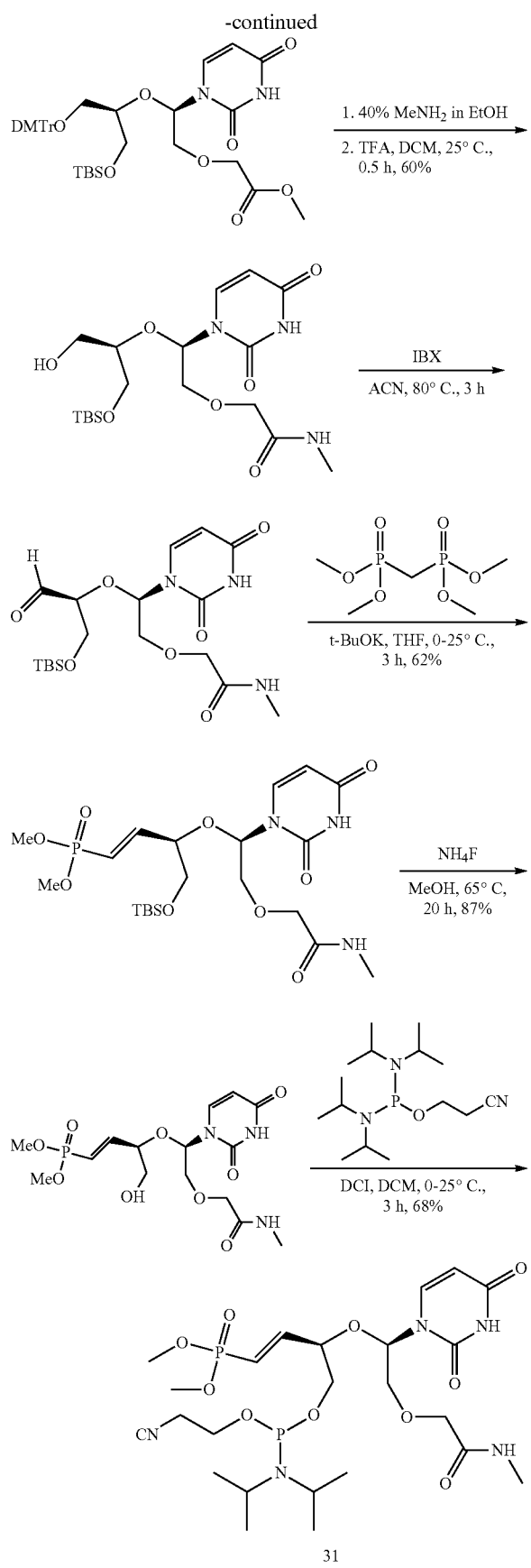
Example 25. Preparation of Compound 32
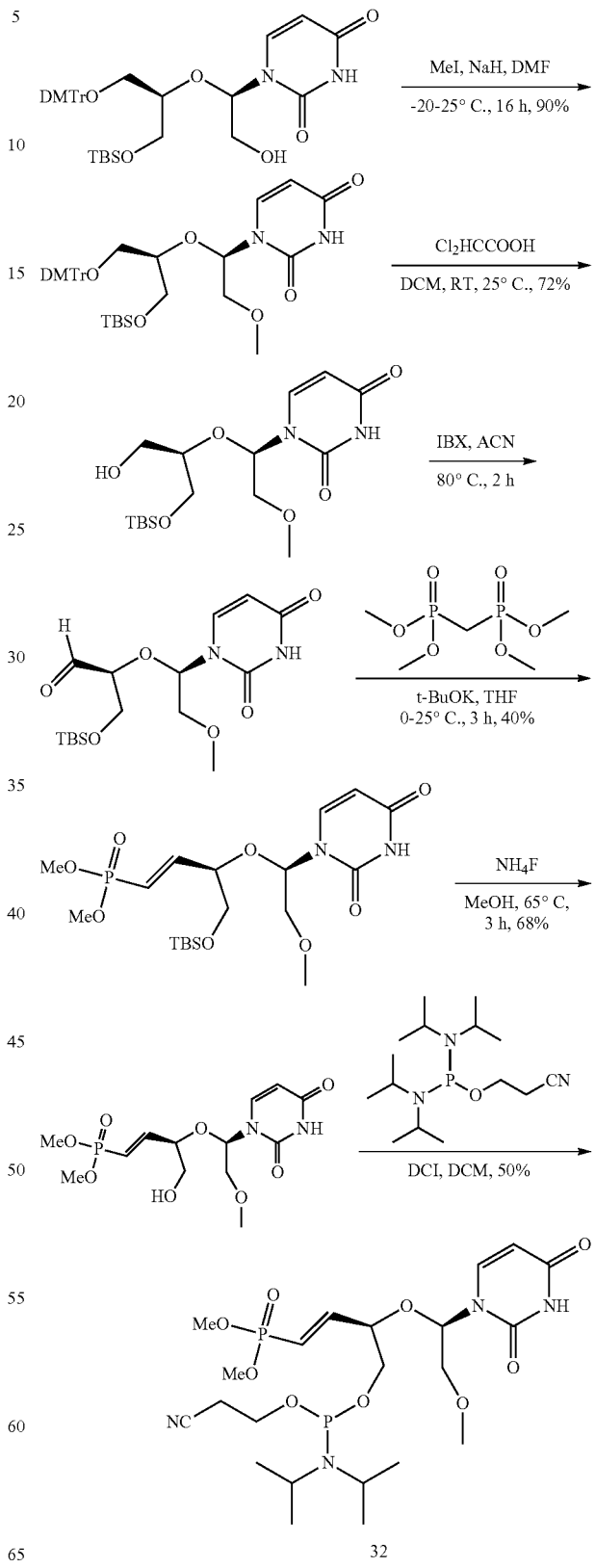

Example 26. Synthetic Protocol for Preparation of Compound 26

Example 27. Analytical Data $^{31}$P decoupled $^1$H NMR, $^{31}$P NMR and MS (ESI) data for various of the compounds described herein are presented below:

| Chemical structure | Analytical (NMR and MS) data |
|---|---|
| 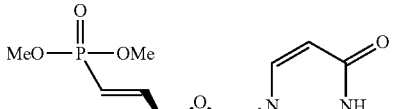 | $^{31}$P decoupled $^1$H NMR (400 MHz, CD$_3$CN): δ 7.39-7.35(dd, J = 7.6 Hz, 1H), δ6.77(m, 1H), 6.0(m, 1H), 5.82-5.78 (dd, J = 3.6, 14 Hz, 1H), 5.66-5.63(dd, J = 4, 8 Hz, 1H), 4.52-4.46(m, 1H), 4.16-4.01(m, 2H), 3.73-3.47(br, 12H), 3.28(s, 3H), 1.26(d, J = 6.4 Hz, 3H), 1.18-1.16(d, J = 6.4 Hz, 6H), 1.09-1.08(d, J = 6.4 Hz, 6H)<br>$^{31}$P NMR (400 MHz, CD$_3$CN) δ125.7, 125.5, 19.09, 18.95<br>MS (ESI) calculated for C$_{24}$H$_{42}$N$_4$O$_{10}$P$_2$ (M + H)+ m/z = 652.2, found 652.2 |
| 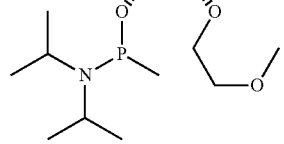 | $^{31}$P decoupled $^1$H NMR (400 MHz, CD$_3$CN): δ7.70-7.61(m, 1H), δ7.55-7.48(m, 1H), 7.08-6.73(br, 1H), 6.01(br, 1H), 5.69(br, 4H), 5.3 (m, 1H), 4.78-4.49(m, 2H), 4.11(br, 3H), 3.90-3.48(br, 14H), 2.83-2.59(Br, 10H), 1.35-1.20(m, 12H)<br>$^{31}$P NMR (400 MHz, CD$_3$CN) δ150.75, 150.71, 150.05, 149.99, 20.54, 20.44, 15.39, 15.29<br>MS (ESI) calculated for C$_{32}$H$_{50}$FN$_8$O$_{13}$P$_3$ (M − H)$^-$ m/z = 865.2, found 865.2 |
| 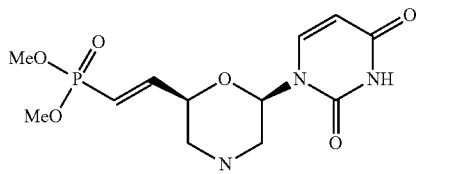 | $^{31}$P decoupled $^1$H NMR (400 MHz, CD$_3$CN): δ 7.42-7.45(dd, J = 8 Hz, 1H), δ 6.42-6.47(dd, J = 17.2 Hz, 1H), 5.97-5.84(m, 2H), 5.54-5.52(d, J = 8 Hz, 1H), 4.27-4.23(m, 1H), 3.75-3.50(br, 12H), 3.36-3.30(br, 2H), 3.18(s, 3H), 2.60-2.57(m, 2H), 1.10-1.09(d, 12H)<br>$^{31}$P NMR (400 MHz, CD$_3$CN) δ148.6, 148.4, 19.24, 19.22<br>MS (ESI) calculated for C$_{24}$H$_{42}$N$_4$O$_{10}$P$_2$ (M − H)$^-$ m/z = 607.2, found 607.2 |

| Chemical structure | Analytical (NMR and MS) data |
|---|---|
| (structure) | $^{31}$P decoupled $^{1}$H NMR (400 MHz, CD$_3$CN): δ 7.55 (dd, J = 8 Hz, 1H), δ 6.58-6.69 (m, J = 17.2 Hz, 1H), 6.11-6.02 (m, 2H), 5.66-5.47 (m, 5H), 4.36-4.38 (m, 1H), 3.88-3.60 (m, 9H), 3.46-3.44 (br, 2H), 3.29 (s, 3H), 2.69 (dt, J = 1.6 Hz, 6 Hz, 2H), 1.20 (m, 30H)<br>$^{31}$P NMR (400 MHz, CD$_3$CN) δ148.69, 148.49, 16.79<br>MS (ESI) calculated for C$_{34}$H$_{58}$N$_4$O$_{14}$P$_2$ (M − H)$^-$ m/z = 807.3, found 807.3 |
| (structure) | $^{31}$P decoupled $^{1}$H NMR (400 MHz, CD$_3$CN): δ 7.55-7.52(dd, J = 8 Hz, 1H), δ 6.58-6.52(dd, J = 17.2 Hz, 1H), 6.08-5.94(m, 2H), 5.67-5.64(d, J = 8 Hz, 1H), 4.39-4.35(m, 1H), 3.95-3.79(br, 4H), 3.75-3.58 (br, 12H), 3.57-3.49(br, 2H), 3.33(br, 3H), 2.68-2.65(t, 2H), 1.18-1.13(m, 12H)<br>$^{31}$P NMR (400 MHz, CD$_3$CN) δ149.05, 148.82, 19.41, 19.38<br>MS (ESI) calculated for C$_{24}$H$_{42}$N$_4$O$_{10}$P$_2$ (M − H)$^-$ m/z = 607.2, found 607.2 |
| (structure) | $^{1}$H NMR (400 MHz, CD$_3$CN): δ7.55 (d, J = 8 Hz, 1H), 6.83 (br, 1H) δ6.57 (ddd, J = 5.2, 17.2, 39.2 Hz, 1H), 6.12-5.95 (m, 2H), 5.68(d, J = 8 Hz, 1H), 4.4 (br, 1H), 3.96 (s, 2H), 3.88-3.52 (br, 14H), 2.35-2.68 (br, 5H), 1.20 (d, J = 6.8 Hz, 12H)<br>$^{31}$P NMR (400 MHz, CD$_3$CN) δ148.6, 148.4, 19.28<br>MS (ESI) calculated for chemical formula: C$_{24}$H$_{41}$N$_5$O$_{10}$P$_2$ (M − H)$^-$ m/z = 620.2, found 620.2 |
| (structure) | $^{1}$H NMR (400 MHz, CD$_3$CN): δ9.02, (br, 1H), δ7.51 (d, J = 8 Hz, 1H), 6.53 (br, 1H) δ6.06 (br, 2H), 5.68(d, J = 8 Hz, 1H), 4.37 (m, 1H), 3.87-3.7 (m, 4H), 3.69-3.63 (m, 10H), 3.35 (s, 3H), 2.70 (m, 2H), 1.22 (m, 12H)<br>$^{31}$P NMR (400 MHz, CD$_3$CN) δ148.7, 148.4, 19.19, 19.15<br>MS (ESI) calculated for chemical formula: C$_{22}$H$_{38}$N$_4$O$_9$P$_2$ (M − H)$^-$ m/z = 563.2, found 563.2 |
| (structure) | $^{1}$H NMR: 400 MHz, DMSO-d$_6$<br>δ ppm 11.35 (s, 1H), 7.72 (d, J = 8.0 Hz, 1H), 7.36-7.41 (m, 2H), 7.32 (t, J = 7.6 Hz, 2H), 7.20-7.28 (m, 5H), 6.90 (d, J = 8.6 Hz, 4H), 5.48 (d, J = 4.8 Hz, 1H), 5.31 (d, J = 8.0 Hz, 1H), 5.14 (d, J = 5.6 Hz, 1H), 4.09 (q, J = 5.4 Hz, 2H), 3.92-3.99 (m, 1H), 3.70-3.78 (m, 6H), 3.18-3.30 (m, 2H). |

| Chemical structure | Analytical (NMR and MS) data |
|---|---|
| (DMTrO, HO, OH, uracil) | ¹H NMR: 400 MHz, DMSO-d₆<br>δ ppm 11.35 (s, 1H), 7.65 (d, J = 8.0 Hz, 1H), 7.28-7.33 (m, 4H), 7.17-7.21 (m, 5H), 6.86 (d, J = 8.0 Hz, 4H), 5.83 (t, J = 6.4 Hz, 1H), 5.53 (d, J = 8.0 Hz, 1H), 5.13 (t, J = 8.0 Hz, 1H), 4.75 (t, J = 5.2 Hz, 1H), 3.76 (s, 6H), 3.68-3.73 (m, 1H), 3.60-3.64 (m, 2H), 3.42 (t, J = 5.2 Hz, 2H), 2.96-3.02 (m, 2H) |
| (DMTrO, TBSO, OH, uracil) | ¹H NMR: 400 MHz, DMSO-d₆<br>δ ppm 11.35 (s, 1H), 7.65 (d, J = 8.0 Hz, 1H), 7.24-7.33 (m, 4H), 7.14-7.22 (m, 5H), 6.82-6.88 (m, 4H), 5.83 (t, J = 5.8 Hz, 1H), 5.47-5.57 (m, 1H), 5.11 (t, J = 5.8 Hz, 1H), 3.72 (d, J = 0.8 Hz, 6H), 3.57-3.67 (m, 4H), 3.46-3.55 (m, 1H), 2.94-3.00 (m, 2H), 0.72-0.78 (m, 9H), −0.04 (d, J = 8.2 Hz, 5H) |
| (DMTrO, TBSO, O-CH₂CH₂OMe, uracil) | ¹H NMR: 400 MHz, DMSO-d₆<br>δ ppm 11.40 (d, J = 1.8 Hz, 1H), 7.68 (d, J = 8.2 Hz, 1H), 7.24-7.33 (m, 5H), 7.14-7.22 (m, 5H), 6.81-6.88 (m, 4H), 5.96-6.02 (m, 1H), 5.55 (dd, J = 8.0, 2.0 Hz, 1H), 3.73 (d, J = 0.8 Hz, 6H), 3.70 (dd, J = 6.0, 2.2 Hz, 2H), 3.62-3.66 (m, 2H), 3.53-3.57 (m, 2H), 3.50-3.53 (m, 1H), 3.38-3.42 (m, 2H), 3.20-3.22 (m, 3H), 2.94-3.00 (m, 2H), 0.72-0.82 (m, 9H), −0.04 (d, J = 7.4 Hz, 5H) |
| (HO, TBSO, O-CH₂CH₂OMe, uracil) | ¹H NMR: 400 MHz, DMSO-d₆<br>δ ppm 11.87 (s, 1H), 8.17 (d, J = 8.2 Hz, 1H), 7.75-7.87 (m, 4H), 7.63-7.74 (m, 5H), 7.36 (dd, J = 9.0, 2.6 Hz, 4H), 6.34 (t, J = 5.8 Hz, 1H), 6.05 (d, J = 8.0 Hz, 1H), 5.62 (t, J = 5.8 Hz, 1H), 4.24 (s, 6H), 4.09-4.20 (m, 4H), 4.02 (d, J = 4.6 Hz, 1H), 3.83 (s, 1H), 2.95-3.09 (m, 4H), 1.28 (s, 9H), 0.48 (d, J = 8.2 Hz, 6H). |
| (MeO)₂P(O)-CH=CH-, TBSO, O-CH₂CH₂OMe, uracil | ¹H NMR: 400 MHz, CDCl₃<br>δ ppm 9.19 (s, 1H), 7.43 (d, J = 8.16 Hz, 1H), 6.51-6.67 (m, 1H), 6.13 (t, J = 4.78 Hz, 1H), 5.82-5.95 (m, 1H), 5.72 (dd, J = 8.04, 1.88 Hz, 1H), 4.20 (s, 1H), 3.63-3.78 (m, 12H), 3.45-3.54 (m, 2H), 3.31-3.37 (m, 3H), 0.82-0.94 (m, 9H), 0.00-0.10 (m, 6H). |
| (MeO)₂P(O)-CH=CH-, HO, O-CH₂CH₂OMe, uracil | ¹H NMR: 400 MHz, DMSO-d₆<br>δ ppm 11.29 (s, 1H) 7.74 (d, J = 8.0 Hz, 1H) 6.42-6.62 (m, 1H) 5.90-5.98 (m, 2H) 5.62 (dd, J = 8.0, 1.2 Hz, 1H) 5.01 (t, J = 5.6 Hz, 1H) 4.18 (d, J = 1.6 Hz, 1H) 4.10 (q, J = 5.2 Hz, 1H) 3.70-3.76 (m, 2H) 3.50-3.58 (m, 8H) 3.43-3.49 (m, 1H) 3.36-3.41 (m, 2H) 3.21 (s, 3H) 3.17 (d, J = 5.2 Hz, 2H) 1.91 (s, 1H) |

| Chemical structure | Analytical (NMR and MS) data |
|---|---|
| | ¹H NMR: 400 MHz, DMSO-d₆<br>δ 11.30 (d, J = 1.8 Hz, 1H), 7.67 (d, J = 8.0 Hz, 1H), 7.61 (br d, J = 4.3 Hz, 1H), 6.03 (t, J = 5.6 Hz, 1H), 5.61 (dd, J = 2.0, 8.0 Hz, 1H), 4.66 (br s, 1H), 3.90 (s, 2H), 3.73-3.57 (m, 4H), 3.49-3.43 (m, 1H), 3.34-3.25 (m, 2H), 2.60 (d, J = 4.8 Hz, 3H), 0.87 (s, 9H), 0.05 (s, 6H) |
| | ¹HNMR: 400 MHz CD₃CN<br>δ 7.52 (d, J = 8.2 Hz, 1H), 6.98 (br s, 1H), 6.61-6.47 (m, 1H), 6.06-5.86 (m, 2H), 5.65 (d, J = 8.2 Hz, 1H), 4.28-4.20 (m, 1H), 3.96 (s, 2H), 3.80-3.51 (m, 10H), 2.73-2.67 (m, 4H)<br>³¹PNMR: 162 MHz CD₃CN, δ 19.71 (s, 1P) |
| | ¹H NMR: 400 MHz, DMSO d₆<br>11.23 (s, 1H), 7.63 (d, J = 8.02 Hz, 1H), 5.85 (dd, J = 6.56, 4.98 Hz, 1H), 5.60 (dd, J = 7.92, 1.66 Hz, 1H), 4.65 (t, J = 5.58 Hz, 1H), 3.63-3.84 (m, 2H), 3.40-3.60 (m, 7H), 3.26 (s, 3H), 0.81 (s, 9H), 0.01 (d, J = 6.66 Hz, 5H). |
| | ¹H NMR: 400 MHz, DMSO d₆<br>7.72 (d, J = 8.22 Hz, 1H), 6.38-6.61 (m, 1H), 5.76-6.09 (m, 2H), 5.61 (dd, J = 8.02, 1.66 Hz, 1H), 4.29-4.43 (m, 1H), 3.66-3.92 (m, 2H), 3.41-3.63 (m, 12H), 3.17-3.26 (m, 3H), 0.73-0.87 (m, 10H), 0.01 (d, J = 7.04 Hz, 7H). |
| | ¹H NMR: 400 MHz, DMSO d₆<br>11.26 (d, J = 1.52 Hz, 1H), 7.71 (d, J = 8.04 Hz, 1H), 6.43-6.58 (m, 1H), 5.88-6.06 (m, 1H), 5.75-5.85 (m, 1H), 5.61 (dd, J = 7.96, 2.08 Hz, 1H), 5.14 (t, J = 6.02 Hz, 1H), 4.34 (br d, J = 1.52 Hz, 1H), 3.42-3.70 (m, 14H), 3.26 (s, 3H) |
| | ¹H NMR: 400 MHz, DMSO-d₆<br>11.31 (s, 1H), 7.72-7.77 (m, 1H), 6.45-6.56 (m, 1H), 5.91-6.03 (m, 2H), 5.62 (dd, J = 8.40, 2.40 Hz, 1H), 4.24 (br s, 1H), 3.72-3.76 (m, 1H), 3.61-3.69 (m, 3H), 3.52-3.59 (m, 6H), 3.26 (s, 3H), 0.87 (s, 9H), 0.06 (d, J = 1.60 Hz, 6H).<br>³¹P NMR: 162 MHz, DMSO-d₆<br>19.93 (s, 1P) |

| Chemical structure | Analytical (NMR and MS) data |
|---|---|
| 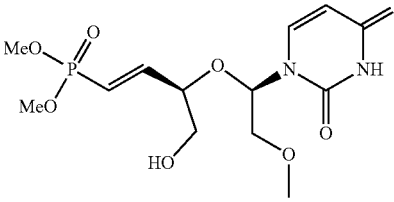 | $^1$H NMR: 400 MHz, DMSO-$d_6$<br>11.31 (s, 1H), 7.74 (d, J = 8.00 Hz, 1H), 6.47-6.58 (m, 1H), 5.87-5.99 (m, 2H), 5.63 (d, J = 8.4 Hz, 1H), 5.04 (s, 1H), 4.10-4.19 (m, 2H), 3.66 (d, J = 6.00 Hz, 2H), 3.56 (dd, J = 11.2, 4.40 Hz, 6H), 3.43-3.48 (m, 1H), 3.28 (s, 3H), 3.17-3.18 (m, 2H).<br>$^{31}$P NMR: 162 MHz, DMSO-$d_6$<br>20.04 (s, 1P). |

Molecular Biology Examples

Example 1. Sequences

Tables 1, 3, 5, 6, and 7 illustrate target sequences described herein. Tables 2, 4, 8, and 9 illustrate polynucleic acid molecule sequences described herein.

TABLE 1

KRAS Target Sequences

| Id # | sequence position in NM_033360.2 | target site in NM_033360.2 | SEQ ID NO: |
|---|---|---|---|
| 182 | 182-200 | AAAUGACUGAAUAUAAACUUGUG | 1 |
| 183 | 183-201 | AAUGACUGAAUAUAAACUUGUGG | 2 |
| 197 | 197-215 | AACUUGUGGUAGUUGGAGCUGGU | 3 |
| 224 | 224-242 | UAGGCAAGAGUGCCUUGACGAUA | 4 |
| 226 | 226-244 | GGCAAGAGUGCCUUGACGAUACA | 5 |
| 227 | 227-245 | GCAAGAGUGCCUUGACGAUACAG | 6 |
| 228 | 228-246 | CAAGAGUGCCUUGACGAUACAGC | 7 |
| 232 | 232-250 | AGUGCCUUGACGAUACAGCUAAU | 8 |
| 233 | 233-251 | GUGCCUUGACGAUACAGCUAAUU | 9 |
| 236 | 236-254 | CCUUGACGAUACAGCUAAUUCAG | 10 |
| 237 | 237-255 | CUUGACGAUACAGCUAAUUCAGA | 11 |
| 245 | 245-263 | UACAGCUAAUUCAGAAUCAUUUU | 12 |
| 266 | 266-284 | UUGUGGACGAAUAUGAUCCAACA | 13 |
| 269 | 269-287 | UGGACGAAUAUGAUCCAACAAUA | 14 |
| 270 | 270-288 | GGACGAAUAUGAUCCAACAAUAG | 15 |

TABLE 2

KRAS siRNA sequences

| Id # | sequence position in NM_033360.2 | sense strand sequence (5'-3') | SEQ ID NO: | antisense strand sequence (5'-3') | SEQ ID NO: |
|---|---|---|---|---|---|
| 182 | 182-200 | AUGACUGAAUAUAAACUUGTT | 16 | CAAGUUUAUAUUCAGUCAUTT | 17 |
| 183 | 183-201 | UGACUGAAUAUAAACUUGUTT | 18 | ACAAGUUUAUAUUCAGUCATT | 19 |
| 197 | 197-215 | CUUGUGGUAGUUGGAGCUGTT | 20 | CAGCUCCAACUACCACAAGTT | 21 |
| 224 | 224-242 | GGCAAGAGUGCCUUGACGATT | 22 | UCGUCAAGGCACUCUUGCCTT | 23 |
| 226 | 226-244 | CAAGAGUGCCUUGACGAUATT | 24 | UAUCGUCAAGGCACUCUUGTT | 25 |
| 227 | 227-245 | AAGAGUGCCUUGACGAUACTT | 26 | GUAUCGUCAAGGCACUCUUTT | 27 |
| 228 | 228-246 | AGAGUGCCUUGACGAUACATT | 28 | UGUAUCGUCAAGGCACUCUTT | 29 |
| 232 | 232-250 | UGCCUUGACGAUACAGCUATT | 30 | UAGCUGUAUCGUCAAGGCATT | 31 |
| 233 | 233-251 | GCCUUGACGAUACAGCUAATT | 32 | UUAGCUGUAUCGUCAAGGCTT | 33 |

TABLE 2-continued

KRAS siRNA sequences

| Id # | sequence position in NM_033360.2 | sense strand sequence (5'-3') | SEQ ID NO: | antisense strand sequence (5'-3') | SEQ ID NO: |
|---|---|---|---|---|---|
| 236 | 236-254 | UUGACGAUACAGCUAAU UCTT | 34 | GAAUUAGCUGUAUCG UCAATT | 35 |
| 237 | 237-255 | UGACGAUACAGCUAAUU CATT | 36 | UGAAUUAGCUGUAUC GUCATT | 37 |
| 245 | 245-263 | CAGCUAAUUCAGAAUCA UUTT | 38 | AAUGAUUCUGAAUUA GCUGTT | 39 |
| 266 | 266-284 | GUGGACGAAUAUGAUCC AATT | 40 | UUGGAUCAUAUUCGU CCACTT | 41 |
| 269 | 269-287 | GACGAAUAUGAUCCAAC AATT | 42 | UUGUUGGAUCAUAUU CGUCTT | 43 |
| 270 | 270-288 | ACGAAUAUGAUCCAACA AUTT | 44 | AUUGUUGGAUCAUAU UCGUTT | 45 |

TABLE 3

EGFR Target Sequences

| hs Id # | 19mer pos. in NM_005228.3 | sequence of total 23mer target site in NM_005228.3 | SEQ ID NO: |
|---|---|---|---|
| 68 | 68-86 | GGCGGCCGGAGUCCCGAGCUAGC | 46 |
| 71 | 71-89 | GGCCGGAGUCCCGAGCUAGCCCC | 47 |
| 72 | 72-90 | GCCGGAGUCCCGAGCUAGCCCCG | 48 |
| 73 | 73-91 | CCGGAGUCCCGAGCUAGCCCCGG | 49 |
| 74 | 74-92 | CGGAGUCCCGAGCUAGCCCCGGC | 50 |
| 75 | 75-93 | GGAGUCCCGAGCUAGCCCCGGCG | 51 |
| 76 | 76-94 | GAGUCCCGAGCUAGCCCCGGCGG | 52 |
| 78 | 78-96 | GUCCCGAGCUAGCCCCGGCGGCC | 53 |
| 114 | 114-132 | CCGGACGACAGGCCACCUCGUCG | 54 |
| 115 | 115-133 | CGGACGACAGGCCACCUCGUCGG | 55 |
| 116 | 116-134 | GGACGACAGGCCACCUCGUCGGC | 56 |
| 117 | 117-135 | GACGACAGGCCACCUCGUCGGCG | 57 |
| 118 | 118-136 | ACGACAGGCCACCUCGUCGGCGU | 58 |
| 120 | 120-138 | GACAGGCCACCUCGUCGGCGUCC | 59 |
| 121 | 121-139 | ACAGGCCACCUCGUCGGCGUCCG | 60 |
| 122 | 122-140 | CAGGCCACCUCGUCGGCGUCCGC | 61 |
| 123 | 123-141 | AGGCCACCUCGUCGGCGUCCGCC | 62 |
| 124 | 124-142 | GGCCACCUCGUCGGCGUCCGCCC | 63 |
| 125 | 125-143 | GCCACCUCGUCGGCGUCCGCCCG | 64 |
| 126 | 126-144 | CCACCUCGUCGGCGUCCGCCCGA | 65 |
| 127 | 127-145 | CACCUCGUCGGCGUCCGCCCGAG | 66 |
| 128 | 128-146 | ACCUCGUCGGCGUCCGCCCGAGU | 67 |

TABLE 3-continued

EGFR Target Sequences

| hs Id # | 19mer pos. in NM_005228.3 | sequence of total 23mer target site in NM_005228.3 | SEQ ID NO: |
|---|---|---|---|
| 129 | 129-147 | CCUCGUCGGCGUCCGCCCGAGUC | 68 |
| 130 | 130-148 | CUCGUCGGCGUCCGCCCGAGUCC | 69 |
| 131 | 131-149 | UCGUCGGCGUCCGCCCGAGUCCC | 70 |
| 132 | 132-150 | CGUCGGCGUCCGCCCGAGUCCCC | 71 |
| 135 | 135-153 | CGGCGUCCGCCCGAGUCCCCGCC | 72 |
| 136 | 136-154 | GGCGUCCGCCCGAGUCCCCGCCU | 73 |
| 141 | 141-159 | CCGCCCGAGUCCCCGCCUCGCCG | 74 |
| 164 | 164-182 | CCAACGCCACAACCACCGCGCAC | 75 |
| 165 | 165-183 | CAACGCCACAACCACCGCGCACG | 76 |
| 166 | 166-184 | AACGCCACAACCACCGCGCACGG | 77 |
| 168 | 168-186 | CGCCACAACCACCGCGCACGGCC | 78 |
| 169 | 169-187 | GCCACAACCACCGCGCACGGCCC | 79 |
| 170 | 170-188 | CCACAACCACCGCGCACGGCCCC | 80 |
| 247 | 247-265 | CGAUGCGACCCUCCGGGACGGCC | 81 |
| 248 | 248-266 | GAUGCGACCCUCCGGGACGGCCG | 82 |
| 249 | 249-267 | AUGCGACCCUCCGGGACGGCCGG | 83 |
| 251 | 251-269 | GCGACCCUCCGGGACGGCCGGGG | 84 |
| 252 | 252-270 | CGACCCUCCGGGACGGCCGGGGC | 85 |
| 254 | 254-272 | ACCCUCCGGGACGGCCGGGGCAG | 86 |
| 329 | 329-347 | AAAGAAAGUUUGCCAAGGCACGA | 87 |
| 330 | 330-348 | AAGAAAGUUUGCCAAGGCACGAG | 88 |
| 332 | 332-350 | GAAAGUUUGCCAAGGCACGAGUA | 89 |

TABLE 3-continued

EGFR Target Sequences

| hs Id # | 19mer pos. in NM_005228.3 | sequence of total 23mer target site in NM_005228.3 | SEQ ID NO: |
|---|---|---|---|
| 333 | 333-351 | AAAGUUUGCCAAGGCACGAGUAA | 90 |
| 334 | 334-352 | AAGUUUGCCAAGGCACGAGUAAC | 91 |
| 335 | 335-353 | AGUUUGCCAAGGCACGAGUAACA | 92 |
| 336 | 336-354 | GUUUGCCAAGGCACGAGUAACAA | 93 |
| 337 | 337-355 | UUUGCCAAGGCACGAGUAACAAG | 94 |
| 338 | 338-356 | UUGCCAAGGCACGAGUAACAAGC | 95 |
| 361 | 361-379 | UCACGCAGUUGGGCACUUUUGAA | 96 |
| 362 | 362-380 | CACGCAGUUGGGCACUUUUGAAG | 97 |
| 363 | 363-381 | ACGCAGUUGGGCACUUUUGAAGA | 98 |
| 364 | 364-382 | CGCAGUUGGGCACUUUUGAAGAU | 99 |
| 365 | 365-383 | GCAGUUGGGCACUUUUGAAGAUC | 100 |
| 366 | 366-384 | CAGUUGGGCACUUUUGAAGAUCA | 101 |
| 367 | 367-385 | AGUUGGGCACUUUUGAAGAUCAU | 102 |
| 368 | 368-386 | GUUGGGCACUUUUGAAGAUCAUU | 103 |
| 369 | 369-387 | UUGGGCACUUUUGAAGAUCAUUU | 104 |
| 377 | 377-395 | UUUUGAAGAUCAUUUUCUCAGCC | 105 |
| 379 | 379-397 | UUGAAGAUCAUUUUCUCAGCCUC | 106 |
| 380 | 380-398 | UGAAGAUCAUUUUCUCAGCCUCC | 107 |
| 385 | 385-403 | AUCAUUUUCUCAGCCUCCAGAGG | 108 |
| 394 | 394-412 | UCAGCCUCCAGAGGAUGUUCAAU | 109 |
| 396 | 396-414 | AGCCUCCAGAGGAUGUUCAAUAA | 110 |
| 397 | 397-415 | GCCUCCAGAGGAUGUUCAAUAAC | 111 |
| 401 | 401-419 | CCAGAGGAUGUUCAAUAACUGUG | 112 |
| 403 | 403-421 | AGAGGAUGUUCAAUAACUGUGAG | 113 |
| 407 | 407-425 | GAUGUUCAAUAACUGUGAGGUGG | 114 |
| 409 | 409-427 | UGUUCAAUAACUGUGAGGUGGUC | 115 |
| 410 | 410-428 | GUUCAAUAACUGUGAGGUGGUCC | 116 |
| 411 | 411-429 | UUCAAUAACUGUGAGGUGGUCCU | 117 |
| 412 | 412-430 | UCAAUAACUGUGAGGUGGUCCUU | 118 |
| 413 | 413-431 | CAAUAACUGUGAGGUGGUCCUUG | 119 |
| 414 | 414-432 | AAUAACUGUGAGGUGGUCCUUGG | 120 |
| 416 | 416-434 | UAACUGUGAGGUGGUCCUUGGGA | 121 |
| 418 | 418-436 | ACUGUGAGGUGGUCCUUGGGAAU | 122 |
| 419 | 419-437 | CUGUGAGGUGGUCCUUGGGAAUU | 123 |
| 425 | 425-443 | GGUGGUCCUUGGGAAUUUGGAAA | 124 |
| 431 | 431-449 | CCUUGGGAAUUUGGAAAUUACCU | 125 |
| 432 | 432-450 | CUUGGGAAUUUGGAAAUUACCUA | 126 |
| 433 | 433-451 | UUGGGAAUUUGGAAAUUACCUAU | 127 |
| 434 | 434-452 | UGGGAAUUUGGAAAUUACCUAUG | 128 |
| 458 | 458-476 | GCAGAGGAAUUAUGAUCUUUCCU | 129 |
| 459 | 459-477 | CAGAGGAAUUAUGAUCUUUCCUU | 130 |
| 463 | 463-481 | GGAAUUAUGAUCUUUCCUUCUUA | 131 |
| 464 | 464-482 | GAAUUAUGAUCUUUCCUUCUUAA | 132 |
| 466 | 466-484 | AUUAUGAUCUUUCCUUCUUAAAG | 133 |
| 468 | 468-486 | UAUGAUCUUUCCUUCUUAAAGAC | 134 |
| 471 | 471-489 | GAUCUUUCCUUCUUAAAGACCAU | 135 |
| 476 | 476-494 | UUCCUUCUUAAAGACCAUCCAGG | 136 |
| 477 | 477-495 | UCCUUCUUAAAGACCAUCCAGGA | 137 |
| 479 | 479-497 | CUUCUUAAAGACCAUCCAGGAGG | 138 |
| 481 | 481-499 | UCUUAAAGACCAUCCAGGAGGUG | 139 |
| 482 | 482-500 | CUUAAAGACCAUCCAGGAGGUGG | 140 |
| 492 | 492-510 | AUCCAGGAGGUGGCUGGUUAUGU | 141 |
| 493 | 493-511 | UCCAGGAGGUGGCUGGUUAUGUC | 142 |
| 494 | 494-512 | CCAGGAGGUGGCUGGUUAUGUCC | 143 |
| 495 | 495-513 | CAGGAGGUGGCUGGUUAUGUCCU | 144 |
| 496 | 496-514 | AGGAGGUGGCUGGUUAUGUCCUC | 145 |
| 497 | 497-515 | GGAGGUGGCUGGUUAUGUCCUCA | 146 |
| 499 | 499-517 | AGGUGGCUGGUUAUGUCCUCAUU | 147 |
| 520 | 520-538 | UUGCCCUCAACACAGUGGAGCGA | 148 |
| 542 | 542-560 | AAUUCCUUUGGAAAACCUGCAGA | 149 |
| 543 | 543-561 | AUUCCUUUGGAAAACCUGCAGAU | 150 |
| 550 | 550-568 | UGGAAAACCUGCAGAUCAUCAGA | 151 |
| 551 | 551-569 | GGAAAACCUGCAGAUCAUCAGAG | 152 |
| 553 | 553-571 | AAAACCUGCAGAUCAUCAGAGGA | 153 |
| 556 | 556-574 | ACCUGCAGAUCAUCAGAGGAAAU | 154 |
| 586 | 586-604 | ACGAAAAUUCCUAUGCCUUAGCA | 155 |
| 587 | 587-605 | CGAAAAUUCCUAUGCCUUAGCAG | 156 |
| 589 | 589-607 | AAAAUUCCUAUGCCUUAGCAGUC | 157 |
| 592 | 592-610 | AUUCCUAUGCCUUAGCAGUCUUA | 158 |
| 593 | 593-611 | UUCCUAUGCCUUAGCAGUCUUAU | 159 |
| 594 | 594-612 | UCCUAUGCCUUAGCAGUCUUAUC | 160 |
| 596 | 596-614 | CUAUGCCUUAGCAGUCUUAUCUA | 161 |
| 597 | 597-615 | UAUGCCUUAGCAGUCUUAUCUAA | 162 |
| 598 | 598-616 | AUGCCUUAGCAGUCUUAUCUAAC | 163 |

TABLE 3-continued

EGFR Target Sequences

| hs Id # | 19mer pos. in NM_005228.3 | sequence of total 23mer target site in NM_005228.3 | SEQ ID NO: |
|---|---|---|---|
| 599 | 599-617 | UGCCUUAGCAGUCUUAUCUAACU | 164 |
| 600 | 600-618 | GCCUUAGCAGUCUUAUCUAACUA | 165 |
| 601 | 601-619 | CCUUAGCAGUCUUAUCUAACUAU | 166 |
| 602 | 602-620 | CUUAGCAGUCUUAUCUAACUAUG | 167 |
| 603 | 603-621 | UUAGCAGUCUUAUCUAACUAUGA | 168 |
| 604 | 604-622 | UAGCAGUCUUAUCUAACUAUGAU | 169 |
| 605 | 605-623 | AGCAGUCUUAUCUAACUAUGAUG | 170 |
| 608 | 608-626 | AGUCUUAUCUAACUAUGAUGCAA | 171 |
| 609 | 609-627 | GUCUUAUCUAACUAUGAUGCAAA | 172 |
| 610 | 610-628 | UCUUAUCUAACUAUGAUGCAAAU | 173 |
| 611 | 611-629 | CUUAUCUAACUAUGAUGCAAAUA | 174 |
| 612 | 612-630 | UUAUCUAACUAUGAUGCAAAUAA | 175 |
| 613 | 613-631 | UAUCUAACUAUGAUGCAAAUAAA | 176 |
| 614 | 614-632 | AUCUAACUAUGAUGCAAAUAAAA | 177 |
| 616 | 616-634 | CUAACUAUGAUGCAAAUAAAACC | 178 |
| 622 | 622-640 | AUGAUGCAAAUAAAACCGGACUG | 179 |
| 623 | 623-641 | UGAUGCAAAUAAAACCGGACUGA | 180 |
| 624 | 624-642 | GAUGCAAAUAAAACCGGACUGAA | 181 |
| 626 | 626-644 | UGCAAAUAAAACCGGACUGAAGG | 182 |
| 627 | 627-645 | GCAAAUAAAACCGGACUGAAGGA | 183 |
| 628 | 628-646 | CAAAUAAAACCGGACUGAAGGAG | 184 |
| 630 | 630-648 | AAUAAAACCGGACUGAAGGAGCU | 185 |
| 631 | 631-649 | AUAAAACCGGACUGAAGGAGCUG | 186 |
| 632 | 632-650 | UAAAACCGGACUGAAGGAGCUGC | 187 |
| 633 | 633-651 | AAAACCGGACUGAAGGAGCUGCC | 188 |
| 644 | 644-662 | GAAGGAGCUGCCCAUGAGAAAUU | 189 |
| 665 | 665-683 | UUUACAGGAAAUCCUGCAUGGCG | 190 |
| 668 | 668-686 | ACAGGAAAUCCUGCAUGGCGCCG | 191 |
| 669 | 669-687 | CAGGAAAUCCUGCAUGGCGCCGU | 192 |
| 670 | 670-688 | AGGAAAUCCUGCAUGGCGCCGUG | 193 |
| 671 | 671-689 | GGAAAUCCUGCAUGGCGCCGUGC | 194 |
| 672 | 672-690 | GAAAUCCUGCAUGGCGCCGUGCG | 195 |
| 674 | 674-692 | AAUCCUGCAUGGCGCCGUGCGGU | 196 |
| 676 | 676-694 | UCCUGCAUGGCGCCGUGCGGUUC | 197 |
| 677 | 677-695 | CCUGCAUGGCGCCGUGCGGUUCA | 198 |
| 678 | 678-696 | CUGCAUGGCGCCGUGCGGUUCAG | 199 |
| 680 | 680-698 | GCAUGGCGCCGUGCGGUUCAGCA | 200 |
| 681 | 681-699 | CAUGGCGCCGUGCGGUUCAGCAA | 201 |
| 682 | 682-700 | AUGGCGCCGUGCGGUUCAGCAAC | 202 |
| 683 | 683-701 | UGGCGCCGUGCGGUUCAGCAACA | 203 |
| 684 | 684-702 | GGCGCCGUGCGGUUCAGCAACAA | 204 |
| 685 | 685-703 | GCGCCGUGCGGUUCAGCAACAAC | 205 |
| 686 | 686-704 | CGCCGUGCGGUUCAGCAACAACC | 206 |
| 688 | 688-706 | CCGUGCGGUUCAGCAACAACCCU | 207 |
| 690 | 690-708 | GUGCGGUUCAGCAACAACCCUGC | 208 |
| 692 | 692-710 | GCGGUUCAGCAACAACCCUGCCC | 209 |
| 698 | 698-716 | CAGCAACAACCCUGCCCUGUGCA | 210 |
| 700 | 700-718 | GCAACAACCCUGCCCUGUGCAAC | 211 |
| 719 | 719-737 | CAACGUGGAGAGCAUCCAGUGGC | 212 |
| 720 | 720-738 | AACGUGGAGAGCAUCCAGUGGCG | 213 |
| 721 | 721-739 | ACGUGGAGAGCAUCCAGUGGCGG | 214 |
| 724 | 724-742 | UGGAGAGCAUCCAGUGGCGGGAC | 215 |
| 725 | 725-743 | GGAGAGCAUCCAGUGGCGGGACA | 216 |
| 726 | 726-744 | GAGAGCAUCCAGUGGCGGGACAU | 217 |
| 733 | 733-751 | UCCAGUGGCGGGACAUAGUCAGC | 218 |
| 734 | 734-752 | CCAGUGGCGGGACAUAGUCAGCA | 219 |
| 736 | 736-754 | AGUGGCGGGACAUAGUCAGCAGU | 220 |
| 737 | 737-755 | GUGGCGGGACAUAGUCAGCAGUG | 221 |
| 763 | 763-781 | UUCUCAGCAACAUGUCGAUGGAC | 222 |
| 765 | 765-783 | CUCAGCAACAUGUCGAUGGACUU | 223 |
| 766 | 766-784 | UCAGCAACAUGUCGAUGGACUUC | 224 |
| 767 | 767-785 | CAGCAACAUGUCGAUGGACUUCC | 225 |
| 769 | 769-787 | GCAACAUGUCGAUGGACUUCCAG | 226 |
| 770 | 770-788 | CAACAUGUCGAUGGACUUCCAGA | 227 |
| 771 | 771-789 | AACAUGUCGAUGGACUUCCAGAA | 228 |
| 772 | 772-790 | ACAUGUCGAUGGACUUCCAGAAC | 229 |
| 775 | 775-793 | UGUCGAUGGACUUCCAGAACCAC | 230 |
| 789 | 789-807 | CAGAACCACCUGGGCAGCUGCCA | 231 |
| 798 | 798-816 | CUGGGCAGCUGCCAAAAGUGUGA | 232 |
| 800 | 800-818 | GGGCAGCUGCCAAAAGUGUGAUC | 233 |
| 805 | 805-823 | GCUGCCAAAAGUGUGAUCCAAGC | 234 |
| 806 | 806-824 | CUGCCAAAAGUGUGAUCCAAGCU | 235 |
| 807 | 807-825 | UGCCAAAAGUGUGAUCCAAGCUG | 236 |
| 810 | 810-828 | CAAAAGUGUGAUCCAAGCUGUCC | 237 |

TABLE 3-continued

EGFR Target Sequences

| hs Id # | 19mer pos. in NM_005228.3 | sequence of total 23mer target site in NM_005228.3 | SEQ ID NO: |
|---|---|---|---|
| 814 | 814-832 | AGUGUGAUCCAAGCUGUCCCAAU | 238 |
| 815 | 815-833 | GUGUGAUCCAAGCUGUCCCAAUG | 239 |
| 817 | 817-835 | GUGAUCCAAGCUGUCCCAAUGGG | 240 |
| 818 | 818-836 | UGAUCCAAGCUGUCCCAAUGGGA | 241 |
| 819 | 819-837 | GAUCCAAGCUGUCCCAAUGGGAG | 242 |
| 820 | 820-838 | AUCCAAGCUGUCCCAAUGGGAGC | 243 |
| 821 | 821-839 | UCCAAGCUGUCCCAAUGGGAGCU | 244 |
| 823 | 823-841 | CAAGCUGUCCCAAUGGGAGCUGC | 245 |
| 826 | 826-844 | GCUGUCCCAAUGGGAGCUGCUGG | 246 |
| 847 | 847-865 | GGGGUGCAGGAGAGGAGAACUGC | 247 |
| 871 | 871-889 | AGAAACUGACCAAAAUCAUCUGU | 248 |
| 872 | 872-890 | GAAACUGACCAAAAUCAUCUGUG | 249 |
| 873 | 873-891 | AAACUGACCAAAAUCAUCUGUGC | 250 |
| 877 | 877-895 | UGACCAAAAUCAUCUGUGCCCAG | 251 |
| 878 | 878-896 | GACCAAAAUCAUCUGUGCCCAGC | 252 |
| 881 | 881-899 | CAAAAUCAUCUGUGCCCAGCAGU | 253 |
| 890 | 890-908 | CUGUGCCCAGCAGUGCUCCGGGC | 254 |
| 892 | 892-910 | GUGCCCAGCAGUGCUCCGGGCGC | 255 |
| 929 | 929-947 | CCCCAGUGACUGCUGCCACAACC | 256 |
| 930 | 930-948 | CCCAGUGACUGCUGCCACAACCA | 257 |
| 979 | 979-997 | GGGAGAGCGACUGCCUGGUCUGC | 258 |
| 980 | 980-998 | GGAGAGCGACUGCCUGGUCUGCC | 259 |
| 981 | 981-999 | GAGAGCGACUGCCUGGUCUGCCG | 260 |
| 982 | 982-1000 | AGAGCGACUGCCUGGUCUGCCGC | 261 |
| 983 | 983-1001 | GAGCGACUGCCUGGUCUGCCGCA | 262 |
| 984 | 984-1002 | AGCGACUGCCUGGUCUGCCGCAA | 263 |
| 989 | 989-1007 | CUGCCUGGUCUGCCGCAAAUUCC | 264 |
| 990 | 990-1008 | UGCCUGGUCUGCCGCAAAUUCCG | 265 |
| 991 | 991-1009 | GCCUGGUCUGCCGCAAAUUCCGA | 266 |
| 992 | 992-1010 | CCUGGUCUGCCGCAAAUUCCGAG | 267 |
| 994 | 994-1012 | UGGUCUGCCGCAAAUUCCGAGAC | 268 |
| 995 | 995-1013 | GGUCUGCCGCAAAUUCCGAGACG | 269 |
| 996 | 996-1014 | GUCUGCCGCAAAUUCCGAGACGA | 270 |
| 997 | 997-1015 | UCUGCCGCAAAUUCCGAGACGAA | 271 |
| 999 | 999-1017 | UGCCGCAAAUUCCGAGACGAAGC | 272 |
| 1004 | 1004-1022 | CAAAUUCCGAGACGAAGCCACGU | 273 |
| 1005 | 1005-1023 | AAAUUCCGAGACGAAGCCACGUG | 274 |
| 1006 | 1006-1024 | AAUUCCGAGACGAAGCCACGUGC | 275 |
| 1007 | 1007-1025 | AUUCCGAGACGAAGCCACGUGCA | 276 |
| 1008 | 1008-1026 | UUCCGAGACGAAGCCACGUGCAA | 277 |
| 1010 | 1010-1028 | CCGAGACGAAGCCACGUGCAAGG | 278 |
| 1013 | 1013-1031 | AGACGAAGCCACGUGCAAGGACA | 279 |
| 1014 | 1014-1032 | GACGAAGCCACGUGCAAGGACAC | 280 |
| 1015 | 1015-1033 | ACGAAGCCACGUGCAAGGACACC | 281 |
| 1016 | 1016-1034 | CGAAGCCACGUGCAAGGACACCU | 282 |
| 1040 | 1040-1058 | CCCCCCACUCAUGCUCUACAACC | 283 |
| 1042 | 1042-1060 | CCCCACUCAUGCUCUACAACCCC | 284 |
| 1044 | 1044-1062 | CCACUCAUGCUCUACAACCCCAC | 285 |
| 1047 | 1047-1065 | CUCAUGCUCUACAACCCCACCAC | 286 |
| 1071 | 1071-1089 | UACCAGAUGGAUGUGAACCCCGA | 287 |
| 1073 | 1073-1091 | CCAGAUGGAUGUGAACCCCGAGG | 288 |
| 1074 | 1074-1092 | CAGAUGGAUGUGAACCCCGAGGG | 289 |
| 1075 | 1075-1093 | AGAUGGAUGUGAACCCCGAGGGC | 290 |
| 1077 | 1077-1095 | AUGGAUGUGAACCCCGAGGGCAA | 291 |
| 1078 | 1078-1096 | UGGAUGUGAACCCCGAGGGCAAA | 292 |
| 1080 | 1080-1098 | GAUGUGAACCCCGAGGGCAAAUA | 293 |
| 1084 | 1084-1102 | UGAACCCCGAGGGCAAAUACAGC | 294 |
| 1085 | 1085-1103 | GAACCCCGAGGGCAAAUACAGCU | 295 |
| 1087 | 1087-1105 | ACCCCGAGGGCAAAUACAGCUUU | 296 |
| 1088 | 1088-1106 | CCCCGAGGGCAAAUACAGCUUUG | 297 |
| 1089 | 1089-1107 | CCCGAGGGCAAAUACAGCUUUGG | 298 |
| 1096 | 1096-1114 | GCAAAUACAGCUUUGGUGCCACC | 299 |
| 1097 | 1097-1115 | CAAAUACAGCUUUGGUGCCACCU | 300 |
| 1098 | 1098-1116 | AAAUACAGCUUUGGUGCCACCUG | 301 |
| 1104 | 1104-1122 | AGCUUUGGUGCCACCUGCGUGAA | 302 |
| 1106 | 1106-1124 | CUUUGGUGCCACCUGCGUGAAGA | 303 |
| 1112 | 1112-1130 | UGCCACCUGCGUGAAGAAGUGUC | 304 |
| 1116 | 1116-1134 | ACCUGCGUGAAGAAGUGUCCCCG | 305 |
| 1117 | 1117-1135 | CCUGCGUGAAGAAGUGUCCCCGU | 306 |
| 1118 | 1118-1136 | CUGCGUGAAGAAGUGUCCCCGUA | 307 |
| 1119 | 1119-1137 | UGCGUGAAGAAGUGUCCCCGUAA | 308 |
| 1120 | 1120-1138 | GCGUGAAGAAGUGUCCCCGUAAU | 309 |
| 1121 | 1121-1139 | CGUGAAGAAGUGUCCCCGUAAUU | 310 |
| 1122 | 1122-1140 | GUGAAGAAGUGUCCCCGUAAUUA | 311 |

TABLE 3-continued

EGFR Target Sequences

| hs Id # | 19mer pos. in NM_005228.3 | sequence of total 23mer target site in NM_005228.3 | SEQ ID NO: |
|---|---|---|---|
| 1123 | 1123-1141 | UGAAGAAGUGUCCCCGUAAUUAU | 312 |
| 1124 | 1124-1142 | GAAGAAGUGUCCCCGUAAUUAUG | 313 |
| 1125 | 1125-1143 | AAGAAGUGUCCCCGUAAUUAUGU | 314 |
| 1126 | 1126-1144 | AGAAGUGUCCCCGUAAUUAUGUG | 315 |
| 1127 | 1127-1145 | GAAGUGUCCCCGUAAUUAUGUGG | 316 |
| 1128 | 1128-1146 | AAGUGUCCCCGUAAUUAUGUGGU | 317 |
| 1129 | 1129-1147 | AGUGUCCCCGUAAUUAUGUGGUG | 318 |
| 1130 | 1130-1148 | GUGUCCCCGUAAUUAUGUGGUGA | 319 |
| 1132 | 1132-1150 | GUCCCCGUAAUUAUGUGGUGACA | 320 |
| 1134 | 1134-1152 | CCCCGUAAUUAUGUGGUGACAGA | 321 |
| 1136 | 1136-1154 | CCGUAAUUAUGUGGUGACAGAUC | 322 |
| 1137 | 1137-1155 | CGUAAUUAUGUGGUGACAGAUCA | 323 |
| 1138 | 1138-1156 | GUAAUUAUGUGGUGACAGAUCAC | 324 |
| 1139 | 1139-1157 | UAAUUAUGUGGUGACAGAUCACG | 325 |
| 1140 | 1140-1158 | AAUUAUGUGGUGACAGAUCACGG | 326 |
| 1142 | 1142-1160 | UUAUGUGGUGACAGAUCACGGCU | 327 |
| 1145 | 1145-1163 | UGUGGUGACAGAUCACGGCUCGU | 328 |
| 1147 | 1147-1165 | UGGUGACAGAUCACGGCUCGUGC | 329 |
| 1148 | 1148-1166 | GGUGACAGAUCACGGCUCGUGCG | 330 |
| 1149 | 1149-1167 | GUGACAGAUCACGGCUCGUGCGU | 331 |
| 1150 | 1150-1168 | UGACAGAUCACGGCUCGUGCGUC | 332 |
| 1151 | 1151-1169 | GACAGAUCACGGCUCGUGCGUCC | 333 |
| 1152 | 1152-1170 | ACAGAUCACGGCUCGUGCGUCCG | 334 |
| 1153 | 1153-1171 | CAGAUCACGGCUCGUGCGUCCGA | 335 |
| 1154 | 1154-1172 | AGAUCACGGCUCGUGCGUCCGAG | 336 |
| 1155 | 1155-1173 | GAUCACGGCUCGUGCGUCCGAGC | 337 |
| 1156 | 1156-1174 | AUCACGGCUCGUGCGUCCGAGCC | 338 |
| 1157 | 1157-1175 | UCACGGCUCGUGCGUCCGAGCCU | 339 |
| 1160 | 1160-1178 | CGGCUCGUGCGUCCGAGCCUGUG | 340 |
| 1200 | 1200-1218 | AUGGAGGAAGACGGCGUCCGCAA | 341 |
| 1201 | 1201-1219 | UGGAGGAAGACGGCGUCCGCAAG | 342 |
| 1203 | 1203-1221 | GAGGAAGACGGCGUCCGCAAGUG | 343 |
| 1204 | 1204-1222 | AGGAAGACGGCGUCCGCAAGUGU | 344 |
| 1205 | 1205-1223 | GGAAGACGGCGUCCGCAAGUGUA | 345 |
| 1207 | 1207-1225 | AAGACGGCGUCCGCAAGUGUAAG | 346 |
| 1208 | 1208-1226 | AGACGGCGUCCGCAAGUGUAAGA | 347 |
| 1211 | 1211-1229 | CGGCGUCCGCAAGUGUAAGAAGU | 348 |
| 1212 | 1212-1230 | GGCGUCCGCAAGUGUAAGAAGUG | 349 |
| 1213 | 1213-1231 | GCGUCCGCAAGUGUAAGAAGUGC | 350 |
| 1214 | 1214-1232 | CGUCCGCAAGUGUAAGAAGUGCG | 351 |
| 1215 | 1215-1233 | GUCCGCAAGUGUAAGAAGUGCGA | 352 |
| 1216 | 1216-1234 | UCCGCAAGUGUAAGAAGUGCGAA | 353 |
| 1217 | 1217-1235 | CCGCAAGUGUAAGAAGUGCGAAG | 354 |
| 1219 | 1219-1237 | GCAAGUGUAAGAAGUGCGAAGGG | 355 |
| 1220 | 1220-1238 | CAAGUGUAAGAAGUGCGAAGGGC | 356 |
| 1221 | 1221-1239 | AAGUGUAAGAAGUGCGAAGGGCC | 357 |
| 1222 | 1222-1240 | AGUGUAAGAAGUGCGAAGGGCCU | 358 |
| 1223 | 1223-1241 | GUGUAAGAAGUGCGAAGGGCCUU | 359 |
| 1224 | 1224-1242 | UGUAAGAAGUGCGAAGGGCCUUG | 360 |
| 1225 | 1225-1243 | GUAAGAAGUGCGAAGGGCCUUGC | 361 |
| 1226 | 1226-1244 | UAAGAAGUGCGAAGGGCCUUGCC | 362 |
| 1229 | 1229-1247 | GAAGUGCGAAGGGCCUUGCCGCA | 363 |
| 1230 | 1230-1248 | AAGUGCGAAGGGCCUUGCCGCAA | 364 |
| 1231 | 1231-1249 | AGUGCGAAGGGCCUUGCCGCAAA | 365 |
| 1232 | 1232-1250 | GUGCGAAGGGCCUUGCCGCAAAG | 366 |
| 1233 | 1233-1251 | UGCGAAGGGCCUUGCCGCAAAGU | 367 |
| 1235 | 1235-1253 | CGAAGGGCCUUGCCGCAAAGUGU | 368 |
| 1236 | 1236-1254 | GAAGGGCCUUGCCGCAAAGUGUG | 369 |
| 1237 | 1237-1255 | AAGGGCCUUGCCGCAAAGUGUGU | 370 |
| 1238 | 1238-1256 | AGGGCCUUGCCGCAAAGUGUGUA | 371 |
| 1239 | 1239-1257 | GGGCCUUGCCGCAAAGUGUGUAA | 372 |
| 1241 | 1241-1259 | GCCUUGCCGCAAAGUGUGUAACG | 373 |
| 1261 | 1261-1279 | ACGGAAUAGGUAUUGGUGAAUUU | 374 |
| 1262 | 1262-1280 | CGGAAUAGGUAUUGGUGAAUUUA | 375 |
| 1263 | 1263-1281 | GGAAUAGGUAUUGGUGAAUUUAA | 376 |
| 1264 | 1264-1282 | GAAUAGGUAUUGGUGAAUUUAAA | 377 |
| 1266 | 1266-1284 | AUAGGUAUUGGUGAAUUUAAAGA | 378 |
| 1267 | 1267-1285 | UAGGUAUUGGUGAAUUUAAAGAC | 379 |
| 1289 | 1289-1307 | CUCACUCUCCAUAAAUGCUACGA | 380 |
| 1313 | 1313-1331 | UAUUAAACACUUCAAAAACUGCA | 381 |
| 1320 | 1320-1338 | CACUUCAAAAACUGCACCUCCAU | 382 |
| 1321 | 1321-1339 | ACUUCAAAAACUGCACCUCCAUC | 383 |
| 1322 | 1322-1340 | CUUCAAAAACUGCACCUCCAUCA | 384 |
| 1323 | 1323-1341 | UUCAAAAACUGCACCUCCAUCAG | 385 |

TABLE 3-continued

EGFR Target Sequences

| hs Id # | 19mer pos. in NM_005228.3 | sequence of total 23mer target site in NM_005228.3 | SEQ ID NO: |
|---|---|---|---|
| 1324 | 1324-1342 | UCAAAAACUGCACCUCCAUCAGU | 386 |
| 1328 | 1328-1346 | AAACUGCACCUCCAUCAGUGGCG | 387 |
| 1332 | 1332-1350 | UGCACCUCCAUCAGUGGCGAUCU | 388 |
| 1333 | 1333-1351 | GCACCUCCAUCAGUGGCGAUCUC | 389 |
| 1335 | 1335-1353 | ACCUCCAUCAGUGGCGAUCUCCA | 390 |
| 1338 | 1338-1356 | UCCAUCAGUGGCGAUCUCCACAU | 391 |
| 1344 | 1344-1362 | AGUGGCGAUCUCCACAUCCUGCC | 392 |
| 1345 | 1345-1363 | GUGGCGAUCUCCACAUCCUGCCG | 393 |
| 1346 | 1346-1364 | UGGCGAUCUCCACAUCCUGCCGG | 394 |
| 1347 | 1347-1365 | GGCGAUCUCCACAUCCUGCCGGU | 395 |
| 1348 | 1348-1366 | GCGAUCUCCACAUCCUGCCGGUG | 396 |
| 1353 | 1353-1371 | CUCCACAUCCUGCCGGUGGCAUU | 397 |
| 1354 | 1354-1372 | UCCACAUCCUGCCGGUGGCAUUU | 398 |
| 1355 | 1355-1373 | CCACAUCCUGCCGGUGGCAUUUA | 399 |
| 1357 | 1357-1375 | ACAUCCUGCCGGUGGCAUUUAGG | 400 |
| 1360 | 1360-1378 | UCCUGCCGGUGGCAUUUAGGGGU | 401 |
| 1361 | 1361-1379 | CCUGCCGGUGGCAUUUAGGGGUG | 402 |
| 1362 | 1362-1380 | CUGCCGGUGGCAUUUAGGGGUGA | 403 |
| 1363 | 1363-1381 | UGCCGGUGGCAUUUAGGGGUGAC | 404 |
| 1366 | 1366-1384 | CGGUGGCAUUUAGGGGUGACUCC | 405 |
| 1369 | 1369-1387 | UGGCAUUUAGGGGUGACUCCUUC | 406 |
| 1370 | 1370-1388 | GGCAUUUAGGGGUGACUCCUUCA | 407 |
| 1371 | 1371-1389 | GCAUUUAGGGGUGACUCCUUCAC | 408 |
| 1372 | 1372-1390 | CAUUUAGGGGUGACUCCUUCACA | 409 |
| 1373 | 1373-1391 | AUUUAGGGGUGACUCCUUCACAC | 410 |
| 1374 | 1374-1392 | UUUAGGGGUGACUCCUUCACACA | 411 |
| 1404 | 1404-1422 | CCUCUGGAUCCACAGGAACUGGA | 412 |
| 1408 | 1408-1426 | UGGAUCCACAGGAACUGGAUAUU | 413 |
| 1409 | 1409-1427 | GGAUCCACAGGAACUGGAUAUUC | 414 |
| 1411 | 1411-1429 | AUCCACAGGAACUGGAUAUUCUG | 415 |
| 1412 | 1412-1430 | UCCACAGGAACUGGAUAUUCUGA | 416 |
| 1419 | 1419-1437 | GAACUGGAUAUUCUGAAAACCGU | 417 |
| 1426 | 1426-1444 | AUAUUCUGAAAACCGUAAAGGAA | 418 |
| 1427 | 1427-1445 | UAUUCUGAAAACCGUAAAGGAAA | 419 |
| 1430 | 1430-1448 | UCUGAAAACCGUAAAGGAAAUCA | 420 |
| 1431 | 1431-1449 | CUGAAAACCGUAAAGGAAAUCAC | 421 |

TABLE 4

EGFR siRNA Sequences

| hs Id # | Sequence position in NM_005228.3 | sense strand sequence (5'-3') | SEQ ID NO: | antisense strand sequence (5'-3') | SEQ ID NO: |
|---|---|---|---|---|---|
| 68 | 68-86 | CGGCCGGAGUCCCGAGCUATT | 422 | UAGCUCGGGACUCCGGCCGTT | 423 |
| 71 | 71-89 | CCGGAGUCCCGAGCUAGCCTT | 424 | GGCUAGCUCGGGACUCCGGTT | 425 |
| 72 | 72-90 | CGGAGUCCCGAGCUAGCCCTT | 426 | GGGCUAGCUCGGGACUCCGTT | 427 |
| 73 | 73-91 | GGAGUCCCGAGCUAGCCCCTT | 428 | GGGGCUAGCUCGGGACUCCTT | 429 |
| 74 | 74-92 | GAGUCCCGAGCUAGCCCCGTT | 430 | CGGGGCUAGCUCGGGACUCTT | 431 |
| 75 | 75-93 | AGUCCCGAGCUAGCCCCGGTT | 432 | CCGGGGCUAGCUCGGGACUTT | 433 |
| 76 | 76-94 | GUCCCGAGCUAGCCCCGGCTT | 434 | GCCGGGGCUAGCUCGGGACTT | 435 |
| 78 | 78-96 | CCCGAGCUAGCCCCGGCGGTT | 436 | CCGCCGGGGCUAGCUCGGGTT | 437 |
| 114 | 114-132 | GGACGACAGGCCACCUCGUTT | 438 | ACGAGGUGGCCUGUCGUCCTT | 439 |

TABLE 4-continued

EGFR siRNA Sequences

| hs Id # | Sequence position in NM_005228.3 | sense strand sequence (5'-3') | SEQ ID NO: | antisense strand sequence (5'-3') | SEQ ID NO: |
|---|---|---|---|---|---|
| 115 | 115-133 | GACGACAGGCCACCUCGUCTT | 440 | GACGAGGUGGCCUGUCGUCTT | 441 |
| 116 | 116-134 | ACGACAGGCCACCUCGUCGTT | 442 | CGACGAGGUGGCCUGUCGUTT | 443 |
| 117 | 117-135 | CGACAGGCCACCUCGUCGGTT | 444 | CCGACGAGGUGGCCUGUCGTT | 445 |
| 118 | 118-136 | GACAGGCCACCUCGUCGGCTT | 446 | GCCGACGAGGUGGCCUGUCTT | 447 |
| 120 | 120-138 | CAGGCCACCUCGUCGGCGUTT | 448 | ACGCCGACGAGGUGGCCUGTT | 449 |
| 121 | 121-139 | AGGCCACCUCGUCGGCGUCTT | 450 | GACGCCGACGAGGUGGCCUTT | 451 |
| 122 | 122-140 | GGCCACCUCGUCGGCGUCCTT | 452 | GGACGCCGACGAGGUGGCCTT | 453 |
| 123 | 123-141 | GCCACCUCGUCGGCGUCCGTT | 454 | CGGACGCCGACGAGGUGGCTT | 455 |
| 124 | 124-142 | CCACCUCGUCGGCGUCCGCTT | 456 | GCGGACGCCGACGAGGUGGTT | 457 |
| 125 | 125-143 | CACCUCGUCGGCGUCCGCCTT | 458 | GGCGGACGCCGACGAGGUGTT | 459 |
| 126 | 126-144 | ACCUCGUCGGCGUCCGCCCTT | 460 | GGGCGGACGCCGACGAGGUTT | 461 |
| 127 | 127-145 | CCUCGUCGGCGUCCGCCCGTT | 462 | CGGGCGGACGCCGACGAGGTT | 463 |
| 128 | 128-146 | CUCGUCGGCGUCCGCCCGATT | 464 | UCGGGCGGACGCCGACGAGTT | 465 |
| 129 | 129-147 | UCGUCGGCGUCCGCCCGAGTT | 466 | CUCGGGCGGACGCCGACGATT | 467 |
| 130 | 130-148 | CGUCGGCGUCCGCCCGAGUTT | 468 | ACUCGGGCGGACGCCGACGTT | 469 |
| 131 | 131-149 | GUCGGCGUCCGCCCGAGUCTT | 470 | GACUCGGGCGGACGCCGACTT | 471 |
| 132 | 132-150 | UCGGCGUCCGCCCGAGUCCTT | 472 | GGACUCGGGCGGACGCCGATT | 473 |
| 135 | 135-153 | GCGUCCGCCCGAGUCCCCGTT | 474 | CGGGGACUCGGGCGGACGCTT | 475 |
| 136 | 136-154 | CGUCCGCCCGAGUCCCCGCTT | 476 | GCGGGGACUCGGGCGGACGTT | 477 |
| 141 | 141-159 | GCCCGAGUCCCCGCCUCGCTT | 478 | GCGAGGCGGGGACUCGGGCTT | 479 |
| 164 | 164-182 | AACGCCACAACCACCGCGCTT | 480 | GCGCGGUGGUUGUGGCGUUTT | 481 |
| 165 | 165-183 | ACGCCACAACCACCGCGCATT | 482 | UGCGCGGUGGUUGUGGCGUTT | 483 |
| 166 | 166-184 | CGCCACAACCACCGCGCACTT | 484 | GUGCGCGGUGGUUGUGGCGTT | 485 |
| 168 | 168-186 | CCACAACCACCGCGCACGGTT | 486 | CCGUGCGCGGUGGUUGUGGTT | 487 |
| 169 | 169-187 | CACAACCACCGCGCACGGCTT | 488 | GCCGUGCGCGGUGGUUGUGTT | 489 |

TABLE 4-continued

EGFR siRNA Sequences

| hs Id # | Sequence position in NM_005228.3 | sense strand sequence (5'-3') | SEQ ID NO: | antisense strand sequence (5'-3') | SEQ ID NO: |
|---|---|---|---|---|---|
| 170 | 170-188 | ACAACCACCGCGCACGGCCTT | 490 | GGCCGUGCGCGGUGGUUGUTT | 491 |
| 247 | 247-265 | AUGCGACCCUCCGGGACGGTT | 492 | CCGUCCCGGAGGGUCGCAUTT | 493 |
| 248 | 248-266 | UGCGACCCUCCGGGACGGCTT | 494 | GCCGUCCCGGAGGGUCGCATT | 495 |
| 249 | 249-267 | GCGACCCUCCGGGACGGCCTT | 496 | GGCCGUCCCGGAGGGUCGCTT | 497 |
| 251 | 251-269 | GACCCUCCGGGACGGCCGGTT | 498 | CCGGCCGUCCCGGAGGGUCTT | 499 |
| 252 | 252-270 | ACCCUCCGGGACGGCCGGTT | 500 | CCCGGCCGUCCCGGAGGGUTT | 501 |
| 254 | 254-272 | CCUCCGGGACGGCCGGGGCTT | 502 | GCCCCGGCCGUCCCGGAGGTT | 503 |
| 329 | 329-347 | AGAAAGUUUGCCAAGGCACTT | 504 | GUGCCUUGGCAAACUUUCUTT | 505 |
| 330 | 330-348 | GAAAGUUUGCCAAGGCACGTT | 506 | CGUGCCUUGGCAAACUUUCTT | 507 |
| 332 | 332-350 | AAGUUUGCCAAGGCACGAGTT | 508 | CUCGUGCCUUGGCAAACUUTT | 509 |
| 333 | 333-351 | AGUUUGCCAAGGCACGAGUTT | 510 | ACUCGUGCCUUGGCAAACUTT | 511 |
| 334 | 334-352 | GUUUGCCAAGGCACGAGUAATT | 512 | UACUCGUGCCUUGGCAAACTT | 513 |
| 335 | 335-353 | UUUGCCAAGGCACGAGUAAATT | 514 | UUACUCGUGCCUUGGCAAATT | 515 |
| 336 | 336-354 | UUGCCAAGGCACGAGUAACTT | 516 | GUUACUCGUGCCUUGGCAATT | 517 |
| 337 | 337-355 | UGCCAAGGCACGAGUAACATT | 518 | UGUUACUCGUGCCUUGGCATT | 519 |
| 338 | 338-356 | GCCAAGGCACGAGUAACAATT | 520 | UUGUUACUCGUGCCUUGGCTT | 521 |
| 361 | 361-379 | ACGCAGUUGGGCACUUUUGTT | 522 | CAAAAGUGCCCAACUGCGUTT | 523 |
| 362 | 362-380 | CGCAGUUGGGCACUUUUGATT | 524 | UCAAAAGUGCCCAACUGCGTT | 525 |
| 363 | 363-381 | GCAGUUGGGCACUUUUGAATT | 526 | UUCAAAAGUGCCCAACUGCTT | 527 |
| 364 | 364-382 | CAGUUGGGCACUUUUGAAGTT | 528 | CUUCAAAAGUGCCCAACUGTT | 529 |
| 365 | 365-383 | AGUUGGGCACUUUUGAAGATT | 530 | UCUUCAAAAGUGCCCAACUTT | 531 |
| 366 | 366-384 | GUUGGGCACUUUUGAAGAUTT | 532 | AUCUUCAAAAGUGCCCAACTT | 533 |
| 367 | 367-385 | UUGGGCACUUUUGAAGAUCTT | 534 | GAUCUUCAAAAGUGCCCATT | 535 |
| 368 | 368-386 | UGGGCACUUUUGAAGAUCATT | 536 | UGAUCUUCAAAAGUGCCCATT | 537 |

TABLE 4-continued

EGFR siRNA Sequences

| hs Id # | Sequence position in NM_005228.3 | sense strand sequence (5'-3') | SEQ ID NO: | antisense strand sequence (5'-3') | SEQ ID NO: |
|---|---|---|---|---|---|
| 369 | 369-387 | GGGCACUUUUGAAGAUCAUTT | 538 | AUGAUCUUCAAAAGUGCCCTT | 539 |
| 377 | 377-395 | UUGAAGAUCAUUUUCUCAGTT | 540 | CUGAGAAAAUGAUCUUCAATT | 541 |
| 379 | 379-397 | GAAGAUCAUUUUCUCAGCCTT | 542 | GGCUGAGAAAAUGAUCUUCTT | 543 |
| 380 | 380-398 | AAGAUCAUUUUCUCAGCCUTT | 544 | AGGCUGAGAAAAUGAUCUUTT | 545 |
| 385 | 385-403 | CAUUUUCUCAGCCUCCAGATT | 546 | UCUGGAGGCUGAGAAAAUGTT | 547 |
| 394 | 394-412 | AGCCUCCAGAGGAUGUUCATT | 548 | UGAACAUCCUCUGGAGGCUTT | 549 |
| 396 | 396-414 | CCUCCAGAGGAUGUUCAAUTT | 550 | AUUGAACAUCCUCUGGAGGTT | 551 |
| 397 | 397-415 | CUCCAGAGGAUGUUCAAUATT | 552 | UAUUGAACAUCCUCUGGAGTT | 553 |
| 401 | 401-419 | AGAGGAUGUUCAAUAACUGTT | 554 | CAGUUAUUGAACAUCCUCUTT | 555 |
| 403 | 403-421 | AGGAUGUUCAAUAACUGUGTT | 556 | CACAGUUAUUGAACAUCCUTT | 557 |
| 407 | 407-425 | UGUUCAAUAACUGUGAGGUTT | 558 | ACCUCACAGUUAUUGAACATT | 559 |
| 409 | 409-427 | UUCAAUAACUGUGAGGUGGTT | 560 | CCACCUCACAGUUAUUGAATT | 561 |
| 410 | 410-428 | UCAAUAACUGUGAGGUGGUTT | 562 | ACCACCUCACAGUUAUUGATT | 563 |
| 411 | 411-429 | CAAUAACUGUGAGGUGGUCTT | 564 | GACCACCUCACAGUUAUUGTT | 565 |
| 412 | 412-430 | AAUAACUGUGAGGUGGUCCTT | 566 | GGACCACCUCACAGUUAUUTT | 567 |
| 413 | 413-431 | AUAACUGUGAGGUGGUCCUTT | 568 | AGGACCACCUCACAGUUAUTT | 569 |
| 414 | 414-432 | UAACUGUGAGGUGGUCCUUTT | 570 | AAGGACCACCUCACAGUUATT | 571 |
| 416 | 416-434 | ACUGUGAGGUGGUCCUUGGTT | 572 | CCAAGGACCACCUCACAGUTT | 573 |
| 418 | 418-436 | UGUGAGGUGGUCCUUGGGATT | 574 | UCCCAAGGACCACCUCACATT | 575 |
| 419 | 419-437 | GUGAGGUGGUCCUUGGGAATT | 576 | UUCCCAAGGACCACCUCACTT | 577 |
| 425 | 425-443 | UGGUCCUUGGGAAUUUGATT | 578 | UCCAAAUUCCAAGGACCATT | 579 |
| 431 | 431-449 | UUGGGAAUUUGGAAAUUACTT | 580 | GUAAUUUCCAAAUUCCCATT | 581 |
| 432 | 432-450 | UGGGAAUUUGGAAAUUACCTT | 582 | GGUAAUUUCCAAAUUCCCATT | 583 |
| 433 | 433-451 | GGGAAUUUGGAAAUUACCUTT | 584 | AGGUAAUUUCCAAAUUCCCTT | 585 |

TABLE 4-continued

EGFR siRNA Sequences

| hs Id # | Sequence position in NM_005228.3 | sense strand sequence (5'-3') | SEQ ID NO: | antisense strand sequence (5'-3') | SEQ ID NO: |
|---|---|---|---|---|---|
| 434 | 434-452 | GGAAUUUGGAAAUUACCUAUT | 586 | UAGGUAAUUUCCAAAUUCCTT | 587 |
| 458 | 458-476 | AGAGGAAUUAUGAUCUUUCTT | 588 | GAAAGAUCAUAAUUCCUCUTT | 589 |
| 459 | 459-477 | GAGGAAUUAUGAUCUUUCCTT | 590 | GGAAAGAUCAUAAUUCCUCTT | 591 |
| 463 | 463-481 | AAUUAUGAUCUUUCCUUCUTT | 592 | AGAAGGAAAGAUCAUAAUUTT | 593 |
| 464 | 464-482 | AUUAUGAUCUUUCCUUCUUTT | 594 | AAGAAGGAAAGAUCAUAAUTT | 595 |
| 466 | 466-484 | UAUGAUCUUUCCUUCUUAATT | 596 | UUAAGAAGGAAAGAUCAUATT | 597 |
| 468 | 468-486 | UGAUCUUUCCUUCUUAAAGTT | 598 | CUUUAAGAAGGAAAGAUCATT | 599 |
| 471 | 471-489 | UCUUUCCUUCUUAAAGACCTT | 600 | GGUCUUUAAGAAGGAAAGATT | 601 |
| 476 | 476-494 | CCUUCUUAAAGACCAUCCATT | 602 | UGGAUGGUCUUUAAGAAGGTT | 603 |
| 477 | 477-495 | CUUCUUAAAGACCAUCCAGTT | 604 | CUGGAUGGUCUUUAAGAAGTT | 605 |
| 479 | 479-497 | UCUUAAAGACCAUCCAGGATT | 606 | UCCUGGAUGGUCUUUAAGATT | 607 |
| 481 | 481-499 | UUAAAGACCAUCCAGGAGGTT | 608 | CCUCCUGGAUGGUCUUUAATT | 609 |
| 482 | 482-500 | UAAAGACCAUCCAGGAGGUTT | 610 | ACCUCCUGGAUGGUCUUUATT | 611 |
| 492 | 492-510 | CCAGGAGGUGGCUGGUUAUTT | 612 | AUAACCAGCCACCUCCUGGTT | 613 |
| 493 | 493-511 | CAGGAGGUGGCUGGUUAUGTT | 614 | CAUAACCAGCCACCUCCUGTT | 615 |
| 494 | 494-512 | AGGAGGUGGCUGGUUAUGUTT | 616 | ACAUAACCAGCCACCUCCUTT | 617 |
| 495 | 495-513 | GGAGGUGGCUGGUUAUGUCTT | 618 | GACAUAACCAGCCACCUCCTT | 619 |
| 496 | 496-514 | GAGGUGGCUGGUUAUGUCCTT | 620 | GGACAUAACCAGCCACCUCTT | 621 |
| 497 | 497-515 | AGGUGGCUGGUUAUGUCCUTT | 622 | AGGACAUAACCAGCCACCUTT | 623 |
| 499 | 499-517 | GUGGCUGGUUAUGUCCUCATT | 624 | UGAGGACAUAACCAGCCACTT | 625 |
| 520 | 520-538 | GCCCUCAACACAGUGGAGCTT | 626 | GCUCCACUGUGUUGAGGGCTT | 627 |
| 542 | 542-560 | UUCCUUUGGAAAACCUGCATT | 628 | UGCAGGUUUUCCAAAGGAATT | 629 |
| 543 | 543-561 | UCCUUUGGAAAACCUGCAGTT | 630 | CUGCAGGUUUUCCAAAGGATT | 631 |
| 550 | 550-568 | GAAAACCUGCAGAUCAUCATT | 632 | UGAUGAUCUGCAGGUUUUCTT | 633 |
| 551 | 551-569 | AAAACCUGCAGAUCAUCAGTT | 634 | CUGAUGAUCUGCAGGUUUUTT | 635 |

TABLE 4-continued

EGFR siRNA Sequences

| hs Id # | Sequence position in NM_005228.3 | sense strand sequence (5'-3') | SEQ ID NO: | antisense strand sequence (5'-3') | SEQ ID NO: |
|---|---|---|---|---|---|
| 553 | 553-571 | AACCUGCAGAUCAUCAGAGTT | 636 | CUCUGAUGAUCUGCAGGUUTT | 637 |
| 556 | 556-574 | CUGCAGAUCAUCAGAGGAATT | 638 | UUCCUCUGAUGAUCUGCAGTT | 639 |
| 586 | 586-604 | GAAAAUUCCUAUGCCUUAGTT | 640 | CUAAGGCAUAGGAAUUUUCTT | 641 |
| 587 | 587-605 | AAAAUUCCUAUGCCUUAGCTT | 642 | GCUAAGGCAUAGGAAUUUUTT | 643 |
| 589 | 589-607 | AAUUCCUAUGCCUUAGCAGTT | 644 | CUGCUAAGGCAUAGGAAUUTT | 645 |
| 592 | 592-610 | UCCUAUGCCUUAGCAGUCUTT | 646 | AGACUGCUAAGGCAUAGGATT | 647 |
| 593 | 593-611 | CCUAUGCCUUAGCAGUCUUTT | 648 | AAGACUGCUAAGGCAUAGGTT | 649 |
| 594 | 594-612 | CUAUGCCUUAGCAGUCUUATT | 650 | UAAGACUGCUAAGGCAUAGTT | 651 |
| 596 | 596-614 | AUGCCUUAGCAGUCUUAUCTT | 652 | GAUAAGACUGCUAAGGCAUTT | 653 |
| 597 | 597-615 | UGCCUUAGCAGUCUUAUCUTT | 654 | AGAUAAGACUGCUAAGGCATT | 655 |
| 598 | 598-616 | GCCUUAGCAGUCUUAUCUATT | 656 | UAGAUAAGACUGCUAAGGCTT | 657 |
| 599 | 599-617 | CCUUAGCAGUCUUAUCUAATT | 658 | UUAGAUAAGACUGCUAAGGTT | 659 |
| 600 | 600-618 | CUUAGCAGUCUUAUCUAACTT | 660 | GUUAGAUAAGACUGCUAAGTT | 661 |
| 601 | 601-619 | UUAGCAGUCUUAUCUAACUTT | 662 | AGUUAGAUAAGACUGCUAATT | 663 |
| 602 | 602-620 | UAGCAGUCUUAUCUAACUATT | 664 | UAGUUAGAUAAGACUGCUATT | 665 |
| 603 | 603-621 | AGCAGUCUUAUCUAACUAUTT | 666 | AUAGUUAGAUAAGACUGCUTT | 667 |
| 604 | 604-622 | GCAGUCUUAUCUAACUAUGTT | 668 | CAUAGUUAGAUAAGACUGCTT | 669 |
| 605 | 605-623 | CAGUCUUAUCUAACUAUGATT | 670 | UCAUAGUUAGAUAAGACUGTT | 671 |
| 608 | 608-626 | UCUUAUCUAACUAUGAUGCTT | 672 | GCAUCAUAGUUAGAUAAGATT | 673 |
| 609 | 609-627 | CUUAUCUAACUAUGAUGCATT | 674 | UGCAUCAUAGUUAGAUAAGTT | 675 |
| 610 | 610-628 | UUAUCUAACUAUGAUGCAATT | 676 | UUGCAUCAUAGUUAGAUAATT | 677 |
| 611 | 611-629 | UAUCUAACUAUGAUGCAAATT | 678 | UUUGCAUCAUAGUUAGAUATT | 679 |
| 612 | 612-630 | AUCUAACUAUGAUGCAAAUTT | 680 | AUUUGCAUCAUAGUUAGAUTT | 681 |
| 613 | 613-631 | UCUAACUAUGAUGCAAAUATT | 682 | UAUUUGCAUCAUAGUUAGATT | 683 |

TABLE 4-continued

EGFR siRNA Sequences

| hs Id # | Sequence position in NM_005228.3 | sense strand sequence (5'-3') | SEQ ID NO: | antisense strand sequence (5'-3') | SEQ ID NO: |
|---|---|---|---|---|---|
| 614 | 614-632 | CUAACUAUGAUGCAAAUAATT | 684 | UUAUUUGCAUCAUAGUUAGTT | 685 |
| 616 | 616-634 | AACUAUGAUGCAAAUAAAATT | 686 | UUUUAUUUGCAUCAUAGUUTT | 687 |
| 622 | 622-640 | GAUGCAAAUAAAACCGGACTT | 688 | GUCCGGUUUUAUUUGCAUCTT | 689 |
| 623 | 623-641 | AUGCAAAUAAAACCGGACUTT | 690 | AGUCCGGUUUUAUUUGCAUTT | 691 |
| 624 | 624-642 | UGCAAAUAAAACCGGACUGTT | 692 | CAGUCCGGUUUUAUUUGCATT | 693 |
| 626 | 626-644 | CAAAUAAAACCGGACUGAATT | 694 | UUCAGUCCGGUUUUAUUUGTT | 695 |
| 627 | 627-645 | AAAUAAAACCGGACUGAAGTT | 696 | CUUCAGUCCGGUUUUAUUUTT | 697 |
| 628 | 628-646 | AAUAAAACCGGACUGAAGGTT | 698 | CCUUCAGUCCGGUUUUAUUTT | 699 |
| 630 | 630-648 | UAAAACCGGACUGAAGGAGTT | 700 | CUCCUUCAGUCCGGUUUUATT | 701 |
| 631 | 631-649 | AAAACCGGACUGAAGGAGCTT | 702 | GCUCCUUCAGUCCGGUUUUTT | 703 |
| 632 | 632-650 | AAACCGGACUGAAGGAGCUTT | 704 | AGCUCCUUCAGUCCGGUUUTT | 705 |
| 633 | 633-651 | AACCGGACUGAAGGAGCUGTT | 706 | CAGCUCCUUCAGUCCGGUUTT | 707 |
| 644 | 644-662 | AGGAGCUGCCCAUGAGAAATT | 708 | UUUCUCAUGGGCAGCUCCUTT | 709 |
| 665 | 665-683 | UACAGGAAAUCCUGCAUGGTT | 710 | CCAUGCAGGAUUUCCUGUATT | 711 |
| 668 | 668-686 | AGGAAAUCCUGCAUGGCGCTT | 712 | GCGCCAUGCAGGAUUUCCUTT | 713 |
| 669 | 669-687 | GGAAAUCCUGCAUGGCGCCTT | 714 | GGCGCCAUGCAGGAUUUCCTT | 715 |
| 670 | 670-688 | GAAAUCCUGCAUGGCGCCGTT | 716 | CGGCGCCAUGCAGGAUUUCTT | 717 |
| 671 | 671-689 | AAAUCCUGCAUGGCGCCGUTT | 718 | ACGGCGCCAUGCAGGAUUUTT | 719 |
| 672 | 672-690 | AAUCCUGCAUGGCGCCGUGTT | 720 | CACGGCGCCAUGCAGGAUUTT | 721 |
| 674 | 674-692 | UCCUGCAUGGCGCCGUGCGTT | 722 | CGCACGGCGCCAUGCAGGATT | 723 |
| 676 | 676-694 | CUGCAUGGCGCCGUGCGGUTT | 724 | ACCGCACGGCGCCAUGCAGTT | 725 |
| 677 | 677-695 | UGCAUGGCGCCGUGCGGUUTT | 726 | AACCGCACGGCGCCAUGCATT | 727 |
| 678 | 678-696 | GCAUGGCGCCGUGCGGUUCTT | 728 | GAACCGCACGGCGCCAUGTT | 729 |
| 680 | 680-698 | AUGGCGCCGUGCGGUUCAGTT | 730 | CUGAACCGCACGGCGCCAUTT | 731 |
| 681 | 681-699 | UGGCGCCGUGCGGUUCAGCTT | 732 | GCUGAACCGCACGGCGCCATT | 733 |

TABLE 4-continued

EGFR siRNA Sequences

| hs Id # | Sequence position in NM_005228.3 | sense strand sequence (5'-3') | SEQ ID NO: | antisense strand sequence (5'-3') | SEQ ID NO: |
|---|---|---|---|---|---|
| 682 | 682-700 | GGCGCCGUGCGGUUCAGCATT | 734 | UGCUGAACCGCACGGCGCCTT | 735 |
| 683 | 683-701 | GCGCCGUGCGGUUCAGCAATT | 736 | UUGCUGAACCGCACGGCGCTT | 737 |
| 684 | 684-702 | CGCCGUGCGGUUCAGCAACTT | 738 | GUUGCUGAACCGCACGGCGTT | 739 |
| 685 | 685-703 | GCCGUGCGGUUCAGCAACATT | 740 | UGUUGCUGAACCGCACGGCTT | 741 |
| 686 | 686-704 | CCGUGCGGUUCAGCAACAATT | 742 | UUGUUGCUGAACCGCACGGTT | 743 |
| 688 | 688-706 | GUGCGGUUCAGCAACAACCTT | 744 | GGUUGUUGCUGAACCGCACTT | 745 |
| 690 | 690-708 | GCGGUUCAGCAACAACCCUTT | 746 | AGGGUUGUUGCUGAACCGCTT | 747 |
| 692 | 692-710 | GGUUCAGCAACAACCCUGCTT | 748 | GCAGGGUUGUUGCUGAACCTT | 749 |
| 698 | 698-716 | GCAACAACCCUGCCCUGUGTT | 750 | CACAGGGCAGGGUUGUUGCTT | 751 |
| 700 | 700-718 | AACAACCCUGCCCUGUGCATT | 752 | UGCACAGGGCAGGGUUGUUTT | 753 |
| 719 | 719-737 | ACGUGGAGAGCAUCCAGUGTT | 754 | CACUGGAUGCUCUCCACGUTT | 755 |
| 720 | 720-738 | CGUGGAGAGCAUCCAGUGGTT | 756 | CCACUGGAUGCUCUCCACGTT | 757 |
| 721 | 721-739 | GUGGAGAGCAUCCAGUGGCTT | 758 | GCCACUGGAUGCUCUCCACTT | 759 |
| 724 | 724-742 | GAGAGCAUCCAGUGGCGGTT | 760 | CCCGCCACUGGAUGCUCUCTT | 761 |
| 725 | 725-743 | AGAGCAUCCAGUGGCGGGATT | 762 | UCCCGCCACUGGAUGCUCUTT | 763 |
| 726 | 726-744 | GAGCAUCCAGUGGCGGGACTT | 764 | GUCCCGCCACUGGAUGCUCTT | 765 |
| 733 | 733-751 | CAGUGGCGGGACAUAGUCATT | 766 | UGACUAUGUCCCGCCACUGTT | 767 |
| 734 | 734-752 | AGUGGCGGGACAUAGUCAGTT | 768 | CUGACUAUGUCCCGCCACUTT | 769 |
| 736 | 736-754 | UGGCGGGACAUAGUCAGCATT | 770 | UGCUGACUAUGUCCCGCCATT | 771 |
| 737 | 737-755 | GGCGGGACAUAGUCAGCAGTT | 772 | CUGCUGACUAUGUCCCGCCTT | 773 |
| 763 | 763-781 | CUCAGCAACAUGUCGAUGGTT | 774 | CCAUCGACAUGUUGCUGAGTT | 775 |
| 765 | 765-783 | CAGCAACAUGUCGAUGGACTT | 776 | GUCCAUCGACAUGUUGCUGTT | 777 |
| 766 | 766-784 | AGCAACAUGUCGAUGGACUTT | 778 | AGUCCAUCGACAUGUUGCUTT | 779 |
| 767 | 767-785 | GCAACAUGUCGAUGGACUUTT | 780 | AAGUCCAUCGACAUGUUGCTT | 781 |

TABLE 4-continued

EGFR siRNA Sequences

| hs Id # | Sequence position in NM_005228.3 | sense strand sequence (5'-3') | SEQ ID NO: | antisense strand sequence (5'-3') | SEQ ID NO: |
|---|---|---|---|---|---|
| 769 | 769-787 | AACAUGUCGAUGGACUUCCTT | 782 | GGAAGUCCAUCGACAUGUUTT | 783 |
| 770 | 770-788 | ACAUGUCGAUGGACUUCCATT | 784 | UGGAAGUCCAUCGACAUGUTT | 785 |
| 771 | 771-789 | CAUGUCGAUGGACUUCCAGTT | 786 | CUGGAAGUCCAUCGACAUGTT | 787 |
| 772 | 772-790 | AUGUCGAUGGACUUCCAGATT | 788 | UCUGGAAGUCCAUCGACAUTT | 789 |
| 775 | 775-793 | UCGAUGGACUUCCAGAACCTT | 790 | GGUUCUGGAAGUCCAUCGATT | 791 |
| 789 | 789-807 | GAACCACCUGGGCAGCUGCTT | 792 | GCAGCUGCCCAGGUGGUUCTT | 793 |
| 798 | 798-816 | GGGCAGCUGCCAAAAGUGUTT | 794 | ACACUUUUGGCAGCUGCCCTT | 795 |
| 800 | 800-818 | GCAGCUGCCAAAAGUGUGATT | 796 | UCACACUUUUGGCAGCUGCTT | 797 |
| 805 | 805-823 | UGCCAAAAGUGUGAUCCAATT | 798 | UUGGAUCACACUUUUGGCATT | 799 |
| 806 | 806-824 | GCCAAAAGUGUGAUCCAAGTT | 800 | CUUGGAUCACACUUUUGGCTT | 801 |
| 807 | 807-825 | CCAAAAGUGUGAUCCAAGCTT | 802 | GCUUGGAUCACACUUUUGGTT | 803 |
| 810 | 810-828 | AAAGUGUGAUCCAAGCUGUTT | 804 | ACAGCUUGGAUCACACUUUTT | 805 |
| 814 | 814-832 | UGUGAUCCAAGCUGUCCCATT | 806 | UGGGACAGCUUGGAUCACATT | 807 |
| 815 | 815-833 | GUGAUCCAAGCUGUCCCAATT | 808 | UUGGGACAGCUUGGAUCACTT | 809 |
| 817 | 817-835 | GAUCCAAGCUGUCCCAAUGTT | 810 | CAUUGGGACAGCUUGGAUCTT | 811 |
| 818 | 818-836 | AUCCAAGCUGUCCCAAUGGTT | 812 | CCAUUGGGACAGCUUGGAUTT | 813 |
| 819 | 819-837 | UCCAAGCUGUCCCAAUGGGTT | 814 | CCCAUUGGGACAGCUUGGATT | 815 |
| 820 | 820-838 | CCAAGCUGUCCCAAUGGGATT | 816 | UCCCAUUGGGACAGCUUGGTT | 817 |
| 821 | 821-839 | CAAGCUGUCCCAAUGGGAGTT | 818 | CUCCCAUUGGGACAGCUUGTT | 819 |
| 823 | 823-841 | AGCUGUCCCAAUGGGAGCUTT | 820 | AGCUCCCAUUGGGACAGCUTT | 821 |
| 826 | 826-844 | UGUCCCAAUGGGAGCUGCUTT | 822 | AGCAGCUCCCAUUGGGACATT | 823 |
| 847 | 847-865 | GGUGCAGGAGAGGAGAACUTT | 824 | AGUUCUCCUCUCCUGCACCTT | 825 |
| 871 | 871-889 | AAACUGACCAAAAUCAUCUTT | 826 | AGAUGAUUUUGGUCAGUUTT | 827 |
| 872 | 872-890 | AACUGACCAAAAUCAUCUGTT | 828 | CAGAUGAUUUUGGUCAGUUTT | 829 |
| 873 | 873-891 | ACUGACCAAAAUCAUCUGUTT | 830 | ACAGAUGAUUUUGGUCAGUTT | 831 |

TABLE 4-continued

EGFR siRNA Sequences

| hs Id # | Sequence position in NM_005228.3 | sense strand sequence (5'-3') | SEQ ID NO: | antisense strand sequence (5'-3') | SEQ ID NO: |
|---|---|---|---|---|---|
| 877 | 877-895 | ACCAAAAUCAUCUGUGCCCTT | 832 | GGGCACAGAUGAUUUUGGUTT | 833 |
| 878 | 878-896 | CCAAAAUCAUCUGUGCCCATT | 834 | UGGGCACAGAUGAUUUUGGTT | 835 |
| 881 | 881-899 | AAAUCAUCUGUGCCCAGCATT | 836 | UGCUGGGCACAGAUGAUUUTT | 837 |
| 890 | 890-908 | GUGCCCAGCAGUGCUCCGTT | 838 | CCGGAGCACUGCUGGGCACTT | 839 |
| 892 | 892-910 | GCCCAGCAGUGCUCCGGGCTT | 840 | GCCCGGAGCACUGCUGGGCTT | 841 |
| 929 | 929-947 | CCAGUGACUGCUGCCACAATT | 842 | UUGUGGCAGCAGUCACUGGTT | 843 |
| 930 | 930-948 | CAGUGACUGCUGCCACAACTT | 844 | GUUGUGGCAGCAGUCACUGTT | 845 |
| 979 | 979-997 | GAGAGCGACUGCCUGGUCUTT | 846 | AGACCAGGCAGUCGCUCUCTT | 847 |
| 980 | 980-998 | AGAGCGACUGCCUGGUCUGTT | 848 | CAGACCAGGCAGUCGCUCUTT | 849 |
| 981 | 981-999 | GAGCGACUGCCUGGUCUGCTT | 850 | GCAGACCAGGCAGUCGCUCTT | 851 |
| 982 | 982-1000 | AGCGACUGCCUGGUCUGCCTT | 852 | GGCAGACCAGGCAGUCGCUTT | 853 |
| 983 | 983-1001 | GCGACUGCCUGGUCUGCCTT | 854 | CGGCAGACCAGGCAGUCGCTT | 855 |
| 984 | 984-1002 | CGACUGCCUGGUCUGCCGTT | 856 | GCGGCAGACCAGGCAGUCGTT | 857 |
| 989 | 989-1007 | GCCUGGUCUGCCGCAAAUTT | 858 | AAUUUGCGGCAGACCAGGCTT | 859 |
| 990 | 990-1008 | CCUGGUCUGCCGCAAAUUCTT | 860 | GAAUUUGCGGCAGACCAGGTT | 861 |
| 991 | 991-1009 | CUGGUCUGCCGCAAAUUCCTT | 862 | GGAAUUUGCGGCAGACCAGTT | 863 |
| 992 | 992-1010 | UGGUCUGCCGCAAAUUCCGTT | 864 | CGGAAUUUGCGGCAGACCATT | 865 |
| 994 | 994-1012 | GUCUGCCGCAAAUUCCGAGTT | 866 | CUCGGAAUUUGCGGCAGACTT | 867 |
| 995 | 995-1013 | UCUGCCGCAAAUUCCGAGATT | 868 | UCUCGGAAUUUGCGGCAGATT | 869 |
| 996 | 996-1014 | CUGCCGCAAAUUCCGAGACTT | 870 | GUCUCGGAAUUUGCGGCAGTT | 871 |
| 997 | 997-1015 | UGCCGCAAAUUCCGAGACGTT | 872 | CGUCUCGGAAUUUGCGGCATT | 873 |
| 999 | 999-1017 | CCGCAAAUUCCGAGACGAATT | 874 | UUCGUCUCGGAAUUUGCGGTT | 875 |
| 1004 | 1004-1022 | AAUUCCGAGACGAAGCCACTT | 876 | GUGGCUUCGUCUCGGAAUUTT | 877 |
| 1005 | 1005-1023 | AUUCCGAGACGAAGCCACGTT | 878 | CGUGGCUUCGUCUCGGAAUTT | 879 |

TABLE 4-continued

EGFR siRNA Sequences

| hs Id # | Sequence position in NM_005228.3 | sense strand sequence (5'-3') | SEQ ID NO: | antisense strand sequence (5'-3') | SEQ ID NO: |
|---|---|---|---|---|---|
| 1006 | 1006-1024 | UUCCGAGACGAAGCCACGUTT | 880 | ACGUGGCUUCGUCUCGGAATT | 881 |
| 1007 | 1007-1025 | UCCGAGACGAAGCCACGUGTT | 882 | CACGUGGCUUCGUCUCGGATT | 883 |
| 1008 | 1008-1026 | CCGAGACGAAGCCACGUGCTT | 884 | GCACGUGGCUUCGUCUCGGTT | 885 |
| 1010 | 1010-1028 | GAGACGAAGCCACGUGCAATT | 886 | UUGCACGUGGCUUCGUCUCTT | 887 |
| 1013 | 1013-1031 | ACGAAGCCACGUGCAAGGATT | 888 | UCCUUGCACGUGGCUUCGUTT | 889 |
| 1014 | 1014-1032 | CGAAGCCACGUGCAAGGACTT | 890 | GUCCUUGCACGUGGCUUCGTT | 891 |
| 1015 | 1015-1033 | GAAGCCACGUGCAAGGACATT | 892 | UGUCCUUGCACGUGGCUUCTT | 893 |
| 1016 | 1016-1034 | AAGCCACGUGCAAGGACACTT | 894 | GUGUCCUUGCACGUGGCUUTT | 895 |
| 1040 | 1040-1058 | CCCCACUCAUGCUCUACAATT | 896 | UUGUAGAGCAUGAGUGGGGTT | 897 |
| 1042 | 1042-1060 | CCACUCAUGCUCUACAACCTT | 898 | GGUUGUAGAGCAUGAGUGGTT | 899 |
| 1044 | 1044-1062 | ACUCAUGCUCUACAACCCCTT | 900 | GGGGUUGUAGAGCAUGAGUTT | 901 |
| 1047 | 1047-1065 | CAUGCUCUACAACCCCACCTT | 902 | GGUGGGGUUGUAGAGCAUGTT | 903 |
| 1071 | 1071-1089 | CCAGAUGGAUGUGAACCCCTT | 904 | GGGGUUCACAUCCAUCUGGTT | 905 |
| 1073 | 1073-1091 | AGAUGGAUGUGAACCCCGATT | 906 | UCGGGGUUCACAUCCAUCUTT | 907 |
| 1074 | 1074-1092 | GAUGGAUGUGAACCCCGAGTT | 908 | CUCGGGGUUCACAUCCAUCTT | 909 |
| 1075 | 1075-1093 | AUGGAUGUGAACCCCGAGGTT | 910 | CCUCGGGGUUCACAUCCAUTT | 911 |
| 1077 | 1077-1095 | GGAUGUGAACCCCGAGGGCTT | 912 | GCCCUCGGGGUUCACAUCTT | 913 |
| 1078 | 1078-1096 | GAUGUGAACCCCGAGGGCATT | 914 | UGCCCUCGGGGUUCACAUCTT | 915 |
| 1080 | 1080-1098 | UGUGAACCCCGAGGGCAAATT | 916 | UUUGCCCUCGGGGUUCACATT | 917 |
| 1084 | 1084-1102 | AACCCCGAGGGCAAAUACATT | 918 | UGUAUUUGCCCUCGGGGUUTT | 919 |
| 1085 | 1085-1103 | ACCCCGAGGGCAAAUACAGTT | 920 | CUGUAUUUGCCCUCGGGGUTT | 921 |
| 1087 | 1087-1105 | CCCGAGGGCAAAUACAGCUTT | 922 | AGCUGUAUUUGCCCUCGGGTT | 923 |
| 1088 | 1088-1106 | CCGAGGGCAAAUACAGCUUTT | 924 | AAGCUGUAUUUGCCCUCGGTT | 925 |
| 1089 | 1089-1107 | CGAGGGCAAAUACAGCUUUTT | 926 | AAAGCUGUAUUUGCCCUCGTT | 927 |
| 1096 | 1096-1114 | AAAUACAGCUUUGGUGCCATT | 928 | UGGCACCAAAGCUGUAUUUTT | 929 |

TABLE 4-continued

EGFR siRNA Sequences

| hs Id # | Sequence position in NM_005228.3 | sense strand sequence (5'-3') | SEQ ID NO: | antisense strand sequence (5'-3') | SEQ ID NO: |
|---|---|---|---|---|---|
| 1097 | 1097-1115 | AAUACAGCUUUGGUGCCACTT | 930 | GUGGCACCAAAGCUGUAUUTT | 931 |
| 1098 | 1098-1116 | AUACAGCUUUGGUGCCACCTT | 932 | GGUGGCACCAAAGCUGUAUTT | 933 |
| 1104 | 1104-1122 | CUUUGGUGCCACCUGCGUGTT | 934 | CACGCAGGUGGCACCAAAGTT | 935 |
| 1106 | 1106-1124 | UUGGUGCCACCUGCGUGAATT | 936 | UUCACGCAGGUGGCACCAATT | 937 |
| 1112 | 1112-1130 | CCACCUGCGUGAAGAAGUGTT | 938 | CACUUCUUCACGCAGGUGGTT | 939 |
| 1116 | 1116-1134 | CUGCGUGAAGAAGUGUCCCTT | 940 | GGGACACUUCUUCACGCAGTT | 941 |
| 1117 | 1117-1135 | UGCGUGAAGAAGUGUCCCCTT | 942 | GGGGACACUUCUUCACGCATT | 943 |
| 1118 | 1118-1136 | GCGUGAAGAAGUGUCCCCGTT | 944 | CGGGGACACUUCUUCACGCTT | 945 |
| 1119 | 1119-1137 | CGUGAAGAAGUGUCCCCGUTT | 946 | ACGGGGACACUUCUUCACGTT | 947 |
| 1120 | 1120-1138 | GUGAAGAAGUGUCCCCGUATT | 948 | UACGGGGACACUUCUUCACTT | 949 |
| 1121 | 1121-1139 | UGAAGAAGUGUCCCCGUAATT | 950 | UUACGGGGACACUUCUUCATT | 951 |
| 1122 | 1122-1140 | GAAGAAGUGUCCCCGUAAUTT | 952 | AUUACGGGGACACUUCUUCTT | 953 |
| 1123 | 1123-1141 | AAGAAGUGUCCCCGUAAUUTT | 954 | AAUUACGGGGACACUUCUUTT | 955 |
| 1124 | 1124-1142 | AGAAGUGUCCCCGUAAUUATT | 956 | UAAUUACGGGGACACUUCUTT | 957 |
| 1125 | 1125-1143 | GAAGUGUCCCCGUAAUUAUTT | 958 | AUAAUUACGGGGACACUUCTT | 959 |
| 1126 | 1126-1144 | AAGUGUCCCCGUAAUUAUGTT | 960 | CAUAAUUACGGGGACACUUTT | 961 |
| 1127 | 1127-1145 | AGUGUCCCCGUAAUUAUGUTT | 962 | ACAUAAUUACGGGGACACUTT | 963 |
| 1128 | 1128-1146 | GUGUCCCCGUAAUUAUGUGTT | 964 | CACAUAAUUACGGGGACACTT | 965 |
| 1129 | 1129-1147 | UGUCCCCGUAAUUAUGUGGTT | 966 | CCACAUAAUUACGGGGACATT | 967 |
| 1130 | 1130-1148 | GUCCCCGUAAUUAUGUGGUTT | 968 | ACCACAUAAUUACGGGGACTT | 969 |
| 1132 | 1132-1150 | CCCCGUAAUUAUGUGGUGATT | 970 | UCACCACAUAAUUACGGGGTT | 971 |
| 1134 | 1134-1152 | CCGUAAUUAUGUGGUGACATT | 972 | UGUCACCACAUAAUUACGGTT | 973 |
| 1136 | 1136-1154 | GUAAUUAUGUGGUGACAGATT | 974 | UCUGUCACCACAUAAUUACTT | 975 |
| 1137 | 1137-1155 | UAAUUAUGUGGUGACAGAUTT | 976 | AUCUGUCACCACAUAAUUATT | 977 |

TABLE 4-continued

EGFR siRNA Sequences

| hs Id # | Sequence position in NM_005228.3 | sense strand sequence (5'-3') | SEQ ID NO: | antisense strand sequence (5'-3') | SEQ ID NO: |
|---|---|---|---|---|---|
| 1138 | 1138-1156 | AAUUAUGUGGUGACAGAUCTT | 978 | GAUCUGUCACCACAUAAUUTT | 979 |
| 1139 | 1139-1157 | AUUAUGUGGUGACAGAUCATT | 980 | UGAUCUGUCACCACAUAAUTT | 981 |
| 1140 | 1140-1158 | UUAUGUGGUGACAGAUCACTT | 982 | GUGAUCUGUCACCACAUAATT | 983 |
| 1142 | 1142-1160 | AUGUGGUGACAGAUCACGGTT | 984 | CCGUGAUCUGUCACCACAUTT | 985 |
| 1145 | 1145-1163 | UGGUGACAGAUCACGGCUCTT | 986 | GAGCCGUGAUCUGUCACCATT | 987 |
| 1147 | 1147-1165 | GUGACAGAUCACGGCUCGUTT | 988 | ACGAGCCGUGAUCUGUCACTT | 989 |
| 1148 | 1148-1166 | UGACAGAUCACGGCUCGUGTT | 990 | CACGAGCCGUGAUCUGUCATT | 991 |
| 1149 | 1149-1167 | GACAGAUCACGGCUCGUGCTT | 992 | GCACGAGCCGUGAUCUGUCTT | 993 |
| 1150 | 1150-1168 | ACAGAUCACGGCUCGUGCGTT | 994 | CGCACGAGCCGUGAUCUGUTT | 995 |
| 1151 | 1151-1169 | CAGAUCACGGCUCGUGCGUTT | 996 | ACGCACGAGCCGUGAUCUGTT | 997 |
| 1152 | 1152-1170 | AGAUCACGGCUCGUGCGUCTT | 998 | GACGCACGAGCCGUGAUCUTT | 999 |
| 1153 | 1153-1171 | GAUCACGGCUCGUGCGUCCTT | 1000 | GGACGCACGAGCCGUGAUCTT | 1001 |
| 1154 | 1154-1172 | AUCACGGCUCGUGCGUCCGTT | 1002 | CGGACGCACGAGCCGUGAUTT | 1003 |
| 1155 | 1155-1173 | UCACGGCUCGUGCGUCCGATT | 1004 | UCGGACGCACGAGCCGUGATT | 1005 |
| 1156 | 1156-1174 | CACGGCUCGUGCGUCCGAGTT | 1006 | CUCGGACGCACGAGCCGUGTT | 1007 |
| 1157 | 1157-1175 | ACGGCUCGUGCGUCCGAGCTT | 1008 | GCUCGGACGCACGAGCCGUTT | 1009 |
| 1160 | 1160-1178 | GCUCGUGCGUCCGAGCCUGTT | 1010 | CAGGCUCGGACGCACGAGCTT | 1011 |
| 1200 | 1200-1218 | GGAGGAAGACGGCGUCCGCTT | 1012 | GCGGACGCCGUCUUCCUCCTT | 1013 |
| 1201 | 1201-1219 | GAGGAAGACGGCGUCCGCATT | 1014 | UGCGGACGCCGUCUUCCUCTT | 1015 |
| 1203 | 1203-1221 | GGAAGACGGCGUCCGCAAGTT | 1016 | CUUGCGGACGCCGUCUUCCTT | 1017 |
| 1204 | 1204-1222 | GAAGACGGCGUCCGCAAGUTT | 1018 | ACUUGCGGACGCCGUCUUCTT | 1019 |
| 1205 | 1205-1223 | AAGACGGCGUCCGCAAGUGTT | 1020 | CACUUGCGGACGCCGUCUUTT | 1021 |
| 1207 | 1207-1225 | GACGGCGUCCGCAAGUGUATT | 1022 | UACACUUGCGGACGCCGUCTT | 1023 |
| 1208 | 1208-1226 | ACGGCGUCCGCAAGUGUAATT | 1024 | UUACACUUGCGGACGCCGUTT | 1025 |
| 1211 | 1211-1229 | GCGUCCGCAAGUGUAAGAATT | 1026 | UUCUUACACUUGCGGACGCTT | 1027 |

TABLE 4-continued

EGFR siRNA Sequences

| hs Id # | Sequence position in NM_005228.3 | sense strand sequence (5'-3') | SEQ ID NO: | antisense strand sequence (5'-3') | SEQ ID NO: |
|---|---|---|---|---|---|
| 1212 | 1212-1230 | CGUCCGCAAGUGUAAGAAGTT | 1028 | CUUCUUACACUUGCGGACGTT | 1029 |
| 1213 | 1213-1231 | GUCCGCAAGUGUAAGAAGUTT | 1030 | ACUUCUUACACUUGCGGACTT | 1031 |
| 1214 | 1214-1232 | UCCGCAAGUGUAAGAAGUGTT | 1032 | CACUUCUUACACUUGCGGATT | 1033 |
| 1215 | 1215-1233 | CCGCAAGUGUAAGAAGUGCTT | 1034 | GCACUUCUUACACUUGCGGTT | 1035 |
| 1216 | 1216-1234 | CGCAAGUGUAAGAAGUGCGTT | 1036 | CGCACUUCUUACACUUGCGTT | 1037 |
| 1217 | 1217-1235 | GCAAGUGUAAGAAGUGCGATT | 1038 | UCGCACUUCUUACACUUGCTT | 1039 |
| 1219 | 1219-1237 | AAGUGUAAGAAGUGCGAAGTT | 1040 | CUUCGCACUUCUUACACUUTT | 1041 |
| 1220 | 1220-1238 | AGUGUAAGAAGUGCGAAGGTT | 1042 | CCUUCGCACUUCUUACACUTT | 1043 |
| 1221 | 1221-1239 | GUGUAAGAAGUGCGAAGGGTT | 1044 | CCCUUCGCACUUCUUACACTT | 1045 |
| 1222 | 1222-1240 | UGUAAGAAGUGCGAAGGGCTT | 1046 | GCCCUUCGCACUUCUUACATT | 1047 |
| 1223 | 1223-1241 | GUAAGAAGUGCGAAGGGCCTT | 1048 | GGCCCUUCGCACUUCUUACTT | 1049 |
| 1224 | 1224-1242 | UAAGAAGUGCGAAGGGCCUTT | 1050 | AGGCCCUUCGCACUUCUUATT | 1051 |
| 1225 | 1225-1243 | AAGAAGUGCGAAGGGCCUUTT | 1052 | AAGGCCCUUCGCACUUCUUTT | 1053 |
| 1226 | 1226-1244 | AGAAGUGCGAAGGGCCUUGTT | 1054 | CAAGGCCCUUCGCACUUCUTT | 1055 |
| 1229 | 1229-1247 | AGUGCGAAGGGCCUUGCCGTT | 1056 | CGGCAAGGCCCUUCGCACUTT | 1057 |
| 1230 | 1230-1248 | GUGCGAAGGGCCUUGCCGCTT | 1058 | GCGGCAAGGCCCUUCGCACTT | 1059 |
| 1231 | 1231-1249 | UGCGAAGGGCCUUGCCGCATT | 1060 | UGCGGCAAGGCCCUUCGCATT | 1061 |
| 1232 | 1232-1250 | GCGAAGGGCCUUGCCGCAATT | 1062 | UUGCGGCAAGGCCCUUCGCTT | 1063 |
| 1233 | 1233-1251 | CGAAGGGCCUUGCCGCAAATT | 1064 | UUUGCGGCAAGGCCCUUCGTT | 1065 |
| 1235 | 1235-1253 | AAGGGCCUUGCCGCAAAGUTT | 1066 | ACUUUGCGGCAAGGCCCUUTT | 1067 |
| 1236 | 1236-1254 | AGGGCCUUGCCGCAAAGUGTT | 1068 | CACUUUGCGGCAAGGCCCUTT | 1069 |
| 1237 | 1237-1255 | GGGCCUUGCCGCAAAGUGUTT | 1070 | ACACUUUGCGGCAAGGCCCTT | 1071 |
| 1238 | 1238-1256 | GGCCUUGCCGCAAAGUGUGTT | 1072 | CACACUUUGCGGCAAGGCTT | 1073 |
| 1239 | 1239-1257 | GCCUUGCCGCAAAGUGUGUTT | 1074 | ACACACUUUGCGGCAAGGCTT | 1075 |

TABLE 4-continued

EGFR siRNA Sequences

| hs Id # | Sequence position in NM_005228.3 | sense strand sequence (5'-3') | SEQ ID NO: | antisense strand sequence (5'-3') | SEQ ID NO: |
|---|---|---|---|---|---|
| 1241 | 1241-1259 | CUUGCCGCAAAGUGUGUAAUU | 1076 | UUACACACUUUGCGGCAAGUU | 1077 |
| 1261 | 1261-1279 | GGAAUAGGUAUUGGUGAAUU | 1078 | AUUCACCAAUACCUAUUCCUU | 1079 |
| 1262 | 1262-1280 | GAAUAGGUAUUGGUGAAUUU | 1080 | AAUUCACCAAUACCUAUUCUU | 1081 |
| 1263 | 1263-1281 | AAUAGGUAUUGGUGAAUUUU | 1082 | AAAUUCACCAAUACCUAUUUU | 1083 |
| 1264 | 1264-1282 | AUAGGUAUUGGUGAAUUUAUU | 1084 | UAAAUUCACCAAUACCUAUU | 1085 |
| 1266 | 1266-1284 | AGGUAUUGGUGAAUUUAAUU | 1086 | UUUAAAUUCACCAAUACCUU | 1087 |
| 1267 | 1267-1285 | GGUAUUGGUGAAUUUAAAGUU | 1088 | CUUUAAAUUCACCAAUACCUU | 1089 |
| 1289 | 1289-1307 | CACUCCAUAAAUGCUACUU | 1090 | GUAGCAUUUAUGGAGAGUGUU | 1091 |
| 1313 | 1313-1331 | UUAAACACUUCAAAAACUGUU | 1092 | CAGUUUUUGAAGUGUUUAAUU | 1093 |
| 1320 | 1320-1338 | CUUCAAAAACUGCACCUCCUU | 1094 | GGAGGUGCAGUUUUUGAAGUU | 1095 |
| 1321 | 1321-1339 | UUCAAAAACUGCACCUCCAUU | 1096 | UGGAGGUGCAGUUUUUGAAUU | 1097 |
| 1322 | 1322-1340 | UCAAAAACUGCACCUCCAUU | 1098 | AUGGAGGUGCAGUUUUUGAUU | 1099 |
| 1323 | 1323-1341 | CAAAAACUGCACCUCCAUCUU | 1100 | GAUGGAGGUGCAGUUUUUGUU | 1101 |
| 1324 | 1324-1342 | AAAAACUGCACCUCCAUCAUU | 1102 | UGAUGGAGGUGCAGUUUUUUU | 1103 |
| 1328 | 1328-1346 | ACUGCACCUCCAUCAGUGGUU | 1104 | CCACUGAUGGAGGUGCAGUUU | 1105 |
| 1332 | 1332-1350 | CACCUCCAUCAGUGGCGAUU | 1106 | AUCGCCACUGAUGGAGGUGUU | 1107 |
| 1333 | 1333-1351 | ACCUCCAUCAGUGGCGAUCUU | 1108 | GAUCGCCACUGAUGGAGGUUU | 1109 |
| 1335 | 1335-1353 | CUCCAUCAGUGGCGAUCUCUU | 1110 | GAGAUCGCCACUGAUGGAGUU | 1111 |
| 1338 | 1338-1356 | CAUCAGUGGCGAUCUCCACUU | 1112 | GUGGAGAUCGCCACUGAUGUU | 1113 |
| 1344 | 1344-1362 | UGGCGAUCUCCACAUCCUGUU | 1114 | CAGGAUGUGGAGAUCGCCAUU | 1115 |
| 1345 | 1345-1363 | GGCGAUCUCCACAUCCUGCUU | 1116 | GCAGGAUGUGGAGAUCGCCUU | 1117 |
| 1346 | 1346-1364 | GCGAUCUCCACAUCCUGCCUU | 1118 | GGCAGGAUGUGGAGAUCGCUU | 1119 |
| 1347 | 1347-1365 | CGAUCUCCACAUCCUGCCGUU | 1120 | CGGCAGGAUGUGGAGAUCGUU | 1121 |
| 1348 | 1348-1366 | GAUCUCCACAUCCUGCCGGUU | 1122 | CCGGCAGGAUGUGGAGAUCUU | 1123 |
| 1353 | 1353-1371 | CCACAUCCUGCCGGUGGCAUU | 1124 | UGCCACCGGCAGGAUGUGGUU | 1125 |

TABLE 4-continued

EGFR siRNA Sequences

| hs Id # | Sequence position in NM_005228.3 | sense strand sequence (5'-3') | SEQ ID NO: | antisense strand sequence (5'-3') | SEQ ID NO: |
|---|---|---|---|---|---|
| 1354 | 1354-1372 | CACAUCCUGCCGGUGGCAUTT | 1126 | AUGCCACCGGCAGGAUGUGTT | 1127 |
| 1355 | 1355-1373 | ACAUCCUGCCGGUGGCAUUTT | 1128 | AAUGCCACCGGCAGGAUGUTT | 1129 |
| 1357 | 1357-1375 | AUCCUGCCGGUGGCAUUUATT | 1130 | UAAAUGCCACCGGCAGGAUTT | 1131 |
| 1360 | 1360-1378 | CUGCCGGUGGCAUUUAGGGTT | 1132 | CCCUAAAUGCCACCGGCAGTT | 1133 |
| 1361 | 1361-1379 | UGCCGGUGGCAUUUAGGGGTT | 1134 | CCCCUAAAUGCCACCGGCATT | 1135 |
| 1362 | 1362-1380 | GCCGGUGGCAUUUAGGGGUTT | 1136 | ACCCCUAAAUGCCACCGGCTT | 1137 |
| 1363 | 1363-1381 | CCGGUGGCAUUUAGGGGUGTT | 1138 | CACCCCUAAAUGCCACCGGTT | 1139 |
| 1366 | 1366-1384 | GUGGCAUUUAGGGGUGACUTT | 1140 | AGUCACCCCUAAAUGCCACTT | 1141 |
| 1369 | 1369-1387 | GCAUUUAGGGGUGACUCCUTT | 1142 | AGGAGUCACCCCUAAAUGCTT | 1143 |
| 1370 | 1370-1388 | CAUUUAGGGGUGACUCCUUTT | 1144 | AAGGAGUCACCCCUAAAUGTT | 1145 |
| 1371 | 1371-1389 | AUUUAGGGGUGACUCCUUCTT | 1146 | GAAGGAGUCACCCCUAAAUTT | 1147 |
| 1372 | 1372-1390 | UUUAGGGGUGACUCCUUCATT | 1148 | UGAAGGAGUCACCCCUAAATT | 1149 |
| 1373 | 1373-1391 | UUAGGGGUGACUCCUUCACTT | 1150 | GUGAAGGAGUCACCCCUAATT | 1151 |
| 1374 | 1374-1392 | UAGGGGUGACUCCUUCACATT | 1152 | UGUGAAGGAGUCACCCCUATT | 1153 |
| 1404 | 1404-1422 | UCUGGAUCCACAGGAACUGTT | 1154 | CAGUUCCUGUGGAUCCAGATT | 1155 |
| 1408 | 1408-1426 | GAUCCACAGGAACUGGAUATT | 1156 | UAUCCAGUUCCUGUGGAUCTT | 1157 |
| 1409 | 1409-1427 | AUCCACAGGAACUGGAUAUTT | 1158 | AUAUCCAGUUCCUGUGGAUTT | 1159 |
| 1411 | 1411-1429 | CCACAGGAACUGGAUAUUCTT | 1160 | GAAUAUCCAGUUCCUGUGGTT | 1161 |
| 1412 | 1412-1430 | CACAGGAACUGGAUAUUCUTT | 1162 | AGAAUAUCCAGUUCCUGUGTT | 1163 |
| 1419 | 1419-1437 | ACUGGAUAUUCUGAAAACCTT | 1164 | GGUUUUCAGAAUAUCCAGUTT | 1165 |
| 1426 | 1426-1444 | AUUCUGAAAACCGUAAAGGTT | 1166 | CCUUUACGGUUUUCAGAAUTT | 1167 |
| 1427 | 1427-1445 | UUCUGAAAACCGUAAAGGATT | 1168 | UCCUUUACGGUUUUCAGAATT | 1169 |
| 1430 | 1430-1448 | UGAAAACCGUAAAGGAAAUTT | 1170 | AUUUCCUUUACGGUUUUCATT | 1171 |
| 1431 | 1431-1449 | GAAAACCGUAAAGGAAAUCTT | 1172 | GAUUUCCUUUACGGUUUUCTT | 1173 |

TABLE 5

AR Target Sequences

| ID | Code | Target Sequence | SEQ ID NO: | NM_000044.3 | Exon | Species |
|---|---|---|---|---|---|---|
| XD-01817K1 | 17 | CAAAGGUUCUCUGCUAGACGACA | 1174 | 1987-2005 | 1 | h |
| XD-01827K1 | 27 | UCUGGGUGUCACUAUGGAGCUCU | 1175 | 2819-2837 | 2 | h |
| XD-01828K1 | 28 | CUGGGUGUCACUAUGGAGCUCUC | 1176 | 2820-2838 | 2 | h |
| XD-01829K1 | 29 | GGGUGUCACUAUGGAGCUCUCAC | 1177 | 2822-2840 | 2 | h |
| XD-01821K1 | 21 | UACUACAACUUUCCACUGGCUCU | 1178 | 2207-2225 | 1 | h |
| XD-01825K1 | 25 | AAGCUUCUGGGUGUCACUAUGGA | 1179 | 2814-2832 | 2 | h, m |
| XD-01826K1 | 26 | CUUCUGGGUGUCACUAUGGAGCU | 1180 | 2817-2835 | 2 | h |

TABLE 6

β-catenin Target Sequences

| R# | Generic name | Gene | Target sequences | | | |
|---|---|---|---|---|---|---|
| R-1146 | 1797mfm | CTNNB1 | CUGUUGGAUUGAUUCGAAAUU | SEQ ID NO. 1181 | UUUCGAAUCAAUCCAACAGUU | SEQ ID NO: 1182 |
| R-1147 | 1870mfm | CTNNB1 | ACGACUAGUUCAGUUGCUUUU | SEQ ID NO: 1183 | AAGCAACUGAACUAGUCGUUU | SEQ ID NO. 1184 |

TABLE 7

PIK3CA* and PIK3CB* Target Sequences

| Gene Symbol | Gene ID | Name | Target Sequences (97-mer) | SEQ ID NO: |
|---|---|---|---|---|
| PIK3CA | 5290 | PIK3CA_1746 | TGCTGTTGACAGTGAGCGCCAGCTCAAAGCAATTTCTACATAGTGAAGCCACAGATGTATGTAGAAATTGCTTTGAGCTGTTGCCTACTGCCTCGGA | 1185 |
| PIK3CA | 5290 | PIK3CA_2328 | TGCTGTTGACAGTGAGCGAAAGGATGAAACACAAAAGGTATAGTGAAGCCACAGATGTATACCTTTTGTGTTTCATCCTTCTGCCTACTGCCTCGGA | 1186 |
| PIK3CA | 5290 | PIK3CA_2522 | TGCTGTTGACAGTGAGCGCCATGTCAGAGTTACTGTTTCATAGTGAAGCCACAGATGTATGAAACAGTAACTCTGACATGATGCCTACTGCCTCGGA | 1187 |
| PIK3CA | 5290 | PIK3CA_3555 | TGCTGTTGACAGTGAGCGCAACTAGTTCATTTCAAAATTATAGTGAAGCCACAGATGTATAATTTTGAAATGAACTAGTTTTGCCTACTGCCTCGGA | 1188 |
| PIK3CA | 5290 | PIK3CA_3484 | TGCTGTTGACAGTGAGCGCACAGCAAGAACAGAAATAAAATAGTGAAGCCACAGATGTATTTTATTTCTGTTCTTGCTGTATGCCTACTGCCTCGGA | 1189 |

TABLE 7-continued

PIK3CA* and PIK3CB* Target Sequences

| Gene Symbol | Gene ID | Name | Target Sequences (97-mer) | SEQ ID NO: |
|---|---|---|---|---|
| PIK3CB | 5291 | PIK3CB_862 | TGCTGTTGACAGTGAGCGACAAGATCAAGAAAAT GTATGATAGTGAAGCCACAGATGTATCATACATTT TCTTGATCTTGCTGCCTACTGCCTCGGA | 1190 |
| PIK3CB | 5291 | PIK3CB_183 | TGCTGTTGACAGTGAGCGCAGCAAGTTCACAATT ACCCAATAGTGAAGCCACAGATGTATTGGGTAAT TGTGAACTTGCTTTGCCTACTGCCTCGGA | 1191 |
| PIK3CB | 5291 | PIK3CB_1520 | TGCTGTTGACAGTGAGCGCCCCTTCGATAAGATTA TTGAATAGTGAAGCCACAGATGTATTCAATAATCT TATCGAAGGGATGCCTACTGCCTCGGA | 1192 |
| PIK3CB | 5291 | PIK3CB_272 | TGCTGTTGACAGTGAGCGAGAGCTTGAAGATGAA ACACGATAGTGAAGCCACAGATGTATCGTGTTTC ATCTTCAAGCTCCTGCCTACTGCCTCGGA | 1193 |
| PIK3CB | 5291 | PIK3CB_948 | TGCTGTTGACAGTGAGCGACACCAAAGAAAACAC GAATTATAGTGAAGCCACAGATGTATAATTCGTG TTTTCTTTGGTGGTGCCTACTGCCTCGGA | 1194 |

*Species is *Homo sapiens*.

TABLE 8

PIK3CA and PIK3CB siRNA Sequences

| Gene Symbol | Gene ID | Name | siRNA Guide | SEQ ID NO: | siRNA passenger | SEQ ID NO: |
|---|---|---|---|---|---|---|
| PIK3CA | 5290 | PIK3CA_1746 | UGUAGAAAUUGCUUUGAGCUGU | 1195 | AGCUCAAAGCAAUUUCUACAUA | 1196 |
| PIK3CA | 5290 | PIK3CA_2328 | UACCUUUUGUGUUUCAUCCUUC | 1197 | AGGAUGAAACACAAAAGGUAUA | 1198 |
| PIK3CA | 5290 | PIK3CA_2522 | UGAAACAGUAACUCUGACAUGA | 1199 | AUGUCAGAGUUACUGUUUCAUA | 1200 |
| PIK3CA | 5290 | PIK3CA_3555 | UAAUUUUGAAAUGAACUAGUUU | 1201 | ACUAGUUCAUUUCAAAAUUAUA | 1202 |
| PIK3CA | 5290 | PIK3CA_3484 | UUUUAUUUCUGUUCUUGCUGUA | 1203 | CAGCAAGAACAGAAAUAAAAUA | 1204 |
| PIK3CB | 5291 | PIK3CB_862 | UCAUACAUUUUCUUGAUCUUGC | 1205 | AAGAUCAAGAAAAUGUAUGAUA | 1206 |
| PIK3CB | 5291 | PIK3CB_183 | UUGGGUAAUUGUGAACUUGCUU | 1207 | GCAAGUUCACAAUUACCCAAUA | 1208 |
| PIK3CB | 5291 | PIK3CB_1520 | UUCAAUAAUCUUAUCGAAGGGA | 1209 | CCUUCGAUAAGAUUAUUGAAUA | 1210 |
| PIK3CB | 5291 | PIK3CB_272 | UCGUGUUUCAUCUUCAAGCUCC | 1211 | AGCUUGAAGAUGAAACACGAUA | 1212 |
| PIK3CB | 5291 | PIK3CB_948 | UAAUUCGUGUUUUCUUUGGUGG | 1213 | ACCAAAGAAAACACGAAUUAUA | 1214 |

TABLE 9

Additional polynucleic acid molecule sequences

| | Base start position | Guide strand | SEQ ID NO: | Passenger strand | SEQ ID NO: |
|---|---|---|---|---|---|
| EGFR R1246 | 333 | ACUCGUGCCUUGGCAA ACUUU | 1215 | AGUUUGCCAAGGCACGA GUUU | 1216 |
| EGFR R1195 | 333 | ACUCGUGCCUUGGCAA ACUUU | 1217 | AGUUUGCCAAGGCACGA GUUU | 1218 |
| EGFR R1449 | 333 | ACUCGUGCCUUGGCAA ACUUU | 1219 | AGUUUGCCAAGGCACGA GUUU | 1220 |
| KRAS R1450 | 237 | UGAAUUAGCUGUAUC GUCAUU | 1221 | TGACGAUACAGCUAAUU CAUU | 1222 |
| KRAS R1443 | 237 | UGAAUUAGCUGUAUC GUCAUU | 1223 | UGACGAUACAGCUAAUU CAUU | 1224 |
| KRAS R1194 | 237 | UGAAUUAGCUGUAUC GUCAUU | 1225 | UGACGAUACAGCUAAUU CAUU | 1226 |
| CTNNB1 R1442 | 1248 | UAAGUAUAGGUCCUCA UUAUU | 1227 | UAAUGAGGACCUAUACU UAUU | 1228 |
| CTNNB1 R1404 | 1797 | TUUCGAAUCAAUCCAA CAGUU | 1229 | CUGUUGGAUUGAUUCGA AAUU | 1230 |
| CTNNB1 R1441 | 1797 | UUUCGAAUCAAUCCAA CAGUU | 1231 | CUGUUGGAUUGAUUCGA AAUU | 1232 |
| CTNNB1 R1523 | 1797 | UUUCGAAUCAAUCCAA CAGUU | 1233 | CUGUUGGAUUGAUUCGA AAUU | 1234 |
| HPRT R1492 | 425 | AUAAAAUCUACAGUCA UAGUU | 1235 | CUAUGACUGUAGAUUUU AUUU | 1236 |
| HPRT R1526 | 425 | UUAAAAUCUACAGUCA UAGUU | 1237 | CUAUGACUGUAGAUUUU AAUU | 1238 |
| HPRT R1527 | 425 | UUAAAAUCUACAGUCA UAGUU | 1239 | CUAUGACUGUAGAUUUU AAUU | 1240 |
| AR R1245 | 2822 | GAGAGCUCCAUAGUGA CACUU | 1241 | GUGUCACUAUGGAGCUC UCUU | 1242 |

Example 2. General Experimental Protocol

Stem-Loop qPCR Assay for Quantification of siRNA

Plasma samples are directly diluted in TE buffer. 50 mg tissue pieces are homogenized in 1 mL of Trizol using a FastPrep-24 tissue homogenizer (MP Biomedicals) and then diluted in TE buffer. Standard curves are generated by spiking siRNA into plasma or homogenized tissue from untreated animals and then serially diluting with TE buffer. The antisense strand of the siRNA is reverse transcribed using a TaqMan MicroRNA reverse transcription kit (Applied Biosystems) with 25 nM of a sequence-specific stem-loop RT primer. The cDNA from the RT step is utilized for real-time PCR using TaqMan Fast Advanced Master Mix (Applied Biosystems) with 1.5 µM of forward primer, 0.75 µM of reverse primer, and 0.2 µM of probe. Quantitative PCR reactions are performed using standard cycling conditions in a ViiA 7 Real-Time PCR System (Life Technologies). The Ct values are transformed into plasma or tissue concentrations using the linear equations derived from the standard curves.

Comparative qPCR Assay for Determination of mRNA Knockdown

Tissue samples are homogenized in Trizol as described above. Total RNA is isolated using RNeasy RNA isolation 96-well plates (Qiagen), then 500 ng RNA is reverse transcribed with a High Capacity RNA to cDNA kit (ThermoFisher). KRAS, EGFR, CTNNB1, and PPIB mRNAs are quantified by TaqMan qPCR analysis performed with a ViiA 7 Real-Time PCR System. The TaqMan primers and probes for EGFR and CTNNB1 are purchased from Applied Biosystems as pre-validated gene expression assays. PPIB (housekeeping gene) is used as an internal RNA loading control, with all TaqMan primers and probes for PPIB purchased from Applied Biosystems as pre-validated gene expression assays. Results are calculated by the comparative Ct method, where the difference between the target gene (KRAS, CTNNB1, or EGFR) Ct value and the PPIB Ct value ($\Delta$Ct) is calculated and then further normalized relative to the PBS control group by taking a second difference ($\Delta\Delta$Ct).

Animals

All animal studies are conducted following protocols in accordance with the Institutional Animal Care and Use Committee (IACUC) at Explora BioLabs, which adhere to the regulations outlined in the USDA Animal Welfare Act as well as the "Guide for the Care and Use of Laboratory Animals" (National Research Council publication, 8th Ed., revised in 2011). All mice are obtained from either Charles River Laboratories or Harlan Laboratories.

H358, HCC827, and Hep-3B2 1-7 Subcutaneous Flank Tumor Model

For the H358 subcutaneous flank tumor model, tumor cells are inoculated and tumors are established according to the following methods. Female NCr nu/nu mice are identified by ear-tag the day before cell injection. Mice are weighed prior to inoculation. H358 cells are cultured with 10% FBS/RPMI medium and harvested with 0.05% Trypsin and Cell Stripper (MediaTech). 5 million H358 cells in 0.05 ml Hank's Balanced Salt Solution (HBSS) with Matrigel (1:1) are injected subcutaneously (SC) into the upper right flank of each mouse. Tumor growth is monitored by tumor volume measurement using a digital caliper starting on day 7 after inoculation, and followed 2 times per week until average tumor volume reaches >100 & ≤300 mm$^3$. Once tumors are to the desired volume (average from 100 to 300 mm$^3$), animals are randomized and mice with very large or small tumors are culled. Mice are divided into the required groups and randomized by tumor volume. Mice are then treated as described in the individual experiments.

For the Hep3B orthotopic liver tumor model, tumor cells are inoculated and tumors are established according to the following methods. Female NCr nu/nu mice are identified by ear-tag the day before, mice will be anesthetized with isoflurane. The mice are then placed in a supine position on a water circulating heating pad to maintain body temperature. A small transverse incision below the sternum will be made to expose the liver. Cancer cells are slowly injected into the upper left lobe of the liver using a 28-gauge needle. The cells are injected at a 30-degree angle into the liver, so that a transparent bleb of cells can be seen through the liver capsule. Hep 3B2.1 7 cells are prepared by suspending in cold PBS (0.1-5×10$^6$ cells) and mixing with diluted matrigel (30× in PBS). 30-50 ul of the cell/matrigel is inoculated. After injection, a small piece of sterile gauze is placed on the injection site, and light pressure was applied for 1 min to prevent bleeding. The abdomen is then closed with a 6-0 silk suture. After tumor cell implantation, animals are kept in a warm cage, observed for 1-2 h, and subsequently returned to the animal room after full recovery from the anesthesia. 7-10 days after tumor implantation animals are randomized, divided into the required groups and then treated as described in the individual experiments.

LNCap Subcutaneous Flank Tumor Model

LNCaP cells (ATCC® CAL-1740™) are grown in RPMI+10% FBS supplemented with non-essential amino acids and sodium pyruvate to a confluency of about 80%. Cells are mixed 1:1 with matrigel and 5-7*106 cells injected subcutaneously into male SCID mice (6-8 weeks). Tumors are usually developed within 3-5 weeks to a size of 100-350 mm$^3$. Animals bearing tumors within this range are randomized and treated with ASCs by injections into the tail vein. For PD studies animals are sacrificed 96 hours after injection and organ fragments harvested, weighted, and frozen in liquid nitrogen. For RNA isolation, organ samples are homogenized in Trizol and RNA prepared using a Qiagen RNeasy 96 Plus kit following the instructions by the manufacturer. RNA concentrations are determined spectroscopically. RNAs are converted into cDNAs by reverse transcription and expression of specific targets quantified by qPCR using the ΔΔCT method and validated Taqman assays (Thermofisher). Samples are standardize to the expression levels of PPIB.

Peptide Synthesis

Peptides are synthesized on solid phase using standard Fmoc chemistry. Both peptides have cysteine at the N-terminus and the cleaved peptides are purified by HPLC and confirmed by mass spectroscopy. INF7 peptide is as illustrated SEQ ID NO: 2055. Melittin peptide is as illustrated SEQ ID NO: 2060.

Anti-EGFR Antibody

Anti-EGFR antibody is a fully human IgG1κ monoclonal antibody directed against the human epidermal growth factor receptor (EGFR). It is produced in the Chinese Hamster Ovary cell line DJT33, which has been derived from the CHO cell line CHO-K1SV by transfection with a GS vector carrying the antibody genes derived from a human anti-EGFR antibody producing hybridoma cell line (2F8). Standard mammalian cell culture and purification technologies are employed in the manufacturing of anti-EGFR antibody.

The theoretical molecular weight (MW) of anti-EGFR antibody without glycans is 146.6 kDa. The experimental MW of the major glycosylated isoform of the antibody is 149 kDa as determined by mass spectrometry. Using SDS-PAGE under reducing conditions the MW of the light chain was found to be approximately 25 kDa and the MW of the heavy chain to be approximately 50 kDa. The heavy chains are connected to each other by two inter-chain disulfide bonds, and one light chain is attached to each heavy chain by a single inter-chain disulfide bond. The light chain has two intra-chain disulfide bonds and the heavy chain has four intra-chain disulfide bonds. The antibody is N-linked glycosylated at Asn305 of the heavy chain with glycans composed of N-acetyl-glucosamine, mannose, fucose and galactose. The predominant glycans present are fucosylated bi-antennary structures containing zero or one terminal galactose residue.

The charged isoform pattern of the IgG1κ antibody has been investigated using imaged capillary IEF, agarose IEF and analytical cation exchange HPLC. Multiple charged isoforms are found, with the main isoform having an isoelectric point of approximately 8.7.

The major mechanism of action of anti-EGFR antibody is a concentration dependent inhibition of EGF-induced EGFR phosphorylation in A431 cancer cells. Additionally, induction of antibody-dependent cell-mediated cytotoxicity (ADCC) at low antibody concentrations has been observed in pre-clinical cellular in vitro studies.

Figure 11:
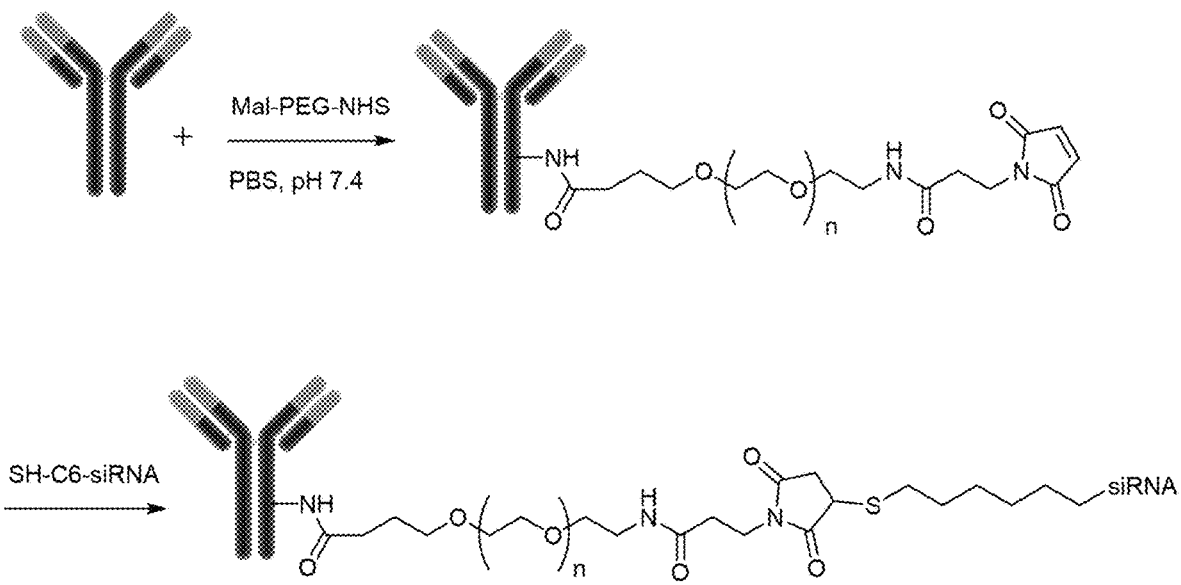
FIGS. 11-15 illustrate conjugation schemes described herein.

Example 3: Synthesis, Purification and Analysis of Antibody-PEG-EGFR and Antibody-EGFR Conjugates Conjugation scheme-1 for generating Antibody-EGFR conjugates is depicted in FIG. 11

Step 1: Antibody Conjugation with Maleimide-PEG-NHS Followed by SH-EGFR

Anti-EGFR antibody (EGFR-Ab) is exchanged with 1× Phosphate buffer (pH 7.4) and made up to 5 mg/ml concentration. To this solution, 2 equivalents of SMCC linker or maleimide-PEGxkDa-NHS (x=1, 5, 10, 20) is added and rotated for 4 hours at room temperature. Unreacted maleimide-PEG is removed by spin filtration using 50 kDa MWCO Amicon spin filters and PBS pH 7.4. The antibody-PEG-Mal conjugate is collected and transferred into a reaction vessel. SH-C6-EGFR (2 equivalents) is added at RT to the antibody-PEG-maleimide in PBS and rotated overnight. The reaction mixture is analyzed by analytical SAX column chromatography and conjugate along with unreacted antibody and siRNA is seen.

Step 2: Purification

The crude reaction mixture is purified by AKTA explorer FPLC using anion exchange chromatography method-1. Fractions containing the antibody-PEG-EGFR conjugate ae pooled, concentrated and buffer exchanged with PBS, pH 7.4. Antibody siRNA conjugates with SMCC linker, PEG1kDa, PEG5kDa and PEG10kDa are separated based on the siRNA loading.

Step-3: Analysis of the Purified Conjugate

The isolated conjugate is characterized by either mass spec or SDS-PAGE. The purity of the conjugate is assessed by analytical HPLC using either anion exchange chromatography method-2 or anion exchange chromatography method-3.

Anion Exchange Chromatography Method-1
1. Column: Tosoh Bioscience, TSKGel SuperQ-SPW, 21.5 mm ID×15 cm, 13 um
2. Solvent A: 20 mM TRIS buffer, pH 8.0; Solvent B: 20 mM TRIS, 1.5 M NaCl, pH 8.0; Flow Rate: 6.0 ml/min

| 3. Gradient: | | |
|---|---|---|
| a. %A | %B | Column Volume |
| b. 100 | 0 | 1.00 |
| c. 60 | 40 | 18.00 |
| d. 40 | 60 | 2.00 |
| e. 40 | 60 | 5.00 |
| f. 0 | 100 | 2.00 |
| g. 100 | 0 | 2.00 |

Anion Exchange Chromatography Method-2
1. Column: Thermo Scientific, ProPac™ SAX-10, Bio LC', 4×250 mm
2. Solvent A: 80% 10 mM TRIS pH 8, 20% ethanol; Solvent B: 80% 10 mM TRIS pH 8, 20% ethanol, 1.5 M NaCl; Flow Rate: 1.0 ml/min

| 3. Gradient: | | |
|---|---|---|
| a. Time | %A | %B |
| b. 0.0 | 90 | 10 |
| c. 3.00 | 90 | 10 |
| d. 11.00 | 40 | 60 |
| e. 13.00 | 40 | 60 |
| f. 15.00 | 90 | 10 |
| g. 20.00 | 90 | 10 |

Anion Exchange Chromatography Method-3
1. Column: Thermo Scientific, ProPac™ SAX-10, Bio LC™, 4×250 mm
2. Solvent A: 80% 10 mM TRIS pH 8, 20% ethanol; Solvent B: 80% 10 mM TRIS pH 8, 20% ethanol, 1.5 M NaCl
3. Flow Rate: 0.75 ml/min

| 4. Gradient: | | |
|---|---|---|
| a. Time | %A | %B |
| b. 0.0 | 90 | 10 |
| c. 3.00 | 90 | 10 |
| d. 11.00 | 40 | 60 |
| e. 23.00 | 40 | 60 |
| f. 25.00 | 90 | 10 |
| g. 30.00 | 90 | 10 |

Figure 12:
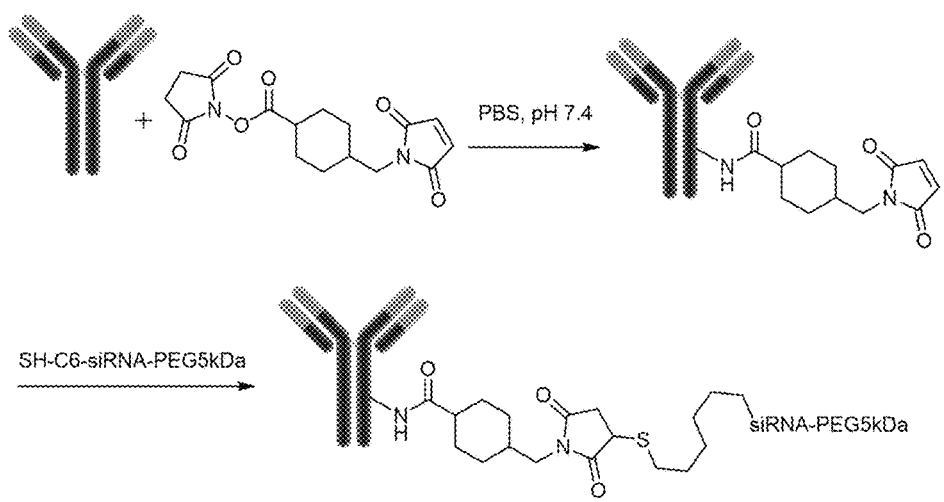

Example 4: Synthesis, Purification and Analysis of Antibody-siRNA-PEG Conjugates Conjugation scheme-2 for generating antibody-siRNA-PEG conjugates is depicted in FIG. 12.

Step 1: Antibody Conjugation with SMCC Linker Followed by SH-KRAS-PEG5kDa

Anti-EGFR antibody is exchanged with 1× Phosphate buffer (pH 7.4) and made up to 5 mg/ml concentration. To this solution, 2 equivalents of SMCC linker (succinimidyl 4-(N-maleimidomethyl)cyclohexane-1-carboxylate) is added and rotated for 4 hours at room temperature. Unreacted SMCC linker is removed by spin filtration using 50 kDa MWCO Amicon spin filters and PBS buffer pH 7.4. The retentate is collected and 2 equivalents of SH-C6-KRAS-PEG5kDa is added at RT and rotated overnight. The reaction mixture is analyzed by analytical SAX column chromatography.

Step 2: Purification

The crude reaction mixture is purified by AKTA explorer FPLC using anion exchange chromatography method-1. Fractions containing the antibody-KRAS-PEG conjugate are pooled, concentrated and buffer exchanged with PBS, pH 7.4.

Step-3: Analysis of the Purified Conjugate

The isolated conjugate is characterized by either mass spec or SDS-PAGE. The purity of the conjugate is assessed by analytical HPLC using anion exchange chromatography method-3 (described in example 1).

Figure 13:
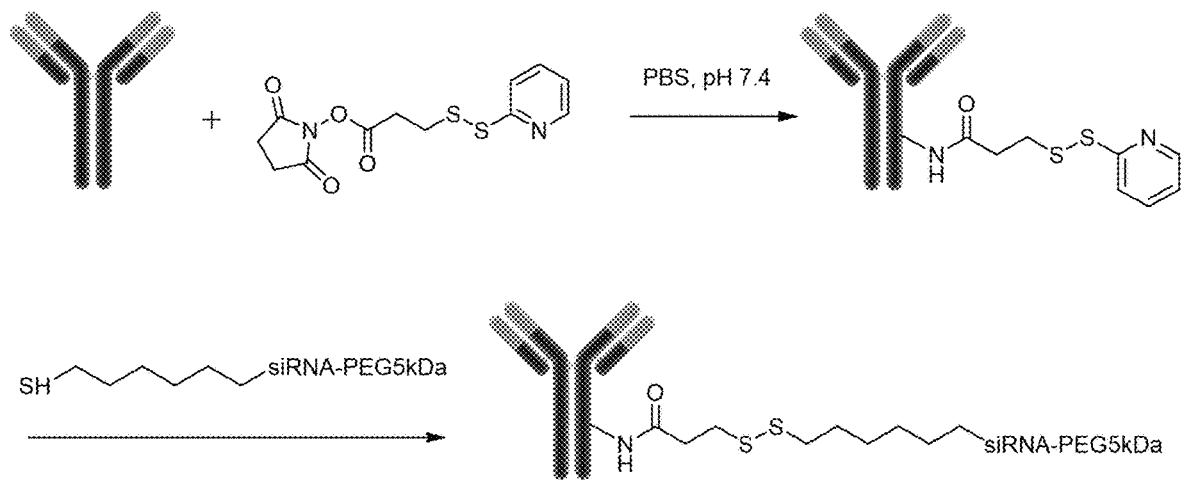

Example 5: Synthesis, Purification and Analysis of Antibody-S-S-siRNA-PEG Conjugates Conjugation scheme-3 for generating antibody-S-S-siRNA-PEG conjugates is depicted in FIG. 13.

Step 1: Antibody Conjugation with SPDP Linker Followed by SH-siRNA-PEG5kDa

Anti-EGFR antibody is exchanged with 1× Phosphate buffer (pH 7.4) and made up to 5 mg/ml concentration. To this solution, 2 equivalents of SPDP linker (succinimidyl 3-(2-pyridyldithio)propionate) is added and rotated for 4 hours at room temperature. Unreacted SPDP linker is removed by spin filtration using 50 kDa MWCO Amicon spin filters and pH 7.4 PBS buffer. The retentate is collected and 2 equivalents of SH-C6-siRNA-PEG5kDa is added at room temperature and rotated overnight. The reaction mixture is analyzed by analytical SAX column chromatography and conjugate along with unreacted antibody determined.

Step 2: Purification

The crude reaction mixture is purified by AKTA explorer FPLC using anion exchange chromatography method-1. Fractions containing the antibody-PEG-siRNA conjugate are pooled, concentrated and buffer exchanged with PBS, pH 7.4.

Step-3: Analysis of the Purified Conjugate

The isolated conjugate is characterized by either mass spec or SDS-PAGE. The purity of the conjugate is assessed by analytical HPLC using anion exchange chromatography method-2.

Example 6: Synthesis, Purification and Analysis of Antibody-SMCC-Endosomal Escape Peptide Conjugates (SEQ ID NOS 1248 and 1277 Disclosed Below, Respectively, in Order of Appearance)

Figure 14:
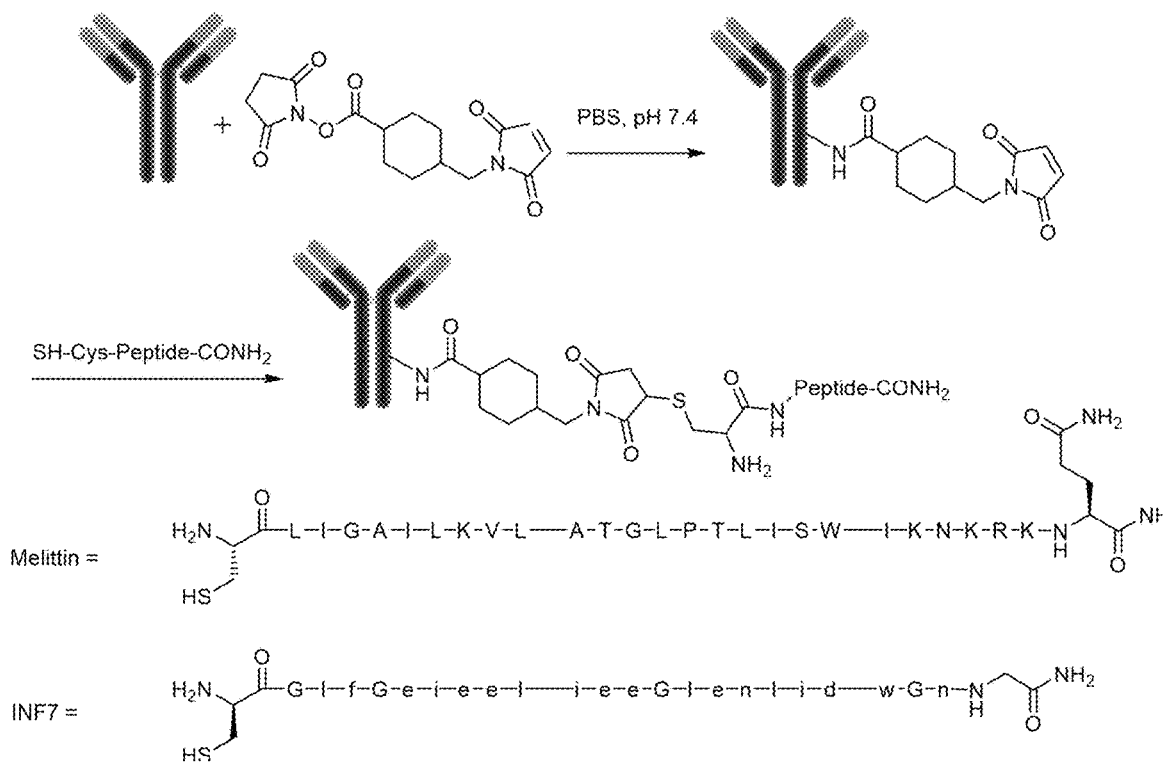

Conjugation scheme-4 for generating antibody-SMCC-Endosomal escape peptide conjugates is depicted in FIG. 14.

Step 1: Antibody Conjugation with SMCC Linker or Maleimide-PEG-NHS Followed by SH-Cys-Peptide-CONH$_2$ Anti-EGFR antibody is exchanged with 1× Phosphate buffer (pH 7.4) and made up to 10 mg/ml concentration. To this solution, 3 equivalents of SMCC linker (succinimidyl 4-(N-maleimidomethyl)cyclohexane-1-carboxylate) or maleimide-PEG1kDa-NHS is added and rotated for 1.5 hours at room temperature. Unreacted SMCC linker or PEG linker is removed by spin filtration using 50 kDa MWCO Amicon spin filters and PBS buffer pH 7.4 (25 mM MES pH=6.1 for Melittin conjugates). The retentate is collected and 3 equivalents of SH-Cys-Peptide-CONH$_2$ is added at RT and rotated overnight. The reaction mixture is then purified by either HIC chromatography or cation exchange chromatography to isolate the anti-EGFR antibody-Peptide or anti-EGFR antibody-PEG1k-Peptide.

Step 2: Purification

The crude reaction mixture is purified by AKTA explorer FPLC using either hydrophobic interaction chromatography (HIC) method-1 or cation exchange chromatography method-1. Fractions containing the antibody-peptide conjugates are pooled, concentrated and buffer exchanged with PBS, pH 7.4 (10 mM Acetate pH=6.0 for Melittin conjugates).

Step-3: Analysis of the Purified Conjugate

The isolated conjugate is characterized by either mass spec or SDS-PAGE. Purity and peptide loading is assessed by analytical HPLC using either HIC method-2 or cation exchange chromatography method-2.

Cation Exchange Chromatography Method-1
1. Column: GE Healthcare HiPrep SP HP 16/10
2. Solvent A: 50 mM MES pH=6.0; Solvent B: 50 mM MES+0.5M NaCl pH=6.0; Flow Rate: 2.0 ml/min

| 3. Gradient: | | | |
|---|---|---|---|
| a. | % A | % B | Column Volume |
| b. | 100 | 0 | 0.1 |
| c. | 100 | 0 | Flush loop 12 ml |
| d. | 100 | 0 | 2.5 |
| e. | 0 | 100 | 15 |
| f. | 0 | 100 | 5 |
| g. | 100 | 0 | 0.5 |
| h. | 100 | 0 | 5 |

Cation Exchange Chromatography Method-2
1. Column: Thermo Scientific, MAbPac™ SCX-10, Bio LC™, 4×250 mm (product #074625)
2. Solvent A: 20 mM MES pH=5.5; Solvent B: 20 mM MES+0.3 M NaCl pH=5.5; Flow Rate: 0.5 ml/min

| 3. Gradient: | | | |
|---|---|---|---|
| a. | Time | % A | % B |
| b. | 0.0 | 100 | 0 |
| c. | 5 | 100 | 0 |
| d. | 50 | 0 | 100 |
| e. | 80 | 0 | 100 |
| f. | 85 | 100 | 0 |
| g. | 90 | 100 | 0 |

Hydrophobic Interaction Chromatography Method-1 (HIC Method-1)
1. Column: GE Healthcare Butyl Sepharose High Performance (17-5432-02) 200 ml
2. Solvent A: 50 mM Sodium Phosphate+0.8M ammonium sulfate (pH=7.0); Solvent B: 80% 50 mM Sodium Phosphate (pH=7.0), 20% IPA; Flow Rate: 3.0 ml/min

| 3. Gradient: | | | |
|---|---|---|---|
| a. | % A | % B | Column Volume |
| b. | 100 | 0 | 0.1 |
| c. | 0 | 100 | 3 |
| d. | 0 | 100 | 1.35 |
| e. | 100 | 0 | 0.1 |
| f. | 100 | 0 | 0.5 |

Hydrophobic Interaction Chromatography Method-2 (HIC Method-2)
1. Column: Tosoh Bioscience TSKgel Butyl-NPR 4.6 mm ID×10 cm 2.5 μm
2. Solvent A: 100 mM Sodium phosphate+1.8 M ammonium sulfate (pH=7.0); Solvent B: 80% 100 mM sodium phosphate (pH=7.0), 20% IPA; Flow Rate: 0.5 ml/min

| 3. Gradient: | | | |
|---|---|---|---|
| a. | Time | % A | % B |
| b. | 0 | 100 | 0 |
| c. | 3 | 50 | 50 |
| d. | 21 | 0 | 100 |
| e. | 23 | 0 | 100 |
| f. | 25 | 100 | 0 |

Figure 15:
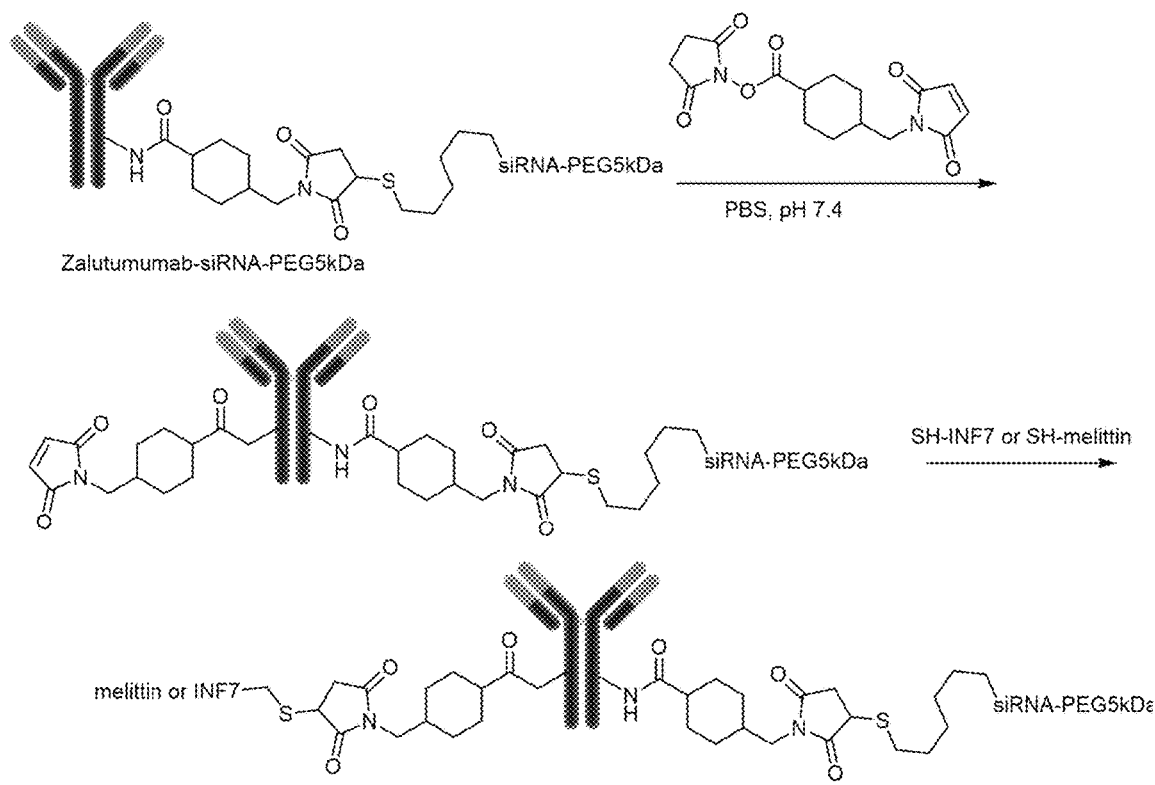

Example 7: Synthesis, Purification and Analysis of EEP-Antibody-siRNA-PEG Conjugates Conjugation scheme-5 for generating EEP-antibody-siRNA-PEG conjugates is depicted in FIG. 15.

Step 1: Conjugation of PEG24 Linker Followed by SH-Cys-Peptide-CONH$_2$ to EGFR-Ab-siRNA-PEG EGFR-Ab-siRNA-PEG5kDa conjugate with a siRNA loading of 1 is conjugated with 4 equivalents of PEG1k linker (succinimidyl 4-(N-maleimidomethyl)cyclohexane-1-carboxylate) in PBS, pH 7.4 buffer and rotated for 1.5 hours at room temperature. Unreacted PEG1k linker is removed by spin filtration using 50 kDa MWCO Amicon spin filters and PBS buffer pH 7.4. The retentate is collected and 4 equivalents of SH-Cys-Peptide-CONH$_2$ is added at RT and rotated overnight.

Step 2: Purification

The reaction mixture is then purified by repeated spin filtration using PBS buffer pH7.4 and 50 kDa Amicon spin filters until the unreacted peptide is removed as monitored by HPLC. The product contains a mixture of conjugates with 0, 1, 2, 3 or more peptides conjugated to the antibody backbone.

Step-3: Analysis of the Purified Conjugate

The isolated conjugate is characterized by either mass spec or SDS-PAGE. The purity and the peptide loading of the conjugate is assessed by analytical HPLC using either HIC method-2 or cation exchange chromatography method-2.

Example 8. Tumor PK/PD Study

Female NCr nu/nu mice bearing subcutaneous flank H358 tumors will be dosed with EGFR antibody-siRNA-EEP conjugates at 0.5 mg/kg (based on siRNA). Multiple EEPs (endosomolytic moieties) will be used to determine the peptide sequence that demonstrates optimal endosomal escape, resulting in the best knockdown of the target gene relative to the control.

Example 9. Formulation of an ABC Conjugate with Nanoparticles

An exemplary ABC conjugate is packaged into self-assembled nanoparticles using cyclodextrin polymers (10 kDa) and an excess of non-conjugated siRNAs (ED 40-60 nm, PDI 0.1-0.2). In these particles, the exemplary ABC conjugate maintains its ability to interact with the antibody target. The stability and target binding competency of the particles in circulation in vivo is regulated through modifications of the packaging siRNAs.

Nanoparticle Formation

Nanoparticles are prepared at a final siRNA concentration of 1.6 mg/mL. siRNA containing CY5-siRNA at a ratio of 1:20 is first diluted to 2× final concentration in water. Cyclodextrin polymer (CDP) is diluted to 2× final concentration necessary to achieve a nitrogen to phosphorus ratio (N:P) of 3:1 in 10 mM phosphate buffer at neutral pH. CDP is added quickly to siRNA and is further mixed by pipetting. Particles are incubated for at least 15 minutes before dosing or analysis.

In Vitro EGFR Binding

Nanoparticles containing various amount of the exemplary ABC conjugate are diluted into Fetal calf serum to a final concentration of 10 nM and are incubated for 1h at RT with Protein G Dynabeads (Thermofisher) loaded with 150 nM of a purified EGFR-Fc protein (Sino Biological). Beads are washed twice with PBS containing 0.01% Tween 20 and 0.05% BSA before bead-bound nanoparticles are disrupted with water containing 0.01% Tween 20 and 100 ug/ml heparin. The amount of CY5-siRNA contained in the input, unbound fraction, washes and bead eluate is quantified by fluorescence using a TECAN Infinite M200 Pro (Excitation 635 nm; Emission 675 nm).

Example 10. siRNA Synthesis

All siRNA single strands were fully assembled on solid phase using standard phospharamidite chemistry and purified using HPLC. Base, sugar and phosphate modifications that are well described in the field of RNAi were used to optimize the potency of the duplex and reduce immunogenicity.

The vinylphosphonate modified nucleotides (compounds 3, 15, 26, 27 and 28) used for examples 11-15 are shown in the table below

| Structure | Cmpd # |
|---|---|
|  | 3 |

-continued

| Structure | Cmpd # |
|---|---|
| 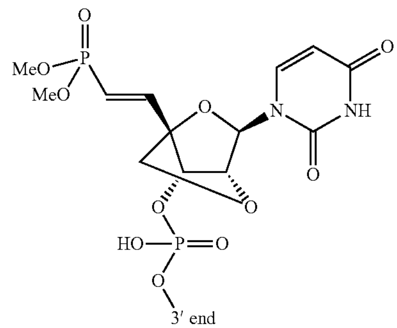  | 15 |
| 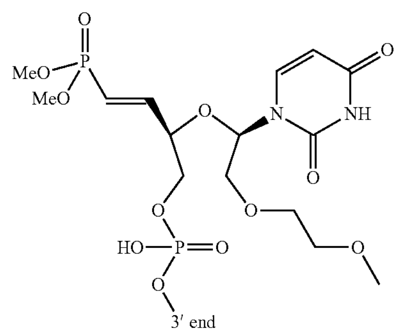  | 26 |
| 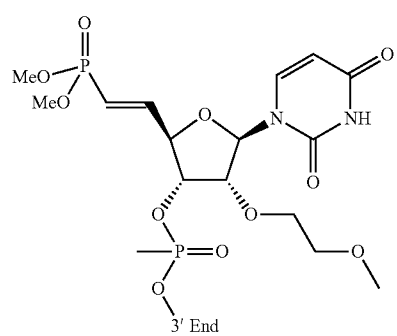  | 27 |
| 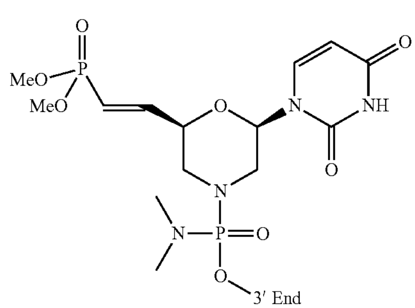  | 28 |

| Structure | Cmpd # |
|---|---|
| [Structure: UU dinucleotide with MeO-P(=O)-vinyl-morpholino-uracil linked via N-P(=O)(NMe2)-O to 2'-F sugar-uracil, 3' End] | |
| [Structure 30: MeO-P(=O)-vinyl linked to sugar-uracil with O-CH2CH2-OMe and O=P(OH)-O-, 3' end] | 30 |
| [Structure 32: MeO-P(=O)-vinyl linked to sugar-uracil with HO-P(=O)-O-, 3' end] | 32 |

Compound 3 was used as a standard for comparison purposes.

Compounds 15, 26, 27, 28, 30 and 32 were incorporated onto individual guide strands.

Compound 28 was incorporated onto the 5' end of the passenger during solid phase synthesis as a dinucleotide.

All the siRNA passenger strands contained a C6-NH$_2$ conjugation handle on the 5' end.

For the 21 mer duplex with 19 bases of complementarity and 3' dinucleotide overhangs, the conjugation handle was connected to siRNA passenger strand via an inverted abasic phosphodiester, (see FIG. 1A).

Figure 1B:
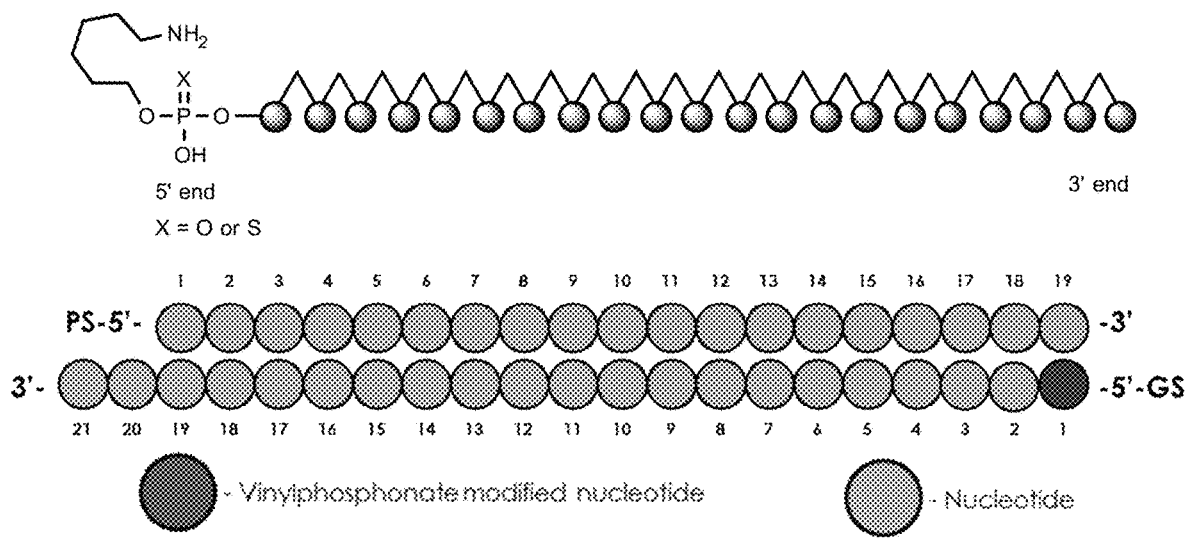
FIG. 1B shows a cartoon representation of the structure of a blunt ended duplex with 19 bases of complementarity and one 3' dinucleotide overhang, as described in molecular biology example 10.

For the blunt ended duplex with 19 bases of complementarity and one 3' dinucleotide overhang the conjugation handle was connected to siRNA passenger strand via a phosphodiester on the terminal base, (see FIG. 1B).

Purified single strands were duplexed to obtain double stranded siRNA.

Example 11. In Vitro Activity of Vinylphosphonate Modified Nucleotide Structures in HCT116 Cells siRNA design and synthesis: A 21 mer HPRT guide strand was designed against mouse HPRT. The sequence (5' to 3') of the guide/antisense strand was (SEQ ID NO: 1275)
UUAAAAUCUACAGUCAUAGUU.

Three versions were prepared incorporating vinylphosphonate modified nucleotide structures (compounds 3, 15 and 27). The guide and fully complementary 0RNA passenger strands were assembled on solid phase using standard phospharamidite chemistry, and purified over HPLC. Base, sugar and phosphate modifications that are well described in the field of RNAi were used to optimize the potency of the duplex and reduce immunogenicity. Purified single strands were duplexed to obtain double stranded siRNA as described in FIG. 1B.

In vitro study: The different siRNAs were transfected into human colorectal carcinoma HCT116 cells at 100 nM, 10 nM, 1 nM, 0.1 nM, 0.01 nM, 0.001 nM, and 0.0001 nM final concentration. The siRNAs were formulated with commercially available transfection reagent, Lipofectamine RNAiMAX (Life Technologies), according to the manufacturer's "forward transfection" instructions. Cells were plated 24 h prior to transfection in triplicate on 24-well tissue culture plates, with 50000 cells per well. At 48 h post-transfection cells were washed with PBS and harvested with TRIzol® reagent (Life Technologies). RNA was isolated using the Direct-zol-96 RNA Kit (Zymo Research) according to the manufacturer's instructions. 10 µl of RNA was reverse transcribed to cDNA using the High Capacity cDNA Reverse Transcription Kit (Applied Biosystems) according to the manufacturer's instructions. cDNA samples were evaluated by qPCR with HPRT-specific and PPIB-specific TaqMan gene expression probes (Thermo Fisher) using TaqMan® Fast Advanced Master Mix (Applied Biosystems). HPRT values were normalized within each sample to PPIB gene expression. The quantification of HPRT down-regulation was performed using the standard $2^{-\Delta\Delta Ct}$ method. All experiments were performed in triplicate.

Figure 2:
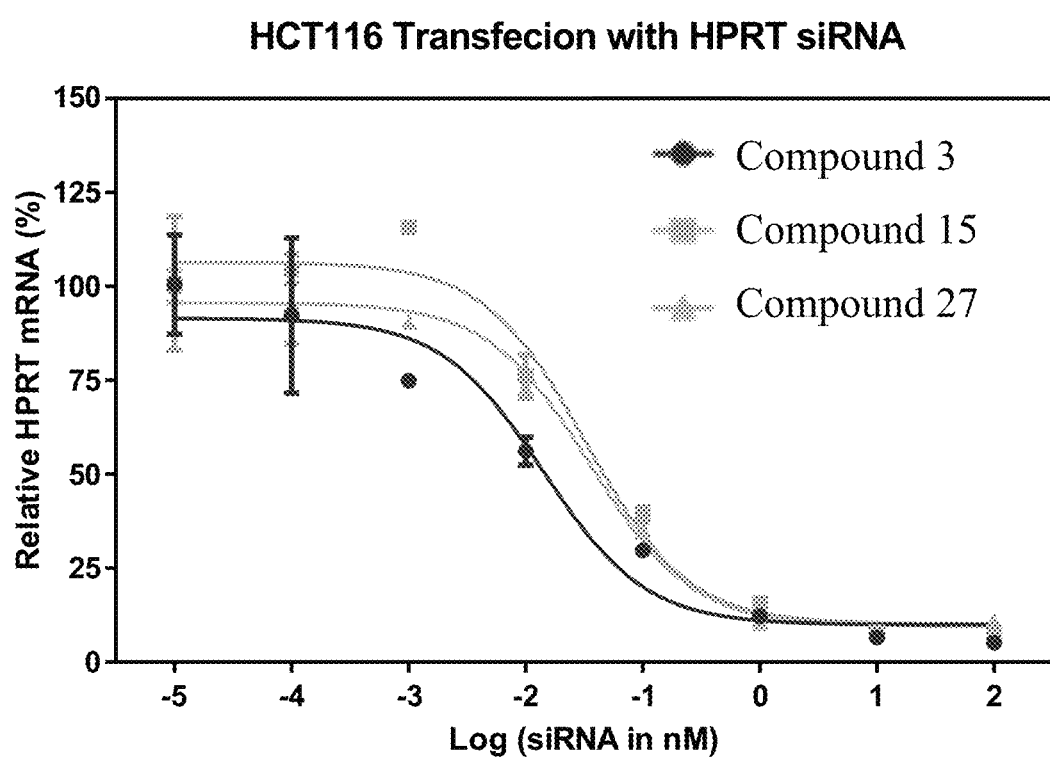
FIG. 2 shows a plot of Log (siRNA in nM) vs relative HPRT mRNA (%) for HCT Transfection with HPRT siRNA as described in example 11

FIG. 2 shows the dose response curves demonstrating that novel vinylphosphonate modified nucleotide structures on the guide strands of an HPRT siRNA, after in vitro transfection of the duplex, can be loaded into RISC and mediate sequence specific down regulation of the target HPRT gene. Activity of the analogues (compounds 15 and 27) was comparable to the standard vinylphosphonate modified nucleotide (compound 3).

Example 12. In Vitro Activity of Vinylphosphonate Modified Nucleotide Structures in Rhabdomyosarcoma Cells siRNA design and synthesis: A 21 mer myostatin (MSTN) guide strand was designed against human MSTN. The sequence (5' to 3') of the guide/antisense strand was UUAUUAUUUGUUCUUUGCCUU (SEQ ID NO: 1273). Five versions were prepared incorporating different structures (compounds 3, 15, 26, 27 and 28). The guide and fully complementary RNA passenger strands were assembled on solid phase using standard phospharamidite chemistry, and purified over HPLC. Base, sugar and phosphate modifications that are well described in the field of RNAi were used to optimize the potency of the duplex and reduce immunogenicity. Purified single strands were duplexed to obtain double stranded siRNA as described in FIG. 1A.

In vitro study: The activity of the siRNAs was evaluated in transfected human rhabdomyosarcoma cells (SJCRH30, ATCC CRL-2061). Cells were grown in RPMI-1640 supplemented with 10% heat inactivated FBS (Gibco) and 10 mM HEPES and 1 mM sodium pyruvate. For siRNA transfections, cells were plated at a density of 20.000 cells/well on 24 well plates plates and transfected with various concentrations of the siRNAs (0.0001-100 nM final concentration) using Lipofectamine RNAiMAX (Life Technologies), according to the manufacturer's "forward transfection" instructions. At 72 h post-transfection cells were washed with PBS and harvested with 300 □l/well TRIzol® reagent (Life Technologies). RNA was isolated using the Direct-zol-96 RNA Kit (Zymo Research) according to the manufacturer's instructions. 10 □l of RNA was reverse transcribed to cDNA using the High Capacity cDNA Reverse Transcription Kit (Applied Biosystems) according to the manufacturer's instructions. cDNA samples were evaluated by qPCR with MSTN-specific and PPIB-specific TaqMan gene expression probes (Thermo Fisher) using TaqMan® Fast Advanced Master Mix (Applied Biosystems) and the ΔΔCt method. Individual experiments were performed in duplicate or triplicate.

The table below shows the the half maximal inhibitory concentrations of the analogs (compounds 15, 26, 27 and 28) and maximum knockdown achieved relative to the standard vinylphosphonate modified nucleotide (compound 3).

| Compound on 5' end of GS | 3 | 28 | 26 | 15 | 27 |
|---|---|---|---|---|---|
| IC50 (pM) | 74.0 | 55.7 | 86.5 | 80.3 | 16.2 |
| Max KD (% untreated control) | 87.77 | 86.51 | 84.61 | 85.47 | 87.24 |

Figure 3:
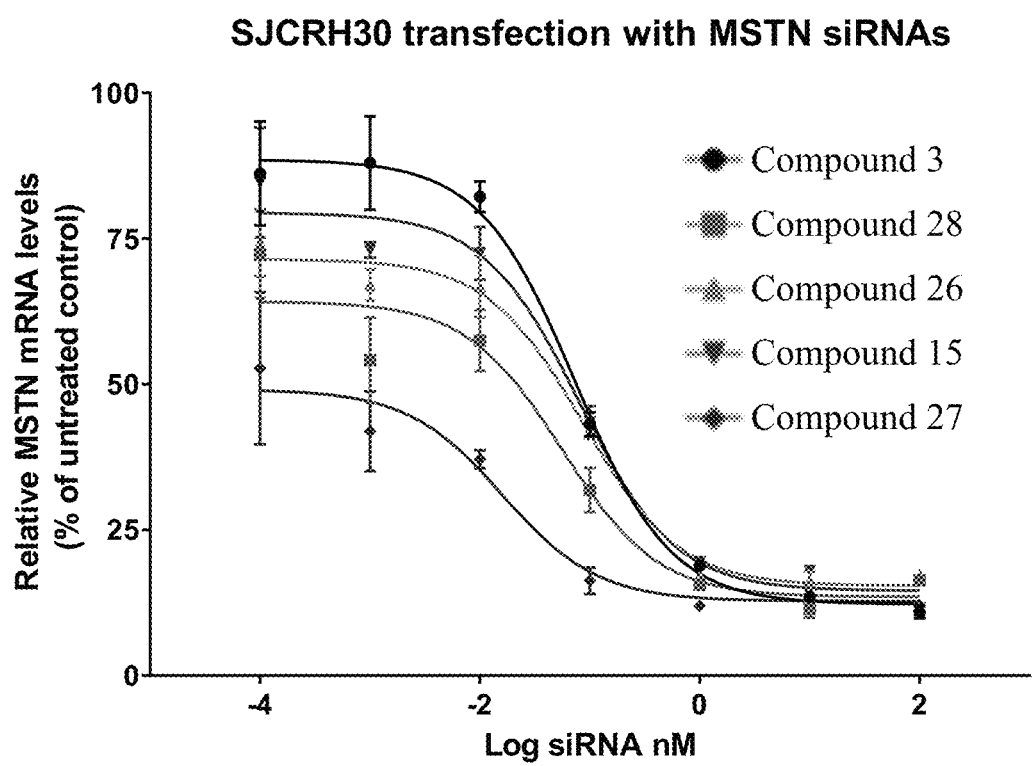
FIG. 3 shows a plot of Log (siRNA in nM) vs relative MSTN mRNA levels (% of untreated control) for SJCRH30 transfection with MSTN siRNAs as described in molecular biology example 12.

FIG. 3 shows the dose response curves, demonstrating that novel vinylphosphonate modified nucleotide structures on the guide strands of an MSTN siRNA, after in vitro transfection of the duplex, can be loaded into RISC and mediate sequence specific down regulation of the target MSTN gene. Activity of the analogs (compounds 15, 26, 27 and 28) was comparable to the standard vinylphosphonate modified nucleotide (compound 3).

Example 13. 2017-PK-407-WT: In Vivo Transferrin mAb Conjugate Delivery of siRNA

For groups 1-4, the 21 mer HPRT guide strand was designed against mouse HPRT. The sequence (5' to 3') of the guide/antisense strand was UUAAAAUCUACAGUCAUAGUU (SEQ ID NO: 1275). The guide and fully complementary RNA passenger strands were assembled on solid phase using standard phospharamidite chemistry and purified over HPLC. Base, sugar and phosphate modifications that are well described in the field of RNAi were used to optimize the potency of the duplex and reduce immunogenicity. Purified single strands were duplexed to obtain double stranded siRNA described above. The guide strand utilized the compound 3 vinylphosphonate modified nucleotide structure. The passenger strand had a conjugation handle on the 5' end via an inverted abasic phosphodiester linkage, see FIG. 1A.

For groups 5-8, the 21 mer HPRT guide strand was designed against mouse HPRT. The sequence (5' to 3') of the guide/antisense strand was UUAAAAUCUACAGUCAUAGUU (SEQ ID NO: 1275). The guide and fully complementary RNA passenger strands were assembled on solid phase using standard phospharamidite chemistry and purified over HPLC. Base, sugar and phosphate modifications that are well described in the field of RNAi were used to optimize the potency of the duplex and reduce immunogenicity. Purified single strands were duplexed to obtain double stranded siRNA described in figure C. The guide strand utilized the compound 15 vinylphosphonate modified nucleotide structure. The passenger strand had a conjugation handle on the 5' end via the phosphodiester linkage on the terminal base, see FIG. 1B.

For groups 9-12, the 21 mer HPRT guide strand was designed against mouse HPRT. The sequence (5' to 3') of the guide/antisense strand was UUAAAAUCUACAGUCAUAGUU (SEQ ID NO: 1275). The guide and fully complementary RNA passenger strands were assembled on solid phase using standard phospharamidite chemistry and purified over HPLC. Base, sugar and phosphate modifications that are well described in the field of RNAi were used to optimize the potency of the duplex and reduce immunogenicity. Purified single strands were duplexed to obtain double stranded siRNA. The guide strand utilized the compound 27 vinylphosphonate modified nucleotide structure. The passenger strand had a conjugation handle on the 5' end via the phosphodiester linkage on the terminal base, see FIG. 1B For groups 13-16, the 21 mer MSTN guide strand was designed against human MSTN. The sequence (5' to 3') of the guide/antisense strand was UUAUUAUUUGUUCUUUGCCUU (SEQ ID NO: 1273). The guide and fully complementary RNA passenger strands were assembled on solid phase using standard phospharamidite chemistry and purified over HPLC. Base, sugar and phosphate modifications that are well described in the field of RNAi were used to optimize the potency of the duplex and reduce immunogenicity. Purified single strands were duplexed to obtain double stranded siRNA. The guide strand utilized the compound 28 vinylphosphonate modified nucleotide structure. The passenger strand had a conjugation handle on the 5' end via an inverted abasic phosphodiester linkage, see FIG. 1A.

For groups 17-20, the 21 mer MSTN guide strand was designed against human MSTN. The sequence (5' to 3') of the guide/antisense strand was UUAUUAUUUGUUCUUUGCCUU (SEQ ID NO: 1273). The guide and fully complementary RNA passenger strands were assembled on solid phase using standard phospharamidite chemistry and purified over HPLC. Base, sugar and phosphate modifications that are well described in the field of RNAi were used to optimize the potency of the duplex and reduce immunogenicity. Purified single strands were duplexed to obtain double stranded siRNA. The guide strand utilized the compound 3 vinylphosphonate modified nucleotide structure. The passenger strand had a conjugation handle on the 5' end via an inverted abasic phosphodiester linkage, see FIG. 1A Antibody siRNA Conjugate Synthesis Using Bis-Maleimide (BisMal) Linker Step 1: Antibody Reduction with TCEP Antibody was buffer exchanged with 25 mM borate buffer (pH 8) with 1 mM DTPA and made up to 10 mg/ml concentration. To this solution, 4 equivalents of TCEP in the same borate buffer were added and incubated for 2 hours at 37° C. The resultant reaction mixture was combined with a solution of BisMal-siRNA (1.25 equivalents) in pH 6.0 10 mM acetate buffer at RT and kept at 4° C. overnight. Analysis of the reaction mixture by analytical SAX column chromatography showed antibody siRNA conjugate along with unreacted antibody and siRNA.

The reaction mixture was treated with 10 EQ of N-ethylmaleimide (in DMSO at 10 mg/mL) to cap any remaining free cysteine residues.

Step 2: Purification

The crude reaction mixture was purified by AKTA Pure FPLC using anion exchange chromatography (SAX) method-1. Fractions containing DAR1 and DAR2 antibody-siRNA conjugates were isolated, concentrated and buffer exchanged with pH 7.4 PBS.

Anion Exchange Chromatography (SAX) Method-1
1. Column: Tosoh Bioscience, TSKGel SuperQ-SPW, 21.5 mm ID×15 cm, 13 um
2. Solvent A: 20 mM TRIS buffer, pH 8.0; Solvent B: 20 mM TRIS, 1.5 M NaCl, pH 8.0; Flow Rate: 6.0 ml/min 3. Gradient:

| a. | % A | % B | Column Volume |
|---|---|---|---|
| b. | 100 | 0 | 1 |
| c. | 81 | 19 | 0.5 |
| d. | 50 | 50 | 13 |
| e. | 40 | 60 | 0.5 |
| f. | 0 | 100 | 0.5 |
| g. | 100 | 0 | 2 |

Anion Exchange Chromatography (SAX) Method-2
1. Column: Thermo Scientific, ProPac™ SAX-10, Bio LC™, 4×250 mm
2. Solvent A: 80% 10 mM TRIS pH 8, 20% ethanol; Solvent B: 80% 10 mM TRIS pH 8, 20% ethanol, 1.5 M NaCl; Flow Rate: 0.75 ml/min 3. Gradient:

| a. | Time | % A | % B |
|---|---|---|---|
| b. | 0.0 | 90 | 10 |
| c. | 3.00 | 90 | 10 |
| d. | 11.00 | 40 | 60 |
| e. | 14.00 | 40 | 60 |
| f. | 15.00 | 20 | 80 |
| g. | 16.00 | 90 | 10 |
| h. | 20.00 | 90 | 10 |

Step-3: Analysis of the Purified Conjugate

The purity of the conjugate was assessed by analytical HPLC using anion exchange chromatography method-2.

| Conjugate | SAX retention time (min) | % purity (by peak area) |
|---|---|---|
| TfR-mAb--compound 3-HPRT DAR 1 | 9.41 | 99 |
| TfR-mAb-compound 15-HPRT DAR 1 | 8.83 | 99 |
| TfR-mAb-compound 27-HPRT DAR 1 | 8.54 | 99 |
| TfR-mAb-compound 28-MSTN DAR 1 | 8.96 | 99 |
| TfR-mAb-compound 3-MSTN DAR 1 | 9.39 | 99 |

In Vivo Study

The conjugates were assessed for their ability to mediate mRNA downregulation of myostatin (MSTN) and HPRT in skeletal muscle, in an in vivo experiment (wild type CD-1 mice). Mice were dosed via intravenous (iv) injection with PBS vehicle control and the indicated ASCs and doses, see table below. After 168 hours, gastrocnemius (gastroc) muscle tissues were harvested and snap-frozen in liquid nitrogen. mRNA knockdown in target tissue was determined using a comparative qPCR assay. Total RNA was extracted from the tissue, reverse transcribed and mRNA levels were quantified using TaqMan qPCR, using the appropriately designed primers and probes. PPIB (housekeeping gene) was used as an internal RNA loading control, results were calculated by the comparative Ct method, where the difference between the target gene Ct value and the PPIB Ct value ($\Delta Ct$) is calculated and then further normalized relative to the PBS control group by taking a second difference ($\Delta\Delta Ct$).

| Group | Test Article | N | siRNA Dose (mg/kg) | Dose Volume (mL/kg) | Harvest Time (h) |
|---|---|---|---|---|---|
| 1 | TfR1-mAb-compound 3-HPRT DAR1 | 4 | 3 | 5.0 | 168 |
| 2 | TfR1-mAb-compound 3-HPRT DAR1 | 4 | 1 | 5.0 | 168 |
| 3 | TfR1-mAb-compound 3-HPRT DAR1 | 4 | 0.3 | 5.0 | 168 |
| 4 | TfR1-mAb-compound 3-HPRT DAR1 | 4 | 0.1 | 5.0 | 168 |
| 5 | TfR1-mAb-compound 15-HPRT DAR1 | 4 | 3.0 | 5.0 | 168 |
| 6 | TfR1-mAb-compound 15-HPRT DAR1 | 4 | 1 | 5.0 | 168 |
| 7 | TfR1-mAb-compound 15-HPRT DAR1 | 4 | 0.3 | 5.0 | 168 |
| 8 | TfR1-mAb-compound 15-HPRT DAR1 | 4 | 0.1 | 5.0 | 168 |
| 9 | TfR1-mAb-compound 27-HPRT DAR1 | 4 | 0.5 | 5.0 | 168 |
| 10 | TfR1-mAb-compound 27-HPRT DAR1 | 4 | 0.5 | 5.0 | 168 |
| 11 | TfR1-mAb-compound 27-HPRT DAR1 | 4 | 0.5 | 5.0 | 168 |
| 12 | TfR1-mAb-compound 27-HPRT DAR1 | 4 | 0.5 | 5.0 | 168 |
| 13 | TfR1-mAb-compound 28-MSTN DAR1 | 4 | 0.5 | 5.0 | 168 |
| 14 | TfR1-mAb-compound 28-MSTN DAR1 | 4 | 0.5 | 5.0 | 168 |
| 15 | TfR1-mAb-compound 28-MSTN DAR1 | 4 | 0.5 | 5.0 | 168 |
| 16 | TfR1-mAb-compound 28-MSTN DAR1 | 4 | 0.5 | 5.0 | 168 |
| 17 | TfR1-mAb-compound 3-MSTN DAR1 | 4 | 0.5 | 5.0 | 168 |
| 18 | TfR1-mAb-compound 3-MSTN DAR1 | 4 | 0.5 | 5.0 | 168 |
| 19 | TfR1-mAb-compound 3-MSTN DAR1 | 4 | 0.5 | 5.0 | 168 |
| 20 | TfR1-mAb-compound 3-MSTN DAR1 | 4 | 0.5 | 5.0 | 168 |
| 21 | PBS control | 5 | | 5.0 | 168 |

Figure 4:
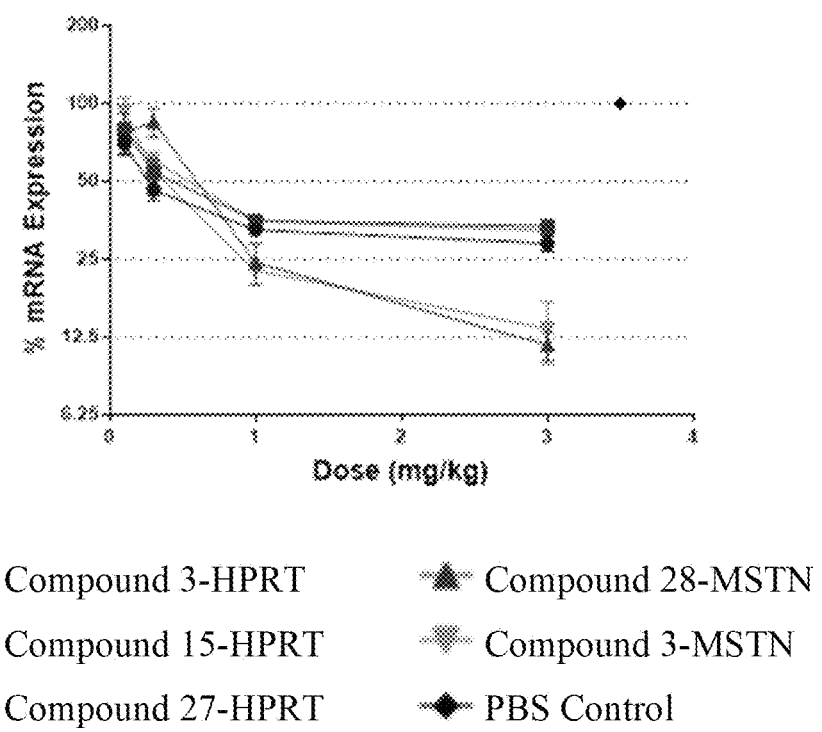
FIG. 4 shows in vivo MSTN and HPRT mRNA downregulation in gastroc muscle, after IV administration of antibody siRNA conjugates, as described in molecular biology example 13.

FIG. 4 shows that the vinylphosphonate modified nucleotide structures on the siRNA guide strands demonstrated dose dependent downregulation of their target gene in gastric muscle when conjugated to an anti-TfR mAb targeting the transferrin receptor. Activity of the analogues was comparable to the standard vinylphosphonate modified nucleotide structure.

Example 14. 2017-PK-421-WT: In Vivo Transferrin mAb Conjugate Delivery of siRNA

For groups 1-12, the 21 mer MSTN guide strand was designed against human/mouse MSTN. The sequence (5' to 3') of the guide/antisense strand was UUAUUAUUU-GUUCUUUGCCUU (SEQ ID NO: 1273). The guide and fully complementary RNA passenger strands were assembled on solid phase using standard phosphoramidite chemistry and purified over HPLC. Base, sugar and phosphate modifications that are well described in the field of RNAi were used to optimize the potency of the duplex and reduce immunogenicity. Purified single strands were duplexed to obtain double stranded siRNA. Three guide strands were produced with three different vinylphosphonate modified nucleotide structures at the 5'end (compounds 3, 15 and 26). The passenger strand had a conjugation handle on the 5' end via a phosphodiester-inverted abasic linkage.

Figure 16:
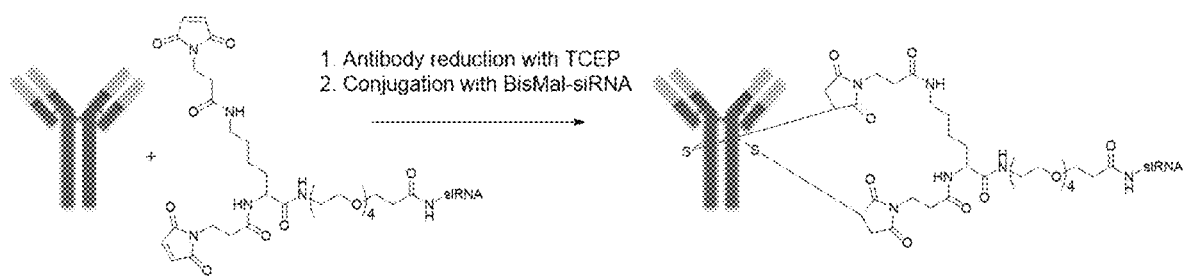
FIG. 16 illustrates a conjugation scheme of anti-TfR1 mAb-MSTN DAR1 conjugate.

The anti-TfR1 mAb-MSTN DAR1 conjugates were synthesized as described in FIG. 16.

Step 1: Antibody Reduction with TCEP

Antibody was buffer exchanged with 25 mM borate buffer (pH 8) with 1 mM DTPA and made up to 10 mg/ml concentration. To this solution, 4 equivalents of TCEP in the same borate buffer were added and incubated for 2 hours at 37° C. The resultant reaction mixture was combined with a solution of BisMal-siRNA (1.25 equivalents) in 10 mM acetate buffer (pH 6) at RT and kept at 4° C. overnight. Analysis of the reaction mixture by analytical SAX column chromatography showed antibody siRNA conjugate along with unreacted antibody and siRNA. The reaction mixture was treated with 10 EQ of N-ethylmaleimide (in DMSO at 10 mg/mL) to cap any remaining free cysteine residues.

Step 2: Purification

The crude reaction mixture was purified by AKTA Pure FPLC using anion exchange chromatography (SAX) method-1. Fractions containing DAR1 and DAR2 antibody-siRNA conjugates were isolated, concentrated and buffer exchanged with pH 7.4 PBS.

Anion Exchange Chromatography (SAX) Method-1.
1. Column: Tosoh Bioscience, TSKGel SuperQ-SPW, 21.5 mm ID×15 cm, 13 um
2. Solvent A: 20 mM TRIS buffer, pH 8.0; Solvent B: 20 mM TRIS, 1.5 M NaCl, pH 8.0; Flow Rate: 6.0 ml/min

| 3. Gradient: | | | |
|---|---|---|---|
| a. | % A | % B | Column Volume |
| b. | 100 | 0 | 1 |
| c. | 81 | 19 | 0.5 |
| d. | 50 | 50 | 13 |
| e. | 40 | 60 | 0.5 |
| f. | 0 | 100 | 0.5 |
| g. | 100 | 0 | 2 |

Anion Exchange Chromatography (SAX) Method-2
1. Column: Thermo Scientific, ProPac™ SAX-10, Bio LC™, 4×250 mm
2. Solvent A: 80% 10 mM TRIS pH 8, 20% ethanol; Solvent B: 80% 10 mM TRIS pH 8, 20% ethanol, 1.5 M NaCl; Flow Rate: 0.75 ml/min

| 3. Gradient: | | | |
|---|---|---|---|
| a. | Time | % A | % B |
| b. | 0.0 | 90 | 10 |
| c. | 3.00 | 90 | 10 |
| d. | 11.00 | 40 | 60 |
| e. | 14.00 | 40 | 60 |
| f. | 15.00 | 20 | 80 |
| g. | 16.00 | 90 | 10 |
| h. | 20.00 | 90 | 10 |

Step-3: Analysis of the Purified Conjugate

The purity of the conjugate was assessed by analytical HPLC using anion exchange chromatography method-2.

| Conjugate | SAX retention time (min) | % purity (by peak area) |
|---|---|---|
| TfR-compound 3-MSTN.mff3s DAR 1 | 8.99 | 99 |
| TfR-compound 15-MSTN DAR 1 | 9.12 | 99 |
| TfR-compound 26-MSTN DAR 1 | 9.09 | 99 |

In Vivo Study

The conjugates were assessed for their ability to mediate mRNA downregulation of myostatin (MSTN) in skeletal muscle, in an in vivo experiment (wild type CD-1 mice). Mice were dosed via intravenous (iv) injection with PBS vehicle control and the indicated ASCs and doses, as noted in the table below. After 168 hours, gastrocnemius (gastroc), quadriceps (quad) and heart muscle tissues were harvested and snap-frozen in liquid nitrogen. mRNA knockdown in target tissue was determined using a comparative qPCR assay as described in the methods section. Total RNA was extracted from the tissue, reverse transcribed and mRNA levels were quantified using TaqMan qPCR, using the appropriately designed primers and probes. PPIB (housekeeping gene) was used as an internal RNA loading control, results were calculated by the comparative Ct method, where the difference between the target gene Ct value and the PPIB Ct value ($\Delta$Ct) is calculated and then further normalized relative to the PBS control group by taking a second difference ($\Delta\Delta$Ct).

| Group | Test Article | N | siRNA Dose (mg/kg) | Dose Volume (mL/kg) | Harvest Time (h) |
|---|---|---|---|---|---|
| 1 | TfR1-mAb-compound 26-MSTN DAR1 | 4 | 3 | 5.0 | 168 |
| 2 | TfR1-mAb-compound 26-MSTN DAR1 | 4 | 1 | 5.0 | 168 |
| 3 | TfR1-mAb-compound 26-MSTN DAR1 | 4 | 0.3 | 5.0 | 168 |
| 4 | TfR1-mAb-compound 26-MSTN DAR1 | 4 | 0.1 | 5.0 | 168 |
| 5 | TfR1-mAb-compound 15-MSTN DAR1 | 4 | 3.0 | 5.0 | 168 |

| Group | Test Article | N | siRNA Dose (mg/kg) | Dose Volume (mL/kg) | Harvest Time (h) |
|---|---|---|---|---|---|
| 6 | TfR1-mAb-compound 15-MSTN DAR1 | 4 | 1 | 5.0 | 168 |
| 7 | TfR1-mAb-compound 15-MSTN DAR1 | 4 | 0.3 | 5.0 | 168 |
| 8 | TfR1-mAb-compound 15-MSTN DAR1 | 4 | 0.1 | 5.0 | 168 |
| 9 | TfR1-mAb-compound 3-MSTN DAR1 | 4 | 0.5 | 5.0 | 168 |
| 10 | TfR1-mAb-compound 3-MSTN DAR1 | 4 | 0.5 | 5.0 | 168 |
| 11 | TfR1-mAb-compound 3-MSTN DAR1 | 4 | 0.5 | 5.0 | 168 |
| 12 | TfR1-mAb-compound 3-MSTN DAR1 | 4 | 0.5 | 5.0 | 168 |
| 13 | PBS control | 5 |  | 5.0 | 168 |

Figure 5:
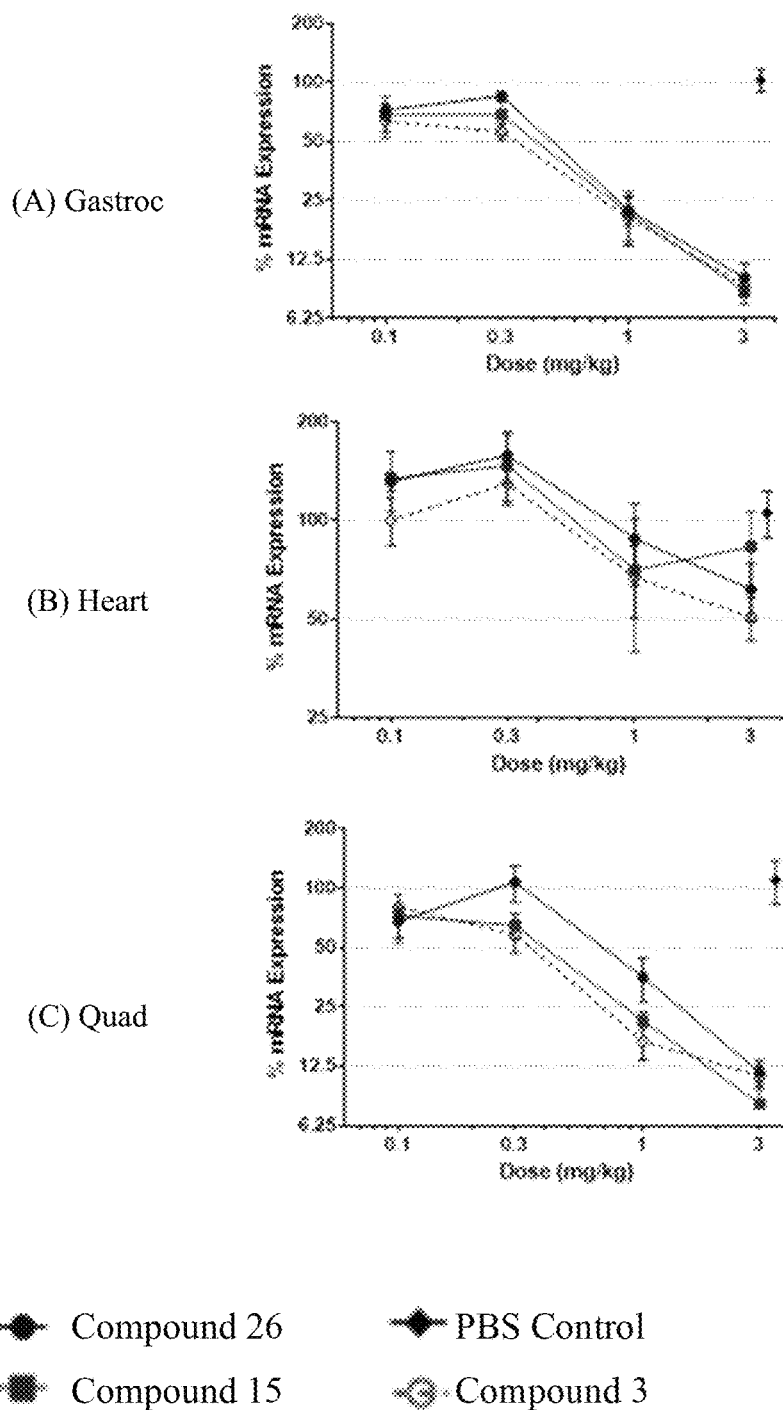
FIG. 5 shows in vivo MSTN mRNA downregulation in (A) gastroc, (B) quad and (C) heart muscle after IV administration of antibody siRNA conjugates, as described in molecular biology example 14.

FIG. 5 demonstrates MSTN mRNA downregulation in gastroc, quad and heart muscle with antibody siRNA conjugates containing different vinylphosphonate modified nucleotide structure on the 5' end of the guide strand. Activity of the analogues was comparable to the standard vinylphosphonate modified nucleotide structure.

Example 15. 2017-PK-422-WT: In Vivo Transferrin mAb Conjugate Delivery of siRNA For groups 1-4 and 9-12, the 21 mer HPRT guide strand was designed against mouse HPRT. The sequence (5' to 3') of the guide/antisense strand was UUAAAAUCUACAGU-CAUAGUU (SEQ ID NO: 1275). The guide and fully complementary RNA passenger strands were assembled on solid phase using standard phospharamidite chemistry and purified over HPLC. Base, sugar and phosphate modifications that are well described in the field of RNAi were used to optimize the potency of the duplex and reduce immunogenicity. Purified single strands were duplexed to obtain double stranded siRNA. The guide strand was produced with compound 3 vinylphosphonate modified nucleotide structures at the 5'end. The passenger strand had a conjugation handle on the 5' end via aphosphorothioate-inverted abasic-phosphodiester linker, see FIG. 1A.

For groups 5-8 and 13-16 a 21 mer HPRT guide strand was designed against mouse HPRT. The sequence (5' to 3') of the guide/antisense strand was UUAAAAUCUACAGU-CAUAGUU (SEQ ID NO: 1275). The guide and fully complementary RNA passenger strands were assembled on solid phase using standard phospharamidite chemistry and purified over HPLC. Base, sugar and phosphate modifications that are well described in the field of RNAi were used to optimize the potency of the duplex and reduce immunogenicity. Purified single strands were duplexed to obtain double stranded siRNA. The guide strand was produced with a compound 26 vinylphosphonate modified nucleotide structures at the 5' end. The passenger strand had a conjugation handle on the 5' end via the terminal phosphorothioate., see FIG. 1B.

The anti-TfR1 mAb-HPRT DAR1 conjugates were synthesized as described in FIG. 16.

Step 1: Antibody Reduction with TCEP

Antibody was buffer exchanged with 25 mM borate buffer (pH 8) with 1 mM DTPA and made up to 10 mg/ml concentration. To this solution, 4 equivalents of TCEP in the same borate buffer were added and incubated for 2 hours at 37° C. The resultant reaction mixture was combined with a solution of BisMal-siRNA (1.25 equivalents) in 10 mM acetate buffer (pH 6) at RT and kept at 4° C. overnight. Analysis of the reaction mixture by analytical SAX column chromatography showed antibody siRNA conjugate along with unreacted antibody and siRNA. The reaction mixture was treated with 10 EQ of N-ethylmaleimide (in DMSO at 10 mg/mL) to cap any remaining free cysteine residues.

Step 2: Purification

The crude reaction mixture was purified by AKTA Pure FPLC using anion exchange chromatography (SAX) method-1. Fractions containing DAR1 and DAR2 antibody-siRNA conjugates were isolated, concentrated and buffer exchanged with pH 7.4 PBS.

Anion Exchange Chromatography (SAX) Method-1.

1. Column: Tosoh Bioscience, TSKGel SuperQ-SPW, 21.5 mm ID×15 cm, 13 um
2. Solvent A: 20 mM TRIS buffer, pH 8.0; Solvent B: 20 mM TRIS, 1.5 M NaCl, pH 8.0; Flow Rate: 6.0 ml/min

| 3. Gradient: | | | |
|---|---|---|---|
| a. | % A | % B | Column Volume |
| b. | 100 | 0 | 1 |
| c. | 81 | 19 | 0.5 |
| d. | 50 | 50 | 13 |
| e. | 40 | 60 | 0.5 |
| f. | 0 | 100 | 0.5 |
| g. | 100 | 0 | 2 |

Anion Exchange Chromatography (SAX) Method-2

1. Column: Thermo Scientific, ProPac™ SAX-10, Bio LC™, 4×250 mm
2. Solvent A: 80% 10 mM TRIS pH 8, 20% ethanol; Solvent B: 80% 10 mM TRIS pH 8, 20% ethanol, 1.5 M NaCl; Flow Rate: 0.75 ml/min

| 3. Gradient: | | | |
|---|---|---|---|
| a. | Time | % A | % B |
| b. | 0.0 | 90 | 10 |
| c. | 3.00 | 90 | 10 |
| d. | 11.00 | 40 | 60 |
| e. | 14.00 | 40 | 60 |
| f. | 15.00 | 20 | 80 |
| g. | 16.00 | 90 | 10 |
| h. | 20.00 | 90 | 10 |

Step-3: Analysis of the Purified Conjugate

The purity of the conjugate was assessed by analytical HPLC using anion exchange chromatography method-2.

| Conjugate | SAX retention time (min) | % purity (by peak area) |
|---|---|---|
| TfR-compound 3-HPRT DAR 1 | 9.14 | 99 |
| TfR-compound 26-HPRT DAR 1 | 8.54 | 99 |
| ASGR-compound 3-HPRT DAR 1 | 9.3 | 99 |
| ASGR-compound 26-MSTN DAR 1 | 8.62 | 99 |

In Vivo Study

The conjugates were assessed for their ability to mediate mRNA downregulation of HPRT in muscle and liver, in an in vivo experiment (wild type CD-1 mice). Mice were dosed via intravenous (iv) injection with PBS vehicle control and the indicated ASCs and doses, as noted in the table below. After 168 hours, gastrocnemius (gastroc), and liver tissues were harvested and snap-frozen in liquid nitrogen. mRNA knockdown in target tissue was determined using a comparative qPCR assay as described in the methods section. Total RNA was extracted from the tissue, reverse transcribed and mRNA levels were quantified using TaqMan qPCR, using the appropriately designed primers and probes. PPIB (housekeeping gene) was used as an internal RNA loading control, results were calculated by the comparative Ct method, where the difference between the target gene Ct value and the PPIB Ct value ($\Delta Ct$) is calculated and then further normalized relative to the PBS control group by taking a second difference ($\Delta\Delta Ct$).

Example 16. In Vitro Activity of Vinylphosphonate Modified Nucleotide Structures in HCT116 Cells siRNA design and synthesis: A 21 mer SSB guide strand was designed against mouse SSB. The sequence (5' to 3') of the guide/antisense strand was UUACAUUAAAGUCU-GUUGUUU (SEQ ID NO: 1274). Three versions were made incorporating vinylphosphonate modified nucleotide structures (compounds 3, 30 and 32). The guide and fully complementary RNA passenger strands were assembled on solid phase using standard phospharamidite chemistry, and purified over HPLC. The vinylphosphonate modified nucleotide structures were incorporated using the amidites described in figure A3. The Base, sugar and phosphate modifications that are well described in the field of RNAi were used to optimize the potency of the duplex and reduce immunogenicity. Purified single strands were duplexed to get the double stranded siRNA described above.

In vitro study: The different siRNAs were transfected into human colorectal carcinoma HCT116 cells at 100 nM, 10 nM, 1 nM, 0.1 nM, 0.01 nM, 0.001 nM, and 0.0001 nM final concentration. The siRNAs were formulated with commercially available transfection reagent.\, Lipofectamine RNAiMAX (Life Technologies), according to the manufacturer's "forward transfection" instructions. Cells were plated 24 h prior to transfection in triplicate on 24-well tissue culture plates, with 50000 cells per well. At 48 h post-transfection cells were washed with PBS and harvested with TRIzol® reagent (Life Technologies). RNA was isolated using the Direct-zol-96 RNA Kit (Zymo Research) according to the manufacturer's instructions. 10 µl of RNA was

| Group | Test Article | N | siRNA Dose (mg/kg) | Dose Volume (mL/kg) | Harvest Time (h) |
|---|---|---|---|---|---|
| 1 | TfR1-mAb-compound 3-HPRT DAR1 | 4 | 1 | 5.0 | 168 |
| 2 | TfR1-mAb-compound 3-HPRT DAR1 | 4 | 0.3 | 5.0 | 168 |
| 3 | TfR1-mAb-compound 3-HPRT DAR1 | 4 | 0.1 | 5.0 | 168 |
| 4 | TfR1-mAb-compound 3-HPRT DAR1 | 4 | 0.03 | 5.0 | 168 |
| 5 | TfR1-mAb-compound 26-HPRT DAR1 | 4 | 1 | 5.0 | 168 |
| 6 | TfR1-mAb-compound 26-HPRT DAR1 | 4 | 0.3 | 5.0 | 168 |
| 7 | TfR1-mAb-compound 26-HPRT DAR1 | 4 | 0.1 | 5.0 | 168 |
| 8 | TfR1-mAb-compound 26-HPRT DAR1 | 4 | 0.03 | 5.0 | 168 |
| 9 | ASGR-mAb-compound 3-HPRT DAR1 | 4 | 1 | 5.0 | 168 |
| 10 | ASGR-mAb-compound 3-HPRT DAR1 | 4 | 0.3 | 5.0 | 168 |
| 11 | ASGR-mAb-compound 3-HPRT DAR1 | 4 | 0.1 | 5.0 | 168 |
| 12 | ASGR-mAb-compound 3-HPRT DAR1 | 4 | 0.03 | 5.0 | 168 |
| 13 | ASGR-mAb-compound 26-HPRT DAR1 | 4 | 1 | 5.0 | 168 |
| 14 | ASGR-mAb-compound 26-HPRT DAR1 | 4 | 0.3 | 5.0 | 168 |
| 15 | ASGR-mAb-compound 26-HPRT DAR1 | 4 | 0.1 | 5.0 | 168 |
| 16 | ASGR-mAb-compound 26-HPRT DAR1 | 4 | 0.03 | 5.0 | 168 |
| 17 | PBS control | 5 | | 5.0 | 168 |

Figure 6:
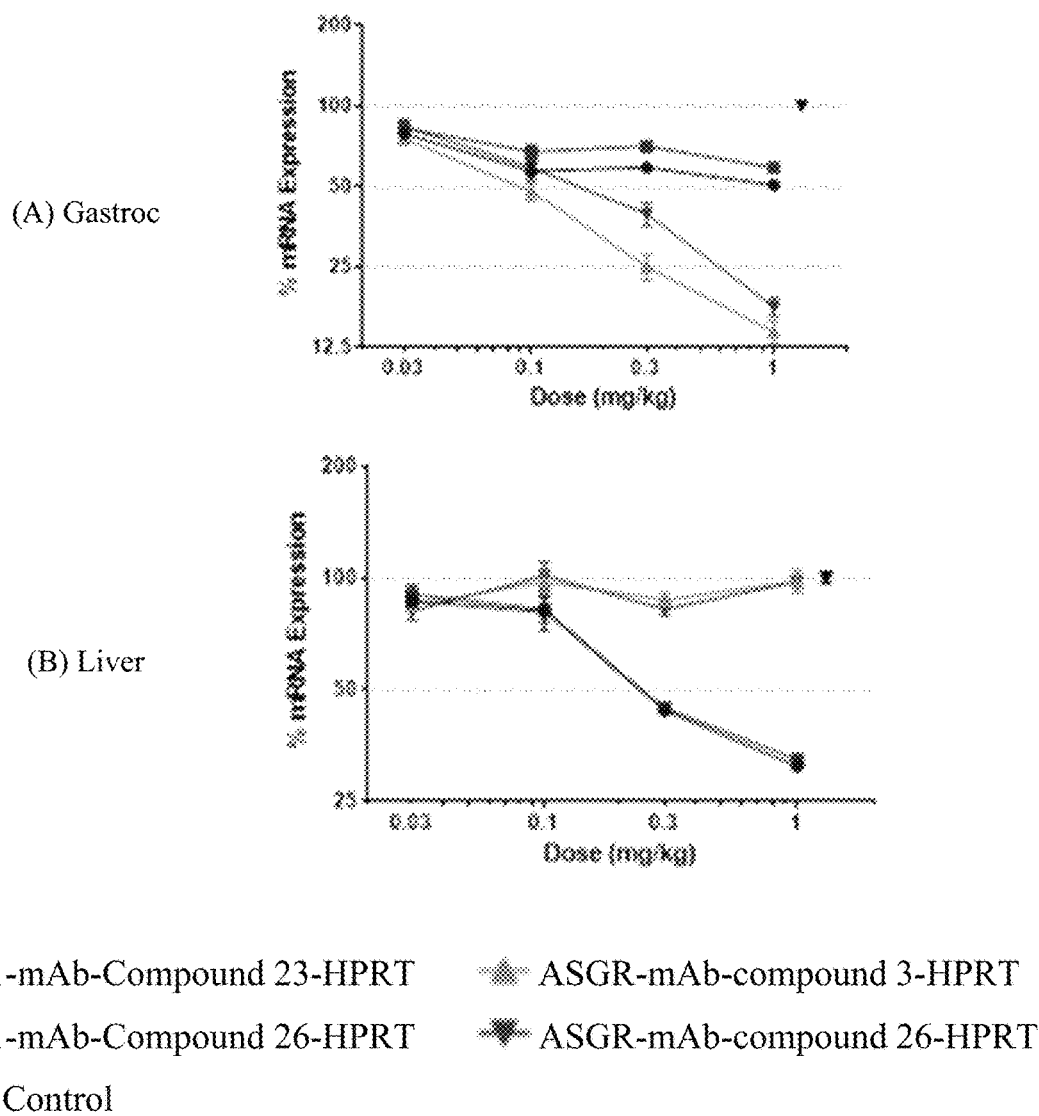
FIG. 6 shows in vivo HPRT mRNA downregulation in (A) gastroc and (B) liver after IV administration of antibody siRNA conjugates, as described in molecular biology example 15.

FIG. 6 demonstrates the modified vinylphosphonate modified nucleotide structures on the siRNA guide strands were able to mediate dose dependent downregulation of the HPRT target gene in the mouse liver and gastroc muscle after IV administration to a mouse. When conjugated to an anti-TfR mAb targeting the transferrin receptor on muscle, the siRNA was able to mediate HPRT downregulation in muscle. When conjugated to an anti-ASGR mAb targeting the ASGR receptor on liver hepatocytes, the siRNA was able to mediate HPRT downregulation in liver.

reverse transcribed to cDNA using the High Capacity cDNA Reverse Transcription Kit (Applied Biosystems) according to the manufacturer's instructions. cDNA samples were evaluated by qPCR with HPRT-specific and PPIB-specific TaqMan gene expression probes (Thermo Fisher) using TaqMan® Fast Advanced Master Mix (Applied Biosystems). HPRT values were normalized within each sample to PPIB gene expression. The quantification of HPRT downregulation was performed using the standard $2^{-\Delta\Delta Ct}$ method. All experiments were performed in triplicate.

EC$_{50}$ values were as follows:

| Sample | EC50 (pM) |
|---|---|
| Compound 3-SSB | 4.00 |
| Compound 30-SSB | 0.44 |
| Compound 32-SSB | 1.46 |

Figure 7:
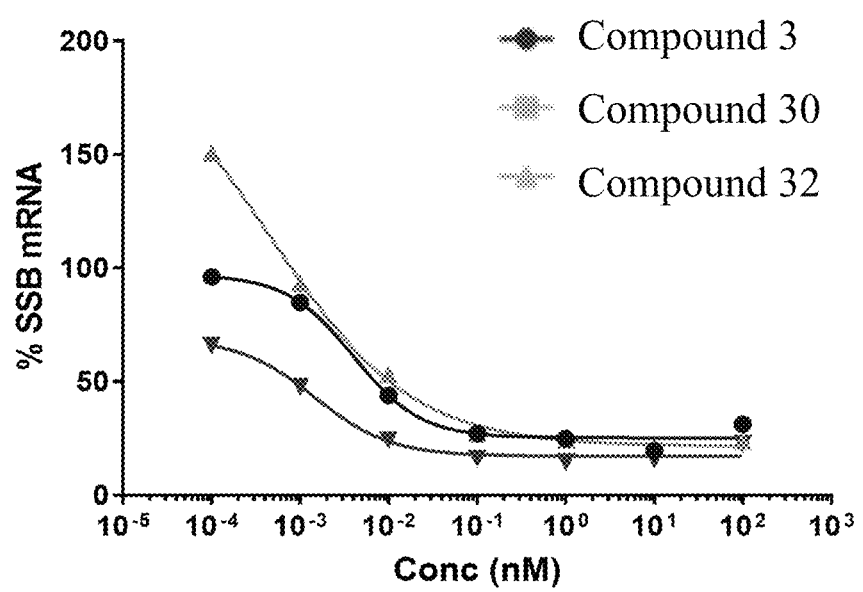
FIG. 7 shows a plot of concentration (nM) vs % SSB mRNA as described in molecular biology example 16.

FIG. 7 shows the dose response curves demonstrating that novel vinylphosphonate modified nucleotide structures on the 5' end of the guide strands of an SSB siRNA, after in vitro transfection of the duplex, can be loaded into RISC and mediate sequence specific down regulation of the target SSB gene. Activity of the analogues (compounds 30 and 32) was comparable to the standard vinylphosphonate modified nucleotide structure (compound 3).

Example 17. In Vitro Activity Vinylphosphonate Modified Nucleotide Structures in Rhabdomyosarcoma Cells siRNA design and synthesis: A 21 mer myostatin (MSTN) guide strand was designed against mouse and human MSTN. The sequence (5' to 3') of the guide/antisense strand was UUAUUAUUUGUUCUUUGCCUU (SEQ ID NO: 1273). Four versions were prepared incorporating different structures (compounds 3, 26, 30 and 32). The guide and fully complementary RNA passenger strands were assembled on solid phase using standard phospharamidite chemistry, and purified using HPLC. The vinylphosphonate modified nucleotide structures were incorporated using the amidites as described above. Base, sugar and phosphate modifications that are well described in the field of RNAi were used to optimize the potency of the duplex and reduce immunogenicity. Purified single strands were duplexed to get the double stranded siRNA as described above.

In addition, a 21 mer SSB guide strand was designed against mouse SSB. The sequence (5' to 3') of the guide/antisense strand was UUACAUUAAAGUCUGUUGUUU (SEQ ID NO: 1274). Three versions were made with different vinylphosphonate modified nucleotide structures (compounds 3, 30 and 32). The guide and fully complementary RNA passenger strands were assembled on solid phase using standard phospharamidite chemistry, and purified over HPLC. The vinylphosphonate modified nucleotide structures were incorporated using the amidites as described herein. The Base, sugar and phosphate modifications that are well described in the field of RNAi were used to optimize the potency of the duplex and reduce immunogenicity. Purified single strands were duplexed to get the double stranded siRNA as described above.

In vitro study: The activity of the siRNAs was evaluated in transfected human rhabdomyosarcoma cells (SJCRH30, ATCC CRL-2061). Cells were grown in RPMI-1640 supplemented with 10% heat inactivated FBS (Gibco) and 10 mM HEPES and 1 mM sodium pyruvate. For siRNA transfections, cells were plated at a density of 20.000 cells/well on 24 well plates plates and transfected with various concentrations of the siRNAs (0.0001-100 nM final concentration) using Lipofectamine RNAiMAX (Life Technologies), according to the manufacturer's "forward transfection" instructions. At 72 h post-transfection cells were washed with PBS and harvested with 300 ul/well TRIzol® reagent (Life Technologies). RNA was isolated using the Direct-zol-96 RNA Kit (Zymo Research) according to the manufacturer's instructions. 10 µl of RNA was reverse transcribed to cDNA using the High Capacity cDNA Reverse Transcription Kit (Applied Biosystems) according to the manufacturer's instructions. cDNA samples were evaluated by qPCR with MSTN-specific and PPIB-specific TaqMan gene expression probes (Thermo Fisher) using TaqMan® Fast Advanced Master Mix (Applied Biosystems) and the ΔΔCt method. Individual experiments were performed in duplicate or triplicate.

Figure 8A:
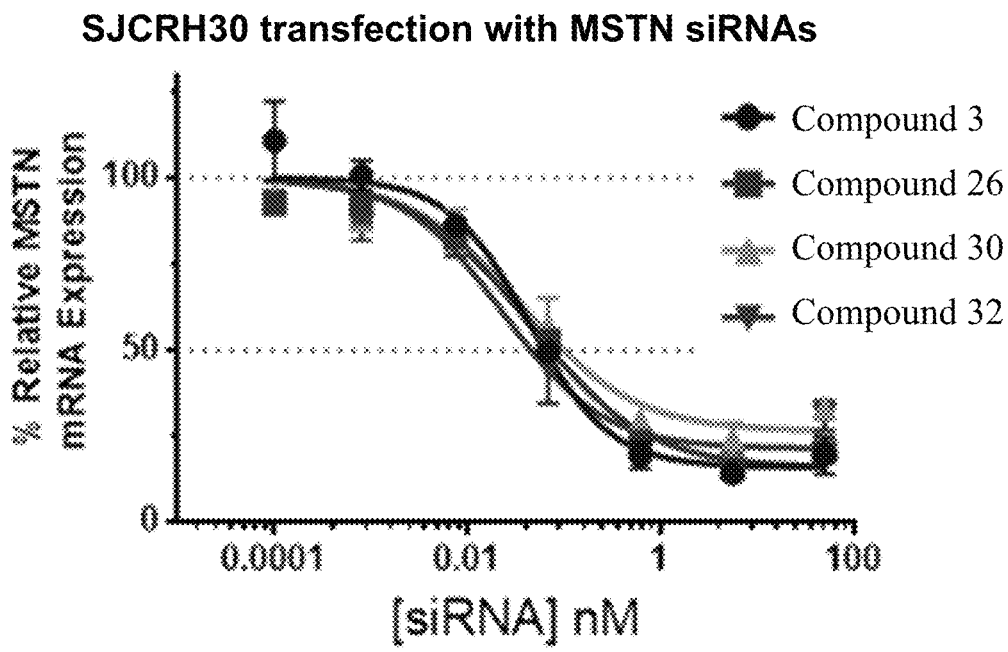
FIGS. 8A-8B shows plots of siRNA concentration (nM) vs relative MSTN (FIG. 8A) and SSB (FIG. 8B) mRNA expression for SJCRH30 transfection, as described in molecular biology example 17.

FIG. 8A shows the dose response curves, demonstrating that the novel vinylphosphonate modified nucleotide structures on the guide strands of an MSTN siRNA, after in vitro transfection of the duplex, can be loaded into RISC and mediate sequence specific down regulation of the target MSTN gene. Activity of the analogues (compounds 26, 30 and 32) was comparable to the standard vinylphosphonate modified nucleotide (compound 3).

Figure 8B:
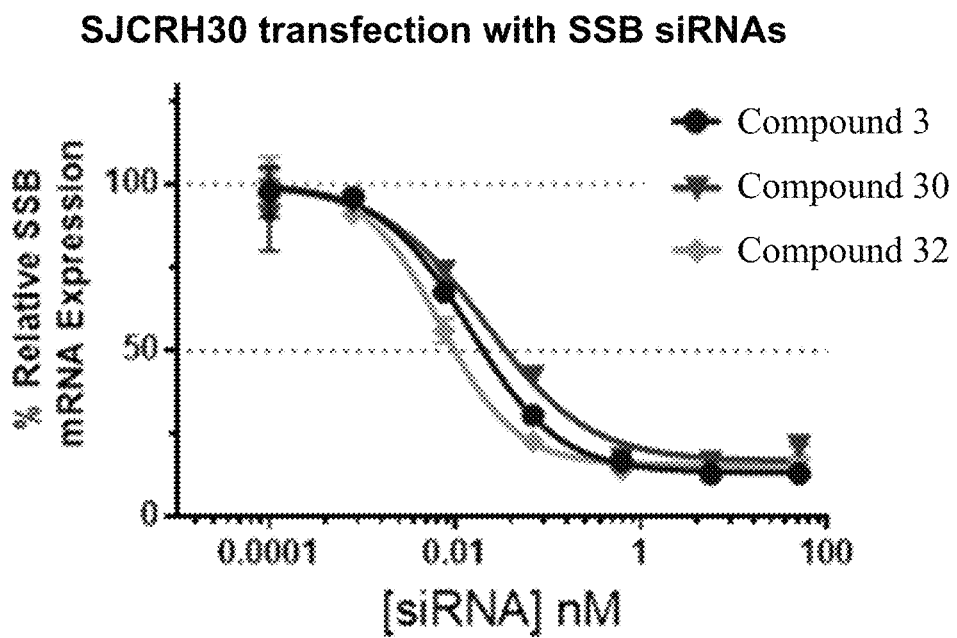

FIG. 8B shows the dose response curves, demonstrating that the novel vinylphosphonate modified nucleotide structures on the guide strands of an SSB siRNA, after in vitro transfection of the duplex, can be loaded into RISC and mediate sequence specific down regulation of the target SSB gene. Activity of the analogues (30 and 32) was comparable to a standard vinylphosphonate modified nucleotide (compound 3).

Example 18. In Vitro Activity of Vinyl Phosphonate Modified Nucleotide Structures in Apparently Healthy Human-Derived Immortalized Skeletal Muscle Myoblast Cells (MB)

siRNA design and synthesis: A 21 mer myostatin (MSTN) guide strand was designed against mouse and human MSTN. The sequence (5' to 3') of the guide/antisense strand was UUAUUAUUUGUUCUUUGCCUU (SEQ ID NO: 1273). Four versions were prepared incorporating different vinylphosphonate modified nucleotide structures (compounds 3, 26, 30 and 32). The guide and fully complementary RNA passenger strands were assembled on solid phase using standard phospharamidite chemistry, and purified using HPLC. The vinylphosphonate modified nucleotide structures were incorporated using the amidites described herein. Base, sugar and phosphate modifications that are well described in the field of RNAi were used to optimize the potency of the duplex and reduce immunogenicity. Purified single strands were duplexed to get the double stranded siRNA as described above.

In addition, a 21 mer SSB guide strand was designed against mouse SSB. The sequence (5' to 3') of the guide/antisense strand was UUACAUUAAAGUCUGUUGUUU (SEQ ID NO: 1274). Three versions were prepared incorporating different vinylphosphonate modified nucleotide structures (compounds 3, 30 and 32). The guide and fully complementary RNA passenger strands were assembled on solid phase using standard phospharamidite chemistry, and purified over HPLC. The vinylphosphonate modified nucleotide structures were incorporated using the amidites described herein. The Base, sugar and phosphate modifications that are well described in the field of RNAi were used to optimize the potency of the duplex and reduce immunogenicity. Purified single strands were duplexed to get the double stranded siRNA as described above.

In vitro study: The activity of the siRNAs was evaluated in apparently healthy human-derived immortalized skeletal muscle myoblasts (MB) (obtained from Denis Furling, Institut de Myologie, France). MB cells were grown in a complete skeletal muscle cell growth medium (PromoCell). Cells were plated 24 h prior to transfection in triplicate on 96-well tissue culture plates, with 4000 (MB) cells per well. siRNAs were transfected into cells 50 nM, 5.5556 nM, 0.6173 nM, 0.0686 nM, 0.0076 nM, 0.0008 nM, and 0.0001 nM final concentration. The siRNAs were formulated with commercially available transfection reagent Lipofectamine RNAiMAX (Life Technologies), according to the manufacturer's "forward transfection" protocol instructions. At 48 h post-transfection cells were washed with PBS and harvested with TRIzol® reagent (Life Technologies). RNA was isolated using the Direct-zol-96 RNA Kit (Zymo Research) according to the manufacturer's instructions. 10 µl of RNA was reverse transcribed to cDNA using the High Capacity cDNA Reverse Transcription Kit (Applied Biosystems) according to the manufacturer's instructions. cDNA samples were evaluated by qPCR with SSB-specific, MSTN-specific and PPIB-specific TaqMan gene expression probes (Thermo Fisher) using TaqMan® Fast Advanced Master Mix (Applied Biosystems). SSB and MSTN expression values were normalized within each sample to PPM gene expression. The quantification of SSB and MSTN downregulation was performed using the standard 2-ΔΔCt method. All experiments were performed in triplicate.

Figure 9A:
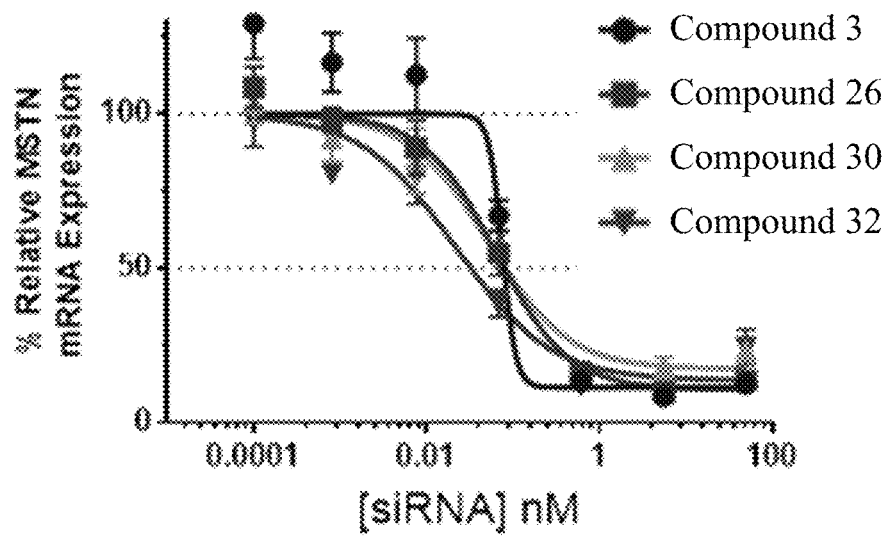
FIGS. 9A-9B shows plots of siRNA concentration (nM) vs relative MSTN (FIG. 9A) and SSB (FIG. 9B) mRNA expression DM1Ctrl Myoblasts, as described in molecular biology example 18.

FIG. 9A shows the dose response curves, demonstrating that the novel vinylphosphonate modified nucleotide structures on the guide strands of an MSTN siRNA, after in vitro transfection of the duplex, can be loaded into RISC and mediate sequence specific down regulation of the target MSTN gene. Activity of the analogues (compounds 26, 30 and 32) was comparable to the standard vinylphosphonate modified nucleotide (compound 3).

Figure 9B:
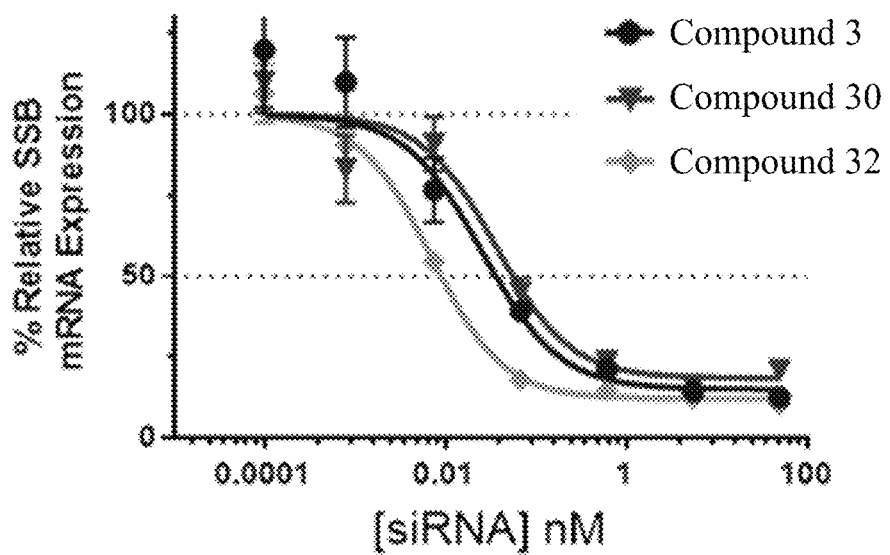

FIG. 9B shows the dose response curves, demonstrating that the novel vinylphosphonate modified nucleotide structures on the guide strands of an SSB siRNA, after in vitro transfection of the duplex, can be loaded into RISC and mediate sequence specific down regulation of the target SSB gene. Activity of the analogues (30 and 32) was comparable to a standard vinylphosphonate modified nucleotide (compound 3).

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. A polynucleotide conjugate molecule comprising a binding moiety, a polynucleotide, a linker selected from succinimidyl-4-(N-maleimidomethyl)cyclohexane-1-carboxylate (SMCC), N-succinimidyl 3-(2-pyridyldithio)propionate (SPDP) or bis-maleimide (BisMal);

wherein the polynucleotide comprises at least one 5'-vinylphosphonate modified non-natural nucleotide, and at least one modified internucleotide linkage or at least one inverted abasic moiety; and wherein the at least one 5'-vinylphosphonate modified non-natural nucleotide is

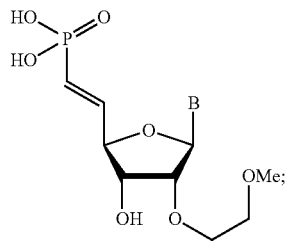

wherein B is a heterocyclic base moiety;

wherein the polynucleotide comprises a double-stranded polynucleic acid molecule comprising a guide strand and a passenger strand, wherein the at least one 5'-vinylphosphonate modified non-natural nucleotide is located at 5'-terminus of the guide strand and the binding moiety is conjugated to 5'-terminus of the passenger strand; and wherein the binding moiety is an antibody or antigen binding fragment thereof that recognizes a cell surface protein.

2. The molecule of claim 1, wherein the at least one modified internucleotide linkage comprises a phosphorothioate linkage, a phosphorodithioate linkage, a phosphorodiamidate linkage, a methylphosphonate linkage, or an amide linkage.

3. The molecule of claim 1, wherein the at least one inverted abasic moiety is located at 5'-terminus of the passenger strand.

4. The molecule of claim 1, wherein the guide strand and the passenger strand are RNA molecules.

5. The molecule of claim 1, wherein the binding moiety is conjugated to the at least one inverted abasic moiety at the 5'-terminus of the passenger strand.

6. The molecule of claim 1, wherein the antibody or antigen binding fragment thereof is an anti-transferrin receptor antibody or antigen binding fragment thereof.

7. The molecule of claim 1, wherein the antibody or antigen binding fragment thereof is a human anti-transferrin receptor antibody or antigen binding fragment thereof.

8. The molecule of claim 1, further comprising a polymer.

9. The molecule of claim 1, wherein the antibody or antigen binding fragment thereof comprises a humanized antibody or antigen binding fragment thereof, a chimeric antibody or antigen binding fragment thereof, a monoclonal antibody or antigen binding fragment thereof, a monovalent Fab', a divalent Fab2, a single-chain variable fragment (scFv), a diabody, a minibody, a nanobody, a single-domain antibody (sdAb), or a camelid antibody or antigen binding fragment thereof.

10. The molecule of claim 8, wherein the polymer is polyethylene glycol.

11. The molecule of claim 8, wherein the polymer has a molecular weight of about 1000 Da, 2000 Da, or 5000 Da.

12. The molecule of claim 1, further comprising an endosomolytic moiety.

* * * * *

SEQUENCE LISTING

```
<160> NUMBER OF SEQ ID NOS: 1277

<210> SEQ ID NO 1
<211> LENGTH: 23
<212> TYPE: RNA
<213> ORGANISM: Homo sapiens

<400> SEQUENCE: 1
aaaugacuga auauaaacuu gug                                           23

<210> SEQ ID NO 2
<211> LENGTH: 23
<212> TYPE: RNA
<213> ORGANISM: Homo sapiens

<400> SEQUENCE: 2
aaugacugaa uauaaacuug ugg                                           23

<210> SEQ ID NO 3
<211> LENGTH: 23
<212> TYPE: RNA
<213> ORGANISM: Homo sapiens

<400> SEQUENCE: 3
aacuuguggu aguuggagcu ggu                                           23

<210> SEQ ID NO 4
<211> LENGTH: 23
<212> TYPE: RNA
<213> ORGANISM: Homo sapiens

<400> SEQUENCE: 4
uaggcaagag ugccuugacg aua                                           23

<210> SEQ ID NO 5
<211> LENGTH: 23
<212> TYPE: RNA
<213> ORGANISM: Homo sapiens
```

-continued

```
<400> SEQUENCE: 5
ggcaagagug ccuugacgau aca                                            23

<210> SEQ ID NO 6
<211> LENGTH: 23
<212> TYPE: RNA
<213> ORGANISM: Homo sapiens

<400> SEQUENCE: 6
gcaagagugc cuugacgaua cag                                            23

<210> SEQ ID NO 7
<211> LENGTH: 23
<212> TYPE: RNA
<213> ORGANISM: Homo sapiens

<400> SEQUENCE: 7
caagagugcc uugacgauac agc                                            23

<210> SEQ ID NO 8
<211> LENGTH: 23
<212> TYPE: RNA
<213> ORGANISM: Homo sapiens

<400> SEQUENCE: 8
agugccuuga cgauacagcu aau                                            23

<210> SEQ ID NO 9
<211> LENGTH: 23
<212> TYPE: RNA
<213> ORGANISM: Homo sapiens

<400> SEQUENCE: 9
gugccuugac gauacagcua auu                                            23

<210> SEQ ID NO 10
<211> LENGTH: 23
<212> TYPE: RNA
<213> ORGANISM: Homo sapiens

<400> SEQUENCE: 10
ccuugacgau acagcuaauu cag                                            23

<210> SEQ ID NO 11
<211> LENGTH: 23
<212> TYPE: RNA
<213> ORGANISM: Homo sapiens

<400> SEQUENCE: 11
cuugacgaua cagcuaauuc aga                                            23

<210> SEQ ID NO 12
<211> LENGTH: 23
<212> TYPE: RNA
<213> ORGANISM: Homo sapiens

<400> SEQUENCE: 12
uacagcuaau ucagaaucau uuu                                            23

<210> SEQ ID NO 13
<211> LENGTH: 23
<212> TYPE: RNA
```

```
<213> ORGANISM: Homo sapiens

<400> SEQUENCE: 13
uuguggacga auaugaucca aca                                               23

<210> SEQ ID NO 14
<211> LENGTH: 23
<212> TYPE: RNA
<213> ORGANISM: Homo sapiens

<400> SEQUENCE: 14
uggacgaaua ugauccaaca aua                                               23

<210> SEQ ID NO 15
<211> LENGTH: 23
<212> TYPE: RNA
<213> ORGANISM: Homo sapiens

<400> SEQUENCE: 15
ggacgaauau gauccaacaa uag                                               23

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 16
augacugaau auaaacuugt t                                                 21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 17
caaguuuaua uucagucaut t                                                 21

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 18
ugacugaaua uaaacuugut t                                                 21

<210> SEQ ID NO 19
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 19
acaaguuuau auucagucat t                                               21

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 20
cuugugguag uuggagcugt t                                               21

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 21
cagcuccaac uaccacaagt t                                               21

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 22
ggcaagagug ccuugacgat t                                               21

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 23
ucgucaaggc acucuugcct t                                               21

<210> SEQ ID NO 24
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 24
caagagugcc uugacgauat t                                              21

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 25
uaucgucaag gcacucuugt t                                              21

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 26
aagagugccu ugacgauact t                                              21

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 27
guaucgucaa ggcacucuut t                                              21

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 28
agagugccuu gacgauacat t                                              21

<210> SEQ ID NO 29
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 29
uguaucguca aggcacucut t                                              21

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 30
ugccuugacg auacagcuat t                                              21

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 31
uagcuguauc gucaaggcat t                                              21

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 32
gccuugacga uacagcuaat t                                              21

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 33
uuagcuguau cgucaaggct t                                              21

<210> SEQ ID NO 34
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 34
uugacgauac agcuaauuct t                                                  21

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 35
gaauuagcug uaucgucaat t                                                  21

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 36
ugacgauaca gcuaauucat t                                                  21

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 37
ugaauuagcu guaucgucat t                                                  21

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 38
cagcuaauuc agaaucauut t                                                  21
```

```
<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 39
aaugauucug aauuagcugt t                                              21

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 40
guggacgaau augauccaat t                                              21

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 41
uuggaucaua uucguccact t                                              21

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 42
gacgaauaug auccaacaat t                                              21

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 43
uuguuggauc auauucguct t                                              21
```

```
<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 44
acgaauauga uccaacaaut t                                                   21

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 45
auuguuggau cauauucgut t                                                   21

<210> SEQ ID NO 46
<211> LENGTH: 23
<212> TYPE: RNA
<213> ORGANISM: Homo sapiens

<400> SEQUENCE: 46
ggcggccgga gucccgagcu agc                                                 23

<210> SEQ ID NO 47
<211> LENGTH: 23
<212> TYPE: RNA
<213> ORGANISM: Homo sapiens

<400> SEQUENCE: 47
ggccggaguc ccgagcuagc ccc                                                 23

<210> SEQ ID NO 48
<211> LENGTH: 23
<212> TYPE: RNA
<213> ORGANISM: Homo sapiens

<400> SEQUENCE: 48
gccggagucc cgagcuagcc ccg                                                 23

<210> SEQ ID NO 49
<211> LENGTH: 23
<212> TYPE: RNA
<213> ORGANISM: Homo sapiens

<400> SEQUENCE: 49
ccggaguccc gagcuagccc cgg                                                 23

<210> SEQ ID NO 50
<211> LENGTH: 23
<212> TYPE: RNA
<213> ORGANISM: Homo sapiens

<400> SEQUENCE: 50
```
cggagucccg agcuagcccc ggc                                               23

<210> SEQ ID NO 51
<211> LENGTH: 23
<212> TYPE: RNA
<213> ORGANISM: Homo sapiens

<400> SEQUENCE: 51
ggagucccga gcuagccccg gcg                                               23

<210> SEQ ID NO 52
<211> LENGTH: 23
<212> TYPE: RNA
<213> ORGANISM: Homo sapiens

<400> SEQUENCE: 52
gagucccgag cuagccccgg cgg                                               23

<210> SEQ ID NO 53
<211> LENGTH: 23
<212> TYPE: RNA
<213> ORGANISM: Homo sapiens

<400> SEQUENCE: 53
gucccgagcu agccccggcg gcc                                               23

<210> SEQ ID NO 54
<211> LENGTH: 23
<212> TYPE: RNA
<213> ORGANISM: Homo sapiens

<400> SEQUENCE: 54
ccggacgaca ggccaccucg ucg                                               23

<210> SEQ ID NO 55
<211> LENGTH: 23
<212> TYPE: RNA
<213> ORGANISM: Homo sapiens

<400> SEQUENCE: 55
cggacgacag gccaccucgu cgg                                               23

<210> SEQ ID NO 56
<211> LENGTH: 23
<212> TYPE: RNA
<213> ORGANISM: Homo sapiens

<400> SEQUENCE: 56
ggacgacagg ccaccucguc ggc                                               23

<210> SEQ ID NO 57
<211> LENGTH: 23
<212> TYPE: RNA
<213> ORGANISM: Homo sapiens

<400> SEQUENCE: 57
gacgacaggc caccucgucg gcg                                               23

<210> SEQ ID NO 58
<211> LENGTH: 23
<212> TYPE: RNA
<213> ORGANISM: Homo sapiens

```
<400> SEQUENCE: 58
acgacaggcc accucgucgg cgu                                        23

<210> SEQ ID NO 59
<211> LENGTH: 23
<212> TYPE: RNA
<213> ORGANISM: Homo sapiens

<400> SEQUENCE: 59
gacaggccac cucgucggcg ucc                                        23

<210> SEQ ID NO 60
<211> LENGTH: 23
<212> TYPE: RNA
<213> ORGANISM: Homo sapiens

<400> SEQUENCE: 60
acaggccacc ucgucggcgu ccg                                        23

<210> SEQ ID NO 61
<211> LENGTH: 23
<212> TYPE: RNA
<213> ORGANISM: Homo sapiens

<400> SEQUENCE: 61
caggccaccu cgucggcguc cgc                                        23

<210> SEQ ID NO 62
<211> LENGTH: 23
<212> TYPE: RNA
<213> ORGANISM: Homo sapiens

<400> SEQUENCE: 62
aggccaccuc gucggcgucc gcc                                        23

<210> SEQ ID NO 63
<211> LENGTH: 23
<212> TYPE: RNA
<213> ORGANISM: Homo sapiens

<400> SEQUENCE: 63
ggccaccucg ucggcguccg ccc                                        23

<210> SEQ ID NO 64
<211> LENGTH: 23
<212> TYPE: RNA
<213> ORGANISM: Homo sapiens

<400> SEQUENCE: 64
gccaccucgu cggcguccgc ccg                                        23

<210> SEQ ID NO 65
<211> LENGTH: 23
<212> TYPE: RNA
<213> ORGANISM: Homo sapiens

<400> SEQUENCE: 65
ccaccucguc ggcguccgcc cga                                        23

<210> SEQ ID NO 66
<211> LENGTH: 23
<212> TYPE: RNA
<213> ORGANISM: Homo sapiens
```

```
<400> SEQUENCE: 66
caccucgucg gcguccgccc gag                                          23

<210> SEQ ID NO 67
<211> LENGTH: 23
<212> TYPE: RNA
<213> ORGANISM: Homo sapiens

<400> SEQUENCE: 67
accucgucgg cguccgcccg agu                                          23

<210> SEQ ID NO 68
<211> LENGTH: 23
<212> TYPE: RNA
<213> ORGANISM: Homo sapiens

<400> SEQUENCE: 68
ccucgucggc guccgcccga guc                                          23

<210> SEQ ID NO 69
<211> LENGTH: 23
<212> TYPE: RNA
<213> ORGANISM: Homo sapiens

<400> SEQUENCE: 69
cucgucggcg uccgcccgag ucc                                          23

<210> SEQ ID NO 70
<211> LENGTH: 23
<212> TYPE: RNA
<213> ORGANISM: Homo sapiens

<400> SEQUENCE: 70
ucgucggcgu ccgcccgagu ccc                                          23

<210> SEQ ID NO 71
<211> LENGTH: 23
<212> TYPE: RNA
<213> ORGANISM: Homo sapiens

<400> SEQUENCE: 71
cgucggcguc cgcccgaguc ccc                                          23

<210> SEQ ID NO 72
<211> LENGTH: 23
<212> TYPE: RNA
<213> ORGANISM: Homo sapiens

<400> SEQUENCE: 72
cggcguccgc ccgaguccccc gcc                                         23

<210> SEQ ID NO 73
<211> LENGTH: 23
<212> TYPE: RNA
<213> ORGANISM: Homo sapiens

<400> SEQUENCE: 73
ggcguccgcc cgaguccccg ccu                                          23

<210> SEQ ID NO 74
<211> LENGTH: 23
<212> TYPE: RNA
```

-continued

```
<213> ORGANISM: Homo sapiens

<400> SEQUENCE: 74
ccgcccgagu ccccgccucg ccg                                              23

<210> SEQ ID NO 75
<211> LENGTH: 23
<212> TYPE: RNA
<213> ORGANISM: Homo sapiens

<400> SEQUENCE: 75
ccaacgccac aaccaccgcg cac                                              23

<210> SEQ ID NO 76
<211> LENGTH: 23
<212> TYPE: RNA
<213> ORGANISM: Homo sapiens

<400> SEQUENCE: 76
caacgccaca accaccgcgc acg                                              23

<210> SEQ ID NO 77
<211> LENGTH: 23
<212> TYPE: RNA
<213> ORGANISM: Homo sapiens

<400> SEQUENCE: 77
aacgccacaa ccaccgcgca cgg                                              23

<210> SEQ ID NO 78
<211> LENGTH: 23
<212> TYPE: RNA
<213> ORGANISM: Homo sapiens

<400> SEQUENCE: 78
cgccacaacc accgcgcacg gcc                                              23

<210> SEQ ID NO 79
<211> LENGTH: 23
<212> TYPE: RNA
<213> ORGANISM: Homo sapiens

<400> SEQUENCE: 79
gccacaacca ccgcgcacgg ccc                                              23

<210> SEQ ID NO 80
<211> LENGTH: 23
<212> TYPE: RNA
<213> ORGANISM: Homo sapiens

<400> SEQUENCE: 80
ccacaaccac cgcgcacggc ccc                                              23

<210> SEQ ID NO 81
<211> LENGTH: 23
<212> TYPE: RNA
<213> ORGANISM: Homo sapiens

<400> SEQUENCE: 81
cgaugcgacc cuccgggacg gcc                                              23

<210> SEQ ID NO 82
<211> LENGTH: 23
```

```
<212> TYPE: RNA
<213> ORGANISM: Homo sapiens

<400> SEQUENCE: 82
gaugcgaccc uccgggacgg ccg                                           23

<210> SEQ ID NO 83
<211> LENGTH: 23
<212> TYPE: RNA
<213> ORGANISM: Homo sapiens

<400> SEQUENCE: 83
augcgacccu ccgggacggc cgg                                           23

<210> SEQ ID NO 84
<211> LENGTH: 23
<212> TYPE: RNA
<213> ORGANISM: Homo sapiens

<400> SEQUENCE: 84
gcgacccucc gggacggccg ggg                                           23

<210> SEQ ID NO 85
<211> LENGTH: 23
<212> TYPE: RNA
<213> ORGANISM: Homo sapiens

<400> SEQUENCE: 85
cgacccuccg ggacggccgg ggc                                           23

<210> SEQ ID NO 86
<211> LENGTH: 23
<212> TYPE: RNA
<213> ORGANISM: Homo sapiens

<400> SEQUENCE: 86
acccuccggg acggccgggg cag                                           23

<210> SEQ ID NO 87
<211> LENGTH: 23
<212> TYPE: RNA
<213> ORGANISM: Homo sapiens

<400> SEQUENCE: 87
aaagaaaguu ugccaaggca cga                                           23

<210> SEQ ID NO 88
<211> LENGTH: 23
<212> TYPE: RNA
<213> ORGANISM: Homo sapiens

<400> SEQUENCE: 88
aagaaaguuu gccaaggcac gag                                           23

<210> SEQ ID NO 89
<211> LENGTH: 23
<212> TYPE: RNA
<213> ORGANISM: Homo sapiens

<400> SEQUENCE: 89
gaaaguuugc caaggcacga gua                                           23

<210> SEQ ID NO 90
```

```
<211> LENGTH: 23
<212> TYPE: RNA
<213> ORGANISM: Homo sapiens

<400> SEQUENCE: 90
aaaguuugcc aaggcacgag uaa                                              23

<210> SEQ ID NO 91
<211> LENGTH: 23
<212> TYPE: RNA
<213> ORGANISM: Homo sapiens

<400> SEQUENCE: 91
aaguuugcca aggcacgagu aac                                              23

<210> SEQ ID NO 92
<211> LENGTH: 23
<212> TYPE: RNA
<213> ORGANISM: Homo sapiens

<400> SEQUENCE: 92
aguuugccaa ggcacgagua aca                                              23

<210> SEQ ID NO 93
<211> LENGTH: 23
<212> TYPE: RNA
<213> ORGANISM: Homo sapiens

<400> SEQUENCE: 93
guuugccaag gcacgaguaa caa                                              23

<210> SEQ ID NO 94
<211> LENGTH: 23
<212> TYPE: RNA
<213> ORGANISM: Homo sapiens

<400> SEQUENCE: 94
uuugccaagg cacgaguaac aag                                              23

<210> SEQ ID NO 95
<211> LENGTH: 23
<212> TYPE: RNA
<213> ORGANISM: Homo sapiens

<400> SEQUENCE: 95
uugccaaggc acgaguaaca agc                                              23

<210> SEQ ID NO 96
<211> LENGTH: 23
<212> TYPE: RNA
<213> ORGANISM: Homo sapiens

<400> SEQUENCE: 96
ucacgcaguu gggcacuuuu gaa                                              23

<210> SEQ ID NO 97
<211> LENGTH: 23
<212> TYPE: RNA
<213> ORGANISM: Homo sapiens

<400> SEQUENCE: 97
cacgcaguug ggcacuuuug aag                                              23
```

```
<210> SEQ ID NO 98
<211> LENGTH: 23
<212> TYPE: RNA
<213> ORGANISM: Homo sapiens

<400> SEQUENCE: 98
acgcaguugg gcacuuuuga aga                                              23

<210> SEQ ID NO 99
<211> LENGTH: 23
<212> TYPE: RNA
<213> ORGANISM: Homo sapiens

<400> SEQUENCE: 99
cgcaguuggg cacuuuugaa gau                                              23

<210> SEQ ID NO 100
<211> LENGTH: 23
<212> TYPE: RNA
<213> ORGANISM: Homo sapiens

<400> SEQUENCE: 100
gcaguugggc acuuuugaag auc                                              23

<210> SEQ ID NO 101
<211> LENGTH: 23
<212> TYPE: RNA
<213> ORGANISM: Homo sapiens

<400> SEQUENCE: 101 cagugggca cuuuugaaga uca                                               23

<210> SEQ ID NO 102
<211> LENGTH: 23
<212> TYPE: RNA
<213> ORGANISM: Homo sapiens

<400> SEQUENCE: 102
aguugggcac uuuugaagau cau                                              23

<210> SEQ ID NO 103
<211> LENGTH: 23
<212> TYPE: RNA
<213> ORGANISM: Homo sapiens

<400> SEQUENCE: 103
guugggcacu uuugaagauc auu                                              23

<210> SEQ ID NO 104
<211> LENGTH: 23
<212> TYPE: RNA
<213> ORGANISM: Homo sapiens

<400> SEQUENCE: 104
uugggcacuu uugaagauca uuu                                              23

<210> SEQ ID NO 105
<211> LENGTH: 23
<212> TYPE: RNA
<213> ORGANISM: Homo sapiens

<400> SEQUENCE: 105
uuuugaagau cauuuucuca gcc                                              23
```

```
<210> SEQ ID NO 106
<211> LENGTH: 23
<212> TYPE: RNA
<213> ORGANISM: Homo sapiens

<400> SEQUENCE: 106
uugaagauca uuucucagc cuc                                           23

<210> SEQ ID NO 107
<211> LENGTH: 23
<212> TYPE: RNA
<213> ORGANISM: Homo sapiens

<400> SEQUENCE: 107
ugaagaucau uuucucagcc ucc                                          23

<210> SEQ ID NO 108
<211> LENGTH: 23
<212> TYPE: RNA
<213> ORGANISM: Homo sapiens

<400> SEQUENCE: 108
aucauuuucu cagccuccag agg                                          23

<210> SEQ ID NO 109
<211> LENGTH: 23
<212> TYPE: RNA
<213> ORGANISM: Homo sapiens

<400> SEQUENCE: 109
ucagccucca gaggauguuc aau                                          23

<210> SEQ ID NO 110
<211> LENGTH: 23
<212> TYPE: RNA
<213> ORGANISM: Homo sapiens

<400> SEQUENCE: 110
agccuccaga ggauguucaa uaa                                          23

<210> SEQ ID NO 111
<211> LENGTH: 23
<212> TYPE: RNA
<213> ORGANISM: Homo sapiens

<400> SEQUENCE: 111
gccuccagag gauguucaau aac                                          23

<210> SEQ ID NO 112
<211> LENGTH: 23
<212> TYPE: RNA
<213> ORGANISM: Homo sapiens

<400> SEQUENCE: 112
ccagaggaug uucaauaacu gug                                          23

<210> SEQ ID NO 113
<211> LENGTH: 23
<212> TYPE: RNA
<213> ORGANISM: Homo sapiens

<400> SEQUENCE: 113
agaggauguu caauaacugu gag                                          23
```

```
<210> SEQ ID NO 114
<211> LENGTH: 23
<212> TYPE: RNA
<213> ORGANISM: Homo sapiens

<400> SEQUENCE: 114
gauguucaau aacugugagg ugg                                               23

<210> SEQ ID NO 115
<211> LENGTH: 23
<212> TYPE: RNA
<213> ORGANISM: Homo sapiens

<400> SEQUENCE: 115
uguucaauaa cugugaggug guc                                               23

<210> SEQ ID NO 116
<211> LENGTH: 23
<212> TYPE: RNA
<213> ORGANISM: Homo sapiens

<400> SEQUENCE: 116
guucaauaac ugugaggugg ucc                                               23

<210> SEQ ID NO 117
<211> LENGTH: 23
<212> TYPE: RNA
<213> ORGANISM: Homo sapiens

<400> SEQUENCE: 117
uucaauaacu gugaggugguc ccu                                              23

<210> SEQ ID NO 118
<211> LENGTH: 23
<212> TYPE: RNA
<213> ORGANISM: Homo sapiens

<400> SEQUENCE: 118
ucaauaacug ugaggugguc cuu                                               23

<210> SEQ ID NO 119
<211> LENGTH: 23
<212> TYPE: RNA
<213> ORGANISM: Homo sapiens

<400> SEQUENCE: 119
caauaacugu gaggguggucc uug                                              23

<210> SEQ ID NO 120
<211> LENGTH: 23
<212> TYPE: RNA
<213> ORGANISM: Homo sapiens

<400> SEQUENCE: 120
aauaacugug aggugguccu ugg                                               23

<210> SEQ ID NO 121
<211> LENGTH: 23
<212> TYPE: RNA
<213> ORGANISM: Homo sapiens

<400> SEQUENCE: 121
``` uacugugag gugguccuug gga                                                23

<210> SEQ ID NO 122
<211> LENGTH: 23
<212> TYPE: RNA
<213> ORGANISM: Homo sapiens

<400> SEQUENCE: 122
acugugaggu gguccuuggg aau                                               23

<210> SEQ ID NO 123
<211> LENGTH: 23
<212> TYPE: RNA
<213> ORGANISM: Homo sapiens

<400> SEQUENCE: 123
cugugaggug guccuuggga auu                                               23

<210> SEQ ID NO 124
<211> LENGTH: 23
<212> TYPE: RNA
<213> ORGANISM: Homo sapiens

<400> SEQUENCE: 124
ggugguccuu gggaauuugg aaa                                               23

<210> SEQ ID NO 125
<211> LENGTH: 23
<212> TYPE: RNA
<213> ORGANISM: Homo sapiens

<400> SEQUENCE: 125
ccuugggaau uggaaauua ccu                                                23

<210> SEQ ID NO 126
<211> LENGTH: 23
<212> TYPE: RNA
<213> ORGANISM: Homo sapiens

<400> SEQUENCE: 126
cuugggaauu uggaaauuac cua                                               23

<210> SEQ ID NO 127
<211> LENGTH: 23
<212> TYPE: RNA
<213> ORGANISM: Homo sapiens

<400> SEQUENCE: 127
uugggaauuu ggaaauuacc uau                                               23

<210> SEQ ID NO 128
<211> LENGTH: 23
<212> TYPE: RNA
<213> ORGANISM: Homo sapiens

<400> SEQUENCE: 128
ugggaauuug gaaauuaccu aug                                               23

<210> SEQ ID NO 129
<211> LENGTH: 23
<212> TYPE: RNA
<213> ORGANISM: Homo sapiens

<400> SEQUENCE: 129

```
gcagaggaau uaugaucuuu ccu                                              23

<210> SEQ ID NO 130
<211> LENGTH: 23
<212> TYPE: RNA
<213> ORGANISM: Homo sapiens

<400> SEQUENCE: 130
cagaggaauu augaucuuuc cuu                                              23

<210> SEQ ID NO 131
<211> LENGTH: 23
<212> TYPE: RNA
<213> ORGANISM: Homo sapiens

<400> SEQUENCE: 131
ggaauuauga ucuuccuuc uua                                               23

<210> SEQ ID NO 132
<211> LENGTH: 23
<212> TYPE: RNA
<213> ORGANISM: Homo sapiens

<400> SEQUENCE: 132
gaauuaugau cuuccuucu uaa                                               23

<210> SEQ ID NO 133
<211> LENGTH: 23
<212> TYPE: RNA
<213> ORGANISM: Homo sapiens

<400> SEQUENCE: 133
auuaugaucu uccuucuua aag                                               23

<210> SEQ ID NO 134
<211> LENGTH: 23
<212> TYPE: RNA
<213> ORGANISM: Homo sapiens

<400> SEQUENCE: 134
uaugaucuuu ccuucuuaaa gac                                              23

<210> SEQ ID NO 135
<211> LENGTH: 23
<212> TYPE: RNA
<213> ORGANISM: Homo sapiens

<400> SEQUENCE: 135 gaucuuccu ucuuaaagac cau                                               23

<210> SEQ ID NO 136
<211> LENGTH: 23
<212> TYPE: RNA
<213> ORGANISM: Homo sapiens

<400> SEQUENCE: 136
uuccuucuua aagaccaucc agg                                              23

<210> SEQ ID NO 137
<211> LENGTH: 23
<212> TYPE: RNA
<213> ORGANISM: Homo sapiens
```

```
<400> SEQUENCE: 137
uccuucuuaa agaccaucca gga                                              23

<210> SEQ ID NO 138
<211> LENGTH: 23
<212> TYPE: RNA
<213> ORGANISM: Homo sapiens

<400> SEQUENCE: 138
cuucuuaaag accauccagg agg                                              23

<210> SEQ ID NO 139
<211> LENGTH: 23
<212> TYPE: RNA
<213> ORGANISM: Homo sapiens

<400> SEQUENCE: 139
ucuuaaagac cauccaggag gug                                              23

<210> SEQ ID NO 140
<211> LENGTH: 23
<212> TYPE: RNA
<213> ORGANISM: Homo sapiens

<400> SEQUENCE: 140
cuuaaagacc auccaggagg ugg                                              23

<210> SEQ ID NO 141
<211> LENGTH: 23
<212> TYPE: RNA
<213> ORGANISM: Homo sapiens

<400> SEQUENCE: 141
auccaggagg uggcuggu ua ugu                                             23

<210> SEQ ID NO 142
<211> LENGTH: 23
<212> TYPE: RNA
<213> ORGANISM: Homo sapiens

<400> SEQUENCE: 142
uccaggaggu ggcugguuau guc                                              23

<210> SEQ ID NO 143
<211> LENGTH: 23
<212> TYPE: RNA
<213> ORGANISM: Homo sapiens

<400> SEQUENCE: 143
ccaggaggug gcugguuaug ucc                                              23

<210> SEQ ID NO 144
<211> LENGTH: 23
<212> TYPE: RNA
<213> ORGANISM: Homo sapiens

<400> SEQUENCE: 144
caggaggugg cugguuaugu ccu                                              23

<210> SEQ ID NO 145
<211> LENGTH: 23
<212> TYPE: RNA
<213> ORGANISM: Homo sapiens
```

```
<400> SEQUENCE: 145
aggagguggc ugguuauguc cuc                                              23

<210> SEQ ID NO 146
<211> LENGTH: 23
<212> TYPE: RNA
<213> ORGANISM: Homo sapiens

<400> SEQUENCE: 146
ggagguggcu gguuaugucc uca                                              23

<210> SEQ ID NO 147
<211> LENGTH: 23
<212> TYPE: RNA
<213> ORGANISM: Homo sapiens

<400> SEQUENCE: 147
agguggcugg uuauguccuc auu                                              23

<210> SEQ ID NO 148
<211> LENGTH: 23
<212> TYPE: RNA
<213> ORGANISM: Homo sapiens

<400> SEQUENCE: 148
uugcccucaa cacaguggag cga                                              23

<210> SEQ ID NO 149
<211> LENGTH: 23
<212> TYPE: RNA
<213> ORGANISM: Homo sapiens

<400> SEQUENCE: 149
aauuccuuug gaaaaccugc aga                                              23

<210> SEQ ID NO 150
<211> LENGTH: 23
<212> TYPE: RNA
<213> ORGANISM: Homo sapiens

<400> SEQUENCE: 150
auuccuuugg aaaaccugca gau                                              23

<210> SEQ ID NO 151
<211> LENGTH: 23
<212> TYPE: RNA
<213> ORGANISM: Homo sapiens

<400> SEQUENCE: 151
uggaaaaccu gcagaucauc aga                                              23

<210> SEQ ID NO 152
<211> LENGTH: 23
<212> TYPE: RNA
<213> ORGANISM: Homo sapiens

<400> SEQUENCE: 152
ggaaaaccug cagaucauca gag                                              23

<210> SEQ ID NO 153
<211> LENGTH: 23
<212> TYPE: RNA
```

```
<213> ORGANISM: Homo sapiens

<400> SEQUENCE: 153
aaaaccugca gaucaucaga gga                                          23

<210> SEQ ID NO 154
<211> LENGTH: 23
<212> TYPE: RNA
<213> ORGANISM: Homo sapiens

<400> SEQUENCE: 154
accugcagau caucagagga aau                                          23

<210> SEQ ID NO 155
<211> LENGTH: 23
<212> TYPE: RNA
<213> ORGANISM: Homo sapiens

<400> SEQUENCE: 155
acgaaaauuc cuaugccuua gca                                          23

<210> SEQ ID NO 156
<211> LENGTH: 23
<212> TYPE: RNA
<213> ORGANISM: Homo sapiens

<400> SEQUENCE: 156
cgaaaauucc uaugccuuag cag                                          23

<210> SEQ ID NO 157
<211> LENGTH: 23
<212> TYPE: RNA
<213> ORGANISM: Homo sapiens

<400> SEQUENCE: 157
aaaauuccua ugccuuagca guc                                          23

<210> SEQ ID NO 158
<211> LENGTH: 23
<212> TYPE: RNA
<213> ORGANISM: Homo sapiens

<400> SEQUENCE: 158
auuccuaugc cuuagcaguc uua                                          23

<210> SEQ ID NO 159
<211> LENGTH: 23
<212> TYPE: RNA
<213> ORGANISM: Homo sapiens

<400> SEQUENCE: 159
uuccuaugcc uuagcagucu uau                                          23

<210> SEQ ID NO 160
<211> LENGTH: 23
<212> TYPE: RNA
<213> ORGANISM: Homo sapiens

<400> SEQUENCE: 160
uccuaugccu uagcagucuu auc                                          23

<210> SEQ ID NO 161
<211> LENGTH: 23
```

```
<212> TYPE: RNA
<213> ORGANISM: Homo sapiens

<400> SEQUENCE: 161
cuaugccuua gcagucuuau cua                                    23

<210> SEQ ID NO 162
<211> LENGTH: 23
<212> TYPE: RNA
<213> ORGANISM: Homo sapiens

<400> SEQUENCE: 162
uaugccuuag cagucuuauc uaa                                    23

<210> SEQ ID NO 163
<211> LENGTH: 23
<212> TYPE: RNA
<213> ORGANISM: Homo sapiens

<400> SEQUENCE: 163
augccuuagc agucuuaucu aac                                    23

<210> SEQ ID NO 164
<211> LENGTH: 23
<212> TYPE: RNA
<213> ORGANISM: Homo sapiens

<400> SEQUENCE: 164
ugccuuagca gucuuaucua acu                                    23

<210> SEQ ID NO 165
<211> LENGTH: 23
<212> TYPE: RNA
<213> ORGANISM: Homo sapiens

<400> SEQUENCE: 165
gccuuagcag ucuuaucuaa cua                                    23

<210> SEQ ID NO 166
<211> LENGTH: 23
<212> TYPE: RNA
<213> ORGANISM: Homo sapiens

<400> SEQUENCE: 166
ccuuagcagu cuuaucuaac uau                                    23

<210> SEQ ID NO 167
<211> LENGTH: 23
<212> TYPE: RNA
<213> ORGANISM: Homo sapiens

<400> SEQUENCE: 167
cuuagcaguc uuaucuaacu aug                                    23

<210> SEQ ID NO 168
<211> LENGTH: 23
<212> TYPE: RNA
<213> ORGANISM: Homo sapiens

<400> SEQUENCE: 168
uuagcagucu uaucuaacua uga                                    23

<210> SEQ ID NO 169
```

```
<211> LENGTH: 23
<212> TYPE: RNA
<213> ORGANISM: Homo sapiens

<400> SEQUENCE: 169
uagcagucuu aucuaacuau gau                                              23

<210> SEQ ID NO 170
<211> LENGTH: 23
<212> TYPE: RNA
<213> ORGANISM: Homo sapiens

<400> SEQUENCE: 170
agcagucuua ucuaacuaug aug                                              23

<210> SEQ ID NO 171
<211> LENGTH: 23
<212> TYPE: RNA
<213> ORGANISM: Homo sapiens

<400> SEQUENCE: 171
agucuuaucu aacuaugaug caa                                              23

<210> SEQ ID NO 172
<211> LENGTH: 23
<212> TYPE: RNA
<213> ORGANISM: Homo sapiens

<400> SEQUENCE: 172
gucuuaucua acuaugaugc aaa                                              23

<210> SEQ ID NO 173
<211> LENGTH: 23
<212> TYPE: RNA
<213> ORGANISM: Homo sapiens

<400> SEQUENCE: 173
ucuuaucuaa cuaugaugca aau                                              23

<210> SEQ ID NO 174
<211> LENGTH: 23
<212> TYPE: RNA
<213> ORGANISM: Homo sapiens

<400> SEQUENCE: 174
cuuaucuaac uaugaugcaa aua                                              23

<210> SEQ ID NO 175
<211> LENGTH: 23
<212> TYPE: RNA
<213> ORGANISM: Homo sapiens

<400> SEQUENCE: 175
uuaucuaacu augaugcaaa uaa                                              23

<210> SEQ ID NO 176
<211> LENGTH: 23
<212> TYPE: RNA
<213> ORGANISM: Homo sapiens

<400> SEQUENCE: 176
uaucuaacua ugaugcaaau aaa                                              23
```

```
<210> SEQ ID NO 177
<211> LENGTH: 23
<212> TYPE: RNA
<213> ORGANISM: Homo sapiens

<400> SEQUENCE: 177
aucuaacuau gaugcaaaua aaa                                              23

<210> SEQ ID NO 178
<211> LENGTH: 23
<212> TYPE: RNA
<213> ORGANISM: Homo sapiens

<400> SEQUENCE: 178
cuaacuauga ugcaaauaaa acc                                              23

<210> SEQ ID NO 179
<211> LENGTH: 23
<212> TYPE: RNA
<213> ORGANISM: Homo sapiens

<400> SEQUENCE: 179
augaugcaaa uaaaaccgga cug                                              23

<210> SEQ ID NO 180
<211> LENGTH: 23
<212> TYPE: RNA
<213> ORGANISM: Homo sapiens

<400> SEQUENCE: 180
ugaugcaaau aaaaccggac uga                                              23

<210> SEQ ID NO 181
<211> LENGTH: 23
<212> TYPE: RNA
<213> ORGANISM: Homo sapiens

<400> SEQUENCE: 181
gaugcaaaua aaaccggacu gaa                                              23

<210> SEQ ID NO 182
<211> LENGTH: 23
<212> TYPE: RNA
<213> ORGANISM: Homo sapiens

<400> SEQUENCE: 182
ugcaaauaaa accggacuga agg                                              23

<210> SEQ ID NO 183
<211> LENGTH: 23
<212> TYPE: RNA
<213> ORGANISM: Homo sapiens

<400> SEQUENCE: 183
gcaaauaaaa ccggacugaa gga                                              23

<210> SEQ ID NO 184
<211> LENGTH: 23
<212> TYPE: RNA
<213> ORGANISM: Homo sapiens

<400> SEQUENCE: 184
caaauaaaac cggacugaag gag                                              23
```

```
<210> SEQ ID NO 185
<211> LENGTH: 23
<212> TYPE: RNA
<213> ORGANISM: Homo sapiens

<400> SEQUENCE: 185
aauaaaaccg gacugaagga gcu                                              23

<210> SEQ ID NO 186
<211> LENGTH: 23
<212> TYPE: RNA
<213> ORGANISM: Homo sapiens

<400> SEQUENCE: 186
auaaaaccgg acugaaggag cug                                              23

<210> SEQ ID NO 187
<211> LENGTH: 23
<212> TYPE: RNA
<213> ORGANISM: Homo sapiens

<400> SEQUENCE: 187
uaaaaccgga cugaaggagc ugc                                              23

<210> SEQ ID NO 188
<211> LENGTH: 23
<212> TYPE: RNA
<213> ORGANISM: Homo sapiens

<400> SEQUENCE: 188
aaaaccggac ugaaggagcu gcc                                              23

<210> SEQ ID NO 189
<211> LENGTH: 23
<212> TYPE: RNA
<213> ORGANISM: Homo sapiens

<400> SEQUENCE: 189
gaaggagcug cccaugagaa auu                                              23

<210> SEQ ID NO 190
<211> LENGTH: 23
<212> TYPE: RNA
<213> ORGANISM: Homo sapiens

<400> SEQUENCE: 190
uuuacaggaa auccugcaug gcg                                              23

<210> SEQ ID NO 191
<211> LENGTH: 23
<212> TYPE: RNA
<213> ORGANISM: Homo sapiens

<400> SEQUENCE: 191
acaggaaauc cugcauggcg ccg                                              23

<210> SEQ ID NO 192
<211> LENGTH: 23
<212> TYPE: RNA
<213> ORGANISM: Homo sapiens

<400> SEQUENCE: 192
caggaaaucc ugcauggcgc cgu                                              23
```

```
<210> SEQ ID NO 193
<211> LENGTH: 23
<212> TYPE: RNA
<213> ORGANISM: Homo sapiens

<400> SEQUENCE: 193
aggaaauccu gcauggcgcc gug                                              23

<210> SEQ ID NO 194
<211> LENGTH: 23
<212> TYPE: RNA
<213> ORGANISM: Homo sapiens

<400> SEQUENCE: 194
ggaaauccug cauggcgccg ugc                                              23

<210> SEQ ID NO 195
<211> LENGTH: 23
<212> TYPE: RNA
<213> ORGANISM: Homo sapiens

<400> SEQUENCE: 195
gaaauccugc auggcgccgu gcg                                              23

<210> SEQ ID NO 196
<211> LENGTH: 23
<212> TYPE: RNA
<213> ORGANISM: Homo sapiens

<400> SEQUENCE: 196
aauccugcau ggcgccgugc ggu                                              23

<210> SEQ ID NO 197
<211> LENGTH: 23
<212> TYPE: RNA
<213> ORGANISM: Homo sapiens

<400> SEQUENCE: 197
uccugcaugg cgccgugcgg uuc                                              23

<210> SEQ ID NO 198
<211> LENGTH: 23
<212> TYPE: RNA
<213> ORGANISM: Homo sapiens

<400> SEQUENCE: 198
ccugcauggc gccgugcggu uca                                              23

<210> SEQ ID NO 199
<211> LENGTH: 23
<212> TYPE: RNA
<213> ORGANISM: Homo sapiens

<400> SEQUENCE: 199
cugcauggcg ccgugcgguu cag                                              23

<210> SEQ ID NO 200
<211> LENGTH: 23
<212> TYPE: RNA
<213> ORGANISM: Homo sapiens

<400> SEQUENCE: 200
```
gcauggcgcc gugcgguuca gca                                           23

<210> SEQ ID NO 201
<211> LENGTH: 23
<212> TYPE: RNA
<213> ORGANISM: Homo sapiens

<400> SEQUENCE: 201
cauggcgccg ugcgguucag caa                                           23

<210> SEQ ID NO 202
<211> LENGTH: 23
<212> TYPE: RNA
<213> ORGANISM: Homo sapiens

<400> SEQUENCE: 202
auggcgccgu gcgguucagc aac                                           23

<210> SEQ ID NO 203
<211> LENGTH: 23
<212> TYPE: RNA
<213> ORGANISM: Homo sapiens

<400> SEQUENCE: 203
uggcgccgug cgguucagca aca                                           23

<210> SEQ ID NO 204
<211> LENGTH: 23
<212> TYPE: RNA
<213> ORGANISM: Homo sapiens

<400> SEQUENCE: 204
ggcgccgugc gguucagcaa caa                                           23

<210> SEQ ID NO 205
<211> LENGTH: 23
<212> TYPE: RNA
<213> ORGANISM: Homo sapiens

<400> SEQUENCE: 205
gcgccgugcg guucagcaac aac                                           23

<210> SEQ ID NO 206
<211> LENGTH: 23
<212> TYPE: RNA
<213> ORGANISM: Homo sapiens

<400> SEQUENCE: 206
cgccgugcgg uucagcaaca acc                                           23

<210> SEQ ID NO 207
<211> LENGTH: 23
<212> TYPE: RNA
<213> ORGANISM: Homo sapiens

<400> SEQUENCE: 207
ccgugcgguu cagcaacaac ccu                                           23

<210> SEQ ID NO 208
<211> LENGTH: 23
<212> TYPE: RNA
<213> ORGANISM: Homo sapiens

<400> SEQUENCE: 208

```
gugcgguuca gcaacaaccc ugc                                         23

<210> SEQ ID NO 209
<211> LENGTH: 23
<212> TYPE: RNA
<213> ORGANISM: Homo sapiens

<400> SEQUENCE: 209
gcgguucagc aacaacccug ccc                                         23

<210> SEQ ID NO 210
<211> LENGTH: 23
<212> TYPE: RNA
<213> ORGANISM: Homo sapiens

<400> SEQUENCE: 210
cagcaacaac ccugcccugu gca                                         23

<210> SEQ ID NO 211
<211> LENGTH: 23
<212> TYPE: RNA
<213> ORGANISM: Homo sapiens

<400> SEQUENCE: 211
gcaacaaccc ugcccugugc aac                                         23

<210> SEQ ID NO 212
<211> LENGTH: 23
<212> TYPE: RNA
<213> ORGANISM: Homo sapiens

<400> SEQUENCE: 212
caacguggag agcauccagu ggc                                         23

<210> SEQ ID NO 213
<211> LENGTH: 23
<212> TYPE: RNA
<213> ORGANISM: Homo sapiens

<400> SEQUENCE: 213
aacguggaga gcauccagug gcg                                         23

<210> SEQ ID NO 214
<211> LENGTH: 23
<212> TYPE: RNA
<213> ORGANISM: Homo sapiens

<400> SEQUENCE: 214
acguggagag cauccagugg cgg                                         23

<210> SEQ ID NO 215
<211> LENGTH: 23
<212> TYPE: RNA
<213> ORGANISM: Homo sapiens

<400> SEQUENCE: 215
uggagagcau ccaguggcgg gac                                         23

<210> SEQ ID NO 216
<211> LENGTH: 23
<212> TYPE: RNA
<213> ORGANISM: Homo sapiens
```

```
<400> SEQUENCE: 216
ggagagcauc caguggcggg aca                                          23

<210> SEQ ID NO 217
<211> LENGTH: 23
<212> TYPE: RNA
<213> ORGANISM: Homo sapiens

<400> SEQUENCE: 217
gagagcaucc aguggcggga cau                                          23

<210> SEQ ID NO 218
<211> LENGTH: 23
<212> TYPE: RNA
<213> ORGANISM: Homo sapiens

<400> SEQUENCE: 218
uccaguggcg ggacauaguc agc                                          23

<210> SEQ ID NO 219
<211> LENGTH: 23
<212> TYPE: RNA
<213> ORGANISM: Homo sapiens

<400> SEQUENCE: 219
ccaguggcgg gacauaguca gca                                          23

<210> SEQ ID NO 220
<211> LENGTH: 23
<212> TYPE: RNA
<213> ORGANISM: Homo sapiens

<400> SEQUENCE: 220
aguggcggga cauagucagc agu                                          23

<210> SEQ ID NO 221
<211> LENGTH: 23
<212> TYPE: RNA
<213> ORGANISM: Homo sapiens

<400> SEQUENCE: 221
guggcgggac auagucagca gug                                          23

<210> SEQ ID NO 222
<211> LENGTH: 23
<212> TYPE: RNA
<213> ORGANISM: Homo sapiens

<400> SEQUENCE: 222
uucucagcaa caugucgaug gac                                          23

<210> SEQ ID NO 223
<211> LENGTH: 23
<212> TYPE: RNA
<213> ORGANISM: Homo sapiens

<400> SEQUENCE: 223
cucagcaaca ugucgaugga cuu                                          23

<210> SEQ ID NO 224
<211> LENGTH: 23
<212> TYPE: RNA
<213> ORGANISM: Homo sapiens
```

```
<400> SEQUENCE: 224
ucagcaacau gucgauggac uuc                                           23

<210> SEQ ID NO 225
<211> LENGTH: 23
<212> TYPE: RNA
<213> ORGANISM: Homo sapiens

<400> SEQUENCE: 225
cagcaacaug ucgauggacu ucc                                           23

<210> SEQ ID NO 226
<211> LENGTH: 23
<212> TYPE: RNA
<213> ORGANISM: Homo sapiens

<400> SEQUENCE: 226
gcaacauguc gauggacuuc cag                                           23

<210> SEQ ID NO 227
<211> LENGTH: 23
<212> TYPE: RNA
<213> ORGANISM: Homo sapiens

<400> SEQUENCE: 227
caacaugucg auggacuucc aga                                           23

<210> SEQ ID NO 228
<211> LENGTH: 23
<212> TYPE: RNA
<213> ORGANISM: Homo sapiens

<400> SEQUENCE: 228
aacaugucga uggacuucca gaa                                           23

<210> SEQ ID NO 229
<211> LENGTH: 23
<212> TYPE: RNA
<213> ORGANISM: Homo sapiens

<400> SEQUENCE: 229
acaugucgau ggacuuccag aac                                           23

<210> SEQ ID NO 230
<211> LENGTH: 23
<212> TYPE: RNA
<213> ORGANISM: Homo sapiens

<400> SEQUENCE: 230
ugucgaugga cuuccagaac cac                                           23

<210> SEQ ID NO 231
<211> LENGTH: 23
<212> TYPE: RNA
<213> ORGANISM: Homo sapiens

<400> SEQUENCE: 231
cagaaccacc ugggcagcug cca                                           23

<210> SEQ ID NO 232
<211> LENGTH: 23
<212> TYPE: RNA
```

```
<213> ORGANISM: Homo sapiens

<400> SEQUENCE: 232
cugggcagcu gccaaaagug uga                                          23

<210> SEQ ID NO 233
<211> LENGTH: 23
<212> TYPE: RNA
<213> ORGANISM: Homo sapiens

<400> SEQUENCE: 233
gggcagcugc caaaagugug auc                                          23

<210> SEQ ID NO 234
<211> LENGTH: 23
<212> TYPE: RNA
<213> ORGANISM: Homo sapiens

<400> SEQUENCE: 234
gcugccaaaa gugugaucca agc                                          23

<210> SEQ ID NO 235
<211> LENGTH: 23
<212> TYPE: RNA
<213> ORGANISM: Homo sapiens

<400> SEQUENCE: 235
cugccaaaag ugugauccaa gcu                                          23

<210> SEQ ID NO 236
<211> LENGTH: 23
<212> TYPE: RNA
<213> ORGANISM: Homo sapiens

<400> SEQUENCE: 236
ugccaaaagu gugauccaag cug                                          23

<210> SEQ ID NO 237
<211> LENGTH: 23
<212> TYPE: RNA
<213> ORGANISM: Homo sapiens

<400> SEQUENCE: 237
caaaagugug auccaagcug ucc                                          23

<210> SEQ ID NO 238
<211> LENGTH: 23
<212> TYPE: RNA
<213> ORGANISM: Homo sapiens

<400> SEQUENCE: 238
agugugaucc aagcugucccaau                                           23

<210> SEQ ID NO 239
<211> LENGTH: 23
<212> TYPE: RNA
<213> ORGANISM: Homo sapiens

<400> SEQUENCE: 239
gugugaucca agcugucccaaug                                           23

<210> SEQ ID NO 240
<211> LENGTH: 23
```

```
<212> TYPE: RNA
<213> ORGANISM: Homo sapiens

<400> SEQUENCE: 240
gugauccaag cugucccaau ggg                                          23

<210> SEQ ID NO 241
<211> LENGTH: 23
<212> TYPE: RNA
<213> ORGANISM: Homo sapiens

<400> SEQUENCE: 241
ugauccaagc ugucccaaug gga                                          23

<210> SEQ ID NO 242
<211> LENGTH: 23
<212> TYPE: RNA
<213> ORGANISM: Homo sapiens

<400> SEQUENCE: 242
gauccaagcu gucccaaugg gag                                          23

<210> SEQ ID NO 243
<211> LENGTH: 23
<212> TYPE: RNA
<213> ORGANISM: Homo sapiens

<400> SEQUENCE: 243
auccaagcug ucccaauggg agc                                          23

<210> SEQ ID NO 244
<211> LENGTH: 23
<212> TYPE: RNA
<213> ORGANISM: Homo sapiens

<400> SEQUENCE: 244
uccaagcugu cccaauggga gcu                                          23

<210> SEQ ID NO 245
<211> LENGTH: 23
<212> TYPE: RNA
<213> ORGANISM: Homo sapiens

<400> SEQUENCE: 245
caagcugucc caaugggagc ugc                                          23

<210> SEQ ID NO 246
<211> LENGTH: 23
<212> TYPE: RNA
<213> ORGANISM: Homo sapiens

<400> SEQUENCE: 246
gcugucccaa ugggagcugc ugg                                          23

<210> SEQ ID NO 247
<211> LENGTH: 23
<212> TYPE: RNA
<213> ORGANISM: Homo sapiens

<400> SEQUENCE: 247
ggggugcagg agaggagaac ugc                                          23

<210> SEQ ID NO 248
```

```
<211> LENGTH: 23
<212> TYPE: RNA
<213> ORGANISM: Homo sapiens

<400> SEQUENCE: 248
agaaacugac caaaaucauc ugu                                              23

<210> SEQ ID NO 249
<211> LENGTH: 23
<212> TYPE: RNA
<213> ORGANISM: Homo sapiens

<400> SEQUENCE: 249
gaaacugacc aaaaucaucu gug                                              23

<210> SEQ ID NO 250
<211> LENGTH: 23
<212> TYPE: RNA
<213> ORGANISM: Homo sapiens

<400> SEQUENCE: 250
aaacugacca aaaucaucug ugc                                              23

<210> SEQ ID NO 251
<211> LENGTH: 23
<212> TYPE: RNA
<213> ORGANISM: Homo sapiens

<400> SEQUENCE: 251
ugaccaaaau caucugugcc cag                                              23

<210> SEQ ID NO 252
<211> LENGTH: 23
<212> TYPE: RNA
<213> ORGANISM: Homo sapiens

<400> SEQUENCE: 252
gaccaaaauc aucugugccc agc                                              23

<210> SEQ ID NO 253
<211> LENGTH: 23
<212> TYPE: RNA
<213> ORGANISM: Homo sapiens

<400> SEQUENCE: 253
caaaaucauc ugugcccagc agu                                              23

<210> SEQ ID NO 254
<211> LENGTH: 23
<212> TYPE: RNA
<213> ORGANISM: Homo sapiens

<400> SEQUENCE: 254
cugugcccag cagugcuccg ggc                                              23

<210> SEQ ID NO 255
<211> LENGTH: 23
<212> TYPE: RNA
<213> ORGANISM: Homo sapiens

<400> SEQUENCE: 255
gugcccagca gugcuccggg cgc                                              23
```

<210> SEQ ID NO 256
<211> LENGTH: 23
<212> TYPE: RNA
<213> ORGANISM: Homo sapiens

<400> SEQUENCE: 256
ccccagugac ugcugccaca acc                                           23

<210> SEQ ID NO 257
<211> LENGTH: 23
<212> TYPE: RNA
<213> ORGANISM: Homo sapiens

<400> SEQUENCE: 257
cccagugacu gcugccacaa cca                                           23

<210> SEQ ID NO 258
<211> LENGTH: 23
<212> TYPE: RNA
<213> ORGANISM: Homo sapiens

<400> SEQUENCE: 258
gggagagcga cugccugguc ugc                                           23

<210> SEQ ID NO 259
<211> LENGTH: 23
<212> TYPE: RNA
<213> ORGANISM: Homo sapiens

<400> SEQUENCE: 259
ggagagcgac ugccuggucu gcc                                           23

<210> SEQ ID NO 260
<211> LENGTH: 23
<212> TYPE: RNA
<213> ORGANISM: Homo sapiens

<400> SEQUENCE: 260
gagagcgacu gccuggucug ccg                                           23

<210> SEQ ID NO 261
<211> LENGTH: 23
<212> TYPE: RNA
<213> ORGANISM: Homo sapiens

<400> SEQUENCE: 261
agagcgacug ccuggucugc cgc                                           23

<210> SEQ ID NO 262
<211> LENGTH: 23
<212> TYPE: RNA
<213> ORGANISM: Homo sapiens

<400> SEQUENCE: 262
gagcgacugc cuggucugcc gca                                           23

<210> SEQ ID NO 263
<211> LENGTH: 23
<212> TYPE: RNA
<213> ORGANISM: Homo sapiens

<400> SEQUENCE: 263
agcgacugcc uggucugccg caa                                           23

```
<210> SEQ ID NO 264
<211> LENGTH: 23
<212> TYPE: RNA
<213> ORGANISM: Homo sapiens

<400> SEQUENCE: 264
cugccugguc ugccgcaaau ucc                                              23

<210> SEQ ID NO 265
<211> LENGTH: 23
<212> TYPE: RNA
<213> ORGANISM: Homo sapiens

<400> SEQUENCE: 265
ugccuggucu gccgcaaauu ccg                                              23

<210> SEQ ID NO 266
<211> LENGTH: 23
<212> TYPE: RNA
<213> ORGANISM: Homo sapiens

<400> SEQUENCE: 266
gccuggucug ccgcaaauuc cga                                              23

<210> SEQ ID NO 267
<211> LENGTH: 23
<212> TYPE: RNA
<213> ORGANISM: Homo sapiens

<400> SEQUENCE: 267
ccuggucugc cgcaaauucc gag                                              23

<210> SEQ ID NO 268
<211> LENGTH: 23
<212> TYPE: RNA
<213> ORGANISM: Homo sapiens

<400> SEQUENCE: 268
uggucugccg caaauuccga gac                                              23

<210> SEQ ID NO 269
<211> LENGTH: 23
<212> TYPE: RNA
<213> ORGANISM: Homo sapiens

<400> SEQUENCE: 269
ggucugccgc aaauuccgag acg                                              23

<210> SEQ ID NO 270
<211> LENGTH: 23
<212> TYPE: RNA
<213> ORGANISM: Homo sapiens

<400> SEQUENCE: 270
gucugccgca aauuccgaga cga                                              23

<210> SEQ ID NO 271
<211> LENGTH: 23
<212> TYPE: RNA
<213> ORGANISM: Homo sapiens

<400> SEQUENCE: 271
ucugccgcaa auuccgagac gaa                                              23
```

```
<210> SEQ ID NO 272
<211> LENGTH: 23
<212> TYPE: RNA
<213> ORGANISM: Homo sapiens

<400> SEQUENCE: 272
ugccgcaaau uccgagacga agc                                            23

<210> SEQ ID NO 273
<211> LENGTH: 23
<212> TYPE: RNA
<213> ORGANISM: Homo sapiens

<400> SEQUENCE: 273
caaauuccga gacgaagcca cgu                                            23

<210> SEQ ID NO 274
<211> LENGTH: 23
<212> TYPE: RNA
<213> ORGANISM: Homo sapiens

<400> SEQUENCE: 274
aaauuccgag acgaagccac gug                                            23

<210> SEQ ID NO 275
<211> LENGTH: 23
<212> TYPE: RNA
<213> ORGANISM: Homo sapiens

<400> SEQUENCE: 275
aauuccgaga cgaagccacg ugc                                            23

<210> SEQ ID NO 276
<211> LENGTH: 23
<212> TYPE: RNA
<213> ORGANISM: Homo sapiens

<400> SEQUENCE: 276
auuccgagac gaagccacgu gca                                            23

<210> SEQ ID NO 277
<211> LENGTH: 23
<212> TYPE: RNA
<213> ORGANISM: Homo sapiens

<400> SEQUENCE: 277
uuccgagacg aagccacgug caa                                            23

<210> SEQ ID NO 278
<211> LENGTH: 23
<212> TYPE: RNA
<213> ORGANISM: Homo sapiens

<400> SEQUENCE: 278
ccgagacgaa gccacgugca agg                                            23

<210> SEQ ID NO 279
<211> LENGTH: 23
<212> TYPE: RNA
<213> ORGANISM: Homo sapiens

<400> SEQUENCE: 279
```

```
agacgaagcc acgugcaagg aca                                              23

<210> SEQ ID NO 280
<211> LENGTH: 23
<212> TYPE: RNA
<213> ORGANISM: Homo sapiens

<400> SEQUENCE: 280
gacgaagcca cgugcaagga cac                                              23

<210> SEQ ID NO 281
<211> LENGTH: 23
<212> TYPE: RNA
<213> ORGANISM: Homo sapiens

<400> SEQUENCE: 281
acgaagccac gugcaaggac acc                                              23

<210> SEQ ID NO 282
<211> LENGTH: 23
<212> TYPE: RNA
<213> ORGANISM: Homo sapiens

<400> SEQUENCE: 282
cgaagccacg ugcaaggaca ccu                                              23

<210> SEQ ID NO 283
<211> LENGTH: 23
<212> TYPE: RNA
<213> ORGANISM: Homo sapiens

<400> SEQUENCE: 283 cccccacuc augcucuaca acc                                               23

<210> SEQ ID NO 284
<211> LENGTH: 23
<212> TYPE: RNA
<213> ORGANISM: Homo sapiens

<400> SEQUENCE: 284
ccccacucau gcucuacaac ccc                                              23

<210> SEQ ID NO 285
<211> LENGTH: 23
<212> TYPE: RNA
<213> ORGANISM: Homo sapiens

<400> SEQUENCE: 285
ccacucaugc ucuacaaccc cac                                              23

<210> SEQ ID NO 286
<211> LENGTH: 23
<212> TYPE: RNA
<213> ORGANISM: Homo sapiens

<400> SEQUENCE: 286
cucaugcucu acaaccccac cac                                              23

<210> SEQ ID NO 287
<211> LENGTH: 23
<212> TYPE: RNA
<213> ORGANISM: Homo sapiens

<400> SEQUENCE: 287
```
uaccagaugg augugaaccc cga   23

<210> SEQ ID NO 288
<211> LENGTH: 23
<212> TYPE: RNA
<213> ORGANISM: Homo sapiens

<400> SEQUENCE: 288
ccagauggau gugaaccccg agg   23

<210> SEQ ID NO 289
<211> LENGTH: 23
<212> TYPE: RNA
<213> ORGANISM: Homo sapiens

<400> SEQUENCE: 289
cagauggaug ugaaccccga ggg   23

<210> SEQ ID NO 290
<211> LENGTH: 23
<212> TYPE: RNA
<213> ORGANISM: Homo sapiens

<400> SEQUENCE: 290
agauggaugu gaaccccgag ggc   23

<210> SEQ ID NO 291
<211> LENGTH: 23
<212> TYPE: RNA
<213> ORGANISM: Homo sapiens

<400> SEQUENCE: 291
auggauguga accccgaggg caa   23

<210> SEQ ID NO 292
<211> LENGTH: 23
<212> TYPE: RNA
<213> ORGANISM: Homo sapiens

<400> SEQUENCE: 292
uggaugugaa ccccgagggc aaa   23

<210> SEQ ID NO 293
<211> LENGTH: 23
<212> TYPE: RNA
<213> ORGANISM: Homo sapiens

<400> SEQUENCE: 293
gaugugaacc ccgagggcaa aua   23

<210> SEQ ID NO 294
<211> LENGTH: 23
<212> TYPE: RNA
<213> ORGANISM: Homo sapiens

<400> SEQUENCE: 294
ugaaccccga gggcaaauac agc   23

<210> SEQ ID NO 295
<211> LENGTH: 23
<212> TYPE: RNA
<213> ORGANISM: Homo sapiens

```
<400> SEQUENCE: 295
gaaccccgag ggcaaauaca gcu                                          23

<210> SEQ ID NO 296
<211> LENGTH: 23
<212> TYPE: RNA
<213> ORGANISM: Homo sapiens

<400> SEQUENCE: 296
accccgaggg caaauacagc uuu                                          23

<210> SEQ ID NO 297
<211> LENGTH: 23
<212> TYPE: RNA
<213> ORGANISM: Homo sapiens

<400> SEQUENCE: 297
ccccgagggc aaauacagcu uug                                          23

<210> SEQ ID NO 298
<211> LENGTH: 23
<212> TYPE: RNA
<213> ORGANISM: Homo sapiens

<400> SEQUENCE: 298 cccgaggggca aauacagcuu ugg                                         23

<210> SEQ ID NO 299
<211> LENGTH: 23
<212> TYPE: RNA
<213> ORGANISM: Homo sapiens

<400> SEQUENCE: 299
gcaaauacag cuuuggugcc acc                                          23

<210> SEQ ID NO 300
<211> LENGTH: 23
<212> TYPE: RNA
<213> ORGANISM: Homo sapiens

<400> SEQUENCE: 300
caaauacagc uuuggugcca ccu                                          23

<210> SEQ ID NO 301
<211> LENGTH: 23
<212> TYPE: RNA
<213> ORGANISM: Homo sapiens

<400> SEQUENCE: 301
aaauacagcu uuggugccac cug                                          23

<210> SEQ ID NO 302
<211> LENGTH: 23
<212> TYPE: RNA
<213> ORGANISM: Homo sapiens

<400> SEQUENCE: 302
agcuuuggug ccaccugcgu gaa                                          23

<210> SEQ ID NO 303
<211> LENGTH: 23
<212> TYPE: RNA
<213> ORGANISM: Homo sapiens
```

```
<400> SEQUENCE: 303
cuuuggugcc accugcguga aga                                              23

<210> SEQ ID NO 304
<211> LENGTH: 23
<212> TYPE: RNA
<213> ORGANISM: Homo sapiens

<400> SEQUENCE: 304
ugccaccugc gugaagaagu guc                                              23

<210> SEQ ID NO 305
<211> LENGTH: 23
<212> TYPE: RNA
<213> ORGANISM: Homo sapiens

<400> SEQUENCE: 305
accugcguga agaagugucc ccg                                              23

<210> SEQ ID NO 306
<211> LENGTH: 23
<212> TYPE: RNA
<213> ORGANISM: Homo sapiens

<400> SEQUENCE: 306
ccugcgugaa gaaguguccc cgu                                              23

<210> SEQ ID NO 307
<211> LENGTH: 23
<212> TYPE: RNA
<213> ORGANISM: Homo sapiens

<400> SEQUENCE: 307
cugcgugaag aaguguccccc gua                                             23

<210> SEQ ID NO 308
<211> LENGTH: 23
<212> TYPE: RNA
<213> ORGANISM: Homo sapiens

<400> SEQUENCE: 308
ugcgugaaga agucccccg uaa                                               23

<210> SEQ ID NO 309
<211> LENGTH: 23
<212> TYPE: RNA
<213> ORGANISM: Homo sapiens

<400> SEQUENCE: 309
gcgugaagaa guguccccgu aau                                              23

<210> SEQ ID NO 310
<211> LENGTH: 23
<212> TYPE: RNA
<213> ORGANISM: Homo sapiens

<400> SEQUENCE: 310
cgugaagaag uguccccgua auu                                              23

<210> SEQ ID NO 311
<211> LENGTH: 23
<212> TYPE: RNA
```

-continued

```
<213> ORGANISM: Homo sapiens

<400> SEQUENCE: 311
gugaagaagu guccccguaa uua                                           23

<210> SEQ ID NO 312
<211> LENGTH: 23
<212> TYPE: RNA
<213> ORGANISM: Homo sapiens

<400> SEQUENCE: 312
ugaagaagug uccccguaau uau                                           23

<210> SEQ ID NO 313
<211> LENGTH: 23
<212> TYPE: RNA
<213> ORGANISM: Homo sapiens

<400> SEQUENCE: 313
gaagaagugu ccccguaauu aug                                           23

<210> SEQ ID NO 314
<211> LENGTH: 23
<212> TYPE: RNA
<213> ORGANISM: Homo sapiens

<400> SEQUENCE: 314
aagaaguguc cccguaauua ugu                                           23

<210> SEQ ID NO 315
<211> LENGTH: 23
<212> TYPE: RNA
<213> ORGANISM: Homo sapiens

<400> SEQUENCE: 315
agaagugucc ccguaauuau gug                                           23

<210> SEQ ID NO 316
<211> LENGTH: 23
<212> TYPE: RNA
<213> ORGANISM: Homo sapiens

<400> SEQUENCE: 316
gaagugcccc cguaauuaug ugg                                           23

<210> SEQ ID NO 317
<211> LENGTH: 23
<212> TYPE: RNA
<213> ORGANISM: Homo sapiens

<400> SEQUENCE: 317
aagugccccc guaauuaugu ggu                                           23

<210> SEQ ID NO 318
<211> LENGTH: 23
<212> TYPE: RNA
<213> ORGANISM: Homo sapiens

<400> SEQUENCE: 318 agugccccg uaauuaugug gug                                            23

<210> SEQ ID NO 319
<211> LENGTH: 23
```

```
<212> TYPE: RNA
<213> ORGANISM: Homo sapiens

<400> SEQUENCE: 319
guguccccgu aauuaugugg uga                                              23

<210> SEQ ID NO 320
<211> LENGTH: 23
<212> TYPE: RNA
<213> ORGANISM: Homo sapiens

<400> SEQUENCE: 320 gucccguaa uuauguggug aca                                               23

<210> SEQ ID NO 321
<211> LENGTH: 23
<212> TYPE: RNA
<213> ORGANISM: Homo sapiens

<400> SEQUENCE: 321
ccccguaauu auggugac aga                                                23

<210> SEQ ID NO 322
<211> LENGTH: 23
<212> TYPE: RNA
<213> ORGANISM: Homo sapiens

<400> SEQUENCE: 322
ccguaauuau guggugacag auc                                              23

<210> SEQ ID NO 323
<211> LENGTH: 23
<212> TYPE: RNA
<213> ORGANISM: Homo sapiens

<400> SEQUENCE: 323
cguaauuaug uggugacaga uca                                              23

<210> SEQ ID NO 324
<211> LENGTH: 23
<212> TYPE: RNA
<213> ORGANISM: Homo sapiens

<400> SEQUENCE: 324
guaauuaugu ggugacagau cac                                              23

<210> SEQ ID NO 325
<211> LENGTH: 23
<212> TYPE: RNA
<213> ORGANISM: Homo sapiens

<400> SEQUENCE: 325
uaauuaugug gugacagauc acg                                              23

<210> SEQ ID NO 326
<211> LENGTH: 23
<212> TYPE: RNA
<213> ORGANISM: Homo sapiens

<400> SEQUENCE: 326
aauuaugugg ugacagauca cgg                                              23

<210> SEQ ID NO 327
```

```
<211> LENGTH: 23
<212> TYPE: RNA
<213> ORGANISM: Homo sapiens

<400> SEQUENCE: 327
uuauguggug acagaucacg gcu                                              23

<210> SEQ ID NO 328
<211> LENGTH: 23
<212> TYPE: RNA
<213> ORGANISM: Homo sapiens

<400> SEQUENCE: 328
uguggugaca gaucacggcu cgu                                              23

<210> SEQ ID NO 329
<211> LENGTH: 23
<212> TYPE: RNA
<213> ORGANISM: Homo sapiens

<400> SEQUENCE: 329
uggugacaga ucacggcucg ugc                                              23

<210> SEQ ID NO 330
<211> LENGTH: 23
<212> TYPE: RNA
<213> ORGANISM: Homo sapiens

<400> SEQUENCE: 330
ggugacagau cacggcucgu gcg                                              23

<210> SEQ ID NO 331
<211> LENGTH: 23
<212> TYPE: RNA
<213> ORGANISM: Homo sapiens

<400> SEQUENCE: 331
gugacagauc acggcucgug cgu                                              23

<210> SEQ ID NO 332
<211> LENGTH: 23
<212> TYPE: RNA
<213> ORGANISM: Homo sapiens

<400> SEQUENCE: 332
ugacagauca cggcucgugc guc                                              23

<210> SEQ ID NO 333
<211> LENGTH: 23
<212> TYPE: RNA
<213> ORGANISM: Homo sapiens

<400> SEQUENCE: 333
gacagaucac ggcucgugcg ucc                                              23

<210> SEQ ID NO 334
<211> LENGTH: 23
<212> TYPE: RNA
<213> ORGANISM: Homo sapiens

<400> SEQUENCE: 334
acagaucacg gcucgugcgu ccg                                              23
```

```
<210> SEQ ID NO 335
<211> LENGTH: 23
<212> TYPE: RNA
<213> ORGANISM: Homo sapiens

<400> SEQUENCE: 335
cagaucacgg cucgugcguc cga                                              23

<210> SEQ ID NO 336
<211> LENGTH: 23
<212> TYPE: RNA
<213> ORGANISM: Homo sapiens

<400> SEQUENCE: 336
agaucacggc ucgugcgucc gag                                              23

<210> SEQ ID NO 337
<211> LENGTH: 23
<212> TYPE: RNA
<213> ORGANISM: Homo sapiens

<400> SEQUENCE: 337
gaucacggcu cgugcguccg agc                                              23

<210> SEQ ID NO 338
<211> LENGTH: 23
<212> TYPE: RNA
<213> ORGANISM: Homo sapiens

<400> SEQUENCE: 338
aucacggcuc gugcguccga gcc                                              23

<210> SEQ ID NO 339
<211> LENGTH: 23
<212> TYPE: RNA
<213> ORGANISM: Homo sapiens

<400> SEQUENCE: 339
ucacggcucg ugcguccgag ccu                                              23

<210> SEQ ID NO 340
<211> LENGTH: 23
<212> TYPE: RNA
<213> ORGANISM: Homo sapiens

<400> SEQUENCE: 340
cggcucgugc guccgagccu gug                                              23

<210> SEQ ID NO 341
<211> LENGTH: 23
<212> TYPE: RNA
<213> ORGANISM: Homo sapiens

<400> SEQUENCE: 341
auggaggaag acggcguccg caa                                              23

<210> SEQ ID NO 342
<211> LENGTH: 23
<212> TYPE: RNA
<213> ORGANISM: Homo sapiens

<400> SEQUENCE: 342
uggaggaaga cggcguccgc aag                                              23
```

```
<210> SEQ ID NO 343
<211> LENGTH: 23
<212> TYPE: RNA
<213> ORGANISM: Homo sapiens

<400> SEQUENCE: 343
gaggaagacg gcguccgcaa gug                                          23

<210> SEQ ID NO 344
<211> LENGTH: 23
<212> TYPE: RNA
<213> ORGANISM: Homo sapiens

<400> SEQUENCE: 344
aggaagacgg cguccgcaag ugu                                          23

<210> SEQ ID NO 345
<211> LENGTH: 23
<212> TYPE: RNA
<213> ORGANISM: Homo sapiens

<400> SEQUENCE: 345
ggaagacggc guccgcaagu gua                                          23

<210> SEQ ID NO 346
<211> LENGTH: 23
<212> TYPE: RNA
<213> ORGANISM: Homo sapiens

<400> SEQUENCE: 346
aagacggcgu ccgcaagugu aag                                          23

<210> SEQ ID NO 347
<211> LENGTH: 23
<212> TYPE: RNA
<213> ORGANISM: Homo sapiens

<400> SEQUENCE: 347
agacggcguc cgcaagugua aga                                          23

<210> SEQ ID NO 348
<211> LENGTH: 23
<212> TYPE: RNA
<213> ORGANISM: Homo sapiens

<400> SEQUENCE: 348
cggcguccgc aaguguaaga agu                                          23

<210> SEQ ID NO 349
<211> LENGTH: 23
<212> TYPE: RNA
<213> ORGANISM: Homo sapiens

<400> SEQUENCE: 349
ggcguccgca aguguaagaa gug                                          23

<210> SEQ ID NO 350
<211> LENGTH: 23
<212> TYPE: RNA
<213> ORGANISM: Homo sapiens

<400> SEQUENCE: 350
gcguccgcaa guguaagaag ugc                                          23
```

```
<210> SEQ ID NO 351
<211> LENGTH: 23
<212> TYPE: RNA
<213> ORGANISM: Homo sapiens

<400> SEQUENCE: 351
cguccgcaag uguaagaagu gcg                                            23

<210> SEQ ID NO 352
<211> LENGTH: 23
<212> TYPE: RNA
<213> ORGANISM: Homo sapiens

<400> SEQUENCE: 352
guccgcaagu guaagaagug cga                                            23

<210> SEQ ID NO 353
<211> LENGTH: 23
<212> TYPE: RNA
<213> ORGANISM: Homo sapiens

<400> SEQUENCE: 353
uccgcaagug uaagaagugc gaa                                            23

<210> SEQ ID NO 354
<211> LENGTH: 23
<212> TYPE: RNA
<213> ORGANISM: Homo sapiens

<400> SEQUENCE: 354
ccgcaagugu aagaagugcg aag                                            23

<210> SEQ ID NO 355
<211> LENGTH: 23
<212> TYPE: RNA
<213> ORGANISM: Homo sapiens

<400> SEQUENCE: 355
gcaaguguaa gaagugcgaa ggg                                            23

<210> SEQ ID NO 356
<211> LENGTH: 23
<212> TYPE: RNA
<213> ORGANISM: Homo sapiens

<400> SEQUENCE: 356
caaguguaag aagugcgaag ggc                                            23

<210> SEQ ID NO 357
<211> LENGTH: 23
<212> TYPE: RNA
<213> ORGANISM: Homo sapiens

<400> SEQUENCE: 357
aaguguaaga agugcgaagg gcc                                            23

<210> SEQ ID NO 358
<211> LENGTH: 23
<212> TYPE: RNA
<213> ORGANISM: Homo sapiens

<400> SEQUENCE: 358
```
aguguaagaa gugcgaaggg ccu                                              23

<210> SEQ ID NO 359
<211> LENGTH: 23
<212> TYPE: RNA
<213> ORGANISM: Homo sapiens

<400> SEQUENCE: 359
guguaagaag ugcgaagggc cuu                                              23

<210> SEQ ID NO 360
<211> LENGTH: 23
<212> TYPE: RNA
<213> ORGANISM: Homo sapiens

<400> SEQUENCE: 360
uguaagaagu gcgaagggcc uug                                              23

<210> SEQ ID NO 361
<211> LENGTH: 23
<212> TYPE: RNA
<213> ORGANISM: Homo sapiens

<400> SEQUENCE: 361
guaagaagug cgaagggccu ugc                                              23

<210> SEQ ID NO 362
<211> LENGTH: 23
<212> TYPE: RNA
<213> ORGANISM: Homo sapiens

<400> SEQUENCE: 362
uaagaagugc gaagggccuu gcc                                              23

<210> SEQ ID NO 363
<211> LENGTH: 23
<212> TYPE: RNA
<213> ORGANISM: Homo sapiens

<400> SEQUENCE: 363
gaagugcgaa gggccuugcc gca                                              23

<210> SEQ ID NO 364
<211> LENGTH: 23
<212> TYPE: RNA
<213> ORGANISM: Homo sapiens

<400> SEQUENCE: 364
aagugcgaag ggccuugccg caa                                              23

<210> SEQ ID NO 365
<211> LENGTH: 23
<212> TYPE: RNA
<213> ORGANISM: Homo sapiens

<400> SEQUENCE: 365
agugcgaagg gccuugccgc aaa                                              23

<210> SEQ ID NO 366
<211> LENGTH: 23
<212> TYPE: RNA
<213> ORGANISM: Homo sapiens

<400> SEQUENCE: 366
gugcgaaggg ccuugccgca aag                                              23

<210> SEQ ID NO 367
<211> LENGTH: 23
<212> TYPE: RNA
<213> ORGANISM: Homo sapiens

<400> SEQUENCE: 367
ugcgaagggc cuugccgcaa agu                                              23

<210> SEQ ID NO 368
<211> LENGTH: 23
<212> TYPE: RNA
<213> ORGANISM: Homo sapiens

<400> SEQUENCE: 368
cgaagggccu ugccgcaaag ugu                                              23

<210> SEQ ID NO 369
<211> LENGTH: 23
<212> TYPE: RNA
<213> ORGANISM: Homo sapiens

<400> SEQUENCE: 369
gaagggccuu gccgcaaagu gug                                              23

<210> SEQ ID NO 370
<211> LENGTH: 23
<212> TYPE: RNA
<213> ORGANISM: Homo sapiens

<400> SEQUENCE: 370
aagggccuug ccgcaaagug ugu                                              23

<210> SEQ ID NO 371
<211> LENGTH: 23
<212> TYPE: RNA
<213> ORGANISM: Homo sapiens

<400> SEQUENCE: 371
agggccuugc cgcaaagugu gua                                              23

<210> SEQ ID NO 372
<211> LENGTH: 23
<212> TYPE: RNA
<213> ORGANISM: Homo sapiens

<400> SEQUENCE: 372
gggccuugcc gcaaagugug uaa                                              23

<210> SEQ ID NO 373
<211> LENGTH: 23
<212> TYPE: RNA
<213> ORGANISM: Homo sapiens

<400> SEQUENCE: 373
gccuugccgc aaagugugua acg                                              23

<210> SEQ ID NO 374
<211> LENGTH: 23
<212> TYPE: RNA
<213> ORGANISM: Homo sapiens

```
<400> SEQUENCE: 374
acggaauagg uauuggugaa uuu                                          23

<210> SEQ ID NO 375
<211> LENGTH: 23
<212> TYPE: RNA
<213> ORGANISM: Homo sapiens

<400> SEQUENCE: 375
cggaauaggu auuggugaau uua                                          23

<210> SEQ ID NO 376
<211> LENGTH: 23
<212> TYPE: RNA
<213> ORGANISM: Homo sapiens

<400> SEQUENCE: 376
ggaauaggua uuggugaauu uaa                                          23

<210> SEQ ID NO 377
<211> LENGTH: 23
<212> TYPE: RNA
<213> ORGANISM: Homo sapiens

<400> SEQUENCE: 377
gaauagguau uggugaauuu aaa                                          23

<210> SEQ ID NO 378
<211> LENGTH: 23
<212> TYPE: RNA
<213> ORGANISM: Homo sapiens

<400> SEQUENCE: 378
auagguauug gugaauuuaa aga                                          23

<210> SEQ ID NO 379
<211> LENGTH: 23
<212> TYPE: RNA
<213> ORGANISM: Homo sapiens

<400> SEQUENCE: 379
uagguauugg ugaauuuaaa gac                                          23

<210> SEQ ID NO 380
<211> LENGTH: 23
<212> TYPE: RNA
<213> ORGANISM: Homo sapiens

<400> SEQUENCE: 380
cucacucucc auaaaugcua cga                                          23

<210> SEQ ID NO 381
<211> LENGTH: 23
<212> TYPE: RNA
<213> ORGANISM: Homo sapiens

<400> SEQUENCE: 381
uauuaaacac uucaaaaacu gca                                          23

<210> SEQ ID NO 382
<211> LENGTH: 23
<212> TYPE: RNA
<213> ORGANISM: Homo sapiens
```

<400> SEQUENCE: 382
cacuucaaaa acugcaccuc cau                                              23

<210> SEQ ID NO 383
<211> LENGTH: 23
<212> TYPE: RNA
<213> ORGANISM: Homo sapiens

<400> SEQUENCE: 383
acuucaaaaa cugcaccucc auc                                              23

<210> SEQ ID NO 384
<211> LENGTH: 23
<212> TYPE: RNA
<213> ORGANISM: Homo sapiens

<400> SEQUENCE: 384
cuucaaaaac ugcaccucca uca                                              23

<210> SEQ ID NO 385
<211> LENGTH: 23
<212> TYPE: RNA
<213> ORGANISM: Homo sapiens

<400> SEQUENCE: 385
uucaaaaacu gcaccuccau cag                                              23

<210> SEQ ID NO 386
<211> LENGTH: 23
<212> TYPE: RNA
<213> ORGANISM: Homo sapiens

<400> SEQUENCE: 386
ucaaaaacug caccuccauc agu                                              23

<210> SEQ ID NO 387
<211> LENGTH: 23
<212> TYPE: RNA
<213> ORGANISM: Homo sapiens

<400> SEQUENCE: 387
aaacugcacc uccaucagug gcg                                              23

<210> SEQ ID NO 388
<211> LENGTH: 23
<212> TYPE: RNA
<213> ORGANISM: Homo sapiens

<400> SEQUENCE: 388
ugcaccucca ucaguggcga ucu                                              23

<210> SEQ ID NO 389
<211> LENGTH: 23
<212> TYPE: RNA
<213> ORGANISM: Homo sapiens

<400> SEQUENCE: 389
gcaccuccau caguggcgau cuc                                              23

<210> SEQ ID NO 390
<211> LENGTH: 23
<212> TYPE: RNA

```
<213> ORGANISM: Homo sapiens

<400> SEQUENCE: 390
accuccauca guggcgaucu cca                                          23

<210> SEQ ID NO 391
<211> LENGTH: 23
<212> TYPE: RNA
<213> ORGANISM: Homo sapiens

<400> SEQUENCE: 391
uccaucagug gcgaucucca cau                                          23

<210> SEQ ID NO 392
<211> LENGTH: 23
<212> TYPE: RNA
<213> ORGANISM: Homo sapiens

<400> SEQUENCE: 392
aguggcgauc uccacauccu gcc                                          23

<210> SEQ ID NO 393
<211> LENGTH: 23
<212> TYPE: RNA
<213> ORGANISM: Homo sapiens

<400> SEQUENCE: 393
guggcgaucu ccacauccug ccg                                          23

<210> SEQ ID NO 394
<211> LENGTH: 23
<212> TYPE: RNA
<213> ORGANISM: Homo sapiens

<400> SEQUENCE: 394
uggcgaucuc cacauccugc cgg                                          23

<210> SEQ ID NO 395
<211> LENGTH: 23
<212> TYPE: RNA
<213> ORGANISM: Homo sapiens

<400> SEQUENCE: 395
ggcgaucucc acauccugcc ggu                                          23

<210> SEQ ID NO 396
<211> LENGTH: 23
<212> TYPE: RNA
<213> ORGANISM: Homo sapiens

<400> SEQUENCE: 396
gcgaucucca cauccugccg gug                                          23

<210> SEQ ID NO 397
<211> LENGTH: 23
<212> TYPE: RNA
<213> ORGANISM: Homo sapiens

<400> SEQUENCE: 397
cuccacaucc ugccgguggc auu                                          23

<210> SEQ ID NO 398
<211> LENGTH: 23
```

```
<212> TYPE: RNA
<213> ORGANISM: Homo sapiens

<400> SEQUENCE: 398
uccacauccu gccgguggca uuu                                          23

<210> SEQ ID NO 399
<211> LENGTH: 23
<212> TYPE: RNA
<213> ORGANISM: Homo sapiens

<400> SEQUENCE: 399
ccacauccug ccgguggcau uua                                          23

<210> SEQ ID NO 400
<211> LENGTH: 23
<212> TYPE: RNA
<213> ORGANISM: Homo sapiens

<400> SEQUENCE: 400
acauccugcc gguggcauuu agg                                          23

<210> SEQ ID NO 401
<211> LENGTH: 23
<212> TYPE: RNA
<213> ORGANISM: Homo sapiens

<400> SEQUENCE: 401
uccugccggu ggcauuuagg ggu                                          23

<210> SEQ ID NO 402
<211> LENGTH: 23
<212> TYPE: RNA
<213> ORGANISM: Homo sapiens

<400> SEQUENCE: 402
ccugccggug gcauuuaggg gug                                          23

<210> SEQ ID NO 403
<211> LENGTH: 23
<212> TYPE: RNA
<213> ORGANISM: Homo sapiens

<400> SEQUENCE: 403
cugccggugg cauuuagggg uga                                          23

<210> SEQ ID NO 404
<211> LENGTH: 23
<212> TYPE: RNA
<213> ORGANISM: Homo sapiens

<400> SEQUENCE: 404
ugccgguggc auuuaggggu gac                                          23

<210> SEQ ID NO 405
<211> LENGTH: 23
<212> TYPE: RNA
<213> ORGANISM: Homo sapiens

<400> SEQUENCE: 405
cgguggcauu uaggggugac ucc                                          23

<210> SEQ ID NO 406
```

```
<211> LENGTH: 23
<212> TYPE: RNA
<213> ORGANISM: Homo sapiens

<400> SEQUENCE: 406
uggcauuuag ggugacuccu uuc                                            23

<210> SEQ ID NO 407
<211> LENGTH: 23
<212> TYPE: RNA
<213> ORGANISM: Homo sapiens

<400> SEQUENCE: 407
ggcauuuagg gugacuccuu uca                                            23

<210> SEQ ID NO 408
<211> LENGTH: 23
<212> TYPE: RNA
<213> ORGANISM: Homo sapiens

<400> SEQUENCE: 408
gcauuuaggg gugacuccuu cac                                            23

<210> SEQ ID NO 409
<211> LENGTH: 23
<212> TYPE: RNA
<213> ORGANISM: Homo sapiens

<400> SEQUENCE: 409
cauuuagggg ugacuccuuc aca                                            23

<210> SEQ ID NO 410
<211> LENGTH: 23
<212> TYPE: RNA
<213> ORGANISM: Homo sapiens

<400> SEQUENCE: 410
auuuaggggu gacuccuuca cac                                            23

<210> SEQ ID NO 411
<211> LENGTH: 23
<212> TYPE: RNA
<213> ORGANISM: Homo sapiens

<400> SEQUENCE: 411
uuuaggggug acuccuucac aca                                            23

<210> SEQ ID NO 412
<211> LENGTH: 23
<212> TYPE: RNA
<213> ORGANISM: Homo sapiens

<400> SEQUENCE: 412
ccucuggauc cacaggaacu gga                                            23

<210> SEQ ID NO 413
<211> LENGTH: 23
<212> TYPE: RNA
<213> ORGANISM: Homo sapiens

<400> SEQUENCE: 413
uggauccaca ggaacuggau auu                                            23
```

```
<210> SEQ ID NO 414
<211> LENGTH: 23
<212> TYPE: RNA
<213> ORGANISM: Homo sapiens

<400> SEQUENCE: 414
ggauccacag gaacuggaua uuc                                              23

<210> SEQ ID NO 415
<211> LENGTH: 23
<212> TYPE: RNA
<213> ORGANISM: Homo sapiens

<400> SEQUENCE: 415
auccacagga acuggauauu cug                                              23

<210> SEQ ID NO 416
<211> LENGTH: 23
<212> TYPE: RNA
<213> ORGANISM: Homo sapiens

<400> SEQUENCE: 416
uccacaggaa cuggauauuc uga                                              23

<210> SEQ ID NO 417
<211> LENGTH: 23
<212> TYPE: RNA
<213> ORGANISM: Homo sapiens

<400> SEQUENCE: 417
gaacuggaua uucugaaaac cgu                                              23

<210> SEQ ID NO 418
<211> LENGTH: 23
<212> TYPE: RNA
<213> ORGANISM: Homo sapiens

<400> SEQUENCE: 418
auauucugaa aaccguaaag gaa                                              23

<210> SEQ ID NO 419
<211> LENGTH: 23
<212> TYPE: RNA
<213> ORGANISM: Homo sapiens

<400> SEQUENCE: 419
uauucugaaa accguaaagg aaa                                              23

<210> SEQ ID NO 420
<211> LENGTH: 23
<212> TYPE: RNA
<213> ORGANISM: Homo sapiens

<400> SEQUENCE: 420
ucugaaaacc guaaaggaaa uca                                              23

<210> SEQ ID NO 421
<211> LENGTH: 23
<212> TYPE: RNA
<213> ORGANISM: Homo sapiens

<400> SEQUENCE: 421
cugaaaaccg uaaaggaaau cac                                              23
```

<210> SEQ ID NO 422
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 422
cggccggagu cccgagcuat t                                              21

<210> SEQ ID NO 423
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 423
uagcucggga cuccggccgt t                                              21

<210> SEQ ID NO 424
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 424
ccggaguccc gagcuagcct t                                              21

<210> SEQ ID NO 425
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 425
ggcuagcucg ggacuccggt t                                              21

<210> SEQ ID NO 426
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 426
cggagucccg agcuagccct t                                              21

<210> SEQ ID NO 427
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 427
gggcuagcuc gggacuccgt t                                              21

<210> SEQ ID NO 428
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 428
ggagucccga gcuagcccct t                                              21

<210> SEQ ID NO 429
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 429
ggggcuagcu cgggacucct t                                              21

<210> SEQ ID NO 430
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 430
gagucccgag cuagccccgt t                                              21

<210> SEQ ID NO 431
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 431
cggggcuagc ucgggacuct t                                              21

<210> SEQ ID NO 432
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 432
agucccgagc uagccccggt t                                              21

<210> SEQ ID NO 433
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 433
ccggggcuag cucgggacut t                                              21

<210> SEQ ID NO 434
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 434
gucccgagcu agccccggct t                                              21

<210> SEQ ID NO 435
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 435
gccggggcua gcucgggact t                                              21

<210> SEQ ID NO 436
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 436
cccgagcuag ccccggcggt t    21

<210> SEQ ID NO 437
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 437
ccgccggggc uagcucgggt t    21

<210> SEQ ID NO 438
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 438
ggacgacagg ccaccucgut t    21

<210> SEQ ID NO 439
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 439
acgagguggc cugucgucct t    21

<210> SEQ ID NO 440
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 440
gacgacaggc caccucguct t    21

<210> SEQ ID NO 441
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 441
gacgaggugg ccugucguct t                                              21

<210> SEQ ID NO 442
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 442
acgacaggcc accucgucgt t                                              21

<210> SEQ ID NO 443
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 443
cgacgaggug gccugucgut t                                              21

<210> SEQ ID NO 444
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 444
cgacaggcca ccucgucggt t                                              21

<210> SEQ ID NO 445
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 445
ccgacgaggu ggccugucgt t                                              21

<210> SEQ ID NO 446
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

```
<400> SEQUENCE: 446
gacaggccac cucgucggct t                                              21

<210> SEQ ID NO 447
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 447
gccgacgagg uggccuguct t                                              21

<210> SEQ ID NO 448
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 448
caggccaccu cgucggcgut t                                              21

<210> SEQ ID NO 449
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 449
acgccgacga gguggccugt t                                              21

<210> SEQ ID NO 450
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 450
aggccaccuc gucggcguct t                                              21

<210> SEQ ID NO 451
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
```

-continued

Synthetic oligonucleotide

<400> SEQUENCE: 451
gacgccgacg agguggccut t                                              21

<210> SEQ ID NO 452
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 452
ggccaccucg ucggcgucct t                                              21

<210> SEQ ID NO 453
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 453
ggacgccgac gagguggcct t                                              21

<210> SEQ ID NO 454
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 454
gccaccucgu cggcguccgt t                                              21

<210> SEQ ID NO 455
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 455
cggacgccga cgagguggct t                                              21

<210> SEQ ID NO 456
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

```
<223> OTHER INFORMATION: Description of Combined DNA/RNA Molecule:
      Synthetic oligonucleotide

<400> SEQUENCE: 456
ccaccucguc ggcguccgct t                                              21

<210> SEQ ID NO 457
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 457
gcggacgccg acgagguggt t                                              21

<210> SEQ ID NO 458
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 458
caccucgucg gcguccgcct t                                              21

<210> SEQ ID NO 459
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 459
ggcggacgcc gacgaggugt t                                              21

<210> SEQ ID NO 460
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 460
accucgucgg cguccgccct t                                              21

<210> SEQ ID NO 461
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide

<400> SEQUENCE: 461
gggcggacgc cgacgaggut t                                              21

<210> SEQ ID NO 462
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 462
ccucgucggc guccgcccgt t                                              21

<210> SEQ ID NO 463
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 463
cgggcggacg ccgacgaggt t                                              21

<210> SEQ ID NO 464
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 464
cucgucggcg uccgcccgat t                                              21

<210> SEQ ID NO 465
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 465
ucgggcggac gccgacgagt t                                              21

<210> SEQ ID NO 466
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
```

Synthetic oligonucleotide

<400> SEQUENCE: 466
ucgucggcgu ccgcccgagt t                                              21

<210> SEQ ID NO 467
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 467
cucgggcgga cgccgacgat t                                              21

<210> SEQ ID NO 468
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 468
cgucggcguc cgcccgagut t                                              21

<210> SEQ ID NO 469
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 469
acucgggcgg acgccgacgt t                                              21

<210> SEQ ID NO 470
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 470
gucggcgucc gcccgaguct t                                              21

<210> SEQ ID NO 471
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

```
<223> OTHER INFORMATION: Description of Combined DNA/RNA Molecule:
      Synthetic oligonucleotide

<400> SEQUENCE: 471
gacucgggcg gacgccgact t                                              21

<210> SEQ ID NO 472
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 472
ucggcguccg cccgagucct t                                              21

<210> SEQ ID NO 473
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 473
ggacucgggc ggacgccgat t                                              21

<210> SEQ ID NO 474
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 474
gcguccgccc gaguccccgt t                                              21

<210> SEQ ID NO 475
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 475
cggggacucg ggcggacgct t                                              21

<210> SEQ ID NO 476
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide

<400> SEQUENCE: 476
cguccgcccg aguccccgct t                                          21

<210> SEQ ID NO 477
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 477
gcggggacuc gggcggacgt t                                          21

<210> SEQ ID NO 478
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 478
gcccgagucc ccgccucgct t                                          21

<210> SEQ ID NO 479
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 479
gcgaggcggg gacucgggct t                                          21

<210> SEQ ID NO 480
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 480
aacgccacaa ccaccgcgct t                                          21

<210> SEQ ID NO 481
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
```

Synthetic oligonucleotide

<400> SEQUENCE: 481
gcgcgguggu uguggcguut t                                    21

<210> SEQ ID NO 482
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 482
acgccacaac caccgcgcat t                                    21

<210> SEQ ID NO 483
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 483
ugcgcggugg uuguggcgut t                                    21

<210> SEQ ID NO 484
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 484
cgccacaacc accgcgcact t                                    21

<210> SEQ ID NO 485
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 485
gugcgcggug guuguggcgt t                                    21

<210> SEQ ID NO 486
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 486
ccacaaccac cgcgcacggt t                                    21

<210> SEQ ID NO 487

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 487
ccgugcgcgg ugguuguggt t                                              21

<210> SEQ ID NO 488
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 488
cacaaccacc gcgcacggct t                                              21

<210> SEQ ID NO 489
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 489
gccgugcgcg gugguugugt t                                              21

<210> SEQ ID NO 490
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 490
acaaccaccg cgcacggcct t                                              21

<210> SEQ ID NO 491
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 491
ggccgugcgc ggugguugut t                                              21

<210> SEQ ID NO 492
<211> LENGTH: 21
<212> TYPE: DNA
<213> ORGANISM: Artificial Sequence
<220> FEATURE:
<223> OTHER INFORMATION: Description of Artificial Sequence: Synthetic
```

```
      oligonucleotide
<220> FEATURE:
<223> OTHER INFORMATION: Description of Combined DNA/RNA Molecule:
      Synthetic oligonucleotide

<400> SEQUENCE: 492
augcgacccu ccgggacggt t                                            21

<210> SEQ ID NO 493
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 493
ccgucccgga gggucgcaut t                                            21

<210> SEQ ID NO 494
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 494
ugcgacccuc cgggacggct t                                            21

<210> SEQ ID NO 495
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 495
gccgucccgg agggucgcat t                                            21

<210> SEQ ID NO 496
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 496
gcgacccucc gggacggcct t                                            21

<210> SEQ ID NO 497
<211> LENGTH: 21
<212> TYPE: DNA
<213> ORGANISM: Artificial Sequence
<220> FEATURE:
```

<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 497
ggccgucccg gagggucgct t                                              21

<210> SEQ ID NO 498
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 498
gacccuccgg gacggccggt t                                              21

<210> SEQ ID NO 499
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 499
ccggccgucc cggaggguct t                                              21

<210> SEQ ID NO 500
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 500
acccuccggg acggccgggt t                                              21

<210> SEQ ID NO 501
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 501
cccggccguc ccggagggut t                                              21

<210> SEQ ID NO 502
<211> LENGTH: 21
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 502
ccuccgggac ggccggggct t                                              21

<210> SEQ ID NO 503
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 503
gccccggccg ucccggaggt t                                              21

<210> SEQ ID NO 504
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 504
agaaaguuug ccaaggcact t                                              21

<210> SEQ ID NO 505
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 505
gugccuuggc aaacuuucut t                                              21

<210> SEQ ID NO 506
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 506
gaaaguuugc caaggcacgt t                                              21

<210> SEQ ID NO 507
<211> LENGTH: 21
<212> TYPE: DNA
```

<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 507
cgugccuugg caaacuuuct t                                              21

<210> SEQ ID NO 508
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 508
aaguuugcca aggcacgagt t                                              21

<210> SEQ ID NO 509
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 509
cucgugccuu ggcaaacuut t                                              21

<210> SEQ ID NO 510
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 510
aguuugccaa ggcacgagut t                                              21

<210> SEQ ID NO 511
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 511
acucgugccu uggcaaacut t                                              21

<210> SEQ ID NO 512
<211> LENGTH: 21

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 512
guuugccaag gcacgaguat t                                              21

<210> SEQ ID NO 513
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 513
uacucgugcc uuggcaaact t                                              21

<210> SEQ ID NO 514
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 514
uuugccaagg cacgaguaat t                                              21

<210> SEQ ID NO 515
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 515
uuacucgugc cuuggcaaat t                                              21

<210> SEQ ID NO 516
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 516
uugccaaggc acgaguaact t                                              21

<210> SEQ ID NO 517
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 517
guuacucgug ccuuggcaat t                                              21

<210> SEQ ID NO 518
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 518
ugccaaggca cgaguaacat t                                              21

<210> SEQ ID NO 519
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 519
uguuacucgu gccuuggcat t                                              21

<210> SEQ ID NO 520
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 520
gccaaggcac gaguaacaat t                                              21

<210> SEQ ID NO 521
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 521
uuguuacucg ugccuuggct t                                              21
```

```
<210> SEQ ID NO 522
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 522
acgcaguugg gcacuuuugt t                                              21

<210> SEQ ID NO 523
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 523
caaaagugcc caacugcgut t                                              21

<210> SEQ ID NO 524
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 524
cgcaguuggg cacuuuugat t                                              21

<210> SEQ ID NO 525
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 525 ucaaaaguge ccaacugcgt t                                              21

<210> SEQ ID NO 526
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 526
gcaguugggc acuuuugaat t                                              21
```

<210> SEQ ID NO 527
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 527
uucaaaagug cccaacugct t                                              21

<210> SEQ ID NO 528
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 528
caguugggca cuuugaagt t                                               21

<210> SEQ ID NO 529
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 529
cuucaaaagu gcccaacugt t                                              21

<210> SEQ ID NO 530
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 530
aguugggcac uuugaagat t                                               21

<210> SEQ ID NO 531
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 531
ucuucaaaag ugcccaacut t                                              21

<210> SEQ ID NO 532
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 532
guugggcacu uugaagaut t                                          21

<210> SEQ ID NO 533
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 533
aucuucaaaa gugcccaact t                                         21

<210> SEQ ID NO 534
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 534
uugggcacuu ugaagauct t                                          21

<210> SEQ ID NO 535
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 535
gaucuucaaa agugcccaat t                                         21

<210> SEQ ID NO 536
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 536
ugggcacuuu ugaagaucat t                21

<210> SEQ ID NO 537
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 537
ugaucuucaa aagugcccat t                21

<210> SEQ ID NO 538
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 538
gggcacuuuu gaagaucaut t                21

<210> SEQ ID NO 539
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 539
augaucuuca aaagugccct t                21

<210> SEQ ID NO 540
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 540
uugaagauca uuuucucagt t                21

<210> SEQ ID NO 541
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 541

```
cugagaaaau gaucuucaat t                                                  21

<210> SEQ ID NO 542
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 542
gaagaucauu uucucagcct t                                                  21

<210> SEQ ID NO 543
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 543
ggcugagaaa augaucuuct t                                                  21

<210> SEQ ID NO 544
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 544
aagaucauuu ucucagccut t                                                  21

<210> SEQ ID NO 545
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 545
aggcugagaa aaugaucuut t                                                  21

<210> SEQ ID NO 546
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

```
<400> SEQUENCE: 546
cauuuucuca gccuccagat t                                              21

<210> SEQ ID NO 547
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 547
ucuggaggcu gagaaaaugt t                                              21

<210> SEQ ID NO 548
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 548
agccuccaga ggauguucat t                                              21

<210> SEQ ID NO 549
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 549
ugaacauccu cuggaggcut t                                              21

<210> SEQ ID NO 550
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 550
ccuccagagg auguucaaut t                                              21

<210> SEQ ID NO 551
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

```
<400> SEQUENCE: 551
auugaacauc cucuggaggt t                                                 21

<210> SEQ ID NO 552
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 552
cuccagagga uguucaauat t                                                 21

<210> SEQ ID NO 553
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 553
uauugaacau ccucuggagt t                                                 21

<210> SEQ ID NO 554
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 554
agaggauguu caauaacugt t                                                 21

<210> SEQ ID NO 555
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 555
caguuauuga acauccucut t                                                 21

<210> SEQ ID NO 556
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
```

```
                              Synthetic oligonucleotide

<400> SEQUENCE: 556
aggauguuca auaacugugt t                                              21

<210> SEQ ID NO 557
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 557
cacaguuauu gaacauccut t                                              21

<210> SEQ ID NO 558
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 558
uguucaauaa cugugaggut t                                              21

<210> SEQ ID NO 559
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 559
accucacagu uauugaacat t                                              21

<210> SEQ ID NO 560
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 560
uucaauaacu gugagguggt t                                              21

<210> SEQ ID NO 561
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

```
<223> OTHER INFORMATION: Description of Combined DNA/RNA Molecule:
      Synthetic oligonucleotide

<400> SEQUENCE: 561
ccaccucaca guuauugaat t                                              21

<210> SEQ ID NO 562
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 562
ucaauaacug ugagguggut t                                              21

<210> SEQ ID NO 563
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 563
accaccucac aguuauugat t                                              21

<210> SEQ ID NO 564
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 564
caauaacugu gaggugguct t                                              21

<210> SEQ ID NO 565
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 565
gaccaccuca caguuauugt t                                              21

<210> SEQ ID NO 566
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide

<400> SEQUENCE: 566
aauaacugug agguggucct t                                               21

<210> SEQ ID NO 567
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 567
ggaccaccuc acaguuauut t                                               21

<210> SEQ ID NO 568
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 568
auaacuguga ggugguccut t                                               21

<210> SEQ ID NO 569
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 569
aggaccaccu cacaguuaut t                                               21

<210> SEQ ID NO 570
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 570
uaacugugag gugguccuut t                                               21

<210> SEQ ID NO 571
<211> LENGTH: 21
<212> TYPE: DNA
<213> ORGANISM: Artificial Sequence
<220> FEATURE:
<223> OTHER INFORMATION: Description of Artificial Sequence: Synthetic
``` oligonucleotide
<220> FEATURE:
<223> OTHER INFORMATION: Description of Combined DNA/RNA Molecule:
    Synthetic oligonucleotide

<400> SEQUENCE: 571
aaggaccacc ucacaguuat t                                              21

<210> SEQ ID NO 572
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 572
acugugaggu gguccuuggt t                                              21

<210> SEQ ID NO 573
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 573
ccaaggacca ccucacagut t                                              21

<210> SEQ ID NO 574
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 574
ugugaggugg uccuugggat t                                              21

<210> SEQ ID NO 575
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 575
ucccaaggac caccucacat t                                              21

<210> SEQ ID NO 576
<211> LENGTH: 21
<212> TYPE: DNA
<213> ORGANISM: Artificial Sequence
<220> FEATURE:

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 576
gugagguggu ccuugggaat t                                                  21

<210> SEQ ID NO 577
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 577
uucccaagga ccaccucact t                                                  21

<210> SEQ ID NO 578
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 578
ugguccuugg gaauuuggat t                                                  21

<210> SEQ ID NO 579
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 579
uccaaauucc caaggaccat t                                                  21

<210> SEQ ID NO 580
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 580
uugggaauuu ggaaauuact t                                                  21

<210> SEQ ID NO 581
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 581
guaauuucca aauucccaat t                                              21

<210> SEQ ID NO 582
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 582 ugggauuug gaaauuacct t                                               21

<210> SEQ ID NO 583
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 583
gguaauuucc aaauucccat t                                              21

<210> SEQ ID NO 584
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 584
gggaauuugg aaauuaccut t                                              21

<210> SEQ ID NO 585
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 585
agguaauuuc caaauuccct t                                              21

<210> SEQ ID NO 586
<211> LENGTH: 21
<212> TYPE: DNA
```

<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 586
ggaauuugga aauuaccuat t                                              21

<210> SEQ ID NO 587
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 587
uagguaauuu ccaaauucct t                                              21

<210> SEQ ID NO 588
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 588
agaggaauua ugaucuuuct t                                              21

<210> SEQ ID NO 589
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 589
gaaagaucau aauuccucut t                                              21

<210> SEQ ID NO 590
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 590
gaggaauuau gaucuuucct t                                              21

<210> SEQ ID NO 591
<211> LENGTH: 21

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 591
ggaaagauca uaauuccuct t                                               21

<210> SEQ ID NO 592
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 592
aauuaugauc uuuccuucut t                                               21

<210> SEQ ID NO 593
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 593
agaaggaaag aucauaauut t                                               21

<210> SEQ ID NO 594
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 594
auuaugaucu uuccuucuut t                                               21

<210> SEQ ID NO 595
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 595
aagaaggaaa gaucauaaut t                                               21

<210> SEQ ID NO 596
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 596
uaugaucuuu ccuucuuaat t                                              21

<210> SEQ ID NO 597
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 597
uuaagaagga aagaucauat t                                              21

<210> SEQ ID NO 598
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 598
ugaucuuucc uucuuaaagt t                                              21

<210> SEQ ID NO 599
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 599
cuuuaagaag gaaagaucat t                                              21

<210> SEQ ID NO 600
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 600
ucuuuccuuc uuaaagacct t                                              21
```

```
<210> SEQ ID NO 601
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 601
ggucuuuaag aaggaaagat t                                              21

<210> SEQ ID NO 602
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 602
ccuucuuaaa gaccauccat t                                              21

<210> SEQ ID NO 603
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 603
uggauggucu uuaagaaggt t                                              21

<210> SEQ ID NO 604
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 604
cuucuuaaag accauccagt t                                              21

<210> SEQ ID NO 605
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 605
cuggaugguc uuuaagaagt t                                              21
```

<210> SEQ ID NO 606
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 606
ucuuaaagac cauccaggat t                                              21

<210> SEQ ID NO 607
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 607
uccuggaugg ucuuuaagat t                                              21

<210> SEQ ID NO 608
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 608
uuaaagacca uccaggaggt t                                              21

<210> SEQ ID NO 609
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 609
ccuccuggau ggucuuuaat t                                              21

<210> SEQ ID NO 610
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 610
uaaagaccau ccaggaggut t                                              21

<210> SEQ ID NO 611
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 611
accuccugga uggucuuuat t                                              21

<210> SEQ ID NO 612
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 612
ccaggaggug gcugguuaut t                                              21

<210> SEQ ID NO 613
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 613
auaaccagcc accuccuggt t                                              21

<210> SEQ ID NO 614
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 614
caggaggugg cugguuaugt t                                              21

<210> SEQ ID NO 615
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 615

```
cauaaccagc caccuccugt t                                          21

<210> SEQ ID NO 616
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 616
aggagguggc ugguuaugut t                                          21

<210> SEQ ID NO 617
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 617
acauaaccag ccaccuccut t                                          21

<210> SEQ ID NO 618
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 618
ggagguggcu gguuauguct t                                          21

<210> SEQ ID NO 619
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 619
gacauaacca gccaccucct t                                          21

<210> SEQ ID NO 620
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 620
```
gagguggcug guuaugucct t                                              21

<210> SEQ ID NO 621
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 621
ggacauaacc agccaccuct t                                              21

<210> SEQ ID NO 622
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 622
agguggcugg uuaugsccut t                                              21

<210> SEQ ID NO 623
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 623
aggacauaac cagccaccut t                                              21

<210> SEQ ID NO 624
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 624
guggcugguu auguccucat t                                              21

<210> SEQ ID NO 625
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide -continued

```
<400> SEQUENCE: 625
ugaggacaua accagccact t                                          21

<210> SEQ ID NO 626
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 626
gcccucaaca caguggagct t                                          21

<210> SEQ ID NO 627
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 627
gcuccacugu guugagggct t                                          21

<210> SEQ ID NO 628
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 628
uuccuuugga aaaccugcat t                                          21

<210> SEQ ID NO 629
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 629
ugcagguuuu ccaaaggaat t                                          21

<210> SEQ ID NO 630
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

<400> SEQUENCE: 630
uccuuuggaa aaccugcagt t                                              21

<210> SEQ ID NO 631
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 631
cugcagguuu uccaaaggat t                                              21

<210> SEQ ID NO 632
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 632
gaaaaccugc agaucaucat t                                              21

<210> SEQ ID NO 633
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 633
ugaugaucug cagguuuuct t                                              21

<210> SEQ ID NO 634
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 634
aaaaccugca gaucaucagt t                                              21

<210> SEQ ID NO 635
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

Synthetic oligonucleotide

<400> SEQUENCE: 635
cugaugaucu gcagguuuut t                                              21

<210> SEQ ID NO 636
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 636
aaccugcaga ucaucagagt t                                              21

<210> SEQ ID NO 637
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 637
cucugaugau cugcagguut t                                              21

<210> SEQ ID NO 638
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 638
cugcagauca ucagaggaat t                                              21

<210> SEQ ID NO 639
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 639
uuccucugau gaucugcagt t                                              21

<210> SEQ ID NO 640
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

<223> OTHER INFORMATION: Description of Combined DNA/RNA Molecule:
      Synthetic oligonucleotide

<400> SEQUENCE: 640
gaaaauuccu augccuuagt t                                              21

<210> SEQ ID NO 641
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 641
cuaaggcaua ggaauuuuct t                                              21

<210> SEQ ID NO 642
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 642
aaaauuccua ugccuuagct t                                              21

<210> SEQ ID NO 643
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 643
gcuaaggcau aggaauuuut t                                              21

<210> SEQ ID NO 644
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 644
aauuccuaug ccuuagcagt t                                              21

<210> SEQ ID NO 645
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

```
<220> FEATURE:
<223> OTHER INFORMATION: Description of Combined DNA/RNA Molecule:
      Synthetic oligonucleotide

<400> SEQUENCE: 645
cugcuaaggc auaggaauut t                                              21

<210> SEQ ID NO 646
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 646
uccuaugccu uagcagucut t                                              21

<210> SEQ ID NO 647
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 647
agacugcuaa ggcauaggat t                                              21

<210> SEQ ID NO 648
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 648
ccuaugccuu agcagucuut t                                              21

<210> SEQ ID NO 649
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 649
aagacugcua aggcauaggt t                                              21

<210> SEQ ID NO 650
<211> LENGTH: 21
<212> TYPE: DNA
<213> ORGANISM: Artificial Sequence
<220> FEATURE:
<223> OTHER INFORMATION: Description of Artificial Sequence: Synthetic
```

```
        oligonucleotide
<220> FEATURE:
<223> OTHER INFORMATION: Description of Combined DNA/RNA Molecule:
      Synthetic oligonucleotide

<400> SEQUENCE: 650
cuaugccuua gcagucuuat t                                              21

<210> SEQ ID NO 651
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 651
uaagacugcu aaggcauagt t                                              21

<210> SEQ ID NO 652
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 652
augccuuagc agucuuauct t                                              21

<210> SEQ ID NO 653
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 653
gauaagacug cuaaggcaut t                                              21

<210> SEQ ID NO 654
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 654
ugccuuagca gucuuaucut t                                              21

<210> SEQ ID NO 655
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 655
agauaagacu gcuaaggcat t                                                  21

<210> SEQ ID NO 656
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 656
gccuuagcag ucuuaucuat t                                                  21

<210> SEQ ID NO 657
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 657
uagauaagac ugcuaaggct t                                                  21

<210> SEQ ID NO 658
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 658
ccuuagcagu cuuaucuaat t                                                  21

<210> SEQ ID NO 659
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 659
uuagauaaga cugcuaaggt t                                                  21

<210> SEQ ID NO 660
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 660
cuuagcaguc uuaucuaact t                                              21

<210> SEQ ID NO 661
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 661
guuagauaag acugcuaagt t                                              21

<210> SEQ ID NO 662
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 662
uuagcagucu uaucuaacut t                                              21

<210> SEQ ID NO 663
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 663
aguuagauaa gacugcuaat t                                              21

<210> SEQ ID NO 664
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 664
uagcagucuu aucuaacuat t                                              21

<210> SEQ ID NO 665
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 665
uaguuagaua agacugcuat t                                                    21

<210> SEQ ID NO 666
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 666
agcagucuua ucuaacuaut t                                                    21

<210> SEQ ID NO 667
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 667
auaguuagau aagacugcut t                                                    21

<210> SEQ ID NO 668
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 668
gcagucuuau cuaacuaugt t                                                    21

<210> SEQ ID NO 669
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 669
cauaguuaga uaagacugct t                                                    21

<210> SEQ ID NO 670
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 670
cagucuuauc uaacuaugat t                                              21

<210> SEQ ID NO 671
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 671
ucauaguuag auaagacugt t                                              21

<210> SEQ ID NO 672
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 672
ucuuaucuaa cuaugaugct t                                              21

<210> SEQ ID NO 673
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 673
gcaucauagu uagauaagat t                                              21

<210> SEQ ID NO 674
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 674
cuuaucuaac uaugaugcat t                                              21

<210> SEQ ID NO 675
```

<210> SEQ ID NO 675
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 675
ugcaucauag uuagauaagt t                                             21

<210> SEQ ID NO 676
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 676
uuaucuaacu augaugcaat t                                             21

<210> SEQ ID NO 677
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 677
uugcaucaua guuagauaat t                                             21

<210> SEQ ID NO 678
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 678
uaucuaacua ugaugcaaat t                                             21

<210> SEQ ID NO 679
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 679
uuugcaucau aguuagauat t                                             21

```
<210> SEQ ID NO 680
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 680
aucuaacuau gaugcaaaut t                                                    21

<210> SEQ ID NO 681
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 681
auuugcauca uaguuagaut t                                                    21

<210> SEQ ID NO 682
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 682
ucuaacuaug augcaaauat t                                                    21

<210> SEQ ID NO 683
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 683
uauuugcauc auaguuagat t                                                    21

<210> SEQ ID NO 684
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 684
cuaacuauga ugcaaauaat t                                                    21
```

<210> SEQ ID NO 685
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 685
uuauuugcau cauaguuagt t                                              21

<210> SEQ ID NO 686
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 686
aacuaugaug caaauaaaat t                                              21

<210> SEQ ID NO 687
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 687
uuuuauuugc aucauaguut t                                              21

<210> SEQ ID NO 688
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 688
gaugcaaaua aaaccggact t                                              21

<210> SEQ ID NO 689
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 689
guccgguuuu auuugcauct t                                              21

<210> SEQ ID NO 690
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 690
augcaaauaa aaccggacut t                                            21

<210> SEQ ID NO 691
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 691
aguccgguuu uauuugcaut t                                            21

<210> SEQ ID NO 692
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 692
ugcaaauaaa accggacugt t                                            21

<210> SEQ ID NO 693
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 693
caguccgguu uuauuugcat t                                            21

<210> SEQ ID NO 694
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 694
caaauaaaac cggacugaat t 21

<210> SEQ ID NO 695
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 695
uucaguccgg uuuuauuugt t 21

<210> SEQ ID NO 696
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 696
aaauaaaacc ggacugaagt t 21

<210> SEQ ID NO 697
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 697
cuucaguccg guuuuauuut t 21

<210> SEQ ID NO 698
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 698
aauaaaaccg gacugaaggt t 21

<210> SEQ ID NO 699
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 699

```
ccuucagucc gguuuuauut t                                          21

<210> SEQ ID NO 700
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 700
uaaaaccgga cugaaggagt t                                          21

<210> SEQ ID NO 701
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 701
cuccuucagu ccgguuuuat t                                          21

<210> SEQ ID NO 702
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 702
aaaaccggac ugaaggagct t                                          21

<210> SEQ ID NO 703
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 703
gcuccuucag uccgguuuut t                                          21

<210> SEQ ID NO 704
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

<400> SEQUENCE: 704
aaaccggacu gaaggagcut t                                               21

<210> SEQ ID NO 705
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 705
agcuccuuca guccgguuut t                                               21

<210> SEQ ID NO 706
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 706
aaccggacug aaggagcugt t                                               21

<210> SEQ ID NO 707
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 707
cagcuccuuc aguccgguut t                                               21

<210> SEQ ID NO 708
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 708
aggagcugcc caugagaaat t                                               21

<210> SEQ ID NO 709
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 709
uuucucaugg gcagcuccut t                                              21

<210> SEQ ID NO 710
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 710
uacaggaaau ccugcauggt t                                              21

<210> SEQ ID NO 711
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 711
ccaugcagga uuuccuguat t                                              21

<210> SEQ ID NO 712
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 712
aggaaauccu gcauggcgct t                                              21

<210> SEQ ID NO 713
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 713
gcgccaugca ggauuuccut t                                              21

<210> SEQ ID NO 714
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

Synthetic oligonucleotide

<400> SEQUENCE: 714
ggaaauccug cauggcgcct t								21

<210> SEQ ID NO 715
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 715
ggcgccaugc aggauuucct t								21

<210> SEQ ID NO 716
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 716
gaaauccugc auggcgccgt t								21

<210> SEQ ID NO 717
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 717
cggcgccaug caggauuuct t								21

<210> SEQ ID NO 718
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 718
aaauccugca uggcgccgut t								21

<210> SEQ ID NO 719
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

```
<223> OTHER INFORMATION: Description of Combined DNA/RNA Molecule:
      Synthetic oligonucleotide

<400> SEQUENCE: 719
acggcgccau gcaggauuut t                                              21

<210> SEQ ID NO 720
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 720
aauccugcau ggcgccgugt t                                              21

<210> SEQ ID NO 721
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 721
cacggcgcca ugcaggauut t                                              21

<210> SEQ ID NO 722
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 722
uccugcaugg cgccgugcgt t                                              21

<210> SEQ ID NO 723
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 723
cgcacggcgc caugcaggat t                                              21

<210> SEQ ID NO 724
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide

<400> SEQUENCE: 724
cugcauggcg ccgugcggut t                                              21

<210> SEQ ID NO 725
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 725
accgcacggc gccaugcagt t                                              21

<210> SEQ ID NO 726
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 726
ugcauggcgc cgugcgguut t                                              21

<210> SEQ ID NO 727
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 727
aaccgcacgg cgccaugcat t                                              21

<210> SEQ ID NO 728
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 728
gcauggcgcc gugcgguuct t                                              21

<210> SEQ ID NO 729
<211> LENGTH: 21
<212> TYPE: DNA
<213> ORGANISM: Artificial Sequence
<220> FEATURE:
<223> OTHER INFORMATION: Description of Artificial Sequence: Synthetic
```

```
                              oligonucleotide
<220> FEATURE:
<223> OTHER INFORMATION: Description of Combined DNA/RNA Molecule:
      Synthetic oligonucleotide

<400> SEQUENCE: 729
gaaccgcacg gcgccaugct t                                              21

<210> SEQ ID NO 730
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 730
auggcgccgu gcgguucagt t                                              21

<210> SEQ ID NO 731
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 731
cugaaccgca cggcgccaut t                                              21

<210> SEQ ID NO 732
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 732
uggcgccgug cgguucagct t                                              21

<210> SEQ ID NO 733
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 733
gcugaaccgc acggcgccat t                                              21

<210> SEQ ID NO 734
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 734
ggcgccgugc gguucagcat t                                             21

<210> SEQ ID NO 735
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 735
ugcugaaccg cacggcgcct t                                             21

<210> SEQ ID NO 736
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 736
gcgccgugcg guucagcaat t                                             21

<210> SEQ ID NO 737
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 737
uugcugaacc gcacggcgct t                                             21

<210> SEQ ID NO 738
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 738
cgccgugcgg uucagcaact t                                             21

<210> SEQ ID NO 739
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 739
guugcugaac cgcacggcgt t                                          21

<210> SEQ ID NO 740
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 740
gccgugcggu ucagcaacat t                                          21

<210> SEQ ID NO 741
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 741
uguugcugaa ccgcacggct t                                          21

<210> SEQ ID NO 742
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 742
ccgugcgguu cagcaacaat t                                          21

<210> SEQ ID NO 743
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 743
uuguugcuga accgcacggt t                                          21

<210> SEQ ID NO 744
<211> LENGTH: 21
<212> TYPE: DNA
```

<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 744
gugcgguuca gcaacaacct t                                              21

<210> SEQ ID NO 745
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 745
gguuguugcu gaaccgcact t                                              21

<210> SEQ ID NO 746
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 746
gcgguucagc aacaacccut t                                              21

<210> SEQ ID NO 747
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 747
aggguuguug cugaaccgct t                                              21

<210> SEQ ID NO 748
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 748
gguucagcaa caaccugct t                                               21

<210> SEQ ID NO 749
<211> LENGTH: 21

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 749
gcaggguugu ugcugaacct t                                           21

<210> SEQ ID NO 750
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 750
gcaacaaccc ugcccugugt t                                           21

<210> SEQ ID NO 751
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 751
cacagggcag gguuguugct t                                           21

<210> SEQ ID NO 752
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 752
aacaacccug cccugugcat t                                           21

<210> SEQ ID NO 753
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 753
ugcacagggc aggguuguut t                                           21

<210> SEQ ID NO 754
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 754
acguggagag cauccagugt t                                              21

<210> SEQ ID NO 755
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 755
cacuggaugc ucuccacgut t                                              21

<210> SEQ ID NO 756
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 756
cguggagagc auccaguggt t                                              21

<210> SEQ ID NO 757
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 757
ccacuggaug cucuccacgt t                                              21

<210> SEQ ID NO 758
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 758
guggagagca uccaguggct t                                              21
```

```
<210> SEQ ID NO 759
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 759
gccacuggau gcucuccact t                                              21

<210> SEQ ID NO 760
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 760
gagagcaucc aguggcgggt t                                              21

<210> SEQ ID NO 761
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 761
cccgccacug gaugcucuct t                                              21

<210> SEQ ID NO 762
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 762
agagcaucca guggcgggat t                                              21

<210> SEQ ID NO 763
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 763
ucccgccacu ggaugcucut t                                              21
```

```
<210> SEQ ID NO 764
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 764
gagcauccag uggcgggact t                                            21

<210> SEQ ID NO 765
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 765
gucccgccac uggaugcuct t                                            21

<210> SEQ ID NO 766
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 766
caguggcggg acauagucat t                                            21

<210> SEQ ID NO 767
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 767
ugacuauguc ccgccacugt t                                            21

<210> SEQ ID NO 768
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 768
aguggcggga cauagucagt t                                            21
```

<210> SEQ ID NO 769
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 769
cugacuaugu cccgccacut t                                               21

<210> SEQ ID NO 770
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 770
uggcgggaca uagucagcat t                                               21

<210> SEQ ID NO 771
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 771
ugcugacuau gucccgccat t                                               21

<210> SEQ ID NO 772
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 772
ggcgggacau agucagcagt t                                               21

<210> SEQ ID NO 773
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 773
cugcugacua ugucccgcct t                                        21

<210> SEQ ID NO 774
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 774
cucagcaaca ugucgauggt t                                        21

<210> SEQ ID NO 775
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 775
ccaucgacau guugcugagt t                                        21

<210> SEQ ID NO 776
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 776
cagcaacaug ucgauggact t                                        21

<210> SEQ ID NO 777
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 777
guccaucgac auguugcugt t                                        21

<210> SEQ ID NO 778
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 778
agcaacaugu cgauggacut t                                              21

<210> SEQ ID NO 779
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 779
aguccaucga cauguugcut t                                              21

<210> SEQ ID NO 780
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 780
gcaacauguc gauggacuut t                                              21

<210> SEQ ID NO 781
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 781
aaguccaucg acauguugct t                                              21

<210> SEQ ID NO 782
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 782
aacaugucga uggacuucct t                                              21

<210> SEQ ID NO 783
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

```
<400> SEQUENCE: 783
ggaaguccau cgacauguut t                                              21

<210> SEQ ID NO 784
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 784
acaugucgau ggacuuccat t                                              21

<210> SEQ ID NO 785
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 785
uggaagucca ucgacaugut t                                              21

<210> SEQ ID NO 786
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 786
caugucgaug gacuuccagt t                                              21

<210> SEQ ID NO 787
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 787
cuggaagucc aucgacaugt t                                              21

<210> SEQ ID NO 788
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

-continued

<400> SEQUENCE: 788
augucgaugg acuuccagat t                                              21

<210> SEQ ID NO 789
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 789
ucuggaaguc caucgacaut t                                              21

<210> SEQ ID NO 790
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 790
ucgauggacu uccagaacct t                                              21

<210> SEQ ID NO 791
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 791
gguucuggaa guccaucgat t                                              21

<210> SEQ ID NO 792
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 792
gaaccaccug ggcagcugct t                                              21

<210> SEQ ID NO 793
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

Synthetic oligonucleotide

<400> SEQUENCE: 793
gcagcugccc aggugguuct t                                              21

<210> SEQ ID NO 794
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 794
gggcagcugc caaaagugut t                                              21

<210> SEQ ID NO 795
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 795
acacuuuugg cagcugccct t                                              21

<210> SEQ ID NO 796
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 796
gcagcugcca aaagugugat t                                              21

<210> SEQ ID NO 797
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 797
ucacacuuuu ggcagcugct t                                              21

<210> SEQ ID NO 798
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

<223> OTHER INFORMATION: Description of Combined DNA/RNA Molecule:
     Synthetic oligonucleotide

<400> SEQUENCE: 798
ugccaaaagu gugauccaat t                                              21

<210> SEQ ID NO 799
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 799
uuggaucaca cuuuggcat t                                               21

<210> SEQ ID NO 800
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 800
gccaaaagug ugauccaagt t                                              21

<210> SEQ ID NO 801
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 801
cuuggaucac acuuuggct t                                               21

<210> SEQ ID NO 802
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 802
ccaaaagugu gauccaagct t                                              21

<210> SEQ ID NO 803
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

```
<220> FEATURE:
<223> OTHER INFORMATION: Description of Combined DNA/RNA Molecule:
      Synthetic oligonucleotide

<400> SEQUENCE: 803
gcuuggauca cacuuuggt t                                                    21

<210> SEQ ID NO 804
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 804
aaagugugau ccaagcugut t                                                   21

<210> SEQ ID NO 805
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 805
acagcuugga ucacacuuut t                                                   21

<210> SEQ ID NO 806
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 806
ugugauccaa gcugucccat t                                                   21

<210> SEQ ID NO 807
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 807
ugggacagcu uggaucacat t                                                   21

<210> SEQ ID NO 808
<211> LENGTH: 21
<212> TYPE: DNA
<213> ORGANISM: Artificial Sequence
<220> FEATURE:
<223> OTHER INFORMATION: Description of Artificial Sequence: Synthetic
```

```
      oligonucleotide
<220> FEATURE:
<223> OTHER INFORMATION: Description of Combined DNA/RNA Molecule:
      Synthetic oligonucleotide

<400> SEQUENCE: 808
gugauccaag cugucccaat t                                              21

<210> SEQ ID NO 809
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 809
uugggacagc uuggaucact t                                              21

<210> SEQ ID NO 810
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 810
gauccaagcu gucccaaugt t                                              21

<210> SEQ ID NO 811
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 811 cauuggggaca gcuuggauct t                                             21

<210> SEQ ID NO 812
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 812
auccaagcug ucccaauggt t                                              21

<210> SEQ ID NO 813
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 813
ccauugggac agcuuggaut t                                               21

<210> SEQ ID NO 814
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 814
uccaagcugu cccaaugggt t                                               21

<210> SEQ ID NO 815
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 815
cccauuggga cagcuuggat t                                               21

<210> SEQ ID NO 816
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 816
ccaagcuguc ccaaugggat t                                               21

<210> SEQ ID NO 817
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 817
ucccauuggg acagcuuggt t                                               21

<210> SEQ ID NO 818
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 818
caagcugucc caaugggagt t                                              21

<210> SEQ ID NO 819
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 819
cucccauugg gacagcuugt t                                              21

<210> SEQ ID NO 820
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 820
agcuguccca augggagcut t                                              21

<210> SEQ ID NO 821
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 821
agcucccauu gggacagcut t                                              21

<210> SEQ ID NO 822
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 822
ugucccaaug ggagcugcut t                                              21

<210> SEQ ID NO 823
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 823
agcagcuccc auuggacat t                                              21

<210> SEQ ID NO 824
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 824
ggugcaggag aggagaacut t                                             21

<210> SEQ ID NO 825
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 825
aguucuccuc uccugcacct t                                             21

<210> SEQ ID NO 826
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 826
aaacugacca aaaucaucut t                                             21

<210> SEQ ID NO 827
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 827
agaugauuuu ggucaguuut t                                             21

<210> SEQ ID NO 828
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 828
aacugaccaa aaucaucugt t                                            21

<210> SEQ ID NO 829
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 829
cagaugauuu uggucaguut t                                            21

<210> SEQ ID NO 830
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 830
acugaccaaa aucaucugut t                                            21

<210> SEQ ID NO 831
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 831
acagaugauu uuggucagut t                                            21

<210> SEQ ID NO 832
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 832
accaaaauca ucugugccct t                                            21

<210> SEQ ID NO 833
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 833
gggcacagau gauuuuggut t                                              21

<210> SEQ ID NO 834
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 834
ccaaaaucau cugugcccat t                                              21

<210> SEQ ID NO 835
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 835
ugggcacaga ugauuuuggt t                                              21

<210> SEQ ID NO 836
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 836
aaaucaucug ugcccagcat t                                              21

<210> SEQ ID NO 837
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 837
ugcugggcac agaugauuut t                                              21
```

```
<210> SEQ ID NO 838
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 838
gugcccagca gugcuccggt t                                              21

<210> SEQ ID NO 839
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 839
ccggagcacu gcugggcact t                                              21

<210> SEQ ID NO 840
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 840
gcccagcagu gcuccgggct t                                              21

<210> SEQ ID NO 841
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 841
gcccggagca cugcugggct t                                              21

<210> SEQ ID NO 842
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 842
ccagugacug cugccacaat t                                              21
```

<210> SEQ ID NO 843
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 843
uuguggcagc agucacuggt t                                                 21

<210> SEQ ID NO 844
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 844
cagugacugc ugccacaact t                                                 21

<210> SEQ ID NO 845
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 845
guuguggcag cagucacugt t                                                 21

<210> SEQ ID NO 846
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 846
gagagcgacu gccuggucut t                                                 21

<210> SEQ ID NO 847
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 847
agaccaggca gucgcucuct t                                                 21

-continued

<210> SEQ ID NO 848
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 848
agagcgacug ccuggucugt t                                                 21

<210> SEQ ID NO 849
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 849
cagaccaggc agucgcucut t                                                 21

<210> SEQ ID NO 850
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 850
gagcgacugc cuggucugct t                                                 21

<210> SEQ ID NO 851
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 851
gcagaccagg cagucgcuct t                                                 21

<210> SEQ ID NO 852
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 852
agcgacugcc uggucugcct t								21

<210> SEQ ID NO 853
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 853
ggcagaccag gcagucgcut t								21

<210> SEQ ID NO 854
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 854
gcgacugccu ggucugccgt t								21

<210> SEQ ID NO 855
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 855
cggcagacca ggcagucgct t								21

<210> SEQ ID NO 856
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 856
cgacugccug gucugccgct t								21

<210> SEQ ID NO 857
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 857
gcggcagacc aggcagucgt t                                              21

<210> SEQ ID NO 858
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 858
gccuggucug ccgcaaauut t                                              21

<210> SEQ ID NO 859
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 859
aauuugcggc agaccaggct t                                              21

<210> SEQ ID NO 860
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 860
ccuggucugc cgcaaauuct t                                              21

<210> SEQ ID NO 861
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 861
gaauuugcgg cagaccaggt t                                              21

<210> SEQ ID NO 862
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

```
<400> SEQUENCE: 862
cuggucugcc gcaaauucct t                                               21

<210> SEQ ID NO 863
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 863
ggaauuugcg gcagaccagt t                                               21

<210> SEQ ID NO 864
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 864
uggucugccg caaauuccgt t                                               21

<210> SEQ ID NO 865
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 865
cggaauuugc ggcagaccat t                                               21

<210> SEQ ID NO 866
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 866
gucugccgca aauuccgagt t                                               21

<210> SEQ ID NO 867
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

<400> SEQUENCE: 867
cucggaauuu gcggcagact t        21

<210> SEQ ID NO 868
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 868
ucugccgcaa auuccgagat t        21

<210> SEQ ID NO 869
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 869
ucucggaauu ugcggcagat t        21

<210> SEQ ID NO 870
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 870
cugccgcaaa uuccgagact t        21

<210> SEQ ID NO 871
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 871
gucucggaau uugcggcagt t        21

<210> SEQ ID NO 872
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

Synthetic oligonucleotide

<400> SEQUENCE: 872
ugccgcaaau uccgagacgt t          21

<210> SEQ ID NO 873
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 873
cgucucggaa uuugcggcat t          21

<210> SEQ ID NO 874
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 874
ccgcaaauuc cgagacgaat t          21

<210> SEQ ID NO 875
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 875
uucgucucgg aauuugcggt t          21

<210> SEQ ID NO 876
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 876
aauuccgaga cgaagccact t          21

<210> SEQ ID NO 877
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

<223> OTHER INFORMATION: Description of Combined DNA/RNA Molecule:
      Synthetic oligonucleotide

<400> SEQUENCE: 877
guggcuucgu cucggaauut t                                              21

<210> SEQ ID NO 878
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 878
auuccgagac gaagccacgt t                                              21

<210> SEQ ID NO 879
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 879
cguggcuucg ucucggaaut t                                              21

<210> SEQ ID NO 880
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 880
uuccgagacg aagccacgut t                                              21

<210> SEQ ID NO 881
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 881
acguggcuuc gucucggaat t                                              21

<210> SEQ ID NO 882
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

```
<220> FEATURE:
<223> OTHER INFORMATION: Description of Combined DNA/RNA Molecule:
      Synthetic oligonucleotide

<400> SEQUENCE: 882
uccgagacga agccacgugt t                                              21

<210> SEQ ID NO 883
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 883
cacguggcuu cgucucggat t                                              21

<210> SEQ ID NO 884
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 884
ccgagacgaa gccacgugct t                                              21

<210> SEQ ID NO 885
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 885
gcacguggcu ucgucucggt t                                              21

<210> SEQ ID NO 886
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 886
gagacgaagc cacgugcaat t                                              21

<210> SEQ ID NO 887
<211> LENGTH: 21
<212> TYPE: DNA
<213> ORGANISM: Artificial Sequence
<220> FEATURE:
<223> OTHER INFORMATION: Description of Artificial Sequence: Synthetic
```

```
      oligonucleotide
<220> FEATURE:
<223> OTHER INFORMATION: Description of Combined DNA/RNA Molecule:
      Synthetic oligonucleotide

<400> SEQUENCE: 887
uugcacgugg cuucgucuct t                                             21

<210> SEQ ID NO 888
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 888
acgaagccac gugcaaggat t                                             21

<210> SEQ ID NO 889
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 889
uccuugcacg uggcuucgut t                                             21

<210> SEQ ID NO 890
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 890
cgaagccacg ugcaaggact t                                             21

<210> SEQ ID NO 891
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 891
guccuugcac guggcuucgt t                                             21

<210> SEQ ID NO 892
<211> LENGTH: 21
<212> TYPE: DNA
<213> ORGANISM: Artificial Sequence
<220> FEATURE:
```

<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 892
gaagccacgu gcaaggacat t                                              21

<210> SEQ ID NO 893
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 893
uguccuugca cguggcuuct t                                              21

<210> SEQ ID NO 894
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 894
aagccacgug caaggacact t                                              21

<210> SEQ ID NO 895
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 895
guguccuugc acguggcuut t                                              21

<210> SEQ ID NO 896
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 896
ccccacucau gcucuacaat t                                              21

<210> SEQ ID NO 897
<211> LENGTH: 21
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 897
uuguagagca ugagugggt t                                              21

<210> SEQ ID NO 898
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 898
ccacucaugc ucuacaacct t                                             21

<210> SEQ ID NO 899
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 899
gguuguagag caugaguggt t                                             21

<210> SEQ ID NO 900
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 900
acucaugcuc uacaacccct t                                             21

<210> SEQ ID NO 901
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 901
gggguuguag agcaugagut t                                             21

<210> SEQ ID NO 902
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 902
caugcucuac aaccccacct t                                             21

<210> SEQ ID NO 903
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 903
ggugggguug uagagcaugt t                                             21

<210> SEQ ID NO 904
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 904
ccagauggau gugaaccect t                                             21

<210> SEQ ID NO 905
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 905
gggguucaca uccaucuggt t                                             21

<210> SEQ ID NO 906
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 906
agauggaugu gaaccccgat t                                             21

<210> SEQ ID NO 907
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 907
ucgggguuca cauccaucut t                                              21

<210> SEQ ID NO 908
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 908
gauggaugug aaccccgagt t                                              21

<210> SEQ ID NO 909
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 909 cucggguuc acauccauct t                                               21

<210> SEQ ID NO 910
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 910
auggauguga accccgaggt t                                              21

<210> SEQ ID NO 911
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 911
ccucgggguu cacauccaut t                                              21

<210> SEQ ID NO 912
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 912
ggaugugaac cccgagggct t                                              21

<210> SEQ ID NO 913
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 913
gcccucgggg uucacaucct t                                              21

<210> SEQ ID NO 914
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 914
gaugugaacc ccgagggcat t                                              21

<210> SEQ ID NO 915
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 915
ugcccucggg guucacauct t                                              21

<210> SEQ ID NO 916
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 916
ugugaacccc gagggcaaat t                                              21
```

```
<210> SEQ ID NO 917
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 917
uuugcccucg ggguucacat t                                              21

<210> SEQ ID NO 918
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 918
aaccccgagg gcaaauacat t                                              21

<210> SEQ ID NO 919
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 919
uguauuugcc cucgggguut t                                              21

<210> SEQ ID NO 920
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 920
accccgaggg caaauacagt t                                              21

<210> SEQ ID NO 921
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 921
cuguauuugc ccucgggut t                                               21
```

```
<210> SEQ ID NO 922
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 922
cccgagggca aauacagcut t                                           21

<210> SEQ ID NO 923
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 923
agcuguauuu gcccucgggt t                                           21

<210> SEQ ID NO 924
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 924
ccgagggcaa auacagcuut t                                           21

<210> SEQ ID NO 925
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 925
aagcuguauu ugcccucggt t                                           21

<210> SEQ ID NO 926
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 926
cgagggcaaa uacagcuuut t                                           21
```

<210> SEQ ID NO 927
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 927
aaagcuguau uugcccucgt t                                              21

<210> SEQ ID NO 928
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 928
aaauacagcu uuggugccat t                                              21

<210> SEQ ID NO 929
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 929
uggcaccaaa gcuguauuut t                                              21

<210> SEQ ID NO 930
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 930
aauacagcuu uggugccact t                                              21

<210> SEQ ID NO 931
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 931

```
guggcaccaa agcuguauut t                                              21
```

<210> SEQ ID NO 932
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 932

```
auacagcuuu ggugccacct t                                              21
```

<210> SEQ ID NO 933
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 933

```
gguggcacca aagcuguaut t                                              21
```

<210> SEQ ID NO 934
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 934

```
cuuuggugcc accugcgugt t                                              21
```

<210> SEQ ID NO 935
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 935

```
cacgcaggug gcaccaaagt t                                              21
```

<210> SEQ ID NO 936
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 936
uuggugccac cugcgugaat t					21

<210> SEQ ID NO 937
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 937
uucacgcagg uggcaccaat t					21

<210> SEQ ID NO 938
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 938
ccaccugcgu gaagaagugt t					21

<210> SEQ ID NO 939
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 939
cacuucuuca cgcagguggt t					21

<210> SEQ ID NO 940
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 940
cugcgugaag aagugcccct t					21

<210> SEQ ID NO 941
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

```
<400> SEQUENCE: 941
gggacacuuc uucacgcagt t                                              21

<210> SEQ ID NO 942
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 942
ugcgugaaga aguguccccu t                                              21

<210> SEQ ID NO 943
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 943
ggggacacuu cuucacgcat t                                              21

<210> SEQ ID NO 944
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 944
gcgugaagaa gugucccegt t                                              21

<210> SEQ ID NO 945
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 945
cggggacacu ucuucacgct t                                              21

<210> SEQ ID NO 946
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

<400> SEQUENCE: 946
cgugaagaag ugucccgut t                              21

<210> SEQ ID NO 947
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 947
acggggacac uucuucacgt t                             21

<210> SEQ ID NO 948
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 948
gugaagaagu gucccguat t                              21

<210> SEQ ID NO 949
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 949
uacggggaca cuucuucact t                             21

<210> SEQ ID NO 950
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 950
ugaagaagug uccccguaat t                             21

<210> SEQ ID NO 951
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

Synthetic oligonucleotide

<400> SEQUENCE: 951
uuacggggac acuucuucat t          21

<210> SEQ ID NO 952
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 952
gaagaagugu ccccguaaut t          21

<210> SEQ ID NO 953
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 953
auuacgggga cacuucuuct t          21

<210> SEQ ID NO 954
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 954
aagaaguguc cccguaauut t          21

<210> SEQ ID NO 955
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 955
aauuacgggg acacuucuut t          21

<210> SEQ ID NO 956
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

```
<223> OTHER INFORMATION: Description of Combined DNA/RNA Molecule:
      Synthetic oligonucleotide

<400> SEQUENCE: 956
agaagugucc ccguaauuat t                                              21

<210> SEQ ID NO 957
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 957
uaauuacggg gacacuucut t                                              21

<210> SEQ ID NO 958
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 958
gaagugcccc cguaauuaut t                                              21

<210> SEQ ID NO 959
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 959
auaauuacgg ggacacuuct t                                              21

<210> SEQ ID NO 960
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 960
aagugccccc guaauuaugt t                                              21

<210> SEQ ID NO 961
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide

<400> SEQUENCE: 961
cauaauuacg gggacacuut t                                               21

<210> SEQ ID NO 962
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 962
aguguccccg uaauuaugut t                                               21

<210> SEQ ID NO 963
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 963
acauaauuac ggggacacut t                                               21

<210> SEQ ID NO 964
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 964
guguccccgu aauuaugugt t                                               21

<210> SEQ ID NO 965
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 965
cacauaauua cggggacact t                                               21

<210> SEQ ID NO 966
<211> LENGTH: 21
<212> TYPE: DNA
<213> ORGANISM: Artificial Sequence
<220> FEATURE:
<223> OTHER INFORMATION: Description of Artificial Sequence: Synthetic
``` oligonucleotide
<220> FEATURE:
<223> OTHER INFORMATION: Description of Combined DNA/RNA Molecule:
    Synthetic oligonucleotide

<400> SEQUENCE: 966 ugucccgua auuauguggt t                                              21

<210> SEQ ID NO 967
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 967
ccacauaauu acgggacat t                                              21

<210> SEQ ID NO 968
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 968 gucccguaa uuauguggut t                                              21

<210> SEQ ID NO 969
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 969
accacauaau uacggggact t                                             21

<210> SEQ ID NO 970
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 970
ccccguaauu auggugat t                                               21

<210> SEQ ID NO 971
<211> LENGTH: 21
<212> TYPE: DNA
<213> ORGANISM: Artificial Sequence
<220> FEATURE:

-continued

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 971
ucaccacaua auuacggggt t                                              21

<210> SEQ ID NO 972
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 972
ccguaauuau guggugacat t                                              21

<210> SEQ ID NO 973
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 973
ugucaccaca uaauuacggt t                                              21

<210> SEQ ID NO 974
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 974
guaauuaugu ggugacagat t                                              21

<210> SEQ ID NO 975
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 975
ucugucacca cauaauuact t                                              21

<210> SEQ ID NO 976
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 976
uaauuaugug gugacagaut t                                              21

<210> SEQ ID NO 977
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 977
aucugucacc acauaauuat t                                              21

<210> SEQ ID NO 978
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 978
aauuaugugg ugacagauct t                                              21

<210> SEQ ID NO 979
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 979
gaucugucac cacauaauut t                                              21

<210> SEQ ID NO 980
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 980
auuauguggu gacagaucat t                                              21

<210> SEQ ID NO 981
<211> LENGTH: 21
<212> TYPE: DNA
```

<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 981
ugaucuguca ccacauaaut t          21

<210> SEQ ID NO 982
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 982
uuauguggug acagaucact t          21

<210> SEQ ID NO 983
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 983
gugaucuguc accacauaat t          21

<210> SEQ ID NO 984
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 984
auguggugac agaucacggt t          21

<210> SEQ ID NO 985
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 985
ccgugaucug ucaccacaut t          21

<210> SEQ ID NO 986
<211> LENGTH: 21

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 986
uggugacaga ucacggcuct t                                             21

<210> SEQ ID NO 987
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 987
gagccgugau cugucaccat t                                             21

<210> SEQ ID NO 988
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 988
gugacagauc acggcucgut t                                             21

<210> SEQ ID NO 989
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 989
acgagccgug aucugucact t                                             21

<210> SEQ ID NO 990
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 990
ugacagauca cggcucgugt t                                             21

<210> SEQ ID NO 991
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 991
cacgagccgu gaucugucat t                                              21

<210> SEQ ID NO 992
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 992
gacagaucac ggcucgugct t                                              21

<210> SEQ ID NO 993
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 993
gcacgagccg ugaucuguct t                                              21

<210> SEQ ID NO 994
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 994
acagaucacg gcucgugcgt t                                              21

<210> SEQ ID NO 995
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 995
cgcacgagcc gugaucugut t                                              21
```

```
<210> SEQ ID NO 996
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 996
cagaucacgg cucgugcgut t                                           21

<210> SEQ ID NO 997
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 997
acgcacgagc cgugaucugt t                                           21

<210> SEQ ID NO 998
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 998
agaucacggc ucgugcguct t                                           21

<210> SEQ ID NO 999
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 999
gacgcacgag ccgugaucut t                                           21

<210> SEQ ID NO 1000
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1000
gaucacggcu cgugcgucct t                                           21
```

```
<210> SEQ ID NO 1001
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1001
ggacgcacga gccgugauct t                                                    21

<210> SEQ ID NO 1002
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1002
aucacggcuc gugcguccgt t                                                    21

<210> SEQ ID NO 1003
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1003
cggacgcacg agccgugaut t                                                    21

<210> SEQ ID NO 1004
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1004
ucacggcucg ugcguccgat t                                                    21

<210> SEQ ID NO 1005
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1005
ucggacgcac gagccgugat t                                                    21
```

```
<210> SEQ ID NO 1006
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1006
cacggcucgu gcguccgagt t                                            21

<210> SEQ ID NO 1007
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1007
cucggacgca cgagccgugt t                                            21

<210> SEQ ID NO 1008
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1008
acggcucgug cguccgagct t                                            21

<210> SEQ ID NO 1009
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1009
gcucggacgc acgagccgut t                                            21

<210> SEQ ID NO 1010
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1010
```
gcucgugcgu ccgagccugt t				21

<210> SEQ ID NO 1011
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1011
caggcucgga cgcacgagct t				21

<210> SEQ ID NO 1012
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1012
ggaggaagac ggcguccgct t				21

<210> SEQ ID NO 1013
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1013
gcggacgccg ucuuccucct t				21

<210> SEQ ID NO 1014
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1014
gaggaagacg gcguccgcat t				21

<210> SEQ ID NO 1015
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1015

-continued ugcggacgcc gucuuccuct t                                    21

<210> SEQ ID NO 1016
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1016
ggaagacggc guccgcaagt t                                    21

<210> SEQ ID NO 1017
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1017
cuugcggacg ccgucuucct t                                    21

<210> SEQ ID NO 1018
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1018
gaagacggcg uccgcaagut t                                    21

<210> SEQ ID NO 1019
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1019
acuugcggac gccgucuuct t                                    21

<210> SEQ ID NO 1020
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

```
<400> SEQUENCE: 1020
aagacggcgu ccgcaagugt t                                              21

<210> SEQ ID NO 1021
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1021
cacuugcgga cgccgucuut t                                              21

<210> SEQ ID NO 1022
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1022
gacggcgucc gcaaguguat t                                              21

<210> SEQ ID NO 1023
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1023
uacacuugcg gacgccguct t                                              21

<210> SEQ ID NO 1024
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1024
acggcguccg caaguguaat t                                              21

<210> SEQ ID NO 1025
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

<400> SEQUENCE: 1025
uuacacuugc ggacgccgut t                     21

<210> SEQ ID NO 1026
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1026
gcguccgcaa guguaagaat t                     21

<210> SEQ ID NO 1027
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1027
uucuuacacu ugcggacgct t                     21

<210> SEQ ID NO 1028
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1028
cguccgcaag uguaagaagt t                     21

<210> SEQ ID NO 1029
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1029
cuucuuacac uugcggacgt t                     21

<210> SEQ ID NO 1030
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

Synthetic oligonucleotide

<400> SEQUENCE: 1030
guccgcaagu guaagaagut t                                              21

<210> SEQ ID NO 1031
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1031
acuucuuaca cuugcggact t                                              21

<210> SEQ ID NO 1032
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1032
uccgcaagug uaagaagugt t                                              21

<210> SEQ ID NO 1033
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1033
cacuucuuac acuugcggat t                                              21

<210> SEQ ID NO 1034
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1034
ccgcaagugu aagaagugct t                                              21

<210> SEQ ID NO 1035
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

```
<223> OTHER INFORMATION: Description of Combined DNA/RNA Molecule:
      Synthetic oligonucleotide

<400> SEQUENCE: 1035
gcacuucuua cacuugcggt t                                              21

<210> SEQ ID NO 1036
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1036
cgcaagugua agaagugcgt t                                              21

<210> SEQ ID NO 1037
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1037
cgcacuucuu acacuugcgt t                                              21

<210> SEQ ID NO 1038
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1038
gcaaguguaa gaagugcgat t                                              21

<210> SEQ ID NO 1039
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1039
ucgcacuucu uacacuugct t                                              21

<210> SEQ ID NO 1040
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide

<400> SEQUENCE: 1040
aaguguaaga agugcgaagt t                                                    21

<210> SEQ ID NO 1041
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1041
cuucgcacuu cuuacacuut t                                                    21

<210> SEQ ID NO 1042
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1042
aguguaagaa gugcgaaggt t                                                    21

<210> SEQ ID NO 1043
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1043
ccuucgcacu ucuuacacut t                                                    21

<210> SEQ ID NO 1044
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1044
guguaagaag ugcgaagggt t                                                    21

<210> SEQ ID NO 1045
<211> LENGTH: 21
<212> TYPE: DNA
<213> ORGANISM: Artificial Sequence
<220> FEATURE:
<223> OTHER INFORMATION: Description of Artificial Sequence: Synthetic
```

```
      oligonucleotide
<220> FEATURE:
<223> OTHER INFORMATION: Description of Combined DNA/RNA Molecule:
      Synthetic oligonucleotide

<400> SEQUENCE: 1045
cccuucgcac uucuuacact t                                            21

<210> SEQ ID NO 1046
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1046
uguaagaagu gcgaagggct t                                            21

<210> SEQ ID NO 1047
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1047
gcccuucgca cuucuuacat t                                            21

<210> SEQ ID NO 1048
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1048
guaagaagug cgaagggcct t                                            21

<210> SEQ ID NO 1049
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1049
ggcccuucgc acuucuuact t                                            21

<210> SEQ ID NO 1050
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1050
uaagaagugc gaagggccut t                                              21

<210> SEQ ID NO 1051
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1051
aggcccuucg cacuucuuat t                                              21

<210> SEQ ID NO 1052
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1052
aagaagugcg aagggccuut t                                              21

<210> SEQ ID NO 1053
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1053
aaggcccuuc gcacuucuut t                                              21

<210> SEQ ID NO 1054
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1054
agaagugcga agggccuugt t                                              21

<210> SEQ ID NO 1055
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1055
caaggcccuu cgcacuucut t                                              21

<210> SEQ ID NO 1056
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1056
agugcgaagg gccuugccgt t                                              21

<210> SEQ ID NO 1057
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1057
cggcaaggcc cuucgcacut t                                              21

<210> SEQ ID NO 1058
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1058
gugcgaaggg ccuugccgct t                                              21

<210> SEQ ID NO 1059
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1059
gcggcaaggc cuucgcact t                                               21

<210> SEQ ID NO 1060
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1060
ugcgaagggc uugccgcat t                                              21

<210> SEQ ID NO 1061
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1061
ugcggcaagg cccuucgcat t                                             21

<210> SEQ ID NO 1062
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1062
gcgaagggcc uugccgcaat t                                             21

<210> SEQ ID NO 1063
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1063
uugcggcaag gcccuucgct t                                             21

<210> SEQ ID NO 1064
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1064
cgaagggccu ugccgcaaat t                                             21

<210> SEQ ID NO 1065
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1065
uuugcggcaa ggcccuucgt t                                              21

<210> SEQ ID NO 1066
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1066
aagggccuug ccgcaaagut t                                              21

<210> SEQ ID NO 1067
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1067
acuuugcggc aaggcccuut t                                              21

<210> SEQ ID NO 1068
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1068
agggccuugc cgcaaagugt t                                              21

<210> SEQ ID NO 1069
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1069
cacuuugcgg caaggcccut t                                              21

<210> SEQ ID NO 1070
```

```
<210> SEQ ID NO 1070
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1070
gggccuugcc gcaaagugut t                                                   21

<210> SEQ ID NO 1071
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1071
acacuuugcg gcaaggccct t                                                   21

<210> SEQ ID NO 1072
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1072
ggccuugccg caaagugugt t                                                   21

<210> SEQ ID NO 1073
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1073
cacacuuugc ggcaaggcct t                                                   21

<210> SEQ ID NO 1074
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1074
gccuugccgc aaagugugut t                                                   21
```

```
<210> SEQ ID NO 1075
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1075
acacacuuug cggcaaggct t                                              21

<210> SEQ ID NO 1076
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1076
cuugccgcaa aguguguaat t                                              21

<210> SEQ ID NO 1077
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1077
uuacacacuu ugcggcaagt t                                              21

<210> SEQ ID NO 1078
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1078
ggaauaggua uuggugaaut t                                              21

<210> SEQ ID NO 1079
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1079
auucaccaau accuauucct t                                              21
```

<210> SEQ ID NO 1080
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1080
gaauagguau uggugaauut t                                              21

<210> SEQ ID NO 1081
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1081
aauucaccaa uaccuauuct t                                              21

<210> SEQ ID NO 1082
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1082
aauagguauu ggugaauuut t                                              21

<210> SEQ ID NO 1083
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1083
aaauucacca auaccuauut t                                              21

<210> SEQ ID NO 1084
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1084
auagguauug gugaauuuat t                                              21

<210> SEQ ID NO 1085
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1085
uaaauucacc aauaccuaut t                                              21

<210> SEQ ID NO 1086
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1086
agguauuggu gaauuuaaat t                                              21

<210> SEQ ID NO 1087
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1087
uuuaaauuca ccaauaccut t                                              21

<210> SEQ ID NO 1088
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1088
gguauuggug aauuuaaagt t                                              21

<210> SEQ ID NO 1089
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1089

-continued cuuuaaauuc accaauacct t                                    21

<210> SEQ ID NO 1090
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1090
cacucuccau aaaugcuact t                                    21

<210> SEQ ID NO 1091
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1091
guagcauuua uggagagugt t                                    21

<210> SEQ ID NO 1092
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1092
uuaaacacuu caaaaacugt t                                    21

<210> SEQ ID NO 1093
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1093
caguuuuuga aguguuuaat t                                    21

<210> SEQ ID NO 1094
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1094

```
cuucaaaaac ugcaccucct t                                              21

<210> SEQ ID NO 1095
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1095
ggaggugcag uuuuugaagt t                                              21

<210> SEQ ID NO 1096
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1096
uucaaaaacu gcaccuccat t                                              21

<210> SEQ ID NO 1097
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1097
uggaggugca guuuuugaat t                                              21

<210> SEQ ID NO 1098
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1098
ucaaaaacug caccuccaut t                                              21

<210> SEQ ID NO 1099
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

-continued

```
<400> SEQUENCE: 1099
auggaggugc aguuuugat t                                               21

<210> SEQ ID NO 1100
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1100
caaaaacugc accuccauct t                                              21

<210> SEQ ID NO 1101
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1101
gauggaggug caguuuuugt t                                              21

<210> SEQ ID NO 1102
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1102
aaaaacugca ccuccaucat t                                              21

<210> SEQ ID NO 1103
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1103
ugauggaggu gcaguuuuut t                                              21

<210> SEQ ID NO 1104
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

<400> SEQUENCE: 1104
acugcaccuc caucaguggt t                                                  21

<210> SEQ ID NO 1105
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1105
ccacugaugg aggugcagut t                                                  21

<210> SEQ ID NO 1106
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1106
caccuccauc aguggcgaut t                                                  21

<210> SEQ ID NO 1107
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1107
aucgccacug auggaggugt t                                                  21

<210> SEQ ID NO 1108
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1108
accuccauca guggcgauct t                                                  21

<210> SEQ ID NO 1109
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

Synthetic oligonucleotide

<400> SEQUENCE: 1109
gaucgccacu gauggaggut t                                              21

<210> SEQ ID NO 1110
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1110
cuccaucagu ggcgaucuct t                                              21

<210> SEQ ID NO 1111
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1111
gagaucgcca cugauggagt t                                              21

<210> SEQ ID NO 1112
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1112
caucaguggc gaucuccact t                                              21

<210> SEQ ID NO 1113
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1113
guggagaucg ccacugaugt t                                              21

<210> SEQ ID NO 1114
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

```
<223> OTHER INFORMATION: Description of Combined DNA/RNA Molecule:
      Synthetic oligonucleotide

<400> SEQUENCE: 1114
uggcgaucuc cacauccugt t                                              21

<210> SEQ ID NO 1115
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1115
caggaugugg agaucgccat t                                              21

<210> SEQ ID NO 1116
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1116
ggcgaucucc acauccugct t                                              21

<210> SEQ ID NO 1117
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1117
gcaggaugug gagaucgcct t                                              21

<210> SEQ ID NO 1118
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1118
gcgaucucca cauccugcct t                                              21

<210> SEQ ID NO 1119
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide

<400> SEQUENCE: 1119
ggcaggaugu ggagaucgct t                                            21

<210> SEQ ID NO 1120
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1120
cgaucuccac auccugccgt t                                            21

<210> SEQ ID NO 1121
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1121
cggcaggaug uggagaucgt t                                            21

<210> SEQ ID NO 1122
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1122
gaucuccaca uccugccggt t                                            21

<210> SEQ ID NO 1123
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1123
ccggcaggau guggagauct t                                            21

<210> SEQ ID NO 1124
<211> LENGTH: 21
<212> TYPE: DNA
<213> ORGANISM: Artificial Sequence
<220> FEATURE:
<223> OTHER INFORMATION: Description of Artificial Sequence: Synthetic
```

```
        oligonucleotide
<220> FEATURE:
<223> OTHER INFORMATION: Description of Combined DNA/RNA Molecule:
      Synthetic oligonucleotide

<400> SEQUENCE: 1124
ccacauccug ccgguggcat t                                              21

<210> SEQ ID NO 1125
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1125
ugccaccggc aggauguggt t                                              21

<210> SEQ ID NO 1126
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1126
cacauccugc cgguggcaut t                                              21

<210> SEQ ID NO 1127
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1127
augccaccgg caggaugugt t                                              21

<210> SEQ ID NO 1128
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1128
acauccugcc gguggcauut t                                              21

<210> SEQ ID NO 1129
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1129
aaugccaccg gcaggaugut t                                            21

<210> SEQ ID NO 1130
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1130
auccugccgg uggcauuuat t                                            21

<210> SEQ ID NO 1131
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1131
uaaaugccac cggcaggaut t                                            21

<210> SEQ ID NO 1132
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1132
cugccggugg cauuuagggt t                                            21

<210> SEQ ID NO 1133
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1133
cccuaaaugc caccggcagt t                                            21

<210> SEQ ID NO 1134
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1134
ugccgguggc auuuaggggt t                                              21

<210> SEQ ID NO 1135
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1135
ccccuaaaug ccaccggcat t                                              21

<210> SEQ ID NO 1136
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1136
gccgguggca uuuaggggut t                                              21

<210> SEQ ID NO 1137
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1137
accccuaaau gccaccggct t                                              21

<210> SEQ ID NO 1138
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1138
ccgguggcau uuaggggugt t                                              21

<210> SEQ ID NO 1139
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1139
caccccuaaa ugccaccggt t                                              21

<210> SEQ ID NO 1140
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1140
guggcauuua ggggugacut t                                              21

<210> SEQ ID NO 1141
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1141
agucaccccu aaaugccact t                                              21

<210> SEQ ID NO 1142
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1142
gcauuuaggg gugacuccut t                                              21

<210> SEQ ID NO 1143
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1143
aggagucacc ccuaaaugct t                                              21

<210> SEQ ID NO 1144
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1144
cauuuagggg ugacuccuut t                                           21

<210> SEQ ID NO 1145
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1145
aaggagucac cccuaaaugt t                                           21

<210> SEQ ID NO 1146
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1146
auuuaggggu gacuccuuct t                                           21

<210> SEQ ID NO 1147
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1147
gaaggaguca ccccuaaaut t                                           21

<210> SEQ ID NO 1148
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1148
uuuaggggug acuccuucat t                                           21

<210> SEQ ID NO 1149
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1149
ugaaggaguc accccuaaat t                                              21

<210> SEQ ID NO 1150
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1150
uuaggggtga cuccuucact t                                              21

<210> SEQ ID NO 1151
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1151
gugaaggagu caccccuaat t                                              21

<210> SEQ ID NO 1152
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1152 uagggguugac uccuucacat t                                             21

<210> SEQ ID NO 1153
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1153
ugugaaggag ucaccccuat t                                              21
```

```
<210> SEQ ID NO 1154
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1154
ucuggaucca caggaacugt t                                                   21

<210> SEQ ID NO 1155
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1155
caguuccugu ggauccagat t                                                   21

<210> SEQ ID NO 1156
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1156
gauccacagg aacuggauat t                                                   21

<210> SEQ ID NO 1157
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1157
uauccaguuc cuguggauct t                                                   21

<210> SEQ ID NO 1158
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1158
auccacagga acuggauaut t                                                   21
```

<210> SEQ ID NO 1159
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1159
auauccaguu ccugggaut t                                                  21

<210> SEQ ID NO 1160
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1160
ccacaggaac uggauauuct t                                                 21

<210> SEQ ID NO 1161
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1161
gaauauccag uuccuguggt t                                                 21

<210> SEQ ID NO 1162
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1162
cacaggaacu ggauauucut t                                                 21

<210> SEQ ID NO 1163
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1163
agaauaucca guuccugugt t                                                 21

<210> SEQ ID NO 1164
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1164
acuggauauu cugaaaacct t                                              21

<210> SEQ ID NO 1165
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1165
gguuuucaga auauccagut t                                              21

<210> SEQ ID NO 1166
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1166
auucugaaaa ccguaaaggt t                                              21

<210> SEQ ID NO 1167
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1167
ccuuuacggu uuucagaaut t                                              21

<210> SEQ ID NO 1168
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1168
uucugaaaac cguaaaggat t            21

<210> SEQ ID NO 1169
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1169
uccuuuacgg uuuucagaat t            21

<210> SEQ ID NO 1170
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1170
ugaaaaccgu aaaggaaaut t            21

<210> SEQ ID NO 1171
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1171
auuuccuuua cgguuuucat t            21

<210> SEQ ID NO 1172
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1172
gaaaaccgua aaggaaauct t            21

<210> SEQ ID NO 1173
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1173

```
gauuuccuuu acgguuuuct t                                         21

<210> SEQ ID NO 1174
<211> LENGTH: 23
<212> TYPE: RNA
<213> ORGANISM: Homo sapiens

<400> SEQUENCE: 1174
caaagguucu cugcuagacg aca                                       23

<210> SEQ ID NO 1175
<211> LENGTH: 23
<212> TYPE: RNA
<213> ORGANISM: Homo sapiens

<400> SEQUENCE: 1175
ucuggguguc acuauggagc ucu                                       23

<210> SEQ ID NO 1176
<211> LENGTH: 23
<212> TYPE: RNA
<213> ORGANISM: Homo sapiens

<400> SEQUENCE: 1176
cuggguguca cuauggagcu cuc                                       23

<210> SEQ ID NO 1177
<211> LENGTH: 23
<212> TYPE: RNA
<213> ORGANISM: Homo sapiens

<400> SEQUENCE: 1177
gggugucacu auggagcucu cac                                       23

<210> SEQ ID NO 1178
<211> LENGTH: 23
<212> TYPE: RNA
<213> ORGANISM: Homo sapiens

<400> SEQUENCE: 1178
uacuacaacu uuccacuggc ucu                                       23

<210> SEQ ID NO 1179
<211> LENGTH: 23
<212> TYPE: RNA
<213> ORGANISM: Unknown
<220> FEATURE:
<223> OTHER INFORMATION: Description of Unknown:
      XD-01825K1 Human or Mouse target sequence

<400> SEQUENCE: 1179
aagcuucugg gugucacuau gga                                       23

<210> SEQ ID NO 1180
<211> LENGTH: 23
<212> TYPE: RNA
<213> ORGANISM: Homo sapiens

<400> SEQUENCE: 1180 cuucggguguc acuaugga gcu                                        23

<210> SEQ ID NO 1181
<211> LENGTH: 21
```

```
<212> TYPE: RNA
<213> ORGANISM: Unknown
<220> FEATURE:
<223> OTHER INFORMATION: Description of Unknown:
      Beta-catenin target sequence

<400> SEQUENCE: 1181
cuguuggauu gauucgaaau u                                              21

<210> SEQ ID NO 1182
<211> LENGTH: 21
<212> TYPE: RNA
<213> ORGANISM: Unknown
<220> FEATURE:
<223> OTHER INFORMATION: Description of Unknown:
      Beta-catenin target sequence

<400> SEQUENCE: 1182
uuucgaauca auccaacagu u                                              21

<210> SEQ ID NO 1183
<211> LENGTH: 21
<212> TYPE: RNA
<213> ORGANISM: Unknown
<220> FEATURE:
<223> OTHER INFORMATION: Description of Unknown:
      Beta-catenin target sequence

<400> SEQUENCE: 1183
acgacuaguu caguugcuuu u                                              21

<210> SEQ ID NO 1184
<211> LENGTH: 21
<212> TYPE: RNA
<213> ORGANISM: Unknown
<220> FEATURE:
<223> OTHER INFORMATION: Description of Unknown:
      Beta-catenin target sequence

<400> SEQUENCE: 1184
aagcaacuga acuagucguu u                                              21

<210> SEQ ID NO 1185
<211> LENGTH: 97
<212> TYPE: DNA
<213> ORGANISM: Homo sapiens

<400> SEQUENCE: 1185
tgctgttgac agtgagcgcc agctcaaagc aatttctaca tagtgaagcc acagatgtat    60
gtagaaattg ctttgagctg ttgcctactg cctcgga                             97

<210> SEQ ID NO 1186
<211> LENGTH: 97
<212> TYPE: DNA
<213> ORGANISM: Homo sapiens

<400> SEQUENCE: 1186
tgctgttgac agtgagcgaa aggatgaaac acaaaaggta tagtgaagcc acagatgtat    60 acctttgtg tttcatcctt ctgcctactg cctcgga                              97

<210> SEQ ID NO 1187
<211> LENGTH: 97
<212> TYPE: DNA
<213> ORGANISM: Homo sapiens
```

<400> SEQUENCE: 1187
tgctgttgac agtgagcgcc atgtcagagt tactgtttca tagtgaagcc acagatgtat     60
gaaacagtaa ctctgacatg atgcctactg cctcgga                             97

<210> SEQ ID NO 1188
<211> LENGTH: 97
<212> TYPE: DNA
<213> ORGANISM: Homo sapiens

<400> SEQUENCE: 1188
tgctgttgac agtgagcgca actagttcat ttcaaaatta tagtgaagcc acagatgtat     60
aattttgaaa tgaactagtt ttgcctactg cctcgga                             97

<210> SEQ ID NO 1189
<211> LENGTH: 97
<212> TYPE: DNA
<213> ORGANISM: Homo sapiens

<400> SEQUENCE: 1189
tgctgttgac agtgagcgca cagcaagaac agaaataaaa tagtgaagcc acagatgtat     60
tttatttctg ttcttgctgt atgcctactg cctcgga                             97

<210> SEQ ID NO 1190
<211> LENGTH: 97
<212> TYPE: DNA
<213> ORGANISM: Homo sapiens

<400> SEQUENCE: 1190
tgctgttgac agtgagcgac aagatcaaga aaatgtatga tagtgaagcc acagatgtat     60
catacatttt cttgatcttg ctgcctactg cctcgga                             97

<210> SEQ ID NO 1191
<211> LENGTH: 97
<212> TYPE: DNA
<213> ORGANISM: Homo sapiens

<400> SEQUENCE: 1191
tgctgttgac agtgagcgca gcaagttcac aattacccaa tagtgaagcc acagatgtat     60
tgggtaattg tgaacttgct ttgcctactg cctcgga                             97

<210> SEQ ID NO 1192
<211> LENGTH: 97
<212> TYPE: DNA
<213> ORGANISM: Homo sapiens

<400> SEQUENCE: 1192
tgctgttgac agtgagcgcc ccttcgataa gattattgaa tagtgaagcc acagatgtat     60
tcaataatct tatcgaaggg atgcctactg cctcgga                             97

<210> SEQ ID NO 1193
<211> LENGTH: 97
<212> TYPE: DNA
<213> ORGANISM: Homo sapiens

<400> SEQUENCE: 1193
tgctgttgac agtgagcgag agcttgaaga tgaaacacga tagtgaagcc acagatgtat     60
cgtgtttcat cttcaagctc ctgcctactg cctcgga                             97

```
<210> SEQ ID NO 1194
<211> LENGTH: 97
<212> TYPE: DNA
<213> ORGANISM: Homo sapiens

<400> SEQUENCE: 1194
tgctgttgac agtgagcgac accaaagaaa acacgaatta tagtgaagcc acagatgtat    60
aattcgtgtt ttctttggtg gtgcctactg cctcgga                            97

<210> SEQ ID NO 1195
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1195
uguagaaauu gcuugagcu gu                                              22

<210> SEQ ID NO 1196
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1196
agcucaaagc aauuucuaca ua                                             22

<210> SEQ ID NO 1197
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1197
uaccuuuugu guuucauccu uc                                             22

<210> SEQ ID NO 1198
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1198
aggaugaaac acaaaaggua ua                                             22

<210> SEQ ID NO 1199
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1199
ugaaacagua acucugacau ga                                             22

<210> SEQ ID NO 1200
<211> LENGTH: 22
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1200
augucagagu uacuguuuca ua                                              22

<210> SEQ ID NO 1201
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1201
uaauuuugaa augaacuagu uu                                              22

<210> SEQ ID NO 1202
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1202
acuaguucau uucaaaauua ua                                              22

<210> SEQ ID NO 1203
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1203
uuuuauuucu guucuugcug ua                                              22

<210> SEQ ID NO 1204
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1204
cagcaagaac agaaauaaaa ua                                              22

<210> SEQ ID NO 1205
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1205
ucauacauuu ucuugaucuu gc                                              22

<210> SEQ ID NO 1206
<211> LENGTH: 22
<212> TYPE: RNA
```

<213> ORGANISM: Artificial Sequence
<220> FEATURE:
<223> OTHER INFORMATION: Description of Artificial Sequence: Synthetic
      oligonucleotide

<400> SEQUENCE: 1206
aagaucaaga aaauguauga ua                                              22

<210> SEQ ID NO 1207
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1207
uuggguaauu gugaacuugc uu                                              22

<210> SEQ ID NO 1208
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1208
gcaaguucac aauuaccaa ua                                               22

<210> SEQ ID NO 1209
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1209
uucaauaauc uuaucgaagg ga                                              22

<210> SEQ ID NO 1210
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1210
ccuucgauaa gauuauugaa ua                                              22

<210> SEQ ID NO 1211
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1211
ucguguuuca ucuucaagcu cc                                              22

<210> SEQ ID NO 1212
<211> LENGTH: 22
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 1212
agcuugaaga ugaaacacga ua                                              22

<210> SEQ ID NO 1213
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1213
uaauucgugu uuucuuuggu gg                                              22

<210> SEQ ID NO 1214
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1214
accaaagaaa acacgaauua ua                                              22

<210> SEQ ID NO 1215
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1215
acucgugccu uggcaaacuu u                                               21

<210> SEQ ID NO 1216
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1216
aguuugccaa ggcacgaguu u                                               21

<210> SEQ ID NO 1217
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1217
acucgugccu uggcaaacuu u                                               21

<210> SEQ ID NO 1218
<211> LENGTH: 21
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 1218
aguuugccaa ggcacgaguu u                                             21

<210> SEQ ID NO 1219
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1219
acucgugccu uggcaaacuu u                                             21

<210> SEQ ID NO 1220
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1220
aguuugccaa ggcacgaguu u                                             21

<210> SEQ ID NO 1221
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1221
ugaauuagcu guaucgucau u                                             21

<210> SEQ ID NO 1222
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1222
tgacgauaca gcuaauucau u                                             21

<210> SEQ ID NO 1223
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1223
ugaauuagcu guaucgucau u                                             21

<210> SEQ ID NO 1224
<211> LENGTH: 21
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 1224
ugacgauaca gcuaauucau u                                              21

<210> SEQ ID NO 1225
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1225
ugaauuagcu guaucgucau u                                              21

<210> SEQ ID NO 1226
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1226
ugacgauaca gcuaauucau u                                              21

<210> SEQ ID NO 1227
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1227
uaaguauagg uccucauuau u                                              21

<210> SEQ ID NO 1228
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1228
uaaugaggac cuauacuuau u                                              21

<210> SEQ ID NO 1229
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1229
tuucgaauca auccaacagu u                                              21

<210> SEQ ID NO 1230
```

```
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1230 cguuggauu gauucgaaau u                                              21

<210> SEQ ID NO 1231
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1231
uuucgaauca auccaacagu u                                             21

<210> SEQ ID NO 1232
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1232 cguuggauu gauucgaaau u                                              21

<210> SEQ ID NO 1233
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1233
uuucgaauca auccaacagu u                                             21

<210> SEQ ID NO 1234
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1234 cguuggauu gauucgaaau u                                              21

<210> SEQ ID NO 1235
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1235
auaaaaucua cagucauagu u                                             21

<210> SEQ ID NO 1236
<211> LENGTH: 21
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1236
cuaugacugu agauuuuauu u                                              21

<210> SEQ ID NO 1237
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1237
uuaaaaucua cagucauagu u                                              21

<210> SEQ ID NO 1238
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1238
cuaugacugu agauuuuaau u                                              21

<210> SEQ ID NO 1239
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1239
uuaaaaucua cagucauagu u                                              21

<210> SEQ ID NO 1240
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1240
cuaugacugu agauuuuaau u                                              21

<210> SEQ ID NO 1241
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1241
gagagcucca uagugacacu u                                              21

<210> SEQ ID NO 1242
<211> LENGTH: 21
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 1242
gugucacuau ggagcucucu u                                                   21

<210> SEQ ID NO 1243
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1243

Cys Gly Ile Phe Gly Glu Ile Glu Glu Leu Ile Glu Glu Gly Leu Glu
1               5                   10                  15

Asn Leu Ile Asp Trp Gly Asn Ala
            20

<210> SEQ ID NO 1244
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1244

Gly Leu Phe Glu Ala Ile Glu Gly Phe Ile Glu Asn Gly Trp Glu Gly
1               5                   10                  15

Met Ile Asp Gly Trp Tyr Gly Cys
            20

<210> SEQ ID NO 1245
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1245

Gly Leu Phe Glu Ala Ile Glu Gly Phe Ile Glu Asn Gly Trp Glu Gly
1               5                   10                  15

Met Ile Trp Asp Tyr Gly Ser Gly Ser Cys Gly
            20                  25

<210> SEQ ID NO 1246
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1246

Gly Leu Phe Glu Ala Ile Glu Gly Phe Ile Glu Asn Gly Trp Glu Gly
1               5                   10                  15

Met Ile Asp Gly Trp Tyr Gly
            20

<210> SEQ ID NO 1247
```

```
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1247

Gly Leu Phe Glu Ala Ile Glu Gly Phe Ile Glu Asn Gly Trp Glu Gly
1               5                   10                  15

Met Ile Trp Asp Tyr Gly Ser Gly Ser Cys Lys
            20                  25

<210> SEQ ID NO 1248
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1248

Cys Leu Ile Gly Ala Ile Leu Lys Val Leu Ala Thr Gly Leu Pro Thr
1               5                   10                  15

Leu Ile Ser Trp Ile Lys Asn Lys Arg Lys Gln
            20                  25

<210> SEQ ID NO 1249
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1249

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 1250
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1250

Ile Phe Gly Ala Ile Ala Gly Leu Leu Lys Asn Ile Phe
1               5                   10

<210> SEQ ID NO 1251
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1251

Phe Phe Gly His Leu Phe Lys Leu Ala Thr Lys Ile Ile Pro Ser Leu
1               5                   10                  15

Phe Gln
```

<210> SEQ ID NO 1252
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1252

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 1253
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1253

Leu Leu Ile Ile Leu Arg Arg Arg Arg Ile Arg Lys Gln Ala His Ala
1               5                   10                  15

His Ser Lys

<210> SEQ ID NO 1254
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1254

Asp Pro Lys Gly Asp Pro Lys Gly Val Thr Val Thr Val Thr Val Thr
1               5                   10                  15

Val Thr Gly Lys Gly Asp Pro Lys Pro Asp
            20                  25

<210> SEQ ID NO 1255
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1255

Cys Ser Ile Pro Pro Glu Val Lys Phe Asn Lys Pro Phe Val Tyr Leu
1               5                   10                  15

Ile

<210> SEQ ID NO 1256
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1256

Gly Trp Thr Leu Asn Ser Ala Gly Tyr Leu Leu Gly Lys Ile Asn Leu
1               5                   10                  15

```
Lys Ala Leu Ala Ala Leu Ala Lys Lys Ile Leu
            20                  25

<210> SEQ ID NO 1257
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1257

Ala Gly Tyr Leu Leu Gly Lys Ile Asn Leu Lys Ala Leu Ala Ala Leu
1               5                   10                  15

Ala Lys Lys Ile Leu
            20

<210> SEQ ID NO 1258
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1258

Gly Ala Leu Phe Leu Gly Phe Leu Gly Ala Ala Gly Ser Thr Met Gly
1               5                   10                  15

Ala

<210> SEQ ID NO 1259
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1259

His Gly Leu Ala Ser Thr Leu Thr Arg Trp Ala His Tyr Asn Ala Leu
1               5                   10                  15

Ile Arg Ala Phe
            20

<210> SEQ ID NO 1260
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1260

Gly Leu Trp Arg Ala Leu Trp Arg Leu Leu Arg Ser Leu Trp Arg Leu
1               5                   10                  15

Leu Trp Arg Ala
            20

<210> SEQ ID NO 1261
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 1261

Trp Glu Ala Ala Leu Ala Glu Ala Leu Ala Glu Ala Leu Ala Glu His
1               5                   10                  15

Leu Ala Glu Ala Leu Ala Glu Ala Leu Glu Ala Leu Ala Ala
            20                  25                  30

<210> SEQ ID NO 1262
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1262

Gly Leu Phe Glu Ala Ile Glu Gly Phe Ile Glu Asn Gly Trp Glu Gly
1               5                   10                  15

Met Ile Asp Gly Trp Tyr Gly Cys
            20

<210> SEQ ID NO 1263
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1263

Gly Leu Phe Gly Ala Ile Ala Gly Phe Ile Glu Asn Gly Trp Glu Gly
1               5                   10                  15

Met Ile Asp Gly Trp Tyr Gly
            20

<210> SEQ ID NO 1264
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1264

Gly Leu Phe Gly Ala Ile Ala Gly Phe Ile Glu Asn Gly Trp Glu Gly
1               5                   10                  15

Met Ile Asp Gly Arg Gln Ile Lys Ile Trp Phe Gln Asn Arg Arg Met
            20                  25                  30

Lys Trp Lys Lys
        35

<210> SEQ ID NO 1265
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1265

Gly Leu Phe Gly Ala Ile Ala Gly Phe Ile Glu Asn Gly Trp Glu Gly
1               5                   10                  15

Met Ile Asp Gly Ser Ser Lys Lys Lys Lys
            20                  25

```
<210> SEQ ID NO 1266
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1266

Gly Leu Phe Glu Ala Ile Ala Gly Phe Ile Glu Asn Gly Trp Glu Gly
1               5                   10                  15

Met Ile Asp Gly Gly Gly Tyr Cys
            20

<210> SEQ ID NO 1267
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1267

Gly Leu Phe His Ala Ile Ala His Phe Ile His Gly Gly Trp His Gly
1               5                   10                  15

Leu Ile His Gly Trp Tyr Gly
            20

<210> SEQ ID NO 1268
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1268

Gly Leu Phe Glu Ala Ile Glu Gly Phe Ile Glu Asn Gly Trp Glu Gly
1               5                   10                  15

Leu Ala Glu Ala Leu Ala Glu Ala Leu Glu Ala Leu Ala Ala
            20                  25                  30

<210> SEQ ID NO 1269
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1269

Lys Trp Lys Leu Phe Lys Lys Ile Gly Ala Val Leu Lys Val Leu Thr
1               5                   10                  15

Thr Gly Tyr Gly Arg Lys Lys Arg Arg Gln Arg Arg Arg
            20                  25

<210> SEQ ID NO 1270
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1270
```

```
Gly Gly Phe Gly
1

<210> SEQ ID NO 1271
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1271

Ala Leu Ala Leu
1

<210> SEQ ID NO 1272
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1272

Gly Phe Leu Gly
1

<210> SEQ ID NO 1273
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1273
uuauuauuug uucuuugccu u                                              21

<210> SEQ ID NO 1274
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1274
uuacauuaaa gucuguuguu u                                              21

<210> SEQ ID NO 1275
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1275
uuaaaaucua cagucauagu u                                              21

<210> SEQ ID NO 1276
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 1276

Glu Ala Phe Gln
1

<210> SEQ ID NO 1277
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1277

Cys Gly Ile Phe Gly Glu Ile Glu Glu Leu Ile Glu Glu Gly Leu Glu
1               5                   10                  15

Asn Leu Ile Asp Trp Gly Asn Gly
            20
```